US011286483B2

(12) United States Patent
Van Der Wal et al.

(10) Patent No.: US 11,286,483 B2
(45) **Date of Patent: *Mar. 29, 2022**

(54) ENZYMATIC REPLACEMENT THERAPY AND ANTISENSE THERAPY FOR POMPE DISEASE

(71) Applicant: ERASMUS UNIVERSITY MEDICAL CENTER ROTTERDAM, Rotterdam (NL)

(72) Inventors: Erik Van Der Wal, Schiedam (NL); Atze Jacobus Bergsma, Utrecht (NL); Wilhelmus Wenceslaus Matthias Pijnappel, Vleuten (NL); Antje Tjitske Van Der Ploeg, Poortugaal (NL)

(73) Assignee: ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/622,670

(22) PCT Filed: Jun. 14, 2018

(86) PCT No.: PCT/NL2018/050392

§ 371 (c)(1),
(2) Date: Dec. 13, 2019

(87) PCT Pub. No.: WO2018/231060

PCT Pub. Date: Dec. 20, 2018

(65) Prior Publication Data

US 2020/0138846 A1 May 7, 2020

(30) Foreign Application Priority Data

Jun. 14, 2017 (NL) ..................................... 2019069

(51) Int. Cl.

| | |
|---|---|
| *C07H 21/04* | (2006.01) |
| *C12N 15/113* | (2010.01) |
| *A61P 21/00* | (2006.01) |
| *A61K 31/712* | (2006.01) |
| *A61K 31/7125* | (2006.01) |
| *A61K 48/00* | (2006.01) |

(52) U.S. Cl.

CPC .......... *C12N 15/113* (2013.01); *A61K 31/712* (2013.01); *A61K 31/7125* (2013.01); *A61K 48/0058* (2013.01); *A61P 21/00* (2018.01); *C12N 15/1137* (2013.01); *C12N 2310/11* (2013.01); *C12N 2310/315* (2013.01); *C12N 2310/346* (2013.01); *C12N 2310/351* (2013.01); *C12N 2320/31* (2013.01); *C12N 2320/33* (2013.01); *C12Y 302/0102* (2013.01)

(58) Field of Classification Search

None

See application file for complete search history.

(56) References Cited

U.S. PATENT DOCUMENTS

| | | | |
|---|---|---|---|
| 9,404,100 B2 * | 8/2016 | Valenzano ....... | C12Y 302/0102 |
| 10,308,940 B2 * | 6/2019 | Bergsma ................ | A61P 25/00 |
| 10,696,967 B2 | 6/2020 | Pijnappel | |

FOREIGN PATENT DOCUMENTS

| | | |
|---|---|---|
| WO | 2015035231 A1 | 3/2015 |
| WO | 2015036451 A1 | 3/2015 |
| WO | 2015190921 A2 | 12/2015 |
| WO | 2015190922 A1 | 12/2015 |
| WO | 2017099579 A1 | 6/2017 |
| WO | 2018026284 A1 | 2/2018 |

OTHER PUBLICATIONS

Laura E. Case, et al., "Safety and Efficacy of Alternative Alglucosidase Alfa Regimens in Pompe Disease", Neuromuscular Disorders, vol. 25. No. 4, pp. 321-332, 2015, XP055434772.
Erik Van Der Wal et al, "Antisense Oligonucleotides Promote Exon Inclusion and Correct the Common C.-32-13T>G GAA Splicing Variant in Pompe Disease", Molecular Therapy—Nucleic Acids, vol. 7, pp. 90-100, 2017, XP055370420.
Erik Van Der Wal et al, "GAA Deficiency in Pompe Disease is Alleviated by Exon Inclusion in IPSC-Derived Skeletal Muscle Cells", Molecular Therapy—Nucleic Acids, vol. 7, pp. 101-115, 2017, XP055370418.
Atze J. Bergsma et al, "From Cryptic Toward Canonical PRE-mRNA Splicing in Pompe Disease: A Pipeline for the Development of Antisense Oligonucleotides", Molecular Therapy—Nucleic Acids, vol. 5, pp. e361, 2016, XP055370150.
Nicholas P. Clayton et al., "Antisense Oligonucleotide-Mediated Suppression of Muscle Glycogen Synthase 1 Synthesis as an Approach for Substrate Reduction Therapy of Pompe Disease", Molecular Therapy—Nucleic Acids, vol. 3, No. 10, pp. e206, 2014, XP055154181.

(Continued)

*Primary Examiner* — Kimberly Chong
(74) *Attorney, Agent, or Firm* — Lucas & Mercanti, LLP

(57) ABSTRACT

The invention relates to method for repairing aberrant; splicing, wherein such aberrant: splicing is caused by the presence of a natural pseudo exon, comprising blocking of either the natural cryptic 3' splice site or the natural cryptic 5' splice site of said natural pseudo exon with an antisense oligomeric compound (AON). Further, the invention comprises an antisense oligomeric compound targeting SEQ ID NO: 1 or SEQ ID NO: 171, preferably selected from the sequences of SEQ ID NO: 267-2040, sequences that are complementary to said sequences or sequences that have an identity of 80% with said sequences or the complementary sequences. The invention further envisages the use of two antisense oligomeric compounds, a first AON targeting SEQ ID NO: 1 and a second targeting AON or SEQ ID NO: 171. These AONs are specifically for use in the treatment of Pompe disease. It is an aspect of the invention that antisense therapy using the above AONs or combinations thereof is used in combination with ERT.

16 Claims, 67 Drawing Sheets

Specification includes a Sequence Listing.

(56) References Cited

OTHER PUBLICATIONS

Deniz Gungor, et al., "Impact of Enzyme Replacement Therapy on Survival in Adults With Pompe Disease: Results From a Prospective International Observational Study", Orphanet Journal of Rare Diseases, vol. 8, No. 1, pp. 49, 2013, XP021147222.
International Search Report and Written Opinion for Corresponding International Application No. PCT/NL2018/050392 (12 Pages) (dated Oct. 10, 2018).

* cited by examiner

WT
IVS1
1000
850
650
500
400
300
200
100
Normal transcript (N)
Splice variant 3 (SV3)
Splice variant 2 (SV2)
GAA Pre-mRNA
GAA mRNA
c.-32-13T>G
AGCCCGCTTGCTTGTCCCGCAG
ATG
1
2
3

ISE
ISS
ESE
ESS
yunay
yyyyyyy yag
G
AG
guragu
U7-antisense c.-30
c.-10
c.10
c.30
c.50
c.70
c.90
c.110
c.130
c.150
c.170
c.190
c.210
c.230
c.250
c.270
c.290
c.310
c.330
c.350
c.370
c.390
c.410
c.430
c.450
c.470
c.490
c.510
c.530
-319
-299
-279
-259
-239
-219
-199
-179
-159
-138
-119
-99
-79
-59
-39
-19
GAA Intron 1
GAA Exon 2 qPCR
1
2
3
GAA (N) expression
GAA enzyme activity
Fold change compared to NT
1.6
1.4
1.2
1.0
0.8
0.6
0.4
0.2
0.0
-319
-299
-279
-259
-239
-219
-199
-179
-159
-138
-119
-99
-79
-59
-39
-19
c.-30
c.-10
c.10
c.30
c.50
c.70
c.90
c.110
c.130
c.150
c.170
c.190
c.210
c.230
c.250
c.270
c.290
c.310
c.330
c.350
c.370
c.390
c.410
c.430
c.450
c.470
c.490
c.510
c.530
GAA Intron 1
GAA Exon 2
c.-32-13T>G RT-PCR
GAA
β-Actin
N
SV3
SV2
H2O

| Name: | cDNA location | sequence 5′ to 3′ | nucleotides |
|---|---|---|---|
| *CypA* 1 | *CypA* c.165_173+11 | TGTACCCTTACCACTCAGTC | 20 |
| *CypA* 2 | *CypA* c.165_173+16 | CATGTTGTACCCTTACCACTCAGTC | 25 |
| AON 1 | *GAA* c.-32-219_-200 | GAGTGCAGAGCACTTGCACA | 20 |
| AON 2 | *GAA* c.-32-224_-200 | GAGTGCAGAGCACTTGCACAGTCTG | 25 |
| AON 3 | *GAA* c.-32-187_-167 | CCAGAAGGAAGGGCGAGAAAA | 21 |
| AON 4 | *GAA* c.-32-190_-166 | GCCAGAAGGAAGGGCGAGAAAAGCT | 25 |
| AON 5 | *GAA* c.-32-64_-40 | TTTGAGAGCCCCGTGAGTGCCGCCC | 25 | reference sequence for cDNA annotation is NM_000152.3

Fig. 8a(Cont. I)
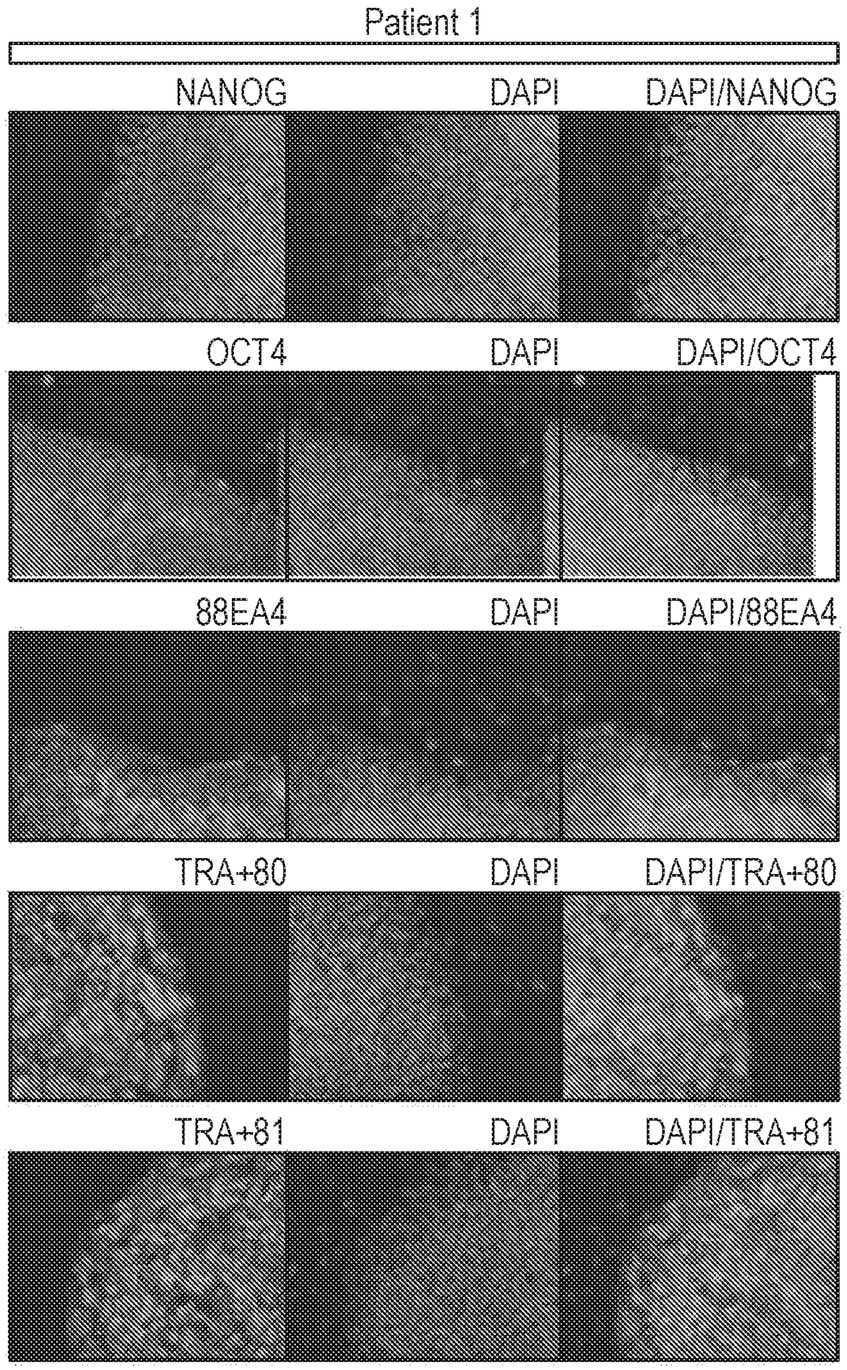

Fig. 8a(Cont. II)
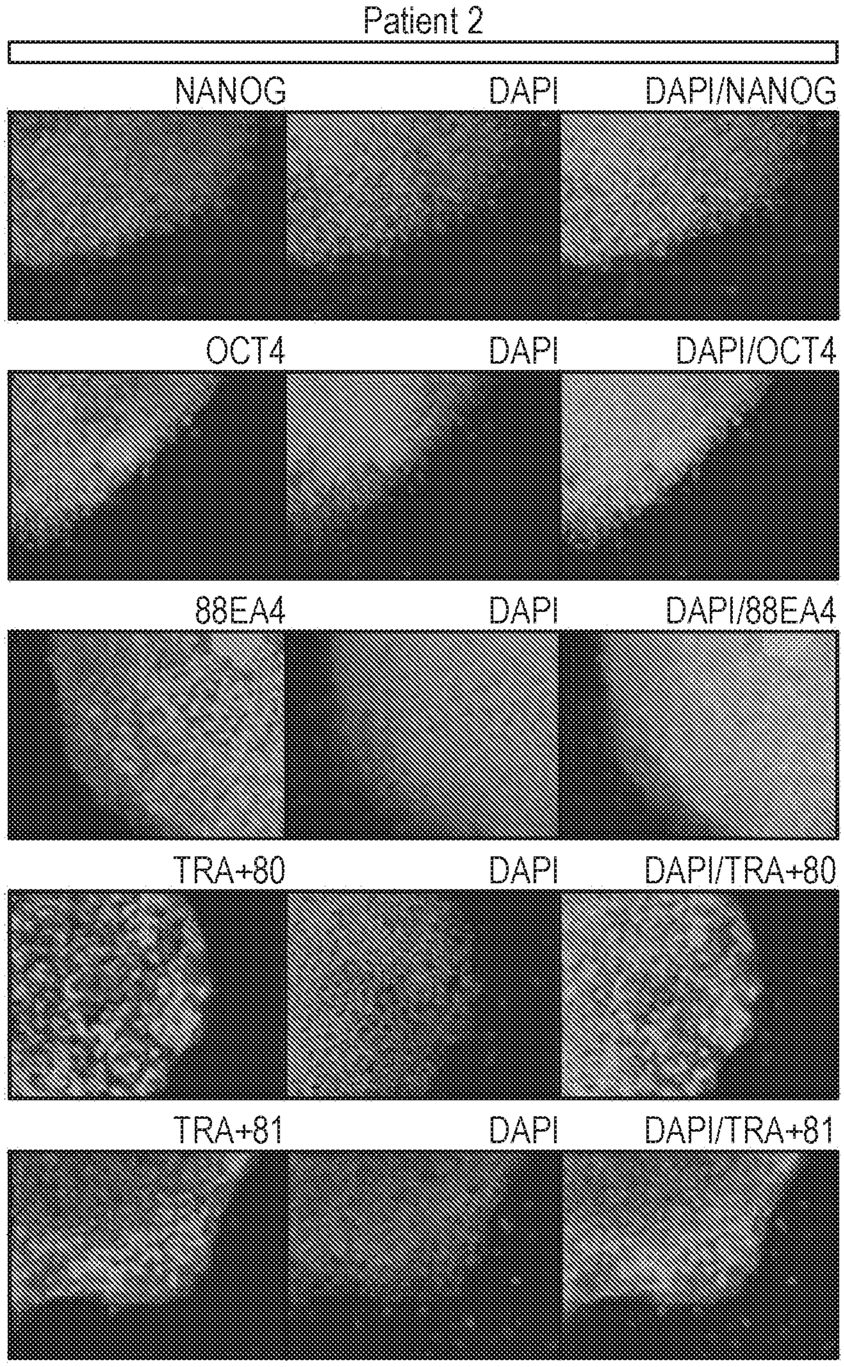

Fig. 8b(Cont. I)
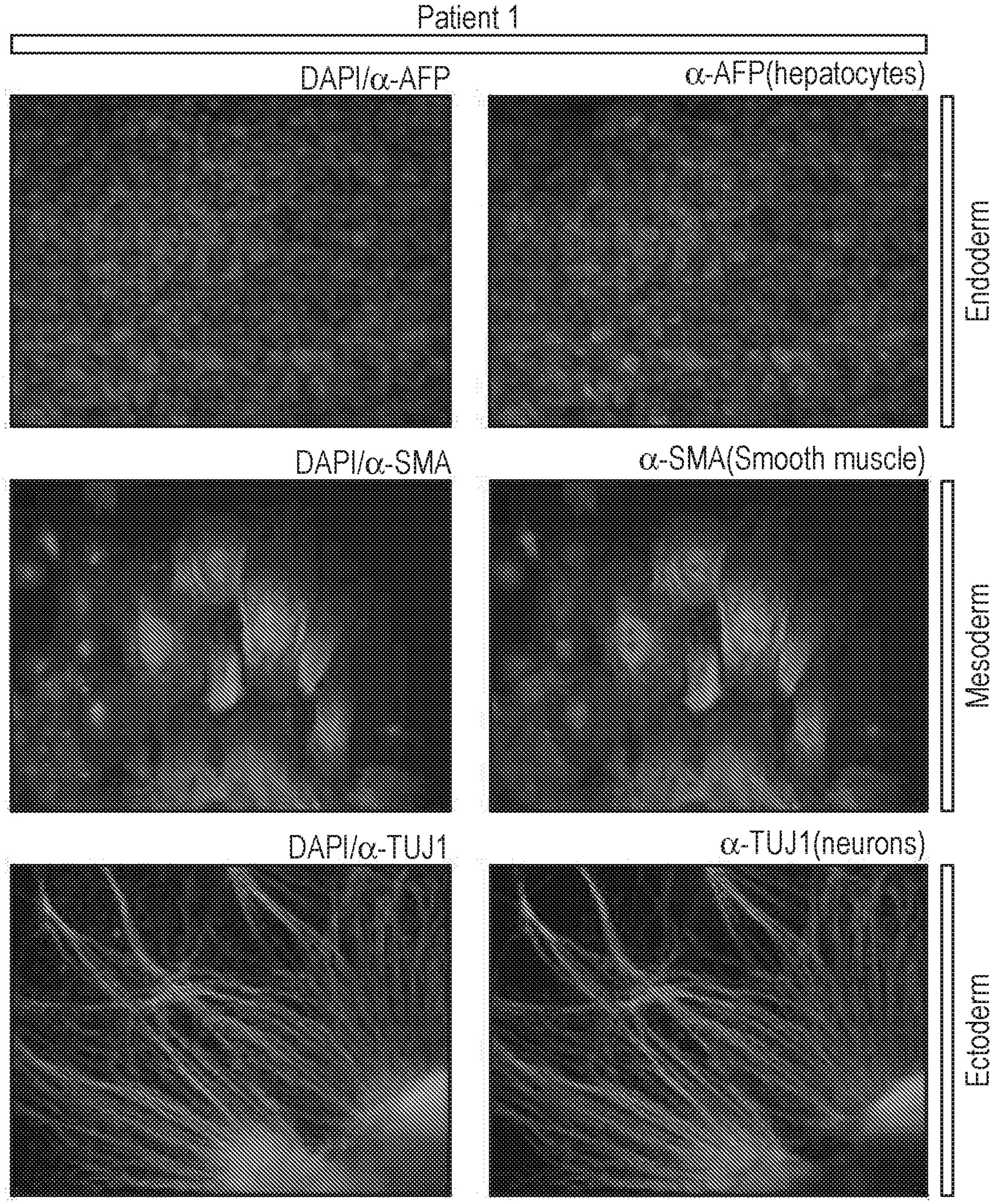

Fig. 8b(Cont. II)
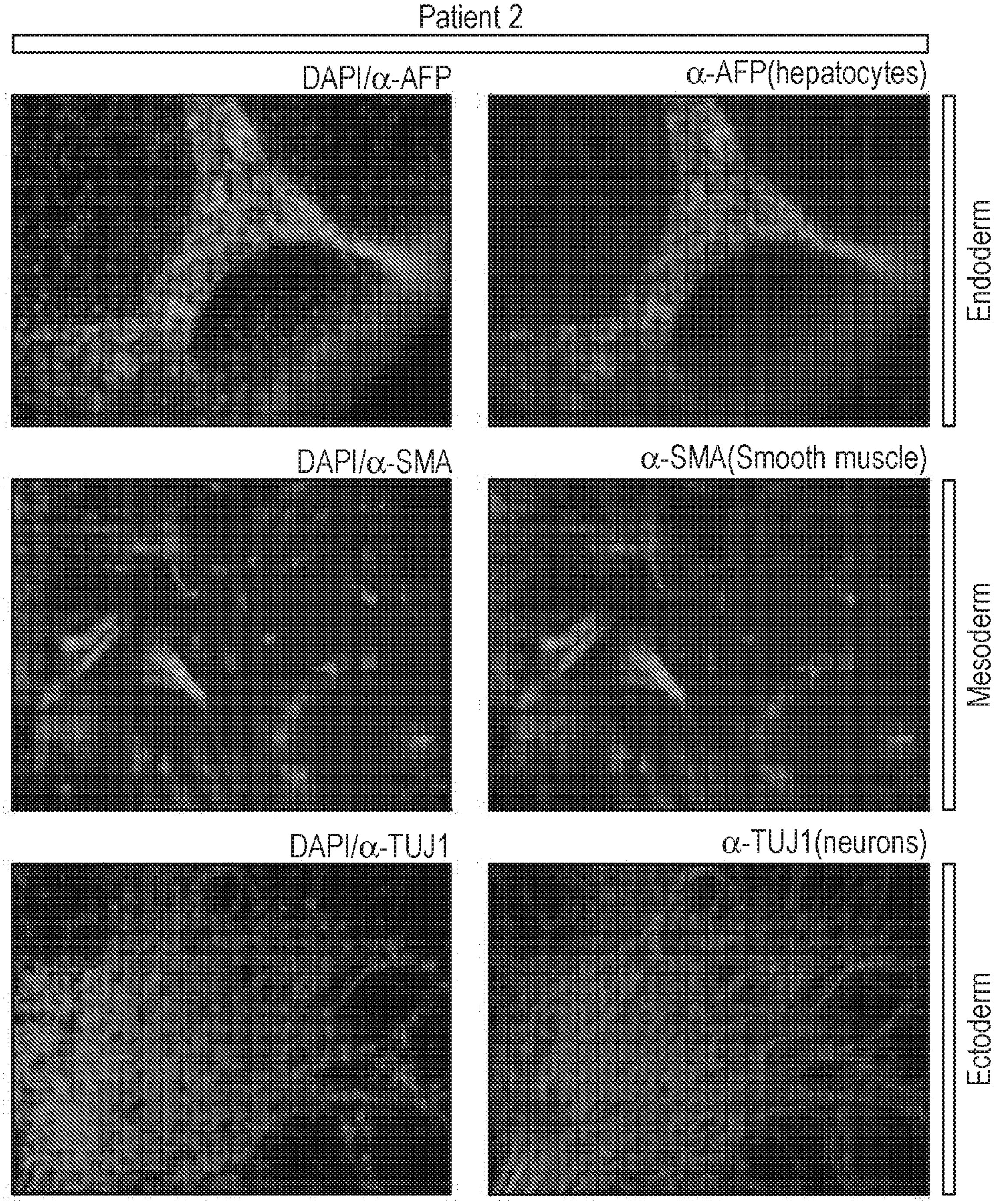

Fig. 8i(Cont. I)
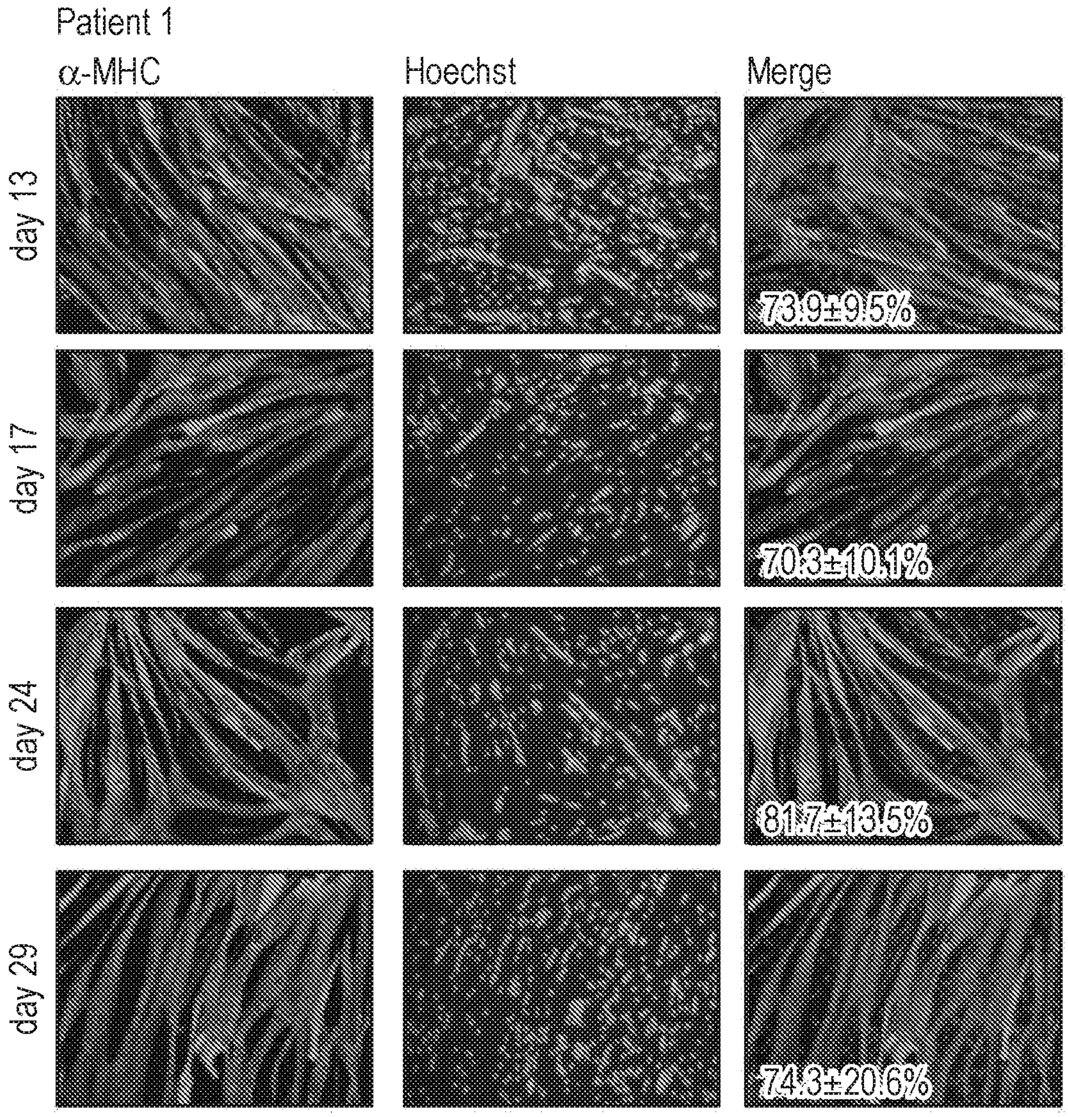

Fig. 8i(Cont. II)
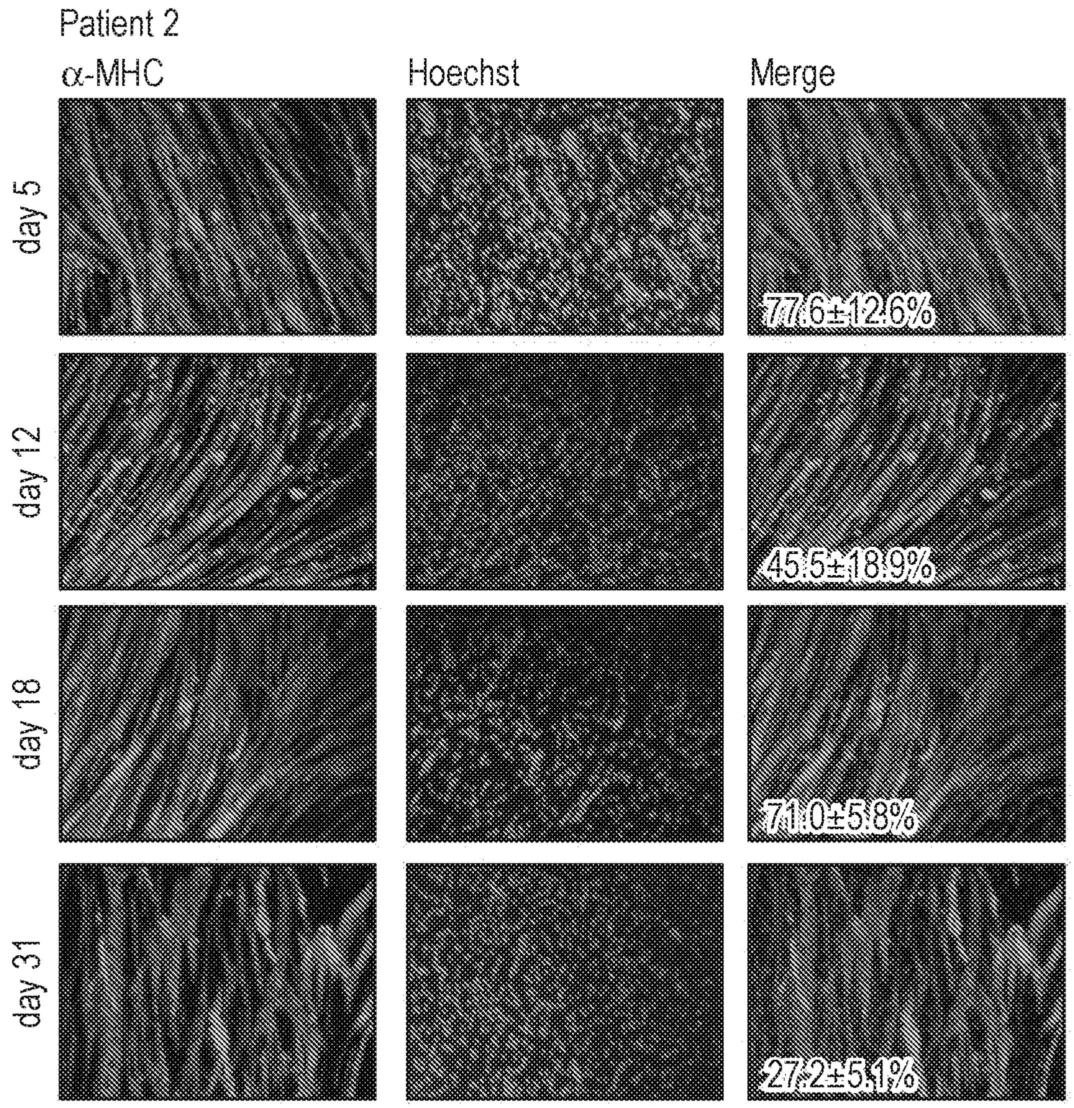

Control 1 day 26
α-MHC/hoechst

Fig. 10d(Cont. I)
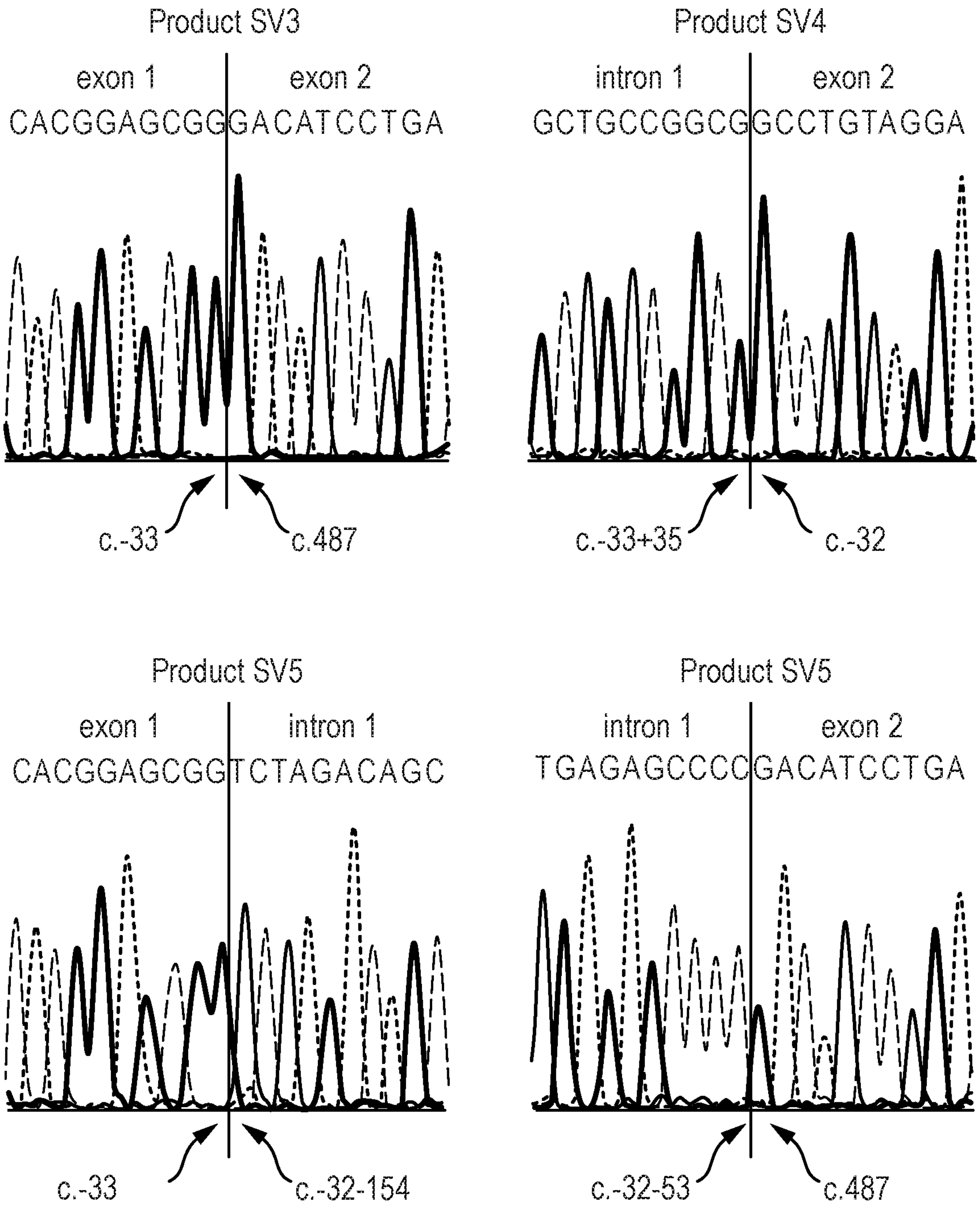

Fig. 10d(Cont. II)
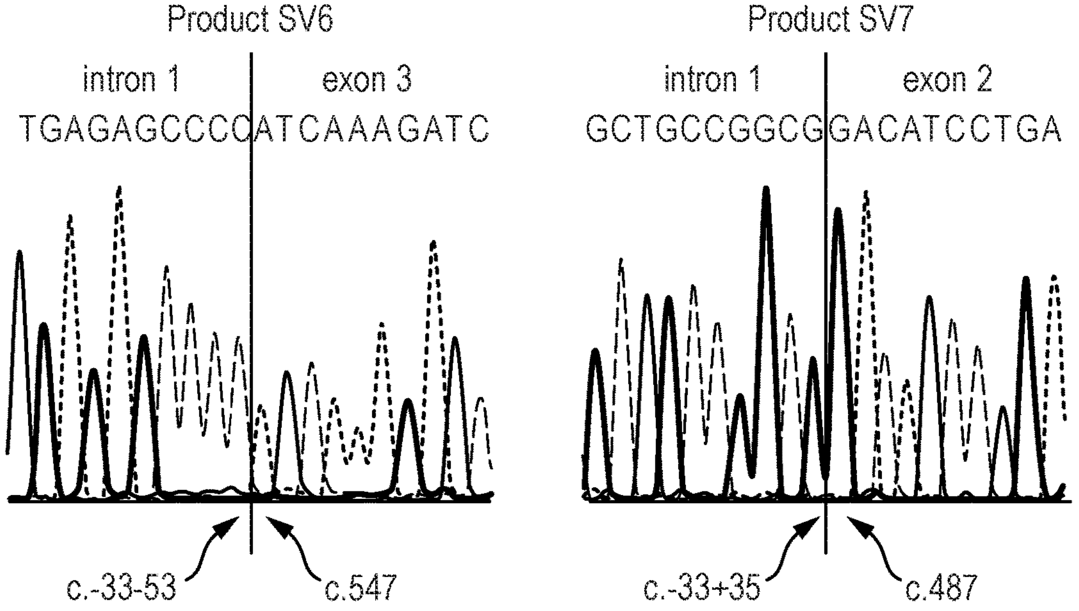
Fig. 10e
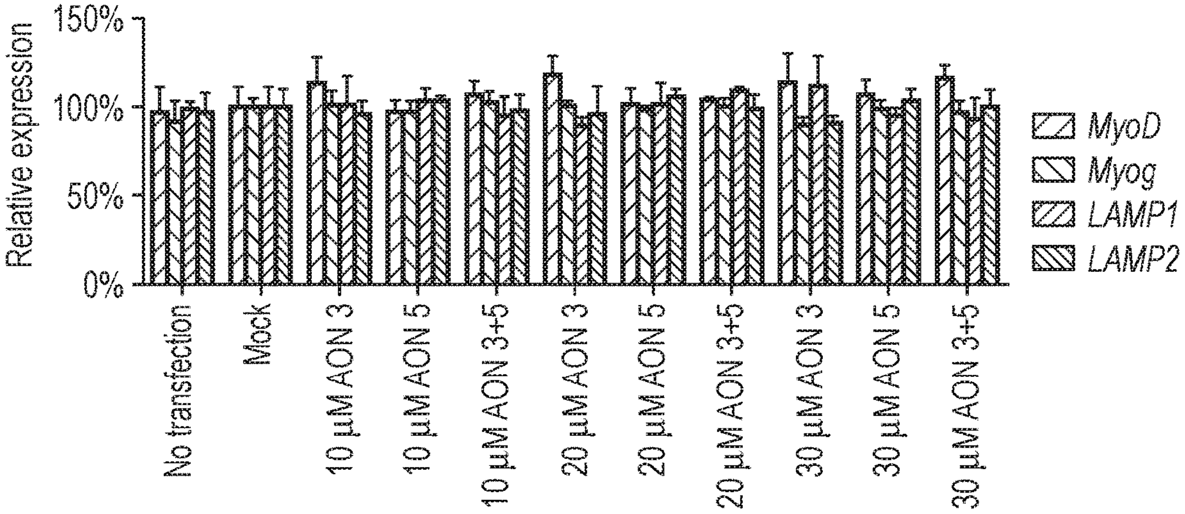

SEQUENCE LISTING

```
<160> NUMBER OF SEQ ID NOS: 2085

<210> SEQ ID NO 1
<211> LENGTH: 82
<212> TYPE: DNA
<213> ORGANISM: Artificial Sequence
<220> FEATURE:
<223> OTHER INFORMATION: target c-32-212_-113

<400> SEQUENCE: 1

gtgctctgca ctcccctgct ggagcttttc tcgcccttcc ttctggccct ctccccagtc     60

tagacagcag ggcaacaccc ac                                              82


<210> SEQ ID NO 2
<211> LENGTH: 55
<212> TYPE: DNA
<213> ORGANISM: Artificial Sequence
<220> FEATURE:
<223> OTHER INFORMATION: Sequence in cDNA to which AON anneals

<400> SEQUENCE: 2

gctctgcact cccctgctgg agcttttctc gcccttcctt ctggccctct cccca          55


<210> SEQ ID NO 3
<211> LENGTH: 45
<212> TYPE: DNA
<213> ORGANISM: Artificial Sequence
<220> FEATURE:
<223> OTHER INFORMATION: Sequence in cDNA to which AON anneals

<400> SEQUENCE: 3

gctctgcact cccctgctgg agcttttctc gcccttcctt ctggc                     45


<210> SEQ ID NO 4
<211> LENGTH: 31
<212> TYPE: DNA
<213> ORGANISM: Artificial Sequence
<220> FEATURE:
<223> OTHER INFORMATION: Sequence in cDNA to which AON anneals

<400> SEQUENCE: 4

tgcactcccc tgctggagct tttctcgccc t                                    31


<210> SEQ ID NO 5
<211> LENGTH: 36
<212> TYPE: DNA
<213> ORGANISM: Artificial Sequence
<220> FEATURE:
<223> OTHER INFORMATION: Sequence in cDNA to which AON anneals

<400> SEQUENCE: 5

tgcactcccc tgctggagct tttctcgccc ttcctt                               36


<210> SEQ ID NO 6
```

<211> LENGTH: 31
<212> TYPE: DNA
<213> ORGANISM: Artificial Sequence
<220> FEATURE:
<223> OTHER INFORMATION: Sequence in cDNA to which AON anneals

<400> SEQUENCE: 6
tcccctgctg gagcttttct cgcccttcct t 31

<210> SEQ ID NO 7
<211> LENGTH: 32
<212> TYPE: DNA
<213> ORGANISM: Artificial Sequence
<220> FEATURE:
<223> OTHER INFORMATION: target c.32-209_-178

<400> SEQUENCE: 7
cttttctcgc ccttccttct ggccctctcc cc 32

<210> SEQ ID NO 8
<211> LENGTH: 25
<212> TYPE: DNA
<213> ORGANISM: Artificial Sequence
<220> FEATURE:
<223> OTHER INFORMATION: target sequence

<400> SEQUENCE: 8
gtgctctgca ctcccctgct ggagc 25

<210> SEQ ID NO 9
<211> LENGTH: 25
<212> TYPE: DNA
<213> ORGANISM: Artificial Sequence
<220> FEATURE:
<223> OTHER INFORMATION: target sequence

<400> SEQUENCE: 9
tgctctgcac tcccctgctg gagct 25

<210> SEQ ID NO 10
<211> LENGTH: 25
<212> TYPE: DNA
<213> ORGANISM: Artificial Sequence
<220> FEATURE:
<223> OTHER INFORMATION: target sequence

<400> SEQUENCE: 10
gctctgcact cccctgctgg agctt 25

<210> SEQ ID NO 11
<211> LENGTH: 25
<212> TYPE: DNA
<213> ORGANISM: Artificial Sequence
<220> FEATURE:
<223> OTHER INFORMATION: target sequence

<400> SEQUENCE: 11
ctctgcactc ccctgctgga gcttt 25

<210> SEQ ID NO 12
<211> LENGTH: 25
<212> TYPE: DNA
<213> ORGANISM: Artificial Sequence
<220> FEATURE:
<223> OTHER INFORMATION: target sequence

<400> SEQUENCE: 12
tctgcactcc cctgctggag ctttt 25

<210> SEQ ID NO 13
<211> LENGTH: 25
<212> TYPE: DNA
<213> ORGANISM: Artificial Sequence
<220> FEATURE:
<223> OTHER INFORMATION: target sequence

<400> SEQUENCE: 13
ctgcactccc ctgctggagc ttttc 25

<210> SEQ ID NO 14
<211> LENGTH: 25
<212> TYPE: DNA
<213> ORGANISM: Artificial Sequence
<220> FEATURE:
<223> OTHER INFORMATION: target sequence

<400> SEQUENCE: 14
tgcactcccc tgctggagct tttct 25

<210> SEQ ID NO 15
<211> LENGTH: 25
<212> TYPE: DNA
<213> ORGANISM: Artificial Sequence
<220> FEATURE:
<223> OTHER INFORMATION: target sequence

<400> SEQUENCE: 15
gcactcccct gctggagctt ttctc 25

<210> SEQ ID NO 16
<211> LENGTH: 25
<212> TYPE: DNA
<213> ORGANISM: Artificial Sequence
<220> FEATURE:
<223> OTHER INFORMATION: target sequence

<400> SEQUENCE: 16
cactcccctg ctggagcttt tctcg 25

<210> SEQ ID NO 17
<211> LENGTH: 25
<212> TYPE: DNA
<213> ORGANISM: Artificial Sequence
<220> FEATURE:
<223> OTHER INFORMATION: target sequence

<400> SEQUENCE: 17
actcccctgc tggagctttt ctcgc 25

<210> SEQ ID NO 18
<211> LENGTH: 25
<212> TYPE: DNA
<213> ORGANISM: Artificial Sequence
<220> FEATURE:
<223> OTHER INFORMATION: target sequence

<400> SEQUENCE: 18
ctcccctgct ggagcttttc tcgcc 25

<210> SEQ ID NO 19
<211> LENGTH: 25
<212> TYPE: DNA

<213> ORGANISM: Artificial Sequence
<220> FEATURE:
<223> OTHER INFORMATION: target sequence

<400> SEQUENCE: 19
tcccctgctg gagcttttct cgccc 25

<210> SEQ ID NO 20
<211> LENGTH: 25
<212> TYPE: DNA
<213> ORGANISM: Artificial Sequence
<220> FEATURE:
<223> OTHER INFORMATION: target sequence

<400> SEQUENCE: 20
cccctgctgg agcttttctc gccct 25

<210> SEQ ID NO 21
<211> LENGTH: 25
<212> TYPE: DNA
<213> ORGANISM: Artificial Sequence
<220> FEATURE:
<223> OTHER INFORMATION: target sequence

<400> SEQUENCE: 21
ccctgctgga gcttttctcg ccctt 25

<210> SEQ ID NO 22
<211> LENGTH: 25
<212> TYPE: DNA
<213> ORGANISM: Artificial Sequence
<220> FEATURE:
<223> OTHER INFORMATION: target sequence

<400> SEQUENCE: 22
cctgctggag cttttctcgc ccttc 25

<210> SEQ ID NO 23
<211> LENGTH: 25
<212> TYPE: DNA
<213> ORGANISM: Artificial Sequence
<220> FEATURE:
<223> OTHER INFORMATION: target sequence

<400> SEQUENCE: 23
ctgctggagc ttttctcgcc cttcc 25

<210> SEQ ID NO 24
<211> LENGTH: 25
<212> TYPE: DNA
<213> ORGANISM: Artificial Sequence
<220> FEATURE:
<223> OTHER INFORMATION: target sequence

<400> SEQUENCE: 24
tgctggagct tttctcgccc ttcct 25

<210> SEQ ID NO 25
<211> LENGTH: 25
<212> TYPE: DNA
<213> ORGANISM: Artificial Sequence
<220> FEATURE:
<223> OTHER INFORMATION: target sequence

<400> SEQUENCE: 25
gctggagctt ttctcgccct tcctt 25

<210> SEQ ID NO 26
<211> LENGTH: 25
<212> TYPE: DNA
<213> ORGANISM: Artificial Sequence
<220> FEATURE:
<223> OTHER INFORMATION: target sequence

<400> SEQUENCE: 26
ctggagcttt tctcgccctt ccttc 25

<210> SEQ ID NO 27
<211> LENGTH: 25
<212> TYPE: DNA
<213> ORGANISM: Artificial Sequence
<220> FEATURE:
<223> OTHER INFORMATION: target sequence

<400> SEQUENCE: 27
tggagctttt ctcgcccttc cttct 25

<210> SEQ ID NO 28
<211> LENGTH: 25
<212> TYPE: DNA
<213> ORGANISM: Artificial Sequence
<220> FEATURE:
<223> OTHER INFORMATION: target sequence

<400> SEQUENCE: 28
ggagcttttc tcgcccttcc ttctg 25

<210> SEQ ID NO 29
<211> LENGTH: 25
<212> TYPE: DNA
<213> ORGANISM: Artificial Sequence
<220> FEATURE:
<223> OTHER INFORMATION: target sequence

<400> SEQUENCE: 29
gagcttttct cgcccttcct tctgg 25

<210> SEQ ID NO 30
<211> LENGTH: 25
<212> TYPE: DNA
<213> ORGANISM: Artificial Sequence
<220> FEATURE:
<223> OTHER INFORMATION: target sequence

<400> SEQUENCE: 30
agcttttctc gcccttcctt ctggc 25

<210> SEQ ID NO 31
<211> LENGTH: 25
<212> TYPE: DNA
<213> ORGANISM: Artificial Sequence
<220> FEATURE:
<223> OTHER INFORMATION: target sequence

<400> SEQUENCE: 31
gcttttctcg cccttccttc tggcc 25

<210> SEQ ID NO 32
<211> LENGTH: 25
<212> TYPE: DNA
<213> ORGANISM: Artificial Sequence
<220> FEATURE:

<223> OTHER INFORMATION: target sequence

<400> SEQUENCE: 32
cttttctcgc ccttccttct ggccc 25

<210> SEQ ID NO 33
<211> LENGTH: 25
<212> TYPE: DNA
<213> ORGANISM: Artificial Sequence
<220> FEATURE:
<223> OTHER INFORMATION: target sequence

<400> SEQUENCE: 33
ttttctcgcc cttccttctg gccct 25

<210> SEQ ID NO 34
<211> LENGTH: 25
<212> TYPE: DNA
<213> ORGANISM: Artificial Sequence
<220> FEATURE:
<223> OTHER INFORMATION: target sequence

<400> SEQUENCE: 34
tttctcgccc ttccttctgg ccctc 25

<210> SEQ ID NO 35
<211> LENGTH: 25
<212> TYPE: DNA
<213> ORGANISM: Artificial Sequence
<220> FEATURE:
<223> OTHER INFORMATION: target sequence

<400> SEQUENCE: 35
ttctcgccct tccttctggc cctct 25

<210> SEQ ID NO 36
<211> LENGTH: 25
<212> TYPE: DNA
<213> ORGANISM: Artificial Sequence
<220> FEATURE:
<223> OTHER INFORMATION: target sequence

<400> SEQUENCE: 36
tctcgccctt ccttctggcc ctctc 25

<210> SEQ ID NO 37
<211> LENGTH: 25
<212> TYPE: DNA
<213> ORGANISM: Artificial Sequence
<220> FEATURE:
<223> OTHER INFORMATION: target sequence

<400> SEQUENCE: 37
ctcgcccttc cttctggccc tctcc 25

<210> SEQ ID NO 38
<211> LENGTH: 25
<212> TYPE: DNA
<213> ORGANISM: Artificial Sequence
<220> FEATURE:
<223> OTHER INFORMATION: target sequence

<400> SEQUENCE: 38
tcgcccttcc ttctggccct ctccc 25

<210> SEQ ID NO 39
<211> LENGTH: 25
<212> TYPE: DNA
<213> ORGANISM: Artificial Sequence
<220> FEATURE:
<223> OTHER INFORMATION: target sequence

<400> SEQUENCE: 39
cgcccttcct tctggccctc tcccc 25

<210> SEQ ID NO 40
<211> LENGTH: 25
<212> TYPE: DNA
<213> ORGANISM: Artificial Sequence
<220> FEATURE:
<223> OTHER INFORMATION: target sequence

<400> SEQUENCE: 40
gcccttcctt ctggccctct cccca 25

<210> SEQ ID NO 41
<211> LENGTH: 25
<212> TYPE: DNA
<213> ORGANISM: Artificial Sequence
<220> FEATURE:
<223> OTHER INFORMATION: target sequence

<400> SEQUENCE: 41
cccttccttc tggccctctc cccag 25

<210> SEQ ID NO 42
<211> LENGTH: 25
<212> TYPE: DNA
<213> ORGANISM: Artificial Sequence
<220> FEATURE:
<223> OTHER INFORMATION: target sequence

<400> SEQUENCE: 42
ccttccttct ggccctctcc ccagt 25

<210> SEQ ID NO 43
<211> LENGTH: 25
<212> TYPE: DNA
<213> ORGANISM: Artificial Sequence
<220> FEATURE:
<223> OTHER INFORMATION: target sequence

<400> SEQUENCE: 43
cttccttctg gccctctccc cagtc 25

<210> SEQ ID NO 44
<211> LENGTH: 25
<212> TYPE: DNA
<213> ORGANISM: Artificial Sequence
<220> FEATURE:
<223> OTHER INFORMATION: target sequence

<400> SEQUENCE: 44
ttccttctgg ccctctcccc agtct 25

<210> SEQ ID NO 45
<211> LENGTH: 25
<212> TYPE: DNA
<213> ORGANISM: Artificial Sequence
<220> FEATURE:
<223> OTHER INFORMATION: target sequence

<400> SEQUENCE: 45
tccttctggc cctctcccca gtcta 25

<210> SEQ ID NO 46
<211> LENGTH: 25
<212> TYPE: DNA
<213> ORGANISM: Artificial Sequence
<220> FEATURE:
<223> OTHER INFORMATION: target sequence

<400> SEQUENCE: 46
ccttctggcc ctctccccag tctag 25

<210> SEQ ID NO 47
<211> LENGTH: 25
<212> TYPE: DNA
<213> ORGANISM: Artificial Sequence
<220> FEATURE:
<223> OTHER INFORMATION: target sequence

<400> SEQUENCE: 47
cttctggccc tctccccagt ctaga 25

<210> SEQ ID NO 48
<211> LENGTH: 25
<212> TYPE: DNA
<213> ORGANISM: Artificial Sequence
<220> FEATURE:
<223> OTHER INFORMATION: target sequence

<400> SEQUENCE: 48
ttctggccct ctccccagtc tagac 25

<210> SEQ ID NO 49
<211> LENGTH: 25
<212> TYPE: DNA
<213> ORGANISM: Artificial Sequence
<220> FEATURE:
<223> OTHER INFORMATION: target sequence

<400> SEQUENCE: 49
tctggccctc tccccagtct agaca 25

<210> SEQ ID NO 50
<211> LENGTH: 25
<212> TYPE: DNA
<213> ORGANISM: Artificial Sequence
<220> FEATURE:
<223> OTHER INFORMATION: target sequence

<400> SEQUENCE: 50
ctggccctct ccccagtcta gacag 25

<210> SEQ ID NO 51
<211> LENGTH: 25
<212> TYPE: DNA
<213> ORGANISM: Artificial Sequence
<220> FEATURE:
<223> OTHER INFORMATION: target sequence

<400> SEQUENCE: 51
tggccctctc cccagtctag acagc 25

<210> SEQ ID NO 52
<211> LENGTH: 25

<212> TYPE: DNA
<213> ORGANISM: Artificial Sequence
<220> FEATURE:
<223> OTHER INFORMATION: target sequence

<400> SEQUENCE: 52
ggccctctcc ccagtctaga cagca 25

<210> SEQ ID NO 53
<211> LENGTH: 25
<212> TYPE: DNA
<213> ORGANISM: Artificial Sequence
<220> FEATURE:
<223> OTHER INFORMATION: target sequence

<400> SEQUENCE: 53
gccctctccc cagtctagac agcag 25

<210> SEQ ID NO 54
<211> LENGTH: 25
<212> TYPE: DNA
<213> ORGANISM: Artificial Sequence
<220> FEATURE:
<223> OTHER INFORMATION: target sequence

<400> SEQUENCE: 54
ccctctcccc agtctagaca gcagg 25

<210> SEQ ID NO 55
<211> LENGTH: 25
<212> TYPE: DNA
<213> ORGANISM: Artificial Sequence
<220> FEATURE:
<223> OTHER INFORMATION: target sequence

<400> SEQUENCE: 55
cctctcccca gtctagacag caggg 25

<210> SEQ ID NO 56
<211> LENGTH: 25
<212> TYPE: DNA
<213> ORGANISM: Artificial Sequence
<220> FEATURE:
<223> OTHER INFORMATION: target sequence

<400> SEQUENCE: 56
ctctccccag tctagacagc agggc 25

<210> SEQ ID NO 57
<211> LENGTH: 25
<212> TYPE: DNA
<213> ORGANISM: Artificial Sequence
<220> FEATURE:
<223> OTHER INFORMATION: target sequence

<400> SEQUENCE: 57
tctccccagt ctagacagca gggca 25

<210> SEQ ID NO 58
<211> LENGTH: 25
<212> TYPE: DNA
<213> ORGANISM: Artificial Sequence
<220> FEATURE:
<223> OTHER INFORMATION: target sequence

<400> SEQUENCE: 58
ctccccagtc tagacagcag ggcaa 25

<210> SEQ ID NO 59
<211> LENGTH: 25
<212> TYPE: DNA
<213> ORGANISM: Artificial Sequence
<220> FEATURE:
<223> OTHER INFORMATION: target sequence

<400> SEQUENCE: 59
tccccagtct agacagcagg gcaac 25

<210> SEQ ID NO 60
<211> LENGTH: 25
<212> TYPE: DNA
<213> ORGANISM: Artificial Sequence
<220> FEATURE:
<223> OTHER INFORMATION: target sequence

<400> SEQUENCE: 60
ccccagtcta gacagcaggg caaca 25

<210> SEQ ID NO 61
<211> LENGTH: 25
<212> TYPE: DNA
<213> ORGANISM: Artificial Sequence
<220> FEATURE:
<223> OTHER INFORMATION: target sequence

<400> SEQUENCE: 61
cccagtctag acagcagggc aacac 25

<210> SEQ ID NO 62
<211> LENGTH: 25
<212> TYPE: DNA
<213> ORGANISM: Artificial Sequence
<220> FEATURE:
<223> OTHER INFORMATION: target sequence

<400> SEQUENCE: 62
ccagtctaga cagcagggca acacc 25

<210> SEQ ID NO 63
<211> LENGTH: 25
<212> TYPE: DNA
<213> ORGANISM: Artificial Sequence
<220> FEATURE:
<223> OTHER INFORMATION: target sequence

<400> SEQUENCE: 63
cagtctagac agcagggcaa caccc 25

<210> SEQ ID NO 64
<211> LENGTH: 25
<212> TYPE: DNA
<213> ORGANISM: Artificial Sequence
<220> FEATURE:
<223> OTHER INFORMATION: target sequence

<400> SEQUENCE: 64
agtctagaca gcagggcaac accca 25

<210> SEQ ID NO 65
<211> LENGTH: 25
<212> TYPE: DNA
<213> ORGANISM: Artificial Sequence
<220> FEATURE:
<223> OTHER INFORMATION: target sequence

<400> SEQUENCE: 65
gtctagacag cagggcaaca cccac 25

<210> SEQ ID NO 66
<211> LENGTH: 21
<212> TYPE: DNA
<213> ORGANISM: Artificial Sequence
<220> FEATURE:
<223> OTHER INFORMATION: target sequence

<400> SEQUENCE: 66
tctgcactcc cctgctggag c 21

<210> SEQ ID NO 67
<211> LENGTH: 21
<212> TYPE: DNA
<213> ORGANISM: Artificial Sequence
<220> FEATURE:
<223> OTHER INFORMATION: target sequence

<400> SEQUENCE: 67
ctgcactccc ctgctggagc t 21

<210> SEQ ID NO 68
<211> LENGTH: 21
<212> TYPE: DNA
<213> ORGANISM: Artificial Sequence
<220> FEATURE:
<223> OTHER INFORMATION: target sequence

<400> SEQUENCE: 68
tgcactcccc tgctggagct t 21

<210> SEQ ID NO 69
<211> LENGTH: 21
<212> TYPE: DNA
<213> ORGANISM: Artificial Sequence
<220> FEATURE:
<223> OTHER INFORMATION: target sequence

<400> SEQUENCE: 69
gcactcccct gctggagctt t 21

<210> SEQ ID NO 70
<211> LENGTH: 21
<212> TYPE: DNA
<213> ORGANISM: Artificial Sequence
<220> FEATURE:
<223> OTHER INFORMATION: target sequence

<400> SEQUENCE: 70
cactcccctg ctggagcttt t 21

<210> SEQ ID NO 71
<211> LENGTH: 21
<212> TYPE: DNA
<213> ORGANISM: Artificial Sequence
<220> FEATURE:
<223> OTHER INFORMATION: target sequence

<400> SEQUENCE: 71
actcccctgc tggagctttt c 21

<210> SEQ ID NO 72
<211> LENGTH: 21
<212> TYPE: DNA
<213> ORGANISM: Artificial Sequence
<220> FEATURE:
<223> OTHER INFORMATION: target sequence

<400> SEQUENCE: 72
ctcccctgct ggagcttttc t 21

<210> SEQ ID NO 73
<211> LENGTH: 21
<212> TYPE: DNA
<213> ORGANISM: Artificial Sequence
<220> FEATURE:
<223> OTHER INFORMATION: target sequence

<400> SEQUENCE: 73
tcccctgctg gagcttttct c 21

<210> SEQ ID NO 74
<211> LENGTH: 21
<212> TYPE: DNA
<213> ORGANISM: Artificial Sequence
<220> FEATURE:
<223> OTHER INFORMATION: target sequence

<400> SEQUENCE: 74
cccctgctgg agcttttctc g 21

<210> SEQ ID NO 75
<211> LENGTH: 21
<212> TYPE: DNA
<213> ORGANISM: Artificial Sequence
<220> FEATURE:
<223> OTHER INFORMATION: target sequence

<400> SEQUENCE: 75
ccctgctgga gcttttctcg c 21

<210> SEQ ID NO 76
<211> LENGTH: 21
<212> TYPE: DNA
<213> ORGANISM: Artificial Sequence
<220> FEATURE:
<223> OTHER INFORMATION: target sequence

<400> SEQUENCE: 76
cctgctggag cttttctcgc c 21

<210> SEQ ID NO 77
<211> LENGTH: 21
<212> TYPE: DNA
<213> ORGANISM: Artificial Sequence
<220> FEATURE:
<223> OTHER INFORMATION: target sequence

<400> SEQUENCE: 77
ctgctggagc ttttctcgcc c 21

<210> SEQ ID NO 78
<211> LENGTH: 21
<212> TYPE: DNA
<213> ORGANISM: Artificial Sequence
<220> FEATURE:
<223> OTHER INFORMATION: target sequence -continued

<400> SEQUENCE: 78
tgctggagct tttctcgccc t 21

<210> SEQ ID NO 79
<211> LENGTH: 21
<212> TYPE: DNA
<213> ORGANISM: Artificial Sequence
<220> FEATURE:
<223> OTHER INFORMATION: target sequence

<400> SEQUENCE: 79
gctggagctt ttctcgccct t 21

<210> SEQ ID NO 80
<211> LENGTH: 21
<212> TYPE: DNA
<213> ORGANISM: Artificial Sequence
<220> FEATURE:
<223> OTHER INFORMATION: target sequence

<400> SEQUENCE: 80
ctggagcttt tctcgccctt c 21

<210> SEQ ID NO 81
<211> LENGTH: 21
<212> TYPE: DNA
<213> ORGANISM: Artificial Sequence
<220> FEATURE:
<223> OTHER INFORMATION: target sequence

<400> SEQUENCE: 81
tggagctttt ctcgcccttc c 21

<210> SEQ ID NO 82
<211> LENGTH: 21
<212> TYPE: DNA
<213> ORGANISM: Artificial Sequence
<220> FEATURE:
<223> OTHER INFORMATION: target sequence

<400> SEQUENCE: 82
ggagcttttc tcgcccttcc t 21

<210> SEQ ID NO 83
<211> LENGTH: 21
<212> TYPE: DNA
<213> ORGANISM: Artificial Sequence
<220> FEATURE:
<223> OTHER INFORMATION: target sequence

<400> SEQUENCE: 83
gagcttttct cgcccttcct t 21

<210> SEQ ID NO 84
<211> LENGTH: 21
<212> TYPE: DNA
<213> ORGANISM: Artificial Sequence
<220> FEATURE:
<223> OTHER INFORMATION: target sequence

<400> SEQUENCE: 84
agcttttctc gcccttcctt c 21

<210> SEQ ID NO 85

<211> LENGTH: 21
<212> TYPE: DNA
<213> ORGANISM: Artificial Sequence
<220> FEATURE:
<223> OTHER INFORMATION: target sequence

<400> SEQUENCE: 85
gcttttctcg cccttccttc t 21

<210> SEQ ID NO 86
<211> LENGTH: 21
<212> TYPE: DNA
<213> ORGANISM: Artificial Sequence
<220> FEATURE:
<223> OTHER INFORMATION: target sequence

<400> SEQUENCE: 86
cttttctcgc ccttccttct g 21

<210> SEQ ID NO 87
<211> LENGTH: 21
<212> TYPE: DNA
<213> ORGANISM: Artificial Sequence
<220> FEATURE:
<223> OTHER INFORMATION: target sequence

<400> SEQUENCE: 87
ttttctcgcc cttccttctg g 21

<210> SEQ ID NO 88
<211> LENGTH: 21
<212> TYPE: DNA
<213> ORGANISM: Artificial Sequence
<220> FEATURE:
<223> OTHER INFORMATION: target sequence

<400> SEQUENCE: 88
tttctcgccc ttccttctgg c 21

<210> SEQ ID NO 89
<211> LENGTH: 21
<212> TYPE: DNA
<213> ORGANISM: Artificial Sequence
<220> FEATURE:
<223> OTHER INFORMATION: target sequence

<400> SEQUENCE: 89
ttctcgccct tccttctggc c 21

<210> SEQ ID NO 90
<211> LENGTH: 21
<212> TYPE: DNA
<213> ORGANISM: Artificial Sequence
<220> FEATURE:
<223> OTHER INFORMATION: target sequence

<400> SEQUENCE: 90
tctcgccctt ccttctggcc c 21

<210> SEQ ID NO 91
<211> LENGTH: 21
<212> TYPE: DNA
<213> ORGANISM: Artificial Sequence
<220> FEATURE:
<223> OTHER INFORMATION: target sequence

<400> SEQUENCE: 91
ctcgcccttc cttctggccc t 21

<210> SEQ ID NO 92
<211> LENGTH: 21
<212> TYPE: DNA
<213> ORGANISM: Artificial Sequence
<220> FEATURE:
<223> OTHER INFORMATION: target sequence

<400> SEQUENCE: 92
tcgcccttcc ttctggccct c 21

<210> SEQ ID NO 93
<211> LENGTH: 21
<212> TYPE: DNA
<213> ORGANISM: Artificial Sequence
<220> FEATURE:
<223> OTHER INFORMATION: target sequence

<400> SEQUENCE: 93
cgcccttcct tctggccctc t 21

<210> SEQ ID NO 94
<211> LENGTH: 21
<212> TYPE: DNA
<213> ORGANISM: Artificial Sequence
<220> FEATURE:
<223> OTHER INFORMATION: target sequence

<400> SEQUENCE: 94
gcccttcctt ctggccctct c 21

<210> SEQ ID NO 95
<211> LENGTH: 21
<212> TYPE: DNA
<213> ORGANISM: Artificial Sequence
<220> FEATURE:
<223> OTHER INFORMATION: target sequence

<400> SEQUENCE: 95
cccttccttc tggccctctc c 21

<210> SEQ ID NO 96
<211> LENGTH: 21
<212> TYPE: DNA
<213> ORGANISM: Artificial Sequence
<220> FEATURE:
<223> OTHER INFORMATION: target sequence

<400> SEQUENCE: 96
ccttccttct ggccctctcc c 21

<210> SEQ ID NO 97
<211> LENGTH: 21
<212> TYPE: DNA
<213> ORGANISM: Artificial Sequence
<220> FEATURE:
<223> OTHER INFORMATION: target sequence

<400> SEQUENCE: 97
cttccttctg gccctctccc c 21

<210> SEQ ID NO 98
<211> LENGTH: 21
<212> TYPE: DNA

<213> ORGANISM: Artificial Sequence
<220> FEATURE:
<223> OTHER INFORMATION: target sequence

<400> SEQUENCE: 98
ttccttctgg ccctctcccc a 21

<210> SEQ ID NO 99
<211> LENGTH: 21
<212> TYPE: DNA
<213> ORGANISM: Artificial Sequence
<220> FEATURE:
<223> OTHER INFORMATION: target sequence

<400> SEQUENCE: 99
tccttctggc cctctcccca g 21

<210> SEQ ID NO 100
<211> LENGTH: 21
<212> TYPE: DNA
<213> ORGANISM: Artificial Sequence
<220> FEATURE:
<223> OTHER INFORMATION: target sequence

<400> SEQUENCE: 100
ccttctggcc ctctccccag t 21

<210> SEQ ID NO 101
<211> LENGTH: 21
<212> TYPE: DNA
<213> ORGANISM: Artificial Sequence
<220> FEATURE:
<223> OTHER INFORMATION: target sequence

<400> SEQUENCE: 101
cttctggccc tctccccagt c 21

<210> SEQ ID NO 102
<211> LENGTH: 21
<212> TYPE: DNA
<213> ORGANISM: Artificial Sequence
<220> FEATURE:
<223> OTHER INFORMATION: target sequence

<400> SEQUENCE: 102
ttctggccct ctccccagtc t 21

<210> SEQ ID NO 103
<211> LENGTH: 21
<212> TYPE: DNA
<213> ORGANISM: Artificial Sequence
<220> FEATURE:
<223> OTHER INFORMATION: target sequence

<400> SEQUENCE: 103
tctggccctc tccccagtct a 21

<210> SEQ ID NO 104
<211> LENGTH: 21
<212> TYPE: DNA
<213> ORGANISM: Artificial Sequence
<220> FEATURE:
<223> OTHER INFORMATION: target sequence

<400> SEQUENCE: 104
ctggccctct ccccagtcta g 21

<210> SEQ ID NO 105
<211> LENGTH: 21
<212> TYPE: DNA
<213> ORGANISM: Artificial Sequence
<220> FEATURE:
<223> OTHER INFORMATION: target sequence

<400> SEQUENCE: 105
tggccctctc cccagtctag a 21

<210> SEQ ID NO 106
<211> LENGTH: 21
<212> TYPE: DNA
<213> ORGANISM: Artificial Sequence
<220> FEATURE:
<223> OTHER INFORMATION: target sequence

<400> SEQUENCE: 106
ggccctctcc ccagtctaga c 21

<210> SEQ ID NO 107
<211> LENGTH: 21
<212> TYPE: DNA
<213> ORGANISM: Artificial Sequence
<220> FEATURE:
<223> OTHER INFORMATION: target sequence

<400> SEQUENCE: 107
gccctctccc cagtctagac a 21

<210> SEQ ID NO 108
<211> LENGTH: 21
<212> TYPE: DNA
<213> ORGANISM: Artificial Sequence
<220> FEATURE:
<223> OTHER INFORMATION: target sequence

<400> SEQUENCE: 108
ccctctcccc agtctagaca g 21

<210> SEQ ID NO 109
<211> LENGTH: 21
<212> TYPE: DNA
<213> ORGANISM: Artificial Sequence
<220> FEATURE:
<223> OTHER INFORMATION: target sequence

<400> SEQUENCE: 109
cctctcccca gtctagacag c 21

<210> SEQ ID NO 110
<211> LENGTH: 21
<212> TYPE: DNA
<213> ORGANISM: Artificial Sequence
<220> FEATURE:
<223> OTHER INFORMATION: target sequence

<400> SEQUENCE: 110
ctctccccag tctagacagc a 21

<210> SEQ ID NO 111
<211> LENGTH: 21
<212> TYPE: DNA
<213> ORGANISM: Artificial Sequence
<220> FEATURE:

<223> OTHER INFORMATION: target sequence

<400> SEQUENCE: 111
tctccccagt ctagacagca g 21

<210> SEQ ID NO 112
<211> LENGTH: 21
<212> TYPE: DNA
<213> ORGANISM: Artificial Sequence
<220> FEATURE:
<223> OTHER INFORMATION: target sequence

<400> SEQUENCE: 112
ctccccagtc tagacagcag g 21

<210> SEQ ID NO 113
<211> LENGTH: 21
<212> TYPE: DNA
<213> ORGANISM: Artificial Sequence
<220> FEATURE:
<223> OTHER INFORMATION: target sequence

<400> SEQUENCE: 113
tccccagtct agacagcagg g 21

<210> SEQ ID NO 114
<211> LENGTH: 21
<212> TYPE: DNA
<213> ORGANISM: Artificial Sequence
<220> FEATURE:
<223> OTHER INFORMATION: target sequence

<400> SEQUENCE: 114
ccccagtcta gacagcaggg c 21

<210> SEQ ID NO 115
<211> LENGTH: 21
<212> TYPE: DNA
<213> ORGANISM: Artificial Sequence
<220> FEATURE:
<223> OTHER INFORMATION: target sequence

<400> SEQUENCE: 115
cccagtctag acagcagggc a 21

<210> SEQ ID NO 116
<211> LENGTH: 21
<212> TYPE: DNA
<213> ORGANISM: Artificial Sequence
<220> FEATURE:
<223> OTHER INFORMATION: target sequence

<400> SEQUENCE: 116
ccagtctaga cagcagggca a 21

<210> SEQ ID NO 117
<211> LENGTH: 21
<212> TYPE: DNA
<213> ORGANISM: Artificial Sequence
<220> FEATURE:
<223> OTHER INFORMATION: target sequence

<400> SEQUENCE: 117
cagtctagac agcagggcaa c 21

<210> SEQ ID NO 118
<211> LENGTH: 21
<212> TYPE: DNA
<213> ORGANISM: Artificial Sequence
<220> FEATURE:
<223> OTHER INFORMATION: target sequence

<400> SEQUENCE: 118
agtctagaca gcagggcaac a 21

<210> SEQ ID NO 119
<211> LENGTH: 21
<212> TYPE: DNA
<213> ORGANISM: Artificial Sequence
<220> FEATURE:
<223> OTHER INFORMATION: target sequence

<400> SEQUENCE: 119
gtctagacag cagggcaaca c 21

<210> SEQ ID NO 120
<211> LENGTH: 18
<212> TYPE: DNA
<213> ORGANISM: Artificial Sequence
<220> FEATURE:
<223> OTHER INFORMATION: target sequence

<400> SEQUENCE: 120
gcactcccct gctggagc 18

<210> SEQ ID NO 121
<211> LENGTH: 18
<212> TYPE: DNA
<213> ORGANISM: Artificial Sequence
<220> FEATURE:
<223> OTHER INFORMATION: target sequence

<400> SEQUENCE: 121
cactcccctg ctggagct 18

<210> SEQ ID NO 122
<211> LENGTH: 18
<212> TYPE: DNA
<213> ORGANISM: Artificial Sequence
<220> FEATURE:
<223> OTHER INFORMATION: target sequence

<400> SEQUENCE: 122
actcccctgc tggagctt 18

<210> SEQ ID NO 123
<211> LENGTH: 18
<212> TYPE: DNA
<213> ORGANISM: Artificial Sequence
<220> FEATURE:
<223> OTHER INFORMATION: target sequence

<400> SEQUENCE: 123
ctcccctgct ggagcttt 18

<210> SEQ ID NO 124
<211> LENGTH: 18
<212> TYPE: DNA
<213> ORGANISM: Artificial Sequence
<220> FEATURE:
<223> OTHER INFORMATION: target sequence

<400> SEQUENCE: 124
tcccctgctg gagctttt 18

<210> SEQ ID NO 125
<211> LENGTH: 18
<212> TYPE: DNA
<213> ORGANISM: Artificial Sequence
<220> FEATURE:
<223> OTHER INFORMATION: target sequence

<400> SEQUENCE: 125
cccctgctgg agcttttc 18

<210> SEQ ID NO 126
<211> LENGTH: 18
<212> TYPE: DNA
<213> ORGANISM: Artificial Sequence
<220> FEATURE:
<223> OTHER INFORMATION: target sequence

<400> SEQUENCE: 126
ccctgctgga gcttttct 18

<210> SEQ ID NO 127
<211> LENGTH: 18
<212> TYPE: DNA
<213> ORGANISM: Artificial Sequence
<220> FEATURE:
<223> OTHER INFORMATION: target sequence

<400> SEQUENCE: 127
cctgctggag cttttctc 18

<210> SEQ ID NO 128
<211> LENGTH: 18
<212> TYPE: DNA
<213> ORGANISM: Artificial Sequence
<220> FEATURE:
<223> OTHER INFORMATION: target sequence

<400> SEQUENCE: 128
ctgctggagc ttttctcg 18

<210> SEQ ID NO 129
<211> LENGTH: 18
<212> TYPE: DNA
<213> ORGANISM: Artificial Sequence
<220> FEATURE:
<223> OTHER INFORMATION: target sequence

<400> SEQUENCE: 129
tgctggagct tttctcgc 18

<210> SEQ ID NO 130
<211> LENGTH: 18
<212> TYPE: DNA
<213> ORGANISM: Artificial Sequence
<220> FEATURE:
<223> OTHER INFORMATION: target sequence

<400> SEQUENCE: 130
gctggagctt ttctcgcc 18

<210> SEQ ID NO 131
<211> LENGTH: 18

<212> TYPE: DNA
<213> ORGANISM: Artificial Sequence
<220> FEATURE:
<223> OTHER INFORMATION: target sequence

<400> SEQUENCE: 131
ctggagcttt tctcgccc 18

<210> SEQ ID NO 132
<211> LENGTH: 18
<212> TYPE: DNA
<213> ORGANISM: Artificial Sequence
<220> FEATURE:
<223> OTHER INFORMATION: target sequence

<400> SEQUENCE: 132
tggagctttt ctcgccct 18

<210> SEQ ID NO 133
<211> LENGTH: 18
<212> TYPE: DNA
<213> ORGANISM: Artificial Sequence
<220> FEATURE:
<223> OTHER INFORMATION: target sequence

<400> SEQUENCE: 133
ggagcttttc tcgccctt 18

<210> SEQ ID NO 134
<211> LENGTH: 18
<212> TYPE: DNA
<213> ORGANISM: Artificial Sequence
<220> FEATURE:
<223> OTHER INFORMATION: target sequence

<400> SEQUENCE: 134
gagcttttct cgcccttc 18

<210> SEQ ID NO 135
<211> LENGTH: 18
<212> TYPE: DNA
<213> ORGANISM: Artificial Sequence
<220> FEATURE:
<223> OTHER INFORMATION: target sequence

<400> SEQUENCE: 135
agcttttctc gcccttcc 18

<210> SEQ ID NO 136
<211> LENGTH: 18
<212> TYPE: DNA
<213> ORGANISM: Artificial Sequence
<220> FEATURE:
<223> OTHER INFORMATION: target sequence

<400> SEQUENCE: 136
gcttttctcg cccttcct 18

<210> SEQ ID NO 137
<211> LENGTH: 18
<212> TYPE: DNA
<213> ORGANISM: Artificial Sequence
<220> FEATURE:
<223> OTHER INFORMATION: target sequence

<400> SEQUENCE: 137
cttttctcgc ccttcctt 18

<210> SEQ ID NO 138
<211> LENGTH: 18
<212> TYPE: DNA
<213> ORGANISM: Artificial Sequence
<220> FEATURE:
<223> OTHER INFORMATION: target sequence

<400> SEQUENCE: 138
ttttctcgcc cttccttc 18

<210> SEQ ID NO 139
<211> LENGTH: 18
<212> TYPE: DNA
<213> ORGANISM: Artificial Sequence
<220> FEATURE:
<223> OTHER INFORMATION: target sequence

<400> SEQUENCE: 139
tttctcgccc ttccttct 18

<210> SEQ ID NO 140
<211> LENGTH: 18
<212> TYPE: DNA
<213> ORGANISM: Artificial Sequence
<220> FEATURE:
<223> OTHER INFORMATION: target sequence

<400> SEQUENCE: 140
ttctcgccct tccttctg 18

<210> SEQ ID NO 141
<211> LENGTH: 18
<212> TYPE: DNA
<213> ORGANISM: Artificial Sequence
<220> FEATURE:
<223> OTHER INFORMATION: target sequence

<400> SEQUENCE: 141
tctcgccctt ccttctgg 18

<210> SEQ ID NO 142
<211> LENGTH: 18
<212> TYPE: DNA
<213> ORGANISM: Artificial Sequence
<220> FEATURE:
<223> OTHER INFORMATION: target sequence

<400> SEQUENCE: 142
ctcgcccttc cttctggc 18

<210> SEQ ID NO 143
<211> LENGTH: 18
<212> TYPE: DNA
<213> ORGANISM: Artificial Sequence
<220> FEATURE:
<223> OTHER INFORMATION: target sequence

<400> SEQUENCE: 143
tcgcccttcc ttctggcc 18

<210> SEQ ID NO 144
<211> LENGTH: 18
<212> TYPE: DNA
<213> ORGANISM: Artificial Sequence
<220> FEATURE:
<223> OTHER INFORMATION: target sequence

<400> SEQUENCE: 144
cgcccttcct tctggccc 18

<210> SEQ ID NO 145
<211> LENGTH: 18
<212> TYPE: DNA
<213> ORGANISM: Artificial Sequence
<220> FEATURE:
<223> OTHER INFORMATION: target sequence

<400> SEQUENCE: 145
gcccttcctt ctggccct 18

<210> SEQ ID NO 146
<211> LENGTH: 18
<212> TYPE: DNA
<213> ORGANISM: Artificial Sequence
<220> FEATURE:
<223> OTHER INFORMATION: target sequence

<400> SEQUENCE: 146
cccttccttc tggccctc 18

<210> SEQ ID NO 147
<211> LENGTH: 18
<212> TYPE: DNA
<213> ORGANISM: Artificial Sequence
<220> FEATURE:
<223> OTHER INFORMATION: target sequence

<400> SEQUENCE: 147
ccttccttct ggccctct 18

<210> SEQ ID NO 148
<211> LENGTH: 18
<212> TYPE: DNA
<213> ORGANISM: Artificial Sequence
<220> FEATURE:
<223> OTHER INFORMATION: target sequence

<400> SEQUENCE: 148
cttccttctg gccctctc 18

<210> SEQ ID NO 149
<211> LENGTH: 18
<212> TYPE: DNA
<213> ORGANISM: Artificial Sequence
<220> FEATURE:
<223> OTHER INFORMATION: target sequence

<400> SEQUENCE: 149
ttccttctgg ccctctcc 18

<210> SEQ ID NO 150
<211> LENGTH: 18
<212> TYPE: DNA
<213> ORGANISM: Artificial Sequence
<220> FEATURE:
<223> OTHER INFORMATION: target sequence

<400> SEQUENCE: 150
tccttctggc cctctccc 18

<210> SEQ ID NO 151
<211> LENGTH: 18
<212> TYPE: DNA
<213> ORGANISM: Artificial Sequence
<220> FEATURE:
<223> OTHER INFORMATION: target sequence

<400> SEQUENCE: 151
ccttctggcc ctctcccc 18

<210> SEQ ID NO 152
<211> LENGTH: 18
<212> TYPE: DNA
<213> ORGANISM: Artificial Sequence
<220> FEATURE:
<223> OTHER INFORMATION: target sequence

<400> SEQUENCE: 152
cttctggccc tctcccca 18

<210> SEQ ID NO 153
<211> LENGTH: 18
<212> TYPE: DNA
<213> ORGANISM: Artificial Sequence
<220> FEATURE:
<223> OTHER INFORMATION: target sequence

<400> SEQUENCE: 153
ttctggccct ctccccag 18

<210> SEQ ID NO 154
<211> LENGTH: 18
<212> TYPE: DNA
<213> ORGANISM: Artificial Sequence
<220> FEATURE:
<223> OTHER INFORMATION: target sequence

<400> SEQUENCE: 154
tctggccctc tccccagt 18

<210> SEQ ID NO 155
<211> LENGTH: 18
<212> TYPE: DNA
<213> ORGANISM: Artificial Sequence
<220> FEATURE:
<223> OTHER INFORMATION: target sequence

<400> SEQUENCE: 155
ctggccctct ccccagtc 18

<210> SEQ ID NO 156
<211> LENGTH: 18
<212> TYPE: DNA
<213> ORGANISM: Artificial Sequence
<220> FEATURE:
<223> OTHER INFORMATION: target sequence

<400> SEQUENCE: 156
tggccctctc cccagtct 18

<210> SEQ ID NO 157
<211> LENGTH: 18
<212> TYPE: DNA
<213> ORGANISM: Artificial Sequence
<220> FEATURE:
<223> OTHER INFORMATION: target sequence

<400> SEQUENCE: 157
ggccctctcc ccagtcta 18

<210> SEQ ID NO 158
<211> LENGTH: 18
<212> TYPE: DNA
<213> ORGANISM: Artificial Sequence
<220> FEATURE:
<223> OTHER INFORMATION: target sequence

<400> SEQUENCE: 158
gccctctccc cagtctag 18

<210> SEQ ID NO 159
<211> LENGTH: 18
<212> TYPE: DNA
<213> ORGANISM: Artificial Sequence
<220> FEATURE:
<223> OTHER INFORMATION: target sequence

<400> SEQUENCE: 159
ccctctcccc agtctaga 18

<210> SEQ ID NO 160
<211> LENGTH: 18
<212> TYPE: DNA
<213> ORGANISM: Artificial Sequence
<220> FEATURE:
<223> OTHER INFORMATION: target sequence

<400> SEQUENCE: 160
cctctcccca gtctagac 18

<210> SEQ ID NO 161
<211> LENGTH: 18
<212> TYPE: DNA
<213> ORGANISM: Artificial Sequence
<220> FEATURE:
<223> OTHER INFORMATION: target sequence

<400> SEQUENCE: 161
ctctccccag tctagaca 18

<210> SEQ ID NO 162
<211> LENGTH: 18
<212> TYPE: DNA
<213> ORGANISM: Artificial Sequence
<220> FEATURE:
<223> OTHER INFORMATION: target sequence

<400> SEQUENCE: 162
tctccccagt ctagacag 18

<210> SEQ ID NO 163
<211> LENGTH: 18
<212> TYPE: DNA
<213> ORGANISM: Artificial Sequence
<220> FEATURE:
<223> OTHER INFORMATION: target sequence

<400> SEQUENCE: 163
ctccccagtc tagacagc 18

<210> SEQ ID NO 164

<211> LENGTH: 18
<212> TYPE: DNA
<213> ORGANISM: Artificial Sequence
<220> FEATURE:
<223> OTHER INFORMATION: target sequence

<400> SEQUENCE: 164
tccccagtct agacagca 18

<210> SEQ ID NO 165
<211> LENGTH: 18
<212> TYPE: DNA
<213> ORGANISM: Artificial Sequence
<220> FEATURE:
<223> OTHER INFORMATION: target sequence

<400> SEQUENCE: 165
ccccagtcta gacagcag 18

<210> SEQ ID NO 166
<211> LENGTH: 18
<212> TYPE: DNA
<213> ORGANISM: Artificial Sequence
<220> FEATURE:
<223> OTHER INFORMATION: target sequence

<400> SEQUENCE: 166
cccagtctag acagcagg 18

<210> SEQ ID NO 167
<211> LENGTH: 18
<212> TYPE: DNA
<213> ORGANISM: Artificial Sequence
<220> FEATURE:
<223> OTHER INFORMATION: target sequence

<400> SEQUENCE: 167
ccagtctaga cagcaggg 18

<210> SEQ ID NO 168
<211> LENGTH: 18
<212> TYPE: DNA
<213> ORGANISM: Artificial Sequence
<220> FEATURE:
<223> OTHER INFORMATION: target sequence

<400> SEQUENCE: 168
cagtctagac agcagggc 18

<210> SEQ ID NO 169
<211> LENGTH: 18
<212> TYPE: DNA
<213> ORGANISM: Artificial Sequence
<220> FEATURE:
<223> OTHER INFORMATION: target sequence

<400> SEQUENCE: 169
agtctagaca gcagggca 18

<210> SEQ ID NO 170
<211> LENGTH: 18
<212> TYPE: DNA
<213> ORGANISM: Artificial Sequence
<220> FEATURE:
<223> OTHER INFORMATION: target sequence

<400> SEQUENCE: 170
gtctagacag cagggcaa 18

<210> SEQ ID NO 171
<211> LENGTH: 50
<212> TYPE: DNA
<213> ORGANISM: Artificial Sequence
<220> FEATURE:
<223> OTHER INFORMATION: target sequence c.-32-77_-28

<400> SEQUENCE: 171
gtctcagagc tgctttgaga gccccgtgag tgccgcccct cccgcctccc 50

<210> SEQ ID NO 172
<211> LENGTH: 25
<212> TYPE: DNA
<213> ORGANISM: Artificial Sequence
<220> FEATURE:
<223> OTHER INFORMATION: target sequence

<400> SEQUENCE: 172
gtctcagagc tgctttgaga gcccc 25

<210> SEQ ID NO 173
<211> LENGTH: 25
<212> TYPE: DNA
<213> ORGANISM: Artificial Sequence
<220> FEATURE:
<223> OTHER INFORMATION: target sequence

<400> SEQUENCE: 173
tctcagagct gctttgagag ccccg 25

<210> SEQ ID NO 174
<211> LENGTH: 25
<212> TYPE: DNA
<213> ORGANISM: Artificial Sequence
<220> FEATURE:
<223> OTHER INFORMATION: target sequence

<400> SEQUENCE: 174
ctcagagctg ctttgagagc cccgt 25

<210> SEQ ID NO 175
<211> LENGTH: 25
<212> TYPE: DNA
<213> ORGANISM: Artificial Sequence
<220> FEATURE:
<223> OTHER INFORMATION: target sequence

<400> SEQUENCE: 175
tcagagctgc tttgagagcc ccgtg 25

<210> SEQ ID NO 176
<211> LENGTH: 25
<212> TYPE: DNA
<213> ORGANISM: Artificial Sequence
<220> FEATURE:
<223> OTHER INFORMATION: target sequence

<400> SEQUENCE: 176
cagagctgct ttgagagccc cgtga 25

<210> SEQ ID NO 177
<211> LENGTH: 25
<212> TYPE: DNA

<213> ORGANISM: Artificial Sequence
<220> FEATURE:
<223> OTHER INFORMATION: target sequence

<400> SEQUENCE: 177
agagctgctt tgagagcccc gtgag 25

<210> SEQ ID NO 178
<211> LENGTH: 25
<212> TYPE: DNA
<213> ORGANISM: Artificial Sequence
<220> FEATURE:
<223> OTHER INFORMATION: target sequence

<400> SEQUENCE: 178
gagctgcttt gagagccccg tgagt 25

<210> SEQ ID NO 179
<211> LENGTH: 25
<212> TYPE: DNA
<213> ORGANISM: Artificial Sequence
<220> FEATURE:
<223> OTHER INFORMATION: target sequence

<400> SEQUENCE: 179
agctgctttg agagccccgt gagtg 25

<210> SEQ ID NO 180
<211> LENGTH: 25
<212> TYPE: DNA
<213> ORGANISM: Artificial Sequence
<220> FEATURE:
<223> OTHER INFORMATION: target sequence

<400> SEQUENCE: 180
gctgctttga gagccccgtg agtgc 25

<210> SEQ ID NO 181
<211> LENGTH: 25
<212> TYPE: DNA
<213> ORGANISM: Artificial Sequence
<220> FEATURE:
<223> OTHER INFORMATION: target sequence

<400> SEQUENCE: 181
ctgctttgag agccccgtga gtgcc 25

<210> SEQ ID NO 182
<211> LENGTH: 25
<212> TYPE: DNA
<213> ORGANISM: Artificial Sequence
<220> FEATURE:
<223> OTHER INFORMATION: target sequence

<400> SEQUENCE: 182
tgctttgaga gccccgtgag tgccg 25

<210> SEQ ID NO 183
<211> LENGTH: 25
<212> TYPE: DNA
<213> ORGANISM: Artificial Sequence
<220> FEATURE:
<223> OTHER INFORMATION: target sequence

<400> SEQUENCE: 183
gctttgagag ccccgtgagt gccgc 25

<210> SEQ ID NO 184
<211> LENGTH: 25
<212> TYPE: DNA
<213> ORGANISM: Artificial Sequence
<220> FEATURE:
<223> OTHER INFORMATION: target sequence

<400> SEQUENCE: 184
ctttgagagc cccgtgagtg ccgcc 25

<210> SEQ ID NO 185
<211> LENGTH: 25
<212> TYPE: DNA
<213> ORGANISM: Artificial Sequence
<220> FEATURE:
<223> OTHER INFORMATION: target sequence

<400> SEQUENCE: 185
tttgagagcc ccgtgagtgc cgccc 25

<210> SEQ ID NO 186
<211> LENGTH: 25
<212> TYPE: DNA
<213> ORGANISM: Artificial Sequence
<220> FEATURE:
<223> OTHER INFORMATION: target sequence

<400> SEQUENCE: 186
ttgagagccc cgtgagtgcc gcccc 25

<210> SEQ ID NO 187
<211> LENGTH: 25
<212> TYPE: DNA
<213> ORGANISM: Artificial Sequence
<220> FEATURE:
<223> OTHER INFORMATION: target sequence

<400> SEQUENCE: 187
tgagagcccc gtgagtgccg cccct 25

<210> SEQ ID NO 188
<211> LENGTH: 25
<212> TYPE: DNA
<213> ORGANISM: Artificial Sequence
<220> FEATURE:
<223> OTHER INFORMATION: target sequence

<400> SEQUENCE: 188
gagagccccg tgagtgccgc ccctc 25

<210> SEQ ID NO 189
<211> LENGTH: 25
<212> TYPE: DNA
<213> ORGANISM: Artificial Sequence
<220> FEATURE:
<223> OTHER INFORMATION: target sequence

<400> SEQUENCE: 189
agagccccgt gagtgccgcc cctcc 25

<210> SEQ ID NO 190
<211> LENGTH: 25
<212> TYPE: DNA
<213> ORGANISM: Artificial Sequence
<220> FEATURE:

<223> OTHER INFORMATION: target sequence

<400> SEQUENCE: 190
gagccccgtg agtgccgccc ctccc 25

<210> SEQ ID NO 191
<211> LENGTH: 25
<212> TYPE: DNA
<213> ORGANISM: Artificial Sequence
<220> FEATURE:
<223> OTHER INFORMATION: target sequence

<400> SEQUENCE: 191
agccccgtga gtgccgcccc tcccg 25

<210> SEQ ID NO 192
<211> LENGTH: 25
<212> TYPE: DNA
<213> ORGANISM: Artificial Sequence
<220> FEATURE:
<223> OTHER INFORMATION: target sequence

<400> SEQUENCE: 192
gccccgtgag tgccgcccct cccgc 25

<210> SEQ ID NO 193
<211> LENGTH: 25
<212> TYPE: DNA
<213> ORGANISM: Artificial Sequence
<220> FEATURE:
<223> OTHER INFORMATION: target sequence

<400> SEQUENCE: 193
ccccgtgagt gccgcccctc ccgcc 25

<210> SEQ ID NO 194
<211> LENGTH: 25
<212> TYPE: DNA
<213> ORGANISM: Artificial Sequence
<220> FEATURE:
<223> OTHER INFORMATION: target sequence

<400> SEQUENCE: 194
cccgtgagtg ccgcccctcc cgcct 25

<210> SEQ ID NO 195
<211> LENGTH: 25
<212> TYPE: DNA
<213> ORGANISM: Artificial Sequence
<220> FEATURE:
<223> OTHER INFORMATION: target sequence

<400> SEQUENCE: 195
ccgtgagtgc cgcccctccc gcctc 25

<210> SEQ ID NO 196
<211> LENGTH: 25
<212> TYPE: DNA
<213> ORGANISM: Artificial Sequence
<220> FEATURE:
<223> OTHER INFORMATION: target sequence

<400> SEQUENCE: 196
cgtgagtgcc gcccctcccg cctcc 25

<210> SEQ ID NO 197
<211> LENGTH: 25
<212> TYPE: DNA
<213> ORGANISM: Artificial Sequence
<220> FEATURE:
<223> OTHER INFORMATION: target sequence

<400> SEQUENCE: 197
gtgagtgccg cccctcccgc ctccc 25

<210> SEQ ID NO 198
<211> LENGTH: 21
<212> TYPE: DNA
<213> ORGANISM: Artificial Sequence
<220> FEATURE:
<223> OTHER INFORMATION: target sequence

<400> SEQUENCE: 198
gtctcagagc tgctttgaga g 21

<210> SEQ ID NO 199
<211> LENGTH: 21
<212> TYPE: DNA
<213> ORGANISM: Artificial Sequence
<220> FEATURE:
<223> OTHER INFORMATION: target sequence

<400> SEQUENCE: 199
tctcagagct gctttgagag c 21

<210> SEQ ID NO 200
<211> LENGTH: 21
<212> TYPE: DNA
<213> ORGANISM: Artificial Sequence
<220> FEATURE:
<223> OTHER INFORMATION: target sequence

<400> SEQUENCE: 200
ctcagagctg ctttgagagc c 21

<210> SEQ ID NO 201
<211> LENGTH: 21
<212> TYPE: DNA
<213> ORGANISM: Artificial Sequence
<220> FEATURE:
<223> OTHER INFORMATION: target sequence

<400> SEQUENCE: 201
tcagagctgc tttgagagcc c 21

<210> SEQ ID NO 202
<211> LENGTH: 21
<212> TYPE: DNA
<213> ORGANISM: Artificial Sequence
<220> FEATURE:
<223> OTHER INFORMATION: target sequence

<400> SEQUENCE: 202
cagagctgct ttgagagccc c 21

<210> SEQ ID NO 203
<211> LENGTH: 21
<212> TYPE: DNA
<213> ORGANISM: Artificial Sequence
<220> FEATURE:
<223> OTHER INFORMATION: target sequence

<400> SEQUENCE: 203
agagctgctt tgagagcccc g 21

<210> SEQ ID NO 204
<211> LENGTH: 21
<212> TYPE: DNA
<213> ORGANISM: Artificial Sequence
<220> FEATURE:
<223> OTHER INFORMATION: target sequence

<400> SEQUENCE: 204
gagctgcttt gagagccccg t 21

<210> SEQ ID NO 205
<211> LENGTH: 21
<212> TYPE: DNA
<213> ORGANISM: Artificial Sequence
<220> FEATURE:
<223> OTHER INFORMATION: target sequence

<400> SEQUENCE: 205
agctgctttg agagccccgt g 21

<210> SEQ ID NO 206
<211> LENGTH: 21
<212> TYPE: DNA
<213> ORGANISM: Artificial Sequence
<220> FEATURE:
<223> OTHER INFORMATION: target sequence

<400> SEQUENCE: 206
gctgctttga gagccccgtg a 21

<210> SEQ ID NO 207
<211> LENGTH: 21
<212> TYPE: DNA
<213> ORGANISM: Artificial Sequence
<220> FEATURE:
<223> OTHER INFORMATION: target sequence

<400> SEQUENCE: 207
ctgctttgag agccccgtga g 21

<210> SEQ ID NO 208
<211> LENGTH: 21
<212> TYPE: DNA
<213> ORGANISM: Artificial Sequence
<220> FEATURE:
<223> OTHER INFORMATION: target sequence

<400> SEQUENCE: 208
tgctttgaga gccccgtgag t 21

<210> SEQ ID NO 209
<211> LENGTH: 21
<212> TYPE: DNA
<213> ORGANISM: Artificial Sequence
<220> FEATURE:
<223> OTHER INFORMATION: target sequence

<400> SEQUENCE: 209
gctttgagag ccccgtgagt g 21

<210> SEQ ID NO 210
<211> LENGTH: 21

<212> TYPE: DNA
<213> ORGANISM: Artificial Sequence
<220> FEATURE:
<223> OTHER INFORMATION: target sequence

<400> SEQUENCE: 210
ctttgagagc cccgtgagtg c 21

<210> SEQ ID NO 211
<211> LENGTH: 21
<212> TYPE: DNA
<213> ORGANISM: Artificial Sequence
<220> FEATURE:
<223> OTHER INFORMATION: target sequence

<400> SEQUENCE: 211
tttgagagcc ccgtgagtgc c 21

<210> SEQ ID NO 212
<211> LENGTH: 21
<212> TYPE: DNA
<213> ORGANISM: Artificial Sequence
<220> FEATURE:
<223> OTHER INFORMATION: target sequence

<400> SEQUENCE: 212
ttgagagccc cgtgagtgcc g 21

<210> SEQ ID NO 213
<211> LENGTH: 21
<212> TYPE: DNA
<213> ORGANISM: Artificial Sequence
<220> FEATURE:
<223> OTHER INFORMATION: target sequence

<400> SEQUENCE: 213
tgagagcccc gtgagtgccg c 21

<210> SEQ ID NO 214
<211> LENGTH: 21
<212> TYPE: DNA
<213> ORGANISM: Artificial Sequence
<220> FEATURE:
<223> OTHER INFORMATION: target sequence

<400> SEQUENCE: 214
gagagccccg tgagtgccgc c 21

<210> SEQ ID NO 215
<211> LENGTH: 21
<212> TYPE: DNA
<213> ORGANISM: Artificial Sequence
<220> FEATURE:
<223> OTHER INFORMATION: target sequence

<400> SEQUENCE: 215
agagccccgt gagtgccgcc c 21

<210> SEQ ID NO 216
<211> LENGTH: 21
<212> TYPE: DNA
<213> ORGANISM: Artificial Sequence
<220> FEATURE:
<223> OTHER INFORMATION: target sequence

<400> SEQUENCE: 216
gagccccgtg agtgccgccc c 21

<210> SEQ ID NO 217
<211> LENGTH: 21
<212> TYPE: DNA
<213> ORGANISM: Artificial Sequence
<220> FEATURE:
<223> OTHER INFORMATION: target sequence

<400> SEQUENCE: 217
agccccgtga gtgccgcccc t 21

<210> SEQ ID NO 218
<211> LENGTH: 21
<212> TYPE: DNA
<213> ORGANISM: Artificial Sequence
<220> FEATURE:
<223> OTHER INFORMATION: target sequence

<400> SEQUENCE: 218
gccccgtgag tgccgcccct c 21

<210> SEQ ID NO 219
<211> LENGTH: 21
<212> TYPE: DNA
<213> ORGANISM: Artificial Sequence
<220> FEATURE:
<223> OTHER INFORMATION: target sequence

<400> SEQUENCE: 219
ccccgtgagt gccgcccctc c 21

<210> SEQ ID NO 220
<211> LENGTH: 21
<212> TYPE: DNA
<213> ORGANISM: Artificial Sequence
<220> FEATURE:
<223> OTHER INFORMATION: target sequence

<400> SEQUENCE: 220
cccgtgagtg ccgcccctcc c 21

<210> SEQ ID NO 221
<211> LENGTH: 21
<212> TYPE: DNA
<213> ORGANISM: Artificial Sequence
<220> FEATURE:
<223> OTHER INFORMATION: target sequence

<400> SEQUENCE: 221
ccgtgagtgc cgcccctccc g 21

<210> SEQ ID NO 222
<211> LENGTH: 21
<212> TYPE: DNA
<213> ORGANISM: Artificial Sequence
<220> FEATURE:
<223> OTHER INFORMATION: target sequence

<400> SEQUENCE: 222
cgtgagtgcc gcccctcccg c 21

<210> SEQ ID NO 223
<211> LENGTH: 21
<212> TYPE: DNA
<213> ORGANISM: Artificial Sequence
<220> FEATURE:
<223> OTHER INFORMATION: target sequence

<400> SEQUENCE: 223
gtgagtgccg cccctcccgc c 21

<210> SEQ ID NO 224
<211> LENGTH: 21
<212> TYPE: DNA
<213> ORGANISM: Artificial Sequence
<220> FEATURE:
<223> OTHER INFORMATION: target sequence

<400> SEQUENCE: 224
tgagtgccgc ccctcccgcc t 21

<210> SEQ ID NO 225
<211> LENGTH: 21
<212> TYPE: DNA
<213> ORGANISM: Artificial Sequence
<220> FEATURE:
<223> OTHER INFORMATION: target sequence

<400> SEQUENCE: 225
gagtgccgcc cctcccgcct c 21

<210> SEQ ID NO 226
<211> LENGTH: 21
<212> TYPE: DNA
<213> ORGANISM: Artificial Sequence
<220> FEATURE:
<223> OTHER INFORMATION: target sequence

<400> SEQUENCE: 226
agtgccgccc ctcccgcctc c 21

<210> SEQ ID NO 227
<211> LENGTH: 21
<212> TYPE: DNA
<213> ORGANISM: Artificial Sequence
<220> FEATURE:
<223> OTHER INFORMATION: target sequence

<400> SEQUENCE: 227
gtgccgcccc tcccgcctcc c 21

<210> SEQ ID NO 228
<211> LENGTH: 18
<212> TYPE: DNA
<213> ORGANISM: Artificial Sequence
<220> FEATURE:
<223> OTHER INFORMATION: target sequence

<400> SEQUENCE: 228
gtctcagagc tgctttga 18

<210> SEQ ID NO 229
<211> LENGTH: 18
<212> TYPE: DNA
<213> ORGANISM: Artificial Sequence
<220> FEATURE:
<223> OTHER INFORMATION: target sequence

<400> SEQUENCE: 229
tctcagagct gctttgag 18

<210> SEQ ID NO 230
<211> LENGTH: 18
<212> TYPE: DNA
<213> ORGANISM: Artificial Sequence
<220> FEATURE:
<223> OTHER INFORMATION: target sequence

<400> SEQUENCE: 230
ctcagagctg ctttgaga 18

<210> SEQ ID NO 231
<211> LENGTH: 18
<212> TYPE: DNA
<213> ORGANISM: Artificial Sequence
<220> FEATURE:
<223> OTHER INFORMATION: target sequence

<400> SEQUENCE: 231
tcagagctgc tttgagag 18

<210> SEQ ID NO 232
<211> LENGTH: 18
<212> TYPE: DNA
<213> ORGANISM: Artificial Sequence
<220> FEATURE:
<223> OTHER INFORMATION: target sequence

<400> SEQUENCE: 232
cagagctgct ttgagagc 18

<210> SEQ ID NO 233
<211> LENGTH: 18
<212> TYPE: DNA
<213> ORGANISM: Artificial Sequence
<220> FEATURE:
<223> OTHER INFORMATION: target sequence

<400> SEQUENCE: 233
agagctgctt tgagagcc 18

<210> SEQ ID NO 234
<211> LENGTH: 18
<212> TYPE: DNA
<213> ORGANISM: Artificial Sequence
<220> FEATURE:
<223> OTHER INFORMATION: target sequence

<400> SEQUENCE: 234
gagctgcttt gagagccc 18

<210> SEQ ID NO 235
<211> LENGTH: 18
<212> TYPE: DNA
<213> ORGANISM: Artificial Sequence
<220> FEATURE:
<223> OTHER INFORMATION: target sequence

<400> SEQUENCE: 235
agctgctttg agagcccc 18

<210> SEQ ID NO 236
<211> LENGTH: 18
<212> TYPE: DNA
<213> ORGANISM: Artificial Sequence
<220> FEATURE:
<223> OTHER INFORMATION: target sequence

<400> SEQUENCE: 236
gctgctttga gagccccg 18

<210> SEQ ID NO 237
<211> LENGTH: 18
<212> TYPE: DNA
<213> ORGANISM: Artificial Sequence
<220> FEATURE:
<223> OTHER INFORMATION: target sequence

<400> SEQUENCE: 237
ctgctttgag agccccgt 18

<210> SEQ ID NO 238
<211> LENGTH: 18
<212> TYPE: DNA
<213> ORGANISM: Artificial Sequence
<220> FEATURE:
<223> OTHER INFORMATION: target sequence

<400> SEQUENCE: 238
tgctttgaga gccccgtg 18

<210> SEQ ID NO 239
<211> LENGTH: 18
<212> TYPE: DNA
<213> ORGANISM: Artificial Sequence
<220> FEATURE:
<223> OTHER INFORMATION: target sequence

<400> SEQUENCE: 239
gctttgagag ccccgtga 18

<210> SEQ ID NO 240
<211> LENGTH: 18
<212> TYPE: DNA
<213> ORGANISM: Artificial Sequence
<220> FEATURE:
<223> OTHER INFORMATION: target sequence

<400> SEQUENCE: 240
ctttgagagc cccgtgag 18

<210> SEQ ID NO 241
<211> LENGTH: 18
<212> TYPE: DNA
<213> ORGANISM: Artificial Sequence
<220> FEATURE:
<223> OTHER INFORMATION: target sequence

<400> SEQUENCE: 241
tttgagagcc ccgtgagt 18

<210> SEQ ID NO 242
<211> LENGTH: 18
<212> TYPE: DNA
<213> ORGANISM: Artificial Sequence
<220> FEATURE:
<223> OTHER INFORMATION: target sequence

<400> SEQUENCE: 242
ttgagagccc cgtgagtg 18

<210> SEQ ID NO 243

<211> LENGTH: 18
<212> TYPE: DNA
<213> ORGANISM: Artificial Sequence
<220> FEATURE:
<223> OTHER INFORMATION: target sequence

<400> SEQUENCE: 243
tgagagcccc gtgagtgc 18

<210> SEQ ID NO 244
<211> LENGTH: 18
<212> TYPE: DNA
<213> ORGANISM: Artificial Sequence
<220> FEATURE:
<223> OTHER INFORMATION: target sequence

<400> SEQUENCE: 244
gagagccccg tgagtgcc 18

<210> SEQ ID NO 245
<211> LENGTH: 18
<212> TYPE: DNA
<213> ORGANISM: Artificial Sequence
<220> FEATURE:
<223> OTHER INFORMATION: target sequence

<400> SEQUENCE: 245
agagccccgt gagtgccg 18

<210> SEQ ID NO 246
<211> LENGTH: 18
<212> TYPE: DNA
<213> ORGANISM: Artificial Sequence
<220> FEATURE:
<223> OTHER INFORMATION: target sequence

<400> SEQUENCE: 246
gagccccgtg agtgccgc 18

<210> SEQ ID NO 247
<211> LENGTH: 18
<212> TYPE: DNA
<213> ORGANISM: Artificial Sequence
<220> FEATURE:
<223> OTHER INFORMATION: target sequence

<400> SEQUENCE: 247
agccccgtga gtgccgcc 18

<210> SEQ ID NO 248
<211> LENGTH: 18
<212> TYPE: DNA
<213> ORGANISM: Artificial Sequence
<220> FEATURE:
<223> OTHER INFORMATION: target sequence

<400> SEQUENCE: 248
gccccgtgag tgccgccc 18

<210> SEQ ID NO 249
<211> LENGTH: 18
<212> TYPE: DNA
<213> ORGANISM: Artificial Sequence
<220> FEATURE:
<223> OTHER INFORMATION: target sequence

<400> SEQUENCE: 249
ccccgtgagt gccgcccc 18

<210> SEQ ID NO 250
<211> LENGTH: 18
<212> TYPE: DNA
<213> ORGANISM: Artificial Sequence
<220> FEATURE:
<223> OTHER INFORMATION: target sequence

<400> SEQUENCE: 250
cccgtgagtg ccgcccct 18

<210> SEQ ID NO 251
<211> LENGTH: 18
<212> TYPE: DNA
<213> ORGANISM: Artificial Sequence
<220> FEATURE:
<223> OTHER INFORMATION: target sequence

<400> SEQUENCE: 251
ccgtgagtgc cgcccctc 18

<210> SEQ ID NO 252
<211> LENGTH: 18
<212> TYPE: DNA
<213> ORGANISM: Artificial Sequence
<220> FEATURE:
<223> OTHER INFORMATION: target sequence

<400> SEQUENCE: 252
cgtgagtgcc gcccctcc 18

<210> SEQ ID NO 253
<211> LENGTH: 18
<212> TYPE: DNA
<213> ORGANISM: Artificial Sequence
<220> FEATURE:
<223> OTHER INFORMATION: target sequence

<400> SEQUENCE: 253
gtgagtgccg cccctccc 18

<210> SEQ ID NO 254
<211> LENGTH: 18
<212> TYPE: DNA
<213> ORGANISM: Artificial Sequence
<220> FEATURE:
<223> OTHER INFORMATION: target sequence

<400> SEQUENCE: 254
tgagtgccgc ccctcccg 18

<210> SEQ ID NO 255
<211> LENGTH: 18
<212> TYPE: DNA
<213> ORGANISM: Artificial Sequence
<220> FEATURE:
<223> OTHER INFORMATION: target sequence

<400> SEQUENCE: 255
gagtgccgcc cctcccgc 18

<210> SEQ ID NO 256
<211> LENGTH: 18
<212> TYPE: DNA

<213> ORGANISM: Artificial Sequence
<220> FEATURE:
<223> OTHER INFORMATION: target sequence

<400> SEQUENCE: 256
agtgccgccc ctcccgcc 18

<210> SEQ ID NO 257
<211> LENGTH: 18
<212> TYPE: DNA
<213> ORGANISM: Artificial Sequence
<220> FEATURE:
<223> OTHER INFORMATION: target sequence

<400> SEQUENCE: 257
gtgccgcccc tcccgcct 18

<210> SEQ ID NO 258
<211> LENGTH: 18
<212> TYPE: DNA
<213> ORGANISM: Artificial Sequence
<220> FEATURE:
<223> OTHER INFORMATION: target sequence

<400> SEQUENCE: 258
tgccgcccct cccgcctc 18

<210> SEQ ID NO 259
<211> LENGTH: 18
<212> TYPE: DNA
<213> ORGANISM: Artificial Sequence
<220> FEATURE:
<223> OTHER INFORMATION: target sequence

<400> SEQUENCE: 259
gccgcccctc ccgcctcc 18

<210> SEQ ID NO 260
<211> LENGTH: 18
<212> TYPE: DNA
<213> ORGANISM: Artificial Sequence
<220> FEATURE:
<223> OTHER INFORMATION: target sequence

<400> SEQUENCE: 260
ccgcccctcc cgcctccc 18

<210> SEQ ID NO 261
<211> LENGTH: 368
<212> TYPE: DNA
<213> ORGANISM: Artificial Sequence
<220> FEATURE:
<223> OTHER INFORMATION: sequence of region (5'-> 3')

<400> SEQUENCE: 261
aaccccagag ctgcttccct tccagatgtg gtcctgcagc cgagccctgc ccttagctgg 60
aggtcgacag gtgggatcct ggatgtctac atcttcctgg gcccagagcc caagagcgtg 120
gtgcagcagt acctggacgt tgtgggtagg gcctgctccc tggccgcggc ccccgcccca 180
aggctccctc ctccctccct catgaagtcg gcgttggcct gcaggatacc cgttcatgcc 240
gccatactgg ggcctgggct tccacctgtg ccgctggggc tactcctcca ccgctatcac 300
ccgccaggtg gtggagaaca tgaccagggc ccacttcccc ctggtgagtt ggggtggtgg 360
caggggag 368

<210> SEQ ID NO 262
<211> LENGTH: 74
<212> TYPE: DNA
<213> ORGANISM: Artificial Sequence
<220> FEATURE:
<223> OTHER INFORMATION: sequence of region (5'-> 3')

<400> SEQUENCE: 262
aaccccagag ctgcttccct tccagatgtg gtcctgcagc cgagccctgc ccttagctgg 60
aggtcgacag gtgg 74

<210> SEQ ID NO 263
<211> LENGTH: 74
<212> TYPE: DNA
<213> ORGANISM: Artificial Sequence
<220> FEATURE:
<223> OTHER INFORMATION: sequence of region (5'-> 3')

<400> SEQUENCE: 263
gatcctggat gtctacatct tcctgggccc agagcccaag agcgtggtgc agcagtacct 60
ggacgttgtg ggta 74

<210> SEQ ID NO 264
<211> LENGTH: 74
<212> TYPE: DNA
<213> ORGANISM: Artificial Sequence
<220> FEATURE:
<223> OTHER INFORMATION: sequence of region (5'-> 3')

<400> SEQUENCE: 264
gggcctgctc cctggccgcg gcccccgccc caaggctccc tcctccctcc ctcatgaagt 60
cggcgttggc ctgc 74

<210> SEQ ID NO 265
<211> LENGTH: 74
<212> TYPE: DNA
<213> ORGANISM: Artificial Sequence
<220> FEATURE:
<223> OTHER INFORMATION: sequence of region (5'-> 3')

<400> SEQUENCE: 265
aggatacccg ttcatgccgc catactgggg cctgggcttc cacctgtgcc gctggggcta 60
ctcctccacc gcta 74

<210> SEQ ID NO 266
<211> LENGTH: 72
<212> TYPE: DNA
<213> ORGANISM: Artificial Sequence
<220> FEATURE:
<223> OTHER INFORMATION: sequence of region (5'-> 3')

<400> SEQUENCE: 266
tcacccgcca ggtggtggag aacatgacca gggcccactt ccccctggtg agttggggtg 60
gtggcagggg ag 72

<210> SEQ ID NO 267
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 267
tggggagagg gccagaagga agggc 25

<210> SEQ ID NO 268
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 268
ggggagaggg ccagaaggaa gggcg 25

<210> SEQ ID NO 269
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 269
gggagagggc cagaaggaag ggcga 25

<210> SEQ ID NO 270
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 270
ggagagggcc agaaggaagg gcgag 25

<210> SEQ ID NO 271
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 271
gagagggcca gaaggaaggg cgaga 25

<210> SEQ ID NO 272
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 272
agagggccag aaggaagggc gagaa 25

<210> SEQ ID NO 273
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 273
gagggccaga aggaagggcg agaaa 25

<210> SEQ ID NO 274
<211> LENGTH: 25

<212> TYPE: DNA
<213> ORGANISM: Artificial Sequence
<220> FEATURE:
<223> OTHER INFORMATION: sequence of AON (5'-> 3')

<400> SEQUENCE: 274
agggccagaa ggaagggcga gaaaa 25

<210> SEQ ID NO 275
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 275
gggccagaag gaagggcgag aaaag 25

<210> SEQ ID NO 276
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 276
ggccagaagg aagggcgaga aaagc 25

<210> SEQ ID NO 277
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 277
gccagaagga agggcgagaa aagct 25

<210> SEQ ID NO 278
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 278
ccagaaggaa gggcgagaaa agctc 25

<210> SEQ ID NO 279
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 279
cagaaggaag ggcgagaaaa gctcc 25

<210> SEQ ID NO 280
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 280
agaaggaagg gcgagaaaag ctcca 25

<210> SEQ ID NO 281
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 281
gaaggaaggg cgagaaaagc tccag 25

<210> SEQ ID NO 282
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 282
aaggaagggc gagaaaagct ccagc 25

<210> SEQ ID NO 283
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 283
aggaagggcg agaaaagctc cagca 25

<210> SEQ ID NO 284
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 284
ggaagggcga gaaaagctcc agcag 25

<210> SEQ ID NO 285
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 285
gaagggcgag aaaagctcca gcagg 25

<210> SEQ ID NO 286
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 286
aagggcgaga aaagctccag caggg 25

<210> SEQ ID NO 287
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 287
agggcgagaa aagctccagc agggg 25

<210> SEQ ID NO 288
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 288
gggcgagaaa agctccagca gggga 25

<210> SEQ ID NO 289
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 289
ggcgagaaaa gctccagcag gggag 25

<210> SEQ ID NO 290
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 290
gcgagaaaag ctccagcagg ggagt 25

<210> SEQ ID NO 291
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 291
cgagaaaagc tccagcaggg gagtg 25

<210> SEQ ID NO 292
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 292
gagaaaagct ccagcagggg agtgc 25

<210> SEQ ID NO 293
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 293
agaaaagctc cagcagggga gtgca 25

<210> SEQ ID NO 294
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 294
gaaaagctcc agcaggggag tgcag 25

<210> SEQ ID NO 295
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 295
aaaagctcca gcaggggagt gcaga 25

<210> SEQ ID NO 296
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 296
aaagctccag caggggagtg cagag 25

<210> SEQ ID NO 297
<211> LENGTH: 25
<212> TYPE: DNA
<213> ORGANISM: Artificial Sequence
<220> FEATURE:
<223> OTHER INFORMATION: sequence of AON (5'-> 3')

<400> SEQUENCE: 297
aagctccagc aggggagtgc agagc 25

<210> SEQ ID NO 298
<211> LENGTH: 21
<212> TYPE: DNA
<213> ORGANISM: Artificial Sequence
<220> FEATURE:
<223> OTHER INFORMATION: sequence of AON (5'-> 3')

<400> SEQUENCE: 298
ccagaaggaa gggcgagaaa a 21

<210> SEQ ID NO 299
<211> LENGTH: 20
<212> TYPE: DNA
<213> ORGANISM: Artificial Sequence
<220> FEATURE:
<223> OTHER INFORMATION: AON

<400> SEQUENCE: 299
gagtgcagag cacttgcaca 20

<210> SEQ ID NO 300
<211> LENGTH: 20
<212> TYPE: DNA
<213> ORGANISM: Artificial Sequence
<220> FEATURE:
<223> OTHER INFORMATION: AON

<400> SEQUENCE: 300
cgagaaaagc tccagcaggg 20

<210> SEQ ID NO 301
<211> LENGTH: 20
<212> TYPE: DNA
<213> ORGANISM: Artificial Sequence
<220> FEATURE:
<223> OTHER INFORMATION: AON

<400> SEQUENCE: 301
gagagggcca gaaggaaggg 20

<210> SEQ ID NO 302
<211> LENGTH: 20
<212> TYPE: DNA
<213> ORGANISM: Artificial Sequence
<220> FEATURE:
<223> OTHER INFORMATION: AON

<400> SEQUENCE: 302
gccctgctgt ctagactggg 20

<210> SEQ ID NO 303
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 303
agagcacttg cacagtctgc 20

<210> SEQ ID NO 304
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 304
gcagagcact tgcacagtct 20

<210> SEQ ID NO 305
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 305
gtgcagagca cttgcacagt 20

<210> SEQ ID NO 306
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 306
gggagtgcag agcacttgca 20

<210> SEQ ID NO 307

-continued

<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 307
aggggagtgc agagcacttg 20

<210> SEQ ID NO 308
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 308
gcaggggagt gcagagcact 20

<210> SEQ ID NO 309
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 309
gccagaagga agggcgagaa 20

<210> SEQ ID NO 310
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 310
gggccagaag gaagggcgag 20

<210> SEQ ID NO 311
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 311
gagggccaga aggaagggcg 20

<210> SEQ ID NO 312
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 312
gggagagggc cagaaggaag 20

<210> SEQ ID NO 313
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 313
tggggagagg gccagaagga 20

<210> SEQ ID NO 314
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 314
actggggaga gggccagaag 20

<210> SEQ ID NO 315
<211> LENGTH: 25
<212> TYPE: DNA
<213> ORGANISM: Artificial Sequence
<220> FEATURE:
<223> OTHER INFORMATION: AON

<400> SEQUENCE: 315
gctccagcag gggagtgcag agcac 25

<210> SEQ ID NO 316
<211> LENGTH: 25
<212> TYPE: DNA
<213> ORGANISM: Artificial Sequence
<220> FEATURE:
<223> OTHER INFORMATION: AON

<400> SEQUENCE: 316
agctccagca ggggagtgca gagca 25

<210> SEQ ID NO 317
<211> LENGTH: 25
<212> TYPE: DNA
<213> ORGANISM: Artificial Sequence
<220> FEATURE:
<223> OTHER INFORMATION: AON

<400> SEQUENCE: 317
ctggggagag ggccagaagg aaggg 25

<210> SEQ ID NO 318
<211> LENGTH: 25
<212> TYPE: DNA
<213> ORGANISM: Artificial Sequence
<220> FEATURE:
<223> OTHER INFORMATION: AON

<400> SEQUENCE: 318
actggggaga gggccagaag gaagg 25

<210> SEQ ID NO 319
<211> LENGTH: 25
<212> TYPE: DNA
<213> ORGANISM: Artificial Sequence
<220> FEATURE:
<223> OTHER INFORMATION: AON

<400> SEQUENCE: 319
gactggggag agggccagaa ggaag 25

<210> SEQ ID NO 320
<211> LENGTH: 25
<212> TYPE: DNA

<213> ORGANISM: Artificial Sequence
<220> FEATURE:
<223> OTHER INFORMATION: AON

<400> SEQUENCE: 320
agactgggga gagggccaga aggaa 25

<210> SEQ ID NO 321
<211> LENGTH: 25
<212> TYPE: DNA
<213> ORGANISM: Artificial Sequence
<220> FEATURE:
<223> OTHER INFORMATION: AON

<400> SEQUENCE: 321
tagactgggg agagggccag aagga 25

<210> SEQ ID NO 322
<211> LENGTH: 25
<212> TYPE: DNA
<213> ORGANISM: Artificial Sequence
<220> FEATURE:
<223> OTHER INFORMATION: AON

<400> SEQUENCE: 322
ctagactggg gagagggcca gaagg 25

<210> SEQ ID NO 323
<211> LENGTH: 25
<212> TYPE: DNA
<213> ORGANISM: Artificial Sequence
<220> FEATURE:
<223> OTHER INFORMATION: AON

<400> SEQUENCE: 323
tctagactgg ggagagggcc agaag 25

<210> SEQ ID NO 324
<211> LENGTH: 25
<212> TYPE: DNA
<213> ORGANISM: Artificial Sequence
<220> FEATURE:
<223> OTHER INFORMATION: AON

<400> SEQUENCE: 324
gtctagactg gggagagggc cagaa 25

<210> SEQ ID NO 325
<211> LENGTH: 25
<212> TYPE: DNA
<213> ORGANISM: Artificial Sequence
<220> FEATURE:
<223> OTHER INFORMATION: AON

<400> SEQUENCE: 325
tgtctagact ggggagaggg ccaga 25

<210> SEQ ID NO 326
<211> LENGTH: 25
<212> TYPE: DNA
<213> ORGANISM: Artificial Sequence
<220> FEATURE:
<223> OTHER INFORMATION: AON

<400> SEQUENCE: 326
ctgtctagac tggggagagg gccag 25

<210> SEQ ID NO 327
<211> LENGTH: 25
<212> TYPE: DNA
<213> ORGANISM: Artificial Sequence
<220> FEATURE:
<223> OTHER INFORMATION: AON

<400> SEQUENCE: 327
gctgtctaga ctggggagag ggcca 25

<210> SEQ ID NO 328
<211> LENGTH: 25
<212> TYPE: DNA
<213> ORGANISM: Artificial Sequence
<220> FEATURE:
<223> OTHER INFORMATION: AON

<400> SEQUENCE: 328
tgctgtctag actggggaga gggcc 25

<210> SEQ ID NO 329
<211> LENGTH: 25
<212> TYPE: DNA
<213> ORGANISM: Artificial Sequence
<220> FEATURE:
<223> OTHER INFORMATION: AON

<400> SEQUENCE: 329
ctgctgtcta gactggggag agggc 25

<210> SEQ ID NO 330
<211> LENGTH: 25
<212> TYPE: DNA
<213> ORGANISM: Artificial Sequence
<220> FEATURE:
<223> OTHER INFORMATION: AON

<400> SEQUENCE: 330
cctgctgtct agactgggga gaggg 25

<210> SEQ ID NO 331
<211> LENGTH: 25
<212> TYPE: DNA
<213> ORGANISM: Artificial Sequence
<220> FEATURE:
<223> OTHER INFORMATION: AON

<400> SEQUENCE: 331
ccctgctgtc tagactgggg agagg 25

<210> SEQ ID NO 332
<211> LENGTH: 25
<212> TYPE: DNA
<213> ORGANISM: Artificial Sequence
<220> FEATURE:
<223> OTHER INFORMATION: AON

<400> SEQUENCE: 332
gccctgctgt ctagactggg gagag 25

<210> SEQ ID NO 333
<211> LENGTH: 25
<212> TYPE: DNA
<213> ORGANISM: Artificial Sequence
<220> FEATURE:

<223> OTHER INFORMATION: AON

<400> SEQUENCE: 333
tgccctgctg tctagactgg ggaga 25

<210> SEQ ID NO 334
<211> LENGTH: 25
<212> TYPE: DNA
<213> ORGANISM: Artificial Sequence
<220> FEATURE:
<223> OTHER INFORMATION: AON

<400> SEQUENCE: 334
ttgccctgct gtctagactg gggag 25

<210> SEQ ID NO 335
<211> LENGTH: 25
<212> TYPE: DNA
<213> ORGANISM: Artificial Sequence
<220> FEATURE:
<223> OTHER INFORMATION: AON

<400> SEQUENCE: 335
gttgccctgc tgtctagact gggga 25

<210> SEQ ID NO 336
<211> LENGTH: 25
<212> TYPE: DNA
<213> ORGANISM: Artificial Sequence
<220> FEATURE:
<223> OTHER INFORMATION: AON

<400> SEQUENCE: 336
tgttgccctg ctgtctagac tgggg 25

<210> SEQ ID NO 337
<211> LENGTH: 25
<212> TYPE: DNA
<213> ORGANISM: Artificial Sequence
<220> FEATURE:
<223> OTHER INFORMATION: AON

<400> SEQUENCE: 337
gtgttgccct gctgtctaga ctggg 25

<210> SEQ ID NO 338
<211> LENGTH: 25
<212> TYPE: DNA
<213> ORGANISM: Artificial Sequence
<220> FEATURE:
<223> OTHER INFORMATION: AON

<400> SEQUENCE: 338
ggtgttgccc tgctgtctag actgg 25

<210> SEQ ID NO 339
<211> LENGTH: 25
<212> TYPE: DNA
<213> ORGANISM: Artificial Sequence
<220> FEATURE:
<223> OTHER INFORMATION: AON

<400> SEQUENCE: 339
gggtgttgcc ctgctgtcta gactg 25

<210> SEQ ID NO 340
<211> LENGTH: 25
<212> TYPE: DNA
<213> ORGANISM: Artificial Sequence
<220> FEATURE:
<223> OTHER INFORMATION: AON

<400> SEQUENCE: 340
tgggtgttgc cctgctgtct agact 25

<210> SEQ ID NO 341
<211> LENGTH: 25
<212> TYPE: DNA
<213> ORGANISM: Artificial Sequence
<220> FEATURE:
<223> OTHER INFORMATION: AON

<400> SEQUENCE: 341
gtgggtgttg ccctgctgtc tagac 25

<210> SEQ ID NO 342
<211> LENGTH: 21
<212> TYPE: DNA
<213> ORGANISM: Artificial Sequence
<220> FEATURE:
<223> OTHER INFORMATION: AON

<400> SEQUENCE: 342
gctccagcag gggagtgcag a 21

<210> SEQ ID NO 343
<211> LENGTH: 21
<212> TYPE: DNA
<213> ORGANISM: Artificial Sequence
<220> FEATURE:
<223> OTHER INFORMATION: AON

<400> SEQUENCE: 343
agctccagca ggggagtgca g 21

<210> SEQ ID NO 344
<211> LENGTH: 21
<212> TYPE: DNA
<213> ORGANISM: Artificial Sequence
<220> FEATURE:
<223> OTHER INFORMATION: AON

<400> SEQUENCE: 344
aagctccagc aggggagtgc a 21

<210> SEQ ID NO 345
<211> LENGTH: 21
<212> TYPE: DNA
<213> ORGANISM: Artificial Sequence
<220> FEATURE:
<223> OTHER INFORMATION: AON

<400> SEQUENCE: 345
aaagctccag caggggagtg c 21

<210> SEQ ID NO 346
<211> LENGTH: 21
<212> TYPE: DNA
<213> ORGANISM: Artificial Sequence
<220> FEATURE:
<223> OTHER INFORMATION: AON

<400> SEQUENCE: 346
aaaagctcca gcaggggagt g 21

<210> SEQ ID NO 347
<211> LENGTH: 21
<212> TYPE: DNA
<213> ORGANISM: Artificial Sequence
<220> FEATURE:
<223> OTHER INFORMATION: AON

<400> SEQUENCE: 347
gaaaagctcc agcaggggag t 21

<210> SEQ ID NO 348
<211> LENGTH: 21
<212> TYPE: DNA
<213> ORGANISM: Artificial Sequence
<220> FEATURE:
<223> OTHER INFORMATION: AON

<400> SEQUENCE: 348
agaaaagctc cagcagggga g 21

<210> SEQ ID NO 349
<211> LENGTH: 21
<212> TYPE: DNA
<213> ORGANISM: Artificial Sequence
<220> FEATURE:
<223> OTHER INFORMATION: AON

<400> SEQUENCE: 349
gagaaaagct ccagcagggg a 21

<210> SEQ ID NO 350
<211> LENGTH: 21
<212> TYPE: DNA
<213> ORGANISM: Artificial Sequence
<220> FEATURE:
<223> OTHER INFORMATION: AON

<400> SEQUENCE: 350
cgagaaaagc tccagcaggg g 21

<210> SEQ ID NO 351
<211> LENGTH: 21
<212> TYPE: DNA
<213> ORGANISM: Artificial Sequence
<220> FEATURE:
<223> OTHER INFORMATION: AON

<400> SEQUENCE: 351
gcgagaaaag ctccagcagg g 21

<210> SEQ ID NO 352
<211> LENGTH: 21
<212> TYPE: DNA
<213> ORGANISM: Artificial Sequence
<220> FEATURE:
<223> OTHER INFORMATION: AON

<400> SEQUENCE: 352
ggcgagaaaa gctccagcag g 21

<210> SEQ ID NO 353
<211> LENGTH: 21

<212> TYPE: DNA
<213> ORGANISM: Artificial Sequence
<220> FEATURE:
<223> OTHER INFORMATION: AON

<400> SEQUENCE: 353
gggcgagaaa agctccagca g 21

<210> SEQ ID NO 354
<211> LENGTH: 21
<212> TYPE: DNA
<213> ORGANISM: Artificial Sequence
<220> FEATURE:
<223> OTHER INFORMATION: AON

<400> SEQUENCE: 354
agggcgagaa aagctccagc a 21

<210> SEQ ID NO 355
<211> LENGTH: 21
<212> TYPE: DNA
<213> ORGANISM: Artificial Sequence
<220> FEATURE:
<223> OTHER INFORMATION: AON

<400> SEQUENCE: 355
aagggcgaga aaagctccag c 21

<210> SEQ ID NO 356
<211> LENGTH: 21
<212> TYPE: DNA
<213> ORGANISM: Artificial Sequence
<220> FEATURE:
<223> OTHER INFORMATION: AON

<400> SEQUENCE: 356
gaagggcgag aaaagctcca g 21

<210> SEQ ID NO 357
<211> LENGTH: 21
<212> TYPE: DNA
<213> ORGANISM: Artificial Sequence
<220> FEATURE:
<223> OTHER INFORMATION: AON

<400> SEQUENCE: 357
ggaagggcga gaaaagctcc a 21

<210> SEQ ID NO 358
<211> LENGTH: 21
<212> TYPE: DNA
<213> ORGANISM: Artificial Sequence
<220> FEATURE:
<223> OTHER INFORMATION: AON

<400> SEQUENCE: 358
aggaagggcg agaaaagctc c 21

<210> SEQ ID NO 359
<211> LENGTH: 21
<212> TYPE: DNA
<213> ORGANISM: Artificial Sequence
<220> FEATURE:
<223> OTHER INFORMATION: AON

<400> SEQUENCE: 359
aaggaagggc gagaaaagct c 21

<210> SEQ ID NO 360
<211> LENGTH: 21
<212> TYPE: DNA
<213> ORGANISM: Artificial Sequence
<220> FEATURE:
<223> OTHER INFORMATION: AON

<400> SEQUENCE: 360
gaaggaaggg cgagaaaagc t 21

<210> SEQ ID NO 361
<211> LENGTH: 21
<212> TYPE: DNA
<213> ORGANISM: Artificial Sequence
<220> FEATURE:
<223> OTHER INFORMATION: AON

<400> SEQUENCE: 361
agaaggaagg gcgagaaaag c 21

<210> SEQ ID NO 362
<211> LENGTH: 21
<212> TYPE: DNA
<213> ORGANISM: Artificial Sequence
<220> FEATURE:
<223> OTHER INFORMATION: AON

<400> SEQUENCE: 362
cagaaggaag ggcgagaaaa g 21

<210> SEQ ID NO 363
<211> LENGTH: 21
<212> TYPE: DNA
<213> ORGANISM: Artificial Sequence
<220> FEATURE:
<223> OTHER INFORMATION: AON

<400> SEQUENCE: 363
gccagaagga agggcgagaa a 21

<210> SEQ ID NO 364
<211> LENGTH: 21
<212> TYPE: DNA
<213> ORGANISM: Artificial Sequence
<220> FEATURE:
<223> OTHER INFORMATION: AON

<400> SEQUENCE: 364
ggccagaagg aagggcgaga a 21

<210> SEQ ID NO 365
<211> LENGTH: 21
<212> TYPE: DNA
<213> ORGANISM: Artificial Sequence
<220> FEATURE:
<223> OTHER INFORMATION: AON

<400> SEQUENCE: 365
gggccagaag gaagggcgag a 21

<210> SEQ ID NO 366
<211> LENGTH: 21
<212> TYPE: DNA
<213> ORGANISM: Artificial Sequence

<220> FEATURE:
<223> OTHER INFORMATION: AON

<400> SEQUENCE: 366
agggccagaa ggaagggcga g 21

<210> SEQ ID NO 367
<211> LENGTH: 21
<212> TYPE: DNA
<213> ORGANISM: Artificial Sequence
<220> FEATURE:
<223> OTHER INFORMATION: AON

<400> SEQUENCE: 367
gagggccaga aggaagggcg a 21

<210> SEQ ID NO 368
<211> LENGTH: 21
<212> TYPE: DNA
<213> ORGANISM: Artificial Sequence
<220> FEATURE:
<223> OTHER INFORMATION: AON

<400> SEQUENCE: 368
agagggccag aaggaagggc g 21

<210> SEQ ID NO 369
<211> LENGTH: 21
<212> TYPE: DNA
<213> ORGANISM: Artificial Sequence
<220> FEATURE:
<223> OTHER INFORMATION: AON

<400> SEQUENCE: 369
gagagggcca gaaggaaggg c 21

<210> SEQ ID NO 370
<211> LENGTH: 21
<212> TYPE: DNA
<213> ORGANISM: Artificial Sequence
<220> FEATURE:
<223> OTHER INFORMATION: AON

<400> SEQUENCE: 370
ggagagggcc agaaggaagg g 21

<210> SEQ ID NO 371
<211> LENGTH: 21
<212> TYPE: DNA
<213> ORGANISM: Artificial Sequence
<220> FEATURE:
<223> OTHER INFORMATION: AON

<400> SEQUENCE: 371
gggagagggc cagaaggaag g 21

<210> SEQ ID NO 372
<211> LENGTH: 21
<212> TYPE: DNA
<213> ORGANISM: Artificial Sequence
<220> FEATURE:
<223> OTHER INFORMATION: AON

<400> SEQUENCE: 372
ggggagaggg ccagaaggaa g 21

<210> SEQ ID NO 373
<211> LENGTH: 21
<212> TYPE: DNA
<213> ORGANISM: Artificial Sequence
<220> FEATURE:
<223> OTHER INFORMATION: AON

<400> SEQUENCE: 373
tggggagagg gccagaagga a 21

<210> SEQ ID NO 374
<211> LENGTH: 21
<212> TYPE: DNA
<213> ORGANISM: Artificial Sequence
<220> FEATURE:
<223> OTHER INFORMATION: AON

<400> SEQUENCE: 374
ctggggagag ggccagaagg a 21

<210> SEQ ID NO 375
<211> LENGTH: 21
<212> TYPE: DNA
<213> ORGANISM: Artificial Sequence
<220> FEATURE:
<223> OTHER INFORMATION: AON

<400> SEQUENCE: 375
actggggaga gggccagaag g 21

<210> SEQ ID NO 376
<211> LENGTH: 21
<212> TYPE: DNA
<213> ORGANISM: Artificial Sequence
<220> FEATURE:
<223> OTHER INFORMATION: AON

<400> SEQUENCE: 376
gactggggag agggccagaa g 21

<210> SEQ ID NO 377
<211> LENGTH: 21
<212> TYPE: DNA
<213> ORGANISM: Artificial Sequence
<220> FEATURE:
<223> OTHER INFORMATION: AON

<400> SEQUENCE: 377
agactgggga gagggccaga a 21

<210> SEQ ID NO 378
<211> LENGTH: 21
<212> TYPE: DNA
<213> ORGANISM: Artificial Sequence
<220> FEATURE:
<223> OTHER INFORMATION: AON

<400> SEQUENCE: 378
tagactgggg agagggccag a 21

<210> SEQ ID NO 379
<211> LENGTH: 21
<212> TYPE: DNA
<213> ORGANISM: Artificial Sequence
<220> FEATURE:
<223> OTHER INFORMATION: AON

<400> SEQUENCE: 379
ctagactggg gagagggcca g 21

<210> SEQ ID NO 380
<211> LENGTH: 21
<212> TYPE: DNA
<213> ORGANISM: Artificial Sequence
<220> FEATURE:
<223> OTHER INFORMATION: AON

<400> SEQUENCE: 380
tctagactgg ggagagggcc a 21

<210> SEQ ID NO 381
<211> LENGTH: 21
<212> TYPE: DNA
<213> ORGANISM: Artificial Sequence
<220> FEATURE:
<223> OTHER INFORMATION: AON

<400> SEQUENCE: 381
gtctagactg gggagagggc c 21

<210> SEQ ID NO 382
<211> LENGTH: 21
<212> TYPE: DNA
<213> ORGANISM: Artificial Sequence
<220> FEATURE:
<223> OTHER INFORMATION: AON

<400> SEQUENCE: 382
tgtctagact ggggagaggg c 21

<210> SEQ ID NO 383
<211> LENGTH: 21
<212> TYPE: DNA
<213> ORGANISM: Artificial Sequence
<220> FEATURE:
<223> OTHER INFORMATION: AON

<400> SEQUENCE: 383
ctgtctagac tggggagagg g 21

<210> SEQ ID NO 384
<211> LENGTH: 21
<212> TYPE: DNA
<213> ORGANISM: Artificial Sequence
<220> FEATURE:
<223> OTHER INFORMATION: AON

<400> SEQUENCE: 384
gctgtctaga ctggggagag g 21

<210> SEQ ID NO 385
<211> LENGTH: 21
<212> TYPE: DNA
<213> ORGANISM: Artificial Sequence
<220> FEATURE:
<223> OTHER INFORMATION: AON

<400> SEQUENCE: 385
tgctgtctag actggggaga g 21

<210> SEQ ID NO 386

<211> LENGTH: 21
<212> TYPE: DNA
<213> ORGANISM: Artificial Sequence
<220> FEATURE:
<223> OTHER INFORMATION: AON

<400> SEQUENCE: 386
ctgctgtcta gactggggag a 21

<210> SEQ ID NO 387
<211> LENGTH: 21
<212> TYPE: DNA
<213> ORGANISM: Artificial Sequence
<220> FEATURE:
<223> OTHER INFORMATION: AON

<400> SEQUENCE: 387
cctgctgtct agactgggga g 21

<210> SEQ ID NO 388
<211> LENGTH: 21
<212> TYPE: DNA
<213> ORGANISM: Artificial Sequence
<220> FEATURE:
<223> OTHER INFORMATION: AON

<400> SEQUENCE: 388
ccctgctgtc tagactgggg a 21

<210> SEQ ID NO 389
<211> LENGTH: 21
<212> TYPE: DNA
<213> ORGANISM: Artificial Sequence
<220> FEATURE:
<223> OTHER INFORMATION: AON

<400> SEQUENCE: 389
gccctgctgt ctagactggg g 21

<210> SEQ ID NO 390
<211> LENGTH: 21
<212> TYPE: DNA
<213> ORGANISM: Artificial Sequence
<220> FEATURE:
<223> OTHER INFORMATION: AON

<400> SEQUENCE: 390
tgccctgctg tctagactgg g 21

<210> SEQ ID NO 391
<211> LENGTH: 21
<212> TYPE: DNA
<213> ORGANISM: Artificial Sequence
<220> FEATURE:
<223> OTHER INFORMATION: AON

<400> SEQUENCE: 391
ttgccctgct gtctagactg g 21

<210> SEQ ID NO 392
<211> LENGTH: 21
<212> TYPE: DNA
<213> ORGANISM: Artificial Sequence
<220> FEATURE:
<223> OTHER INFORMATION: AON

<400> SEQUENCE: 392
gttgccctgc tgtctagact g 21

<210> SEQ ID NO 393
<211> LENGTH: 21
<212> TYPE: DNA
<213> ORGANISM: Artificial Sequence
<220> FEATURE:
<223> OTHER INFORMATION: AON

<400> SEQUENCE: 393
tgttgccctg ctgtctagac t 21

<210> SEQ ID NO 394
<211> LENGTH: 21
<212> TYPE: DNA
<213> ORGANISM: Artificial Sequence
<220> FEATURE:
<223> OTHER INFORMATION: AON

<400> SEQUENCE: 394
gtgttgccct gctgtctaga c 21

<210> SEQ ID NO 395
<211> LENGTH: 18
<212> TYPE: DNA
<213> ORGANISM: Artificial Sequence
<220> FEATURE:
<223> OTHER INFORMATION: AON

<400> SEQUENCE: 395
gctccagcag gggagtgc 18

<210> SEQ ID NO 396
<211> LENGTH: 18
<212> TYPE: DNA
<213> ORGANISM: Artificial Sequence
<220> FEATURE:
<223> OTHER INFORMATION: AON

<400> SEQUENCE: 396
agctccagca ggggagtg 18

<210> SEQ ID NO 397
<211> LENGTH: 18
<212> TYPE: DNA
<213> ORGANISM: Artificial Sequence
<220> FEATURE:
<223> OTHER INFORMATION: AON

<400> SEQUENCE: 397
aagctccagc aggggagt 18

<210> SEQ ID NO 398
<211> LENGTH: 18
<212> TYPE: DNA
<213> ORGANISM: Artificial Sequence
<220> FEATURE:
<223> OTHER INFORMATION: AON

<400> SEQUENCE: 398
aaagctccag caggggag 18

<210> SEQ ID NO 399
<211> LENGTH: 18
<212> TYPE: DNA

<213> ORGANISM: Artificial Sequence
<220> FEATURE:
<223> OTHER INFORMATION: AON

<400> SEQUENCE: 399
aaaagctcca gcagggga 18

<210> SEQ ID NO 400
<211> LENGTH: 18
<212> TYPE: DNA
<213> ORGANISM: Artificial Sequence
<220> FEATURE:
<223> OTHER INFORMATION: AON

<400> SEQUENCE: 400
gaaaagctcc agcagggg 18

<210> SEQ ID NO 401
<211> LENGTH: 18
<212> TYPE: DNA
<213> ORGANISM: Artificial Sequence
<220> FEATURE:
<223> OTHER INFORMATION: AON

<400> SEQUENCE: 401
agaaaagctc cagcaggg 18

<210> SEQ ID NO 402
<211> LENGTH: 18
<212> TYPE: DNA
<213> ORGANISM: Artificial Sequence
<220> FEATURE:
<223> OTHER INFORMATION: AON

<400> SEQUENCE: 402
gagaaaagct ccagcagg 18

<210> SEQ ID NO 403
<211> LENGTH: 18
<212> TYPE: DNA
<213> ORGANISM: Artificial Sequence
<220> FEATURE:
<223> OTHER INFORMATION: AON

<400> SEQUENCE: 403
cgagaaaagc tccagcag 18

<210> SEQ ID NO 404
<211> LENGTH: 18
<212> TYPE: DNA
<213> ORGANISM: Artificial Sequence
<220> FEATURE:
<223> OTHER INFORMATION: AON

<400> SEQUENCE: 404
gcgagaaaag ctccagca 18

<210> SEQ ID NO 405
<211> LENGTH: 18
<212> TYPE: DNA
<213> ORGANISM: Artificial Sequence
<220> FEATURE:
<223> OTHER INFORMATION: AON

<400> SEQUENCE: 405
ggcgagaaaa gctccagc 18

<210> SEQ ID NO 406
<211> LENGTH: 18
<212> TYPE: DNA
<213> ORGANISM: Artificial Sequence
<220> FEATURE:
<223> OTHER INFORMATION: AON

<400> SEQUENCE: 406
gggcgagaaa agctccag 18

<210> SEQ ID NO 407
<211> LENGTH: 18
<212> TYPE: DNA
<213> ORGANISM: Artificial Sequence
<220> FEATURE:
<223> OTHER INFORMATION: AON

<400> SEQUENCE: 407
agggcgagaa aagctcca 18

<210> SEQ ID NO 408
<211> LENGTH: 18
<212> TYPE: DNA
<213> ORGANISM: Artificial Sequence
<220> FEATURE:
<223> OTHER INFORMATION: AON

<400> SEQUENCE: 408
aagggcgaga aaagctcc 18

<210> SEQ ID NO 409
<211> LENGTH: 18
<212> TYPE: DNA
<213> ORGANISM: Artificial Sequence
<220> FEATURE:
<223> OTHER INFORMATION: AON

<400> SEQUENCE: 409
gaagggcgag aaaagctc 18

<210> SEQ ID NO 410
<211> LENGTH: 18
<212> TYPE: DNA
<213> ORGANISM: Artificial Sequence
<220> FEATURE:
<223> OTHER INFORMATION: AON

<400> SEQUENCE: 410
ggaagggcga gaaaagct 18

<210> SEQ ID NO 411
<211> LENGTH: 18
<212> TYPE: DNA
<213> ORGANISM: Artificial Sequence
<220> FEATURE:
<223> OTHER INFORMATION: AON

<400> SEQUENCE: 411
aggaagggcg agaaaagc 18

<210> SEQ ID NO 412
<211> LENGTH: 18
<212> TYPE: DNA
<213> ORGANISM: Artificial Sequence
<220> FEATURE:

<223> OTHER INFORMATION: AON

<400> SEQUENCE: 412
aaggaagggc gagaaaag 18

<210> SEQ ID NO 413
<211> LENGTH: 18
<212> TYPE: DNA
<213> ORGANISM: Artificial Sequence
<220> FEATURE:
<223> OTHER INFORMATION: AON

<400> SEQUENCE: 413
gaaggaaggg cgagaaaa 18

<210> SEQ ID NO 414
<211> LENGTH: 18
<212> TYPE: DNA
<213> ORGANISM: Artificial Sequence
<220> FEATURE:
<223> OTHER INFORMATION: AON

<400> SEQUENCE: 414
agaaggaagg gcgagaaa 18

<210> SEQ ID NO 415
<211> LENGTH: 18
<212> TYPE: DNA
<213> ORGANISM: Artificial Sequence
<220> FEATURE:
<223> OTHER INFORMATION: AON

<400> SEQUENCE: 415
cagaaggaag ggcgagaa 18

<210> SEQ ID NO 416
<211> LENGTH: 18
<212> TYPE: DNA
<213> ORGANISM: Artificial Sequence
<220> FEATURE:
<223> OTHER INFORMATION: AON

<400> SEQUENCE: 416
ccagaaggaa gggcgaga 18

<210> SEQ ID NO 417
<211> LENGTH: 18
<212> TYPE: DNA
<213> ORGANISM: Artificial Sequence
<220> FEATURE:
<223> OTHER INFORMATION: AON

<400> SEQUENCE: 417
gccagaagga agggcgag 18

<210> SEQ ID NO 418
<211> LENGTH: 18
<212> TYPE: DNA
<213> ORGANISM: Artificial Sequence
<220> FEATURE:
<223> OTHER INFORMATION: AON

<400> SEQUENCE: 418
ggccagaagg aagggcga 18

<210> SEQ ID NO 419
<211> LENGTH: 18
<212> TYPE: DNA
<213> ORGANISM: Artificial Sequence
<220> FEATURE:
<223> OTHER INFORMATION: AON

<400> SEQUENCE: 419
gggccagaag gaagggcg 18

<210> SEQ ID NO 420
<211> LENGTH: 18
<212> TYPE: DNA
<213> ORGANISM: Artificial Sequence
<220> FEATURE:
<223> OTHER INFORMATION: AON

<400> SEQUENCE: 420
agggccagaa ggaagggc 18

<210> SEQ ID NO 421
<211> LENGTH: 18
<212> TYPE: DNA
<213> ORGANISM: Artificial Sequence
<220> FEATURE:
<223> OTHER INFORMATION: AON

<400> SEQUENCE: 421
gagggccaga aggaaggg 18

<210> SEQ ID NO 422
<211> LENGTH: 18
<212> TYPE: DNA
<213> ORGANISM: Artificial Sequence
<220> FEATURE:
<223> OTHER INFORMATION: AON

<400> SEQUENCE: 422
agagggccag aaggaagg 18

<210> SEQ ID NO 423
<211> LENGTH: 18
<212> TYPE: DNA
<213> ORGANISM: Artificial Sequence
<220> FEATURE:
<223> OTHER INFORMATION: AON

<400> SEQUENCE: 423
gagagggcca gaaggaag 18

<210> SEQ ID NO 424
<211> LENGTH: 18
<212> TYPE: DNA
<213> ORGANISM: Artificial Sequence
<220> FEATURE:
<223> OTHER INFORMATION: AON

<400> SEQUENCE: 424
ggagagggcc agaaggaa 18

<210> SEQ ID NO 425
<211> LENGTH: 18
<212> TYPE: DNA
<213> ORGANISM: Artificial Sequence
<220> FEATURE:
<223> OTHER INFORMATION: AON

<400> SEQUENCE: 425
gggagagggc cagaagga 18

<210> SEQ ID NO 426
<211> LENGTH: 18
<212> TYPE: DNA
<213> ORGANISM: Artificial Sequence
<220> FEATURE:
<223> OTHER INFORMATION: AON

<400> SEQUENCE: 426
ggggagaggg ccagaagg 18

<210> SEQ ID NO 427
<211> LENGTH: 18
<212> TYPE: DNA
<213> ORGANISM: Artificial Sequence
<220> FEATURE:
<223> OTHER INFORMATION: AON

<400> SEQUENCE: 427
tggggagagg gccagaag 18

<210> SEQ ID NO 428
<211> LENGTH: 18
<212> TYPE: DNA
<213> ORGANISM: Artificial Sequence
<220> FEATURE:
<223> OTHER INFORMATION: AON

<400> SEQUENCE: 428
ctggggagag ggccagaa 18

<210> SEQ ID NO 429
<211> LENGTH: 18
<212> TYPE: DNA
<213> ORGANISM: Artificial Sequence
<220> FEATURE:
<223> OTHER INFORMATION: AON

<400> SEQUENCE: 429
actggggaga gggccaga 18

<210> SEQ ID NO 430
<211> LENGTH: 18
<212> TYPE: DNA
<213> ORGANISM: Artificial Sequence
<220> FEATURE:
<223> OTHER INFORMATION: AON

<400> SEQUENCE: 430
gactggggag agggccag 18

<210> SEQ ID NO 431
<211> LENGTH: 18
<212> TYPE: DNA
<213> ORGANISM: Artificial Sequence
<220> FEATURE:
<223> OTHER INFORMATION: AON

<400> SEQUENCE: 431
agactgggga gagggcca 18

<210> SEQ ID NO 432
<211> LENGTH: 18

<212> TYPE: DNA
<213> ORGANISM: Artificial Sequence
<220> FEATURE:
<223> OTHER INFORMATION: AON

<400> SEQUENCE: 432
tagactgggg agagggcc 18

<210> SEQ ID NO 433
<211> LENGTH: 18
<212> TYPE: DNA
<213> ORGANISM: Artificial Sequence
<220> FEATURE:
<223> OTHER INFORMATION: AON

<400> SEQUENCE: 433
ctagactggg gagagggc 18

<210> SEQ ID NO 434
<211> LENGTH: 18
<212> TYPE: DNA
<213> ORGANISM: Artificial Sequence
<220> FEATURE:
<223> OTHER INFORMATION: AON

<400> SEQUENCE: 434
tctagactgg ggagaggg 18

<210> SEQ ID NO 435
<211> LENGTH: 18
<212> TYPE: DNA
<213> ORGANISM: Artificial Sequence
<220> FEATURE:
<223> OTHER INFORMATION: AON

<400> SEQUENCE: 435
gtctagactg gggagagg 18

<210> SEQ ID NO 436
<211> LENGTH: 18
<212> TYPE: DNA
<213> ORGANISM: Artificial Sequence
<220> FEATURE:
<223> OTHER INFORMATION: AON

<400> SEQUENCE: 436
tgtctagact ggggagag 18

<210> SEQ ID NO 437
<211> LENGTH: 18
<212> TYPE: DNA
<213> ORGANISM: Artificial Sequence
<220> FEATURE:
<223> OTHER INFORMATION: AON

<400> SEQUENCE: 437
ctgtctagac tggggaga 18

<210> SEQ ID NO 438
<211> LENGTH: 18
<212> TYPE: DNA
<213> ORGANISM: Artificial Sequence
<220> FEATURE:
<223> OTHER INFORMATION: AON

<400> SEQUENCE: 438
gctgtctaga ctggggag 18

<210> SEQ ID NO 439
<211> LENGTH: 18
<212> TYPE: DNA
<213> ORGANISM: Artificial Sequence
<220> FEATURE:
<223> OTHER INFORMATION: AON

<400> SEQUENCE: 439
tgctgtctag actgggga 18

<210> SEQ ID NO 440
<211> LENGTH: 18
<212> TYPE: DNA
<213> ORGANISM: Artificial Sequence
<220> FEATURE:
<223> OTHER INFORMATION: AON

<400> SEQUENCE: 440
ctgctgtcta gactgggg 18

<210> SEQ ID NO 441
<211> LENGTH: 18
<212> TYPE: DNA
<213> ORGANISM: Artificial Sequence
<220> FEATURE:
<223> OTHER INFORMATION: AON

<400> SEQUENCE: 441
cctgctgtct agactggg 18

<210> SEQ ID NO 442
<211> LENGTH: 18
<212> TYPE: DNA
<213> ORGANISM: Artificial Sequence
<220> FEATURE:
<223> OTHER INFORMATION: AON

<400> SEQUENCE: 442
ccctgctgtc tagactgg 18

<210> SEQ ID NO 443
<211> LENGTH: 18
<212> TYPE: DNA
<213> ORGANISM: Artificial Sequence
<220> FEATURE:
<223> OTHER INFORMATION: AON

<400> SEQUENCE: 443
gccctgctgt ctagactg 18

<210> SEQ ID NO 444
<211> LENGTH: 18
<212> TYPE: DNA
<213> ORGANISM: Artificial Sequence
<220> FEATURE:
<223> OTHER INFORMATION: AON

<400> SEQUENCE: 444
tgccctgctg tctagact 18

<210> SEQ ID NO 445
<211> LENGTH: 18
<212> TYPE: DNA
<213> ORGANISM: Artificial Sequence

<220> FEATURE:
<223> OTHER INFORMATION: AON

<400> SEQUENCE: 445
ttgccctgct gtctagac 18

<210> SEQ ID NO 446
<211> LENGTH: 20
<212> TYPE: DNA
<213> ORGANISM: Artificial Sequence
<220> FEATURE:
<223> OTHER INFORMATION: AON

<400> SEQUENCE: 446
tcaaagcagc tctgagacat 20

<210> SEQ ID NO 447
<211> LENGTH: 20
<212> TYPE: DNA
<213> ORGANISM: Artificial Sequence
<220> FEATURE:
<223> OTHER INFORMATION: AON

<400> SEQUENCE: 447
gggcggcact cacggggctc 20

<210> SEQ ID NO 448
<211> LENGTH: 20
<212> TYPE: DNA
<213> ORGANISM: Artificial Sequence
<220> FEATURE:
<223> OTHER INFORMATION: AON

<400> SEQUENCE: 448
gctcagcagg gaggcgggag 20

<210> SEQ ID NO 449
<211> LENGTH: 21
<212> TYPE: DNA
<213> ORGANISM: Artificial Sequence
<220> FEATURE:
<223> OTHER INFORMATION: AON

<400> SEQUENCE: 449
ctctcaaagc agctctgaga c 21

<210> SEQ ID NO 450
<211> LENGTH: 21
<212> TYPE: DNA
<213> ORGANISM: Artificial Sequence
<220> FEATURE:
<223> OTHER INFORMATION: AON

<400> SEQUENCE: 450
gctctcaaag cagctctgag a 21

<210> SEQ ID NO 451
<211> LENGTH: 21
<212> TYPE: DNA
<213> ORGANISM: Artificial Sequence
<220> FEATURE:
<223> OTHER INFORMATION: AON

<400> SEQUENCE: 451
ggctctcaaa gcagctctga g 21

<210> SEQ ID NO 452
<211> LENGTH: 21
<212> TYPE: DNA
<213> ORGANISM: Artificial Sequence
<220> FEATURE:
<223> OTHER INFORMATION: AON

<400> SEQUENCE: 452
gggctctcaa agcagctctg a 21

<210> SEQ ID NO 453
<211> LENGTH: 21
<212> TYPE: DNA
<213> ORGANISM: Artificial Sequence
<220> FEATURE:
<223> OTHER INFORMATION: AON

<400> SEQUENCE: 453
ggggctctca aagcagctct g 21

<210> SEQ ID NO 454
<211> LENGTH: 21
<212> TYPE: DNA
<213> ORGANISM: Artificial Sequence
<220> FEATURE:
<223> OTHER INFORMATION: AON

<400> SEQUENCE: 454
cggggctctc aaagcagctc t 21

<210> SEQ ID NO 455
<211> LENGTH: 21
<212> TYPE: DNA
<213> ORGANISM: Artificial Sequence
<220> FEATURE:
<223> OTHER INFORMATION: AON

<400> SEQUENCE: 455
acggggctct caaagcagct c 21

<210> SEQ ID NO 456
<211> LENGTH: 21
<212> TYPE: DNA
<213> ORGANISM: Artificial Sequence
<220> FEATURE:
<223> OTHER INFORMATION: AON

<400> SEQUENCE: 456
cacggggctc tcaaagcagc t 21

<210> SEQ ID NO 457
<211> LENGTH: 21
<212> TYPE: DNA
<213> ORGANISM: Artificial Sequence
<220> FEATURE:
<223> OTHER INFORMATION: AON

<400> SEQUENCE: 457
tcacggggct ctcaaagcag c 21

<210> SEQ ID NO 458
<211> LENGTH: 21
<212> TYPE: DNA
<213> ORGANISM: Artificial Sequence
<220> FEATURE:
<223> OTHER INFORMATION: AON

<400> SEQUENCE: 458
ctcacggggc tctcaaagca g 21

<210> SEQ ID NO 459
<211> LENGTH: 21
<212> TYPE: DNA
<213> ORGANISM: Artificial Sequence
<220> FEATURE:
<223> OTHER INFORMATION: AON

<400> SEQUENCE: 459
actcacgggg ctctcaaagc a 21

<210> SEQ ID NO 460
<211> LENGTH: 21
<212> TYPE: DNA
<213> ORGANISM: Artificial Sequence
<220> FEATURE:
<223> OTHER INFORMATION: AON

<400> SEQUENCE: 460
cactcacggg gctctcaaag c 21

<210> SEQ ID NO 461
<211> LENGTH: 21
<212> TYPE: DNA
<213> ORGANISM: Artificial Sequence
<220> FEATURE:
<223> OTHER INFORMATION: AON

<400> SEQUENCE: 461
gcactcacgg ggctctcaaa g 21

<210> SEQ ID NO 462
<211> LENGTH: 21
<212> TYPE: DNA
<213> ORGANISM: Artificial Sequence
<220> FEATURE:
<223> OTHER INFORMATION: AON

<400> SEQUENCE: 462
ggcactcacg gggctctcaa a 21

<210> SEQ ID NO 463
<211> LENGTH: 21
<212> TYPE: DNA
<213> ORGANISM: Artificial Sequence
<220> FEATURE:
<223> OTHER INFORMATION: AON

<400> SEQUENCE: 463
cggcactcac ggggctctca a 21

<210> SEQ ID NO 464
<211> LENGTH: 21
<212> TYPE: DNA
<213> ORGANISM: Artificial Sequence
<220> FEATURE:
<223> OTHER INFORMATION: AON

<400> SEQUENCE: 464
gcggcactca cggggctctc a 21

<210> SEQ ID NO 465

<211> LENGTH: 21
<212> TYPE: DNA
<213> ORGANISM: Artificial Sequence
<220> FEATURE:
<223> OTHER INFORMATION: AON

<400> SEQUENCE: 465
ggcggcactc acggggctct c 21

<210> SEQ ID NO 466
<211> LENGTH: 21
<212> TYPE: DNA
<213> ORGANISM: Artificial Sequence
<220> FEATURE:
<223> OTHER INFORMATION: AON

<400> SEQUENCE: 466
gggcggcact cacggggctc t 21

<210> SEQ ID NO 467
<211> LENGTH: 21
<212> TYPE: DNA
<213> ORGANISM: Artificial Sequence
<220> FEATURE:
<223> OTHER INFORMATION: AON

<400> SEQUENCE: 467
ggggcggcac tcacggggct c 21

<210> SEQ ID NO 468
<211> LENGTH: 21
<212> TYPE: DNA
<213> ORGANISM: Artificial Sequence
<220> FEATURE:
<223> OTHER INFORMATION: AON

<400> SEQUENCE: 468
aggggcggca ctcacggggc t 21

<210> SEQ ID NO 469
<211> LENGTH: 21
<212> TYPE: DNA
<213> ORGANISM: Artificial Sequence
<220> FEATURE:
<223> OTHER INFORMATION: AON

<400> SEQUENCE: 469
gaggggcggc actcacgggg c 21

<210> SEQ ID NO 470
<211> LENGTH: 21
<212> TYPE: DNA
<213> ORGANISM: Artificial Sequence
<220> FEATURE:
<223> OTHER INFORMATION: AON

<400> SEQUENCE: 470
ggaggggcgg cactcacggg g 21

<210> SEQ ID NO 471
<211> LENGTH: 21
<212> TYPE: DNA
<213> ORGANISM: Artificial Sequence
<220> FEATURE:
<223> OTHER INFORMATION: AON

<400> SEQUENCE: 471
gggaggggcg gcactcacgg g 21

<210> SEQ ID NO 472
<211> LENGTH: 21
<212> TYPE: DNA
<213> ORGANISM: Artificial Sequence
<220> FEATURE:
<223> OTHER INFORMATION: AON

<400> SEQUENCE: 472
cgggaggggc ggcactcacg g 21

<210> SEQ ID NO 473
<211> LENGTH: 21
<212> TYPE: DNA
<213> ORGANISM: Artificial Sequence
<220> FEATURE:
<223> OTHER INFORMATION: AON

<400> SEQUENCE: 473
gcgggagggg cggcactcac g 21

<210> SEQ ID NO 474
<211> LENGTH: 21
<212> TYPE: DNA
<213> ORGANISM: Artificial Sequence
<220> FEATURE:
<223> OTHER INFORMATION: AON

<400> SEQUENCE: 474
ggcgggaggg gcggcactca c 21

<210> SEQ ID NO 475
<211> LENGTH: 21
<212> TYPE: DNA
<213> ORGANISM: Artificial Sequence
<220> FEATURE:
<223> OTHER INFORMATION: AON

<400> SEQUENCE: 475
aggcgggagg ggcggcactc a 21

<210> SEQ ID NO 476
<211> LENGTH: 21
<212> TYPE: DNA
<213> ORGANISM: Artificial Sequence
<220> FEATURE:
<223> OTHER INFORMATION: AON

<400> SEQUENCE: 476
gaggcgggag gggcggcact c 21

<210> SEQ ID NO 477
<211> LENGTH: 21
<212> TYPE: DNA
<213> ORGANISM: Artificial Sequence
<220> FEATURE:
<223> OTHER INFORMATION: AON

<400> SEQUENCE: 477
ggaggcggga ggggcggcac t 21

<210> SEQ ID NO 478
<211> LENGTH: 21
<212> TYPE: DNA

<213> ORGANISM: Artificial Sequence
<220> FEATURE:
<223> OTHER INFORMATION: AON

<400> SEQUENCE: 478
gggaggcggg aggggcggca c 21

<210> SEQ ID NO 479
<211> LENGTH: 18
<212> TYPE: DNA
<213> ORGANISM: Artificial Sequence
<220> FEATURE:
<223> OTHER INFORMATION: AON

<400> SEQUENCE: 479
tcaaagcagc tctgagac 18

<210> SEQ ID NO 480
<211> LENGTH: 18
<212> TYPE: DNA
<213> ORGANISM: Artificial Sequence
<220> FEATURE:
<223> OTHER INFORMATION: AON

<400> SEQUENCE: 480
ctcaaagcag ctctgaga 18

<210> SEQ ID NO 481
<211> LENGTH: 18
<212> TYPE: DNA
<213> ORGANISM: Artificial Sequence
<220> FEATURE:
<223> OTHER INFORMATION: AON

<400> SEQUENCE: 481
tctcaaagca gctctgag 18

<210> SEQ ID NO 482
<211> LENGTH: 18
<212> TYPE: DNA
<213> ORGANISM: Artificial Sequence
<220> FEATURE:
<223> OTHER INFORMATION: AON

<400> SEQUENCE: 482
ctctcaaagc agctctga 18

<210> SEQ ID NO 483
<211> LENGTH: 18
<212> TYPE: DNA
<213> ORGANISM: Artificial Sequence
<220> FEATURE:
<223> OTHER INFORMATION: AON

<400> SEQUENCE: 483
gctctcaaag cagctctg 18

<210> SEQ ID NO 484
<211> LENGTH: 18
<212> TYPE: DNA
<213> ORGANISM: Artificial Sequence
<220> FEATURE:
<223> OTHER INFORMATION: AON

<400> SEQUENCE: 484
ggctctcaaa gcagctct 18

<210> SEQ ID NO 485
<211> LENGTH: 18
<212> TYPE: DNA
<213> ORGANISM: Artificial Sequence
<220> FEATURE:
<223> OTHER INFORMATION: AON

<400> SEQUENCE: 485
gggctctcaa agcagctc 18

<210> SEQ ID NO 486
<211> LENGTH: 18
<212> TYPE: DNA
<213> ORGANISM: Artificial Sequence
<220> FEATURE:
<223> OTHER INFORMATION: AON

<400> SEQUENCE: 486
ggggctctca aagcagct 18

<210> SEQ ID NO 487
<211> LENGTH: 18
<212> TYPE: DNA
<213> ORGANISM: Artificial Sequence
<220> FEATURE:
<223> OTHER INFORMATION: AON

<400> SEQUENCE: 487
cggggctctc aaagcagc 18

<210> SEQ ID NO 488
<211> LENGTH: 18
<212> TYPE: DNA
<213> ORGANISM: Artificial Sequence
<220> FEATURE:
<223> OTHER INFORMATION: AON

<400> SEQUENCE: 488
acggggctct caaagcag 18

<210> SEQ ID NO 489
<211> LENGTH: 18
<212> TYPE: DNA
<213> ORGANISM: Artificial Sequence
<220> FEATURE:
<223> OTHER INFORMATION: AON

<400> SEQUENCE: 489
cacggggctc tcaaagca 18

<210> SEQ ID NO 490
<211> LENGTH: 18
<212> TYPE: DNA
<213> ORGANISM: Artificial Sequence
<220> FEATURE:
<223> OTHER INFORMATION: AON

<400> SEQUENCE: 490
tcacggggct ctcaaagc 18

<210> SEQ ID NO 491
<211> LENGTH: 18
<212> TYPE: DNA
<213> ORGANISM: Artificial Sequence
<220> FEATURE:

<223> OTHER INFORMATION: AON

<400> SEQUENCE: 491
ctcacggggc tctcaaag 18

<210> SEQ ID NO 492
<211> LENGTH: 18
<212> TYPE: DNA
<213> ORGANISM: Artificial Sequence
<220> FEATURE:
<223> OTHER INFORMATION: AON

<400> SEQUENCE: 492
actcacgggg ctctcaaa 18

<210> SEQ ID NO 493
<211> LENGTH: 18
<212> TYPE: DNA
<213> ORGANISM: Artificial Sequence
<220> FEATURE:
<223> OTHER INFORMATION: AON

<400> SEQUENCE: 493
cactcacggg gctctcaa 18

<210> SEQ ID NO 494
<211> LENGTH: 18
<212> TYPE: DNA
<213> ORGANISM: Artificial Sequence
<220> FEATURE:
<223> OTHER INFORMATION: AON

<400> SEQUENCE: 494
gcactcacgg ggctctca 18

<210> SEQ ID NO 495
<211> LENGTH: 18
<212> TYPE: DNA
<213> ORGANISM: Artificial Sequence
<220> FEATURE:
<223> OTHER INFORMATION: AON

<400> SEQUENCE: 495
ggcactcacg gggctctc 18

<210> SEQ ID NO 496
<211> LENGTH: 18
<212> TYPE: DNA
<213> ORGANISM: Artificial Sequence
<220> FEATURE:
<223> OTHER INFORMATION: AON

<400> SEQUENCE: 496
cggcactcac ggggctct 18

<210> SEQ ID NO 497
<211> LENGTH: 18
<212> TYPE: DNA
<213> ORGANISM: Artificial Sequence
<220> FEATURE:
<223> OTHER INFORMATION: AON

<400> SEQUENCE: 497
gcggcactca cggggctc 18

<210> SEQ ID NO 498
<211> LENGTH: 18
<212> TYPE: DNA
<213> ORGANISM: Artificial Sequence
<220> FEATURE:
<223> OTHER INFORMATION: AON

<400> SEQUENCE: 498
ggcggcactc acggggct 18

<210> SEQ ID NO 499
<211> LENGTH: 18
<212> TYPE: DNA
<213> ORGANISM: Artificial Sequence
<220> FEATURE:
<223> OTHER INFORMATION: AON

<400> SEQUENCE: 499
gggcggcact cacggggc 18

<210> SEQ ID NO 500
<211> LENGTH: 18
<212> TYPE: DNA
<213> ORGANISM: Artificial Sequence
<220> FEATURE:
<223> OTHER INFORMATION: AON

<400> SEQUENCE: 500
ggggcggcac tcacgggg 18

<210> SEQ ID NO 501
<211> LENGTH: 18
<212> TYPE: DNA
<213> ORGANISM: Artificial Sequence
<220> FEATURE:
<223> OTHER INFORMATION: AON

<400> SEQUENCE: 501
aggggcggca ctcacggg 18

<210> SEQ ID NO 502
<211> LENGTH: 18
<212> TYPE: DNA
<213> ORGANISM: Artificial Sequence
<220> FEATURE:
<223> OTHER INFORMATION: AON

<400> SEQUENCE: 502
gaggggcggc actcacgg 18

<210> SEQ ID NO 503
<211> LENGTH: 18
<212> TYPE: DNA
<213> ORGANISM: Artificial Sequence
<220> FEATURE:
<223> OTHER INFORMATION: AON

<400> SEQUENCE: 503
ggaggggcgg cactcacg 18

<210> SEQ ID NO 504
<211> LENGTH: 18
<212> TYPE: DNA
<213> ORGANISM: Artificial Sequence
<220> FEATURE:
<223> OTHER INFORMATION: AON

<400> SEQUENCE: 504
gggaggggcg gcactcac 18

<210> SEQ ID NO 505
<211> LENGTH: 18
<212> TYPE: DNA
<213> ORGANISM: Artificial Sequence
<220> FEATURE:
<223> OTHER INFORMATION: AON

<400> SEQUENCE: 505
cgggaggggc ggcactca 18

<210> SEQ ID NO 506
<211> LENGTH: 18
<212> TYPE: DNA
<213> ORGANISM: Artificial Sequence
<220> FEATURE:
<223> OTHER INFORMATION: AON

<400> SEQUENCE: 506
gcgggagggg cggcactc 18

<210> SEQ ID NO 507
<211> LENGTH: 18
<212> TYPE: DNA
<213> ORGANISM: Artificial Sequence
<220> FEATURE:
<223> OTHER INFORMATION: AON

<400> SEQUENCE: 507
ggcgggaggg gcggcact 18

<210> SEQ ID NO 508
<211> LENGTH: 18
<212> TYPE: DNA
<213> ORGANISM: Artificial Sequence
<220> FEATURE:
<223> OTHER INFORMATION: AON

<400> SEQUENCE: 508
aggcgggagg ggcggcac 18

<210> SEQ ID NO 509
<211> LENGTH: 18
<212> TYPE: DNA
<213> ORGANISM: Artificial Sequence
<220> FEATURE:
<223> OTHER INFORMATION: AON

<400> SEQUENCE: 509
gaggcgggag gggcggca 18

<210> SEQ ID NO 510
<211> LENGTH: 18
<212> TYPE: DNA
<213> ORGANISM: Artificial Sequence
<220> FEATURE:
<223> OTHER INFORMATION: AON

<400> SEQUENCE: 510
ggaggcggga ggggcggc 18

<210> SEQ ID NO 511
<211> LENGTH: 18

<212> TYPE: DNA
<213> ORGANISM: Artificial Sequence
<220> FEATURE:
<223> OTHER INFORMATION: AON

<400> SEQUENCE: 511
gggaggcggg aggggcgg 18

<210> SEQ ID NO 512
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 512
ggctctcaaa gcagctctga gacat 25

<210> SEQ ID NO 513
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 513
ggggctctca aagcagctct gagac 25

<210> SEQ ID NO 514
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 514
acggggctct caaagcagct ctgag 25

<210> SEQ ID NO 515
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 515
tcacggggct ctcaaagcag ctctg 25

<210> SEQ ID NO 516
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 516
actcacgggg ctctcaaagc agctc 25

<210> SEQ ID NO 517
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 517
gcactcacgg ggctctcaaa gcagc 25

<210> SEQ ID NO 518
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 518
cggcactcac ggggctctca aagca 25

<210> SEQ ID NO 519
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 519
ggcggcactc acggggctct caaag 25

<210> SEQ ID NO 520
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 520
ggggcggcac tcacggggct ctcaa 25

<210> SEQ ID NO 521
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 521
gaggggcggc actcacgggg ctctc 25

<210> SEQ ID NO 522
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 522
gggaggggcg gcactcacgg ggctc 25

<210> SEQ ID NO 523
<211> LENGTH: 25
<212> TYPE: DNA
<213> ORGANISM: Artificial Sequence
<220> FEATURE:

<223> OTHER INFORMATION: AON sequence designed to block the region surrounding the identified splice element (5' -> 3')

<400> SEQUENCE: 523
gcgggagggg cggcactcac ggggc 25

<210> SEQ ID NO 524
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 524
aggcgggagg ggcggcactc acggg 25

<210> SEQ ID NO 525
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 525
ggaggcggga ggggcggcac tcacg 25

<210> SEQ ID NO 526
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 526
agggaggcgg gaggggcggc actca 25

<210> SEQ ID NO 527
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 527
gcagggaggc gggaggggcg gcact 25

<210> SEQ ID NO 528
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 528
cagcagggag gcgggagggg cggca 25

<210> SEQ ID NO 529
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 529
ctcagcaggg aggcgggagg ggcgg 25

<210> SEQ ID NO 530
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 530
ggctcagcag ggaggcggga ggggc 25

<210> SEQ ID NO 531
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 531
cgggctcagc agggaggcgg gaggg 25

<210> SEQ ID NO 532
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 532
agcgggctca gcagggaggc gggag 25

<210> SEQ ID NO 533
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 533
aaagcgggct cagcagggag gcggg 25

<210> SEQ ID NO 534
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 534
agaaagcggg ctcagcaggg aggcg 25

<210> SEQ ID NO 535
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 535
gaagaaagcg ggctcagcag ggagg 25

<210> SEQ ID NO 536
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 536
gagaagaaag cgggctcagc aggga 25

<210> SEQ ID NO 537
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 537
gggagaagaa agcgggctca gcagg 25

<210> SEQ ID NO 538
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 538
gcgggagaag aaagcgggct cagca 25

<210> SEQ ID NO 539
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 539
ctgcgggaga agaaagcggg ctcag 25

<210> SEQ ID NO 540
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 540
gcctgcggga gaagaaagcg ggctc 25

<210> SEQ ID NO 541
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 541
aggcctgcgg gagaagaaag cgggc 25

<210> SEQ ID NO 542
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 542
actcccatgg ttggagatgg cctgg 25

<210> SEQ ID NO 543
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 543
tcactcccat ggttggagat ggcct 25

<210> SEQ ID NO 544
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 544
cctcactccc atggttggag atggc 25

<210> SEQ ID NO 545
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 545
tgcctcactc ccatggttgg agatg 25

<210> SEQ ID NO 546
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 546
ggtgcctcac tcccatggtt ggaga 25

<210> SEQ ID NO 547
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 547
cgggtgcctc actcccatgg ttgga 25

<210> SEQ ID NO 548
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 548
ggcgggtgcc tcactcccat ggttg 25

<210> SEQ ID NO 549
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 549
agggcgggtg cctcactccc atggt 25

<210> SEQ ID NO 550
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 550
gcagggcggg tgcctcactc ccatg 25

<210> SEQ ID NO 551
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 551
gagcagggcg ggtgcctcac tccca 25

<210> SEQ ID NO 552
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 552
gggagcaggg cgggtgcctc actcc 25

<210> SEQ ID NO 553
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 553
gtgggagcag ggcgggtgcc tcact 25

<210> SEQ ID NO 554
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 554
cggtgggagc agggcgggtg cctca 25

<210> SEQ ID NO 555
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 555
gccggtggga gcagggcggg tgcct 25

<210> SEQ ID NO 556
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 556
gagccggtgg gagcagggcg ggtgc 25

<210> SEQ ID NO 557
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 557
aggagccggt gggagcaggg cgggt 25

<210> SEQ ID NO 558
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 558
ccaggagccg gtgggagcag ggcgg 25

<210> SEQ ID NO 559
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 559
ggccaggagc cggtgggagc agggc 25

<210> SEQ ID NO 560
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 560
acggccagga gccggtggga gcagg 25

<210> SEQ ID NO 561
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 561
agacggccag gagccggtgg gagca 25

<210> SEQ ID NO 562
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 562
gcagacggcc aggagccggt gggag 25

<210> SEQ ID NO 563
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 563
gcgcagacgg ccaggagccg gtggg 25

<210> SEQ ID NO 564
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 564
gggcgcagac ggccaggagc cggtg 25

<210> SEQ ID NO 565
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 565
gagggcgcag acggccagga gccgg 25

<210> SEQ ID NO 566
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 566
acgagggcgc agacggccag gagcc 25

<210> SEQ ID NO 567
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 567
acacgagggc gcagacggcc aggag 25

<210> SEQ ID NO 568
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 568
ggacacgagg gcgcagacgg ccagg 25

<210> SEQ ID NO 569
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 569
aaggacacga gggcgcagac ggcca 25

<210> SEQ ID NO 570
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 570
ccaaggacac gagggcgcag acggc 25

<210> SEQ ID NO 571
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 571
tgccaaggac acgagggcgc agacg 25

<210> SEQ ID NO 572
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 572
gctctcaaag cagctctgag acatc 25

<210> SEQ ID NO 573
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 573
gggctctcaa agcagctctg agaca 25

<210> SEQ ID NO 574
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 574
ctcacggggc tctcaaagca gctct 25

<210> SEQ ID NO 575
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 575
cactcacggg gctctcaaag cagct 25

<210> SEQ ID NO 576
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 576
ggcactcacg gggctctcaa agcag 25

<210> SEQ ID NO 577
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 577
gcggcactca cggggctctc aaagc 25

<210> SEQ ID NO 578

<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 578
gggcggcact cacggggctc tcaaa 25

<210> SEQ ID NO 579
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 579
aggggcggca ctcacggggc tctca 25

<210> SEQ ID NO 580
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 580
ggaggggcgg cactcacggg gctct 25

<210> SEQ ID NO 581
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 581
cgggaggggc ggcactcacg gggct 25

<210> SEQ ID NO 582
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 582
ggcgggaggg gcggcactca cgggg 25

<210> SEQ ID NO 583
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 583
gaggcgggag gggcggcact cacgg 25

<210> SEQ ID NO 584
<211> LENGTH: 25

<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 584
gggaggcggg aggggcggca ctcac 25

<210> SEQ ID NO 585
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 585
cagggaggcg ggaggggcgg cactc 25

<210> SEQ ID NO 586
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 586
agcagggagg cgggaggggc ggcac 25

<210> SEQ ID NO 587
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 587
tcagcaggga ggcgggaggg gcggc 25

<210> SEQ ID NO 588
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 588
gctcagcagg gaggcgggag gggcg 25

<210> SEQ ID NO 589
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 589
gggctcagca gggaggcggg agggg 25

<210> SEQ ID NO 590
<211> LENGTH: 25
<212> TYPE: DNA

<213> ORGANISM: Artificial Sequence
<220> FEATURE:
<223> OTHER INFORMATION: AON sequence designed to block the region surrounding the identified splice element (5' -> 3')

<400> SEQUENCE: 590
gcgggctcag cagggaggcg ggagg 25

<210> SEQ ID NO 591
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 591
aagcgggctc agcagggagg cggga 25

<210> SEQ ID NO 592
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 592
gaaagcgggc tcagcaggga ggcgg 25

<210> SEQ ID NO 593
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 593
aagaaagcgg gctcagcagg gaggc 25

<210> SEQ ID NO 594
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 594
agaagaaagc gggctcagca gggag 25

<210> SEQ ID NO 595
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 595
ggagaagaaa gcgggctcag caggg 25

<210> SEQ ID NO 596
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 596
cgggagaaga aagcgggctc agcag 25

<210> SEQ ID NO 597
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 597
tgcgggagaa gaaagcgggc tcagc 25

<210> SEQ ID NO 598
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 598
cctgcgggag aagaaagcgg gctca 25

<210> SEQ ID NO 599
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 599
ggcctgcggg agaagaaagc gggct 25

<210> SEQ ID NO 600
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 600
caggcctgcg ggagaagaaa gcggg 25

<210> SEQ ID NO 601
<211> LENGTH: 25
<212> TYPE: DNA
<213> ORGANISM: Artificial Sequence
<220> FEATURE:
<223> OTHER INFORMATION: AON sequence designed to block the region
      surrounding the identified splice element (5' -> 3')

<400> SEQUENCE: 601
cggggctctc aaagcagctc tgaga 25

<210> SEQ ID NO 602
<211> LENGTH: 25
<212> TYPE: DNA
<213> ORGANISM: Artificial Sequence
<220> FEATURE:

<223> OTHER INFORMATION: AON sequence designed to block the region
      surrounding the identified splice element (5' -> 3')

<400> SEQUENCE: 602
cacggggctc tcaaagcagc tctga 25

<210> SEQ ID NO 603
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 603
ccaaacagct gtcgcctggg 20

<210> SEQ ID NO 604
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 604
aggtagacac ttgaaacagg 20

<210> SEQ ID NO 605
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 605
cccaggaaga ccagcaaggc 20

<210> SEQ ID NO 606
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 606
tcaaacacgc ttagaatgtc 20

<210> SEQ ID NO 607
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 607
gtctgctaaa atgttacaaa 20

<210> SEQ ID NO 608
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 608
aggtggccag ggtgggtgtt 20

<210> SEQ ID NO 609
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 609
gcacccaggc aggtggggta 20

<210> SEQ ID NO 610
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 610
caaccgcggc tggcactgca 20

<210> SEQ ID NO 611
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 611
cctgcgggag aagaaagcgg 20

<210> SEQ ID NO 612
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 612
gcctggacag ctcctacagg 20

<210> SEQ ID NO 613
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 613
cactcccatg gttggagatg 20

<210> SEQ ID NO 614
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 614
tgggagcagg gcgggtgcct 20

<210> SEQ ID NO 615
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 615
cgcagacggc caggagccgg 20

<210> SEQ ID NO 616
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 616
ggttgccaag gacacgaggg 20

<210> SEQ ID NO 617
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 617
atgtgcccca ggagtgcagc 20

<210> SEQ ID NO 618
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 618
gcaggaaatc atggagtagg 20

<210> SEQ ID NO 619
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 619
actcagctct cggggaacca 20

<210> SEQ ID NO 620
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 620
tccaggactg gggaggagcc 20

<210> SEQ ID NO 621
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 621
ggtgagctgg gtgagtctcc 20

<210> SEQ ID NO 622

<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 622
tggtctgctg gctccctgct 20

<210> SEQ ID NO 623
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 623
gcctgggcat cccggggccc 20

<210> SEQ ID NO 624
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 624
ctctgggacg gccggggtgt 20

<210> SEQ ID NO 625
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 625
gtcgcactgt gtgggcactg 20

<210> SEQ ID NO 626
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 626
aagcggctgt tggggggac 20

<210> SEQ ID NO 627
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 627
ccttgtcagg ggcgcaatcg 20

<210> SEQ ID NO 628
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 628
gcactgttcc tgggtgatgg 20

<210> SEQ ID NO 629
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 629
tagcaacagc cgcgggcctc 20

<210> SEQ ID NO 630
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 630
gcccctgctt tgcagggatg 20

<210> SEQ ID NO 631
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 631
ccccatctgg gctccctgca 20

<210> SEQ ID NO 632
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 632
gggaagaagc accagggctg 20

<210> SEQ ID NO 633
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 633
tgtagctggg gtagctgggt 20

<210> SEQ ID NO 634
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 634
ggagctcagg ttctccagct 20

<210> SEQ ID NO 635
<211> LENGTH: 20
<212> TYPE: DNA

<213> ORGANISM: Artificial Sequence
<220> FEATURE:
<223> OTHER INFORMATION: AON sequence 5' -> 3'

<400> SEQUENCE: 635
gccgtgtagc ccatttcaga 20

<210> SEQ ID NO 636
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 636
gggtggtacg ggtcagggtg 20

<210> SEQ ID NO 637
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 637
gtccttgggg aagaaggtgg 20

<210> SEQ ID NO 638
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 638
tccagccgca gggtcaggat 20

<210> SEQ ID NO 639
<211> LENGTH: 20
<212> TYPE: DNA
<213> ORGANISM: Artificial Sequence
<220> FEATURE:
<223> OTHER INFORMATION: AON sequence 5' -> 3'

<400> SEQUENCE: 639
tctcagtctc catcatcacg 20

<210> SEQ ID NO 640
<211> LENGTH: 16
<212> TYPE: DNA
<213> ORGANISM: Artificial Sequence
<220> FEATURE:
<223> OTHER INFORMATION: AON sequence 5' -> 3'

<400> SEQUENCE: 640
gtgaagtgga ggcggt 16

<210> SEQ ID NO 641
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 641
cacccaggca ggtggggtaa ggtgg 25

<210> SEQ ID NO 642
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 642
agcacccagg caggtggggt aaggt 25

<210> SEQ ID NO 643
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 643
gcagcaccca ggcaggtggg gtaag 25

<210> SEQ ID NO 644
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 644
ctgcagcacc caggcaggtg gggta 25

<210> SEQ ID NO 645
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 645
cactgcagca cccaggcagg tgggg 25

<210> SEQ ID NO 646
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 646
ggcactgcag cacccaggca ggtgg 25

<210> SEQ ID NO 647
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 647
ctggcactgc agcacccagg caggt 25

<210> SEQ ID NO 648
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 648
ggctggcact gcagcaccca ggcag 25

<210> SEQ ID NO 649
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 649
gcggctggca ctgcagcacc caggc 25

<210> SEQ ID NO 650
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 650
ccgcggctgg cactgcagca cccag 25

<210> SEQ ID NO 651
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 651
tcaaccgcgg ctggcactgc agcac 25

<210> SEQ ID NO 652
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 652
acccaggcag gtggggtaag gtggc 25

<210> SEQ ID NO 653
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 653
gcacccaggc aggtggggta aggtg 25

<210> SEQ ID NO 654
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 654
cagcacccag gcaggtgggg taagg 25

<210> SEQ ID NO 655
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 655
tgcagcaccc aggcaggtgg ggtaa 25

<210> SEQ ID NO 656
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 656
actgcagcac ccaggcaggt ggggt 25

<210> SEQ ID NO 657
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 657
gcactgcagc acccaggcag gtggg 25

<210> SEQ ID NO 658
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 658
tggcactgca gcacccaggc aggtg 25

<210> SEQ ID NO 659
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 659
gctggcactg cagcacccag gcagg 25

<210> SEQ ID NO 660
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 660
cggctggcac tgcagcaccc aggca 25

<210> SEQ ID NO 661
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 661
cgcggctggc actgcagcac ccagg 25

<210> SEQ ID NO 662
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 662
accgcggctg gcactgcagc accca 25

<210> SEQ ID NO 663
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 663
caaccgcggc tggcactgca gcacc 25

<210> SEQ ID NO 664
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 664
atcaaccgcg gctggcactg cagca 25

<210> SEQ ID NO 665
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 665
ctcccatggt tggagatggc ctgga 25

<210> SEQ ID NO 666

<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 666
cactcccatg gttggagatg gcctg 25

<210> SEQ ID NO 667
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 667
ctcactccca tggttggaga tggcc 25

<210> SEQ ID NO 668
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 668
gcctcactcc catggttgga gatgg 25

<210> SEQ ID NO 669
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 669
gtgcctcact cccatggttg gagat 25

<210> SEQ ID NO 670
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 670
gggtgcctca ctcccatggt tggag 25

<210> SEQ ID NO 671
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 671
gcgggtgcct cactcccatg gttgg 25

<210> SEQ ID NO 672
<211> LENGTH: 25

<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 672
gggcgggtgc ctcactccca tggtt 25

<210> SEQ ID NO 673
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 673
cagggcgggt gcctcactcc catgg 25

<210> SEQ ID NO 674
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 674
agcagggcgg gtgcctcact cccat 25

<210> SEQ ID NO 675
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 675
ggagcagggc gggtgcctca ctccc 25

<210> SEQ ID NO 676
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 676
tgggagcagg gcgggtgcct cactc 25

<210> SEQ ID NO 677
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 677
ggtgggagca gggcgggtgc ctcac 25

<210> SEQ ID NO 678
<211> LENGTH: 25
<212> TYPE: DNA

<213> ORGANISM: Artificial Sequence
<220> FEATURE:
<223> OTHER INFORMATION: AON sequence designed to block the region surrounding the identified splice element (5' -> 3')

<400> SEQUENCE: 678
ccggtgggag cagggcgggt gcctc 25

<210> SEQ ID NO 679
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 679
agccggtggg agcagggcgg gtgcc 25

<210> SEQ ID NO 680
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 680
ggagccggtg ggagcagggc gggtg 25

<210> SEQ ID NO 681
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 681
caggagccgg tgggagcagg gcggg 25

<210> SEQ ID NO 682
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 682
gccaggagcc ggtgggagca gggcg 25

<210> SEQ ID NO 683
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 683
cggccaggag ccggtgggag caggg 25

<210> SEQ ID NO 684
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 684
gacggccagg agccggtggg agcag 25

<210> SEQ ID NO 685
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 685
cagacggcca ggagccggtg ggagc 25

<210> SEQ ID NO 686
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 686
cgcagacggc caggagccgg tggga 25

<210> SEQ ID NO 687
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 687
ggcgcagacg gccaggagcc ggtgg 25

<210> SEQ ID NO 688
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 688
agggcgcaga cggccaggag ccggt 25

<210> SEQ ID NO 689
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 689
cgagggcgca gacggccagg agccg 25

<210> SEQ ID NO 690
<211> LENGTH: 25
<212> TYPE: DNA
<213> ORGANISM: Artificial Sequence
<220> FEATURE:

<223> OTHER INFORMATION: AON sequence designed to block the region
surrounding the identified splice element (5' -> 3')

<400> SEQUENCE: 690
cacgagggcg cagacggcca ggagc 25

<210> SEQ ID NO 691
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 691
gacacgaggg cgcagacggc cagga 25

<210> SEQ ID NO 692
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 692
aggacacgag ggcgcagacg gccag 25

<210> SEQ ID NO 693
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 693
caaggacacg agggcgcaga cggcc 25

<210> SEQ ID NO 694
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 694
gccaaggaca cgagggcgca gacgg 25

<210> SEQ ID NO 695
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 695
ttgccaagga cacgagggcg cagac 25

<210> SEQ ID NO 696
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 696
ggatgtgccc caggagtgca gcggt 25

<210> SEQ ID NO 697
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 697
taggatgtgc cccaggagtg cagcg 25

<210> SEQ ID NO 698
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 698
agtaggatgt gccccaggag tgcag 25

<210> SEQ ID NO 699
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 699
ggagtaggat gtgccccagg agtgc 25

<210> SEQ ID NO 700
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 700
atggagtagg atgtgcccca ggagt 25

<210> SEQ ID NO 701
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 701
tcatggagta ggatgtgccc cagga 25

<210> SEQ ID NO 702
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 702
aatcatggag taggatgtgc cccag 25

<210> SEQ ID NO 703
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 703
gaaatcatgg agtaggatgt gcccc 25

<210> SEQ ID NO 704
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 704
aggaaatcat ggagtaggat gtgcc 25

<210> SEQ ID NO 705
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 705
gcaggaaatc atggagtagg atgtg 25

<210> SEQ ID NO 706
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 706
cagcaggaaa tcatggagta ggatg 25

<210> SEQ ID NO 707
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 707
accagcagga aatcatggag tagga 25

<210> SEQ ID NO 708
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 708
gaaccagcag gaaatcatgg agtag 25

<210> SEQ ID NO 709
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 709
gggaaccagc aggaaatcat ggagt 25

<210> SEQ ID NO 710
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 710
cggggaacca gcaggaaatc atgga 25

<210> SEQ ID NO 711
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 711
ctcggggaac cagcaggaaa tcatg 25

<210> SEQ ID NO 712
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 712
ctctcgggga accagcagga aatca 25

<210> SEQ ID NO 713
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 713
agctctcggg gaaccagcag gaaat 25

<210> SEQ ID NO 714
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 714
tcagctctcg gggaaccagc aggaa 25

<210> SEQ ID NO 715
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 715
actcagctct cggggaacca gcagg 25

<210> SEQ ID NO 716
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 716
ccactcagct ctcggggaac cagca 25

<210> SEQ ID NO 717
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 717
agccactcag ctctcgggga accag 25

<210> SEQ ID NO 718
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 718
ggagccactc agctctcggg gaacc 25

<210> SEQ ID NO 719
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 719
gaggagccac tcagctctcg gggaa 25

<210> SEQ ID NO 720
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 720
gggaggagcc actcagctct cgggg 25

<210> SEQ ID NO 721
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 721
tggggaggag ccactcagct ctcgg 25

<210> SEQ ID NO 722
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 722
actggggagg agccactcag ctctc 25

<210> SEQ ID NO 723
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 723
ggactgggga ggagccactc agctc 25

<210> SEQ ID NO 724
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 724
caggactggg gaggagccac tcagc 25

<210> SEQ ID NO 725
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 725
tccaggactg gggaggagcc actca 25

<210> SEQ ID NO 726
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 726
cctccaggac tggggaggag ccact 25

<210> SEQ ID NO 727
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 727
ctcctccagg actggggagg agcca 25

<210> SEQ ID NO 728
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 728
gtctcctcca ggactgggga ggagc 25

<210> SEQ ID NO 729
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 729
gagtctcctc caggactggg gagga 25

<210> SEQ ID NO 730
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 730
gtgagtctcc tccaggactg gggag 25

<210> SEQ ID NO 731
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 731
gggtgagtct cctccaggac tgggg 25

<210> SEQ ID NO 732
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 732
ctgggtgagt ctcctccagg actgg 25

<210> SEQ ID NO 733
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 733
agctgggtga gtctcctcca ggact 25

<210> SEQ ID NO 734
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 734
tgagctgggt gagtctcctc cagga 25

<210> SEQ ID NO 735
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 735
ggtgagctgg gtgagtctcc tccag 25

<210> SEQ ID NO 736
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 736
ctggtgagct gggtgagtct cctcc 25

<210> SEQ ID NO 737
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 737
tgctggtgag ctgggtgagt ctcct 25

<210> SEQ ID NO 738
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 738
cctgctggtg agctgggtga gtctc 25

<210> SEQ ID NO 739
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 739
tccctgctgg tgagctgggt gagtc 25

<210> SEQ ID NO 740
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 740
gctccctgct ggtgagctgg gtgag 25

<210> SEQ ID NO 741
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 741
tggctccctg ctggtgagct gggtg 25

<210> SEQ ID NO 742
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 742
gctggctccc tgctggtgag ctggg 25

<210> SEQ ID NO 743
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 743
ctgctggctc cctgctggtg agctg 25

<210> SEQ ID NO 744
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 744
gtctgctggc tccctgctgg tgagc 25

<210> SEQ ID NO 745

<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 745
gatgtgcccc aggagtgcag cggtt 25

<210> SEQ ID NO 746
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 746
aggatgtgcc ccaggagtgc agcgg 25

<210> SEQ ID NO 747
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 747
gtaggatgtg ccccaggagt gcagc 25

<210> SEQ ID NO 748
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 748
gagtaggatg tgccccagga gtgca 25

<210> SEQ ID NO 749
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 749
tggagtagga tgtgccccag gagtg 25

<210> SEQ ID NO 750
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 750
catggagtag gatgtgcccc aggag 25

<210> SEQ ID NO 751
<211> LENGTH: 25

<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 751
atcatggagt aggatgtgcc ccagg 25

<210> SEQ ID NO 752
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 752
aaatcatgga gtaggatgtg cccca 25

<210> SEQ ID NO 753
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 753
ggaaatcatg gagtaggatg tgccc 25

<210> SEQ ID NO 754
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 754
caggaaatca tggagtagga tgtgc 25

<210> SEQ ID NO 755
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 755
agcaggaaat catggagtag gatgt 25

<210> SEQ ID NO 756
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 756
ccagcaggaa atcatggagt aggat 25

<210> SEQ ID NO 757
<211> LENGTH: 25
<212> TYPE: DNA

<213> ORGANISM: Artificial Sequence
<220> FEATURE:
<223> OTHER INFORMATION: AON sequence designed to block the region surrounding the identified splice element (5' -> 3')

<400> SEQUENCE: 757
aaccagcagg aaatcatgga gtagg 25

<210> SEQ ID NO 758
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 758
ggaaccagca ggaaatcatg gagta 25

<210> SEQ ID NO 759
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 759
ggggaaccag caggaaatca tggag 25

<210> SEQ ID NO 760
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 760
tcggggaacc agcaggaaat catgg 25

<210> SEQ ID NO 761
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 761
tctcggggaa ccagcaggaa atcat 25

<210> SEQ ID NO 762
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 762
gctctcgggg aaccagcagg aaatc 25

<210> SEQ ID NO 763
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 763
cagctctcgg ggaaccagca ggaaa 25

<210> SEQ ID NO 764
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 764
ctcagctctc ggggaaccag cagga 25

<210> SEQ ID NO 765
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 765
cactcagctc tcggggaacc agcag 25

<210> SEQ ID NO 766
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 766
gccactcagc tctcggggaa ccagc 25

<210> SEQ ID NO 767
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 767
gagccactca gctctcgggg aacca 25

<210> SEQ ID NO 768
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 768
aggagccact cagctctcgg ggaac 25

<210> SEQ ID NO 769
<211> LENGTH: 25
<212> TYPE: DNA
<213> ORGANISM: Artificial Sequence
<220> FEATURE:

<223> OTHER INFORMATION: AON sequence designed to block the region
surrounding the identified splice element (5' -> 3')

<400> SEQUENCE: 769
ggaggagcca ctcagctctc gggga 25

<210> SEQ ID NO 770
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 770
ggggaggagc cactcagctc tcggg 25

<210> SEQ ID NO 771
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 771
ctggggagga gccactcagc tctcg 25

<210> SEQ ID NO 772
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 772
gactggggag gagccactca gctct 25

<210> SEQ ID NO 773
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 773
aggactgggg aggagccact cagct 25

<210> SEQ ID NO 774
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 774
ccaggactgg ggaggagcca ctcag 25

<210> SEQ ID NO 775
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 775
ctccaggact ggggaggagc cactc 25

<210> SEQ ID NO 776
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 776
tcctccagga ctggggagga gccac 25

<210> SEQ ID NO 777
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 777
tctcctccag gactggggag gagcc 25

<210> SEQ ID NO 778
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 778
agtctcctcc aggactgggg aggag 25

<210> SEQ ID NO 779
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 779
tgagtctcct ccaggactgg ggagg 25

<210> SEQ ID NO 780
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 780
ggtgagtctc ctccaggact gggga 25

<210> SEQ ID NO 781
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 781
tgggtgagtc tcctccagga ctggg 25

<210> SEQ ID NO 782
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 782
gctgggtgag tctcctccag gactg 25

<210> SEQ ID NO 783
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 783
gagctgggtg agtctcctcc aggac 25

<210> SEQ ID NO 784
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 784
gtgagctggg tgagtctcct ccagg 25

<210> SEQ ID NO 785
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 785
tggtgagctg ggtgagtctc ctcca 25

<210> SEQ ID NO 786
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 786
gctggtgagc tgggtgagtc tcctc 25

<210> SEQ ID NO 787
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 787
ctgctggtga gctgggtgag tctcc 25

<210> SEQ ID NO 788
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 788
ccctgctggt gagctgggtg agtct 25

<210> SEQ ID NO 789
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 789
ctccctgctg gtgagctggg tgagt 25

<210> SEQ ID NO 790
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 790
ggctccctgc tggtgagctg ggtga 25

<210> SEQ ID NO 791
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 791
ctggctccct gctggtgagc tgggt 25

<210> SEQ ID NO 792
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 792
tgctggctcc ctgctggtga gctgg 25

<210> SEQ ID NO 793
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 793
tctgctggct ccctgctggt gagct 25

<210> SEQ ID NO 794
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 794
ggtctgctgg ctccctgctg gtgag 25

<210> SEQ ID NO 795
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 795
agcccctgct ttgcagggat gtagc 25

<210> SEQ ID NO 796
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 796
gcagcccctg ctttgcaggg atgta 25

<210> SEQ ID NO 797
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 797
ctgcagcccc tgctttgcag ggatg 25

<210> SEQ ID NO 798
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 798
ccctgcagcc cctgctttgc aggga 25

<210> SEQ ID NO 799
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 799
ctccctgcag cccctgcttt gcagg 25

<210> SEQ ID NO 800
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 800
ggctccctgc agcccctgct ttgca 25

<210> SEQ ID NO 801
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 801
tgggctccct gcagcccctg ctttg 25

<210> SEQ ID NO 802
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 802
tctgggctcc ctgcagcccc tgctt 25

<210> SEQ ID NO 803
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 803
catctgggct ccctgcagcc cctgc 25

<210> SEQ ID NO 804
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 804
cccatctggg ctccctgcag cccct 25

<210> SEQ ID NO 805
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 805
gccccatctg ggctccctgc agccc 25

<210> SEQ ID NO 806
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 806
ctgccccatc tgggctccct gcagc 25

<210> SEQ ID NO 807
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 807
ggctgcccca tctgggctcc ctgca 25

<210> SEQ ID NO 808
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 808
agggctgccc catctgggct ccctg 25

<210> SEQ ID NO 809
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 809
ccagggctgc cccatctggg ctccc 25

<210> SEQ ID NO 810
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 810
caccagggct gccccatctg ggctc 25

<210> SEQ ID NO 811
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 811
agcaccaggg ctgccccatc tgggc 25

<210> SEQ ID NO 812
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 812
gaagcaccag ggctgcccca tctgg 25

<210> SEQ ID NO 813
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 813
aagaagcacc agggctgccc catct 25

<210> SEQ ID NO 814
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 814
ggaagaagca ccagggctgc cccat 25

<210> SEQ ID NO 815
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 815
tgggaagaag caccagggct gcccc 25

<210> SEQ ID NO 816
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 816
ggtgggaaga agcaccaggg ctgcc 25

<210> SEQ ID NO 817
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 817
tgggtgggaa gaagcaccag ggctg 25

<210> SEQ ID NO 818
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 818
gctgggtggg aagaagcacc agggc 25

<210> SEQ ID NO 819
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 819
gcccctgctt tgcagggatg tagca 25

<210> SEQ ID NO 820
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 820
cagcccctgc tttgcaggga tgtag 25

<210> SEQ ID NO 821
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 821
tgcagcccct gctttgcagg gatgt 25

<210> SEQ ID NO 822
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 822
cctgcagccc ctgctttgca gggat 25

<210> SEQ ID NO 823
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 823
tccctgcagc ccctgctttg caggg 25

<210> SEQ ID NO 824

<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 824
gctccctgca gcccctgctt tgcag 25

<210> SEQ ID NO 825
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 825
gggctccctg cagcccctgc tttgc 25

<210> SEQ ID NO 826
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 826
ctgggctccc tgcagcccct gcttt 25

<210> SEQ ID NO 827
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 827
atctgggctc cctgcagccc ctgct 25

<210> SEQ ID NO 828
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 828
ccatctgggc tccctgcagc ccctg 25

<210> SEQ ID NO 829
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 829
ccccatctgg gctccctgca gcccc 25

<210> SEQ ID NO 830
<211> LENGTH: 25

<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 830
tgccccatct gggctccctg cagcc 25

<210> SEQ ID NO 831
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 831
gctgccccat ctgggctccc tgcag 25

<210> SEQ ID NO 832
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 832
gggctgcccc atctgggctc cctgc 25

<210> SEQ ID NO 833
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 833
cagggctgcc ccatctgggc tccct 25

<210> SEQ ID NO 834
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 834
accagggctg ccccatctgg gctcc 25

<210> SEQ ID NO 835
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 835
gcaccagggc tgccccatct gggct 25

<210> SEQ ID NO 836
<211> LENGTH: 25
<212> TYPE: DNA

<213> ORGANISM: Artificial Sequence
<220> FEATURE:
<223> OTHER INFORMATION: AON sequence designed to block the region surrounding the identified splice element (5' -> 3')

<400> SEQUENCE: 836
aagcaccagg gctgccccat ctggg 25

<210> SEQ ID NO 837
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 837
agaagcacca gggctgcccc atctg 25

<210> SEQ ID NO 838
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 838
gaagaagcac cagggctgcc ccatc 25

<210> SEQ ID NO 839
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 839
gggaagaagc accagggctg cccca 25

<210> SEQ ID NO 840
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 840
gtgggaagaa gcaccagggc tgccc 25

<210> SEQ ID NO 841
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 841
gggtgggaag aagcaccagg gctgc 25

<210> SEQ ID NO 842
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 842
ctgggtggga agaagcacca gggct 25

<210> SEQ ID NO 843
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 843
agctgggtgg gaagaagcac caggg 25

<210> SEQ ID NO 844
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 844
cagcttgtag ctggggtagc tgggt 25

<210> SEQ ID NO 845
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 845
tccagcttgt agctggggta gctgg 25

<210> SEQ ID NO 846
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 846
tctccagctt gtagctgggg tagct 25

<210> SEQ ID NO 847
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 847
gttctccagc ttgtagctgg ggtag 25

<210> SEQ ID NO 848
<211> LENGTH: 25
<212> TYPE: DNA
<213> ORGANISM: Artificial Sequence
<220> FEATURE:

<223> OTHER INFORMATION: AON sequence designed to block the region
surrounding the identified splice element (5' -> 3')

<400> SEQUENCE: 848
aggttctcca gcttgtagct ggggt 25

<210> SEQ ID NO 849
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 849
tcaggttctc cagcttgtag ctggg 25

<210> SEQ ID NO 850
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 850
gctcaggttc tccagcttgt agctg 25

<210> SEQ ID NO 851
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 851
gagctcaggt tctccagctt gtagc 25

<210> SEQ ID NO 852
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 852
aggagctcag gttctccagc ttgta 25

<210> SEQ ID NO 853
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 853
agaggagctc aggttctcca gcttg 25

<210> SEQ ID NO 854
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 854
tcagaggagc tcaggttctc cagct 25

<210> SEQ ID NO 855
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 855
tttcagagga gctcaggttc tccag 25

<210> SEQ ID NO 856
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 856
agcttgtagc tggggtagct gggtg 25

<210> SEQ ID NO 857
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 857
ccagcttgta gctggggtag ctggg 25

<210> SEQ ID NO 858
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 858
ctccagcttg tagctggggt agctg 25

<210> SEQ ID NO 859
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 859
ttctccagct tgtagctggg gtagc 25

<210> SEQ ID NO 860
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 860
ggttctccag cttgtagctg gggta 25

<210> SEQ ID NO 861
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 861
caggttctcc agcttgtagc tgggg 25

<210> SEQ ID NO 862
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 862
ctcaggttct ccagcttgta gctgg 25

<210> SEQ ID NO 863
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 863
agctcaggtt ctccagcttg tagct 25

<210> SEQ ID NO 864
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 864
ggagctcagg ttctccagct tgtag 25

<210> SEQ ID NO 865
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 865
gaggagctca ggttctccag cttgt 25

<210> SEQ ID NO 866
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 866
cagaggagct caggttctcc agctt 25

<210> SEQ ID NO 867
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 867
ttcagaggag ctcaggttct ccagc 25

<210> SEQ ID NO 868
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 868
atttcagagg agctcaggtt ctcca 25

<210> SEQ ID NO 869
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 869
ggggtggtac gggtcagggt ggccg 25

<210> SEQ ID NO 870
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 870
tgggggtggt acgggtcagg gtggc 25

<210> SEQ ID NO 871
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 871
ggtgggggtg gtacgggtca gggtg 25

<210> SEQ ID NO 872
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 872
aaggtggggg tggtacgggt caggg 25

<210> SEQ ID NO 873
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 873
agaaggtggg ggtggtacgg gtcag 25

<210> SEQ ID NO 874
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 874
gaagaaggtg ggggtggtac gggtc 25

<210> SEQ ID NO 875
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 875
gggaagaagg tgggggtggt acggg 25

<210> SEQ ID NO 876
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 876
tggggaagaa ggtgggggtg gtacg 25

<210> SEQ ID NO 877
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 877
cttggggaag aaggtggggg tggta 25

<210> SEQ ID NO 878
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 878
tccttgggga agaaggtggg ggtgg 25

<210> SEQ ID NO 879
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 879
tgtccttggg gaagaaggtg ggggt 25

<210> SEQ ID NO 880
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 880
gatgtccttg gggaagaagg tgggg 25

<210> SEQ ID NO 881
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 881
aggatgtcct tggggaagaa ggtgg 25

<210> SEQ ID NO 882
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 882
tcaggatgtc cttggggaag aaggt 25

<210> SEQ ID NO 883
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 883
ggtcaggatg tccttgggga agaag 25

<210> SEQ ID NO 884
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 884
agggtcagga tgtccttggg gaaga 25

<210> SEQ ID NO 885
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 885
gcagggtcag gatgtccttg gggaa 25

<210> SEQ ID NO 886
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 886
ccgcagggtc aggatgtcct tgggg 25

<210> SEQ ID NO 887
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 887
agccgcaggg tcaggatgtc cttgg 25

<210> SEQ ID NO 888
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 888
gggtggtacg ggtcagggtg gccgt 25

<210> SEQ ID NO 889
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 889
gggggtggta cgggtcaggg tggcc 25

<210> SEQ ID NO 890
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 890
gtgggggtgg tacgggtcag ggtgg 25

<210> SEQ ID NO 891
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 891
aggtgggggt ggtacgggtc agggt 25

<210> SEQ ID NO 892
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 892
gaaggtgggg gtggtacggg tcagg 25

<210> SEQ ID NO 893
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 893
aagaaggtgg gggtggtacg ggtca 25

<210> SEQ ID NO 894
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 894
ggaagaaggt gggggtggta cgggt 25

<210> SEQ ID NO 895
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 895
ggggaagaag gtgggggtgg tacgg 25

<210> SEQ ID NO 896
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 896
ttggggaaga aggtgggggt ggtac 25

<210> SEQ ID NO 897
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 897
ccttggggaa gaaggtgggg gtggt 25

<210> SEQ ID NO 898
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 898
gtccttgggg aagaaggtgg gggtg 25

<210> SEQ ID NO 899
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 899
atgtccttgg ggaagaaggt ggggg 25

<210> SEQ ID NO 900
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 900
ggatgtcctt ggggaagaag gtggg 25

<210> SEQ ID NO 901
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 901
caggatgtcc ttggggaaga aggtg 25

<210> SEQ ID NO 902
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 902
gtcaggatgt ccttggggaa gaagg 25

<210> SEQ ID NO 903

<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 903
gggtcaggat gtccttgggg aagaa 25

<210> SEQ ID NO 904
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 904
cagggtcagg atgtccttgg ggaag 25

<210> SEQ ID NO 905
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 905
cgcagggtca ggatgtcctt gggga 25

<210> SEQ ID NO 906
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 906
gccgcagggt caggatgtcc ttggg 25

<210> SEQ ID NO 907
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 907
cagccgcagg gtcaggatgt ccttg 25

<210> SEQ ID NO 908
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 908
cgtccagccg cagggtcagg atgtc 25

<210> SEQ ID NO 909
<211> LENGTH: 25

<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 909
cacgtccagc cgcagggtca ggatg 25

<210> SEQ ID NO 910
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 910
atcacgtcca gccgcagggt cagga 25

<210> SEQ ID NO 911
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 911
tcatcacgtc cagccgcagg gtcag 25

<210> SEQ ID NO 912
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 912
catcatcacg tccagccgca gggtc 25

<210> SEQ ID NO 913
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 913
tccatcatca cgtccagccg caggg 25

<210> SEQ ID NO 914
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 914
tctccatcat cacgtccagc cgcag 25

<210> SEQ ID NO 915
<211> LENGTH: 25
<212> TYPE: DNA

<213> ORGANISM: Artificial Sequence
<220> FEATURE:
<223> OTHER INFORMATION: AON sequence designed to block the region surrounding the identified splice element (5' -> 3')

<400> SEQUENCE: 915
agtctccatc atcacgtcca gccgc 25

<210> SEQ ID NO 916
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 916
tcagtctcca tcatcacgtc cagcc 25

<210> SEQ ID NO 917
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 917
tctcagtctc catcatcacg tccag 25

<210> SEQ ID NO 918
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 918
gttctcagtc tccatcatca cgtcc 25

<210> SEQ ID NO 919
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 919
cggttctcag tctccatcat cacgt 25

<210> SEQ ID NO 920
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 920
ggcggttctc agtctccatc atcac 25

<210> SEQ ID NO 921
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 921
gaggcggttc tcagtctcca tcatc 25

<210> SEQ ID NO 922
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 922
tggaggcggt tctcagtctc catca 25

<210> SEQ ID NO 923
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 923
agtggaggcg gttctcagtc tccat 25

<210> SEQ ID NO 924
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 924
gaagtggagg cggttctcag tctcc 25

<210> SEQ ID NO 925
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 925
gtccagccgc agggtcagga tgtcc 25

<210> SEQ ID NO 926
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 926
acgtccagcc gcagggtcag gatgt 25

<210> SEQ ID NO 927
<211> LENGTH: 25
<212> TYPE: DNA
<213> ORGANISM: Artificial Sequence
<220> FEATURE:

<223> OTHER INFORMATION: AON sequence designed to block the region surrounding the identified splice element (5' -> 3')

<400> SEQUENCE: 927
tcacgtccag ccgcagggtc aggat 25

<210> SEQ ID NO 928
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 928
catcacgtcc agccgcaggg tcagg 25

<210> SEQ ID NO 929
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 929
atcatcacgt ccagccgcag ggtca 25

<210> SEQ ID NO 930
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 930
ccatcatcac gtccagccgc agggt 25

<210> SEQ ID NO 931
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 931
ctccatcatc acgtccagcc gcagg 25

<210> SEQ ID NO 932
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 932
gtctccatca tcacgtccag ccgca 25

<210> SEQ ID NO 933
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 933
cagtctccat catcacgtcc agccg 25

<210> SEQ ID NO 934
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 934
ctcagtctcc atcatcacgt ccagc 25

<210> SEQ ID NO 935
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 935
ttctcagtct ccatcatcac gtcca 25

<210> SEQ ID NO 936
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 936
ggttctcagt ctccatcatc acgtc 25

<210> SEQ ID NO 937
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 937
gcggttctca gtctccatca tcacg 25

<210> SEQ ID NO 938
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 938
aggcggttct cagtctccat catca 25

<210> SEQ ID NO 939
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 939
ggaggcggtt ctcagtctcc atcat 25

<210> SEQ ID NO 940
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 940
gtggaggcgg ttctcagtct ccatc 25

<210> SEQ ID NO 941
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 941
aagtggaggc ggttctcagt ctcca 25

<210> SEQ ID NO 942
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 942
tgaagtggag gcggttctca gtctc 25

<210> SEQ ID NO 943
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 943
tgccctgccc accgtgaagt ggagg 25

<210> SEQ ID NO 944
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 944
cctgccctgc ccaccgtgaa gtgga 25

<210> SEQ ID NO 945
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 945
cccctgccct gcccaccgtg aagtg 25

<210> SEQ ID NO 946
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 946
cgcccctgcc ctgcccaccg tgaag 25

<210> SEQ ID NO 947
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 947
cccgcccctg ccctgcccac cgtga 25

<210> SEQ ID NO 948
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 948
gccctgccca ccgtgaagtg gaggc 25

<210> SEQ ID NO 949
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 949
ctgccctgcc caccgtgaag tggag 25

<210> SEQ ID NO 950
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 950
ccctgccctg cccaccgtga agtgg 25

<210> SEQ ID NO 951
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 951
gcccctgccc tgcccaccgt gaagt 25

<210> SEQ ID NO 952
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 952
ccgcccctgc cctgcccacc gtgaa 25

<210> SEQ ID NO 953
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 953
ccccgcccct gccctgccca ccgtg 25

<210> SEQ ID NO 954
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 954
gcccccgccc ctgccctgcc caccg 25

<210> SEQ ID NO 955
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 955
ccgcccccgc ccctgccctg cccac 25

<210> SEQ ID NO 956
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 956
cgccgccccc gcccctgccc tgccc 25

<210> SEQ ID NO 957
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 957
gccgccgccc ccgcccctgc cctgc 25

<210> SEQ ID NO 958
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 958
tggccgccgc ccccgcccct gccct 25

<210> SEQ ID NO 959
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 959
cctggccgcc gcccccgccc ctgcc 25

<210> SEQ ID NO 960
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 960
gccctggccg ccgcccccgc ccctg 25

<210> SEQ ID NO 961
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 961
ctgccctggc cgccgccccc gcccc 25

<210> SEQ ID NO 962
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 962
ctctgccctg gccgccgccc ccgcc 25

<210> SEQ ID NO 963
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 963
ccctctgccc tggccgccgc ccccg 25

<210> SEQ ID NO 964
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 964
caccctctgc cctggccgcc gcccc 25

<210> SEQ ID NO 965
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 965
cgcaccctct gccctggccg ccgcc 25

<210> SEQ ID NO 966
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 966
cgcgcaccct ctgccctggc cgccg 25

<210> SEQ ID NO 967
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 967
cccccgcccc tgccctgccc accgt 25

<210> SEQ ID NO 968
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 968
cgcccccgcc cctgccctgc ccacc 25

<210> SEQ ID NO 969
<211> LENGTH: 25
<212> TYPE: DNA
<213> ORGANISM: Artificial Sequence
<220> FEATURE:
<223> OTHER INFORMATION: AON sequence designed to block the region
surrounding the identified splice element (5' -> 3')

<400> SEQUENCE: 969
gccgcccccg cccctgccct gccca 25

<210> SEQ ID NO 970
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 970
ccgccgcccc cgcccctgcc ctgcc 25

<210> SEQ ID NO 971
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 971
ggccgccgcc cccgcccctg ccctg 25

<210> SEQ ID NO 972
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 972
ctggccgccg cccccgcccc tgccc 25

<210> SEQ ID NO 973
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 973
ccctggccgc cgcccccgcc cctgc 25

<210> SEQ ID NO 974
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 974
tgccctggcc gccgcccccg cccct 25

<210> SEQ ID NO 975
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 975
tctgccctgg ccgccgcccc cgccc 25

<210> SEQ ID NO 976
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 976
cctctgccct ggccgccgcc cccgc 25

<210> SEQ ID NO 977
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 977
accctctgcc ctggccgccg ccccc 25

<210> SEQ ID NO 978
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 978
gcaccctctg ccctggccgc cgccc 25

<210> SEQ ID NO 979
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 979
gcgcaccctc tgccctggcc gccgc 25

<210> SEQ ID NO 980
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 980
agagatgggg gtttattgat gttcc 25

<210> SEQ ID NO 981
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 981
gaagagatgg gggtttattg atgtt 25

<210> SEQ ID NO 982

<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 982
tagaagagat gggggtttat tgatg 25

<210> SEQ ID NO 983
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 983
tctagaagag atgggggttt attga 25

<210> SEQ ID NO 984
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 984
gatctagaag agatgggggt ttatt 25

<210> SEQ ID NO 985
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 985
ttgatctaga agagatgggg gttta 25

<210> SEQ ID NO 986
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 986
ctttgatcta gaagagatgg gggtt 25

<210> SEQ ID NO 987
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 987
atctttgatc tagaagagat ggggg 25

<210> SEQ ID NO 988
<211> LENGTH: 25

<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 988
ggatctttga tctagaagag atggg 25

<210> SEQ ID NO 989
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 989
ctggatcttt gatctagaag agatg 25

<210> SEQ ID NO 990
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 990
agctggatct ttgatctaga agaga 25

<210> SEQ ID NO 991
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 991
ttagctggat ctttgatcta gaaga 25

<210> SEQ ID NO 992
<211> LENGTH: 25
<212> TYPE: DNA
<213> ORGANISM: Artificial Sequence
<220> FEATURE:
<223> OTHER INFORMATION: AON sequence designed to block the region surrounding the identified splice element (5' -> 3')

<400> SEQUENCE: 992
tgttagctgg atctttgatc tagaa 25

<210> SEQ ID NO 993
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 993
ctggaaggga agcagctctg gggtt 25

<210> SEQ ID NO 994
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 994
tctggaaggg aagcagctct ggggt 25

<210> SEQ ID NO 995
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 995
atctggaagg gaagcagctc tgggg 25

<210> SEQ ID NO 996
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 996
catctggaag ggaagcagct ctggg 25

<210> SEQ ID NO 997
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 997
acatctggaa gggaagcagc tctgg 25

<210> SEQ ID NO 998
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 998
cacatctgga agggaagcag ctctg 25

<210> SEQ ID NO 999
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 999
ccacatctgg aagggaagca gctct 25

<210> SEQ ID NO 1000
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1000
accacatctg gaagggaagc agctc 25

<210> SEQ ID NO 1001
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1001
gaccacatct ggaagggaag cagct 25

<210> SEQ ID NO 1002
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1002
ggaccacatc tggaagggaa gcagc 25

<210> SEQ ID NO 1003
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1003
aggaccacat ctggaaggga agcag 25

<210> SEQ ID NO 1004
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1004
caggaccaca tctggaaggg aagca 25

<210> SEQ ID NO 1005
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1005
gcaggaccac atctggaagg gaagc 25

<210> SEQ ID NO 1006
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1006
tgcaggacca catctggaag ggaag 25

<210> SEQ ID NO 1007
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1007
ctgcaggacc acatctggaa gggaa 25

<210> SEQ ID NO 1008
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1008
gctgcaggac cacatctgga aggga 25

<210> SEQ ID NO 1009
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1009
ggctgcagga ccacatctgg aaggg 25

<210> SEQ ID NO 1010
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1010
cggctgcagg accacatctg gaagg 25

<210> SEQ ID NO 1011
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1011
tcggctgcag gaccacatct ggaag 25

<210> SEQ ID NO 1012
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1012
ctcggctgca ggaccacatc tggaa 25

<210> SEQ ID NO 1013
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1013
gctcggctgc aggaccacat ctgga 25

<210> SEQ ID NO 1014

<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1014
ggctcggctg caggaccaca tctgg 25

<210> SEQ ID NO 1015
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1015
gggctcggct gcaggaccac atctg 25

<210> SEQ ID NO 1016
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1016
agggctcggc tgcaggacca catct 25

<210> SEQ ID NO 1017
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1017
cagggctcgg ctgcaggacc acatc 25

<210> SEQ ID NO 1018
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1018
gcagggctcg gctgcaggac cacat 25

<210> SEQ ID NO 1019
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1019
ggcagggctc ggctgcagga ccaca 25

<210> SEQ ID NO 1020
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1020
gggcagggct cggctgcagg accac 25

<210> SEQ ID NO 1021
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1021
agggcagggc tcggctgcag gacca 25

<210> SEQ ID NO 1022
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1022
aagggcaggg ctcggctgca ggacc 25

<210> SEQ ID NO 1023
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1023
taagggcagg gctcggctgc aggac 25

<210> SEQ ID NO 1024
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1024
ctaagggcag ggctcggctg cagga 25

<210> SEQ ID NO 1025
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1025
gctaagggca gggctcggct gcagg 25

<210> SEQ ID NO 1026
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1026
agctaagggc agggctcggc tgcag 25

<210> SEQ ID NO 1027
<211> LENGTH: 25
<212> TYPE: DNA

<213> ORGANISM: Artificial Sequence
<220> FEATURE:
<223> OTHER INFORMATION: AON sequence 5' -> 3'

<400> SEQUENCE: 1027
cagctaaggg cagggctcgg ctgca 25

<210> SEQ ID NO 1028
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1028
ccagctaagg gcagggctcg gctgc 25

<210> SEQ ID NO 1029
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1029
tccagctaag ggcagggctc ggctg 25

<210> SEQ ID NO 1030
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1030
ctccagctaa gggcagggct cggct 25

<210> SEQ ID NO 1031
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1031
cctccagcta agggcagggc tcggc 25

<210> SEQ ID NO 1032
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1032
acctccagct aagggcaggg ctcgg 25

<210> SEQ ID NO 1033
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1033
gacctccagc taagggcagg gctcg 25

<210> SEQ ID NO 1034
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1034
gacctccagc taagggcagg gctcg 25

<210> SEQ ID NO 1035
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1035
tcgacctcca gctaagggca gggct 25

<210> SEQ ID NO 1036
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1036
gtcgacctcc agctaagggc agggc 25

<210> SEQ ID NO 1037
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1037
tgtcgacctc cagctaaggg caggg 25

<210> SEQ ID NO 1038
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1038
ctgtcgacct ccagctaagg gcagg 25

<210> SEQ ID NO 1039
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1039
cctgtcgacc tccagctaag ggcag 25

<210> SEQ ID NO 1040
<211> LENGTH: 25
<212> TYPE: DNA
<213> ORGANISM: Artificial Sequence
<220> FEATURE:

<223> OTHER INFORMATION: AON sequence 5' -> 3'

<400> SEQUENCE: 1040
acctgtcgac ctccagctaa gggca 25

<210> SEQ ID NO 1041
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1041
cacctgtcga cctccagcta agggc 25

<210> SEQ ID NO 1042
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1042
ccacctgtcg acctccagct aaggg 25

<210> SEQ ID NO 1043
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1043
cccacctgtc gacctccagc taagg 25

<210> SEQ ID NO 1044
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1044
tcccacctgt cgacctccag ctaag 25

<210> SEQ ID NO 1045
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1045
atcccacctg tcgacctcca gctaa 25

<210> SEQ ID NO 1046
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1046
gatcccacct gtcgacctcc agcta 25

<210> SEQ ID NO 1047
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1047
ggatcccacc tgtcgacctc cagct 25

<210> SEQ ID NO 1048
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1048
aggatcccac ctgtcgacct ccagc 25

<210> SEQ ID NO 1049
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1049
caggatccca cctgtcgacc tccag 25

<210> SEQ ID NO 1050
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1050
ccaggatccc acctgtcgac ctcca 25

<210> SEQ ID NO 1051
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1051
tccaggatcc cacctgtcga cctcc 25

<210> SEQ ID NO 1052
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1052
atccaggatc ccacctgtcg acctc 25

<210> SEQ ID NO 1053
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1053
catccaggat cccacctgtc gacct 25

<210> SEQ ID NO 1054
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1054
acatccagga tcccacctgt cgacc 25

<210> SEQ ID NO 1055
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1055
gacatccagg atcccacctg tcgac 25

<210> SEQ ID NO 1056
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1056
agacatccag gatcccacct gtcga 25

<210> SEQ ID NO 1057
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1057
tagacatcca ggatcccacc tgtcg 25

<210> SEQ ID NO 1058
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1058
gtagacatcc aggatcccac ctgtc 25

<210> SEQ ID NO 1059
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1059
tgtagacatc caggatccca cctgt 25

<210> SEQ ID NO 1060
<211> LENGTH: 25

<212> TYPE: DNA
<213> ORGANISM: Artificial Sequence
<220> FEATURE:
<223> OTHER INFORMATION: AON sequence 5' -> 3'

<400> SEQUENCE: 1060
atgtagacat ccaggatccc acctg 25

<210> SEQ ID NO 1061
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1061
gatgtagaca tccaggatcc cacct 25

<210> SEQ ID NO 1062
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1062
agatgtagac atccaggatc ccacc 25

<210> SEQ ID NO 1063
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1063
aagatgtaga catccaggat cccac 25

<210> SEQ ID NO 1064
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1064
gaagatgtag acatccagga tccca 25

<210> SEQ ID NO 1065
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1065
ggaagatgta gacatccagg atccc 25

<210> SEQ ID NO 1066
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1066
aggaagatgt agacatccag gatcc 25

<210> SEQ ID NO 1067
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1067
caggaagatg tagacatcca ggatc 25

<210> SEQ ID NO 1068
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1068
ccaggaagat gtagacatcc aggat 25

<210> SEQ ID NO 1069
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1069
cccaggaaga tgtagacatc cagga 25

<210> SEQ ID NO 1070
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1070
gcccaggaag atgtagacat ccagg 25

<210> SEQ ID NO 1071
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1071
ggcccaggaa gatgtagaca tccag 25

<210> SEQ ID NO 1072
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1072
gggcccagga agatgtagac atcca 25

<210> SEQ ID NO 1073
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1073
tgggcccagg aagatgtaga catcc 25

<210> SEQ ID NO 1074
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1074
ctgggcccag gaagatgtag acatc 25

<210> SEQ ID NO 1075
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1075
tctgggccca ggaagatgta gacat 25

<210> SEQ ID NO 1076
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1076
ctctgggccc aggaagatgt agaca 25

<210> SEQ ID NO 1077
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1077
gctctgggcc caggaagatg tagac 25

<210> SEQ ID NO 1078
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1078
ggctctgggc ccaggaagat gtaga 25

<210> SEQ ID NO 1079
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1079
gggctctggg cccaggaaga tgtag 25

<210> SEQ ID NO 1080
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1080
tgggctctgg gcccaggaag atgta 25

<210> SEQ ID NO 1081
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1081
ttgggctctg ggcccaggaa gatgt 25

<210> SEQ ID NO 1082
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1082
cttgggctct gggcccagga agatg 25

<210> SEQ ID NO 1083
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1083
tcttgggctc tgggcccagg aagat 25

<210> SEQ ID NO 1084
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1084
ctcttgggct ctgggcccag gaaga 25

<210> SEQ ID NO 1085
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1085
gctcttgggc tctgggccca ggaag 25

<210> SEQ ID NO 1086
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1086
cgctcttggg ctctgggccc aggaa 25

<210> SEQ ID NO 1087
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1087
acgctcttgg gctctgggcc cagga 25

<210> SEQ ID NO 1088
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1088
cacgctcttg ggctctgggc ccagg 25

<210> SEQ ID NO 1089
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1089
ccacgctctt gggctctggg cccag 25

<210> SEQ ID NO 1090
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1090
accacgctct tgggctctgg gccca 25

<210> SEQ ID NO 1091
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1091
caccacgctc ttgggctctg ggccc 25

<210> SEQ ID NO 1092
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1092
gcaccacgct cttgggctct gggcc 25

<210> SEQ ID NO 1093

<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1093
tgcaccacgc tcttgggctc tgggc 25

<210> SEQ ID NO 1094
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1094
ctgcaccacg ctcttgggct ctggg 25

<210> SEQ ID NO 1095
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1095
gctgcaccac gctcttgggc tctgg 25

<210> SEQ ID NO 1096
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1096
tgctgcacca cgctcttggg ctctg 25

<210> SEQ ID NO 1097
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1097
ctgctgcacc acgctcttgg gctct 25

<210> SEQ ID NO 1098
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1098
actgctgcac cacgctcttg ggctc 25

<210> SEQ ID NO 1099
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1099
tactgctgca ccacgctctt gggct 25

<210> SEQ ID NO 1100
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1100
gtactgctgc accacgctct tgggc 25

<210> SEQ ID NO 1101
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1101
ggtactgctg caccacgctc ttggg 25

<210> SEQ ID NO 1102
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1102
aggtactgct gcaccacgct cttgg 25

<210> SEQ ID NO 1103
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1103
caggtactgc tgcaccacgc tcttg 25

<210> SEQ ID NO 1104
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1104
ccaggtactg ctgcaccacg ctctt 25

<210> SEQ ID NO 1105
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1105
tccaggtact gctgcaccac gctct 25

<210> SEQ ID NO 1106
<211> LENGTH: 25
<212> TYPE: DNA

<213> ORGANISM: Artificial Sequence
<220> FEATURE:
<223> OTHER INFORMATION: AON sequence 5' -> 3'

<400> SEQUENCE: 1106
gtccaggtac tgctgcacca cgctc 25

<210> SEQ ID NO 1107
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1107
cgtccaggta ctgctgcacc acgct 25

<210> SEQ ID NO 1108
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1108
acgtccaggt actgctgcac cacgc 25

<210> SEQ ID NO 1109
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1109
aacgtccagg tactgctgca ccacg 25

<210> SEQ ID NO 1110
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1110
caacgtccag gtactgctgc accac 25

<210> SEQ ID NO 1111
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1111
acaacgtcca ggtactgctg cacca 25

<210> SEQ ID NO 1112
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1112
cacaacgtcc aggtactgct gcacc 25

<210> SEQ ID NO 1113
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1113
ccacaacgtc caggtactgc tgcac 25

<210> SEQ ID NO 1114
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1114
cccacaacgt ccaggtactg ctgca 25

<210> SEQ ID NO 1115
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1115
acccacaacg tccaggtact gctgc 25

<210> SEQ ID NO 1116
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1116
tacccacaac gtccaggtac tgctg 25

<210> SEQ ID NO 1117
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1117
ctacccacaa cgtccaggta ctgct 25

<210> SEQ ID NO 1118
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1118
cctacccaca acgtccaggt actgc 25

<210> SEQ ID NO 1119
<211> LENGTH: 25
<212> TYPE: DNA
<213> ORGANISM: Artificial Sequence
<220> FEATURE:

<223> OTHER INFORMATION: AON sequence 5' -> 3'

<400> SEQUENCE: 1119
ccctacccac aacgtccagg tactg 25

<210> SEQ ID NO 1120
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1120
gccctaccca caacgtccag gtact 25

<210> SEQ ID NO 1121
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1121
ggccctaccc acaacgtcca ggtac 25

<210> SEQ ID NO 1122
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1122
aggccctacc cacaacgtcc aggta 25

<210> SEQ ID NO 1123
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1123
caggccctac ccacaacgtc caggt 25

<210> SEQ ID NO 1124
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1124
gcaggcccta cccacaacgt ccagg 25

<210> SEQ ID NO 1125
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1125
agcaggccct acccacaacg tccag 25

<210> SEQ ID NO 1126
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1126
gagcaggccc tacccacaac gtcca 25

<210> SEQ ID NO 1127
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1127
ggagcaggcc ctacccacaa cgtcc 25

<210> SEQ ID NO 1128
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1128
gggagcaggc cctacccaca acgtc 25

<210> SEQ ID NO 1129
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1129
agggagcagg ccctacccac aacgt 25

<210> SEQ ID NO 1130
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1130
cagggagcag gccctaccca caacg 25

<210> SEQ ID NO 1131
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1131
ccagggagca ggccctaccc acaac 25

<210> SEQ ID NO 1132
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1132
gccagggagc aggccctacc cacaa 25

<210> SEQ ID NO 1133
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1133
ggccagggag caggccctac ccaca 25

<210> SEQ ID NO 1134
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1134
cggccaggga gcaggcccta cccac 25

<210> SEQ ID NO 1135
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1135
gcggccaggg agcaggccct accca 25

<210> SEQ ID NO 1136
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1136
cgcggccagg gagcaggccc taccc 25

<210> SEQ ID NO 1137
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1137
ccgcggccag ggagcaggcc ctacc 25

<210> SEQ ID NO 1138
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1138
gccgcggcca gggagcaggc cctac 25

<210> SEQ ID NO 1139
<211> LENGTH: 25

<212> TYPE: DNA
<213> ORGANISM: Artificial Sequence
<220> FEATURE:
<223> OTHER INFORMATION: AON sequence 5' -> 3'

<400> SEQUENCE: 1139
ggccgcggcc agggagcagg cccta 25

<210> SEQ ID NO 1140
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1140
gggccgcggc cagggagcag gccct 25

<210> SEQ ID NO 1141
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1141
ggggccgcgg ccagggagca ggccc 25

<210> SEQ ID NO 1142
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1142
gggggccgcg gccagggagc aggcc 25

<210> SEQ ID NO 1143
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1143
cgggggccgc ggccagggag caggc 25

<210> SEQ ID NO 1144
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1144
gcgggggccg cggccaggga gcagg 25

<210> SEQ ID NO 1145
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1145
ggcgggggcc gcggccaggg agcag 25

<210> SEQ ID NO 1146
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1146
gggcgggggc cgcggccagg gagca 25

<210> SEQ ID NO 1147
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1147
ggggcggggg ccgcggccag ggagc 25

<210> SEQ ID NO 1148
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1148
tggggcgggg gccgcggcca gggag 25

<210> SEQ ID NO 1149
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1149
ttggggcggg ggccgcggcc aggga 25

<210> SEQ ID NO 1150
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1150
cttggggcgg gggccgcggc caggg 25

<210> SEQ ID NO 1151
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1151
ccttggggcg ggggccgcgg ccagg 25

<210> SEQ ID NO 1152
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1152
gccttggggc gggggccgcg gccag 25

<210> SEQ ID NO 1153
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1153
agccttgggg cgggggccgc ggcca 25

<210> SEQ ID NO 1154
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1154
gagccttggg gcgggggccg cggcc 25

<210> SEQ ID NO 1155
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1155
ggagccttgg ggcgggggcc gcggc 25

<210> SEQ ID NO 1156
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1156
gggagccttg gggcgggggc cgcgg 25

<210> SEQ ID NO 1157
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1157
agggagcctt ggggcggggg ccgcg 25

<210> SEQ ID NO 1158
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1158
gagggagcct tggggcgggg gccgc 25

<210> SEQ ID NO 1159
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1159
ggagggagcc ttggggcggg ggccg 25

<210> SEQ ID NO 1160
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1160
aggagggagc cttggggcgg gggcc 25

<210> SEQ ID NO 1161
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1161
gaggagggag ccttggggcg ggggc 25

<210> SEQ ID NO 1162
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1162
ggaggaggga gccttggggc ggggg 25

<210> SEQ ID NO 1163
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1163
gggaggaggg agccttgggg cgggg 25

<210> SEQ ID NO 1164
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1164
agggaggagg gagccttggg gcggg 25

<210> SEQ ID NO 1165
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1165
gagggaggag ggagccttgg ggcgg 25

<210> SEQ ID NO 1166
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1166
ggagggagga gggagccttg gggcg 25

<210> SEQ ID NO 1167
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1167
gggagggagg agggagcctt ggggc 25

<210> SEQ ID NO 1168
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1168
agggagggag gagggagcct tgggg 25

<210> SEQ ID NO 1169
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1169
gagggaggga ggagggagcc ttggg 25

<210> SEQ ID NO 1170
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1170
tgagggaggg aggagggagc cttgg 25

<210> SEQ ID NO 1171
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1171
atgagggagg gaggagggag ccttg 25

<210> SEQ ID NO 1172

<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1172
catgagggag ggaggaggga gcctt 25

<210> SEQ ID NO 1173
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1173
tcatgaggga gggaggaggg agcct 25

<210> SEQ ID NO 1174
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1174
ttcatgaggg agggaggagg gagcc 25

<210> SEQ ID NO 1175
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1175
cttcatgagg gagggaggag ggagc 25

<210> SEQ ID NO 1176
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1176
acttcatgag ggagggagga gggag 25

<210> SEQ ID NO 1177
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1177
gacttcatga gggagggagg aggga 25

<210> SEQ ID NO 1178
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1178
cgacttcatg agggagggag gaggg 25

<210> SEQ ID NO 1179
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1179
ccgacttcat gagggaggga ggagg 25

<210> SEQ ID NO 1180
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1180
gccgacttca tgagggaggg aggag 25

<210> SEQ ID NO 1181
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1181
cgccgacttc atgagggagg gagga 25

<210> SEQ ID NO 1182
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1182
acgccgactt catgagggag ggagg 25

<210> SEQ ID NO 1183
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1183
aacgccgact tcatgaggga gggag 25

<210> SEQ ID NO 1184
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1184
caacgccgac ttcatgaggg aggga 25

<210> SEQ ID NO 1185
<211> LENGTH: 25
<212> TYPE: DNA

<213> ORGANISM: Artificial Sequence
<220> FEATURE:
<223> OTHER INFORMATION: AON sequence 5' -> 3'

<400> SEQUENCE: 1185
ccaacgccga cttcatgagg gaggg 25

<210> SEQ ID NO 1186
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1186
gccaacgccg acttcatgag ggagg 25

<210> SEQ ID NO 1187
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1187
ggccaacgcc gacttcatga gggag 25

<210> SEQ ID NO 1188
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1188
aggccaacgc cgacttcatg aggga 25

<210> SEQ ID NO 1189
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1189
caggccaacg ccgacttcat gaggg 25

<210> SEQ ID NO 1190
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1190
gcaggccaac gccgacttca tgagg 25

<210> SEQ ID NO 1191
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1191
tgcaggccaa cgccgacttc atgag 25

<210> SEQ ID NO 1192
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1192
ctgcaggcca acgccgactt catga 25

<210> SEQ ID NO 1193
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1193
cctgcaggcc aacgccgact tcatg 25

<210> SEQ ID NO 1194
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1194
tcctgcaggc caacgccgac ttcat 25

<210> SEQ ID NO 1195
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1195
atcctgcagg ccaacgccga cttca 25

<210> SEQ ID NO 1196
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1196
tatcctgcag gccaacgccg acttc 25

<210> SEQ ID NO 1197
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1197
gtatcctgca ggccaacgcc gactt 25

<210> SEQ ID NO 1198
<211> LENGTH: 25
<212> TYPE: DNA
<213> ORGANISM: Artificial Sequence
<220> FEATURE:

<223> OTHER INFORMATION: AON sequence 5' -> 3'

<400> SEQUENCE: 1198
ggtatcctgc aggccaacgc cgact 25

<210> SEQ ID NO 1199
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1199
gggtatcctg caggccaacg ccgac 25

<210> SEQ ID NO 1200
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1200
cgggtatcct gcaggccaac gccga 25

<210> SEQ ID NO 1201
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1201
acgggtatcc tgcaggccaa cgccg 25

<210> SEQ ID NO 1202
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1202
aacgggtatc ctgcaggcca acgcc 25

<210> SEQ ID NO 1203
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1203
gaacgggtat cctgcaggcc aacgc 25

<210> SEQ ID NO 1204
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1204
tgaacgggta tcctgcaggc caacg 25

<210> SEQ ID NO 1205
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1205
atgaacgggt atcctgcagg ccaac 25

<210> SEQ ID NO 1206
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1206
catgaacggg tatcctgcag gccaa 25

<210> SEQ ID NO 1207
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1207
gcatgaacgg gtatcctgca ggcca 25

<210> SEQ ID NO 1208
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1208
ggcatgaacg ggtatcctgc aggcc 25

<210> SEQ ID NO 1209
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1209
cggcatgaac gggtatcctg caggc 25

<210> SEQ ID NO 1210
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1210
gcggcatgaa cgggtatcct gcagg 25

<210> SEQ ID NO 1211
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1211
ggcggcatga acgggtatcc tgcag 25

<210> SEQ ID NO 1212
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1212
tggcggcatg aacgggtatc ctgca 25

<210> SEQ ID NO 1213
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1213
atggcggcat gaacgggtat cctgc 25

<210> SEQ ID NO 1214
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1214
tatggcggca tgaacgggta tcctg 25

<210> SEQ ID NO 1215
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1215
gtatggcggc atgaacgggt atcct 25

<210> SEQ ID NO 1216
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1216
agtatggcgg catgaacggg tatcc 25

<210> SEQ ID NO 1217
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1217
cagtatggcg gcatgaacgg gtatc 25

<210> SEQ ID NO 1218
<211> LENGTH: 25

<212> TYPE: DNA
<213> ORGANISM: Artificial Sequence
<220> FEATURE:
<223> OTHER INFORMATION: AON sequence 5' -> 3'

<400> SEQUENCE: 1218
ccagtatggc ggcatgaacg ggtat 25

<210> SEQ ID NO 1219
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1219
cccagtatgg cggcatgaac gggta 25

<210> SEQ ID NO 1220
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1220
ccccagtatg gcggcatgaa cgggt 25

<210> SEQ ID NO 1221
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1221
gccccagtat ggcggcatga acggg 25

<210> SEQ ID NO 1222
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1222
ggccccagta tggcggcatg aacgg 25

<210> SEQ ID NO 1223
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1223
aggccccagt atggcggcat gaacg 25

<210> SEQ ID NO 1224
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1224
caggccccag tatggcggca tgaac 25

<210> SEQ ID NO 1225
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1225
ccaggcccca gtatggcggc atgaa 25

<210> SEQ ID NO 1226
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1226
cccaggcccc agtatggcgg catga 25

<210> SEQ ID NO 1227
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1227
gcccaggccc cagtatggcg gcatg 25

<210> SEQ ID NO 1228
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1228
agcccaggcc ccagtatggc ggcat 25

<210> SEQ ID NO 1229
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1229
aagcccaggc cccagtatgg cggca 25

<210> SEQ ID NO 1230
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1230
gaagcccagg ccccagtatg gcggc 25

<210> SEQ ID NO 1231
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1231
ggaagcccag gccccagtat ggcgg 25

<210> SEQ ID NO 1232
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1232
tggaagccca ggccccagta tggcg 25

<210> SEQ ID NO 1233
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1233
gtggaagccc aggccccagt atggc 25

<210> SEQ ID NO 1234
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1234
ggtggaagcc caggccccag tatgg 25

<210> SEQ ID NO 1235
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1235
aggtggaagc ccaggcccca gtatg 25

<210> SEQ ID NO 1236
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1236
caggtggaag cccaggcccc agtat 25

<210> SEQ ID NO 1237
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1237
acaggtggaa gcccaggccc cagta 25

<210> SEQ ID NO 1238
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1238
cacaggtgga agcccaggcc ccagt 25

<210> SEQ ID NO 1239
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1239
gcacaggtgg aagcccaggc cccag 25

<210> SEQ ID NO 1240
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1240
ggcacaggtg gaagcccagg cccca 25

<210> SEQ ID NO 1241
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1241
cggcacaggt ggaagcccag gcccc 25

<210> SEQ ID NO 1242
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1242
gcggcacagg tggaagccca ggccc 25

<210> SEQ ID NO 1243
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1243
agcggcacag gtggaagccc aggcc 25

<210> SEQ ID NO 1244
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1244
cagcggcaca ggtggaagcc caggc 25

<210> SEQ ID NO 1245
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1245
ccagcggcac aggtggaagc ccagg 25

<210> SEQ ID NO 1246
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1246
cccagcggca caggtggaag cccag 25

<210> SEQ ID NO 1247
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1247
ccccagcggc acaggtggaa gccca 25

<210> SEQ ID NO 1248
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1248
gccccagcgg cacaggtgga agccc 25

<210> SEQ ID NO 1249
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1249
agccccagcg gcacaggtgg aagcc 25

<210> SEQ ID NO 1250
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1250
tagccccagc ggcacaggtg gaagc 25

<210> SEQ ID NO 1251

<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1251
gtagccccag cggcacaggt ggaag 25

<210> SEQ ID NO 1252
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1252
agtagcccca gcggcacagg tggaa 25

<210> SEQ ID NO 1253
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1253
gagtagcccc agcggcacag gtgga 25

<210> SEQ ID NO 1254
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1254
ggagtagccc cagcggcaca ggtgg 25

<210> SEQ ID NO 1255
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1255
aggagtagcc ccagcggcac aggtg 25

<210> SEQ ID NO 1256
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1256
gaggagtagc cccagcggca caggt 25

<210> SEQ ID NO 1257
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1257
ggaggagtag ccccagcggc acagg 25

<210> SEQ ID NO 1258
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1258
tggaggagta gccccagcgg cacag 25

<210> SEQ ID NO 1259
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1259
gtggaggagt agccccagcg gcaca 25

<210> SEQ ID NO 1260
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1260
ggtggaggag tagccccagc ggcac 25

<210> SEQ ID NO 1261
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1261
cggtggagga gtagccccag cggca 25

<210> SEQ ID NO 1262
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1262
gcggtggagg agtagcccca gcggc 25

<210> SEQ ID NO 1263
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1263
agcggtggag gagtagcccc agcgg 25

<210> SEQ ID NO 1264
<211> LENGTH: 25
<212> TYPE: DNA

<213> ORGANISM: Artificial Sequence
<220> FEATURE:
<223> OTHER INFORMATION: AON sequence 5' -> 3'

<400> SEQUENCE: 1264
tagcggtgga ggagtagccc cagcg 25

<210> SEQ ID NO 1265
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1265
atagcggtgg aggagtagcc ccagc 25

<210> SEQ ID NO 1266
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1266
gatagcggtg gaggagtagc cccag 25

<210> SEQ ID NO 1267
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1267
tgatagcggt ggaggagtag cccca 25

<210> SEQ ID NO 1268
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1268
gtgatagcgg tggaggagta gcccc 25

<210> SEQ ID NO 1269
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1269
ggtgatagcg gtggaggagt agccc 25

<210> SEQ ID NO 1270
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1270
gggtgatagc ggtggaggag tagcc 25

<210> SEQ ID NO 1271
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1271
cgggtgatag cggtggagga gtagc 25

<210> SEQ ID NO 1272
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1272
gcgggtgata gcggtggagg agtag 25

<210> SEQ ID NO 1273
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1273
ggcgggtgat agcggtggag gagta 25

<210> SEQ ID NO 1274
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1274
tggcgggtga tagcggtgga ggagt 25

<210> SEQ ID NO 1275
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1275
ctggcgggtg atagcggtgg aggag 25

<210> SEQ ID NO 1276
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1276
cctggcgggt gatagcggtg gagga 25

<210> SEQ ID NO 1277
<211> LENGTH: 25
<212> TYPE: DNA
<213> ORGANISM: Artificial Sequence
<220> FEATURE:

<223> OTHER INFORMATION: AON sequence 5' -> 3'

<400> SEQUENCE: 1277
acctggcggg tgatagcggt ggagg 25

<210> SEQ ID NO 1278
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1278
cacctggcgg gtgatagcgg tggag 25

<210> SEQ ID NO 1279
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1279
ccacctggcg ggtgatagcg gtgga 25

<210> SEQ ID NO 1280
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1280
accacctggc gggtgatagc ggtgg 25

<210> SEQ ID NO 1281
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1281
caccacctgg cgggtgatag cggtg 25

<210> SEQ ID NO 1282
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1282
ccaccacctg gcgggtgata gcggt 25

<210> SEQ ID NO 1283
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1283
tccaccacct ggcgggtgat agcgg 25

<210> SEQ ID NO 1284
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1284
ctccaccacc tggcgggtga tagcg 25

<210> SEQ ID NO 1285
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1285
tctccaccac ctggcgggtg atagc 25

<210> SEQ ID NO 1286
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1286
ttctccacca cctggcgggt gatag 25

<210> SEQ ID NO 1287
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1287
gttctccacc acctggcggg tgata 25

<210> SEQ ID NO 1288
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1288
tgttctccac cacctggcgg gtgat 25

<210> SEQ ID NO 1289
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1289
atgttctcca ccacctggcg ggtga 25

<210> SEQ ID NO 1290
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1290
catgttctcc accacctggc gggtg 25

<210> SEQ ID NO 1291
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1291
tcatgttctc caccacctgg cgggt 25

<210> SEQ ID NO 1292
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1292
gtcatgttct ccaccacctg gcggg 25

<210> SEQ ID NO 1293
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1293
ggtcatgttc tccaccacct ggcgg 25

<210> SEQ ID NO 1294
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1294
tggtcatgtt ctccaccacc tggcg 25

<210> SEQ ID NO 1295
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1295
ctggtcatgt tctccaccac ctggc 25

<210> SEQ ID NO 1296
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1296
cctggtcatg ttctccacca cctgg 25

<210> SEQ ID NO 1297
<211> LENGTH: 25

<212> TYPE: DNA
<213> ORGANISM: Artificial Sequence
<220> FEATURE:
<223> OTHER INFORMATION: AON sequence 5' -> 3'

<400> SEQUENCE: 1297
ccctggtcat gttctccacc acctg 25

<210> SEQ ID NO 1298
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1298
gccctggtca tgttctccac cacct 25

<210> SEQ ID NO 1299
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1299
ggccctggtc atgttctcca ccacc 25

<210> SEQ ID NO 1300
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1300
gggccctggt catgttctcc accac 25

<210> SEQ ID NO 1301
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1301
tgggccctgg tcatgttctc cacca 25

<210> SEQ ID NO 1302
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1302
gtgggccctg gtcatgttct ccacc 25

<210> SEQ ID NO 1303
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1303
agtgggccct ggtcatgttc tccac 25

<210> SEQ ID NO 1304
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1304
aagtgggccc tggtcatgtt ctcca 25

<210> SEQ ID NO 1305
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1305
gaagtgggcc ctggtcatgt tctcc 25

<210> SEQ ID NO 1306
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1306
ggaagtgggc cctggtcatg ttctc 25

<210> SEQ ID NO 1307
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1307
gggaagtggg ccctggtcat gttct 25

<210> SEQ ID NO 1308
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1308
ggggaagtgg gccctggtca tgttc 25

<210> SEQ ID NO 1309
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1309
gggggaagtg ggccctggtc atgtt 25

<210> SEQ ID NO 1310
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1310
agggggaagt gggccctggt catgt 25

<210> SEQ ID NO 1311
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1311
cagggggaag tgggccctgg tcatg 25

<210> SEQ ID NO 1312
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1312
ccagggggaa gtgggccctg gtcat 25

<210> SEQ ID NO 1313
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1313
accaggggga agtgggccct ggtca 25

<210> SEQ ID NO 1314
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1314
caccaggggg aagtgggccc tggtc 25

<210> SEQ ID NO 1315
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1315
tcaccagggg gaagtgggcc ctggt 25

<210> SEQ ID NO 1316
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1316
ctcaccaggg ggaagtgggc cctgg 25

<210> SEQ ID NO 1317
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1317
actcaccagg gggaagtggg ccctg 25

<210> SEQ ID NO 1318
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1318
aactcaccag ggggaagtgg gccct 25

<210> SEQ ID NO 1319
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1319
caactcacca gggggaagtg ggccc 25

<210> SEQ ID NO 1320
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1320
ccaactcacc agggggaagt gggcc 25

<210> SEQ ID NO 1321
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1321
cccaactcac cagggggaag tgggc 25

<210> SEQ ID NO 1322
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1322
ccccaactca ccagggggaa gtggg 25

<210> SEQ ID NO 1323
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1323
accccaactc accaggggga agtgg 25

<210> SEQ ID NO 1324
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1324
caccccaact caccaggggg aagtg 25

<210> SEQ ID NO 1325
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1325
ccaccccaac tcaccagggg gaagt 25

<210> SEQ ID NO 1326
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1326
accaccccaa ctcaccaggg ggaag 25

<210> SEQ ID NO 1327
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1327
caccacccca actcaccagg gggaa 25

<210> SEQ ID NO 1328
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1328
ccaccacccc aactcaccag gggga 25

<210> SEQ ID NO 1329
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1329
gccaccaccc caactcacca ggggg 25

<210> SEQ ID NO 1330

<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1330
tgccaccacc ccaactcacc agggg 25

<210> SEQ ID NO 1331
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1331
ctgccaccac cccaactcac caggg 25

<210> SEQ ID NO 1332
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1332
cctgccacca ccccaactca ccagg 25

<210> SEQ ID NO 1333
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1333
ccctgccacc accccaactc accag 25

<210> SEQ ID NO 1334
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1334
cccctgccac caccccaact cacca 25

<210> SEQ ID NO 1335
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1335
tcccctgcca ccaccccaac tcacc 25

<210> SEQ ID NO 1336
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 1336
ctcccctgcc accaccccaa ctcac 25

<210> SEQ ID NO 1337
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1337
aagggaagca gctctggggt t 21

<210> SEQ ID NO 1338
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1338
gaagggaagc agctctgggg t 21

<210> SEQ ID NO 1339
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1339
ggaagggaag cagctctggg g 21

<210> SEQ ID NO 1340
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1340
tggaagggaa gcagctctgg g 21

<210> SEQ ID NO 1341
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1341
ctggaaggga agcagctctg g 21

<210> SEQ ID NO 1342
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1342
tctggaaggg aagcagctct g 21

<210> SEQ ID NO 1343
<211> LENGTH: 21
<212> TYPE: DNA

<213> ORGANISM: Artificial Sequence
<220> FEATURE:
<223> OTHER INFORMATION: AON sequence 5' -> 3'

<400> SEQUENCE: 1343
atctggaagg gaagcagctc t 21

<210> SEQ ID NO 1344
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1344
catctggaag ggaagcagct c 21

<210> SEQ ID NO 1345
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1345
acatctggaa gggaagcagc t 21

<210> SEQ ID NO 1346
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1346
cacatctgga agggaagcag c 21

<210> SEQ ID NO 1347
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1347
ccacatctgg aagggaagca g 21

<210> SEQ ID NO 1348
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1348
accacatctg gaagggaagc a 21

<210> SEQ ID NO 1349
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1349
gaccacatct ggaagggaag c 21

<210> SEQ ID NO 1350
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1350
ggaccacatc tggaagggaa g 21

<210> SEQ ID NO 1351
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1351
aggaccacat ctggaaggga a 21

<210> SEQ ID NO 1352
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1352
caggaccaca tctggaaggg a 21

<210> SEQ ID NO 1353
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1353
gcaggaccac atctggaagg g 21

<210> SEQ ID NO 1354
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1354
tgcaggacca catctggaag g 21

<210> SEQ ID NO 1355
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1355
ctgcaggacc acatctggaa g 21

<210> SEQ ID NO 1356
<211> LENGTH: 21
<212> TYPE: DNA
<213> ORGANISM: Artificial Sequence
<220> FEATURE:

<223> OTHER INFORMATION: AON sequence 5' -> 3'

<400> SEQUENCE: 1356
gctgcaggac cacatctgga a 21

<210> SEQ ID NO 1357
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1357
ggctgcagga ccacatctgg a 21

<210> SEQ ID NO 1358
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1358
cggctgcagg accacatctg g 21

<210> SEQ ID NO 1359
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1359
tcggctgcag gaccacatct g 21

<210> SEQ ID NO 1360
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1360
ctcggctgca ggaccacatc t 21

<210> SEQ ID NO 1361
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1361
gctcggctgc aggaccacat c 21

<210> SEQ ID NO 1362
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1362
ggctcggctg caggaccaca t 21

<210> SEQ ID NO 1363
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1363
gggctcggct gcaggaccac a 21

<210> SEQ ID NO 1364
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1364
agggctcggc tgcaggacca c 21

<210> SEQ ID NO 1365
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1365
cagggctcgg ctgcaggacc a 21

<210> SEQ ID NO 1366
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1366
gcagggctcg gctgcaggac c 21

<210> SEQ ID NO 1367
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1367
ggcagggctc ggctgcagga c 21

<210> SEQ ID NO 1368
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1368
gggcagggct cggctgcagg a 21

<210> SEQ ID NO 1369
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1369
agggcagggc tcggctgcag g 21

<210> SEQ ID NO 1370
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1370
aagggcaggg ctcggctgca g 21

<210> SEQ ID NO 1371
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1371
taagggcagg gctcggctgc a 21

<210> SEQ ID NO 1372
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1372
ctaagggcag ggctcggctg c 21

<210> SEQ ID NO 1373
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1373
gctaagggca gggctcggct g 21

<210> SEQ ID NO 1374
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1374
agctaagggc agggctcggc t 21

<210> SEQ ID NO 1375
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1375
cagctaaggg cagggctcgg c 21

<210> SEQ ID NO 1376
<211> LENGTH: 21

<212> TYPE: DNA
<213> ORGANISM: Artificial Sequence
<220> FEATURE:
<223> OTHER INFORMATION: AON sequence 5' -> 3'

<400> SEQUENCE: 1376
ccagctaagg gcagggctcg g 21

<210> SEQ ID NO 1377
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1377
tccagctaag ggcagggctc g 21

<210> SEQ ID NO 1378
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1378
ctccagctaa gggcagggct c 21

<210> SEQ ID NO 1379
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1379
cctccagcta agggcagggc t 21

<210> SEQ ID NO 1380
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1380
acctccagct aagggcaggg c 21

<210> SEQ ID NO 1381
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1381
gacctccagc taagggcagg g 21

<210> SEQ ID NO 1382
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1382
cgacctccag ctaagggcag g 21

<210> SEQ ID NO 1383
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1383
tcgacctcca gctaagggca g 21

<210> SEQ ID NO 1384
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1384
gtcgacctcc agctaagggc a 21

<210> SEQ ID NO 1385
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1385
tgtcgacctc cagctaaggg c 21

<210> SEQ ID NO 1386
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1386
ctgtcgacct ccagctaagg g 21

<210> SEQ ID NO 1387
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1387
cctgtcgacc tccagctaag g 21

<210> SEQ ID NO 1388
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1388
acctgtcgac ctccagctaa g 21

<210> SEQ ID NO 1389
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1389
cacctgtcga cctccagcta a 21

<210> SEQ ID NO 1390
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1390
ccacctgtcg acctccagct a 21

<210> SEQ ID NO 1391
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1391
cccacctgtc gacctccagc t 21

<210> SEQ ID NO 1392
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1392
tcccacctgt cgacctccag c 21

<210> SEQ ID NO 1393
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1393
atcccacctg tcgacctcca g 21

<210> SEQ ID NO 1394
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1394
gatcccacct gtcgacctcc a 21

<210> SEQ ID NO 1395
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1395
ggatcccacc tgtcgacctc c 21

<210> SEQ ID NO 1396
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1396
aggatcccac ctgtcgacct c 21

<210> SEQ ID NO 1397
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1397
caggatccca cctgtcgacc t 21

<210> SEQ ID NO 1398
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1398
ccaggatccc acctgtcgac c 21

<210> SEQ ID NO 1399
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1399
tccaggatcc cacctgtcga c 21

<210> SEQ ID NO 1400
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1400
atccaggatc ccacctgtcg a 21

<210> SEQ ID NO 1401
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1401
catccaggat cccacctgtc g 21

<210> SEQ ID NO 1402
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1402
acatccagga tcccacctgt c 21

<210> SEQ ID NO 1403
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1403
gacatccagg atcccacctg t 21

<210> SEQ ID NO 1404
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1404
agacatccag gatcccacct g 21

<210> SEQ ID NO 1405
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1405
tagacatcca ggatcccacc t 21

<210> SEQ ID NO 1406
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1406
gtagacatcc aggatcccac c 21

<210> SEQ ID NO 1407
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1407
tgtagacatc caggatccca c 21

<210> SEQ ID NO 1408
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1408
atgtagacat ccaggatccc a 21

<210> SEQ ID NO 1409

<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1409
gatgtagaca tccaggatcc c 21

<210> SEQ ID NO 1410
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1410
agatgtagac atccaggatc c 21

<210> SEQ ID NO 1411
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1411
aagatgtaga catccaggat c 21

<210> SEQ ID NO 1412
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1412
gaagatgtag acatccagga t 21

<210> SEQ ID NO 1413
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1413
ggaagatgta gacatccagg a 21

<210> SEQ ID NO 1414
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1414
aggaagatgt agacatccag g 21

<210> SEQ ID NO 1415
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1415
caggaagatg tagacatcca g 21

<210> SEQ ID NO 1416
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1416
ccaggaagat gtagacatcc a 21

<210> SEQ ID NO 1417
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1417
cccaggaaga tgtagacatc c 21

<210> SEQ ID NO 1418
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1418
gcccaggaag atgtagacat c 21

<210> SEQ ID NO 1419
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1419
ggcccaggaa gatgtagaca t 21

<210> SEQ ID NO 1420
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1420
gggcccagga agatgtagac a 21

<210> SEQ ID NO 1421
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1421
tgggcccagg aagatgtaga c 21

<210> SEQ ID NO 1422
<211> LENGTH: 21
<212> TYPE: DNA

<213> ORGANISM: Artificial Sequence
<220> FEATURE:
<223> OTHER INFORMATION: AON sequence 5' -> 3'

<400> SEQUENCE: 1422
ctgggcccag gaagatgtag a 21

<210> SEQ ID NO 1423
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1423
tctgggccca ggaagatgta g 21

<210> SEQ ID NO 1424
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1424
ctctgggccc aggaagatgt a 21

<210> SEQ ID NO 1425
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1425
gctctgggcc caggaagatg t 21

<210> SEQ ID NO 1426
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1426
ggctctgggc ccaggaagat g 21

<210> SEQ ID NO 1427
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1427
gggctctggg cccaggaaga t 21

<210> SEQ ID NO 1428
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1428
tgggctctgg gcccaggaag a 21

<210> SEQ ID NO 1429
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1429
ttgggctctg ggcccaggaa g 21

<210> SEQ ID NO 1430
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1430
cttgggctct gggcccagga a 21

<210> SEQ ID NO 1431
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1431
tcttgggctc tgggcccagg a 21

<210> SEQ ID NO 1432
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1432
ctcttgggct ctgggcccag g 21

<210> SEQ ID NO 1433
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1433
gctcttgggc tctgggccca g 21

<210> SEQ ID NO 1434
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1434
cgctcttggg ctctgggccc a 21

<210> SEQ ID NO 1435
<211> LENGTH: 21
<212> TYPE: DNA
<213> ORGANISM: Artificial Sequence
<220> FEATURE:

<223> OTHER INFORMATION: AON sequence 5' -> 3'

<400> SEQUENCE: 1435
acgctcttgg gctctgggcc c 21

<210> SEQ ID NO 1436
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1436
cacgctcttg ggctctgggc c 21

<210> SEQ ID NO 1437
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1437
ccacgctctt gggctctggg c 21

<210> SEQ ID NO 1438
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1438
accacgctct tgggctctgg g 21

<210> SEQ ID NO 1439
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1439
caccacgctc ttgggctctg g 21

<210> SEQ ID NO 1440
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1440
gcaccacgct cttgggctct g 21

<210> SEQ ID NO 1441
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1441
tgcaccacgc tcttgggctc t 21

<210> SEQ ID NO 1442
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1442
ctgcaccacg ctcttgggct c 21

<210> SEQ ID NO 1443
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1443
gctgcaccac gctcttgggc t 21

<210> SEQ ID NO 1444
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1444
tgctgcacca cgctcttggg c 21

<210> SEQ ID NO 1445
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1445
ctgctgcacc acgctcttgg g 21

<210> SEQ ID NO 1446
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1446
actgctgcac cacgctcttg g 21

<210> SEQ ID NO 1447
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1447
tactgctgca ccacgctctt g 21

<210> SEQ ID NO 1448
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1448
gtactgctgc accacgctct t 21

<210> SEQ ID NO 1449
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1449
ggtactgctg caccacgctc t 21

<210> SEQ ID NO 1450
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1450
aggtactgct gcaccacgct c 21

<210> SEQ ID NO 1451
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1451
caggtactgc tgcaccacgc t 21

<210> SEQ ID NO 1452
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1452
ccaggtactg ctgcaccacg c 21

<210> SEQ ID NO 1453
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1453
tccaggtact gctgcaccac g 21

<210> SEQ ID NO 1454
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1454
gtccaggtac tgctgcacca c 21

<210> SEQ ID NO 1455
<211> LENGTH: 21

<212> TYPE: DNA
<213> ORGANISM: Artificial Sequence
<220> FEATURE:
<223> OTHER INFORMATION: AON sequence 5' -> 3'

<400> SEQUENCE: 1455
cgtccaggta ctgctgcacc a 21

<210> SEQ ID NO 1456
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1456
acgtccaggt actgctgcac c 21

<210> SEQ ID NO 1457
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1457
aacgtccagg tactgctgca c 21

<210> SEQ ID NO 1458
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1458
caacgtccag gtactgctgc a 21

<210> SEQ ID NO 1459
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1459
acaacgtcca ggtactgctg c 21

<210> SEQ ID NO 1460
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1460
cacaacgtcc aggtactgct g 21

<210> SEQ ID NO 1461
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1461
ccacaacgtc caggtactgc t 21

<210> SEQ ID NO 1462
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1462
cccacaacgt ccaggtactg c 21

<210> SEQ ID NO 1463
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1463
acccacaacg tccaggtact g 21

<210> SEQ ID NO 1464
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1464
tacccacaac gtccaggtac t 21

<210> SEQ ID NO 1465
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1465
ctacccacaa cgtccaggta c 21

<210> SEQ ID NO 1466
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1466
cctacccaca acgtccaggt a 21

<210> SEQ ID NO 1467
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1467
ccctacccac aacgtccagg t 21

<210> SEQ ID NO 1468
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1468
gccctaccca caacgtccag g 21

<210> SEQ ID NO 1469
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1469
ggccctaccc acaacgtcca g 21

<210> SEQ ID NO 1470
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1470
aggccctacc cacaacgtcc a 21

<210> SEQ ID NO 1471
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1471
caggccctac ccacaacgtc c 21

<210> SEQ ID NO 1472
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1472
gcaggcccta cccacaacgt c 21

<210> SEQ ID NO 1473
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1473
agcaggccct acccacaacg t 21

<210> SEQ ID NO 1474
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1474
gagcaggccc tacccacaac g 21

<210> SEQ ID NO 1475
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1475
ggagcaggcc ctacccacaa c 21

<210> SEQ ID NO 1476
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1476
gggagcaggc cctacccaca a 21

<210> SEQ ID NO 1477
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1477
agggagcagg ccctacccac a 21

<210> SEQ ID NO 1478
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1478
cagggagcag gccctaccca c 21

<210> SEQ ID NO 1479
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1479
ccagggagca ggccctaccc a 21

<210> SEQ ID NO 1480
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1480
gccagggagc aggccctacc c 21

<210> SEQ ID NO 1481
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1481
ggccagggag caggccctac c 21

<210> SEQ ID NO 1482
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1482
cggccaggga gcaggcccta c 21

<210> SEQ ID NO 1483
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1483
gcggccaggg agcaggccct a 21

<210> SEQ ID NO 1484
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1484
cgcggccagg gagcaggccc t 21

<210> SEQ ID NO 1485
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1485
ccgcggccag ggagcaggcc c 21

<210> SEQ ID NO 1486
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1486
gccgcggcca gggagcaggc c 21

<210> SEQ ID NO 1487
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1487
ggccgcggcc agggagcagg c 21

<210> SEQ ID NO 1488

<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1488
gggccgcggc cagggagcag g 21

<210> SEQ ID NO 1489
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1489
ggggccgcgg ccagggagca g 21

<210> SEQ ID NO 1490
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1490
gggggccgcg gccagggagc a 21

<210> SEQ ID NO 1491
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1491
cgggggccgc ggccagggag c 21

<210> SEQ ID NO 1492
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1492
gcgggggccg cggccaggga g 21

<210> SEQ ID NO 1493
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1493
ggcgggggcc gcggccaggg a 21

<210> SEQ ID NO 1494
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1494
gggcgggggc cgcggccagg g 21

<210> SEQ ID NO 1495
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1495
ggggcggggg ccgcggccag g 21

<210> SEQ ID NO 1496
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1496
tggggcgggg gccgcggcca g 21

<210> SEQ ID NO 1497
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1497
ttggggcggg ggccgcggcc a 21

<210> SEQ ID NO 1498
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1498
cttggggcgg gggccgcggc c 21

<210> SEQ ID NO 1499
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1499
ccttggggcg ggggccgcgg c 21

<210> SEQ ID NO 1500
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1500
gccttggggc gggggccgcg g 21

<210> SEQ ID NO 1501
<211> LENGTH: 21
<212> TYPE: DNA

<213> ORGANISM: Artificial Sequence
<220> FEATURE:
<223> OTHER INFORMATION: AON sequence 5' -> 3'

<400> SEQUENCE: 1501
agccttgggg cgggggccgc g 21

<210> SEQ ID NO 1502
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1502
gagccttggg gcgggggccg c 21

<210> SEQ ID NO 1503
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1503
ggagccttgg ggcgggggcc g 21

<210> SEQ ID NO 1504
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1504
gggagccttg gggcgggggc c 21

<210> SEQ ID NO 1505
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1505
agggagcctt ggggcggggg c 21

<210> SEQ ID NO 1506
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1506
gagggagcct tggggcgggg g 21

<210> SEQ ID NO 1507
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1507
ggagggagcc ttggggcggg g 21

<210> SEQ ID NO 1508
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1508
aggagggagc cttggggcgg g 21

<210> SEQ ID NO 1509
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1509
gaggagggag ccttggggcg g 21

<210> SEQ ID NO 1510
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1510
ggaggaggga gccttggggc g 21

<210> SEQ ID NO 1511
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1511
gggaggaggg agccttgggg c 21

<210> SEQ ID NO 1512
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1512
agggaggagg gagccttggg g 21

<210> SEQ ID NO 1513
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1513
gagggaggag ggagccttgg g 21

<210> SEQ ID NO 1514
<211> LENGTH: 21
<212> TYPE: DNA
<213> ORGANISM: Artificial Sequence
<220> FEATURE:

<223> OTHER INFORMATION: AON sequence 5' -> 3'

<400> SEQUENCE: 1514
ggagggagga gggagccttg g 21

<210> SEQ ID NO 1515
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1515
gggagggagg agggagcctt g 21

<210> SEQ ID NO 1516
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1516
agggagggag gagggagcct t 21

<210> SEQ ID NO 1517
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1517
gagggaggga ggagggagcc t 21

<210> SEQ ID NO 1518
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1518
tgagggaggg aggagggagc c 21

<210> SEQ ID NO 1519
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1519
atgagggagg gaggagggag c 21

<210> SEQ ID NO 1520
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1520
catgagggag ggaggaggga g 21

<210> SEQ ID NO 1521
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1521
tcatgaggga gggaggaggg a 21

<210> SEQ ID NO 1522
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1522
ttcatgaggg agggaggagg g 21

<210> SEQ ID NO 1523
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1523
cttcatgagg gagggaggag g 21

<210> SEQ ID NO 1524
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1524
acttcatgag ggagggagga g 21

<210> SEQ ID NO 1525
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1525
gacttcatga gggagggagg a 21

<210> SEQ ID NO 1526
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1526
cgacttcatg agggagggag g 21

<210> SEQ ID NO 1527
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1527
ccgacttcat gagggaggga g 21

<210> SEQ ID NO 1528
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1528
gccgacttca tgagggaggg a 21

<210> SEQ ID NO 1529
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1529
cgccgacttc atgagggagg g 21

<210> SEQ ID NO 1530
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1530
acgccgactt catgagggag g 21

<210> SEQ ID NO 1531
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1531
aacgccgact tcatgaggga g 21

<210> SEQ ID NO 1532
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1532
caacgccgac ttcatgaggg a 21

<210> SEQ ID NO 1533
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1533
ccaacgccga cttcatgagg g 21

<210> SEQ ID NO 1534
<211> LENGTH: 21

<212> TYPE: DNA
<213> ORGANISM: Artificial Sequence
<220> FEATURE:
<223> OTHER INFORMATION: AON sequence 5' -> 3'

<400> SEQUENCE: 1534
gccaacgccg acttcatgag g 21

<210> SEQ ID NO 1535
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1535
ggccaacgcc gacttcatga g 21

<210> SEQ ID NO 1536
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1536
aggccaacgc cgacttcatg a 21

<210> SEQ ID NO 1537
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1537
caggccaacg ccgacttcat g 21

<210> SEQ ID NO 1538
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1538
gcaggccaac gccgacttca t 21

<210> SEQ ID NO 1539
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1539
tgcaggccaa cgccgacttc a 21

<210> SEQ ID NO 1540
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1540
ctgcaggcca acgccgactt c 21

<210> SEQ ID NO 1541
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1541
cctgcaggcc aacgccgact t 21

<210> SEQ ID NO 1542
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1542
tcctgcaggc caacgccgac t 21

<210> SEQ ID NO 1543
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1543
atcctgcagg ccaacgccga c 21

<210> SEQ ID NO 1544
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1544
tatcctgcag gccaacgccg a 21

<210> SEQ ID NO 1545
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1545
gtatcctgca ggccaacgcc g 21

<210> SEQ ID NO 1546
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1546
ggtatcctgc aggccaacgc c 21

<210> SEQ ID NO 1547
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1547
gggtatcctg caggccaacg c 21

<210> SEQ ID NO 1548
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1548
cgggtatcct gcaggccaac g 21

<210> SEQ ID NO 1549
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1549
acgggtatcc tgcaggccaa c 21

<210> SEQ ID NO 1550
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1550
aacgggtatc ctgcaggcca a 21

<210> SEQ ID NO 1551
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1551
gaacgggtat cctgcaggcc a 21

<210> SEQ ID NO 1552
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1552
tgaacgggta tcctgcaggc c 21

<210> SEQ ID NO 1553
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1553
atgaacgggt atcctgcagg c 21

<210> SEQ ID NO 1554
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1554
catgaacggg tatcctgcag g 21

<210> SEQ ID NO 1555
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1555
gcatgaacgg gtatcctgca g 21

<210> SEQ ID NO 1556
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1556
ggcatgaacg ggtatcctgc a 21

<210> SEQ ID NO 1557
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1557
cggcatgaac gggtatcctg c 21

<210> SEQ ID NO 1558
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1558
gcggcatgaa cgggtatcct g 21

<210> SEQ ID NO 1559
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1559
ggcggcatga acgggtatcc t 21

<210> SEQ ID NO 1560
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1560
tggcggcatg aacgggtatc c 21

<210> SEQ ID NO 1561
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1561
atggcggcat gaacgggtat c 21

<210> SEQ ID NO 1562
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1562
tatggcggca tgaacgggta t 21

<210> SEQ ID NO 1563
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1563
gtatggcggc atgaacgggt a 21

<210> SEQ ID NO 1564
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1564
agtatggcgg catgaacggg t 21

<210> SEQ ID NO 1565
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1565
cagtatggcg gcatgaacgg g 21

<210> SEQ ID NO 1566
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1566
ccagtatggc ggcatgaacg g 21

<210> SEQ ID NO 1567

<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1567
cccagtatgg cggcatgaac g 21

<210> SEQ ID NO 1568
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1568
ccccagtatg gcggcatgaa c 21

<210> SEQ ID NO 1569
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1569
gccccagtat ggcggcatga a 21

<210> SEQ ID NO 1570
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1570
ggccccagta tggcggcatg a 21

<210> SEQ ID NO 1571
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1571
aggccccagt atggcggcat g 21

<210> SEQ ID NO 1572
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1572
caggccccag tatggcggca t 21

<210> SEQ ID NO 1573
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1573
ccaggcccca gtatggcggc a 21

<210> SEQ ID NO 1574
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1574
cccaggcccc agtatggcgg c 21

<210> SEQ ID NO 1575
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1575
gcccaggccc cagtatggcg g 21

<210> SEQ ID NO 1576
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1576
agcccaggcc ccagtatggc g 21

<210> SEQ ID NO 1577
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1577
aagcccaggc cccagtatgg c 21

<210> SEQ ID NO 1578
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1578
gaagcccagg ccccagtatg g 21

<210> SEQ ID NO 1579
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1579
ggaagcccag gccccagtat g 21

<210> SEQ ID NO 1580
<211> LENGTH: 21
<212> TYPE: DNA

<213> ORGANISM: Artificial Sequence
<220> FEATURE:
<223> OTHER INFORMATION: AON sequence 5' -> 3'

<400> SEQUENCE: 1580
tggaagccca ggccccagta t 21

<210> SEQ ID NO 1581
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1581
gtggaagccc aggccccagt a 21

<210> SEQ ID NO 1582
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1582
ggtggaagcc caggccccag t 21

<210> SEQ ID NO 1583
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1583
aggtggaagc ccaggcccca g 21

<210> SEQ ID NO 1584
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1584
caggtggaag cccaggcccc a 21

<210> SEQ ID NO 1585
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1585
acaggtggaa gcccaggccc c 21

<210> SEQ ID NO 1586
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1586
cacaggtgga agcccaggcc c 21

<210> SEQ ID NO 1587
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1587
gcacaggtgg aagcccaggc c 21

<210> SEQ ID NO 1588
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1588
ggcacaggtg gaagcccagg c 21

<210> SEQ ID NO 1589
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1589
cggcacaggt ggaagcccag g 21

<210> SEQ ID NO 1590
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1590
gcggcacagg tggaagccca g 21

<210> SEQ ID NO 1591
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1591
agcggcacag gtggaagccc a 21

<210> SEQ ID NO 1592
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1592
cagcggcaca ggtggaagcc c 21

<210> SEQ ID NO 1593
<211> LENGTH: 21
<212> TYPE: DNA
<213> ORGANISM: Artificial Sequence
<220> FEATURE:

<223> OTHER INFORMATION: AON sequence 5' -> 3'

<400> SEQUENCE: 1593
ccagcggcac aggtggaagc c 21

<210> SEQ ID NO 1594
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1594
cccagcggca caggtggaag c 21

<210> SEQ ID NO 1595
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1595
ccccagcggc acaggtggaa g 21

<210> SEQ ID NO 1596
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1596
gccccagcgg cacaggtgga a 21

<210> SEQ ID NO 1597
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1597
agccccagcg gcacaggtgg a 21

<210> SEQ ID NO 1598
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1598
tagccccagc ggcacaggtg g 21

<210> SEQ ID NO 1599
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1599
gtagccccag cggcacaggt g 21

<210> SEQ ID NO 1600
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1600
agtagcccca gcggcacagg t 21

<210> SEQ ID NO 1601
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1601
gagtagcccc agcggcacag g 21

<210> SEQ ID NO 1602
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1602
ggagtagccc cagcggcaca g 21

<210> SEQ ID NO 1603
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1603
aggagtagcc ccagcggcac a 21

<210> SEQ ID NO 1604
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1604
gaggagtagc cccagcggca c 21

<210> SEQ ID NO 1605
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1605
ggaggagtag ccccagcggc a 21

<210> SEQ ID NO 1606
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1606
tggaggagta gccccagcgg c 21

<210> SEQ ID NO 1607
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1607
gtggaggagt agccccagcg g 21

<210> SEQ ID NO 1608
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1608
ggtggaggag tagccccagc g 21

<210> SEQ ID NO 1609
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1609
cggtggagga gtagccccag c 21

<210> SEQ ID NO 1610
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1610
gcggtggagg agtagcccca g 21

<210> SEQ ID NO 1611
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1611
agcggtggag gagtagcccc a 21

<210> SEQ ID NO 1612
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1612
tagcggtgga ggagtagccc c 21

<210> SEQ ID NO 1613
<211> LENGTH: 21

<212> TYPE: DNA
<213> ORGANISM: Artificial Sequence
<220> FEATURE:
<223> OTHER INFORMATION: AON sequence 5' -> 3'

<400> SEQUENCE: 1613
atagcggtgg aggagtagcc c 21

<210> SEQ ID NO 1614
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1614
gatagcggtg gaggagtagc c 21

<210> SEQ ID NO 1615
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1615
tgatagcggt ggaggagtag c 21

<210> SEQ ID NO 1616
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1616
gtgatagcgg tggaggagta g 21

<210> SEQ ID NO 1617
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1617
ggtgatagcg gtggaggagt a 21

<210> SEQ ID NO 1618
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1618
gggtgatagc ggtggaggag t 21

<210> SEQ ID NO 1619
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1619
cgggtgatag cggtggagga g 21

<210> SEQ ID NO 1620
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1620
gcgggtgata gcggtggagg a 21

<210> SEQ ID NO 1621
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1621
ggcgggtgat agcggtggag g 21

<210> SEQ ID NO 1622
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1622
tggcgggtga tagcggtgga g 21

<210> SEQ ID NO 1623
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1623
ctggcgggtg atagcggtgg a 21

<210> SEQ ID NO 1624
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1624
cctggcgggt gatagcggtg g 21

<210> SEQ ID NO 1625
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1625
acctggcggg tgatagcggt g 21

<210> SEQ ID NO 1626
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1626
cacctggcgg gtgatagcgg t 21

<210> SEQ ID NO 1627
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1627
ccacctggcg ggtgatagcg g 21

<210> SEQ ID NO 1628
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1628
accacctggc gggtgatagc g 21

<210> SEQ ID NO 1629
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1629
caccacctgg cgggtgatag c 21

<210> SEQ ID NO 1630
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1630
ccaccacctg gcgggtgata g 21

<210> SEQ ID NO 1631
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1631
tccaccacct ggcgggtgat a 21

<210> SEQ ID NO 1632
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1632
ctccaccacc tggcgggtga t 21

<210> SEQ ID NO 1633
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1633
tctccaccac ctggcgggtg a 21

<210> SEQ ID NO 1634
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1634
ttctccacca cctggcgggt g 21

<210> SEQ ID NO 1635
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1635
gttctccacc acctggcggg t 21

<210> SEQ ID NO 1636
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1636
tgttctccac cacctggcgg g 21

<210> SEQ ID NO 1637
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1637
atgttctcca ccacctggcg g 21

<210> SEQ ID NO 1638
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1638
catgttctcc accacctggc g 21

<210> SEQ ID NO 1639
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1639
tcatgttctc caccacctgg c 21

<210> SEQ ID NO 1640
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1640
gtcatgttct ccaccacctg g 21

<210> SEQ ID NO 1641
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1641
ggtcatgttc tccaccacct g 21

<210> SEQ ID NO 1642
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1642
tggtcatgtt ctccaccacc t 21

<210> SEQ ID NO 1643
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1643
ctggtcatgt tctccaccac c 21

<210> SEQ ID NO 1644
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1644
cctggtcatg ttctccacca c 21

<210> SEQ ID NO 1645
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1645
ccctggtcat gttctccacc a 21

<210> SEQ ID NO 1646

<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1646
gccctggtca tgttctccac c 21

<210> SEQ ID NO 1647
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1647
ggccctggtc atgttctcca c 21

<210> SEQ ID NO 1648
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1648
gggccctggt catgttctcc a 21

<210> SEQ ID NO 1649
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1649
tgggccctgg tcatgttctc c 21

<210> SEQ ID NO 1650
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1650
gtgggccctg gtcatgttct c 21

<210> SEQ ID NO 1651
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1651
agtgggccct ggtcatgttc t 21

<210> SEQ ID NO 1652
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1652
aagtgggccc tggtcatgtt c 21

<210> SEQ ID NO 1653
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1653
gaagtgggcc ctggtcatgt t 21

<210> SEQ ID NO 1654
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1654
ggaagtgggc cctggtcatg t 21

<210> SEQ ID NO 1655
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1655
gggaagtggg ccctggtcat g 21

<210> SEQ ID NO 1656
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1656
ggggaagtgg gccctggtca t 21

<210> SEQ ID NO 1657
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1657
gggggaagtg ggccctggtc a 21

<210> SEQ ID NO 1658
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1658
agggggaagt gggccctggt c 21

<210> SEQ ID NO 1659
<211> LENGTH: 21
<212> TYPE: DNA

<213> ORGANISM: Artificial Sequence
<220> FEATURE:
<223> OTHER INFORMATION: AON sequence 5' -> 3'

<400> SEQUENCE: 1659 caggggaag tgggccctgg t 21

<210> SEQ ID NO 1660
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1660
ccagggggaa gtgggccctg g 21

<210> SEQ ID NO 1661
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1661
accaggggga agtgggccct g 21

<210> SEQ ID NO 1662
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1662
caccaggggg aagtgggccc t 21

<210> SEQ ID NO 1663
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1663
tcaccagggg gaagtgggcc c 21

<210> SEQ ID NO 1664
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1664
ctcaccaggg ggaagtgggc c 21

<210> SEQ ID NO 1665
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1665
actcaccagg gggaagtggg c 21

<210> SEQ ID NO 1666
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1666
aactcaccag ggggaagtgg g 21

<210> SEQ ID NO 1667
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1667
caactcacca gggggaagtg g 21

<210> SEQ ID NO 1668
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1668
ccaactcacc agggggaagt g 21

<210> SEQ ID NO 1669
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1669
cccaactcac cagggggaag t 21

<210> SEQ ID NO 1670
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1670
ccccaactca ccagggggaa g 21

<210> SEQ ID NO 1671
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1671
accccaactc accaggggga a 21

<210> SEQ ID NO 1672
<211> LENGTH: 21
<212> TYPE: DNA
<213> ORGANISM: Artificial Sequence
<220> FEATURE:

<223> OTHER INFORMATION: AON sequence 5' -> 3'

<400> SEQUENCE: 1672
caccccaact caccaggggg a 21

<210> SEQ ID NO 1673
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1673
ccaccccaac tcaccagggg g 21

<210> SEQ ID NO 1674
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1674
accaccccaa ctcaccaggg g 21

<210> SEQ ID NO 1675
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1675
caccacccca actcaccagg g 21

<210> SEQ ID NO 1676
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1676
ccaccacccc aactcaccag g 21

<210> SEQ ID NO 1677
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1677
gccaccaccc caactcacca g 21

<210> SEQ ID NO 1678
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1678
tgccaccacc ccaactcacc a 21

<210> SEQ ID NO 1679
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1679
ctgccaccac cccaactcac c 21

<210> SEQ ID NO 1680
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1680
cctgccacca ccccaactca c 21

<210> SEQ ID NO 1681
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1681
ccctgccacc accccaactc a 21

<210> SEQ ID NO 1682
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1682
cccctgccac caccccaact c 21

<210> SEQ ID NO 1683
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1683
tcccctgcca ccaccccaac t 21

<210> SEQ ID NO 1684
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 1684
ctcccctgcc accaccccaa c 21

<210> SEQ ID NO 1685
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1685
ggaagcagct ctggggtt 18

<210> SEQ ID NO 1686
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1686
gggaagcagc tctggggt 18

<210> SEQ ID NO 1687
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1687
agggaagcag ctctgggg 18

<210> SEQ ID NO 1688
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1688
aagggaagca gctctggg 18

<210> SEQ ID NO 1689
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1689
gaagggaagc agctctgg 18

<210> SEQ ID NO 1690
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1690
ggaagggaag cagctctg 18

<210> SEQ ID NO 1691
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1691
tggaagggaa gcagctct 18

<210> SEQ ID NO 1692
<211> LENGTH: 18

<212> TYPE: DNA
<213> ORGANISM: Artificial Sequence
<220> FEATURE:
<223> OTHER INFORMATION: AON sequence 5' -> 3'

<400> SEQUENCE: 1692
ctggaaggga agcagctc 18

<210> SEQ ID NO 1693
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1693
tctggaaggg aagcagct 18

<210> SEQ ID NO 1694
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1694
atctggaagg gaagcagc 18

<210> SEQ ID NO 1695
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1695
catctggaag ggaagcag 18

<210> SEQ ID NO 1696
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1696
acatctggaa gggaagca 18

<210> SEQ ID NO 1697
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1697
cacatctgga agggaagc 18

<210> SEQ ID NO 1698
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1698
ccacatctgg aagggaag 18

<210> SEQ ID NO 1699
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1699
accacatctg gaagggaa 18

<210> SEQ ID NO 1700
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1700
gaccacatct ggaaggga 18

<210> SEQ ID NO 1701
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1701
ggaccacatc tggaaggg 18

<210> SEQ ID NO 1702
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1702
aggaccacat ctggaagg 18

<210> SEQ ID NO 1703
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1703
caggaccaca tctggaag 18

<210> SEQ ID NO 1704
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1704
gcaggaccac atctggaa 18

<210> SEQ ID NO 1705
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1705
tgcaggacca catctgga 18

<210> SEQ ID NO 1706
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1706
ctgcaggacc acatctgg 18

<210> SEQ ID NO 1707
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1707
gctgcaggac cacatctg 18

<210> SEQ ID NO 1708
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1708
ggctgcagga ccacatct 18

<210> SEQ ID NO 1709
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1709
cggctgcagg accacatc 18

<210> SEQ ID NO 1710
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1710
tcggctgcag gaccacat 18

<210> SEQ ID NO 1711
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1711
ctcggctgca ggaccaca 18

<210> SEQ ID NO 1712
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1712
gctcggctgc aggaccac 18

<210> SEQ ID NO 1713
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1713
ggctcggctg caggacca 18

<210> SEQ ID NO 1714
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1714
gggctcggct gcaggacc 18

<210> SEQ ID NO 1715
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1715
agggctcggc tgcaggac 18

<210> SEQ ID NO 1716
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1716
cagggctcgg ctgcagga 18

<210> SEQ ID NO 1717
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1717
gcagggctcg gctgcagg 18

<210> SEQ ID NO 1718
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1718
ggcagggctc ggctgcag 18

<210> SEQ ID NO 1719
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1719
gggcagggct cggctgca 18

<210> SEQ ID NO 1720
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1720
agggcagggc tcggctgc 18

<210> SEQ ID NO 1721
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1721
aagggcaggg ctcggctg 18

<210> SEQ ID NO 1722
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1722
taagggcagg gctcggct 18

<210> SEQ ID NO 1723
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1723
ctaagggcag ggctcggc 18

<210> SEQ ID NO 1724
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1724
gctaagggca gggctcgg 18

<210> SEQ ID NO 1725

<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1725
agctaagggc agggctcg 18

<210> SEQ ID NO 1726
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1726
cagctaaggg cagggctc 18

<210> SEQ ID NO 1727
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1727
ccagctaagg gcagggct 18

<210> SEQ ID NO 1728
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1728
tccagctaag ggcagggc 18

<210> SEQ ID NO 1729
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1729
ctccagctaa gggcaggg 18

<210> SEQ ID NO 1730
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1730
cctccagcta agggcagg 18

<210> SEQ ID NO 1731
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1731
acctccagct aagggcag 18

<210> SEQ ID NO 1732
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1732
gacctccagc taagggca 18

<210> SEQ ID NO 1733
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1733
cgacctccag ctaagggc 18

<210> SEQ ID NO 1734
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1734
tcgacctcca gctaaggg 18

<210> SEQ ID NO 1735
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1735
gtcgacctcc agctaagg 18

<210> SEQ ID NO 1736
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1736
tgtcgacctc cagctaag 18

<210> SEQ ID NO 1737
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1737
ctgtcgacct ccagctaa 18

<210> SEQ ID NO 1738
<211> LENGTH: 18
<212> TYPE: DNA

<213> ORGANISM: Artificial Sequence
<220> FEATURE:
<223> OTHER INFORMATION: AON sequence 5' -> 3'

<400> SEQUENCE: 1738
cctgtcgacc tccagcta 18

<210> SEQ ID NO 1739
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1739
acctgtcgac ctccagct 18

<210> SEQ ID NO 1740
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1740
cacctgtcga cctccagc 18

<210> SEQ ID NO 1741
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1741
ccacctgtcg acctccag 18

<210> SEQ ID NO 1742
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1742
cccacctgtc gacctcca 18

<210> SEQ ID NO 1743
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1743
tcccacctgt cgacctcc 18

<210> SEQ ID NO 1744
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1744
atcccacctg tcgacctc 18

<210> SEQ ID NO 1745
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1745
gatcccacct gtcgacct 18

<210> SEQ ID NO 1746
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1746
ggatcccacc tgtcgacc 18

<210> SEQ ID NO 1747
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1747
aggatcccac ctgtcgac 18

<210> SEQ ID NO 1748
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1748
caggatccca cctgtcga 18

<210> SEQ ID NO 1749
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1749
ccaggatccc acctgtcg 18

<210> SEQ ID NO 1750
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1750
tccaggatcc cacctgtc 18

<210> SEQ ID NO 1751
<211> LENGTH: 18
<212> TYPE: DNA
<213> ORGANISM: Artificial Sequence
<220> FEATURE:

<223> OTHER INFORMATION: AON sequence 5' -> 3'

<400> SEQUENCE: 1751
atccaggatc ccacctgt 18

<210> SEQ ID NO 1752
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1752
catccaggat cccacctg 18

<210> SEQ ID NO 1753
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1753
acatccagga tcccacct 18

<210> SEQ ID NO 1754
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1754
gacatccagg atcccacc 18

<210> SEQ ID NO 1755
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1755
agacatccag gatcccac 18

<210> SEQ ID NO 1756
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1756
tagacatcca ggatccca 18

<210> SEQ ID NO 1757
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1757
gtagacatcc aggatccc 18

<210> SEQ ID NO 1758
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1758
tgtagacatc caggatcc 18

<210> SEQ ID NO 1759
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1759
atgtagacat ccaggatc 18

<210> SEQ ID NO 1760
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1760
gatgtagaca tccaggat 18

<210> SEQ ID NO 1761
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1761
agatgtagac atccagga 18

<210> SEQ ID NO 1762
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1762
aagatgtaga catccagg 18

<210> SEQ ID NO 1763
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1763
gaagatgtag acatccag 18

<210> SEQ ID NO 1764
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1764
ggaagatgta gacatcca 18

<210> SEQ ID NO 1765
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1765
aggaagatgt agacatcc 18

<210> SEQ ID NO 1766
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1766
caggaagatg tagacatc 18

<210> SEQ ID NO 1767
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1767
ccaggaagat gtagacat 18

<210> SEQ ID NO 1768
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1768
cccaggaaga tgtagaca 18

<210> SEQ ID NO 1769
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1769
gcccaggaag atgtagac 18

<210> SEQ ID NO 1770
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1770
ggcccaggaa gatgtaga 18

<210> SEQ ID NO 1771
<211> LENGTH: 18

<212> TYPE: DNA
<213> ORGANISM: Artificial Sequence
<220> FEATURE:
<223> OTHER INFORMATION: AON sequence 5' -> 3'

<400> SEQUENCE: 1771
gggcccagga agatgtag 18

<210> SEQ ID NO 1772
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1772
tgggcccagg aagatgta 18

<210> SEQ ID NO 1773
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1773
ctgggcccag gaagatgt 18

<210> SEQ ID NO 1774
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1774
tctgggccca ggaagatg 18

<210> SEQ ID NO 1775
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1775
ctctgggccc aggaagat 18

<210> SEQ ID NO 1776
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1776
gctctgggcc caggaaga 18

<210> SEQ ID NO 1777
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1777
ggctctgggc ccaggaag 18

<210> SEQ ID NO 1778
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1778
gggctctggg cccaggaa 18

<210> SEQ ID NO 1779
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1779
tgggctctgg gcccagga 18

<210> SEQ ID NO 1780
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1780
ttgggctctg ggcccagg 18

<210> SEQ ID NO 1781
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1781
cttgggctct gggcccag 18

<210> SEQ ID NO 1782
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1782
tcttgggctc tgggccca 18

<210> SEQ ID NO 1783
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1783
ctcttgggct ctgggccc 18

<210> SEQ ID NO 1784
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1784
gctcttgggc tctgggcc 18

<210> SEQ ID NO 1785
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1785
cgctcttggg ctctgggc 18

<210> SEQ ID NO 1786
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1786
acgctcttgg gctctggg 18

<210> SEQ ID NO 1787
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1787
cacgctcttg ggctctgg 18

<210> SEQ ID NO 1788
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1788
ccacgctctt gggctctg 18

<210> SEQ ID NO 1789
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1789
accacgctct tgggctct 18

<210> SEQ ID NO 1790
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1790
caccacgctc ttgggctc 18

<210> SEQ ID NO 1791
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1791
gcaccacgct cttgggct 18

<210> SEQ ID NO 1792
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1792
tgcaccacgc tcttgggc 18

<210> SEQ ID NO 1793
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1793
ctgcaccacg ctcttggg 18

<210> SEQ ID NO 1794
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1794
gctgcaccac gctcttgg 18

<210> SEQ ID NO 1795
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1795
tgctgcacca cgctcttg 18

<210> SEQ ID NO 1796
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1796
ctgctgcacc acgctctt 18

<210> SEQ ID NO 1797
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1797
actgctgcac cacgctct 18

<210> SEQ ID NO 1798
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1798
tactgctgca ccacgctc 18

<210> SEQ ID NO 1799
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1799
gtactgctgc accacgct 18

<210> SEQ ID NO 1800
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1800
ggtactgctg caccacgc 18

<210> SEQ ID NO 1801
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1801
aggtactgct gcaccacg 18

<210> SEQ ID NO 1802
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1802
caggtactgc tgcaccac 18

<210> SEQ ID NO 1803
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1803
ccaggtactg ctgcacca 18

<210> SEQ ID NO 1804

<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1804
tccaggtact gctgcacc 18

<210> SEQ ID NO 1805
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1805
gtccaggtac tgctgcac 18

<210> SEQ ID NO 1806
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1806
cgtccaggta ctgctgca 18

<210> SEQ ID NO 1807
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1807
acgtccaggt actgctgc 18

<210> SEQ ID NO 1808
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1808
aacgtccagg tactgctg 18

<210> SEQ ID NO 1809
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1809
caacgtccag gtactgct 18

<210> SEQ ID NO 1810
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1810
acaacgtcca ggtactgc 18

<210> SEQ ID NO 1811
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1811
cacaacgtcc aggtactg 18

<210> SEQ ID NO 1812
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1812
ccacaacgtc caggtact 18

<210> SEQ ID NO 1813
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1813
cccacaacgt ccaggtac 18

<210> SEQ ID NO 1814
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1814
acccacaacg tccaggta 18

<210> SEQ ID NO 1815
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1815
tacccacaac gtccaggt 18

<210> SEQ ID NO 1816
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1816
ctacccacaa cgtccagg 18

<210> SEQ ID NO 1817
<211> LENGTH: 18
<212> TYPE: DNA

<213> ORGANISM: Artificial Sequence
<220> FEATURE:
<223> OTHER INFORMATION: AON sequence 5' -> 3'

<400> SEQUENCE: 1817
cctacccaca acgtccag 18

<210> SEQ ID NO 1818
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1818
ccctacccac aacgtcca 18

<210> SEQ ID NO 1819
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1819
gccctaccca caacgtcc 18

<210> SEQ ID NO 1820
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1820
ggccctaccc acaacgtc 18

<210> SEQ ID NO 1821
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1821
aggccctacc cacaacgt 18

<210> SEQ ID NO 1822
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1822
caggccctac ccacaacg 18

<210> SEQ ID NO 1823
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1823
gcaggcccta cccacaac 18

<210> SEQ ID NO 1824
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1824
agcaggccct acccacaa 18

<210> SEQ ID NO 1825
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1825
gagcaggccc tacccaca 18

<210> SEQ ID NO 1826
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1826
ggagcaggcc ctacccac 18

<210> SEQ ID NO 1827
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1827
gggagcaggc cctaccca 18

<210> SEQ ID NO 1828
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1828
agggagcagg ccctaccc 18

<210> SEQ ID NO 1829
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1829
cagggagcag gccctacc 18

<210> SEQ ID NO 1830
<211> LENGTH: 18
<212> TYPE: DNA
<213> ORGANISM: Artificial Sequence
<220> FEATURE:

<223> OTHER INFORMATION: AON sequence 5' -> 3'

<400> SEQUENCE: 1830
ccagggagca ggccctac 18

<210> SEQ ID NO 1831
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1831
gccagggagc aggcccta 18

<210> SEQ ID NO 1832
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1832
ggccagggag caggccct 18

<210> SEQ ID NO 1833
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1833
cggccaggga gcaggccc 18

<210> SEQ ID NO 1834
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1834
gcggccaggg agcaggcc 18

<210> SEQ ID NO 1835
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1835
cgcggccagg gagcaggc 18

<210> SEQ ID NO 1836
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1836
ccgcggccag ggagcagg 18

<210> SEQ ID NO 1837
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1837
gccgcggcca gggagcag 18

<210> SEQ ID NO 1838
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1838
ggccgcggcc agggagca 18

<210> SEQ ID NO 1839
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1839
gggccgcggc cagggagc 18

<210> SEQ ID NO 1840
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1840
ggggccgcgg ccagggag 18

<210> SEQ ID NO 1841
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1841
gggggccgcg gccaggga 18

<210> SEQ ID NO 1842
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1842
cgggggccgc ggccaggg 18

<210> SEQ ID NO 1843
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1843
gcgggggccg cggccagg 18

<210> SEQ ID NO 1844
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1844
ggcgggggcc gcggccag 18

<210> SEQ ID NO 1845
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1845
gggcgggggc cgcggcca 18

<210> SEQ ID NO 1846
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1846
ggggcggggg ccgcggcc 18

<210> SEQ ID NO 1847
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1847
tggggcgggg gccgcggc 18

<210> SEQ ID NO 1848
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1848
ttggggcggg ggccgcgg 18

<210> SEQ ID NO 1849
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1849
cttggggcgg gggccgcg 18

<210> SEQ ID NO 1850
<211> LENGTH: 18

<212> TYPE: DNA
<213> ORGANISM: Artificial Sequence
<220> FEATURE:
<223> OTHER INFORMATION: AON sequence 5' -> 3'

<400> SEQUENCE: 1850
ccttggggcg ggggccgc 18

<210> SEQ ID NO 1851
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1851
gccttggggc gggggccg 18

<210> SEQ ID NO 1852
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1852
agccttgggg cgggggcc 18

<210> SEQ ID NO 1853
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1853
gagccttggg gcgggggc 18

<210> SEQ ID NO 1854
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1854
ggagccttgg ggcggggg 18

<210> SEQ ID NO 1855
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1855
gggagccttg gggcgggg 18

<210> SEQ ID NO 1856
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1856
agggagcctt ggggcggg 18

<210> SEQ ID NO 1857
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1857
gagggagcct tggggcgg 18

<210> SEQ ID NO 1858
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1858
ggagggagcc ttggggcg 18

<210> SEQ ID NO 1859
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1859
aggagggagc cttggggc 18

<210> SEQ ID NO 1860
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1860
gaggagggag ccttgggg 18

<210> SEQ ID NO 1861
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1861
ggaggaggga gccttggg 18

<210> SEQ ID NO 1862
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1862
gggaggaggg agccttgg 18

<210> SEQ ID NO 1863
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1863
agggaggagg gagccttg 18

<210> SEQ ID NO 1864
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1864
gagggaggag ggagcctt 18

<210> SEQ ID NO 1865
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1865
ggagggagga gggagcct 18

<210> SEQ ID NO 1866
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1866
gggagggagg agggagcc 18

<210> SEQ ID NO 1867
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1867
agggagggag gagggagc 18

<210> SEQ ID NO 1868
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1868
gagggaggga ggagggag 18

<210> SEQ ID NO 1869
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1869
tgagggaggg aggaggga 18

<210> SEQ ID NO 1870
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1870
atgagggagg gaggaggg 18

<210> SEQ ID NO 1871
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1871
catgagggag ggaggagg 18

<210> SEQ ID NO 1872
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1872
tcatgaggga gggaggag 18

<210> SEQ ID NO 1873
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1873
ttcatgaggg agggagga 18

<210> SEQ ID NO 1874
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1874
cttcatgagg gagggagg 18

<210> SEQ ID NO 1875
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1875
acttcatgag ggagggag 18

<210> SEQ ID NO 1876
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1876
gacttcatga gggaggga 18

<210> SEQ ID NO 1877
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1877
cgacttcatg agggaggg 18

<210> SEQ ID NO 1878
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1878
ccgacttcat gagggagg 18

<210> SEQ ID NO 1879
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1879
gccgacttca tgagggag 18

<210> SEQ ID NO 1880
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1880
cgccgacttc atgaggga 18

<210> SEQ ID NO 1881
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1881
acgccgactt catgaggg 18

<210> SEQ ID NO 1882
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1882
aacgccgact tcatgagg 18

<210> SEQ ID NO 1883

-continued

<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1883
caacgccgac ttcatgag 18

<210> SEQ ID NO 1884
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1884
ccaacgccga cttcatga 18

<210> SEQ ID NO 1885
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1885
gccaacgccg acttcatg 18

<210> SEQ ID NO 1886
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1886
ggccaacgcc gacttcat 18

<210> SEQ ID NO 1887
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1887
aggccaacgc cgacttca 18

<210> SEQ ID NO 1888
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1888
caggccaacg ccgacttc 18

<210> SEQ ID NO 1889
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1889
gcaggccaac gccgactt 18

<210> SEQ ID NO 1890
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1890
tgcaggccaa cgccgact 18

<210> SEQ ID NO 1891
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1891
ctgcaggcca acgccgac 18

<210> SEQ ID NO 1892
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1892
cctgcaggcc aacgccga 18

<210> SEQ ID NO 1893
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1893
tcctgcaggc caacgccg 18

<210> SEQ ID NO 1894
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1894
atcctgcagg ccaacgcc 18

<210> SEQ ID NO 1895
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1895
tatcctgcag gccaacgc 18

<210> SEQ ID NO 1896
<211> LENGTH: 18
<212> TYPE: DNA

-continued

<213> ORGANISM: Artificial Sequence
<220> FEATURE:
<223> OTHER INFORMATION: AON sequence 5' -> 3'

<400> SEQUENCE: 1896
gtatcctgca ggccaacg 18

<210> SEQ ID NO 1897
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1897
ggtatcctgc aggccaac 18

<210> SEQ ID NO 1898
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1898
gggtatcctg caggccaa 18

<210> SEQ ID NO 1899
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1899
cgggtatcct gcaggcca 18

<210> SEQ ID NO 1900
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1900
acgggtatcc tgcaggcc 18

<210> SEQ ID NO 1901
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1901
aacgggtatc ctgcaggc 18

<210> SEQ ID NO 1902
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1902
gaacgggtat cctgcagg 18

<210> SEQ ID NO 1903
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1903
tgaacgggta tcctgcag 18

<210> SEQ ID NO 1904
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1904
atgaacgggt atcctgca 18

<210> SEQ ID NO 1905
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1905
catgaacggg tatcctgc 18

<210> SEQ ID NO 1906
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1906
gcatgaacgg gtatcctg 18

<210> SEQ ID NO 1907
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1907
ggcatgaacg ggtatcct 18

<210> SEQ ID NO 1908
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1908
cggcatgaac gggtatcc 18

<210> SEQ ID NO 1909
<211> LENGTH: 18
<212> TYPE: DNA
<213> ORGANISM: Artificial Sequence
<220> FEATURE:

<223> OTHER INFORMATION: AON sequence 5' -> 3'

<400> SEQUENCE: 1909
gcggcatgaa cgggtatc 18

<210> SEQ ID NO 1910
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1910
ggcggcatga acgggtat 18

<210> SEQ ID NO 1911
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1911
tggcggcatg aacgggta 18

<210> SEQ ID NO 1912
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1912
atggcggcat gaacgggt 18

<210> SEQ ID NO 1913
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1913
tatggcggca tgaacggg 18

<210> SEQ ID NO 1914
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1914
gtatggcggc atgaacgg 18

<210> SEQ ID NO 1915
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1915
agtatggcgg catgaacg 18

<210> SEQ ID NO 1916
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1916
cagtatggcg gcatgaac 18

<210> SEQ ID NO 1917
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1917
ccagtatggc ggcatgaa 18

<210> SEQ ID NO 1918
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1918
cccagtatgg cggcatga 18

<210> SEQ ID NO 1919
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1919
ccccagtatg gcggcatg 18

<210> SEQ ID NO 1920
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1920
gccccagtat ggcggcat 18

<210> SEQ ID NO 1921
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1921
ggccccagta tggcggca 18

<210> SEQ ID NO 1922
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1922
aggccccagt atggcggc 18

<210> SEQ ID NO 1923
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1923
caggccccag tatggcgg 18

<210> SEQ ID NO 1924
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1924
ccaggcccca gtatggcg 18

<210> SEQ ID NO 1925
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1925
cccaggcccc agtatggc 18

<210> SEQ ID NO 1926
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1926
gcccaggccc cagtatgg 18

<210> SEQ ID NO 1927
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1927
agcccaggcc ccagtatg 18

<210> SEQ ID NO 1928
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1928
aagcccaggc cccagtat 18

<210> SEQ ID NO 1929
<211> LENGTH: 18

<212> TYPE: DNA
<213> ORGANISM: Artificial Sequence
<220> FEATURE:
<223> OTHER INFORMATION: AON sequence 5' -> 3'

<400> SEQUENCE: 1929
gaagcccagg ccccagta 18

<210> SEQ ID NO 1930
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1930
ggaagcccag gccccagt 18

<210> SEQ ID NO 1931
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1931
tggaagccca ggccccag 18

<210> SEQ ID NO 1932
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1932
gtggaagccc aggcccca 18

<210> SEQ ID NO 1933
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1933
ggtggaagcc caggcccc 18

<210> SEQ ID NO 1934
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1934
aggtggaagc ccaggccc 18

<210> SEQ ID NO 1935
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1935
caggtggaag cccaggcc 18

<210> SEQ ID NO 1936
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1936
acaggtggaa gcccaggc 18

<210> SEQ ID NO 1937
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1937
cacaggtgga agcccagg 18

<210> SEQ ID NO 1938
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1938
gcacaggtgg aagcccag 18

<210> SEQ ID NO 1939
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1939
ggcacaggtg gaagccca 18

<210> SEQ ID NO 1940
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1940
cggcacaggt ggaagccc 18

<210> SEQ ID NO 1941
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1941
gcggcacagg tggaagcc 18

<210> SEQ ID NO 1942
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1942
agcggcacag gtggaagc 18

<210> SEQ ID NO 1943
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1943
cagcggcaca ggtggaag 18

<210> SEQ ID NO 1944
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1944
ccagcggcac aggtggaa 18

<210> SEQ ID NO 1945
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1945
cccagcggca caggtgga 18

<210> SEQ ID NO 1946
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1946
ccccagcggc acaggtgg 18

<210> SEQ ID NO 1947
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1947
gccccagcgg cacaggtg 18

<210> SEQ ID NO 1948
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1948
agccccagcg gcacaggt 18

<210> SEQ ID NO 1949
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1949
tagccccagc ggcacagg 18

<210> SEQ ID NO 1950
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1950
gtagccccag cggcacag 18

<210> SEQ ID NO 1951
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1951
agtagcccca gcggcaca 18

<210> SEQ ID NO 1952
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1952
gagtagcccc agcggcac 18

<210> SEQ ID NO 1953
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1953
ggagtagccc cagcggca 18

<210> SEQ ID NO 1954
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1954
aggagtagcc ccagcggc 18

<210> SEQ ID NO 1955
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1955
gaggagtagc cccagcgg 18

<210> SEQ ID NO 1956
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1956
ggaggagtag ccccagcg 18

<210> SEQ ID NO 1957
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1957
tggaggagta gccccagc 18

<210> SEQ ID NO 1958
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1958
gtggaggagt agccccag 18

<210> SEQ ID NO 1959
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1959
ggtggaggag tagcccca 18

<210> SEQ ID NO 1960
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1960
cggtggagga gtagcccc 18

<210> SEQ ID NO 1961
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1961
gcggtggagg agtagccc 18

<210> SEQ ID NO 1962

<211> LENGTH: 36
<212> TYPE: DNA
<213> ORGANISM: Artificial Sequence
<220> FEATURE:
<223> OTHER INFORMATION: AON sequence 5' -> 3'

<400> SEQUENCE: 1962
agcggtggag gagtagccag cggtggagga gtagcc 36

<210> SEQ ID NO 1963
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1963
tagcggtgga ggagtagc 18

<210> SEQ ID NO 1964
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1964
atagcggtgg aggagtag 18

<210> SEQ ID NO 1965
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1965
gatagcggtg gaggagta 18

<210> SEQ ID NO 1966
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1966
tgatagcggt ggaggagt 18

<210> SEQ ID NO 1967
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1967
gtgatagcgg tggaggag 18

<210> SEQ ID NO 1968
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1968
ggtgatagcg gtggagga 18

<210> SEQ ID NO 1969
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1969
gggtgatagc ggtggagg 18

<210> SEQ ID NO 1970
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1970
cgggtgatag cggtggag 18

<210> SEQ ID NO 1971
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1971
gcgggtgata gcggtgga 18

<210> SEQ ID NO 1972
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1972
ggcgggtgat agcggtgg 18

<210> SEQ ID NO 1973
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1973
tggcgggtga tagcggtg 18

<210> SEQ ID NO 1974
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1974
ctggcgggtg atagcggt 18

<210> SEQ ID NO 1975
<211> LENGTH: 18
<212> TYPE: DNA

<213> ORGANISM: Artificial Sequence
<220> FEATURE:
<223> OTHER INFORMATION: AON sequence 5' -> 3'

<400> SEQUENCE: 1975
cctggcgggt gatagcgg 18

<210> SEQ ID NO 1976
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1976
acctggcggg tgatagcg 18

<210> SEQ ID NO 1977
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1977
cacctggcgg gtgatagc 18

<210> SEQ ID NO 1978
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1978
ccacctggcg ggtgatag 18

<210> SEQ ID NO 1979
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1979
accacctggc gggtgata 18

<210> SEQ ID NO 1980
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1980
caccacctgg cgggtgat 18

<210> SEQ ID NO 1981
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1981
ccaccacctg gcgggtga 18

<210> SEQ ID NO 1982
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1982
tccaccacct ggcgggtg 18

<210> SEQ ID NO 1983
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1983
ctccaccacc tggcgggt 18

<210> SEQ ID NO 1984
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1984
tctccaccac ctggcggg 18

<210> SEQ ID NO 1985
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1985
ttctccacca cctggcgg 18

<210> SEQ ID NO 1986
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1986
gttctccacc acctggcg 18

<210> SEQ ID NO 1987
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1987
tgttctccac cacctggc 18

<210> SEQ ID NO 1988
<211> LENGTH: 18
<212> TYPE: DNA
<213> ORGANISM: Artificial Sequence
<220> FEATURE:

<223> OTHER INFORMATION: AON sequence 5' -> 3'

<400> SEQUENCE: 1988
atgttctcca ccacctgg 18

<210> SEQ ID NO 1989
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1989
catgttctcc accacctg 18

<210> SEQ ID NO 1990
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1990
tcatgttctc caccacct 18

<210> SEQ ID NO 1991
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1991
gtcatgttct ccaccacc 18

<210> SEQ ID NO 1992
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1992
ggtcatgttc tccaccac 18

<210> SEQ ID NO 1993
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1993
tggtcatgtt ctccacca 18

<210> SEQ ID NO 1994
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1994
ctggtcatgt tctccacc 18

<210> SEQ ID NO 1995
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1995
cctggtcatg ttctccac 18

<210> SEQ ID NO 1996
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1996
ccctggtcat gttctcca 18

<210> SEQ ID NO 1997
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1997
gccctggtca tgttctcc 18

<210> SEQ ID NO 1998
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1998
ggccctggtc atgttctc 18

<210> SEQ ID NO 1999
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 1999
gggccctggt catgttct 18

<210> SEQ ID NO 2000
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2000
tgggccctgg tcatgttc 18

<210> SEQ ID NO 2001
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2001
gtgggccctg gtcatgtt 18

<210> SEQ ID NO 2002
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2002
agtgggccct ggtcatgt 18

<210> SEQ ID NO 2003
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2003
aagtgggccc tggtcatg 18

<210> SEQ ID NO 2004
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2004
gaagtgggcc ctggtcat 18

<210> SEQ ID NO 2005
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2005
ggaagtgggc cctggtca 18

<210> SEQ ID NO 2006
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2006
gggaagtggg ccctggtc 18

<210> SEQ ID NO 2007
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2007
ggggaagtgg gccctggt 18

<210> SEQ ID NO 2008
<211> LENGTH: 18

<212> TYPE: DNA
<213> ORGANISM: Artificial Sequence
<220> FEATURE:
<223> OTHER INFORMATION: AON sequence 5' -> 3'

<400> SEQUENCE: 2008
gggggaagtg ggccctgg 18

<210> SEQ ID NO 2009
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2009
agggggaagt gggccctg 18

<210> SEQ ID NO 2010
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2010
cagggggaag tgggccct 18

<210> SEQ ID NO 2011
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2011
ccagggggaa gtgggccc 18

<210> SEQ ID NO 2012
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2012
accaggggga agtgggcc 18

<210> SEQ ID NO 2013
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2013
caccaggggg aagtgggc 18

<210> SEQ ID NO 2014
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2014

-continued tcaccagggg gaagtggg 18

<210> SEQ ID NO 2015
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2015
ctcaccaggg ggaagtgg 18

<210> SEQ ID NO 2016
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2016
actcaccagg gggaagtg 18

<210> SEQ ID NO 2017
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2017
aactcaccag ggggaagt 18

<210> SEQ ID NO 2018
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2018
caactcacca gggggaag 18

<210> SEQ ID NO 2019
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2019
ccaactcacc agggggaa 18

<210> SEQ ID NO 2020
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2020
cccaactcac caggggga 18

<210> SEQ ID NO 2021
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2021
ccccaactca ccaggggg 18

<210> SEQ ID NO 2022
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2022
accccaactc accagggg 18

<210> SEQ ID NO 2023
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2023
caccccaact caccaggg 18

<210> SEQ ID NO 2024
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2024
ccaccccaac tcaccagg 18

<210> SEQ ID NO 2025
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2025
accaccccaa ctcaccag 18

<210> SEQ ID NO 2026
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2026
caccacccca actcacca 18

<210> SEQ ID NO 2027
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2027
ccaccacccc aactcacc 18

<210> SEQ ID NO 2028
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2028
gccaccaccc caactcac 18

<210> SEQ ID NO 2029
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2029
tgccaccacc ccaactca 18

<210> SEQ ID NO 2030
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2030
ctgccaccac cccaactc 18

<210> SEQ ID NO 2031
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2031
cctgccacca ccccaact 18

<210> SEQ ID NO 2032
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2032
ccctgccacc accccaac 18

<210> SEQ ID NO 2033
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2033
cccctgccac caccccaa 18

<210> SEQ ID NO 2034
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2034
tcccctgcca ccacccca 18

<210> SEQ ID NO 2035
<211> LENGTH: 18
<212> TYPE: DNA
<213> ORGANISM: Artificial Sequence
<220> FEATURE:
<223> OTHER INFORMATION: AON sequence 5' -> 3'

<400> SEQUENCE: 2035
ctcccctgcc accacccc 18

<210> SEQ ID NO 2036
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 2036
tcagtcaagt atctggaaag tacga 25

<210> SEQ ID NO 2037
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 2037
agtcaagtat ctggaaagta c 21

<210> SEQ ID NO 2038
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 2038
ggaagtcccg gaagccaacc ttgtt 25

<210> SEQ ID NO 2039
<211> LENGTH: 21
<212> TYPE: DNA
<213> ORGANISM: Artificial Sequence
<220> FEATURE:
<223> OTHER INFORMATION: AON sequence 5' -> 3'

<400> SEQUENCE: 2039
tgactctgcc cagagtgagg a 21

<210> SEQ ID NO 2040
<211> LENGTH: 25
<212> TYPE: DNA
<213> ORGANISM: Artificial Sequence
<220> FEATURE:
<223> OTHER INFORMATION: AON sequence 5' -> 3'

<400> SEQUENCE: 2040
agctttctgg gatgaggcag aggct 25

<210> SEQ ID NO 2041

<211> LENGTH: 25
<212> TYPE: DNA
<213> ORGANISM: Artificial Sequence
<220> FEATURE:
<223> OTHER INFORMATION: AON c.-32-224_-200

<400> SEQUENCE: 2041
gagtgcagag cacttgcaca gtctg 25

<210> SEQ ID NO 2042
<211> LENGTH: 25
<212> TYPE: DNA
<213> ORGANISM: Artificial Sequence
<220> FEATURE:
<223> OTHER INFORMATION: AON c.-32-86_-62

<400> SEQUENCE: 2042
aaagcagctc tgagacatca accgc 25

<210> SEQ ID NO 2043
<211> LENGTH: 20
<212> TYPE: DNA
<213> ORGANISM: Artificial Sequence
<220> FEATURE:
<223> OTHER INFORMATION: AON c.-32-27_-8

<400> SEQUENCE: 2043
agaagcaagc gggctcagca 20

<210> SEQ ID NO 2044
<211> LENGTH: 21
<212> TYPE: DNA
<213> ORGANISM: Artificial Sequence
<220> FEATURE:
<223> OTHER INFORMATION: AON c.5-25

<400> SEQUENCE: 2044
agcagggcgg gtgcctcact c 21

<210> SEQ ID NO 2045
<211> LENGTH: 20
<212> TYPE: DNA
<213> ORGANISM: Artificial Sequence
<220> FEATURE:
<223> OTHER INFORMATION: AON CypA c.165_173+11

<400> SEQUENCE: 2045
tgtaccctta ccactcagtc 20

<210> SEQ ID NO 2046
<211> LENGTH: 30
<212> TYPE: DNA
<213> ORGANISM: Artificial Sequence
<220> FEATURE:
<223> OTHER INFORMATION: target c.-32-188_-159

<400> SEQUENCE: 2046
cttttctcgc ccttccttct ggccctctcc 30

<210> SEQ ID NO 2047
<211> LENGTH: 12
<212> TYPE: PRT
<213> ORGANISM: Artificial Sequence
<220> FEATURE:
<223> OTHER INFORMATION: TAT sequence

<400> SEQUENCE: 2047

Cys Tyr Gly Arg Lys Lys Arg Arg Gln Arg Arg Arg
1 5 10

<210> SEQ ID NO 2048
<211> LENGTH: 19
<212> TYPE: DNA
<213> ORGANISM: Artificial Sequence
<220> FEATURE:
<223> OTHER INFORMATION: primer

<400> SEQUENCE: 2048
aaccgcgaga agatgaccc 19

<210> SEQ ID NO 2049
<211> LENGTH: 21
<212> TYPE: DNA
<213> ORGANISM: Artificial Sequence
<220> FEATURE:
<223> OTHER INFORMATION: primer

<400> SEQUENCE: 2049
gccagaggcg tacagggata g 21

<210> SEQ ID NO 2050
<211> LENGTH: 18
<212> TYPE: DNA
<213> ORGANISM: Artificial Sequence
<220> FEATURE:
<223> OTHER INFORMATION: primer

<400> SEQUENCE: 2050
aaactgaggc acggagcg 18

<210> SEQ ID NO 2051
<211> LENGTH: 18
<212> TYPE: DNA
<213> ORGANISM: Artificial Sequence
<220> FEATURE:
<223> OTHER INFORMATION: primer

<400> SEQUENCE: 2051
gagtgcagcg gttgccaa 18

<210> SEQ ID NO 2052
<211> LENGTH: 16
<212> TYPE: DNA
<213> ORGANISM: Artificial Sequence
<220> FEATURE:
<223> OTHER INFORMATION: primer

<400> SEQUENCE: 2052
ggcacggagc gggaca 16

<210> SEQ ID NO 2053
<211> LENGTH: 24
<212> TYPE: DNA
<213> ORGANISM: Artificial Sequence
<220> FEATURE:
<223> OTHER INFORMATION: primer

<400> SEQUENCE: 2053
ctgttagctg gatctttgat cgtg 24

<210> SEQ ID NO 2054
<211> LENGTH: 17

<212> TYPE: DNA
<213> ORGANISM: Artificial Sequence
<220> FEATURE:
<223> OTHER INFORMATION: primer

<400> SEQUENCE: 2054
aggcacggag cggatca 17

<210> SEQ ID NO 2055
<211> LENGTH: 20
<212> TYPE: DNA
<213> ORGANISM: Artificial Sequence
<220> FEATURE:
<223> OTHER INFORMATION: primer

<400> SEQUENCE: 2055
tcggagaact ccacgctgta 20

<210> SEQ ID NO 2056
<211> LENGTH: 18
<212> TYPE: DNA
<213> ORGANISM: Artificial Sequence
<220> FEATURE:
<223> OTHER INFORMATION: primer

<400> SEQUENCE: 2056
aaactgaggc acggagcg 18

<210> SEQ ID NO 2057
<211> LENGTH: 21
<212> TYPE: DNA
<213> ORGANISM: Artificial Sequence
<220> FEATURE:
<223> OTHER INFORMATION: primer

<400> SEQUENCE: 2057
gcagctctga gacatcaacc g 21

<210> SEQ ID NO 2058
<211> LENGTH: 20
<212> TYPE: DNA
<213> ORGANISM: Artificial Sequence
<220> FEATURE:
<223> OTHER INFORMATION: primer

<400> SEQUENCE: 2058
gagacagcgg ctaacaggat 20

<210> SEQ ID NO 2059
<211> LENGTH: 20
<212> TYPE: DNA
<213> ORGANISM: Artificial Sequence
<220> FEATURE:
<223> OTHER INFORMATION: primer

<400> SEQUENCE: 2059
attccaaaag ctcactcgct 20

<210> SEQ ID NO 2060
<211> LENGTH: 21
<212> TYPE: DNA
<213> ORGANISM: Artificial Sequence
<220> FEATURE:
<223> OTHER INFORMATION: primer

<400> SEQUENCE: 2060
gtccagaacc tcccctactc c 21

<210> SEQ ID NO 2061
<211> LENGTH: 21
<212> TYPE: DNA
<213> ORGANISM: Artificial Sequence
<220> FEATURE:
<223> OTHER INFORMATION: primer

<400> SEQUENCE: 2061
cgaaaaccgg agtcggaact t 21

<210> SEQ ID NO 2062
<211> LENGTH: 21
<212> TYPE: DNA
<213> ORGANISM: Artificial Sequence
<220> FEATURE:
<223> OTHER INFORMATION: primer

<400> SEQUENCE: 2062
ccatgctgct ggctgtggga t 21

<210> SEQ ID NO 2063
<211> LENGTH: 25
<212> TYPE: DNA
<213> ORGANISM: Artificial Sequence
<220> FEATURE:
<223> OTHER INFORMATION: primer

<400> SEQUENCE: 2063
agcagtacaa cacaggtgct cttgc 25

<210> SEQ ID NO 2064
<211> LENGTH: 20
<212> TYPE: DNA
<213> ORGANISM: Artificial Sequence
<220> FEATURE:
<223> OTHER INFORMATION: primer

<400> SEQUENCE: 2064
caaaaacggg ggcttcttcc 20

<210> SEQ ID NO 2065
<211> LENGTH: 20
<212> TYPE: DNA
<213> ORGANISM: Artificial Sequence
<220> FEATURE:
<223> OTHER INFORMATION: primer

<400> SEQUENCE: 2065
gccaggtaac ggttagcaca 20

<210> SEQ ID NO 2066
<211> LENGTH: 21
<212> TYPE: DNA
<213> ORGANISM: Artificial Sequence
<220> FEATURE:
<223> OTHER INFORMATION: primer

<400> SEQUENCE: 2066
gagctgcaac ttggccacga c 21

<210> SEQ ID NO 2067
<211> LENGTH: 21
<212> TYPE: DNA
<213> ORGANISM: Artificial Sequence
<220> FEATURE:
<223> OTHER INFORMATION: primer

<400> SEQUENCE: 2067
gagacggaga ggaattcaga c 21

<210> SEQ ID NO 2068
<211> LENGTH: 20
<212> TYPE: DNA
<213> ORGANISM: Artificial Sequence
<220> FEATURE:
<223> OTHER INFORMATION: primer

<400> SEQUENCE: 2068
cactccggtc ccaaatgtag 20

<210> SEQ ID NO 2069
<211> LENGTH: 20
<212> TYPE: DNA
<213> ORGANISM: Artificial Sequence
<220> FEATURE:
<223> OTHER INFORMATION: primer

<400> SEQUENCE: 2069
ttccctgtag caccacacac 20

<210> SEQ ID NO 2070
<211> LENGTH: 20
<212> TYPE: DNA
<213> ORGANISM: Artificial Sequence
<220> FEATURE:
<223> OTHER INFORMATION: primer

<400> SEQUENCE: 2070
cactccctca cctccatcgt 20

<210> SEQ ID NO 2071
<211> LENGTH: 19
<212> TYPE: DNA
<213> ORGANISM: Artificial Sequence
<220> FEATURE:
<223> OTHER INFORMATION: primer

<400> SEQUENCE: 2071
catctgggaa ggccacaga 19

<210> SEQ ID NO 2072
<211> LENGTH: 20
<212> TYPE: DNA
<213> ORGANISM: Artificial Sequence
<220> FEATURE:
<223> OTHER INFORMATION: primer

<400> SEQUENCE: 2072
gtgttagtgg cacccaggtc 20

<210> SEQ ID NO 2073
<211> LENGTH: 20
<212> TYPE: DNA
<213> ORGANISM: Artificial Sequence
<220> FEATURE:
<223> OTHER INFORMATION: primer

<400> SEQUENCE: 2073
ggaaggcctg tcttgttcac 20

<210> SEQ ID NO 2074
<211> LENGTH: 20
<212> TYPE: DNA
<213> ORGANISM: Artificial Sequence
<220> FEATURE:
<223> OTHER INFORMATION: primer

<400> SEQUENCE: 2074
cctggattgc gaattttacc 20

<210> SEQ ID NO 2075
<211> LENGTH: 20
<212> TYPE: DNA
<213> ORGANISM: Artificial Sequence
<220> FEATURE:
<223> OTHER INFORMATION: primer

<400> SEQUENCE: 2075
atggaattct gatggccaaa 20

<210> SEQ ID NO 2076
<211> LENGTH: 38
<212> TYPE: DNA
<213> ORGANISM: Artificial Sequence
<220> FEATURE:
<223> OTHER INFORMATION: primer

<400> SEQUENCE: 2076
gctcttttag aatttttgga gcaggttttc tgacttcg 38

<210> SEQ ID NO 2077
<211> LENGTH: 38
<212> TYPE: DNA
<213> ORGANISM: Artificial Sequence
<220> FEATURE:
<223> OTHER INFORMATION: primer

<400> SEQUENCE: 2077
cgaagtcaga aaacctgctc caaaaattct aaaagagc 38

<210> SEQ ID NO 2078
<211> LENGTH: 37
<212> TYPE: DNA
<213> ORGANISM: Artificial Sequence
<220> FEATURE:
<223> OTHER INFORMATION: primer

<400> SEQUENCE: 2078
cctggctcgc tacagatgca taggaggacg gaggacg 37

<210> SEQ ID NO 2079
<211> LENGTH: 37
<212> TYPE: DNA
<213> ORGANISM: Artificial Sequence
<220> FEATURE:
<223> OTHER INFORMATION: primer

<400> SEQUENCE: 2079
cgtcctccgt cctcctatgc atctgtagcg agccagg 37

<210> SEQ ID NO 2080
<211> LENGTH: 17
<212> TYPE: DNA
<213> ORGANISM: Artificial Sequence
<220> FEATURE:
<223> OTHER INFORMATION: primer -continued

<400> SEQUENCE: 2080
gtaaaacgac gggccag 17

<210> SEQ ID NO 2081
<211> LENGTH: 17
<212> TYPE: DNA
<213> ORGANISM: Artificial Sequence
<220> FEATURE:
<223> OTHER INFORMATION: primer

<400> SEQUENCE: 2081
caggaaacag ctatgac 17

<210> SEQ ID NO 2082
<211> LENGTH: 27
<212> TYPE: DNA
<213> ORGANISM: Artificial Sequence
<220> FEATURE:
<223> OTHER INFORMATION: primer

<400> SEQUENCE: 2082
aggttctcct cgtccgcccg ttgttca 27

<210> SEQ ID NO 2083
<211> LENGTH: 27
<212> TYPE: DNA
<213> ORGANISM: Artificial Sequence
<220> FEATURE:
<223> OTHER INFORMATION: primer

<400> SEQUENCE: 2083
tccaagggca cctcgtagcg cctgtta 27

<210> SEQ ID NO 2084
<211> LENGTH: 29
<212> TYPE: DNA
<213> ORGANISM: Artificial Sequence
<220> FEATURE:
<223> OTHER INFORMATION: primer

<400> SEQUENCE: 2084
gcgcctgcag taacaacata ggagctgtg 29

<210> SEQ ID NO 2085
<211> LENGTH: 30
<212> TYPE: DNA
<213> ORGANISM: Artificial Sequence
<220> FEATURE:
<223> OTHER INFORMATION: primer

<400> SEQUENCE: 2085
gcgcgtcgac cagatacgcg tttcctagga 30

ENZYMATIC REPLACEMENT THERAPY AND ANTISENSE THERAPY FOR POMPE DISEASE

CROSS-REFERENCE TO RELATED APPLICATIONS

This application is a 371 of PCT/NL2018/050392, filed Jun. 14, 2018, which claims the benefit of Netherlands Patent Application No. 2019069, filed Jun. 14, 2017.

FIELD OF THE INVENTION

The invention is related to a combination of enzymatic replacement therapy (ERT) or gene therapy and antisense oligonucleotides that are useful for the treatment of aberrant gene splicing, especially aberrant splicing in Pompe disease and to pharmaceutical compositions comprising the antisense oligonucleotides and, optionally, enzymes. The invention is also related to a method to modulate splicing, especially splicing of pre-mRNA of the GAA gene and to treatment of Pompe disease.

BACKGROUND OF THE INVENTION

Pompe disease, also known as acid maltase deficiency or Glycogen storage disease type II, is an autosomal recessive metabolic disorder which damages muscle and nerve cells throughout the body. It is caused by an accumulation of glycogen in the lysosome due to a deficiency of the lysosomal acid α-glucosidase enzyme. The build-up of glycogen causes progressive muscle weakness (myopathy) throughout the body and affects various body tissues, particularly in the heart, skeletal muscles, liver and nervous system.

In Pompe disease, a protein, α-D-glucoside glucohydrolase or, in short, α-glucosidase (EC 3.2.1.20, also known as acid maltase), which is a lysosomal hydrolase, is defective. The protein is an enzyme that normally degrades the α-1,4 and α-1,6 linkages in glycogen, maltose and isomaltose and is required for the degradation of 1-3% of cellular glycogen. The deficiency of this enzyme results in the accumulation of structurally normal glycogen in lysosomes and cytoplasm in affected individuals. Excessive glycogen storage within lysosomes may interrupt normal functioning of other organelles and lead to cellular injury. The defective protein is the result of alternative splicing which is caused by mutations in the GAA gene on long arm of chromosome 17 at 17q25.2-q25.3 (base pair chr17:80, 101,526 to 80,119,882 build GRCh38/hg38). The gene spans approximately 18 kb and contains 20 exons with the first exon being noncoding.

The defective α-glucosidase protein or reduced amount or activity of α-glucosidase protein is the result of mutations (or variations) with in the GAA gene. Some of these GAA mutations may lead to alternative splicing and thereby to absent or a reduced amount or activity of α-glucosidase protein. The GAA gene is located on the long arm of chromosome 17 at 17q25.2-q25.3 (base pair 75,689,876 to 75,708,272). The gene contains 20 exons with the first exon being noncoding.

The Pompe Center at the Erasmus University in Rotterdam, the Netherlands, maintains an up-to-date catalog of the GAA mutations. The current list (May 2016) can be found on its website at http://www.erasmusme.nl/klnische_genetica/research/lijnen/pompe_center/?lang=en. Although over 460 GAA mutations have been described (http://cluster15.erasmusmc.nl/klgn/pompe/mutations.html), only a few splicing mutations have been characterized. Severe mutations that completely abrogate GAA enzyme activity cause a classic infantile disease course with hypertrophic cardiomyopathy, general skeletal muscle weakness, and respiratory failure and result in death within 1.5 years of life. Milder mutations leave partial GAA enzyme activity which results in a milder phenotype with onset varying from childhood to adult. In general, a higher residual enzyme activity in primary fibroblasts is associated with later onset of Pompe disease.

Enzyme replacement therapy (ERT) has been developed for Pompe disease, in which recombinant human GAA protein is administered intravenously every two weeks. This treatment is aimed to increase the intracellular level of n-glucosidase activity in affected cells and tissues and thereby reduce or prevent glycogen accumulation and eventually symptoms of the disease. The treatment can rescue the lives of classic infantile patients and delay disease progression of later onset patients, but the effects are heterogeneous.

Pompe disease is an autosomal recessive inheritable disorder. One of the most common mutations in Pompe disease is the IVS1 mutation, c.-32-13T'>G, a transversion (T to C) mutation and occurs among infants, children, juveniles and adults with this disorder (Huie M L, et al., 1994. Hum Mol Genet. 3(12):2231.6). This mutation interrupts a site of RNA splicing.

Antisense oligonucleotides (antisense oligomeric compounds) are currently being tested in clinical trials for their ability to modulate splicing. A classical example is (treatment of) Duchenne muscular dystrophy. In this disease, mutation hotspots are present in certain exons. Using antisense oligomeric compounds, the mutated exon is skipped and the mutation is bypassed. This results in a slightly shorter protein that is still partially functional. It is straightforward to induce exon skipping using antisense oligomeric compounds, because it is evident that the antisense oligomeric compound must be targeted to the relevant splice site. Also in Epidermolysis bullosa (WO2013053819) and in Leber congenital amaurosis symptoms (WO2012168435) antisense oligonucleotides are used for exon skipping.

However, with the IVS1 mutation, such a strategy does not work. The IVS1 mutation causes a skipping of exon 2 resulting in the deletion of the canonical translation start side and leads to non-sense mediated decay and thus no protein is transcribed. For antisense therapy to work for the IVS1 mutation in Pompe disease, it needs to induce exon inclusion. i.e. an effect strongly contrasting with exon skipping. However, it is very difficult to induce exon inclusion, because it relies on targeting a splicing repressor sequence, which cannot be reliably predicted. Splicing repressor sequences may be present anywhere in the gene, either in an exon (termed exonic splicing silencer or ESS) or in an intron (termed intronic splicing silencer or ISS) and maybe close to the mutation or far away or maybe close to the affected splice site or far away from it.

Although a number of antisense compounds that are capable of modulating splicing of a target gene in vitro have been reported, there remains a need to identify compounds that may modulate the splicing of the GAA gene.

Enzyme replacement therapy (ERT) with acid α-glucosidase (GAA), has been used or treatment of infantile (infantile-onset or 'classic infantile'), childhood (delayed-onset) and adult (late onset) Pompe patients. The ERT modifies the natural course of the disease. Targeting of the main target tissues and cells is, however, a challenge. For example 15-40% of the body is composed of skeletal muscle and for the treatment to be effective each individual cell in the body needs to reached and loaded with exogenous (AA. The cells must take up the enzyme via endocytosis, which seems most efficient when receptors on the cell surface such as the mannose 6-phosphate/IGF II receptor are targeted. The mannose 6-phosphate/IGF II receptor recognizes various ligands such as mannose 6-phosphate. IGF II and Gluc-NAC, and ERT wherein these ligands are bound to (AA show a better uptake of the enzyme. The current registered ERT is targeted at the M6P part of the M6P/IGF II receptor, but there is also ERT under development with an increased amount of M6P ligands or with IGF II linked to it. Another problem with ERT is that some patients develop antibodies to the administered GAA enzyme reducing the effect or ERT and these patients respond poorly to the treatment. In addition, ERT requires purified recombinant human GAA which is difficult to produce and therefore expensive. Furthermore, recombinant human GAA has a relative short half life ranging from 2-3 hours in blood to several dyes in cells and must therefore be administered intravenously every 2 weeks (or every week), which is cumbersome for patients. It is a further problem with ERT that acid α-glucosidase (GAA) enzyme accumulation within target cells shows saturation, such that further increase of the external enzyme concentration does not result in higher intracellular enzyme concentrations. Furthermore, under clinical conditions using standard dosages. ERT results in levels and/or activities of intracellular GAA enzyme that are still lower than those observed in normal, healthy subjects, or obtained when using antisense therapy to induce exon inclusion in IVS1 mutations as shown herein and e.g. in Van der Wal et al. 2017 Molecular Therapy: Nucleic Acids Vol. 7:90-100.

It is therefore an object of the invention to provide an improved treatment for Pompe Disease. Another object of the invention is to provide an improved ERT treatment of Pompe Disease. Another object of the invention is to provide an antisense compound that is capable of improving GAA exon 2 inclusion in the context of the IVS1 mutation. Yet another object of the invention is to provide a antisense compound that is capable of targeting the IVS-1 mutation. It is further an object of the invention to improve the enzyme replacement therapy of GAA enzyme in patients. It is a further object to improve ERT such that higher levels and/or activity of GAA is achieved when using current clinical dosages of GAA in ERT. It is a further object to increase the intracellular levels and/or activities of GAA in cells of Pompe patients to levels beyond the maximum attainable by ERT. The present invention meets one or more of the objects.

The present invention combines two strategies which are different. ERT or gene therapy enhances glycogen breakdown by administration of a foreign GAA enzyme, whereas antisense therapy improves or enhances the intracellular production of the patients own GAA enzyme.

Our earlier research has led to the discovery of sites in the genomic sequence of the GAA gene that cause aberrant splicing and in a co-pending patent application it has been shown that antisense oligonucleotide-based compounds directed to those sites may be able to restore the aberrant splicing. There is, however, still room for improving GAA gene expression or GAA activity in Pompe patients.

Also other diseases that are caused by or characterized by aberrant pre-mRNA splicing that cannot be completely restored by known antisense approaches (such as exon skipping) may be in need of new techniques for improving correct splicing.

SUMMARY OF THE INVENTION

The inventors now have found that the GAA IVS1 mutation causes novel aberrant splicing. Besides the already known splice products N (leaky wild type splicing), SV1 (alternative splice donor from exon 1, perfect skipping of exon 2), SV2 (full skipping of exon 2), and SV3 (partial skipping of exon 2), the inventors found that the IVS1 mutation results in the usage of a natural pseudo exon that is present in GAA intron 1. Blocking of either the natural cryptic 3' splice site or the natural cryptic 5' splice site of this natural pseudo exon with AONs restores wild type GAA splicing in cells carrying the IVS1 allele. Blocking of both natural cryptic splice sites simultaneously is more effective in restoration of splicing and GAA enzyme activity.

Therefore, the present invention relates to method for repairing aberrant splicing, wherein such aberrant splicing is caused by the expression of a natural pseudo exon, comprising blocking of either the natural cryptic 3' splice site or the natural cryptic 5' splice site of said natural pseudo exon with an antisense oligomeric compound (AON).

In a further aspect, the invention relates to a method for repairing aberrant splicing, wherein such aberrant splicing is caused by the expression of a natural pseudo exon, comprising providing a pair of AONs, in which the first AON is directed to the acceptor splice site of said natural pseudo exon (i.e. 3' splice site of the natural pseudo exon) and wherein the second AON is directed to the donor splice site of said natural pseudo exon (i.e. the 5' splice site of the natural pseudo exon), wherein the application of said pair of AONs provides for a silencing of the expression of the natural pseudo exon, and promotes canonical splicing.

In a preferred embodiment said natural pseudo exon is comprised in an intron of a gene. In another preferred embodiment the aberrant splicing is related to a probably is the cause of a disease selected from the group consisting of mucopolysaccharidoses (MPS I, MPS II, MPS IV), familial dysautonomia, congenital disorder of glycosylation (CDG1A), ataxia telangiectasia, spinal muscular atrophy, medium-chain acyl-CoA dehydrogenase (MCAD) deficiency, cystic fibrosis, Factor VII deficiency, Fanconi anemia, Hutchinson-Gilford progeria syndrome, growth hormone insensitivity, hyperphenylalaninemia (HPABH4A), Menkes disease, hypobetalipoproteinemia (FHBL), megalencephalic leukoencephalopathy with subcortical cysts (MLC1), methylmalonic aciduria, frontotemporal dementia, Parkinsonism related to chromosome 17 (FTDP-17), Alzheimer's disease, tauopathies, myotonic dystrophy, afibrinogenemia, Bardet-Biedl syndrome, β-thalassemia, muscular dystrophies, such as Duchenne muscular dystrophy, myopathy with lactic acidosis, neurofibromatosis, Fukuyama congenital muscular dystrophy, muscle wasting diseases, dystrophic epidermolysis bullosa, Myoshi myopathy, retinitis pigmentosa, ocular albinism type 1, hypercholesterolemia, Hemaophilis A, propionic academia, Prader-Willi syndrome, Niemann-Pick type C, Usher syndrome, autosomal dominant polycystic kidney disease (ADPKD), cancer such as solid tumours, retinitis pigmentosa, viral infections such as HIV, Zika, hepatitis, encephalitis, yellow fever, infectious diseases like malaria or Lyme disease. More preferably in the present invention the disease is Pompe disease, even more preferably wherein the Pompe disease is characterized by the IVS1 mutation.

In one aspect of the invention an antisense oligomeric compound (AON) is directed against the natural cryptic donor splice site chosen from the sequences SEQ ID NO: 1 and/or 171.

In a further aspect of the present invention an AON is directed against the cryptic acceptor site chosen from the sequences SEQ ID NO: 267-445. Preferably, the AON is chosen from the sequences SEQ ID NO: 267-298 or sequences that have an identity of 80% with said sequences, or, alternatively the AON is chosen from the sequences SEQ ID NO: 299-445 or sequences that have an identity of 80% with said sequences.

In a further embodiment, the invention comprises a method according to the invention wherein a pair of AONs is formed by selecting a first AON from the sequences of SEQ ID NO: 267-298 or sequences that have an identity of 80% with said sequences and a second AON from the sequences of SEQ ID NO: 299-445 or sequences that have an identity of 80% with said sequences.

In a further aspect, the invention is related to an antisense oligomeric compound targeting SEQ ID NO: 1 or SEQ ID NO: 171. In a further embodiment the antisense oligomeric compound targets any of the sequences of SEQ ID NO: 2-170 or SEQ ID NO: 172-260, which sequences are a part of SEQ ID NO: 1 or SEQ ID NO: 171, respectively.

In a still further aspect the invention is related to a pair of antisense oligomeric compounds of which a first AON targets one of the sequences of SEQ ID NO: 1-170 and of which the second AON targets one of the sequences of SEQ ID NO: 171-260.

Preferably, in embodiments of aspects of the invention, said AON may be selected from the sequences of SEQ ID NO: 267-2040, sequences that are complementary to said sequences or sequences that have an identity of 80% with said sequences or the complementary sequences. It is to be understood that in all embodiments of aspects of this invention, the AON as indicated in any of the tables herein may be used in the form of a reverse complement, in which case reference is made to embodiments including the complementary sequence. Preferably, in a further aspect of the invention, a combination of at least 2 AONs is used wherein a first AON is selected from the sequences of SEQ ID NO: 267-298, sequences that are complementary thereto or sequences that have an identity of 80% therewith, and wherein a second AON is selected from the sequences of SEQ ID NO: 299-602, sequences that are complementary thereto or sequences that have an identity of 80% therewith, more preferably a first AON selected from SEQ ID NOs: 514, 519, and 578 as the AON targeting the splice donor site or a sequence complimentary thereto or sequences having a sequence identity of at least 80% therewith or with the complementary sequence, and a second AON selected from SEQ ID NOs: 277 and 298 as the AON targeting the splice acceptor site, or sequences complimentary thereto or sequences having a sequence identity of at least 80% therewith or with the complementary sequences.

In a further preferred embodiment, the invention comprises a pair of AONs of which a first member is selected from the sequences of SEQ ID NO: 267-445, sequences that are complementary to said sequences or sequences that have an identity of 80% with said sequences or the complementary sequences and of which a second AON is selected from the sequences of SEQ ID NO: 446-602, sequences that are complementary to said sequences or sequences that have an identity of 80% with said sequences or the complementary sequences.

In a further aspect, the invention provides an AON that modulate splicing by promotion of exon 6 inclusion wherein the AON targets a sequence selected from any one of SEQ ID NO: 261-266. Exemplary embodiments of such sequences include the SEQ ID NOs: 993-2040.

In a further aspect, the invention comprises an AON selected from the sequences of SEQ ID NO: 641-992, sequences that are complementary to said sequences or sequences that have an identity of 80% with said sequences or the complementary sequences and a second AON from the sequences of SEQ ID NO: 641-992, sequences that are complementary to said sequences or sequences that have an identity of 80% with said sequences or the complementary sequences for use in the treatment of Pompe disease, wherein said AON sequences are able to block the region surrounding specific splice element variants that affect aberrant splicing of exon 2 caused by IVS1 in GAA exon 1-3 minigene system.

These splice element variants may include splice element variants represented by mutations c.-32-13T>G, c.-32-3C>G c.-32-102T>C. c.-32-56C>T, c.-32-46G>A, c.-32-28>A, c.-32-28C>T, c.-32-21G>A, c.7G>A, c, 11G>A, c.15-17AAA, c.17C>T, c.19_21AAA, c.26-28AAA, c.33-35AAA, c.39G>A, c.42C>T, c.90C>T, c, 112G>A, c, 137C>T, c, 16-4C>T, c.348G>A, c.373C>T, c.413T>A, c.469C>T, c.476T>C. c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, c.1552-30, c.1256A>T, c.1551+1G>T, c.546G>T, .17C>T, c.469C>T, c.546+23C>A, c.-32-102T>C, c.–32-56C>T, c, 11G>A, c.112G>A, or c, 137C>T.

In a still further aspect, the invention comprises a pair of AONs as described above, of which a first member is selected from the sequences of SEQ ID NO: 267-445, sequences that are complementary to said sequences or sequences that have an identity of 80% with said sequences or the complementary sequences and of which a second AON is selected from the sequences of SEQ ID NO: 446-602, sequences that are complementary to said sequences or sequences that have an identity of 80% with said sequences or the complementary sequences for use in the treatment of Pompe disease, more preferably wherein said pair comprises an AON selected from SEQ ID NOs: 514, 519, and 578 and an AON selected from SEQ ID NOs: 277 and 298, or sequences complimentary thereto or sequences having an identity of 80% with said sequences or the complementary sequences.

In a preferred embodiment each of said AON or pair of AONs according to the invention, or AON or pair of AONs for use according to the invention is uniformly modified, preferably wherein the sugar of one or more nucleotides is modified, more preferably wherein the sugar modification is 2'-O-methyl or 2'-O-methoxyethy, or alternatively or in combination wherein the base of one or more nucleotides is modified, or alternatively or in combination wherein the backbone of the oligomeric compound is modified, more preferably wherein the backbone is a Morpholino, referring to the presence of a six-membered morpholine ring, such as in the form of morpholino phosphorothioates, or morpholino phosphorodiamidate.

In a further aspect, the invention relates to a pharmaceutical composition comprising an AON or pair of AONs according to the invention, preferably wherein said pharmaceutical composition further provides a pharmaceutical acceptable excipient and/or a cell delivery agent.

In still a further aspect of the invention, a method is provided for treating Pompe disease comprising antisense therapy by administering any one of the AONs or pairs of AONs as described above in combination with ERT.

In the combination therapy described herein, preferred administration dosages for AON include 1-60 mg/kg, preferably 1-50 mg/kg, more preferably about 10-50 mg/kg, and still more preferably around 10 mg/kg. Preferably, the AON is administered in said dosage once every 1 week, more preferably once every 2 weeks, and si ill more preferably once every month. A pair of AONs may be used at the same or each at half the dosage of the preferred regimes, preferably at, half the dosage each.

In the combination therapy described herein, preferred administration dosages for ERT enzyme include 5-60 mg/kg, preferably 5-40 mg/kg, more preferably about 10-30 mg/kg, and still more preferably around 20 mg/kg. Preferably, the ERT enzyme is administered in said dosage once every week, and more preferably once every 2 weeks.

Preferred embodiments of AONs used in aspects of the present invention include AONs having SEQ ID Nos: 277, 298, 514, 519, and 578.

Figures 1A, 1B, 1C:
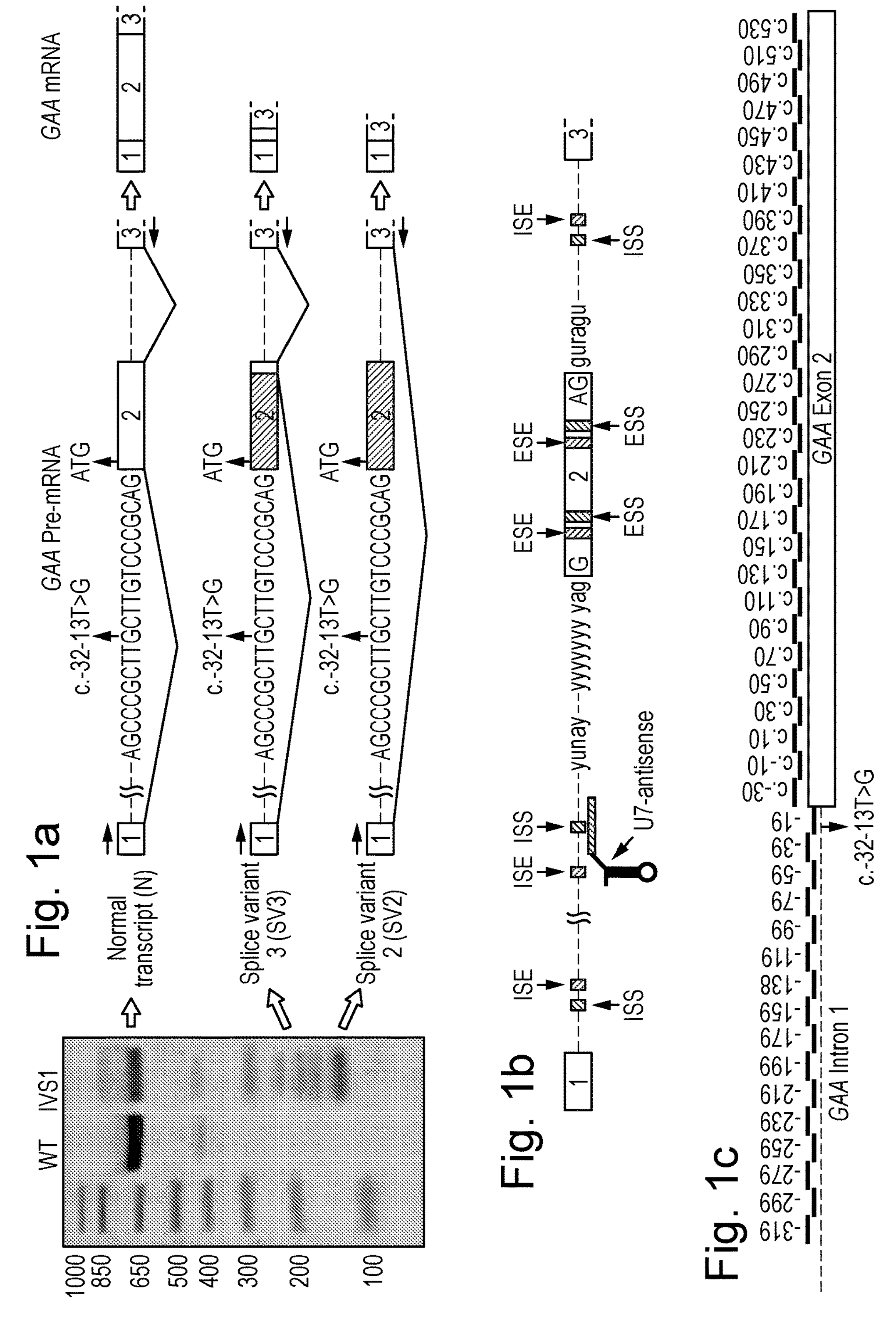
FIG. 1. Screen to identify silencers of GAA exon 2 splicing.

(a) Outline of the three major splicing products of the GAA pre-mRNA caused by the IVS1 variant in patient-derived primary fibroblasts known to date. The gel illustrates the results of flanking exon RT-PCR analysis of exon 2 using primers that anneal to exon 1 and exon 3. WT: control fibroblasts; IVS1: fibroblasts from patient 1. Left lane: DNA size markers (in basepairs). Cartoons of pre-mRNAs illustrate splicing events as described 22, 23, 24, 25. The location of the c.-32-13C>T (IVS1) variant in the pY tract is indicated. Spliced mRNA cartoons are shown on the far right with sizes of the PCR products shown below the cartoons. Sizes of introns and exons in the cartoon are not to scale.

(b) Cartoon showing hypothetical splicing regulatory elements that may be subject to modulation e.g. by a U7 snRNA 56.

(c) Locations of U7 snRNA-based AONs used in the screen in (d).

(d) Screen to identify splicing silencers of GAA exon 2. Primary fibroblasts from patient 1 (IVS1, c.525delT) were transduced with 200 ng U7 snRNA-expressing lentiviruses. The effects on GAA exon 2 expression were measured using RT-qPCR (black line; GAA (N) expression; primers indicated in the upper left cartoon). Effects on GAA enzymatic activity are indicated by the red line. The cartoon of GAA pre-mRNA below the graph indicates the positions of the AONs tested. Data are expressed relative to non-transduced (NT) fibroblasts and represent means+/−SD of three biological replicates. Samples were normalized for β-Actin expression.

(e) The experiment of (d) was also analyzed by flanking exon RT-PCR of GAA exon 2. β-Actin mRNA was used as loading control $*P<0.05$ and $**P<0.01$ ($n=3$).

FIG. 2. Splicing correction of GAA exon 2 in fibroblasts using PMO-based AONs.

(a) Positions in the GAA pre-mRNA to which PMO-based AONs1-4 anneal (PMO refers to phosphorodiamidate morpholino oligomer).

(b) Effect of AONs 1-4 in fibroblasts from patient 1. GAA exon 2 inclusion in the mRNA was measured using RT-qPCR analysis (see FIG. 2*d*) (GAA (N) mRNA level), and GAA enzymatic activity using 4-MU as substrate. Data are expressed relative to levels in healthy control fibroblasts and were corrected for β-Actin expression.

Figure 2A:
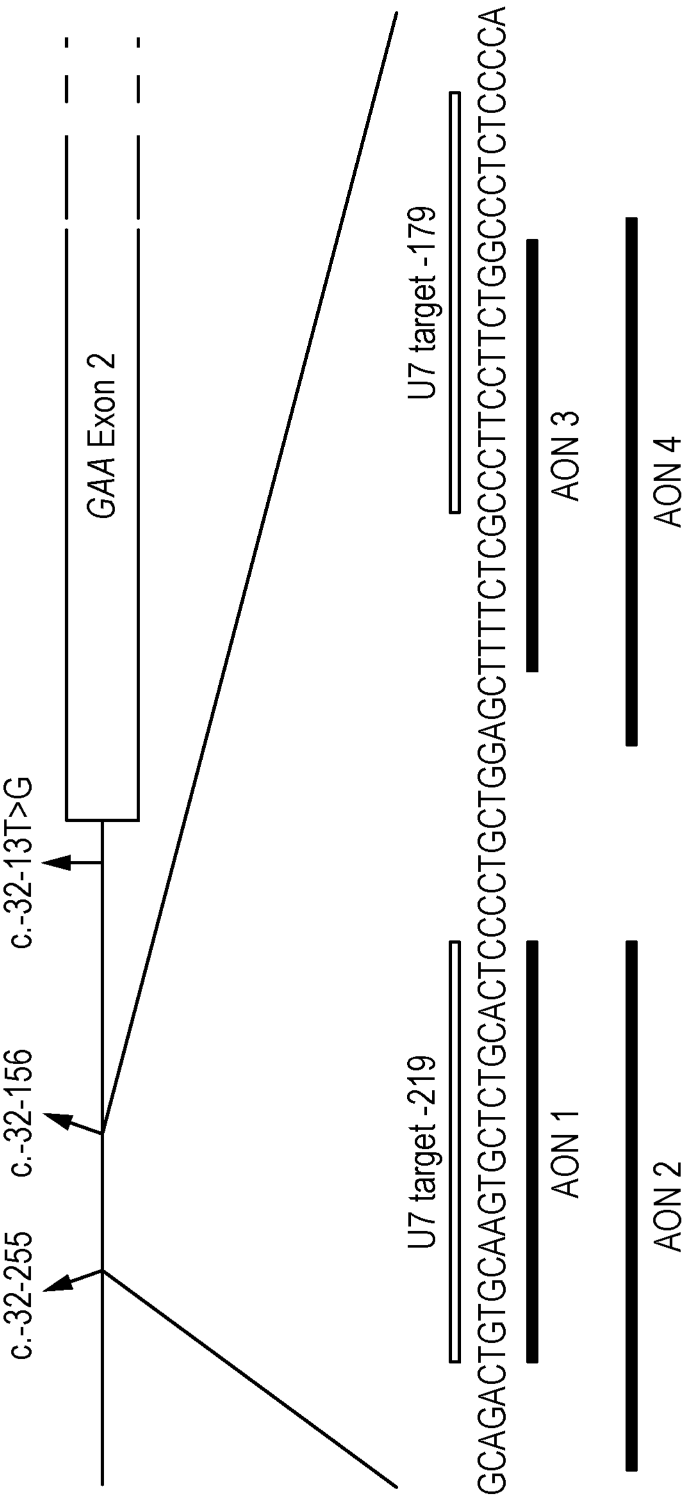
Figure 2B:
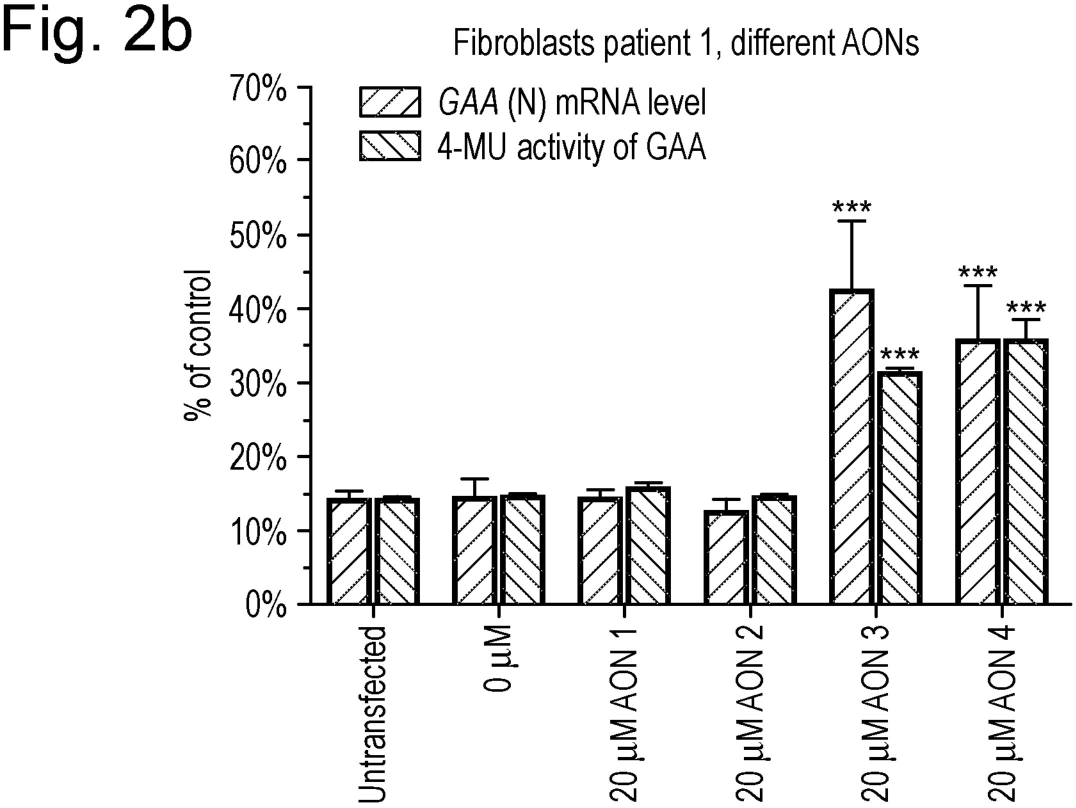
Figure 2C:
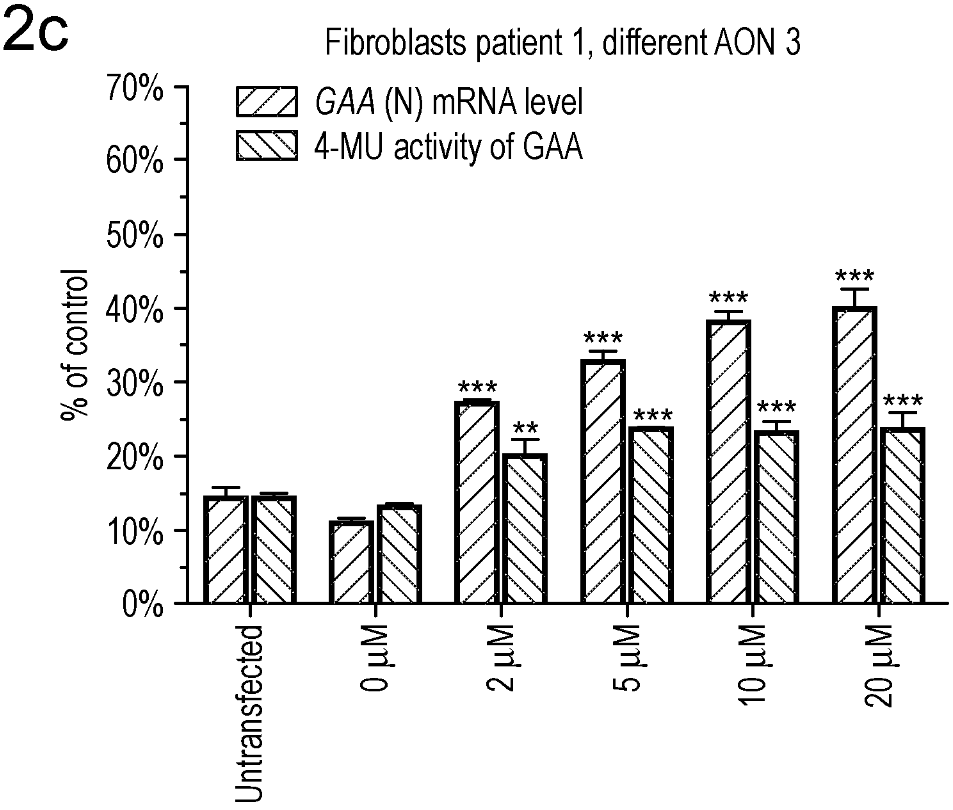

(c) As in FIG. 2*b*, but now using a concentration range of AON 3.

(d) As in FIG. 2*b*, but now using a concentration range of AON 4.

(e) Flanking exon RT-PCR analysis (as in FIG. 2*a*) of the effect of AON 4 on GAA exon 2 inclusion in fibroblasts from patient 1 and 2. −: 0 μM AON, +: 20 μM AON. (1) RT-qPCR analysis of individual splicing products of GAA exon 2 splicing. The N, SV2, and SV3 products were quantified using primers as outlined in the cartoon, and the effect of AON 4 on GAA exon 2 splicing was determined in fibroblasts from patients 1 and 2 and control 1. Data are corrected for β-Actin expression and normalized per splicing variant for expression in untreated cells to visualize the effect per variant. Note that patient 2 carried a missense GAA variant on the second allele which shows mRNA expression (partially masking effects on the IVS1 allele), whereas patient 1 has no GAA mRNA expression from the second allele due to NMD. Data are means+/−SDs of three biological replicates, $*p<0.05$, $p<0.01$, $*p<0.001$.

FIG. 3. Expansion of purified iPS-derived myogenic progenitors and differentiation into multinucleated myotubes.

(a) I. Scheme for differentiation of iPS cells into myogenic progenitors and FACS purification: II, Scheme for expansion of purified myogenic progenitors. The expansion medium is indicated. The average passage (IP) number and fold expansion are also indicated.

(b) Linear proliferation curves for all four iPS-derived myogenic progenitor lines during expansion. The single R2 shown was calculated for all datapoints of the 4 lines, and indicates high concordance between the four lines.

(c) mRNA expression of iPS-derived myogenic progenitors and myotubes. Equal amounts of total RNA were isolated from fibroblasts (F), myogenic progenitors (MP), and myotubes (MT), and mRNA expression of the indicated genes was determined by RT-qPCR analysis. Log fold change was calculated compared to Control 1 sample 1. Symbols are as in (b). Biological duplicates are shown.

(d) Karyotype analysis after expansion of purified myogenic progenitors at day 35 (a representative example of 15 nuclei).

(e) Myogenic progenitors retain their capacity to differentiate into multinucleated myotubes during expansion. Myogenic progenitors were expanded, and at several time points during expansion a subculture was differentiated for 4 days and stained for expression of the myogenic differentiation marker MHC (MF-20 antibody; red). Nuclei were stained with Hoechst (blue). The white arrowheads point to examples of aligned nuclei present in a single myotube.

FIG. 4. Quantitative analysis of GAA exon 2 splicing in expanded iPS-derived myotubes.

(a) Comparison of aberrant GAA splicing in fibroblasts and myotubes. Equal amounts of total RNA from primary fibroblasts (F) and their corresponding iPS-derived myotubes (MT), derived from patient 1 or a healthy control, were analyzed by flanking exon RT-PCR of exon 2 as described in FIG. 1*a*.

(b), as (a) but now as analyzed by RT-qPCR of individual splicing products. To facilitate comparison between different cell types, no normalization was used, and all products were compared to the value of average control fibroblast product N levels using the delta-Ct method. (c-i) Quantitative analysis of splicing correction in iPS-derived myotubes.

(c) Effect of AON 3 on GAA exon 2 splicing in myotubes from patient 1 as analyzed with RT-qPCR analysis of individual splicing products. Data were normalized against expression of four genes that showed no consistent changes in expression: MyoD, Myogenin, LAMP1, and LAMP2 (see FIG. 9*h*).

(d) As (c), but now for AON 4.

(e) Effect of AONs 3 and 4 on GAA exon 2 splicing in myotubes from control 1 as analyzed with RT-qPCR analysis of splice product N. Control cells have undetectable levels of aberrant splice products SV2 and SV3.

(f) Flanking exon RT-PCR analysis of the effect of AON 3 on GAA exon 2 splicing in myotubes from patient 1 and control 1.

(g) Effects of AON 3 and 4 on GAA enzymatic activity in myotubes from patient 1.

(h) As (g), but now in myotubes from control 1. (i) AON treatment does not affect myogenic differentiation. Immunofluorescent stainings of myotubes after treatment with AONs 3 and 4. Red: MHC (anti-MF-20); green: Myogenin: blue: nuclei (Hoechst). 0 μM: mock transfection. Representative pictures are shown. Quantitative data are means+/−SDs of three biological replicates. *p<0.05, p<0.01, *p<0.001.

FIG. 5. Blocking of a natural pseudo exon restores GAA exon 2 splicing.

(a) The splicing silencer in intron 1 is predicted to be the pY tract of a pseudo exon. Human splice finder was used to predict splice sites around the splicing silencer identified in FIG. 1. Note that predictions were independent of the IVS1 variant. A strong 3' splice site was predicted at c.-32-154, and a strong 5' splice site at c.-32-53, which suggested the presence of a natural pseudo exon, indicated by 'p' in the cartoon. The canonical 3' splice site of exon 2 at c.-32 showed strong prediction and is also indicated.

(b) Blocking of pseudo exon splicing restores GAA exon 2 splicing. AON 5 was designed to block the predicted 5' splice site, and AONs 3 and 5 were tested alone or in combination in myotubes from patient 1. Flanking RT-PCR analysis of GAA exon 2 was performed. Splicing products were identified by TOPO cloning and are indicated in the gel and in the cartoons in (c).

(d). Analysis of the experiment in (c) by RT-qPCR of individual splicing products. Splicing to the pseudo exon is represented by SV5 and SV6 and these products were quantified using a unique PC(R primer.

(e) Analysis of the experiment in (c) on GAA enzyme activity.

(f) Combined treatment with AONs 3 and 5 does not interfere with myogenic differentiation to myotubes. Inmunofluorescent staining results are shown for treatment of iPS-derived myotubes obtained from patient 1. Red: MHC (anti-MF-20); green: Myogenin: blue: nuclei (Hoechst). 0 μM: mock transfection. Representative pictures are shown. Quantitative data are means+/−SDs of three biological replicates. *p<0.05, p<0.01, *p<0.001.

FIG. 6. A U7 snRNA screen to identify splicing repressors.

(a) In silico prediction of exonic and intronic splicing silencers around the GAA IVS1 variant. Algorithms from Human Splicing Finder 2.4.1 are indicated below the graph.

(b) One-step cloning strategy for rapid cloning of AONs in the lentiviral U7 snRNA expression vector. A unique NsiI site was introduced in the U7 snRNA. AON sequences and the NsiI site were part of a forward primer in PCR, and a unique SalI site was included in the reverse PCR primer.

(c) Cartoon of the region of the Cyclophilin A (CypA) gene that was targeted using a U7 snRNA-expressed AON (CyPA-E4) as described previously by Liu et al.[29].

(d) RT-PCR analysis of patient 1 fibroblasts in which the CypA pre-mRNA was targeted using CyPA-E4. As control, and empty, non-transduced U7 lentivirus was used (NT). The PCR strategy is shown above the gel. Sizes of spliced mRNAs are indicated to the right of the gel. β-actin was used as loading control.

(e) RT-qPCR analysis of the samples of (d). The PCR strategy is shown above the figure.

(f) Testing of the optimal viral amount for detection of splicing modulation sequences. Patient 1 fibroblasts were infected with various lentiviruses at the amounts indicated. The optimum amount was determined to be 200 ng lentivirus per ml of medium. Data are means+/−SD of two biological replicates. Data points from 200 ng were taken from FIG. 2*d* (N=3). NT: non-transduced.

Figure 2D:
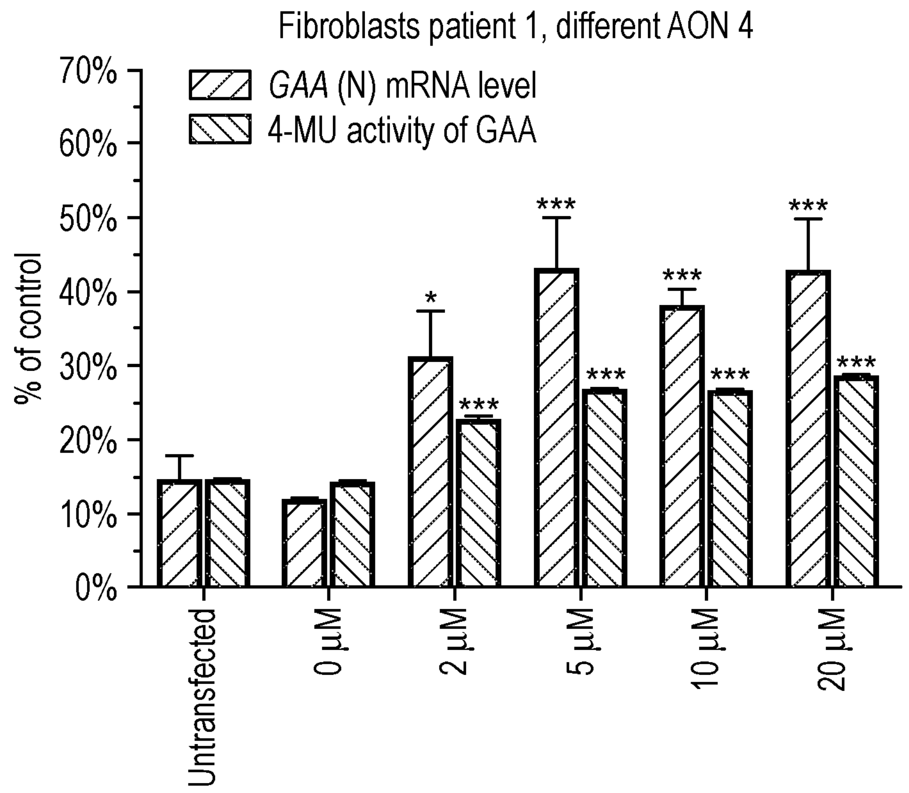

(g) Two hits from the screen shown in FIG. 2*d* were further tested in a microwalk using the U7 snRNA system. Primer locations are shown here.

(h) Results of the microwalk, as analyzed by RT-qPCR (FIG. 2*d*).

(i) As (h), using RT-PCR analyses. Results are expressed relative to non-transduced and represent means+/−SD of three biological replicates. **P<0.01.

FIG. 7. PMO-based AONs promote exon inclusion in primary fibroblasts from Pompe patients.

(a) Sequences of PMO-AONs used.

(b-d) Test of PMO-based AONs on positive control CypA.

(b) Location of AONs designed to block the splice donor of CypA exon 4.

(c) Fibroblasts from patient 1 were transfected with AONs at various concentrations as indicated, and CyPA mRNAs were analyzed by RT-PCR. Cartoons at the right side of the gel indicate sizes of splicing products.

(d) RT-qPCR analysis of exon 4 skipping of the experiment in (c). The cartoon highlights the primer location. Data represent means of 3 technical replicates.

(e-f) Promotion of GAA exon 2 inclusion.

(e) Effect of AON 3 on GAA exon 2 inclusion (measured using RT-qPCR analysis as in FIG. 2*d*) and on GAA enzymatic activity in fibroblasts from patient 2. Note that this patient has genotype IVS1, c.923A>C, and that the c.923A>C allele causes background expression of the N form of GAA mRNA. Data are means+/−SD from three biological replicates.

(f) As (e) but with AON 4. Data for Supplementary FIG. 2*e,f* are means+/−SD from three biological replicates. *p<0.05, p<0.01, *p<0.001.

FIG. 8. Purification and expansion of iPS-derived myogenic progenitors.

(a-d) Generation and characterization of iPS cells.

(a) Immunofluorescent analysis of iPS cells from control 2 and patient 1 and 2 with antibodies to Nanog. Oct 4, SSEA4, TRA-I-60 an TRA-I-81 (red). DAPI was used to stain nuclei (blue). Control 1 iPS cells were published previously[26].

(b) In vitro differentiation potential of iPS lines from (a) into the three germ layers. Stainings for α-Fetoprotein (AFP) show hepatocytes (endoderm: red), stainings for smooth muscle actin (SMA) show smooth muscle cells (mesoderm, red), and neuron-specific class III β-tubulin (TUJ1) stainings show neurons (ectoderm, red). DAPI staining shows nuclei in blue.

(c) Microarray analysis of mRNA expression of pluripotency and fibroblast genes, iPS cell are marked as P2, P1 and C2 (patients 2 and 1, and control 2, respectively). For comparison, human embryonic stem cell lines H1 and H9 and fibroblast line F134 were also analyzed.

(d) Karyotype analysis of the four iPS lines used in this study. All lines have normal karyotypes. Representative karyotypes of 10 nuclei per cell line are shown.

(e-j) Expansion and differentiation of purified iPS-derived myogenic progenitors. (e)

Figure 3A:
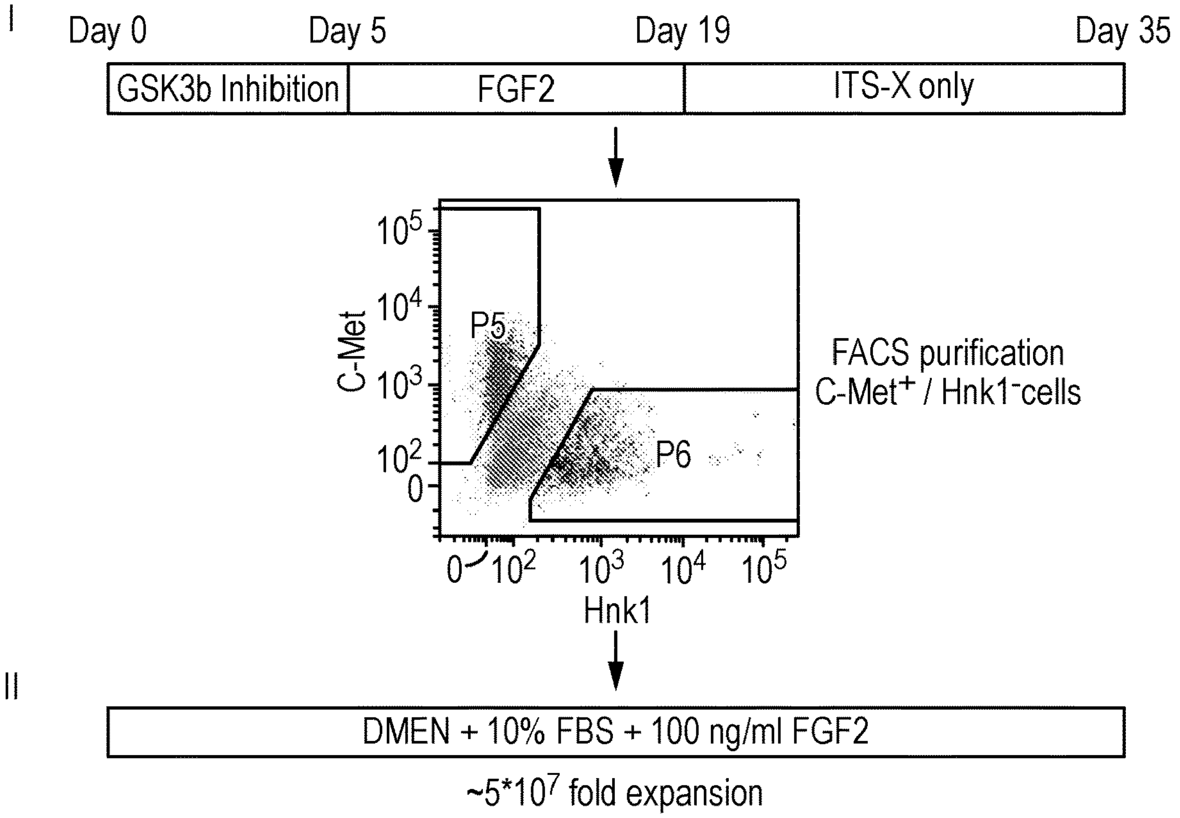

Immunofluorescent staining for Pax7 (in red) in non-purified myogenic progenitors following the 35-day differentiation protocol outlined in FIG. 3A I. Nuclei were stained with Hoechst (blue).

(f) Myogenic progenitors from (e) were purified by FACS sorting for HNK-1-/C-MET+ cells, and differentiated for 4 days into myotubes, which were stained with an MF-20 antibody to MHC (red). Nuclei were stained with Hoechst (blue). Purification yields and differentiation capacities without subsequent expansion were variable and prevented reproducible quantitative analysis.

(g-j) Characterization of expanded myogenic progenitors. Equal amounts of total RNA from fibroblasts (F), purified and expanded myogenic progenitors (MPs) and myotubes (MTs) from purified and expanded MPs were analyzed by RT-qPCR analysis. Biological duplicates are shown. Lines represent means.

(h) Immunofluorescent analysis of MyoD in expanded myogenic progenitors. Myogenic progenitors were expanded in proliferation medium and stained at the start of expansion and after expansion to ~1012 cells. Representative pictures are shown.

(i). Unchanged capacity to differentiate into multinucleated myotubes during expansion. Myogenic progenitors were expanded and at several time points during expansion, and a subculture from the expansion was differentiated for 4 days and stained for MHC expression (anti-MF20, red). Nuclei were stained with Hoechst (blue).

(j) Examples of myogenic differentiation after expansion of myogenic progenitors to ~1012 cells. Staining was as in (i). Multiple aligned myonuclei were seen in extended myotubes.

FIG. 9. Promotion of exon inclusion in patient-derived myotubes.

(a) Morphology of differentiated myotubes, obtained from purified myogenic progenitors from control 1 and patient 1, with and without AON treatment. Cells were stained with antibodies against Myosin Heavy Chain (MHC) and Myogenin. Nuclei were visualized with Hoechst.

(b) Same as (a), but for control 2 and patient 2. (c-g) AONs promote exon 2 inclusion and GAA enzyme activity in patient-derived myotubes but not in myotubes from a healthy control.

(c) Effect of AON 3 on GAA pre-mRNA splicing in myotubes from patient 2, measured with RT-qPCR analysis of individual splicing products.

(d) As (c), but using AON 4.

(e) Effects of AON 3 and 4 on expression of the N form of GAA mRNA in myotubes from control 2.

(f) Effects of AON 3 and 4 on GAA enzymatic activity in myotubes from patient 2. (g) Effects of AON 3 and 4 on (AA enzymatic activity in myotubes from control 2. (h) Effects of AON 3 and 4 on expression of reference genes (MyoD, Myog, LAMP1. LAMP2) in myotubes from patients and controls. In all experiments, data represent means+/−SD of three biological replicates. *p<0.05, *p<0.01, ***p<0.001.

FIG. 10. Identification of a natural pseudo exon that competes with GAA exon inclusion.

(a) Sequence analysis of splicing products from Table 6.

(b) AON treatment does not change expression of reference genes in myotubes. The experiment of FIG. 2*b-e* was analyzed by RT-qPCR for expression of the reference genes shown. Equal amounts of total RNA were used.

(c-e) Mutations in splice sites of the pseudo exon abolish pseudo exon inclusion.

(c) Cartoon of the minigene comprising the 5 kb genomic GAA sequence from exons 1-3. This sequence was obtained by PCR and cloned into pcDNA3.1. The pseudo exon is indicated along with the splice sites that were mutated by site directed mutagenesis.

(d) Splicing prediction of the effect of the mutations shown in (c). Mutation 1 generated a new predicted 3' splice site 5 nt downstream, whereas Mutations 2 and 3 completely abolished predicted 3' and 5' splice site, respectively.

(e) Wild type and mutated minigenes were transfected in HEK293 cells, and expression of GAA splice variants containing the pseudo exon was quantified by RT-qPCR analysis using the primers indicated. While this experiment further validates the identification of the pseudo exon, we found in an extensive set of experiments that GAA splicing regulation from the minigene does not faithfully reproduce endogenous GAA splicing. For example, abolishment of pseudo gene incusion promotes endogenous GAA exon 2 inclusion but not in the context of the minigene. This may be caused by differences in promoters, polyadenylation, and/or chromatin organization, all of which are factors that are known to affect splicing outcome.

Figure 11:
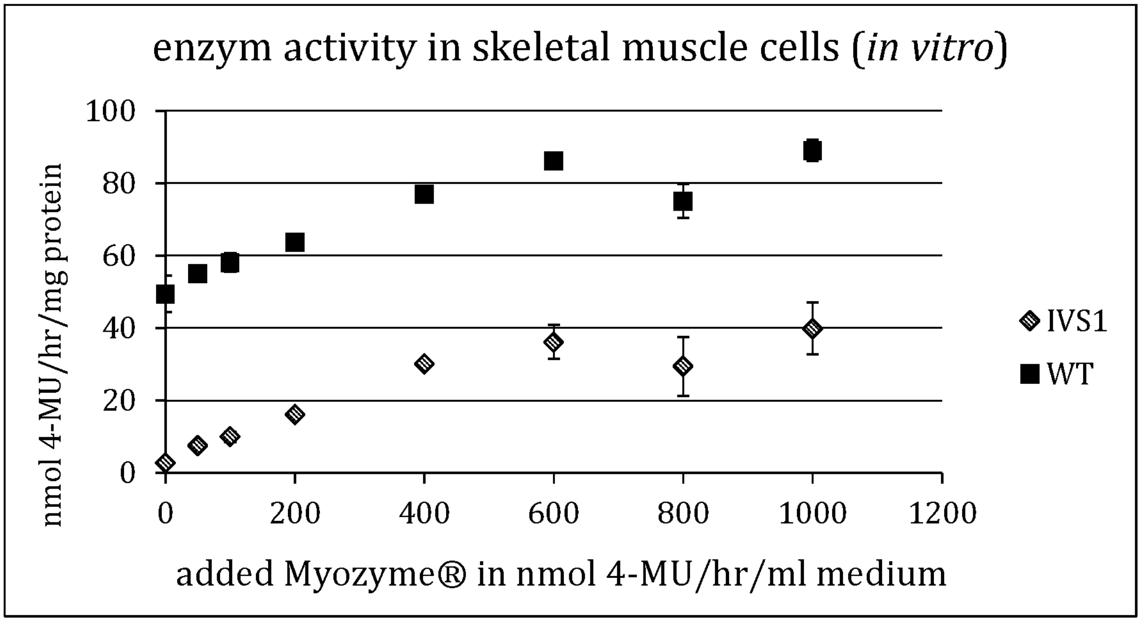

FIG. 11 shows GAA enzyme activity in skeletal muscle cells (in vitro) of an IVS1 patient and a healthy control subject during incubation in medium containing between 0 and 1000 added Myozyme® in nmol 4-MU/hr/ml as described in Example 2.

Figure 12:
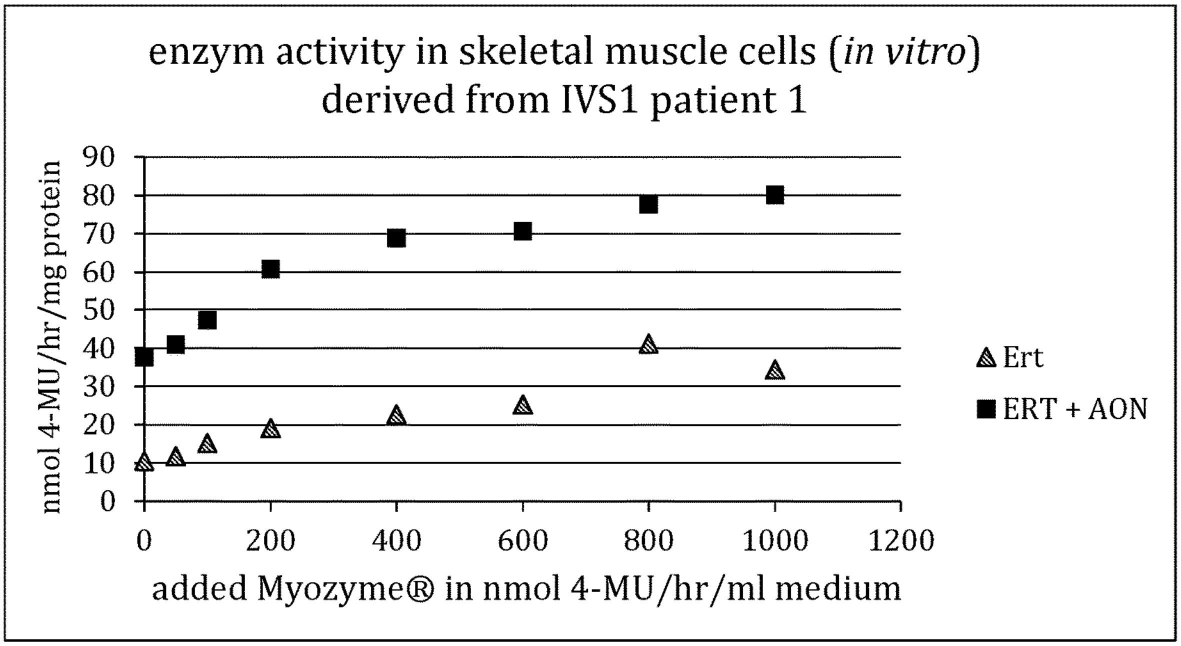
Figure 13:
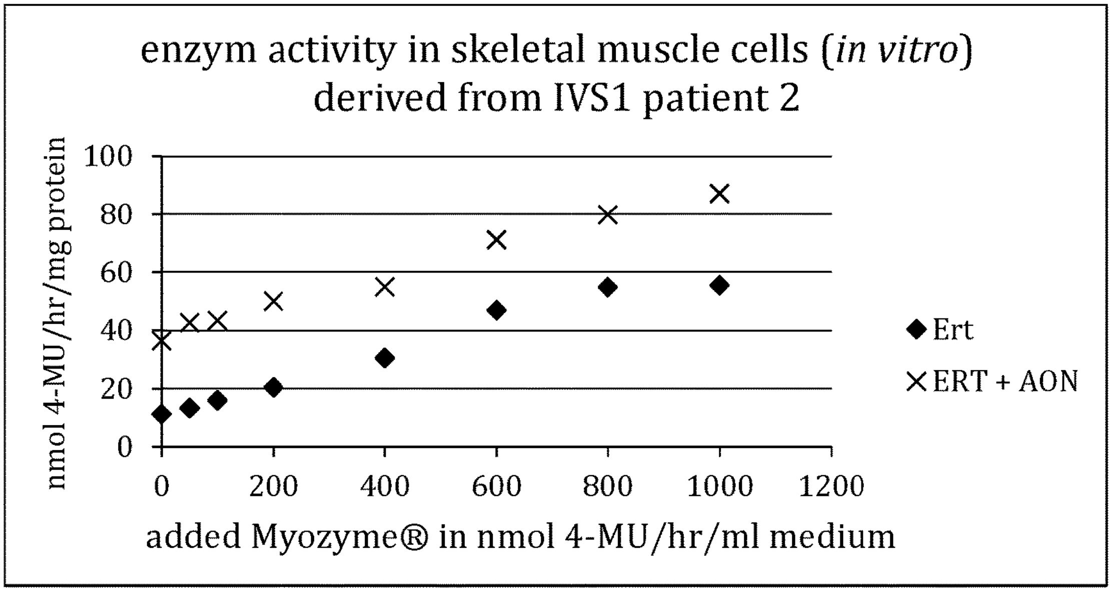
Figure 14:
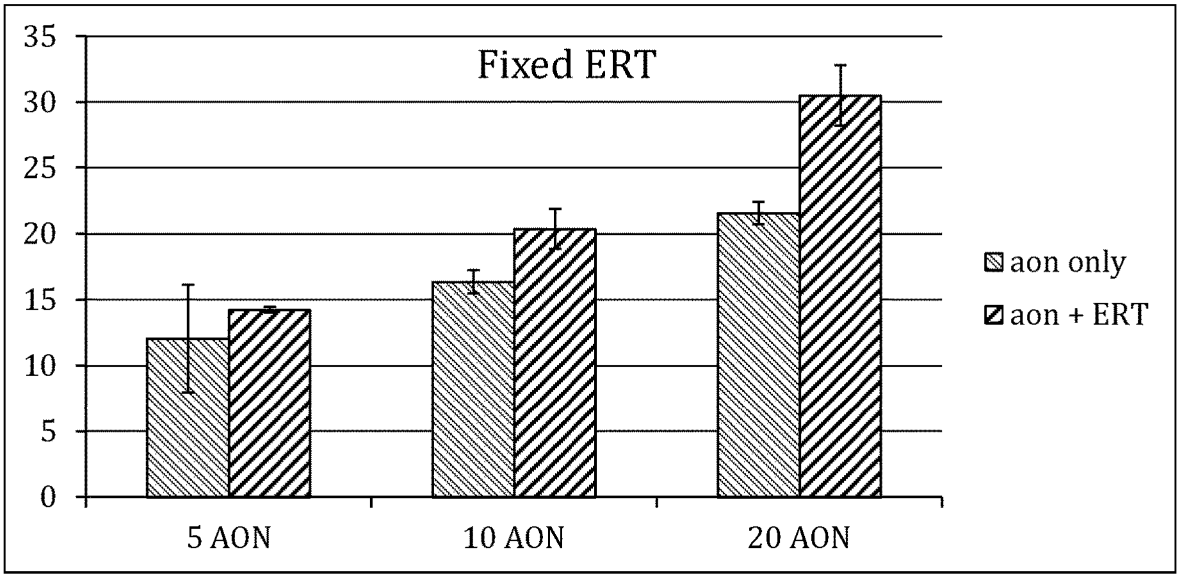

FIGS. 12 and 13 show (GAA enzyme activity in skeletal muscle cells (in vitro) derived from 2 different IVS1 patients, respectively, as described in Example 3, wherein an AON plus ERT combination therapy as described in the present invention was tested against ERT therapy alone. Concentrations of between 0 and 1000 ng added Myozyme® in nmol 4-MU/hr/ml medium were tested at a fixed AON concentration of 20 μM. The therapeutic combination according to the present invention results in an increase in protein level whereby levels well in excess of 40 nmol 4-MU/hr/mg protein (the therapeutic ERT ceiling as shown for ERT therapy alone) can be attained. The advantage is that this allows for the use of reduced concentrations of either AON, ERT, or both, which may help to reduce toxicity of AON and reduce the price of ERT therapy.

Figure 15:
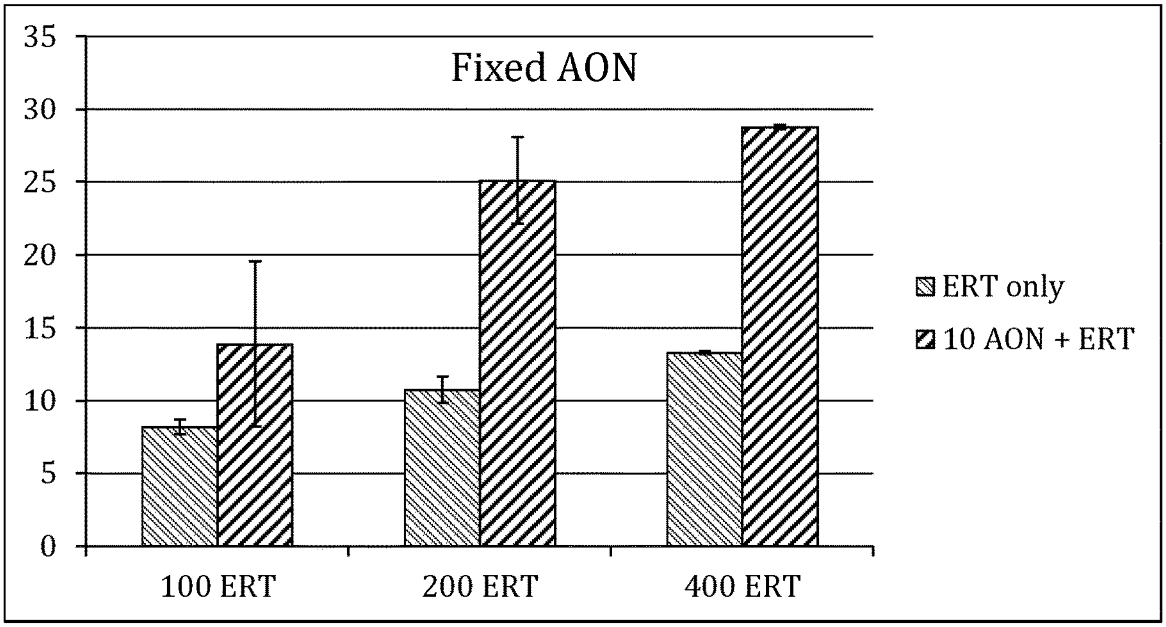
Figure 16:
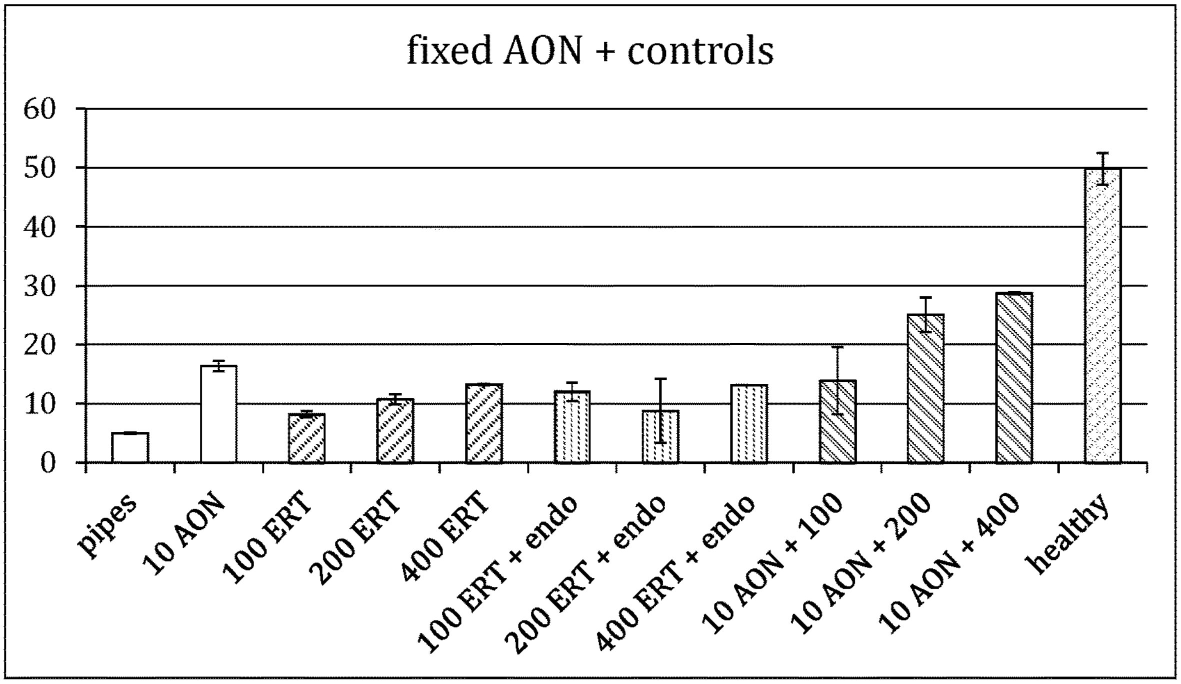
Figure 17:
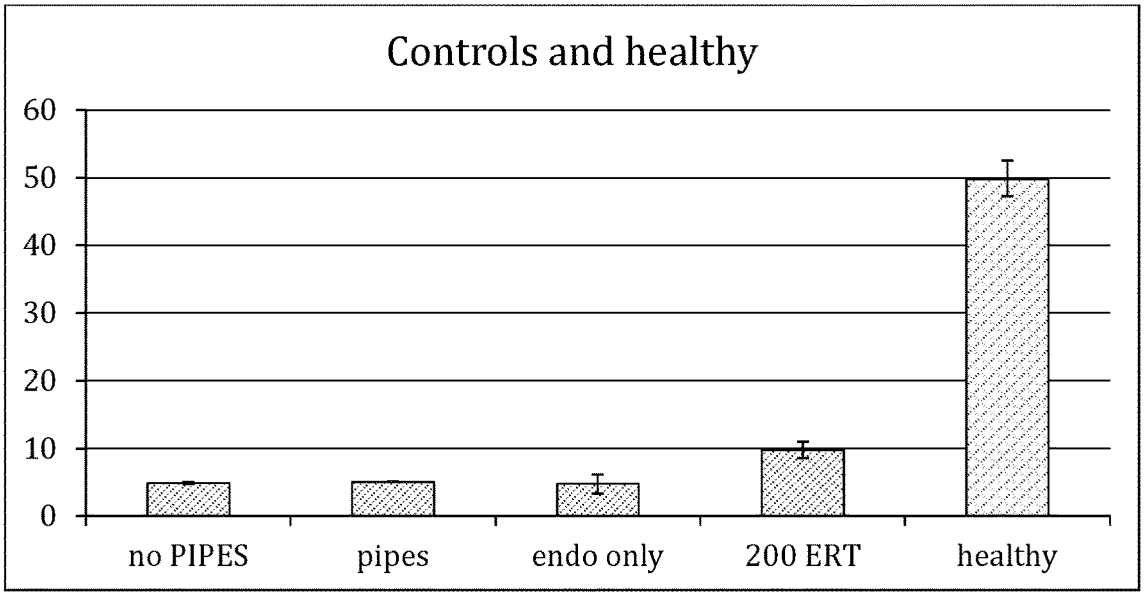

FIGS. 14-17 show the results of enzyme activity measurements in skeletal muscle cells (in vitro) derived from an IVS1 patient, when treated with AON. ERT, or the combination thereof as described herein, wherein the cells were either treated with Myozyme® at a fixed concentration (200 nmol 4-MU/hr/ml medium) and increasing concentrations of AON (FIG. 14), with Myozyme® at several concentrations using a fixed concentration of AON (20 μM) (FIG. 15). A number of controls was included (FIGS. 16 and 17), as described in Example 4, hereinbelow, wherein the results of 10 μM AOM in combination with 100, 200 and 400 ERT (in added Myozyme® in nmol 4-MU/hr/ml) from FIG. 15 was included.

Figure 18:
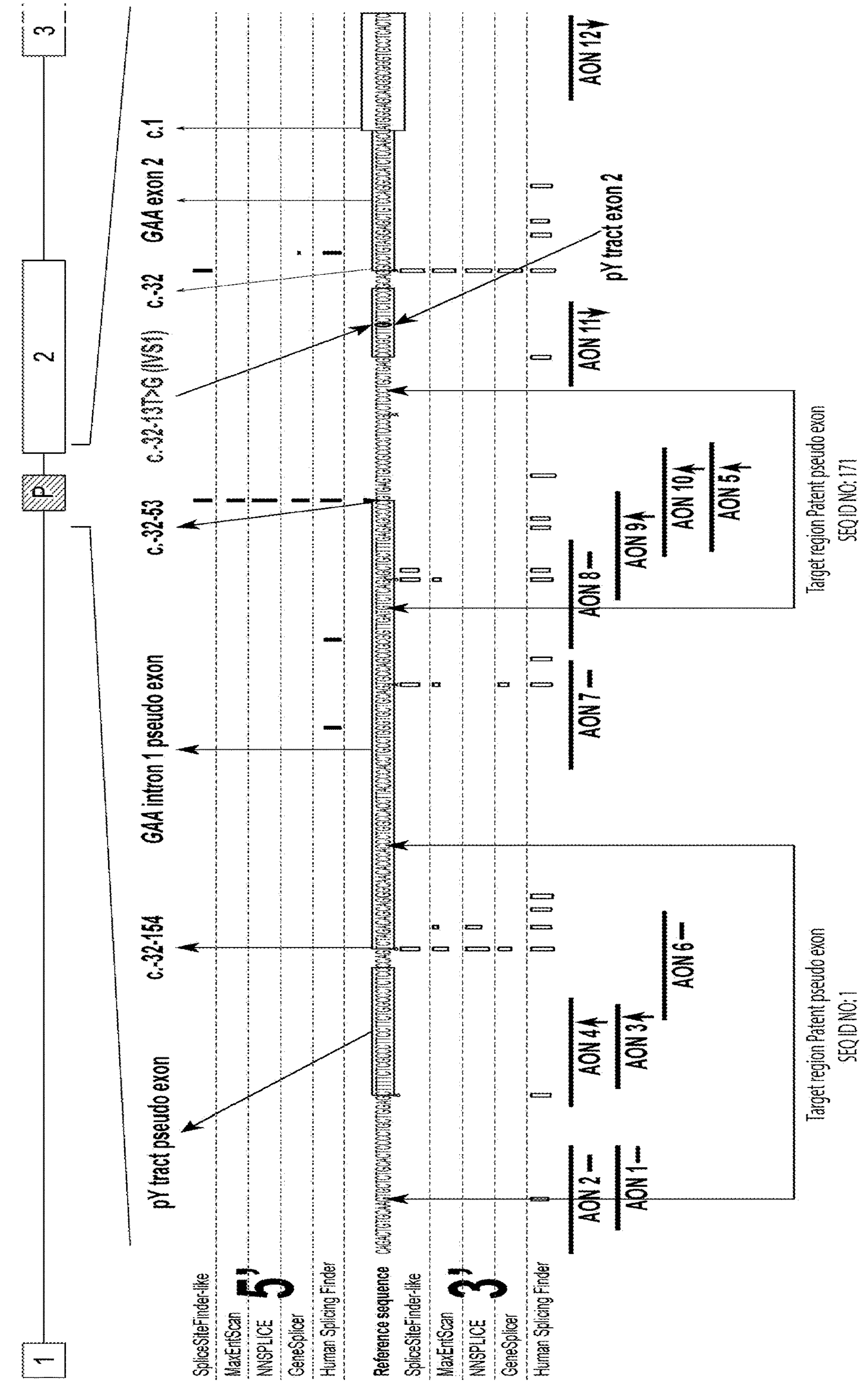

FIG. 18 shows a cartoon of the splicing regulatory region relevant for the IVS1 variant in the GAA gene. The Figure is based on that displayed in FIG. 7*a*. The previously identified splicing silencer in intron 1 (see FIG. 1) is predicted to be the pY tract of a pseudo exon (indicated with ‘P’ in the upper part of the cartoon). Human splice finder was used to predict splice sites around the splicing silencer identified in FIG. 1. Note that predictions were independent of the IVS1 variant. A strong 3' splice site was predicted at c.-32-154, and a strong 5' splice site at c.-32-53, which suggested the presence of a natural pseudo exon ‘P’. The canonical 3' splice site of exon 2 at c.-32 showed strong prediction and is also indicated. Indicated in the cartoon as well are the antisense oligonucleotides (AONs) tested in either primary fibroblasts or iPSC-derived skeletal muscle cells of a Pompe patient carrying the IVS1 variant (details of AONs in Table 19) as described in Example 5 hereinbelow. A minus behind the AON number indicates there was no effect on splicing. An arrow pointing up indicates improved GAA exon 2 inclusion, and an arrow pointing down indicates a negative effect on GAA exon 2 inclusion. Preferred embodiments in aspects of the present invention therefore include AONs 3-5, 9, and 10.

Figure 19:
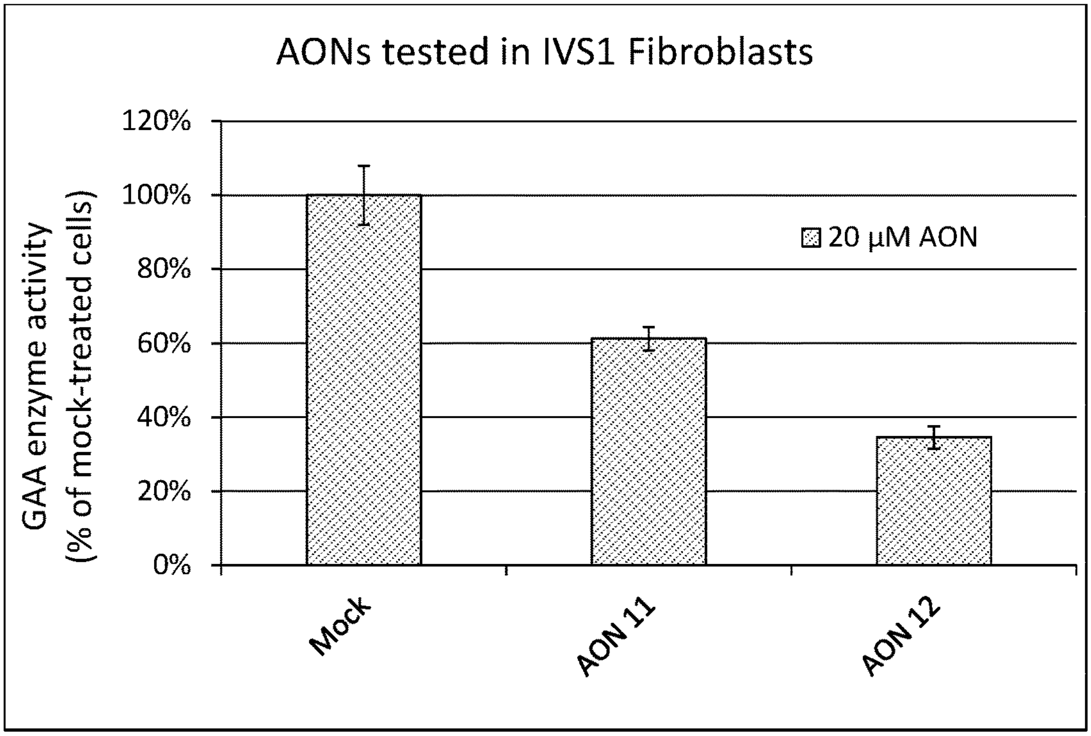

FIG. 19 shows the relative GAA enzymatic activity (compared to mock) measured after transfection of AONs 11 and 12 in IVS1 Pompe patient fibroblasts at a concentration of 20 μM as described in Example 5 hereinbelow. AONs 11 and 12 both show a negative effect on GAA exon 2 inclusion, defining the downstream boundary of the target region of the splice donor site of the pseudo exon (SEQ ID NO: 171).

Figure 20:
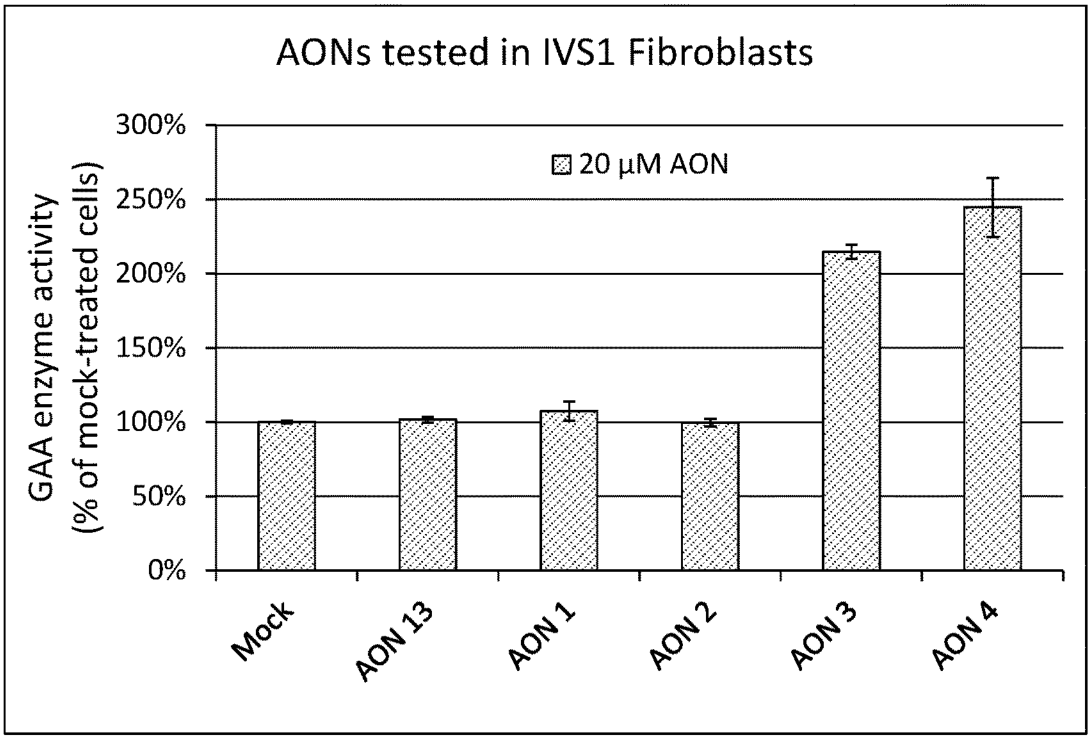

FIG. 20 (similar to FIG. 21B) shows the relative GAA enzymatic activity (compared to mock) measured after transfection of AONs 1 to 4 in IVS1 Pompe patient fibroblasts at a concentration of 20 μM as described in Example 5 hereinbelow. AON 13, targeting a different gene (CypA) was used as a control. AONs 1 and 2 both have no effect on GAA exon 2 splicing, indicating the left boundary of the target region of the splice acceptor site of the pseudo exon (SEQ ID NO: 1). AONs 3 and 4 show a significant effect on exon inclusion, indicating these AONs can be used to promote GAA exon 2 inclusion in primary fibroblasts from Pompe patients carrying the IVS1 variant.

Figure 21:
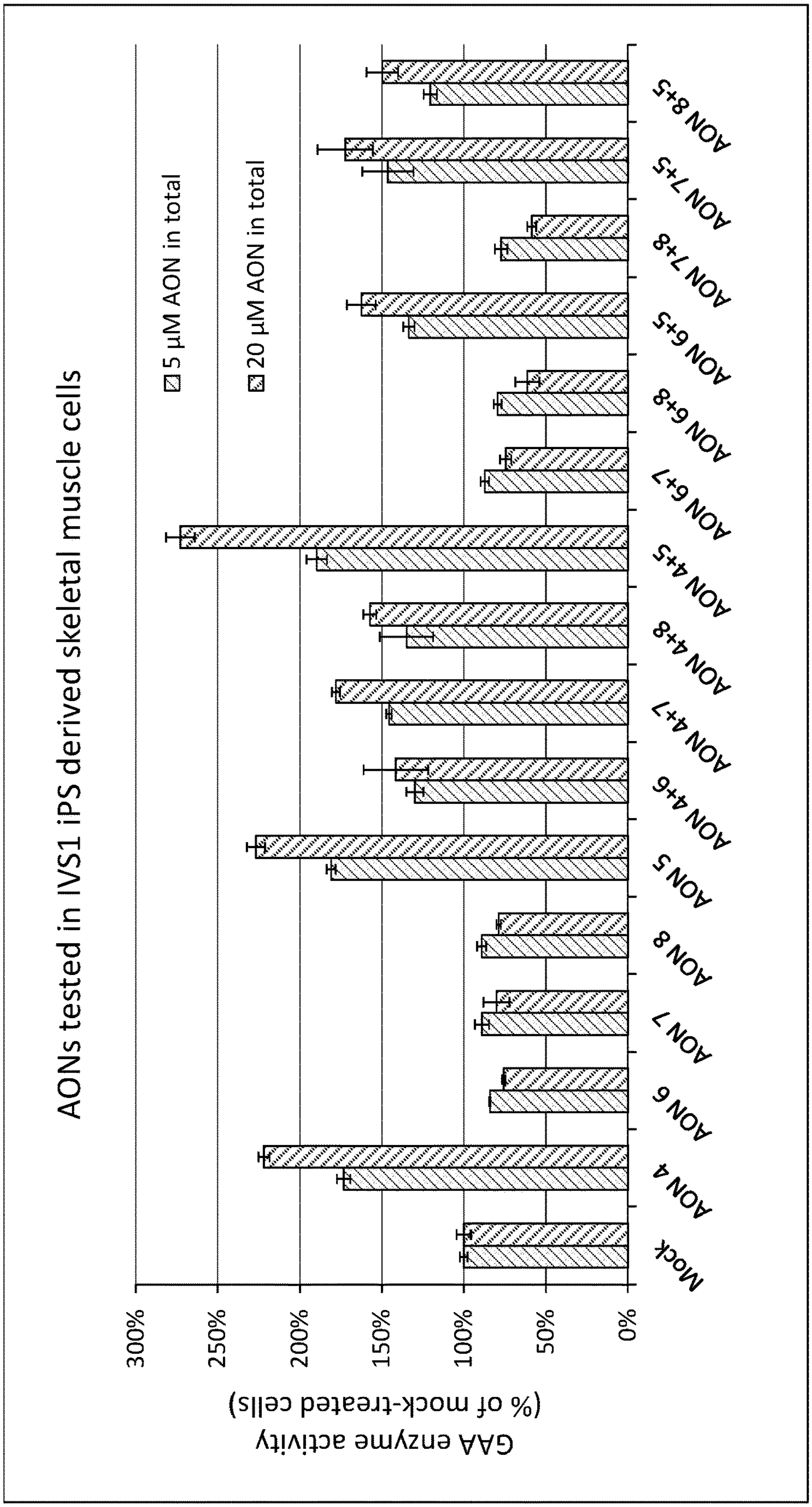

FIG. 21 shows the relative GAA enzymatic activity (compared to mock) measured after transfection of AONs 4-8 in iPSC-derived skeletal muscle cells generated from IVS1 Pompe patient fibroblasts as described in Example 5 hereinbelow. The concentrations indicated are in total 5 μM or 20 μM, so combinations of AONs contain 2.5 μM of each or 10 μM of each AON. AONs 4 and 5, as well as the combination of AONs 4 and 5, show a significant effect on exon inclusion, indicating that these AONs can be used to promote GAA exon 2 inclusion in cells from Pompe patients carrying the IVS1 variant. AONs 6, 7 and 8, or any combination made with these AONs, have either a low, no, or negative effect on GAA, exon 2 inclusion, defining the downstream boundary of the target region of the splice acceptor site of the pseudo exon (SEQ ID NO: 1) and the upstream boundary of the target, region of the splice donor site of the pseudo exon (SEQ ID NO 171).

Figure 22:
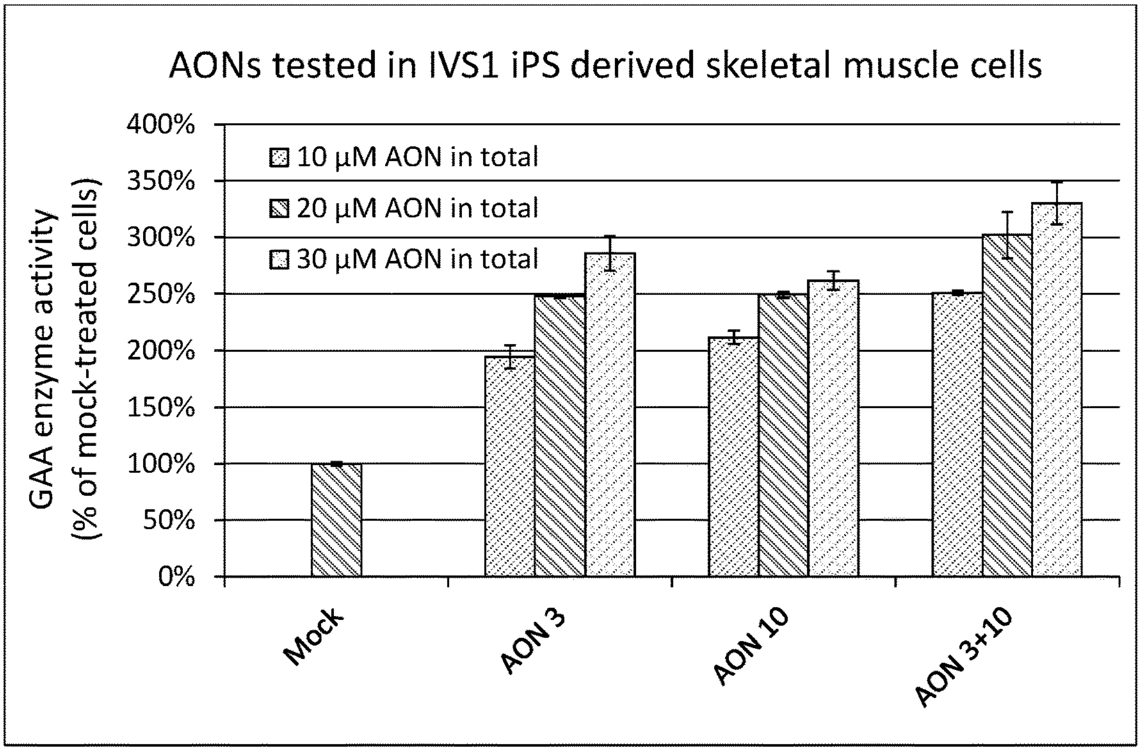

FIG. 22 (similar data as in figure SE) shows the relative GAA enzymatic activity (compared to mock) measured after transfection of AONs 3, 10 and a combination of AONs 3 and 10 in iPSC-derived skeletal muscle cells generated from IVS1 Pompe patient fibroblasts as described in Example 5 hereinbelow. The concentrations indicated are in total 10 μM, 20 μM, and 30 μM, so the combination of AONs contain 5, 10 and 15 μM of each AON. All AONs, or combinations of AONs, show a significant positive effect, on exon inclusion, indicating that these AONs can be used to promote GAA exon 2 inclusion in cells from Pompe patients carrying the IVS1 variant. Importantly, the combination of AONs scores better at all concentrations compared to single AONS at the same total AON concentrations.

Figure 23:
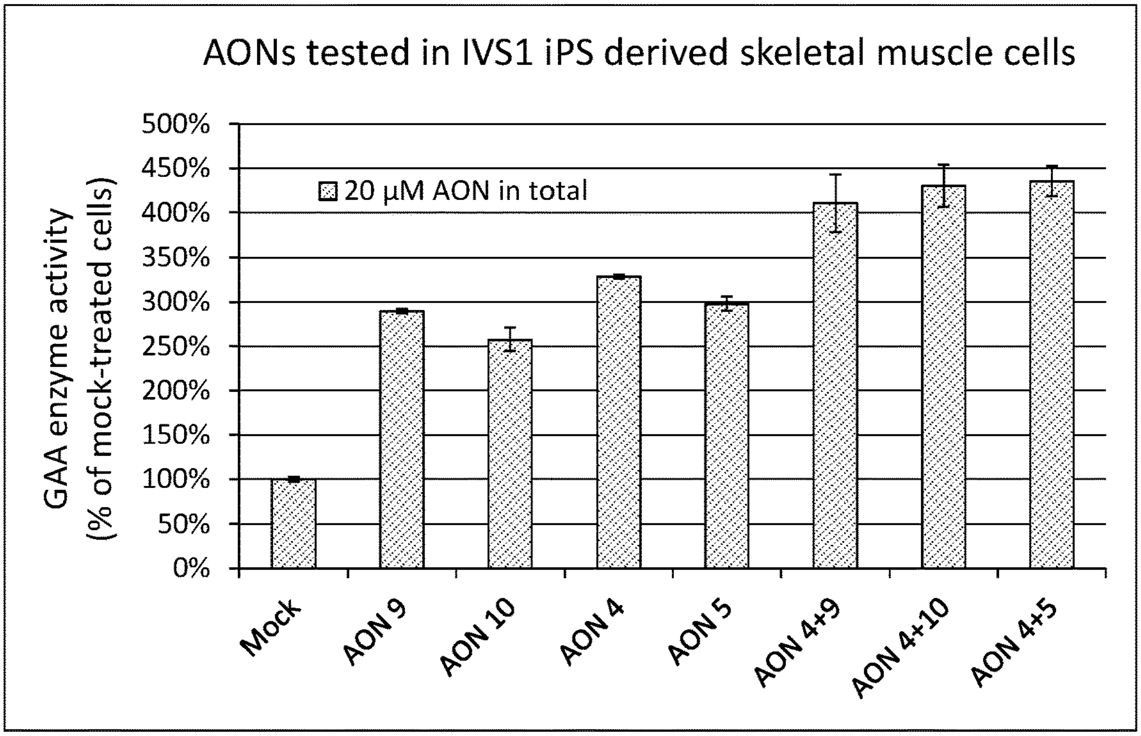

FIG. 23 shows the relative GAA enzymatic activity (compared to mock) measured after transfection of AONs 4, 5, 9 and 10 and combinations thereof in iPSC-derived skeletal muscle cells generated from IVS1 Pompe patient fibroblasts as described in Example 5 hereinbelow. The concentrations indicated are in total 20 μM, so the combination of AONs contain 10 μM of each. All AONs, or combinations of AONs, show a significant effect on exon inclusion, indicating that these AONs can be used to promote (AA exon 2 inclusion in cells from Pompe patients carrying the IVS1 variant. Importantly, the combination of AONs improves GAA exon 2 inclusion significantly better compared to the use of single AONs.

DETAILED DESCRIPTION OF PREFERRED EMBODIMENTS

The present invention is directed to a composition for use for the treatment of Pompe disease, said composition comprising an enzyme or nucleic acid encoding for said enzyme suitable for Enzyme Replacement Therapy for Pompe disease, wherein said treatment is a combination of the administration of said enzyme or said nucleic acid encoding for said enzyme and the administration of an antisense oligomeric that modulates the splicing of acid α-glucosidase (GAA) enzyme.

The present inventors have found that intracellular enzyme concentrations attainable by ERT can be further increased by using AON antisense therapy (using a splice switching antisense oligonucleotide (SSO)) even to levels of intracellular acid α-glucosidase (GAA) enzyme that are comparable to or even higher than normal endogenous levels of healthy subjects (as simulated by AON antisense therapy as disclosed herein).

The present invention is directed to a treatment of Pompe disease by administration of an enzyme or nucleic acid encoding for said enzyme suitable for Enzyme Replacement Therapy for Pompe disease in combination with the administration of an antisense oligomeric compound that modulates the splicing of acid α-glucosidase (GAA) enzyme gene.

Optionally the enzyme suitable for Enzyme Replacement Therapy for Pompe disease is an enzyme that breaks down glycogen such as acid α glycosidase (GAA). The nucleic acid encoding for said enzyme suitable for Enzyme Replacement Therapy for Pompe disease may be used in gene therapy. Optionally the nucleic acid is in a vector or other means that enables the translation of the enzyme. Optionally the modulation of the splicing is to increase the activity of glycogen break-down. Optionally the modulation of the splicing is to increase the activity of acid α-glucosidase (GAA) enzyme gene. Optionally the modulation of the splicing is to increase the activity of GAA to at least 120% of the activity of GAA enzyme without the modulation of the splicing of the GAA gene. Optionally the modulation of the splicing is to increase the activity of GAA to at least 25% of the activity of a wild type GAA enzyme.

Optionally the antisense oligomeric compound modulates aberrant splicing of acid α-glucosidase (GAA) enzyme gene.

Optionally the antisense oligomeric compound modulates splicing by an activity selected from the group consisting of promotion of exon inclusion, inhibition of a cryptic splicing site, inhibition of intron inclusion, recovering of reading frame, inhibition of splicing silencer sequence, activation of spicing enhancer sequence or any combination thereof. Optionally the antisense oligomeric compound modulates splicing by promotion of exon inclusion, optionally exon 2, or exon 6.

Optionally the antisense oligomeric compound modulates splicing by inhibition of a cryptic splicing site.

Optionally the antisense oligomeric compound modulates splicing by inhibition of intron inclusion.

Optionally the antisense oligomeric compound modulates splicing by recovering of the reading frame.

Optionally the antisense oligomeric compound modulates splicing by inhibition of splicing silencer sequence.

Optionally the antisense oligomeric compound modulates splicing by activation of spicing enhancer sequence.

Optionally said enzyme or said nucleic acid encoding for said enzyme and the antisense oligomeric compound are administered simultaneously or sequentially, as part of the same or separate compositions. Optionally said nucleic acid encoding for said enzyme and said antisense oligomeric compound are administered simultaneously or in one treatment composition. Optionally said enzyme and said antisense oligomeric compound are administered simultaneously or in one treatment composition. Optionally said nucleic acid encoding for said enzyme and said antisense oligomeric compound are administered on separate occasions or in separate treatment compositions. Optionally said enzyme and said antisense oligomeric compound are administered on separate occasions or in separate treatment compositions. Optionally the treatment uses said enzyme and said nucleic acid encoding for said enzyme. Optionally said enzyme and said nucleic acid encoding for said enzyme are administered simultaneously or in one treatment composition. Optionally the treatment uses said enzyme and said nucleic acid encoding for said enzyme. Optionally said enzyme and said nucleic acid encoding for said enzyme are administered on separate occasions or in separate treatment compositions. Optionally said enzyme and said nucleic acid encoding for said enzyme and said antisense oligomeric compound are administered simultaneously or in one treatment composition.

Optionally the administration route is selected from the group consisting of oral, parenteral, intravenous, intra-arterial, subcutaneous, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation, or combinations thereof. Optionally the administration route for the enzyme or the nucleic acid encoding for said enzyme is intravenous. Optionally the administration route of said enzyme or said nucleic acid encoding for said enzyme and the administration route of said antisense oligomeric compound are the same or different. Optionally the administration route for said antisense oligomeric compound is intravenous. Optionally the administration route for said antisense oligomeric compound is orally. Optionally the administration route for the enzyme or the nucleic acid encoding for said enzyme is orally. It is explicitly envisioned to combine various administration routes in the present invention.

Optionally the enzyme or the nucleic acid encoding for said enzyme in accordance with the invention is administered once every 1, 2, 3, 4, 5, 6, 7, 8, 9, 10, 11, 12, 13, 14, 15, 16, 17, 18, 19, 20, 21, 22, 23, 24, or 25 days. Optionally said enzyme or said nucleic acid encoding for said enzyme is administered once every 1, 2, 3, 4, 5, 6, 7, 8, 9, 10, 11, 12, 13, 14, 15, 16, 17, 18, 19, 20, 21, 22, 23, 24, or 25 weeks. Optionally said enzyme or said nucleic acid encoding for said enzyme is administered once every 1, 2, 3, 4, 5, 6, 7, 8, 9, 10, 11, 12, 13, 14, 15, 16, 17, 18, 19, 20, 21, 22, 23, 24, or 25 months, Optionally said enzyme or said nucleic acid encoding for said enzyme is administered once every 1, 2, 3, 4, 5, 6, 7, 8, 9, 10, years. It is explicitly envisioned that various frequencies of administration as indicated hereinabove are combined. For example 8 weeks of administration once every week and thereafter 24 weeks of administration of once every 2 weeks.

Optionally said antisense oligomeric compound is administered once every 1, 2, 3, 4, 5, 6, 7, 8, 9, 10, 11, 12, 13, 14, 15, 16, 17, 18, 19, 20, 21, 22, 23, 24, or 25 days. Optionally said antisense oligomeric compound is administered once every 1, 2, 3, 4, 5, 6, 7, 8, 9, 10, 11, 12, 13, 14, 15, 16, 17, 18, 19, 20, 21, 22, 23, 24, or 25 weeks. Optionally said antisense oligomeric compound is administered once every 1, 2, 3, 4, 5, 6, 7, 8, 9, 10, 11, 12, 13, 14, 15, 16, 17, 18, 19, 20, 21, 22, 23, 24, or 25 months. Optionally said antisense oligomeric compound is administered once every 1, 2, 3, 4, 5, 6, 7, 8, 9, 10, years. It is explicitly envisioned that various frequencies of administration as indicated here are combined. For example 8 weeks of administration once every week and thereafter 24 weeks of administration of once every 2 weeks. Also various combinations of the frequencies of administration of the antisense oligomeric compound in combination with various combination of the frequencies of administration of the said enzyme or said nucleic acid encoding for said enzyme are explicitly envisioned in the present invention. For example said enzyme is administered once every two weeks and the antisense oligomeric compound is administered once every 4 weeks.

Optionally said enzyme or said nucleic acid encoding for said enzyme is administered in a dose of about 1-100 mg/kg, optionally 2.90 mg/kg, 3-80 mg/kg, 5-75 mg/kg, 7-70 mg/kg, 10-60 mg/kg, 12-55 mg/kg, 15-50 mg/kg, 17-45 mg/kg, 20-40 mg/kg, 22-35 mg/kg, 25-30 mg/kg.

Optionally said antisense oligomeric compound is administered in a dose of about 0.05 to 1000 mg/kg, optionally about 0.1 to 900 mg/kg, 1-800 mg/kg, 2-750 mg/kg, 3-700 mg/kg, 4-600 mg/kg, 5-500 mg/kg, 7 to 450 mg/kg, 10 to 400 mg/kg, 12 to 350 mg/kg, 15 to 300 mg/kg, 17 to 250 mg/kg, 20 to 220 mg/kg, 22 to 200 mg/kg, 25 to 180 mg/kg, 30 to 150 mg/kg, 35 to 125 mg/kg, 40 to 100 mg/kg, 45 to 75 mg/kg, 50-70 mg/kg, preferably a dose of about 0.05 to 100 mg/kg, optionally about 0.1 to 100 mg/kg, 1-100 mg/kg, 2-100 mg/kg, 3-100 mg/kg, 4-10 mg/kg, 5-100 mg/kg, 7 to 100 mg/kg, 10 to 100 mg/kg, 12 to 100 mg/kg, 15 to 100 mg/kg, 17 to 100 mg/kg, 20 to 100 mg/kg, 22 to 100 mg/kg, 25 to 100 mg/kg, 30 to 100 mg/kg, 35 to 100 mg/kg, 40 to 100 mg/kg, 45 to 75 mg/kg, 50-70 mg/kg. Preferred administration dosages for AON include 1.60 mg/kg, preferably 1-50 mg/kg, more preferably about 10-50 mg/kg, and still more preferably around 30 mg/kg. Preferably, the AON is administered in said dosage once every 1 week, more preferably once every 2 weeks, and still more preferably once every month. A pair of AONs may be used at the same or half the dosage each, preferably half.

Optionally said enzyme or said nucleic acid encoding for said enzyme or said antisense oligomeric compound is administered in combination with a chaperone such as an Active Site-Specific Chaperone (ASSC). Optionally said enzyme is administered in combination with a chaperone. Optionally said nucleic acid encoding for said enzyme is administered in combination with a chaperone. Optionally said antisense oligomeric compound is administered in combination with a chaperone. Suitable chaperones are 1-deoxynojirimycin and derivatives thereof. Suitable examples of chaperones are 1-deoxynojirimycin N-(n-nonyl)deoxynojirimycin (NN-DNJ). N-(n-butyl)deoxynojirimycin (NB-DNJ), N-octyl-4-epi-β-valienamine. N-acetylglucosamine-thiazoline, N-(7-oxodecyl)deoxynojirimycin (NO-DNJ) and N-(n-dodecyl)deoxynojirimycin (ND-DNJ), 1-deoxygalactonojirimycin, N-alkylderivative of 1-deoxynojirimycin, 1-deoxynojirimycin and derivatives thereof are also suitable for substrate reduction.

Optionally the administration is in combination with genistein. Optionally in a dose of genistein of 1-100 mg/kg per day, optionally of 5.90 mg/kg per day, optionally 10-80-mg/kg per day, optionally 15-75 mg/kg per clay, optionally 20-70 mg/kg per day, optionally 25-60 mg/kg per day. 30-55 mg/kg per day. 35-50 mg/kg per clay, 40-45 mg/kg per day. In the combination therapy described herein, preferred administration dosages for ERT enzyme include 5-60 mg/kg, preferably 5-40 mg/kg, more preferably about 10.30 mg/kg, and still more preferably around 20 mg/kg. Preferably, the ERT enzyme is administered in said dosage once every week, and more preferably once every 2 weeks.

Optionally the administration is in combination with cell penetrating peptides, such as PIP-series peptides. Optionally the administration is in combination with a targeting ligand. Optionally said cell penetrating peptide and/or targeting ligand is present on the antisense oligomeric compound. Optionally said cell penetrating peptide and/or targeting ligand is present on said nucleic acid encoding for said enzyme. Optionally said cell penetrating peptide and/or targeting ligand is present on said enzyme.

Optionally the enzyme is an acid α-glucosidase (GAA) enzyme. Optionally said enzyme is a modification, variant, analogue, fragment, port ion, or functional derivative, thereof. Optionally said enzyme is a modification, variant, analogue, fragment, portion, or functional derivative of GAA enzyme. The present invention explicitly encompasses all forms of recombinant human acid α-glucosidase which may be based on all natural or genetically modified forms of either human GAA cDNA, or human GAA gene, or combinations thereof, including those forms that are created by codon optimization. Suitable GAA enzyme include an enzyme selected from the group consisting of Myozyme and lysozyme, neo-GAA (carbohydrate modified forms of alglucosidase-α). BMN-701 (BioMarin: Gilt GAA for Pompe disease, in which rhGAA is fused with an IGF-II peptide) rhGGAA (Oxyrane: recombinant human acid α-glucosidase produced in genetically modified yeast cells and enriched in mannose 6-phosphate content), rhGAA modified by conjugation, for example to mannose-6-phosphate groups or to IGF-II peptides, said enzyme is selected from the group consisting of a recombinant human GAA, Myozyme, Lumizyme, neoGAA, Gilt GAA (BMN-701), or rhGGAA.

Optionally the composition or treatment comprises more than one antisense oligomeric compound. Optionally, 1, 2, 4, 6, 7, 8, 9, 10, 11, 12, 13, 14, 15, or more different antisense oligomeric compounds are used for the composition and/or treatment.

1590 Optionally at least one of the nucleotides of the is antisense oligomeric compound is modified. Optionally all of the nucleotides in the antisense oligomeric compound are modified. Optionally the modifications in the antisense oligomeric compound is the same for each nucleotide or different. Various combinations of modification of the nucleotides is explicitly envisioned in the present invention.

Optionally the sugar of one or more nucleotides of the is antisense oligomeric compound is modified. Optionally the sugar modification is 2'-O-methyl. Optionally the sugar modification 2'-O-methoxyethyl.

Optionally the base of one or more nucleotides of the antisense oligomeric compound is modified.

Optionally the backbone of the antisense oligomeric compound is modified. Optionally the backbone of the antisense oligomeric compound is a morpholino phosphorothioate. Optionally the backbone of the antisense oligomeric compound is a morpholino phosphorodiamidate. Optionally the backbone of the antisense oligomeric compound is a tricyclo-DNA.

Optionally the antisense oligomeric compound and/or the enzyme or nucleic acid coding for said enzyme is present in a carrier selected from the group of exosomes, nanoparticles, micelles, liposomes, or microparticles. The carrier may enhance the uptake of the antisense oligomeric compound and/or the enzyme or nucleic acid coding for said enzyme into the cells. Optionally the composition or the treatment comprises compounds that enhance the uptake of the antisense oligomeric compound and/or the enzyme or nucleic acid coding for said enzyme into the cells. Suitable compounds that enhance the uptake into the cells are Polyethylimine, conjugated pluronic copolymers, lipids, e.g. patisiran, ICAM-targeted nanocariers, peptide Pip6a or cationic nanoemulsions. A skilled person is well suited to find compounds that enhance the uptake of the antisense oligomeric compound and/or the enzyme or nucleic acid coding for said enzyme into the cells.

The present invention is also directed to a pharmaceutical composition comprising at least one antisense oligomeric compound as defined in aspects of the present invention and/or embodiments thereof and a enzyme as defined in aspects of the present invention and/or embodiments thereof.

Optionally the pharmaceutical composition further comprises a pharmaceutical acceptable excipient and/or a cell delivery agent. Suitable cell delivery agents are carriers selected from the group of exosomes, nanoparticles, micelles, liposomes, or microparticles. Optionally the pharmaceutical composition comprises compounds that enhance the uptake of the antisense oligomeric compound and/or the enzyme or nucleic acid coding for said enzyme into the cells. Suitable compounds that enhance the uptake into the cells are Polyethylimine, conjugated pluronic copolymers, lipids, e.g. patisiran, ICAM-targeted nanocariers, peptide Pip6a or cationic nanoemulsions. A skilled person is well suited to find compounds that enhance the uptake of the antisense oligomeric compound and/or the enzyme or nucleic acid codling for said enzyme into the cells.

Optionally the pharmaceutical composition further comprises a chaperone such as a Active Site-Specific Chaperone (ASSC). Suitable chaperones are 1-deoxynojirimycin and derivatives thereof. Suitable examples of chaperones are 1-deoxynojirimycin N-(n-nonyl)deoxynojirimycin (NN-DNJ), N-(n-butyl)deoxynojirimycin (NB-DNJ), N-octyl-4-epi-O-valienamine, N-acetylglucosamine-thiazoline, N-(7-oxadecyl)deoxynojirimycin (NO-DNJ) and N-(n-dodecyl) deoxynojirimycin (ND-DNJ), 1-deoxygalactonojirimycin, N-alkylderivative of 1-deoxynojirimycin. 1-deoxynojirimycin and derivatives thereof are also suitable for substrate reduction.

Optionally the pharmaceutical composition further comprises genistein. Optionally the pharmaceutical composition further comprises genistein in a dose of 1-100 mg/kg per day, optionally of 5-90 mg/kg per day, optionally 10.80-mg/kg per (lay, optionally 15-75 mg/kg per day, optionally 20-70 mg/kg per day, optionally 25-60 mg/kg per day, 30-55 mg/kg per day, 35-50 mg/kg per day, 40-45 mg/kg per day. Optionally the pharmaceutical composition comprises said enzyme or said nucleic acid encoding for said enzyme or said antisense oligomeric compound in combination with a genistein. Optionally the pharmaceutical composition comprises said enzyme in combination with a genistein Optionally the pharmaceutical composition comprises said nucleic acid encoding for said enzyme in combination with a genistein Optionally the pharmaceutical composition comprises said antisense oligomeric compound in combination with a genistein.

Optionally the pharmaceutical composition further comprises cell penetrating peptides. Optionally the pharmaceutical composition further comprises a targeting ligand. Optionally said cell penetrating peptide and/or targeting ligand is present on the antisense oligomeric compound. Optionally said cell penetrating peptide and/or targeting ligand is present on said nucleic acid encoding for said enzyme. Optionally said cell penetrating peptide and/or targeting ligand is present on said enzyme.

Optionally in the pharmaceutical composition the enzyme is an acid α-glucosidase (GAA) enzyme. Optionally said enzyme is a modification, variant, analogue, fragment, portion, or functional derivative, thereof. Optionally said enzyme is a modification, variant, analogue, fragment, portion, or functional derivative of GAA enzyme. The present invention explicitly encompasses all forms of recombinant human acid α-glucosidase which may be based on all natural or genetically modified forms of either human GAA cDNA, or human GAA gene, or combinations thereof, including those forms that are created by codon optimization. Suitable GAA enzyme include an enzyme selected from the group consisting of Myozyme and lysozyme, neo-GA A (carbohydrate modified forms of alglucosidase-α). BMN-701 (BioMarin: Gilt GAA for Pompe disease, in which rhGAA is fused with an IGF-II peptide) rhGGAA (Oxyrane: recombinant human acid α-glucosidase produced in genetically modified yeast cells and enriched in mannose 6-phosphate content), rhGAA modified by conjugation, for example to mannose-6-phosphate groups or to IGF-II peptides, said enzyme is selected from the group consisting of a recombinant human GAA, Myozyme, Lumizyme, neoGAA, Gilt GAA (BMN-701), or rhGAA.

Optionally the pharmaceutical composition comprises the enzyme in an amount of about 1-50 mg/mL enzyme. Optionally the enzyme is present in the pharmaceutical composition in an amount of 2-45 mg/mL, 3-40 mg/mL, 5-35 mg/mL, 7-30 mg/mL, 10-25 ng/mL, 12-22 mg/mL, or 15-20, mg/mL.

Optionally the pharmaceutical composition comprises more than one antisense oligomeric compound, Optionally, the pharmaceutical composition comprises 1, 2, 3, 4, 5, 6, 7, 8, 9, 10, 11, 12, 13, 14, 15, or more different antisense oligomeric compounds.

Optionally the pharmaceutical composition comprises the antisense oligomeric compound in an amount of about 1-50 mg/mL enzyme. Optionally the antisense oligomeric compound is present in the pharmaceutical composition in an amount of 2-45 mg/mL, 3-40 mg/mL, 5-35 mg/mL, 7-30 mg/mL, 10-25 mg/mL, 12.22 mg/mL, or 15-20, mg/mL.

Optionally the pharmaceutical composition comprises a carrier selected from the group consisting of exosomes, nanoparticles, micelles, liposomes, and microparticles.

The present invention is also directed to a sequences selected from the group comprising SEQ ID NO: 267-2045 and sequences having at least 80% identity thereof.

The present invention is also directed to a sequences selected from the group comprising SEQ ID NO: 267-2045 and sequences having at least 80% identity thereof for use in the treatment Pompe disease.

The present invention is also directed to a method of modulating splicing of GAA pre-mRNA in a cell comprising:

contacting the cell with an antisense oligomeric compound selected from the group comprising SEQ ID NO: 267-2045 and sequences having at least 80% identity thereof.

The present invention is also directed to a method for treating Pompe disease in a patient comprising administering said patient with an effective amount of an antisense oligomeric compound selected from the group comprising SEQ ID NO: 267-2045 and sequences having at least 80% identity thereof.

The present invention is also directed to a method to restore the function of GAA in a cell wherein said method comprises the administration of an antisense oligomeric compound selected from the group comprising SEQ ID NO: 267-2045 and sequences having at least 80% identity thereof.

Further preferred embodiments of the above aspects include antisense oligomeric compounds selected from SEQ ID NO: 267-298, 299-445, 446-602, 603-640, 641-992, and 993-2045.

The present invention is also directed to a method of correcting abnormal gene expression in a cell, Optionally a muscular cell, of a subject, the method comprising administering to the subject an antisense oligomeric compound selected from the group comprising SEQ ID NO: 1590-1594 and sequences having at least 80% identity thereof. Optionally in said methods the cell or the patient comprises at least one mutation selected from the group c.-32-13T>G, c.-32-3C>G, c.547-6, c. 1071, c.1254, and c.1552-30, Optionally the cell or patient comprises mutation c.-32-3C>G or c.-32-13T>G. Optionally in said methods exon inclusion is accomplished, optionally inclusion of exon 2.

The present invention is also directed to a pharmaceutical composition comprising at least one antisense oligomeric compound selected from the group comprising SEQ ID NO: 1590-1594 and sequences having at least 80% identify thereof. Optionally the pharmaceutical composition further comprises a pharmaceutical acceptable excipient and/or a cell delivery agent.

DETAILED DESCRIPTION

The principle behind antisense technology is that an antisense compound that hybridizes to a target nucleic acid modulates gene expression activities such as transcription, splicing or translation. This sequence specificity makes antisense compounds extremely attractive as tools for target validation and gene functionalization, as well as therapeutics to selectively modulate the expression of genes or gene products involved in disease.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product are implicated in disease, or where aberrant levels of an aberrant splice product are implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets, mRNA transcripts produced via the process of splicing of two (or more) mRNAs from different, gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

It is also known in the art that alternative RNA transcripts can be produced from the same genomic region of DNA. These alternative transcripts are generally known as "alternative splice transcripts." These are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA transcripts produce smaller mRNA transcripts. Consequently, mRNA alternative splice transcripts are processed pre-mRNA transcripts and each unique pre-mRNA transcript must always produce a unique mRNA transcript as a result of splicing. If no splicing of the pre-mRNA transcript occurs then the pre-mRNA transcript is identical to the mRNA transcript.

It is also known in the art that such alternative splice transcripts can be produced through the use of alternative signals to start or stop transcription and that pre-mRNAs and mRNAs can possess more than one start codon or stop codon. Alternative splice transcripts that originate from a pre-mRNA or mRNA that use alternative start codons are known as "alternative start transcripts" of that pre-mRNA or mRNA. Those transcripts that use an alternative stop codon are known as "alternative stop transcripts" of that pre-mRNA or mRNA. One specific type of alternative stop transcript is the "polyA transcript" in which the multiple transcripts produced result from the alternative selection of one of the "polyA stop signals" by the transcription machinery, thereby producing transcripts that terminate at unique polyA sites.

As used herein, "antisense mechanisms" are all those involving hybridization of a compound with target nucleic acid, wherein the outcome or effect, of the hybridization is either target degradation or target occupancy with concomitant stalling of the cellular machinery involving, for example, transcription or splicing.

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the subject invention. As used herein, the terms "include" and "comprise" are used synonymously.

The articles "a" and "an" are used herein to refer to one or to more than one (i.e., to at least one) of the grammatical object of the article. The use of the alternative (e.g., "or") should be understood to mean either one, both, or any combination thereof of the alternatives.

The terms "individual", "patient", and "subject" are used interchangeably herein and refer to mammals, in particular primates and preferably humans.

The term "exon" refers to a portion of a gene that is present in the mature form of mRNA. Exons include the ORF (open reading frame), i.e., the sequence which encodes protein, as well as the 5' and 3' UTRs (untranslated regions). The UTRs are important for translation of the protein. Algorithms and computer programs are available for predicting exons in DNA sequences (Grail. Grail 2 and Genscan and US 20040219522 for determining exon-intron junctions).

As used herein, the term "protein coding exon" refers to an exon which codes (or at least partially codes) for a protein (or part of a protein). The first protein coding exon in an mRNA is the exon which contains the start codon. The last protein encoding exon in an mRNA is the exon which contains the stop codon. The start and stop codons can be predicted using any number of well-known programs in the art.

As used herein, the term "internal exon" refers to an exon that is flanked on both its 5' and 3' end by another exon. For an mRNA comprising n exons, exon 2 to exon (n−1) are the internal exons. The first and last exons of an mRNA are referred to herein as "external exons".

A "natural cryptic splice site" or "natural pseudo splice site" is a site that is normally not used in pre-mRNA splicing, but can be utilized when canonical splicing has been weakened. It can be located either in an intron or an exon. The term "induced splice site" refers to an RNA sequence that is changed by an (induced) mutation, resulting in the generation of a novel splice site that is used in pre-mRNA splicing. The term "natural pseudo-exon" or "natural cryptic exon" refers to a region in the pre-mRNA that could function as an exon during splicing and is located in an intronic region of the pre-mRNA. The natural pseudo exon is not utilized in normal, healthy cells, but is utilized in diseased cells that carry a mutation in the gene. The strength of the natural cryptic splice sites is usually not affected by the presence or absence of such a mutation, although in some cases its predicted strength can change due to a nearby mutation.

The term "intron" refers to a portion of a gene that is not translated into protein and while present in genomic DNA and pre-mRNA, it is removed in the formation of mature mRNA.

The term "messenger RNA" or "mRNA" refers to RNA that is transcribed from genomic DNA and that carries the coding sequence for protein synthesis. Pre-mRNA (precursor mRNA) is transcribed from genomic DNA. In eukaryotes, pre-mRNA is processed into mRNA, which includes removal of the introns, i.e., "splicing", and modifications to the 5' and 3' end (e.g., polyadenylation). mRNA typically comprises from 5' to 3': a 5' cap (modified guanine nucleotide), 5' UTR (untranslated region), the coding sequence (beginning with a start codon and ending with a stop codon), the 3' UTR, and the poly(A) tail.

The terms "nucleic acid sequence" or "nucleic acid molecule" or "nucleotide sequence" or "polynucleotide" are used interchangeably and refer to a DNA or RNA molecule (or non-natural DNA or RNA variants) in single or double stranded form. An "isolated nucleic acid sequence" refers to a nucleic acid sequence which is no longer in the natural environment from which it was isolated, e.g. the nucleic acid sequence in a cell.

A "mutation" in a nucleic acid molecule is a change of one or more nucleotides compared to the wild type sequence, e.g. by replacement, deletion or insertion of one or more nucleotides. A "point mutation" is the replacement of a single nucleotide, or the insertion or deletion of a single nucleotide.

Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) and share at least a certain minimal percentage of sequence identity (as defined further below). These programs use the Needleman and Wunsch global alignment algorithm to align two sequences over their entire length, maximising the number of matches and minimising the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS (http://www.ebi.ac.uk/fools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences are "highly homogenous" or have "substantial sequence identity" if the percentage sequence identity is at least 70%, 75%, 80%, 85%, 90%, 95%, 98%, 99% or more, preferably at least 90%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins). Such sequences are also referred to as 'homologous sequences' herein, e.g. other variants of a pre-mRNA or homologues or derivatives of antisense oligomeric compounds. It should be understood that, sequences with substantial sequence identity do not necessarily have the same length and may differ in length. For example sequences that have the same nucleotide sequence but of which one has additional nucleotides on the 3'- and/or 5'-side are 100% identical when relating to the shared sequence part.

The term "hybridisation" as used herein is generally used to mean hybridisation of nucleic acids at appropriate conditions of stringency as would be readily evident to those skilled in the art depending upon the nature of the probe sequence and target sequences. Conditions of hybridisation and washing are well known in the art, and the adjustment of conditions depending upon the desired stringency by varying incubation time, temperature and/or ionic strength of the solution are readily accomplished. See, for example. Sambrook, J, et al. Molecular Cloning: A Laboratory Manual, 2nd edition. Cold Spring Harbor Press. Cold Spring Harbor, N.Y., 1989. The choice of conditions is dictated by the length of the sequences being hybridised, in particular, the length of the probe sequence, the relative G-C content of the nucleic acids and the amount of mismatches to be permitted. Low stringency conditions are preferred when partial hybridisation between strands that have lesser degrees of complementarity is desired. When perfect or near perfect complementarity is desired, high stringency conditions are preferred. For typical high stringency conditions, the hybridisation solution contains 6×S.S.C. 0.01 M EDTA, 1×Denhardt's solution and 0.5% SOS, hybridisation Hybridisation is carried out at about 68° C., for about 3 to 4 hours for fragments of cloned DNA and for about 12 to about 16 hours for total eukaryotic DNA. For lower stringencies the temperature of hybridisation is reduced to about 42° C., below the melting temperature (TM) of the duplex. The TM is known to be a function of the G-C content and duplex length as well as the ionic strength of the solution.

The term "allele(s)" means any of one or more alternative forms of a gene at a particular locus, all of which alleles relate to one trait or characteristic at a specific locus. One allele is present on each chromosome of the pair of homologous chromosomes. These may be identical alleles of the gene (homozygous) or two different alleles (heterozygous).

Mutant allele" refers herein to an allele comprising one or more mutations in the sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vive functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different conformation, being targeted to a different sub-cellular compartment, having a modified catalytic domain, having a modified binding activity to nucleic acids or proteins, etc, it may also lead to a different splicing event.

A "fragment" of the gene or nucleotide sequence or antisense oligomeric compound refers to any subset of the molecule, e.g. a shorter polynucleotide or oligonucleotide.

An "AON derivative" refers to a molecule substantially similar to the antisense oligomeric compound or a fragment thereof, such as a nucleotide substitution variant having one or more substituted nucleotides, but which maintains the ability to hybridize with the particular gene. Preferably the AON derivative comprises the mutations as identified by the invention. Derivatives may also include longer sequences.

An "analogue" refers to a non-natural molecule substantially similar to or functioning in relation to either the entire molecule, a variant or a fragment thereof.

As used herein, the terms "precursor mRNA" or "pre-mRNA" refer to an immature single strand of messenger ribonucleic acid (mRNA) that contains one or more intervening sequence(s) (introns). Pre-mRNA is transcribed by an RNA polymerase from a DNA template in the cell nucleus and is comprised of alternating sequences of introns and coding regions (exons). Once a pre-mRNA has been completely processed by the splicing out of introns and joining of exons, it is referred to as "messenger RNA" or "mRNA," which is an RNA that is completely devoid of intron sequences. Eukaryotic pre-mRNAs exist only transiently before being fully processed into mRNA. When a pre-mRNA has been properly processed to an mRNA sequence, it is exported out of the nucleus and eventually translated into a protein by ribosomes in the cytoplasm.

As used herein, the terms "splicing" and "(pre-)mRNA processing" refer to the modification of a pre-mRNA following transcription, in which introns are removed and exons are joined. Pre-mRNA splicing involves two sequential biochemical reactions. Both reactions involve the spliceosomal transesterification between RNA nucleotides. In a first reaction, the 2'-OH of a specific branch-point nucleotide within an intron, which is defined during spliceosome assembly, performs a nucleophilic at tack on the first nucleotide of the intron at the 5' splice site forming a lariat intermediate. In a second react ion, the 3'-OH of the released 5' exon performs a nucleophilic attack at the last nucleotide of the intron at the 3' splice site thus joining the exons and releasing the intron lariat. Pre-mRNA splicing is regulated by intronic silencer sequence (ISS), exonic silencer sequences (ESS) and terminal stem loop (TSL) sequences.

As used herein, the terms "intronic silencer sequences (ISS)" and "exonic silencer sequences (ESS)" refer to sequence elements within introns and exons, respectively, that control alternative splicing by the binding of trans-acting protein factors within a pre-mRNA thereby resulting in differential use of splice sites. Typically, intronic silencer sequences are less conserved than the splice sites at exon-intron junctions.

As used herein, "modulation of splicing" refers to altering the processing of a pre-mRNA transcript such that there is an increase or decrease of one or more splice products, or a change in the ratio of two or more splice products. Modulation of splicing can also refer to altering the processing of a pre-mRNA transcript such that a spliced mRNA molecule contains either a different combination of exons as a result of exon skipping or exon inclusion, a deletion in one or more exons, or additional sequence not normally found in the spliced mRNA (e.g., intron sequence).

As used herein, "splice site" refers to the junction between an exon and an intron in a pre-mRNA (unspliced RNA) molecule (also known as a "splice junction"). A "cryptic splice site" is a splice site that is not typically used but may be used when the usual splice site is blocked or unavailable or when a mutation causes a normally dormant site to become an active splice site. An "aberrant splice site" is a splice site that results from a mutation in the native DNA and pre-mRNA.

As used herein, "splice products" or "splicing products" are the mature mRNA molecules generated from the process of splicing a pre-mRNA. Alternatively spliced pre-mRNAs have at least two different splice products. For example, a first splicing product may contain an additional exon, or portion of an exon, relative to a second splicing product. Splice products of a selected pre-mRNA can be identified by a variety of different techniques well known to those of skill in the art (e.g. Leparc, G. G, and Mitra, R. D. Nucleic Acids Res. 35(21): e146, 2007).

As used herein "splice donor site" refers to a splice site found at the 5' end of an intron, or alternatively, the 3' end of an exon. Splice donor site is used interchangeably with "5' splice site." As used herein "splice acceptor site" refers to a splice site found at the 3' end of an intron, or alternatively, the 5' end of an exon. Splice acceptor site is used interchangeably with "3' splice site."

As used herein, "targeting" or "targeted to" refer to the process of designing an oligomeric compound such that the compound hybridizes with a selected nucleic acid molecule or region of a nucleic acid molecule. Targeting an oligomeric compound to a particular target nucleic acid molecule can be a multistep process. The process usually begins with the identification of a target, nucleic acid whose expression is to be modulated. As used herein, the terms "target nucleic acid" and "nucleic acid encoding GAA" encompass DNA encoding GAA, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes GAA. The GAA protein may be any mammalian enzyme, but it preferably is the human GAA.

The targeting process usually also includes determination of at least one target region, segment, or site within the target nucleic acid for the antisense interaction to occur such that the desired effect, e.g., modulation of expression, will result.

As used herein, "target mRNA" refers to the nucleic acid molecule to which the oligomeric compounds provided herein are designed to hybridize. In the context of the present disclosure, target mRNA is usually unspliced mRNA, or pre-mRNA. In the context of the present invention, the target mRNA is GAA mRNA or GAA pre-mRNA.

"Region" is defined as a portion of the target nucleic acid having at least one identifiable structure, function, or characteristic. Target regions may include, for example, a particular exon or intron, or may include only selected nucleotides within an exon or intron which are identified as appropriate target regions. Target regions may also be splicing repressor sites. Within regions of target nucleic acids are segments. "Segments" are defined as smaller or sub-portions of regions within a target nucleic acid. "Sites." as used in the present invention, are defined as unique nucleobase positions within a target nucleic acid. As used herein, the "target site" of an oligomeric compound is the 5'-most nucleotide of the target nucleic acid to which the compound binds.

Target degradation can include (performance of) an RNase H, which is a cellular endonuclease which cleaves the RNA strand of an RNA:DNA duplex. It is known in the art that single-stranded antisense compounds which are "DNA-like" elicit cleavage by RNAse H. Occupancy-based antisense mechanisms, whereby antisense compounds hybridize yet do not elicit cleavage of the target, include inhibition of translation, modulation of splicing, modulation of poly(A) site selection and disruption of regulatory RNA structure. For the present invention "RNA-like" antisense compounds for use in occupancy-based antisense mechanisms are preferred.

In the context of the present disclosure, an oligomeric compound "targeted to a splice site" refers to a compound that hybridizes with at least a portion of a region of nucleic acid encoding a splice site or a compound that hybridizes with an intron or exon in proximity to a splice site, such that splicing of the mRNA is modulated.

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self-complementarity to allow for hybridization and formation of a fully or partially double-stranded compound.

The term "antisense oligonucleotide. AON, or antisense oligomeric compound" refers to an oligonucleotide that is capable of interacting with and/or hybridizing to a pre-mRNA or an mRNA having a complementary nucleotide sequence thereby modifying gene expression and/or splicing. Enzyme-dependent antisense oligonucleotides include forms that are dependent on RNase H activity to degrade target mRNA, and include single-stranded DNA, RNA, and phosphorothioate antisense. Steric blocking antisense oligonucleotides (RNase-H independent antisense) interfere with gene expression or other mRNA-dependent cellular processes by binding to a target sequence of mRNA. Steric blocking antisense includes 2'-0 alkyl antisense oligonucleotides, morpholino antisense oligonucleotides, and tricyclo-DNA antisense oligonucleotides. Steric blocking antisense oligonucleotides are preferred in the present invention.

As used herein, antisense oligonucleotides that are "RNase H-independent" are those compounds which do not elicit cleavage by RNase H when hybridized to a target nucleic acid. RNase H-independent oligomeric compounds modulate gene expression, such as splicing, by a target occupancy-based mechanism. RNase H-independent antisense oligonucleotides are preferred in the present invention.

As used herein, "hybridization" means the pairing of complementary strands of oligomeric compounds. In the context of the present disclosure, an oligomeric compound is specifically hybridizable when there is a sufficient degree of complementarity to avoid non-specific binding of the oligomeric compound to non-target nucleic acid sequences. One of skill in the art will be able to determine when an oligomeric compound is specifically hybridizable.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. In reference to the antisense oligomeric compound of the present disclosure, the binding free energy for an antisense oligomeric compound with its complementary sequence is sufficient to allow the relevant function of the antisense oligomeric compound to proceed and there is a sufficient degree of complementarity to avoid non-specific binding of the antisense oligomeric compound to non-target sequences under conditions in which specific binding is desired, i.e., under physiological conditions in the case of ex vivo or in vivo therapeutic treatment. Determination of binding free energies for nucleic acid molecules is well known in the art (see e.g. Turner et ah, CSH Symp. Quant. Biol. 1/7:123-133 (1987); Frier et al, Proc. Nat. Acad. Sci. USA 83:9373-77 (1986); and Turner et al, J. Am. Chem. Soc. 109:3783-3785 (1987)). Thus, "complementary" (or "specifically hybridizable") are terms that indicate a sufficient degree of complementarity or precise pairing such that stable and specific binding occurs between a antisense oligomeric compound and a pre-mRNA or mRNA target. It is understood in the art that a nucleic acid molecule need not be 100% complementary to a target nucleic acid sequence to be specifically hybridizable. That is, two or more nucleic acid molecules may be less than fully complementary. Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res. 1997, 7, 649-656). Percent homology, sequence identity or complementarity, can be determined by, for example, the Gap program (Wisconsin Sequence Analysis Package. Version 8 for Unix, Genetics Computer Group. University Research Park, Madison Wis.), using default settings, which uses the algorithm of Smith and Waterman (Adv. Appl. Math., 1981, 2, 482-489). "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

As used herein, "uniformly modified" or "fully modified" refers to an oligomeric compound, an antisense oligonucleotide, or a region of nucleotides wherein essentially each nucleoside is a sugar modified nucleoside having uniform modification.

As used herein, a "chimeric oligomeric compound". "chimeric antisense compound" or "chimeric antisense oligonucleotide compound" is a compound containing two or more chemically distinct regions, each comprising at least one monomer unit (i.e. a nucleotide in the case of an oligonucleotide compound). The term "chimeric antisense compound" specifically refers to an antisense compound, having at least one sugar, nucleobase and/or internucleoside linkage that is differentially modified as compared to the other sugars, nucleotides and internucleoside linkages within the same oligomeric compound. The remainder of the sugars, nucleotides and internucleoside linkages can be independently modified or unmodified. In general a chimeric oligomeric compound will have modified nucleosides that can be in isolated positions or grouped together in regions that will define a particular motif. Chimeric oligomeric compounds typically contain at least one region modified so as to confer increased resistance to nuclease degradation, increased cellular uptake, and/or increased binding affinity for the target nucleic acid. In the context of the present disclosure, a "chimeric RNase H-independent antisense compound" is an antisense compound with at least two chemically distinct regions, but which is not susceptible to cleavage by RNase H when hybridized to a target nucleic acid.

As used herein, a "nucleoside" is a base-sugar combination and "nucleotides" are nucleosides that further include a phosphate group covalently linked to the sugar portion of the nucleoside.

As used herein, a nucleoside with a modified sugar residue is any nucleoside wherein the ribose sugar of the nucleoside has been substituted with a chemically modified sugar moiety. In the context of the present disclosure, the chemically modified sugar moieties include, but are not limited to, 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid.

As used herein, compounds "resistant to RNase H degradation" are antisense compounds having a least one chemical modification that increases resistance of the compound to RNase H cleavage. Such modifications include, but are not limited to, nucleotides with sugar modifications. As used herein, a nucleotide with a modified sugar includes, but is not limited to, any nucleotide wherein the 2'-deoxyribose sugar has been substituted with a chemically modified sugar moiety. In the context of the present invention, chemically modified sugar moieties include, but are not limited to, 2'-O-(2-methoxyethyl), 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido, locked nucleic acid (LNA) and ethylene bridged nucleic acid (ENA). Modified compounds resistant to RNase H cleavage are thoroughly described herein and are well known to those of skill in the art.

In the context of the present disclosure, "cellular uptake" refers to delivery and internalization of oligomeric compounds into cells. The oligomeric compounds can be internalized, for example, by cells grown in culture (in vitro), cells harvested from an animal (ex vivo) or by tissues following administration to an animal (in vivo).

By "subject" is meant an organism, which is a donor or recipient of explanted cells or the cells themselves. "Subject" also refers to an organism to which the nucleic acid molecules of this disclosure can be administered. In one embodiment of the invention and/or embodiments thereof, a subject is a mammal or mammalian cell. In another embodiment, a subject is a human or human cell.

As used herein, the term "therapeutically effective amount" means an amount of antisense oligomeric compound that is sufficient, in the subject (e.g., human) to which it is administered, to treat or prevent the stated disease, disorder, or condition. The antisense oligomeric compound of the instant disclosure, individually, or in combination or in conjunction with other drugs, can be used to treat diseases or conditions discussed herein. For example, to treat a particular disease, disorder, or condition, the antisense oligomeric compound can be administered to a patient or can be administered to other appropriate cells evident to those skilled in the art, individually or in combination with one or more drugs, under conditions suitable for treatment. In the present invention the disease is preferably Pompe disease.

As used herein, the phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "isolated" means that the referenced material is removed from its native environment, e.g. a cell. Thus, an isolated biological material can be free of some or all cellular components, i.e. components of the cells in which the native material occurs naturally (e.g. cytoplasmic or membrane component).

The term "purified" as used herein refers to material that has been isolated under conditions that reduce or eliminate the presence of unrelated materials, i.e. contaminants, including native materials from which the material is obtained (e.g. a tissue culture). For example, a purified DNA antisense oligomeric compound is preferably substantially free of cell or culture components, including tissue culture components, contaminants, and the like. As used herein, the term "substantially free" is used operationally, in the context of analytical testing of the material. Preferably, purified material substantially free of contaminants is at least 50% P pure; more preferably, at least 90% pure, and more preferably still at least 99% pure. Purity can be evaluated by chromatography, gel electrophoresis, immunoassay, composition analysis, biological assay, and other methods known in the art.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

Previous data showed aberrant splicing due to the IVS1 variant. Three major splice products were observed (N, SV2, SV3). Here we found that a natural pseudo exon exists in intron 1. This is not used in control cells, but in the context of the IVS1 mutation it is utilized and competes with canonical splicing of exon 2. It is believed that this phenomenon is not limited to the IVS1 mutation in Pompe disease, but that this may occur also with the c.-32-3C>G and C>A mutations in the GAA gene. Further, it, is believed that this phenomenon occurs in many instances where a disease is caused by aberrant splicing, such as found in many inherited diseases, such as mucopolysaccharidoses (MPS I, MPS II, MPS IV), familial dysautonomia, congenital disorder of glycosylation (CDGIA), ataxia telangiectasia, spinal muscular atrophy, medium-chain acyl-CoA dehydrogenase (MCAD) deficiency, cystic fibrosis. Factor VII deficiency. Fanconi anemia, Hutchinson-Gilford progeria syndrome, growth hormone insensitivity, hyperphenylalaninemia (HPABH4A), Menkes disease, hypobetalipoproteinemia (FHBL), megalencephalic leukoencephalopathy with subcortical cysts (MLC1), methylmalonic aciduria, frontotemporal dementia, Parkinsonism related to chromosome 17 (FTDP-17), Alzheimer's disease, tauopathies, myotonic dystrophy, afibrinogenemia. Bardet-Biedl syndrome, β-thalassemia, muscular dystrophies, such as Duchenne muscular dystrophy, myopathy with lactic acidosis, neurofibromatosis, Fukuyama congenital muscular dystrophy, muscle wasting diseases, dystrophic epidermolysis bullosa, Myoshi myopathy, retinitis pigmentosa, ocular albinism type 1, hypercholesterolemia, Hemaophilis A, propionic academia, Prader-Willi syndrome, Niemann-Pick type C, Usher syndrome, autosomal dominant polycystic kidney disease (ADPKD), cancer such as solid tumours, retinitis pigmentosa, viral infect ions such as HIV, Zika, hepatitis, encephalitis, yellow fever, infectious diseases like malaria or Lyme disease.

As has been shown by Havens, M A et al. 2013. Wiley Interdisciplinary Rev 4(3), 19-03-2013 (see FIG. 1), the use of induced splice sites may in many cases lead to the creation of an extra exon. Expression of this extra exon then causes aberrant protein product ion. In the present invention the discovery was made that in hereditary diseases that are accompanied or caused by splicing aberrations natural pseudo-exons can be present and can be included in the transcript. Such a pseudo-exon was used preferentially when the pY tract of exon 2 was mutated by the IVS1 mutation in Pompe disease. The presence of a natural pseudo exon and its role here is completely unexpected.

It has now been found that the commonly known solution to repair such aberrant splicing. i.e. by blocking the cryptic splice site is greatly improved if both cryptic splice sites of the pseudo-exon, i.e. both the donor and acceptor splice sites, are blocked. As is commonly known in the prior art, blocking splice sites can advantageously be achieved by antisense oligonucleotides (AONs).

As such, the present invention provides a method for repairing aberrant splicing, wherein such aberrant splicing is caused by the expression of a natural pseudo exon, by providing a pair of AONs, in which the first AON is directed to the natural cryptic acceptor splice site of said natural pseudo exon (i.e, the 3' splice site of the natural pseudo exon) and wherein the second AON is directed to the natural cryptic donor splice site of said natural pseudo exon (i.e. the 5' splice site of the natural pseudo exon), wherein the application of said pair of AONs provides for a silencing of the expression of the natural pseudo exon. This also means that the target sites are relatively close; they normally will not be separated by more than 200, preferably 500 nucleotides, i.e. the cryptic exon will normally be less than 200 or 500 nucleotides, respectively. However, larger exons may occasionally occur.

Such a method can be used for any aberrant splicing resulting in the expression of a cryptic exon whether or not this aberrant splicing would cause a disease. However, it is advantageously performed in cases where the aberrant splicing causes a disease, preferably where said disease is selected from the group consisting mucopolysaccharidoses (MPS I, MPS II, MPS IV), familial dysautonomia, congenital disorder of glycosylation (CDG1A), ataxia telangiectasia, spinal muscular atrophy, medium-chain acyl-CoA dehydrogenase (MCAD) deficiency, cystic fibrosis. Factor VII deficiency. Fanconi anemia. Hutchinson-Gilford progeria syndrome, growth hormone insensitivity, hyperphenylalaninemia (HPABH4A). Menkes disease, hypobetalipoproteinemia (FHBL), megalencephalic leukoencephalopathy with subcortical cysts (MLC1), methylmalonic aciduria, frontotemporal dementia, Parkinsonism related to chromosome 17 (FTDP-17), Alzheimers disease, tauopathies, myotonic dystrophy, afibrinogenemia, Bardet-Biedl syndrome, 8-thalassemia, muscular dystrophies, such as Duchenne muscular dystrophy, myopathy with lactic acidosis, neurofibromatosis. Fukuyama congenital muscular dystrophy, muscle wasting diseases, dystrophic epidermolysis bullosa. Myoshi myopathy, retinitis pigmentosa, ocular albinism type 1, hypercholesterolemia. Hemaophilis A, propionic academia, Prader-Willi syndrome, Niemann-Pick type C, Usher syndrome, autosomal dominant polycystic kidney disease (ADPKD)), cancer such as solid tumours, retinitis pigmentosa, viral infect ions such as HIV, Zika, hepatitis, encephalitis, yellow fever, infectious diseases like malaria or Lyme disease.

Preferably, the disease is Pompe disease and the aberrant splicing is caused by the so-called IVS1 mutation. In the case of this mutation a natural pseudo-exon is recognized in the region of the first intron which is spliced at the cryptic splice sites c-32-154 (natural cryptic acceptor splice site), and c.-32-52 (natural cryptic donor splice site). These sites may, according to aspects of this invention, be blocked by using AONs that are for instance targeted to the following regions: SEQ ID NO: 1 for the natural cryptic acceptor splice site and SEQ ID NO: 171 for the natural cryptic donor splice site.

It should be noted that a concentration of the chaperone that is inhibitory during in vitro production, transportation, or storage of the purified therapeutic protein may still constitute an "effective amount" for purposes of this invention because of dilution (and consequent shift in binding due to the change in equilibrium), bioavailability and metabolism of the chaperone upon administration in vivo.

The term 'alkyl' refers to a straight or branched hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl).

The term "alkenyl" refers to a C2-C20 aliphatic hydrocarbon group containing at least one carbon-carbon double bond and which may be a straight or branched chain, e.g., ethenyl, 1-propenyl, 2-propenyl (allyl), iso-propenyl, 2-methyl-1-propenyl, 1-butenyl, 2-butenyl.

The term "cycloalkyl" denotes an unsaturated, non-aromatic mono- or multicyclic hydrocarbon ring system such as cyclopropyl, cyclobutyl, cyclopentyl, cyclohexyl. Examples of multicyclic cycloalkyl groups include perhydronaphthyl, adamantyl and norbornyl groups bridged cyclic group or sprirobicycic groups, e.g., spiro (4,4) non-2-yl.

The term "aryl" refers to aromatic radicals having in the range of about 6 to about 14 carbon atoms such as phenyl, naphthyl, tetrahydronaphthyl, indanyl, biphenyl.

The term "heterocyclic" refers to a stable 3- to 15-membered ring radical which consists of carbon atoms and from one to five heteroatoms selected from the group consisting of nitrogen, oxygen and sulfur. For purposes of this invention, the heterocyclic ring radical may be a monocyclic or bicyclic ring system, which may include fused or bridged ring systems, and the nitrogen, carbon, oxygen or sulfur atoms in the heterocyclic ring radical may be optionally oxidized to various oxidation states. In addition, a nitrogen atom, where present, may be optionally quaternized; and the ring radical may be partially or fully saturated (e.g., heteroaromatic or heteroaryl aromatic). The heterocyclic ring radical may be attached to the main structure at any heteroatom or carbon atom that results in the creation of a stable structure.

The term "heteroaryl" refers to a heterocyclic ring wherein the ring is aromatic.

The substituents in the 'substituted alkyl', 'substituted alkenyl', 'substituted cycloalkyl', 'substituted aryl' and 'substituted heteroaryl' may be the same or different, with one or more selected from the groups hydrogen, halogen, acetyl, nitro, carboxyl, oxo (=0), $CF_3$, $—OCF_3$, $NH_2$, —C(=0)-alkyl$_2$. $OCH_3$, or optionally substituted groups selected from alkyl, alkoxy and aryl. The term "halogen" refers to radicals of fluorine, chlorine, bromine and iodine.

GAA enzyme: Human GAA is synthesized as a 110 kDa precursor (Wisselaar et al. (1993) J. Biol. Chem. 268(3): 2223-31). The mature form of the enzyme is a mixture of monomers of 70 and 76 kD (Wisselaar et al. (1993) J. Biol. Chem. 268(3): 2223-31). The precursor enzyme has seven potential glycosylation sites and four of these are retained in the mature enzyme (Wisselaar et al. (1993) J. Biol. Chem. 268(3): 2223-31). The proteolytic cleavage events which produce the mature enzyme occur in late endosomes or in the lysosome (Wisselaar et al. (199:3) J. Biol. Chem. 268(3): 2223-31). The C-terminal 160 amino acids are absent from the mature 70 and 76 kD species. It has been reported that the C-terminal portion of the protein, although cleaved from the rest of the protein during processing, remains associated with the major species (Moreland et al. (Nov. 1, 2004) J. Biol. Chem. Manuscript 404008200).

The enzyme of GAA may be obtained from a cell endogenously expressing the enzyme or GAA, or the enzyme or GAA may be a recombinant human enzyme or GAA (rhGAA), as described herein. Optionally the recombinant human enzyme or rhGAA is a full length wild-type enzyme. Optionally the recombinant human enzyme or rhGAA comprises a subset of the amino acid residues present in a wild-type enzyme or GAA, wherein the subset includes the amino acid residues of the wild-type enzyme or (GAA that form the active site for substrate binding and/or substrate reduction. As such, the present invention contemplates an recombinant human enzyme or rhGAA that is a fusion protein comprising the wild-type enzyme or GAA active site for substrate binding and/or substrate reduction, as well as other amino acid residues that may or may not be present in the wild type enzyme or GAA.

The enzyme or GAA may be obtained from commercial sources or may be obtained by synthesis techniques known to a person of ordinary skill in the art. The wild-type enzyme can be purified from a recombinant cellular expression system (e.g., mammalian cells or insect cells-see generally U.S. Pat. Nos. 5,580,757; 6,395,884 and 6,458,574, 6,461, 609, 6,210,666; 6,083,725; 6,451,600; 5,236,838; and 5,879,680), human placenta, or animal milk (see e.g. U.S. Pat. No. 6,188,045). After the infusion, the exogenous enzyme is expected to be taken up by tissues through non-specific or receptor-specific mechanism. In general, the uptake efficiency (without use of an chaperone) is not high, and the circulation time of the exogenous protein is short (Ioannu et at Am. J. Hum. Genet. 2001; 68: 14-25). In addition, the exogenous protein is unstable and subject to rapid intracellular degradation in vitro. Other synthesis techniques for obtaining GAA suitable for pharmaceutical may be found, for example, in U.S. Pat. Nos. 7,560,424 and 7,396,811, U.S. Published Application Nos. 2009/0203575, 2009/0029467, 2008/0299640, 2008/0241118, 2006/0121018, and 2005/0244400, U.S. Pat. Nos. 7,423,135, 6,534,300, and 6,537,785: International Published Application No. 2005/077093 and U.S. Published Application Nos. 2007/0280925, and 2004/0029779. These references are hereby incorporated by reference in their entirety.

Optionally the GAA is alglucosidase alfa, which consists of the human enzyme acid α-glucosidase (GAA), encoded by any of nine observed haplotypes of this gene.
The GAA or enzyme suitable for ERT may be a modification, variant, analogue, fragment, portion, or functional derivative, thereof.

The uptake of the enzyme or GAA may be enhanced by functionalizing the enzyme or GAA by targets for receptors selected from the group consisting of mannose 6-phosphate receptor, insulin like growth factor II receptor, mannose receptor, galactose receptor, fucose receptor. N-Acetylglucosamine (GlcNAc) receptor, plasminogen activator receptor. IGF 1 receptor, insulin receptor; transferrin receptor, cation-dependent mannose-6-phosphate receptor (CD-MPR).

Functional derivatives" of the enzyme or GAA as described herein are fragments, variants, analogs, or chemical derivatives of the enzyme which retain at least a portion of the enzyme activity or immunological cross reactivity with an antibody specific for the enzyme.

A fragment or portion of enzyme refers to any subset of the molecule.

The enzyme or GAA may be modified with a compound selected from the group consisting of mannose 6-phosphate, peptide insulin-like growth factor-2.

Peptide insulin-like growth factor-2 is used in glycosylation-independent lysosomal targeting (GILT).

Optionally the enzyme or GAA is produced by recombinant DNA technology in a Chinese hamster ovary cell line.

Optionally the enzyme or GAA is produced by a glycoengineered yeast platform (e.g. based on the yeast *Yarrowria lipolytica*).

Optionally the enzyme or GAA is produced by transgene rabbits and collected via the milk of these transgene rabbits.

GAA enzyme is available as Myozyme (Sanofi) Lumizyme (Sanofi) OXY2810 (Oxyrane), IGF2-GAA (Biomarin) BMN-701 (Biomarin), Reveglucosidase alfa (Biomarin).

Chaperone or ASSC (active site-specific chaperone) may be obtained using synthesis techniques known to one of ordinary skill in the art. For example, ASSC that may be used in the present application, such as 1-DNJ may be prepared as described in U.S. Pat. Nos. 6,274,597 and 6,583,158, and U.S. Published Application No. 200610264467, each of which is hereby incorporated by reference in its entirety.

Optionally, the ASSC is a-homonojirimycin and the GAA is hrGAA (e.g., Myozyme® or Lumizyme®). Optionally the ASSC is castanospermine and the GAA is hrGAA (e.g., Myozyme® or Lumizyme®). The ASSC (e.g. -homonojirimycin and castanospermine) may be obtained from synthetic libraries (see, e.g., Needels et al. Proc. Natl. Acad. Sci. USA 1993: 90: 10700-4; Ohlmeyer et al., Proc. Natl. Acad. Sci. USA 1993: 90: 10922-10926; Lam et al. PCT Publication No. WO 92/00252; Kocis et al., PCT Publication No. WO 94/28028) which provide a source of potential ASSC's. Synthetic compound libraries are commercially available from Maybridge Chemical Co. (Trevillet, Cornwall, UK). Comgenex (Princeton, N. J.). Brandon Associates (Merrimack, N.H.), and Microsource (New Milford, Conn.). A rare chemical library is available from Aldrich (Milwaukee. Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through Res. 1986; 155:1 19-29. Optionally ASSC's useful for the present invention are inhibitors of lysosomal enzymes and include glucose and galactose imino-sugar derivatives as described in Asano et al. J. Med. Chem. 1994; 37:3701-06; Dale et al, Biochemistry 1985; 24:3530-39; Goldman et al., J. Nat. Prod. 1996; 59:1137-42; Legler et al, Carbohydrate Res. 1986: 155; 1 19-29. Such derivatives include those that can be purchased from commercial sources such as Toronto Research Chemicals, Inc. (North York, On. Canada) and Sigma.

Optionally, the route of administration is subcutaneous. Other routes of administration may be oral or parenteral, including intravenous, intraarterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation. Intrapulmonary delivery methods, apparatus and drug preparation are described, for example, in U.S. Pat. Nos. 5,785,049, 5,780,019, and 5,775,320, each incorporated herein by reference. In some embodiments, the method of intradermal delivery is by iontophoretic delivery via patches: one example of such delivery is taught in U.S. Pat. No. 5,843,015, which is incorporated herein by reference. Administration may be by periodic injections of a bolus of the preparation, or as a sustained release dosage form over long periods of time, or by intravenous or intraperitoneal administration, for example, from a reservoir which is external (e.g., an IV bag) or internal (e.g. a bioerodable implant, a bioartificial organ, or a population of implanted GAA production cells). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the GAA preparation described herein can administered in these methods.

Optionally the enzyme or GAA enzyme or nucleic acid encoding the enzyme or GAA enzyme and/or the antisense oligomeric compound may be administered in combination with an Active Site-Specific Chaperone (ASSC) for the GAA enzyme (e.g., 1-deoxynojirimycin (DNJ, 1-DNJ)). The ASSC enables higher concentrations of the enzyme or GAA enzyme or nucleic acid encoding the enzyme or GAA enzyme and/or the antisense oligomeric compound in a pharmaceutical composition. In combination with an ASSC the enzyme or GAA enzyme or nucleic acid encoding the enzyme or GAA enzyme and/or the antisense oligomeric compound may be administered at a concentration between about 5 and about 250 mg/mL. Optionally, the enzyme or GAA enzyme or nucleic acid encoding the enzyme or GAA enzyme and/or the antisense oligomeric compound is combined with an ASSC at a high concentration, for example, at a concentration selected from the group consisting of about 25-240 mg/mL, about 80-200 mg/mL, about 115-160 mg/mL. Optionally, the enzyme or GAA enzyme or nucleic acid encoding the enzyme or GAA enzyme and/or the antisense oligomeric compound is combined with an ASSC, wherein the ASSC is present at a concentration between about 5 mg/mL and about 200 mg/mL, optionally between about 32 mg/mL and about 160 mg/mL. Optionally, the enzyme or GAA enzyme or nucleic acid encoding the enzyme or GAA enzyme and/or the antisense oligomeric compound is combined with an ASSC, wherein the ASSC is present at a concentration between about 0.5 mM and about 20 mM. GAA enzyme combined with an ASSC can remain soluble at a high concentration (e.g. 25 mg/mL) and remain non-aggregated while maintaining a viscosity suitable for injection (e.g., subcutaneous administration). Optionally the compositions of the present invention comprise more than about 5 mg/mL of the enzyme or GAA enzyme or nucleic acid encoding the enzyme or GAA enzyme and/or the antisense oligomeric compound.

Optionally, the compositions of the invention comprise about 5-25 mg/mL the enzyme or GAA enzyme or nucleic acid encoding the enzyme or GAA enzyme and/or the antisense oligomeric compound and optionally about 1-10 mM DNJ.

Optionally the method of treating Pompe Disease comprises administering the enzyme or GAA enzyme or nucleic acid encoding the enzyme or GAA enzyme and/or the antisense oligomeric compound biweekly, weekly or once per two weeks for up to about 10 weeks, optionally in combination with from about 1 to about 5000 mg/kg of an ASSC (e.g., 1-DNJ-HCl) prior to, and in regular intervals after, the infusion of the enzyme or GAA enzyme or nucleic acid encoding the enzyme or GAA enzyme and/or the antisense oligomeric compound. For example, the ASSC could be administered within two hours of the infusion, and then administered at regular intervals once, twice, three-times, four-times, five-times or six-times within 24 hours post-infusion. Optionally, the GAA is Myozyme® and is administered via infusion once per week and the ASSC (e.g., 1-DNJ-HCl) is administered at 10 mg/kg, 100 mg/kg or 1000 mg/kg 30 minutes prior to infusion, and then 8, 16, and 24 hours after each Myozyme® infusion.

Optionally, the GAA is Lumizyme® and is administered via infusion once per week and the ASSC (e.g., 1-DNJ-HCl) is administered at 10 mg/kg, 100 mg/kg or 1000 mg/kg 30 minutes prior to infusion, and then 8, 16, and 24 hours after each Lumizyme® infusion.

It is believed that acid α-glucosidase (GAA) functions to remove terminal glucose residues from lysosomal glycogen. Some genetic mutations reduce GAA trafficking and maturation. The pharmacological chaperone 1-DNJ increases GAA levels by selectively binding and stabilizing the enzyme in a proper conformation which restores proper protein trafficking to the lysosome. Optionally, the ASSC is administered as described in International Publication No. 2008/134628, which is hereby incorporated by reference in its entirety.

The ASSC is a small molecule inhibitor of the GAA enzyme, including reversible competitive inhibitors of the GAA enzyme. Optionally the ASSC may be represented by the formula:

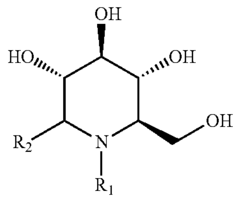

where $R_1$ is H or a straight or branched alkyl, cycloalkyl, alkoxyalkyl or aminoalkyl containing 1-12 carbon atoms optionally substituted with an —OH, —COOH, —Cl, —F, $—CF_a$, $—OCF_3$, —O—C(O)N-$(alkyl)_2$; and $R_2$ is H or a straight or branched alkyl, cycloalkyl, or alkoxyalkyl containing 1-9 carbon atoms; including pharmaceutically acceptable salts, esters and prodrugs thereof. Optionally the ASSC is 1-deoxynojirimycin (1-DNJ), which is represented by the following formula:

or a pharmaceutically acceptable salts, esters or prodrug of 1-deoxynojirimycin. Optionally, the salt is hydrochloride salt (i.e. 1-deoxynojirimycin-HCl). Optionally, the ASSC is N-butyl-deoxynojirimycin (NB-DNJ; Zavesca®, Actelion Pharmaceuticals Ltd. Switzerland), which is represented by the following formula:

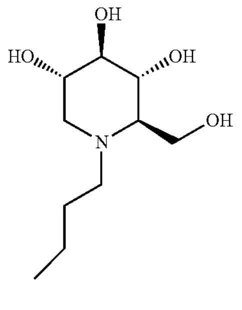

or a pharmaceutically acceptable salt, ester or prodrug of NB-DNJ.

Optionally the ASSC is $C_{10}H_{19}NO_4$, which is represented by the following formula:

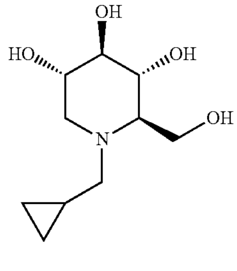 [SMILES: OC[C@@H]1[C@@H](O)[C@H](O)[C@@H](O)CN1CC1CC1]

or a pharmaceutically acceptable salt, ester or prodrug of $C10H_{19}NO_4$. Optionally the salt is hydrochloride salt.

Optionally, the ASSC is $C_{12}H_{23}NO_4$, which is represented by the following formula:

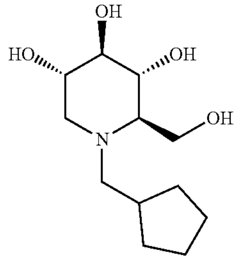 [SMILES: OC[C@@H]1[C@@H](O)[C@H](O)[C@@H](O)CN1CC1CCCC1]

or a pharmaceutically acceptable salt, ester or prodrug of $C_{12}H_{23}NO_4$. Optionally, the salt is hydrochloride salt.

Patients with complete absence of GAA enzyme are cross-reactive immunological material (CRIM) negative, and develop high titer antibody to rhGAA. Patients with GAA protein detectable by western blot are classified as CRIM-positive. Whereas the majority of CRIM-positive patients have sustained therapeutic responses to ERT, or gene therapy CRIM-negative patients almost uniformly do poorly, experiencing rapid clinical decline because of the development of sustained, high-titer antibodies to rhGAA.

A combination of rituximab with methotrexate with or without intravenous gammaglobulins (IVIG) may be used to induce tolerance induction of CRIM negative patients. The treatment may be prophylactically to avoid antibody to rhGAA or may be given to patients that have already developed anti-rhGAA. Rituximab may be given in a dose of 100-1000 mg/kg, or in a dose of 150-900 mg/kg, or in a dose of 200-800 mg/kg, or in a dose of 250-750 mg/kg, or in a dose of 300-600 mg/kg, or in a dose of 350-500 mg/kg, or in a dose of 400-450 mg/kg.

Rituximab may be given once every 1, 2, 3, 4, 5, 6, 7, 8, 9, 10, 11, 12, 13, 14, 15, 16, 17, 18, 19, 20, 21, 22, 23, 24, or 25 days. Optionally Rituximab is administered once every 1, 2, 3, 4, 5, 6, 7, 8, 9, 10, 11, 12, 13, 14, 15, 16, 17, 18, 19, 20, 21, 22, 23, 24, or 25 weeks. Optionally Rituximab is administered once every 1, 2, 3, 4, 5, 6, 7, 8, 9, 10, 11, 12, 13, 14, 15, 16, 17, 18, 19, 20, 21, 22, 23, 24, or 25 months. Optionally Rituximab is administered once every 1, 2, 3, 4, 5, 6, 7, 8, 9, 10, years.

Methotrexate may be given in a dose of 0.1-10 mg/kg, or in a dose of 0.2-5 mg/kg, or in a dose of 0.3-2 mg/kg, or in a dose of 0.4-1 mg/kg or in a dose of 0.5-0.7 mg/kg. Methotrexate may be given once every 1, 2, 3, 4, 5, 6, 7, 8, 9, 10, 11, 12, 13, 14, 15, 16, 17, 18, 19, 20, 21, 22, 23, 24, or 25 days, Optionally Methotrexate is administered once every 1, 2, 3, 4, 5, 6, 7, 8, 9, 10, 11, 12, 13, 14, 15, 16, 17, 18, 19, 20, 21, 22, 23, 24, or 25 weeks. Optionally Methotrexate is administered once every 1, 2, 3, 4, 5, 6, 7, 8, 9, 10, 11, 12, 13, 14, 15, 16, 17, 18, 19, 20, 21, 22, 23, 24, or 25 months. Optionally Methotrexate is administered once every 1, 2, 3, 4, 5, 6, 7, 8, 9, 10, years, Administration of Methotrexate may be based on hematologic tolerance. IVIG may be given in a dose of 0.1-10 mg/kg, or in a dose of 0.2-5 mg/kg, or in a dose of 0.3-2 mg/kg, or in a dose of 0.4-1 mg/kg or in a dose of 0.5-0.7 mg/kg. IVIG may be given once every 1, 2, 3, 4, 5, 6, 7, 8, 9, 10, 11, 12, 13, 14, 15, 16, 17, 18, 19, 20, 21, 22, 23, 24, or 25 days, Optionally IVIG is administered once every 1, 2, 3, 4, 5, 6, 7, 8, 9, 10, 11, 12, 13, 14, 15, 16, 17, 18, 19, 20, 21, 22, 23, 24, or 25 weeks. Optionally IVIG is administered once every 1, 2, 3, 4, 5, 6, 7, 8, 9, 10, 11, 12, 13, 14, 15, 16, 17, 18, 19, 20, 21, 22, 23, 24, or 25 months. Optionally IVIG is administered once every 1, 2, 3, 4, 5, 6, 7, 8, 9, 10, years, Treatment may be given until rhGAA antibody titer is down to zero. Various combinations of administration of the enzyme or GAA and Rituximab, and/or Methotrexate and/or IVIG is explicitly envisioned in the present invention.

In one aspect, the invention is directed to an antisense oligomeric compound. Previous work by others has resulted in the design of antisense oligomeric compounds that promote exon exclusion in several human disorders including Duchenne Muscular Dystrophy (DMD). The strategy is simple and straightforward and relies on blocking a well-defined splice site. This results in exon skipping, thereby removing the exon containing the pathogenic gene variant. The resulting mRNA is a little bit shorter resulting in expression of a truncated protein with considerable residual activity, sufficient to at least partially alleviate the disease. The strategy is simple because canonical splice sites are known for virtually all genes. The only requirement is to design an antisense oligomeric compound that binds to the canonical splice site in the pre-mRNA, which will result in blocking of that site and skipping of the exon involved.

A much more difficult task is the reverse process: to promote inclusion rather than exclusion of an exon. To promote exon inclusion, a splice repressor may be blocked using an antisense oligomeric compound. It is however unknown where splice repressors are located. These can be present in introns or in exons and are named intronic or exonic splice silencers (ISSs or ESSs, respectively). There is software available to predict the presence of such silences but these are very unreliable. This is further illustrated by our own experience using the minigene system containing GAA exon 1-3, which failed to confirm activity of predicted splice silencer motifs. The idea to promote exon 2 inclusion of GAA with an antisense oligomeric compound to treat Pompe disease is entirely novel.

Hence, in aspects of this invention promotion of exon 2 inclusion of GAA to treat Pompe disease may be performed with an antisense oligomeric compound as described herein.

Target Sequences of AONs of the Present Invention

In one aspect or embodiment of aspects and/or embodiments thereof the invention is directed to an antisense oligomeric compound complementary to a genomic nucleic acid sequence of the GAA gene targeting the location that comprises the position of the following mutation c.-32-13T>G, c.-32-3C>G c.-32-102T>C. c.-32-56C>T, c.-32-46G>A, c.-32-28C>A, c.-32-28C>T, c.-32-21G>A, c.7G>A, c.11G>A, c.15-17AAA, c.17C>T, c.19-21AAA, c.26-28AAA, c.33-35AAA, c.39G>A, c.42>T, c.90C>T, c.112>A, c.137C>T, c.164C>T, c.348G>A, c.373C>T, c.413T>A, c.469C>T, c.476T>C, c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, c.1552.30, c.1256A>T, c.1551+1G>T, c.546G>T, 0.17C>T, c.469C>T, c.546+23C>A, c.-32-102T>C, c.-32-56C>T, c.11G>A, c.112G>A, c.137C>T.

The above identified mutations have been found to modulate splicing. Targeting the location of the mutation may also modulate the splicing. It is therefore understand that the antisense oligomeric compound in aspects of this invention targets the location of the mutation.

The nomenclature of the mutation identifies the location and the mutation. It is understood that the antisense oligomeric compound targets the location of the mutation, and the mutation does not need to be present in the genomic sequence or in the pre-mRNA. The location of the mutation is thus the location of the mutated nucleotide, or the location of the wild type nucleotide of the mutation. The antisense oligomeric compound may be targeted to a sequence comprising nucleotides upstream and nucleotides downstream of the location of the mutation. Optionally the antisense oligomeric compounds target a sequence comprising 2-50 nucleotides upstream, and/or 2-50 nucleotides downstream of the location of the mutation. Alternatively, or in addition, or more preferably, the antisense oligomeric compounds target a sequence comprising 3-45 nucleotides upstream, and/or 3-45 nucleotides downstream of the location of the mutation, more Optionally the antisense oligomeric compound target a sequence comprising 5-40 nucleotides upstream, and/or 5-40 nucleotides downstream of the location of the mutation. Alternatively, or in addition, or more preferably, the antisense oligomeric compounds target a sequence comprising 6-35 nucleotides upstream, and/or 6-35 nucleotides downstream of the location of the mutation. For instance, the antisense oligomeric compounds may target a sequence comprising 7-33 nucleotides upstream, and/or 7-33 nucleotides downstream of the location of the mutation, more preferably 8-3) nucleotides upstream, and/or 8-30 nucleotides downstream of the location of the mutation. It is also possible that the antisense oligomeric compounds target a sequence comprising 9-28 nucleotides upstream, and/or 9-28 nucleotides downstream of the location of the mutation, such as 10-25 nucleotides upstream, and/or 10-25 nucleotides downstream, 11.22 nucleotides upstream, and/or 11-22 nucleotides downstream, 12-20 nucleotides upstream, and/or 12.20 nucleotides downstream, 13-18 nucleotides upstream, and/or 13-18 nucleotides downstream, or 14-16 nucleotides upstream, and/or 14-16 nucleotides downstream of the location of the mutation.

The nomenclature is well known to a skilled person and can be found in Dunnen and Antonarakis Human mutation 15:7-12(2000) and Antonarakis SE, the Nomenclature Working Group. 1998. Recommendations for a nomenclature system for human gene mutations. Hum Mutat 11:1-3 and on the website (http://ww.dmd.nl/mutnomen.html. Genomic positions may also be found on www.pompecenter.nl. All of these are incorporated by reference.

A number of genomic nucleic acid sequences of the GAA gene is suitable as target. The genomic nucleic acid sequence acting as target of AONs in the present invention is preferably a pre-mRNA sequence. The genomic nucleic acid is preferably pre-mRNA A large number of antisense oligomeric compounds as referred to herein below, either alone, or in combination, are useful in the treatment of glycogen storage disease type II/Pompe disease. The antisense oligomeric compounds as referred to herein, may target a variety or combination of genomic nucleic acid sequences herein disclosed. It should be noted that also naturally occurring single nucleotide polymorphisms in the genomic nucleic acid sequences are included.

In one aspect, the target sequence may be an intronic splicing silencer or ISS. One such a target sequence (5'-GCTCTGCACTCCCCTGCTG-GAGCTTTTCTCGCCCTTCCTTCTGGCCCTCTCCCCA-3' (SEQ ID NO: 2)), was found to be part of a cryptic acceptor splice site corresponding to a region around c.-32-154 (referred to as the natural cryptic acceptor splice site) 5'-GTGCTCTGCACTCCCCTGCTG-GAGCTTTTCTCGCCCTTCCTTCTGGCCCTCTCCCC-AGTCTAGA CAGCAGGGCAACACCCAC-3' (SEQ ID NO: 1).

In one aspect of this invention the AON targets for antisense gene therapy as envisioned herein, may be sequences of the GAA gene product that are (part of) a cryptic splice site or pseudo exon, in particular the splice acceptor, referred to herein as SEQ ID NO:1. Oligonucleotide sequences used as antisense oligos in aspects of this invention may be sequences targeting SEQ ID NO: 1, and these are able to enhance inclusion of GAA exon 2 in the context of the IVS1 mutation. Also sequences targeting SEQ ID NOs: 2-7 (subsequence targets of SEQ ID NO:1), were found to be able to enhance inclusion of GAA exon 2 in the context of the IVS1 mutation. It is to be noted that "targeting" means that at least part of the sequence SEQ ID NO: 1 is targeted, e.g. by a sequence that hybridizes with at least a part or by the sequence SEQ ID NO: 1, or that binds to at least a part of SEQ ID NO: 1. Sequences that target may be shorter or longer than the target sequence, and may be derivatives and fragments thereof having at least 80% sequence identity, determined over the entire length of the molecule.

Hence, the target for AONs in aspects of this invention may be SEQ ID NO: 1, or a part thereof, such as SEQ ID NO:2, or other parts of SEQ ID NO: 1, such as SEQ ID Nos:3-7, as indicated below merely as examples. It is understood that the antisense oligomeric compound targets the location of the natural cryptic splice site.

The AONs that target these regions hybridize with at, least a part of SEQ ID NO: 1. Sequences that hybridize may be shorter or longer than the target, sequence. A highly preferred region for targeting AONs is the pY tract, of the pseudo exon, which region is indicated by c.-32-188_-159. Preferred embodiments of AONs used in aspects of this invention anneal substantially completely to this region.

TABLE 1

Suitable optional target sequences for use in the present invention associated with a cryptic acceptor splice site in GAA.

| Sequence in target to which AON anneals* | Target sequence (5' → 3'): | SEQ ID NO: |
|---|---|---|
| c-32-212_-113 | GTGCTCTGCACTCCCCTGC TGGAGCTTTTCTCGCCCT TCCTTCTGGCCCTCTC CCCAGTCTAGACAGC AGGGCAACACCCAC | 1 |
| c-32-210_-156 | GCTCTGCACTCCCCTGCTG GAGCTTTTCTCGCCCTTC CTTCTGGCCCTCTCCCCA | 2 |

TABLE 1-continued

Suitable optional target sequences for use in the present invention associated with a cryptic acceptor splice site in GAA.

| Sequence in target to which AON anneals* | Target sequence (5' → 3'): | SEQ ID NO: |
|---|---|---|
| c-32-200_-156 | GCTCTGCACTCCCCTGC TGGAGCTTTTCTCGCC CTTCCTTCTGGC | 3 |
| c-32-190_-160 | TGCACTCCCCTGCTGG AGCTTTTCTCGCCCT | 4 |
| c-32-195_160 | TGCACTCCCCTGCTGGAG CTTTTCTCGCCCTTCCTT | 5 |
| c-32-195_-165 | TCCCCTGCTGGAGCTT TTCTCGCCCTTCCTT | 6 |
| c-32-209_-178 | CTTTTCTCGCCCTTCC TTCTGGCCCTCTCCCC | 7 |

In aspects of the invention, the targets to which an antisense oligomeric compound of the invention may anneal or hybridize, may be an acceptor splice site sequence of the natural pseudo-exon, such as a sequence selected from the group comprising SEQ ID NO: 8.65 as shown in Table 2 and derivatives and fragments having at, least 80% identity thereof.

TABLE 2

25 bp sequences (5' → 3') serving as possible AON targets in the cryptic acceptor splice site in GAA

| Sequence in target to which AON anneals* | Target sequence (5' → 3'): | SEQ ID NO: |
|---|---|---|
| c.-32-212_-188 | GTGCTCTGCACTCCCCTGCTGGAGC | 8 |
| c.-32-211_-187 | TGCTCTGCACTCCCCTGCTGGAGCT | 9 |
| c.-32-210_-186 | GCTCTGCACTCCCCTGCTGGAGCTT | 10 |
| c.-32-209_-185 | CTCTGCACTCCCCTGCTGGAGCTTT | 11 |
| c.-32-208_-184 | TCTGCACTCCCCTGCTGGAGCTTTT | 12 |
| c.-32-207_-183 | CTGCACTCCCCTGCTGGAGCTTTTC | 13 |
| c.-32-206_-182 | TGCACTCCCCTGCTGGAGCTTTTCT | 14 |
| c.-32-205_-181 | GCACTCCCCTGCTGGAGCTTTTCTC | 15 |
| c.-32-204_-180 | CACTCCCCTGCTGGAGCTTTTCTCG | 16 |
| c.-32-203_-179 | ACTCCCCTGCTGGAGCTTTTCTCGC | 17 |
| c.-32-202_-178 | CTCCCCTGCTGGAGCTTTTCTCGCC | 18 |
| c.-32-201_-177 | TCCCCTGCTGGAGCTTTTCTCGCCC | 19 |
| c.-32-200_-176 | CCCCTGCTGGAGCTTTTCTCGCCCT | 20 |
| c.-32-199_-175 | CCCTGCTGGAGCTTTTCTCGCCCTT | 21 |
| c.-32-198_-174 | CCTGCTGGAGCTTTTCTCGCCCTTC | 22 |
| c.-32-197_-173 | CTGCTGGAGCTTTTCTCGCCCTTCC | 23 |
| c.-32-196_-172 | TGCTGGAGCTTTTCTCGCCCTTCCT | 24 |
| c.-32-195_-171 | GCTGGAGCTTTTCTCGCCCTTCCTT | 25 |

TABLE 2-continued 25 bp sequences (5' → 3') serving as possible AON targets in the cryptic acceptor splice site in GAA

| Sequence in target to which AON anneals* | Target sequence (5' → 3'): | SEQ ID NO: |
|---|---|---|
| c.-32-194_-170 | CTGGAGCTTTTCTCGCCCTTCCTTC | 26 |
| c.-32-193_-169 | TGGAGCTTTTCTCGCCCTTCCTTCT | 27 |
| c.-32-192_-168 | GGAGCTTTTCTCGCCCTTCCTTCTG | 28 |
| c.-32-191_-167 | GAGCTTTTCTCGCCCTTCCTTCTGG | 29 |
| c.-32-190_-166 | AGCTTTTCTCGCCCTTCCTTCTGGC | 30 |
| c.-32-189_-165 | GCTTTTCTCGCCCTTCCTTCTGGCC | 31 |
| c.-32-188_-164 | CTTTTCTCGCCCTTCCTTCTGGCCC | 32 |
| c.-32-187_-163 | TTTTCTCGCCCTTCCTTCTGGCCCT | 33 |
| c.-32-186_-162 | TTTCTCGCCCTTCCTTCTGGCCCTC | 34 |
| c.-32-185_-161 | TTCTCGCCCTTCCTTCTGGCCCTCT | 35 |
| c.-32-184_-160 | TCTCGCCCTTCCTTCTGGCCCTCTC | 36 |
| c.-32-183_-159 | CTCGCCCTTCCTTCTGGCCCTCTCC | 37 |
| c.-32-182_-158 | TCGCCCTTCCTTCTGGCCCTCTCCC | 38 |
| c.-32-181_-157 | CGCCCTTCCTTCTGGCCCTCTCCCC | 39 |
| c.-32-180_-156 | GCCCTTCCTTCTGGCCCTCTCCCCA | 40 |
| c.-32-179_-155 | CCCTTCCTTCTGGCCCTCTCCCCAG | 41 |
| c.-32-178_-154 | CCTTCCTTCTGGCCCTCTCCCCAGT | 42 |
| c.-32-177_-153 | CTTCCTTCTGGCCCTCTCCCCAGTC | 43 |
| c.-32-176_-152 | TTCCTTCTGGCCCTCTCCCCAGTCT | 44 |
| c.-32-175_-151 | TCCTTCTGGCCCTCTCCCCAGTCTA | 45 |
| c.-32-174_-150 | CCTTCTGGCCCTCTCCCCAGTCTAG | 46 |
| c.-32-173_-149 | CTTCTGGCCCTCTCCCCAGTCTAGA | 47 |
| c.-32-172_-148 | TTCTGGCCCTCTCCCCAGTCTAGAC | 48 |
| c.-32-171_-147 | TCTGGCCCTCTCCCCAGTCTAGACA | 49 |
| c.-32-170_-146 | CTGGCCCTCTCCCCAGTCTAGACAG | 50 |
| c.-32-169_-145 | TGGCCCTCTCCCCAGTCTAGACAGC | 51 |
| c.-32-168_-144 | GGCCCTCTCCCCAGTCTAGACAGCA | 52 |
| c.-32-167_-143 | GCCCTCTCCCCAGTCTAGACAGCAG | 53 |
| c.-32-166_-142 | CCCTCTCCCCAGTCTAGACAGCAGG | 54 |
| c.-32-165_-141 | CCTCTCCCCAGTCTAGACAGCAGGG | 55 |
| c.-32-164_-140 | CTCTCCCCAGTCTAGACAGCAGGGC | 56 |
| c.-32-163_-139 | TCTCCCCAGTCTAGACAGCAGGGCA | 57 |
| c.-32-162_-138 | CTCCCCAGTCTAGACAGCAGGGCAA | 58 |
| c.-32-161_-137 | TCCCCAGTCTAGACAGCAGGGCAAC | 59 |
| c.-32-160_-136 | CCCCAGTCTAGACAGCAGGGCAACA | 60 |
| c.-32-159_-135 | CCCAGTCTAGACAGCAGGGCAACAC | 61 |

TABLE 2-continued 25 bp sequences (5' → 3') serving as possible AON targets in the cryptic acceptor splice site in GAA

| Sequence in target to which AON anneals* | Target sequence (5' → 3'): | SEQ ID NO: |
|---|---|---|
| c.-32-158_-134 | CCAGTCTAGACAGCAGGGCAACACC | 62 |
| c.-32-157_-133 | CAGTCTAGACAGCAGGGCAACACCC | 63 |
| c.-32-156_-132 | AGTCTAGACAGCAGGGCAACACCCA | 64 |
| c.-32-155_-131 | GTCTAGACAGCAGGGCAACACCCAC | 65 |
| c.-32-188_-159 | CTTTTCTCGCCCTTCCTTCTGGCCC TCTCC | 66 |

It should be noted that it may not be necessary to target the full length of SEQ ID NO: 8-65, target fragments having a shorter or longer sequence are also envisioned. In particular shorter fragments such as fragments with 18, 19, 20, 21, 22, 23, or 24 nucleotides of SEQ ID NO: 8-65 are envisioned, such as depicted in below Tables 3 and 4.

The target sequence of the cryptic acceptor splice site in an especially preferred embodiment of aspects of the invention comprises region c.-.32-188_-159 (5' CTTTCTCGCCCTTCCTTCTGGCCCTCTCC-3': SEQ ID NO. 2046).

TABLE 3

21 bp sequences (5' → 3') serving as possible AON targets in the cryptic acceptor splice site in GAA.

| Sequence in target to which AON anneals* | Target sequence (5' → 3'): | SEQ ID NO: |
|---|---|---|
| c.-32-208_-188 | TCTGCACTCCCCTGCTGGAGC | 66 |
| c.-32-207_-187 | CTGCACTCCCCTGCTGGAGCT | 67 |
| c.-32-206_-186 | TGCACTCCCCTGCTGGAGCTT | 68 |
| c.-32-205_-185 | GCACTCCCCTGCTGGAGCTTT | 69 |
| c.-32-204_-184 | CACTCCCCTGCTGGAGCTTTT | 70 |
| c.-32-203_-183 | ACTCCCCTGCTGGAGCTTTTC | 71 |
| c.-32-202_-182 | CTCCCCTGCTGGAGCTTTTCT | 72 |
| c.-32-201_-181 | TCCCCTGCTGGAGCTTTTCTC | 73 |
| c.-32-200_-180 | CCCCTGCTGGAGCTTTTCTCG | 74 |
| c.-32-199_-179 | CCCTGCTGGAGCTTTTCTCGC | 75 |
| c.-32-198_-178 | CCTGCTGGAGCTTTTCTCGCC | 76 |
| c.-32-197_-177 | CTGCTGGAGCTTTTCTCGCCC | 77 |
| c.-32-196_-176 | TGCTGGAGCTTTTCTCGCCCT | 78 |
| c.-32-195_-175 | GCTGGAGCTTTTCTCGCCCTT | 79 |
| c.-32-194_-174 | CTGGAGCTTTTCTCGCCCTTC | 80 |
| c.-32-193_-173 | TGGAGCTTTTCTCGCCCTTCC | 81 |
| c.-32-192_-172 | GGAGCTTTTCTCGCCCTTCCT | 82 |

TABLE 3-continued 21 bp sequences (5' → 3') serving as possible AON targets in the cryptic acceptor splice site in GAA.

| Sequence in target to which AON anneals* | Target sequence (5' → 3'): | SEQ ID NO: |
|---|---|---|
| c.-32-191_-171 | GAGCTTTTCTCGCCCTTCCTT | 83 |
| c.-32-190_-170 | AGCTTTTCTCGCCCTTCCTTC | 84 |
| c.-32-189_-169 | GCTTTTCTCGCCCTTCCTTCT | 85 |
| c.-32-188_-168 | CTTTTCTCGCCCTTCCTTCTG | 86 |
| c.-32-187_-167 | TTTTCTCGCCCTTCCTTCTGG | 87 |
| c.-32-186_-166 | TTTCTCGCCCTTCCTTCTGGC | 88 |
| c.-32-185_-165 | TTCTCGCCCTTCCTTCTGGCC | 89 |
| c.-32-184_-164 | TCTCGCCCTTCCTTCTGGCCC | 90 |
| c.-32-183_-163 | CTCGCCCTTCCTTCTGGCCCT | 91 |
| c.-32-182_-162 | TCGCCCTTCCTTCTGGCCCTC | 92 |
| c.-32-181_-161 | CGCCCTTCCTTCTGGCCCTCT | 93 |
| c.-32-180_-160 | GCCCTTCCTTCTGGCCCTCTC | 94 |
| c.-32-179_-159 | CCCTTCCTTCTGGCCCTCTCC | 95 |
| c.-32-178_-158 | CCTTCCTTCTGGCCCTCTCCC | 96 |
| c.-32-177_-157 | CTTCCTTCTGGCCCTCTCCCC | 97 |
| c.-32-176_-156 | TTCCTTCTGGCCCTCTCCCCA | 98 |
| c.-32-175_-155 | TCCTTCTGGCCCTCTCCCCAG | 99 |
| c.-32-174_-154 | CCTTCTGGCCCTCTCCCCAGT | 100 |
| c.-32-173_-153 | CTTCTGGCCCTCTCCCCAGTC | 101 |
| c.-32-172_-152 | TTCTGGCCCTCTCCCCAGTCT | 102 |
| c.-32-171_-151 | TCTGGCCCTCTCCCCAGTCTA | 103 |
| c.-32-170_-150 | CTGGCCCTCTCCCCAGTCTAG | 104 |
| c.-32-169_-149 | TGGCCCTCTCCCCAGTCTAGA | 105 |
| c.-32-168_-148 | GGCCCTCTCCCCAGTCTAGAC | 106 |
| c.-32-167_-147 | GCCCTCTCCCCAGTCTAGACA | 107 |
| c.-32-166_-146 | CCCTCTCCCCAGTCTAGACAG | 108 |
| c.-32-165_-145 | CCTCTCCCCAGTCTAGACAGC | 109 |
| c.-32-164_-144 | CTCTCCCCAGTCTAGACAGCA | 110 |
| c.-32-163_-143 | TCTCCCCAGTCTAGACAGCAG | 111 |
| c.-32-162_-142 | CTCCCCAGTCTAGACAGCAGG | 112 |
| c.-32-161_-141 | TCCCCAGTCTAGACAGCAGGG | 113 |
| c.-32-160_-140 | CCCCAGTCTAGACAGCAGGGC | 114 |
| c.-32-159_-139 | CCCAGTCTAGACAGCAGGGCA | 115 |
| c.-32-158_-138 | CCAGTCTAGACAGCAGGGCAA | 116 |

TABLE 3-continued 21 bp sequences (5' → 3') serving as possible AON targets in the cryptic acceptor splice site in GAA.

| Sequence in target to which AON anneals* | Target sequence (5' → 3'): | SEQ ID NO: |
|---|---|---|
| c.-32-157_-137 | CAGTCTAGACAGCAGGGCAAC | 117 |
| c.-32-156_-136 | AGTCTAGACAGCAGGGCAACA | 118 |
| c.-32-155_-135 | GTCTAGACAGCAGGGCAACAC | 119 |

TABLE 4

18 bp sequences (5' → 3') serving as possible AON targets in the cryptic acceptor splice site in GAA.

| Sequence in target to which AON anneals* | Target sequence (5' → 3'): | SEQ ID NO: |
|---|---|---|
| c.-32-205_-188 | GCACTCCCCTGCTGGAGC | 120 |
| c.-32-204_-187 | CACTCCCCTGCTGGAGCT | 121 |
| c.-32-203_-186 | ACTCCCCTGCTGGAGCTT | 122 |
| c.-32-202_-185 | CTCCCCTGCTGGAGCTTT | 123 |
| c.-32-201_-184 | TCCCCTGCTGGAGCTTTT | 124 |
| c.-32-200_-183 | CCCCTGCTGGAGCTTTTC | 125 |
| c.-32-199_-182 | CCCTGCTGGAGCTTTTCT | 126 |
| c.-32-198_-181 | CCTGCTGGAGCTTTTCTC | 127 |
| c.-32-197_-180 | CTGCTGGAGCTTTTCTCG | 128 |
| c.-32-196_-179 | TGCTGGAGCTTTTCTCGC | 129 |
| c.-32-195_-178 | GCTGGAGCTTTTCTCGCC | 130 |
| c.-32-194_-177 | CTGGAGCTTTTCTCGCCC | 131 |
| c.-32-193_-176 | TGGAGCTTTTCTCGCCCT | 132 |
| c.-32-192_-175 | GGAGCTTTTCTCGCCCTT | 133 |
| c.-32-191_-174 | GAGCTTTTCTCGCCCTTC | 134 |
| c.-32-190_-173 | AGCTTTTCTCGCCCTTCC | 135 |
| c.-32-189_-172 | GCTTTTCTCGCCCTTCCT | 136 |
| c.-32-188_-171 | CTTTTCTCGCCCTTCCTT | 137 |
| c.-32-187_-170 | TTTTCTCGCCCTTCCTTC | 138 |
| c.-32-186_-169 | TTTCTCGCCCTTCCTTCT | 139 |
| c.-32-185_-168 | TTCTCGCCCTTCCTTCTG | 140 |
| c.-32-184_-167 | TCTCGCCCTTCCTTCTGG | 141 |
| c.-32-183_-166 | CTCGCCCTTCCTTCTGGC | 142 |
| c.-32-182_-165 | TCGCCCTTCCTTCTGGCC | 143 |
| c.-32-181_-164 | CGCCCTTCCTTCTGGCCC | 144 |
| c.-32-180_-163 | GCCCTTCCTTCTGGCCCT | 145 |
| c.-32-179_-162 | CCCTTCCTTCTGGCCCTC | 146 |

TABLE 4-continued 18 bp sequences (5' → 3') serving as possible AON targets in the cryptic acceptor splice site in GAA.

| Sequence in target to which AON anneals* | Target sequence (5' → 3'): | SEQ ID NO: |
|---|---|---|
| c.-32-178_-161 | CCTTCCTTCTGGCCCTCT | 147 |
| c.-32-177_-160 | CTTCCTTCTGGCCCTCTC | 148 |
| c.-32-176_-159 | TTCCTTCTGGCCCTCTCC | 149 |
| c.-32-175_-158 | TCCTTCTGGCCCTCTCCC | 150 |
| c.-32-174_-157 | CCTTCTGGCCCTCTCCCC | 151 |
| c.-32-173_-156 | CTTCTGGCCCTCTCCCCA | 152 |
| c.-32-172_-155 | TTCTGGCCCTCTCCCCAG | 153 |
| c.-32-171_-154 | TCTGGCCCTCTCCCCAGT | 154 |
| c.-32-170_-153 | CTGGCCCTCTCCCCAGTC | 155 |
| c.-32-169_-152 | TGGCCCTCTCCCCAGTCT | 156 |
| c.-32-168_-151 | GGCCCTCTCCCCAGTCTA | 157 |
| c.-32-167_-150 | GCCCTCTCCCCAGTCTAG | 158 |
| c.-32-166_-149 | CCCTCTCCCCAGTCTAGA | 159 |
| c.-32-165_-148 | CCTCTCCCCAGTCTAGAC | 160 |
| c.-32-164_-147 | CTCTCCCCAGTCTAGACA | 161 |
| c.-32-163_-146 | TCTCCCCAGTCTAGACAG | 162 |
| c.-32-162_-145 | CTCCCCAGTCTAGACAGC | 163 |
| c.-32-161_-144 | TCCCCAGTCTAGACAGCA | 164 |
| c.-32-160_-143 | CCCCAGTCTAGACAGCAG | 165 |
| c.-32-159_-142 | CCCAGTCTAGACAGCAGG | 166 |
| c.-32-158_-141 | CCAGTCTAGACAGCAGGG | 167 |
| c.-32-157_-140 | CAGTCTAGACAGCAGGGC | 168 |
| c.-32-156_-139 | AGTCTAGACAGCAGGGCA | 169 |
| c.-32-155_-138 | GTCTAGACAGCAGGGCAA | 170 |

In addition to the above/referred cryptic acceptor splice site corresponding to a region around c.-32-154, the inventors also discovered the cryptic donor splice site at a region around c.-32-52.

In combination, the cryptic donor splice site and cryptic acceptor splice site cause aberrant splicing. This aberrant splicing is the result of the so-called IVS1 mutation. It was fond that, in the case of this mutation a natural pseudo-exon is recognized in the region of the first intron which is spliced at the cryptic splice sites c-32-154 (natural cryptic acceptor splice site), and c.-32-52 (natural cryptic donor splice site). These sites may suitably be blocked by using a combination of at least two AONs of which a first is targeted to the natural cryptic acceptor splice site described above and second is targeted to the natural cryptic donor splice site, described herein.

Hence, a very suitable alternative, or optionally, additional target for AON therapy as described herein includes the natural cryptic donor splice site at c.-32.52, which is included in SEQ ID NO: 171. A most preferred target site is the region c.-32-77_-28.

TABLE 5

Suitable optional target sequences for use in the present invention associated with a cryptic donor splice site in GAA.

| Sequence in target to which AON anneals* | Target sequence (5' → 3'): | SEQ ID NO: |
|---|---|---|
| c.-32-77_-28 | GTCTCAGAGCTGCTTTGAGAGCCCC GTGAGTGCCGCCCCTCCCGCCTCCC | 171 |

In aspects of the invention, the targets to which an antisense oligomeric compound of the invention may anneal or hybridize, may be a donor splice site sequence of the natural pseudo-exon, such as a sequence selected from the group comprising SEQ ID NO: 172-260 as shown in Tables 6-8 and derivatives and fragments thereof having at least 80% sequence identity therewith over the entire length of the molecule.

It should be noted that it may not be necessary to target the full length of SEQ ID NO: 171-260, target fragments having a shorter or longer sequence are also envisioned. In particular shorter fragments such as fragments with 18, 19, 20, 21, 22, 23, or 24 nucleotides of SEQ ID NO: 171-260 are envisioned, such as depicted in below Tables 6-8.

TABLE 6

25 bp sequences (5' → 3') serving as possible AON targets in the cryptic donor splice site in GAA.

| Sequence in target to which AON anneals* | Target sequence (5' → 3'): | SEQ ID NO: |
|---|---|---|
| c.-32-77_-53 | GTCTCAGAGCTGCTTTGAGAGCCCC | 172 |
| c.-32-76_-52 | TCTCAGAGCTGCTTTGAGAGCCCCG | 173 |
| c.-32-75_-51 | CTCAGAGCTGCTTTGAGAGCCCCGT | 174 |
| c.-32-74_-50 | TCAGAGCTGCTTTGAGAGCCCCGTG | 175 |
| c.-32-73_-49 | CAGAGCTGCTTTGAGAGCCCCGTGA | 176 |
| c.-32-72_-48 | AGAGCTGCTTTGAGAGCCCCGTGAG | 177 |
| c.-32-71_-47 | GAGCTGCTTTGAGAGCCCCGTGAGT | 178 |
| c.-32-70_-46 | AGCTGCTTTGAGAGCCCCGTGAGTG | 179 |
| c.-32-69_-45 | GCTGCTTTGAGAGCCCCGTGAGTGC | 180 |
| c.-32-68_-44 | CTGCTTTGAGAGCCCCGTGAGTGCC | 181 |
| c.-32-67_-43 | TGCTTTGAGAGCCCCGTGAGTGCCG | 182 |
| c.-32-66_-42 | GCTTTGAGAGCCCCGTGAGTGCCGC | 183 |
| c.-32-65_-41 | CTTTGAGAGCCCCGTGAGTGCCGCC | 184 |
| c.-32-64_-40 | TTTGAGAGCCCCGTGAGTGCCGCCC | 185 |
| c.-32-63_-39 | TTGAGAGCCCCGTGAGTGCCGCCCC | 186 |
| c.-32-62_-38 | TGAGAGCCCCGTGAGTGCCGCCCCT | 187 |
| c.-32-61_-37 | GAGAGCCCCGTGAGTGCCGCCCCTC | 188 |

TABLE 6-continued 25 bp sequences (5' → 3') serving as possible AON targets in the cryptic donor splice site in GAA.

| Sequence in target to which AON anneals* | Target sequence (5' → 3'): | SEQ ID NO: |
|---|---|---|
| c.-32-60_-36 | AGAGCCCCGTGAGTGCCGCCCCTCC | 189 |
| c.-32-59_-35 | GAGCCCCGTGAGTGCCGCCCCTCCC | 190 |
| c.-32-58_-34 | AGCCCCGTGAGTGCCGCCCCTCCCG | 191 |
| c.-32-57_-33 | GCCCCGTGAGTGCCGCCCCTCCCGC | 192 |
| c.-32-56_-32 | CCCCGTGAGTGCCGCCCCTCCCGCC | 193 |
| c.-32-55_-31 | CCCGTGAGTGCCGCCCCTCCCGCCT | 194 |
| c.-32-54_-30 | CCGTGAGTGCCGCCCCTCCCGCCTC | 195 |
| c.-32-53_-29 | CGTGAGTGCCGCCCCTCCCGCCTCC | 196 |
| c.-32-52_-28 | GTGAGTGCCGCCCCTCCCGCCTCCC | 197 |

TABLE 7

21 bp sequences (5' → 3') serving as possible AON targets in the cryptic donor splice site in GAA.

| Sequence in target to which AON anneals* | Target sequence (5' → 3'): | SEQ ID NO: |
|---|---|---|
| c.-32-77_-57 | GTCTCAGAGCTGCTTTGAGAG | 198 |
| c.-32-76_-56 | TCTCAGAGCTGCTTTGAGAGC | 199 |
| c.-32-75_-55 | CTCAGAGCTGCTTTGAGAGCC | 200 |
| c.-32-74_-54 | TCAGAGCTGCTTTGAGAGCCC | 201 |
| c.-32-73_-53 | CAGAGCTGCTTTGAGAGCCCC | 202 |
| c.-32-72_-52 | AGAGCTGCTTTGAGAGCCCCG | 203 |
| c.-32-71_-51 | GAGCTGCTTTGAGAGCCCCGT | 204 |
| c.-32-70_-50 | AGCTGCTTTGAGAGCCCCGTG | 205 |
| c.-32-69_-49 | GCTGCTTTGAGAGCCCCGTGA | 206 |
| c.-32-68_-48 | CTGCTTTGAGAGCCCCGTGAG | 207 |
| c.-32-67_-47 | TGCTTTGAGAGCCCCGTGAGT | 208 |
| c.-32-66_-46 | GCTTTGAGAGCCCCGTGAGTG | 209 |
| c.-32-65_-45 | CTTTGAGAGCCCCGTGAGTGC | 210 |
| c.-32-64_-44 | TTTGAGAGCCCCGTGAGTGCC | 211 |
| c.-32-63_-43 | TTGAGAGCCCCGTGAGTGCCG | 212 |
| c.-32-62_-42 | TGAGAGCCCCGTGAGTGCCGC | 213 |
| c.-32-61_-41 | GAGAGCCCCGTGAGTGCCGCC | 214 |
| c.-32-60_-40 | AGAGCCCCGTGAGTGCCGCCC | 215 |
| c.-32-59_-39 | GAGCCCCGTGAGTGCCGCCCC | 216 |
| c.-32-58_-38 | AGCCCCGTGAGTGCCGCCCCT | 217 |

TABLE 7-continued 21 bp sequences (5' → 3') serving as possible AON targets in the cryptic donor splice site in GAA.

| Sequence in target to which AON anneals* | Target sequence (5' → 3'): | SEQ ID NO: |
|---|---|---|
| c.-32-57_-37 | GCCCCGTGAGTGCCGCCCCTC | 218 |
| c.-32-56_-36 | CCCCGTGAGTGCCGCCCCTCC | 219 |
| c.-32-55_-35 | CCCGTGAGTGCCGCCCCTCCC | 220 |
| c.-32-54_-34 | CCGTGAGTGCCGCCCCTCCCG | 221 |
| c.-32-53_-33 | CGTGAGTGCCGCCCCTCCCGC | 222 |
| c.-32-52_-32 | GTGAGTGCCGCCCCTCCCGCC | 223 |
| c.-32-51_-31 | TGAGTGCCGCCCCTCCCGCCT | 224 |
| c.-32-50_-30 | GAGTGCCGCCCCTCCCGCCTC | 225 |
| c.-32-49_-29 | AGTGCCGCCCCTCCCGCCTCC | 226 |
| c.-32-48_-28 | GTGCCGCCCCTCCCGCCTCCC | 227 |

TABLE 8

18 bp sequences (5' → 3') serving as possible AON targets in the cryptic donor splice site in GAA.

| Sequence in target to which AON anneals* | Target sequence (5' → 3'): | SEQ ID NO: |
|---|---|---|
| c.-32-77_-60 | GTCTCAGAGCTGCTTTGA | 228 |
| c.-32-76_-59 | TCTCAGAGCTGCTTTGAG | 229 |
| c.-32-75_-58 | CTCAGAGCTGCTTTGAGA | 230 |
| c.-32-74_-57 | TCAGAGCTGCTTTGAGAG | 231 |
| c.-32-73_-56 | CAGAGCTGCTTTGAGAGC | 232 |
| c.-32-72_-55 | AGAGCTGCTTTGAGAGCC | 233 |
| c.-32-71_-54 | GAGCTGCTTTGAGAGCCC | 234 |
| c.-32-70_-53 | AGCTGCTTTGAGAGCCCC | 235 |
| c.-32-69_-52 | GCTGCTTTGAGAGCCCCG | 236 |
| c.-32-68_-51 | CTGCTTTGAGAGCCCCGT | 237 |
| c.-32-67_-50 | TGCTTTGAGAGCCCCGTG | 238 |
| c.-32-66_-49 | GCTTTGAGAGCCCCGTGA | 239 |
| c.-32-65_-48 | CTTTGAGAGCCCCGTGAG | 240 |
| c.-32-64_-47 | TTTGAGAGCCCCGTGAGT | 241 |
| c.-32-63_-46 | TTGAGAGCCCCGTGAGTG | 242 |
| c.-32-62_-45 | TGAGAGCCCCGTGAGTGC | 243 |
| c.-32-61_-44 | GAGAGCCCCGTGAGTGCC | 244 |
| c.-32-60_-43 | AGAGCCCCGTGAGTGCCG | 245 |
| c.-32-59_-42 | GAGCCCCGTGAGTGCCGC | 246 |
| c.-32-58_-41 | AGCCCCGTGAGTGCCGCC | 247 |

TABLE 8-continued 18 bp sequences (5' → 3') serving as possible AON targets in the cryptic donor splice site in GAA.

| Sequence in target to which AON anneals* | Target sequence (5' → 3'): | SEQ ID NO: |
|---|---|---|
| c.-32-57_-40 | GCCCCGTGAGTGCCGCCC | 248 |
| c.-32-56_-39 | CCCCGTGAGTGCCGCCCC | 249 |
| c.-32-55_-38 | CCCGTGAGTGCCGCCCCT | 250 |
| c.-32-54_-37 | CCGTGAGTGCCGCCCCTC | 251 |
| c.-32-53_-36 | CGTGAGTGCCGCCCCTCC | 252 |
| c.-32-52_-35 | GTGAGTGCCGCCCCTCCC | 253 |
| c.-32-51_-34 | TGAGTGCCGCCCCTCCCG | 254 |
| c.-32-50_-33 | GAGTGCCGCCCCTCCCGC | 255 |
| c.-32-49_-32 | AGTGCCGCCCCTCCCGCC | 256 |
| c.-32-48_-31 | GTGCCGCCCCTCCCGCCT | 257 |
| c.-32-47_-30 | TGCCGCCCCTCCCGCCTC | 258 |
| c.-32-46_-29 | GCCGCCCCTCCCGCCTCC | 259 |
| c.-32-45_-28 | CCGCCCCTCCCGCCTCCC | 260 |

In a further alternative, or additional embodiment of aspects of the invention, the sequences in the GAA gene targeted by the antisense oligomeric compounds of the invention are sites that modulate splicing by promotion of exon 6 inclusion, including SEQ ID NO:261, or parts thereof. Therefore, optionally in the invention and/or embodiments thereof, the target sequence provides exclusion of intron 6. It was found that SEQ ID NO: 261 provides the target sequence for exclusion of intron 6. It should be noted that also naturally occurring single nucleotide polymorphisms are included.

The genomic sequences of Table 9 are target sequences for exclusion of intron 6 of GAA.

TABLE 9

Target sequences that modulate splicing by promotion of exon 6 inclusion useful in the present invention

| Sequence in target to which AON anneals* | Target sequence (5' → 3'): | SEQ ID NO |
|---|---|---|
| c.956-25_1194 + 25 | AACCCCAGAGCTGCTTCCCTTCCAGAT GTGGTCCTGCAGCCGAGCCCTGCCCTT AGCTGGAGGTCGACAGGTGGGATCCTG GATGTCTACATCTTCCTGGGCCCAGAG CCCAAGAGCGTGGTGCAGCAGTACCTG GACGTTGTGGGTAGGGCCTGCTCCCTG GCCGCGGCCCCCGCCCCAAGGCTCCCT CCTCCCTCCCTCATGAAGTCGGCGTTG GCCTGCAGGATACCCGTTCATGCCGCC ATACTGGGGCCTGGGCTTCCACCTGTG CCGCTGGGGCTACTCCTCCACCGCTAT CACCCGCCAGGTGGTGGAGAACATGAC CAGGGCCCACTTCCCCCTGGTGAGTTG GGGTGGTGGCAGGGGAG | 261 |

TABLE 9-continued

Target sequences that modulate splicing by promotion of exon 6 inclusion useful in the present invention

| Sequence in target to which AON anneals* | Target sequence (5' → 3'): | SEQ ID NO |
|---|---|---|
| c.956-25_1004 | AACCCCAGAGCTGCTTCCCTTCCAGAT GTGGTCCTGCAGCCGAGCCCTGCCCTT AGCTGGAGGTCGACAGGTGG | 262 |
| c.1005_1075 + 3 | GATCCTGGATGTCTACATCTTCCTGGG CCCAGAGCCCAAGAGCGTGGTGCAGCA GTACCTGGACGTTGTGGGTA | 263 |
| c.1075 + 4_1076 - 2 | GGGCCTGCTCCCTGGCCGCGGCCCCCG CCCCAAGGCTCCCTCCTCCCTCCCTCA TGAAGTCGGCGTTGGCCTGC | 264 |
| c.1076-2_1147 | AGGATACCCGTTCATGCCGCCATACTG GGGCCTGGGCTTCCACCTGTGCCGCTG GGGCTACTCCTCCACCGCTA | 265 |
| c.1148_1194 + 25 | TCACCCGCCAGGTGGTGGAGAACATGA CCAGGGCCCACTTCCCCCTGGTGAGTT GGGGTGGTGGCAGGGGAG | 266 |

AONs of the Present Invention

In one aspect of this invention AONs may be used that target a sequence of the GAA gene product that is (part of) a cryptic splice site or pseudo exon, in particular the splice acceptor, referred to herein as SEQ ID NO:1. Oligonucleotide sequences used as antisense oligos in aspects of this invention may be sequences targeting (parts of) SEQ ID NO: 1, and these are able to enhance inclusion of GAA exon 2 in the context of the IVS1 mutation. Also AON sequences targeting SEQ ID NOs: 2-7 (subsequence targets of SEG ID NO:1), were found to be able to enhance inclusion of GAA exon 2 in the context, of the IVS1 mutation. It is to be noted that "targeting" means that at least part of the sequence SEQ ID NO: 1 is targeted, e.g. by a sequence that, hybridizes with at least a part or by the sequence SEQ ID NO: 1, or that binds to at, least a part of SEQ ID NO: 1. Sequences that target may be shorter or longer than the target sequence.

AON sequences targeting the target sequences of the invention may be between 18 and 40 nucleotides in length, preferably 18-30, more preferably 20-25 nucleotides in length.

Exemplary antisense oligomeric compounds targeting SEQ ID NO: 1, the sequence of the GAA gene product that is (part, of) a cryptic splice acceptor site of the pseudo exon, are provided in Table 10.

TABLE 10

Exemplary AONs targeting the cryptic acceptor splice site, e.g. targeting SEQ ID NO: 1.

| Sequence in GAA to which AON anneals | AON sequence 5' → 3' | SEQ ID NO |
|---|---|---|
| c.-32-180_-156 | TGGGGAGAGGGCCAGAAGGAAGGGC | 267 |
| c.-32-181_-157 | GGGGAGAGGGCCAGAAGGAAGGGCG | 268 |
| c.-32-182_-158 | GGGAGAGGGCCAGAAGGAAGGGCGA | 269 |
| c.-32-183_-159 | GGAGAGGGCCAGAAGGAAGGGCGAG | 270 |
| c.-32-184_-160 | GAGAGGGCCAGAAGGAAGGGCGAGA | 271 |
| c.-32-185_-161 | AGAGGGCCAGAAGGAAGGGCGAGAA | 272 |
| c.-32-186_-162 | GAGGGCCAGAAGGAAGGGCGAGAAA | 273 |
| c.-32-187_-163 | AGGGCCAGAAGGAAGGGCGAGAAAA | 274 |
| c.-32-188_-164 | GGGCCAGAAGGAAGGGCGAGAAAAG | 275 |
| c.-32-188_-165 | GGCCAGAAGGAAGGGCGAGAAAAGC | 276 |
| c.-32-189_-166 | GCCAGAAGGAAGGGCGAGAAAAGCT | 277 |
| c.-32-190_-167 | CCAGAAGGAAGGGCGAGAAAAGCTC | 278 |
| c.-32-191_-168 | CAGAAGGAAGGGCGAGAAAAGCTCC | 279 |
| c.-32-192_-169 | AGAAGGAAGGGCGAGAAAAGCTCCA | 280 |
| c.-32-193_-170 | GAAGGAAGGGCGAGAAAAGCTCCAG | 281 |
| c.-32-194_-171 | AAGGAAGGGCGAGAAAAGCTCCAGC | 282 |
| c.-32-195_-172 | AGGAAGGGCGAGAAAAGCTCCAGCA | 283 |
| c.-32-196_-173 | GGAAGGGCGAGAAAAGCTCCAGCAG | 284 |
| c.-32-198_-174 | GAAGGGCGAGAAAAGCTCCAGCAGG | 285 |
| c.-32-199_-175 | AAGGGCGAGAAAAGCTCCAGCAGGG | 286 |
| c.-32-200_-176 | AGGGCGAGAAAAGCTCCAGCAGGGG | 287 |
| c.-32-201_-177 | GGGCGAGAAAAGCTCCAGCAGGGGA | 288 |
| c.-32-201_-178 | GGCGAGAAAAGCTCCAGCAGGGGAG | 289 |
| c.-32-202_-179 | GCGAGAAAAGCTCCAGCAGGGGAGT | 290 |
| c.-32-203_-180 | CGAGAAAAGCTCCAGCAGGGGAGTG | 291 |
| c.-32-204_-181 | GAGAAAAGCTCCAGCAGGGGAGTGC | 292 |
| c.-32-205_-182 | AGAAAAGCTCCAGCAGGGGAGTGCA | 293 |
| c.-32-206_-183 | GAAAAGCTCCAGCAGGGGAGTGCAG | 294 |
| c.-32-207_-184 | AAAAGCTCCAGCAGGGGAGTGCAGA | 295 |
| c.-32-208_-185 | AAAGCTCCAGCAGGGGAGTGCAGAG | 296 |
| c.-32-209_-186 | AAGCTCCAGCAGGGGAGTGCAGAGC | 297 |
| c.-32-187_-167 | CCAGAAGGAAGGGCGAGAAAA | 298 |

Nucleotide sequences of SEQ ID NO:267-298 are exemplary AON sequences of oligomers that are able to enhance GAA exon 2 inclusion in the context of the IVS1 mutation. These oligomers are 18-25 nucleotides in length. Two antisense oligomeric compounds, a first one of 21 nucleotides (SEQ ID NO: 298) and a second one of 25 nucleotides (SEQ ID NO: 277), were tested and both were found to enhance exon 2 inclusion in the context of the IVS1 mutation. This was accompanied by enhanced GAA enzyme activity of at least 2 fold. It is known that patients with the IVS1 variant have ~15% leaky wild type splicing. The enhancement of 2 fold results in enzyme activities of ~30%, which are known to be above the disease threshold of 20% and thus are anticipated to restore at least a part, or even fully the lysosomal glycogen degradation.

In the above examples the sequences are 25 nucleotides long however longer variants or shorter fragment are also envisioned. Exemplary is SEQ ID NO: 298 which is only 21 nucleotides long and comprises the same nucleotides as SEQ ID NO: 277 but is shorter. Optionally of the invention and/or embodiments thereof of the present invention and/or embodiments thereof the antisense oligomeric compounds are selected from the group of SEQ ID NO: 267-298 and fragments and variants thereof having at least 80% sequence identity. Optionally of the invention and/or embodiments thereof of the present invention and/or embodiments thereof the antisense oligomeric compounds are selected from the group of SEQ ID NO: 267-298 and fragments and variants thereof having at least 80%, 83%, 85%, 87%, 90%, 92%, 93%, 94%, 95%, 96%, 97%, 98%, 99%, 99.2%, 99.3%, 99.4%, 99.5%, 99.6%, 99.7% sequence identity to SEQ ID NO: 267-298.

The present invention is also directed to sequences that are at least 80% identical to SEQ ID NO: 267-298, preferably at least 85% identical to SEQ ID NO: 267-298, more preferably at least 88% identical to SEQ ID NO: 267-298, more preferably at least 90% identical to SEQ ID NO: 267-298, even more preferably at least 91% identical to SEQ ID NO: 267-298, still more preferably at least 92% identical to SEQ ID NO: 267-298, still more preferably at least 93% identical to SEQ ID NO: 267-298, more preferably at least 94% identical to SEQ ID NO: 267-298, more preferably at least 95% identical to SEQ ID NO: 267-298, more preferably at least 96% identical to SEQ ID NO: 267-298, more preferably at least 97% identical to SEQ ID NO: 267-298, more preferably at least 98% identical to SEQ ID NO: 267-298, more preferably at least 99% identical to SEQ ID NO: 267-298.

Preferred antisense sequences are SEQ ID NO: 277, and SEQ ID NO:298 or sequences that are at least 80% identical thereto, preferably at least 85% identical, more preferably at least 88% identical, more preferably at least 90% identical, more preferably at least 91% identical, more preferably at least 92% identical, more preferably at least 93% identical, more preferably at least 94% identical, more preferably at least 95% identical, more preferably at least 96% identical, more preferably at least 97% identical, more preferably at least 98% identical, more preferably at least 99% identical to SEQ ID NO: 277, and/or 298.

Optionally in the embodiments of aspects of the invention the antisense oligomeric compounds are selected from the group of fragments SEQ ID NO: 267-298, wherein the fragment is 16, 17, 18, 19, 20, 21, 22, 23, or 24 nucleotides long. Optionally of the invention and/or embodiments thereof of the present invention and/or embodiments thereof the antisense oligomeric compounds are selected from the group of fragments SEQ ID NO: 267-298, wherein the fragment is 17, 18, 19, 20, 21, or 22 nucleotides long. Optionally of the invention and/or embodiments thereof of the present invention and/or embodiments thereof the antisense oligomeric compounds are selected from the group of fragments SEQ ID NO: 267-298, wherein the fragment is 19, 20, or 21 nucleotides long.

Preferred embodiments of AONs targeting the cryptic acceptor splice site are SEQ ID Nos: 277 and 298.

Alternative preferred antisense oligomeric compounds may be selected from the group of SEQ ID NOs. as indicated in Table 11.

TABLE 11

Further exemplary AONs targeting the cryptic acceptor splice site, e.g. targeting SEQ ID NO: 1.

| Sequence in GAA to which AON anneals | AON sequence 5' → 3' | SEQ ID NO |
|---|---|---|
| c.-32-219_-200 | GAGTGCAGAGCACTTGCACA | 299 |
| c.-32-199_-180 | GCAGAAAAGCTCCAGCAGGG | 300 |
| c.-32-179_-160 | GAGAGGGCCAGAAGGAAGGG | 301 |
| c.-32-159_-140 | GCCCTGCTGTCTAGACTGGG | 302 |
| c.-32-225_-206 | AGAGCACTTGCACAGTCTGC | 303 |
| c.-32-223_-204 | GCAGAGCACTTGCACAGCT | 304 |
| c.-32-221_-202 | GTGCAGAGCACTTGCACAGT | 305 |
| c.-32-217_-198 | GGGAGTGCAGAGCACTTGCA | 306 |
| c.-32-215_-196 | AGGGGAGTGCAGAGCACTTG | 307 |
| c.-32-213_-194 | GCAGGGGAGTGCAGAGCACT | 308 |
| c.-32-185_-166 | GCCAGAAGGAAGGGCGAGAA | 309 |
| c.-32-183_-164 | GGGCCAGAAGGAAGGGCGAG | 310 |
| c.-32-181_-162 | GAGGGCCAGAAGGAAGGGCG | 311 |
| c.-32-177_-158 | GGGAGAGGGCCAGAAGGAAG | 312 |
| c.-32-175_-156 | TGGGGAGAGGGCCAGAAGGA | 313 |
| c.-32-173_-154 | ACTGGGGAGAGGGCCAGAAG | 314 |
| c.-32-212_-188 | GCTCCAGCAGGGGAGTGCAGAGCAC | 315 |
| c.-32-211_-187 | AGCTCCAGCAGGGGAGTGCAGAGCA | 316 |
| c.-32-179_-155 | CTGGGGAGAGGGCCAGAAGGAAGGG | 317 |
| c.-32-178_-154 | ACTGGGGAGAGGGCCAGAAGGAAGG | 318 |
| c.-32-177_-153 | GACTGGGGAGAGGGCCAGAAGGAAG | 319 |
| c.-32-176_-152 | AGACTGGGGAGAGGGCCAGAAGGAA | 320 |
| c.-32-175_-151 | TAGACTGGGGAGAGGGCCAGAAGGA | 321 |
| c.-32-174_-150 | CTAGACTGGGGAGAGGGCCAGAAGG | 322 |
| c.-32-173_-149 | TCTAGACTGGGGAGAGGGCCAGAAG | 323 |
| c.-32-172_-148 | GTCTAGACTGGGGAGAGGGCCAGAA | 324 |
| c.-32-171_-147 | TGTCTAGACTGGGGAGAGGGCCAGA | 325 |
| c.-32-170_-146 | CTGTCTAGACTGGGGAGAGGGCCAG | 326 |
| c.-32-169_-145 | GCTGTCTAGACTGGGGAGAGGGCCA | 327 |
| c.-32-168_-144 | TGCTGTCTAGACTGGGGAGAGGGCC | 328 |
| c.-32-167_-143 | CTGCTGTCTAGACTGGGGAGAGGGC | 329 |
| c.-32-166_-142 | CCTGCTGTCTAGACTGGGGAGAGGG | 330 |
| c.-32-165_-141 | CCCTGCTGTCTAGACTGGGGAGAGG | 331 |
| c.-32-164_-140 | GCCCTGCTGTCTAGACTGGGGAGAG | 332 |
| c.-32-163_-139 | TGCCCTGCTGTCTAGACTGGGGAGA | 333 |
| c.-32-162_-138 | TTGCCCTGCTGTCTAGACTGGGGAG | 334 |

TABLE 11-continued

Further exemplary AONs targeting the cryptic acceptor splice site, e.g. targeting SEQ ID NO: 1.

| Sequence in GAA to which AON anneals | AON sequence 5' → 3' | SEQ ID NO |
|---|---|---|
| c.-32-161_-137 | GTTGCCCTGCTGTCTAGACTGGGGA | 335 |
| c.-32-160_-136 | TGTTGCCCTGCTGTCTAGACTGGGG | 336 |
| c.-32-159_-135 | GTGTTGCCCTGCTGTCTAGACTGGG | 337 |
| c.-32-158_-134 | GGTGTTGCCCTGCTGTCTAGACTGG | 338 |
| c.-32-157_-133 | GGGTGTTGCCCTGCTGTCTAGACTG | 339 |
| c.-32-156_-132 | TGGGTGTTGCCCTGCTGTCTAGACT | 340 |
| c.-32-155_-131 | GTGGGTGTTGCCCTGCTGTCTAGAC | 341 |
| c.-32-208_-188 | GCTCCAGCAGGGGAGTGCAGA | 342 |
| c.-32-207_-187 | AGCTCCAGCAGGGGAGTGCAG | 343 |
| c.-32-206_-186 | AAGCTCCAGCAGGGGAGTGCA | 344 |
| c.-32-205_-185 | AAAGCTCCAGCAGGGGAGTGC | 345 |
| c.-32-204_-184 | AAAAGCTCCAGCAGGGGAGTG | 346 |
| c.-32-203_-183 | GAAAAGCTCCAGCAGGGGAGT | 347 |
| c.-32-202_-182 | AGAAAAGCTCCAGCAGGGGAG | 348 |
| c.-32-201_-181 | GAGAAAAGCTCCAGCAGGGGA | 349 |
| c.-32-200_-180 | CGAGAAAAGCTCCAGCAGGGG | 350 |
| c.-32-199_-179 | GCGAGAAAAGCTCCAGCAGGG | 351 |
| c.-32-198_-178 | GGCGAGAAAAGCTCCAGCAGG | 352 |
| c.-32-197_-177 | GGGCGAGAAAAGCTCCAGCAG | 353 |
| c.-32-196_-176 | AGGGCGAGAAAAGCTCCAGCA | 354 |
| c.-32-195_-175 | AAGGGCGAGAAAAGCTCCAGC | 355 |
| c.-32-194_-174 | GAAGGGCGAGAAAAGCTCCAG | 356 |
| c.-32-193_-173 | GGAAGGGCGAGAAAAGCTCCA | 357 |
| c.-32-192_-172 | AGGAAGGGCGAGAAAAGCTCC | 358 |
| c.-32-191_-171 | AAGGAAGGGCGAGAAAAGCTC | 359 |
| c.-32-190_-170 | GAAGGAAGGGCGAGAAAAGCT | 360 |
| c.-32-189_-169 | AGAAGGAAGGGCGAGAAAAGC | 361 |
| c.-32-188_-168 | CAGAAGGAAGGGCGAGAAAAG | 362 |
| c.-32-186_-166 | GCCAGAAGGAAGGGCGAGAAA | 363 |
| c.-32-185_-165 | GGCCAGAAGGAAGGGCGAGAA | 364 |
| c.-32-184_-164 | GGGCCAGAAGGAAGGGCGAGA | 365 |
| c.-32-183_-163 | AGGGCCAGAAGGAAGGGCGAG | 366 |
| c.-32-182_-162 | GAGGGCCAGAAGGAAGGGCGA | 367 |
| c.-32-181_-161 | AGAGGGCCAGAAGGAAGGGCG | 368 |
| c.-32-180_-160 | GAGAGGGCCAGAAGGAAGGGC | 369 |
| c.-32-179_-159 | GGAGAGGGCCAGAAGGAAGGG | 370 |
| c.-32-178_-158 | GGGAGAGGGCCAGAAGGAAGG | 371 |
| c.-32-177_-157 | GGGGAGAGGGCCAGAAGGAAG | 372 |
| c.-32-176_-156 | TGGGGAGAGGGCCAGAAGGAA | 373 |
| c.-32-175_-155 | CTGGGGAGAGGGCCAGAAGGA | 374 |
| c.-32-174_-154 | ACTGGGGAGAGGGCCAGAAGG | 375 |
| c.-32-173_-153 | GACTGGGGAGAGGGCCAGAAG | 376 |
| c.-32-172_-152 | AGACTGGGGAGAGGGCCAGAA | 377 |
| c.-32-171_-151 | TAGACTGGGGAGAGGGCCAGA | 378 |
| c.-32-170_-150 | CTAGACTGGGGAGAGGGCCAG | 379 |
| c.-32-169_-149 | TCTAGACTGGGGAGAGGGCCA | 380 |
| c.-32-168_-148 | GTCTAGACTGGGGAGAGGGCC | 381 |
| c.-32-167_-147 | TGTCTAGACTGGGGAGAGGGC | 382 |
| c.-32-166_-146 | CTGTCTAGACTGGGGAGAGGG | 383 |
| c.-32-165_-145 | GCTGTCTAGACTGGGGAGAGG | 384 |
| c.-32-164_-144 | TGCTGTCTAGACTGGGGAGAG | 385 |
| c.-32-163_-143 | CTGCTGTCTAGACTGGGGAGA | 386 |
| c.-32-162_-142 | CCTGCTGTCTAGACTGGGGAG | 387 |
| c.-32-161_-141 | CCCTGCTGTCTAGACTGGGGA | 388 |
| c.-32-160_-140 | GCCCTGCTGTCTAGACTGGGG | 389 |
| c.-32-159_-139 | TGCCCTGCTGTCTAGACTGGG | 390 |
| c.-32-158_-138 | TTGCCCTGCTGTCTAGACTGG | 391 |
| c.-32-157_-137 | GTTGCCCTGCTGTCTAGACTG | 392 |
| c.-32-156_-136 | TGTTGCCCTGCTGTCTAGACT | 393 |
| c.-32-155_-135 | GTGTTGCCCTGCTGTCTAGAC | 394 |
| c.-32-205_-188 | GCTCCAGCAGGGGAGTGC | 395 |
| c.-32-204_-187 | AGCTCCAGCAGGGGAGTG | 396 |
| c.-32-203_-186 | AAGCTCCAGCAGGGGAGT | 397 |
| c.-32-202_-185 | AAAGCTCCAGCAGGGGAG | 398 |
| c.-32-201_-184 | AAAAGCTCCAGCAGGGGA | 399 |
| c.-32-200_-183 | GAAAAGCTCCAGCAGGGG | 400 |
| c.-32-199_-182 | AGAAAAGCTCCAGCAGGG | 401 |
| c.-32-198_-181 | GAGAAAAGCTCCAGCAGG | 402 |
| c.-32-197_-180 | CGAGAAAAGCTCCAGCAG | 403 |
| c.-32-196_-179 | GCGAGAAAAGCTCCAGCA | 404 |
| c.-32-195_-178 | GGCGAGAAAAGCTCCAGC | 405 |
| c.-32-194_-177 | GGGCGAGAAAAGCTCCAG | 406 |

TABLE 11-continued

Further exemplary AONs targeting the cryptic acceptor splice site, e.g. targeting SEQ ID NO: 1.

| Sequence in GAA to which AON anneals | AON sequence 5' → 3' | SEQ ID NO |
|---|---|---|
| c.-32-193_-176 | AGGGCGAGAAAAGCTCCA | 407 |
| c.-32-192_-175 | AAGGGCGAGAAAAGCTCC | 408 |
| c.-32-191_-174 | GAAGGGCGAGAAAAGCTC | 409 |
| c.-32-190_-173 | GGAAGGGCGAGAAAAGCT | 410 |
| c.-32-189_-172 | AGGAAGGGCGAGAAAAGC | 411 |
| c.-32-188_-171 | AAGGAAGGGCGAGAAAAG | 412 |
| c.-32-187_-170 | GAAGGAAGGGCGAGAAAA | 413 |
| c.-32-186_-169 | AGAAGGAAGGGCGAGAAA | 414 |
| c.-32-185_-168 | CAGAAGGAAGGGCGAGAA | 415 |
| c.-32-184_-167 | CCAGAAGGAAGGGCGAGA | 416 |
| c.-32-183_-166 | GCCAGAAGGAAGGGCGAG | 417 |
| c.-32-182_-165 | GGCCAGAAGGAAGGGCGA | 418 |
| c.-32-181_-164 | GGGCCAGAAGGAAGGGCG | 419 |
| c.-32-180_-163 | AGGGCCAGAAGGAAGGGC | 420 |
| c.-32-179_-162 | GAGGGCCAGAAGGAAGGG | 421 |
| c.-32-178_-161 | AGAGGGCCAGAAGGAAGG | 422 |
| c.-32-177_-160 | GAGAGGGCCAGAAGGAAG | 423 |
| c.-32-176_-159 | GGAGAGGGCCAGAAGGAA | 424 |
| c.-32-175_-158 | GGGAGAGGGCCAGAAGGA | 425 |
| c.-32-174_-157 | GGGGAGAGGGCCAGAAGG | 426 |
| c.-32-173_-156 | TGGGGAGAGGGCCAGAAG | 427 |
| c.-32-172_-155 | CTGGGGAGAGGGCCAGAA | 428 |
| c.-32-171_-154 | ACTGGGGAGAGGGCCAGA | 429 |
| c.-32-170_-153 | GACTGGGGAGAGGGCCAG | 430 |
| c.-32-169_-152 | AGACTGGGGAGAGGGCCA | 431 |
| c.-32-168_-151 | TAGACTGGGGAGAGGGCC | 432 |
| c.-32-167_-150 | CTAGACTGGGGAGAGGGC | 433 |
| c.-32-166_- 149 | TCTAGACTGGGGAGAGGG | 434 |
| c.-32-165_-148 | GTCTAGACTGGGGAGAGG | 435 |
| c.-32-164_-147 | TGTCTAGACTGGGGAGAG | 436 |
| c.-32-163_-146 | CTGTCTAGACTGGGGAGA | 437 |
| c.-32-162_-145 | GCTGTCTAGACTGGGGAG | 438 |
| c.-32-161_-144 | TGCTGTCTAGACTGGGGA | 439 |
| c.-32-160_-143 | CTGCTGTCTAGACTGGGG | 440 |
| c.-32-159_-142 | CCTGCTGTCTAGACTGGG | 441 |
| c.-32-158_-141 | CCCTGCTGTCTAGACTGG | 442 |

TABLE 11-continued

Further exemplary AONs targeting the cryptic acceptor splice site, e.g. targeting SEQ ID NO: 1.

| Sequence in GAA to which AON anneals | AON sequence 5' → 3' | SEQ ID NO |
|---|---|---|
| c.-32-157_-140 | GCCCTGCTGTCTAGACTG | 443 |
| c.-32-156_-139 | TGCCCTGCTGTCTAGACT | 444 |
| c.-32-155_-138 | TTGCCCTGCTGTCTAGAC | 445 |

In another or alternative aspect of this invention AONs may be used that target a sequence of the GAA gene product that is (part of) a cryptic splice site or pseudo exon, in particular the splice donor, referred to herein as SEQ ID NO: 171. Oligonucleotide sequences used as antisense oligos in aspects of this invention may be sequences targeting SEQ ID NO: 171, and these are able to enhance inclusion of GAA exon 2 in the context of the IVS1 mutation. Sequences targeting SEQ ID NO: 171 were found to be able to enhance inclusion of GAA exon 2 in the context of the IVS1 mutation. It, is to be noted that “targeting” means that at, least part of the sequence SEQ ID NO: 171 is targeted, e.g. by a sequence that hybridizes with at least a part or by the sequence SEQ ID NO: 171, or that binds to at least a part, of SEQ ID NO): 171. Sequences that target may be shorter or longer than the target sequence.

TABLE 12

AONs targeting the cryptic donor splice site, e.g. targeting SEQ ID NO: 171.

| Sequence in GAA to which AON anneals | AON sequence 5' → 3' | SEQ ID NO |
|---|---|---|
| c.-32-79_-60 | TCAAAGCAGCTCTGAGACAT | 446 |
| c.-32-59_-40 | GGGCGGCACTCACGGGGCTC | 447 |
| c.-32-39_-20 | GCTCAGCAGGGAGGCGGGAG | 448 |
| c.-32-77_-57 | CTCTCAAAGCAGCTCTGAGAC | 449 |
| c.-32-76_-56 | GCTCTCAAAGCAGCTCTGAGA | 450 |
| c.-32-75_-55 | GGCTCTCAAAGCAGCTCTGAG | 451 |
| c.-32-74_-54 | GGGCTCTCAAAGCAGCTCTGA | 452 |
| c.-32-73_-53 | GGGGCTCTCAAAGCAGCTCTG | 453 |
| c.-32-72_-52 | CGGGGCTCTCAAAGCAGCTCT | 454 |
| c.-32-71_-51 | ACGGGGCTCTCAAAGCAGCTC | 455 |
| c.-32-70_-50 | CACGGGGCTCTCAAAGCAGCT | 456 |
| c.-32-69_-49 | TCACGGGGCTCTCAAAGCAGC | 457 |
| c.-32-68_-48 | CTCACGGGGCTCTCAAAGCAG | 458 |
| c.-32-67_-47 | ACTCACGGGGCTCTCAAAGCA | 459 |
| c.-32-66_-46 | CACTCACGGGGCTCTCAAAGC | 460 |
| c.-32-65_-45 | GCACTCACGGGGCTCTCAAAG | 461 |
| c.-32-64_-44 | GGCACTCACGGGGCTCTCAAA | 462 |

TABLE 12-continued

AONs targeting the cryptic donor splice site, e.g. targeting SEQ ID NO: 171.

| Sequence in GAA to which AON anneals | AON sequence 5' → 3' | SEQ ID NO |
|---|---|---|
| c.-32-63_-43 | CGGCACTCACGGGGCTCTCAA | 463 |
| c.-32-62_-42 | GCGGCACTCACGGGGCTCTCA | 464 |
| c.-32-61_-41 | GGCGGCACTCACGGGGCTCTC | 465 |
| c.-32-60_-40 | GGGCGGCACTCACGGGGCTCT | 466 |
| c.-32-59_-39 | GGGGCGGCACTCACGGGGCTC | 467 |
| c.-32-58_-38 | AGGGGCGGCACTCACGGGGCT | 468 |
| c.-32-57_-37 | GAGGGGCGGCACTCACGGGGC | 469 |
| c.-32-56_-36 | GGAGGGGCGGCACTCACGGGG | 470 |
| c.-32-55_-35 | GGGAGGGGCGGCACTCACGGG | 471 |
| c.-32-54_-34 | CGGGAGGGGCGGCACTCACGG | 472 |
| c.-32-53_-33 | GCGGGAGGGGCGGCACTCACG | 473 |
| c.-32-52_-32 | GGCGGGAGGGGCGGCACTCAC | 474 |
| c.-32-51_-31 | AGGCGGGAGGGGCGGCACTCA | 475 |
| c.-32-50_-30 | GAGGCGGGAGGGGCGGCACTC | 476 |
| c.-32-49_-29 | GGAGGCGGGAGGGGCGGCACT | 477 |
| c.-32-48_-28 | GGGAGGCGGGAGGGGCGGCAC | 478 |
| c.-32-77_-60 | TCAAAGCAGCTCTGAGAC | 479 |
| c.-32-76_-59 | CTCAAAGCAGCTCTGAGA | 480 |
| c.-32-75_-58 | TCTCAAAGCAGCTCTGAG | 481 |
| c.-32-74_-57 | CTCTCAAAGCAGCTCTGA | 482 |
| c.-32-73_-56 | GCTCTCAAAGCAGCTCTG | 483 |
| c.-32-72_-55 | GGCTCTCAAAGCAGCTCT | 484 |
| c.-32-71_-54 | GGGCTCTCAAAGCAGCTC | 485 |
| c.-32-70_-53 | GGGGCTCTCAAAGCAGCT | 486 |
| c.-32-69_-52 | CGGGGCTCTCAAAGCAGC | 487 |
| c.-32-68_-51 | ACGGGGCTCTCAAAGCAG | 488 |
| c.-32-67_-50 | CACGGGGCTCTCAAAGCA | 489 |
| c.-32-66_-49 | TCACGGGGCTCTCAAAGC | 490 |
| c.-32-65_-48 | CTCACGGGGCTCTCAAAG | 491 |
| c.-32-64_-47 | ACTCACGGGGCTCTCAAA | 492 |
| c.-32-63_-46 | CACTCACGGGGCTCTCAA | 493 |
| c.-32-62_-45 | GCACTCACGGGGCTCTCA | 494 |
| c.-32-61_-44 | GGCACTCACGGGGCTCTC | 495 |
| c.-32-60_-43 | CGGCACTCACGGGGCTCT | 496 |
| c.-32-59_-42 | GCGGCACTCACGGGGCTC | 497 |
| c.-32-58_-41 | GGCGGCACTCACGGGGCT | 498 |
| c.-32-57_-40 | GGGCGGCACTCACGGGGC | 499 |

TABLE 12-continued

AONs targeting the cryptic donor splice site, e.g. targeting SEQ ID NO: 171.

| Sequence in GAA to which AON anneals | AON sequence 5' → 3' | SEQ ID NO |
|---|---|---|
| c.-32-56_-39 | GGGGCGGCACTCACGGGG | 500 |
| c.-32-55_-38 | AGGGGCGGCACTCACGGG | 501 |
| c.-32-54_-37 | GAGGGGCGGCACTCACGG | 502 |
| c.-32-53_-36 | GGAGGGGCGGCACTCACG | 503 |
| c.-32-52_-35 | GGGAGGGGCGGCACTCAC | 504 |
| c.-32-51_-34 | CGGGAGGGGCGGCACTCA | 505 |
| c.-32-50_-33 | GCGGGAGGGGCGGCACTC | 506 |
| c.-32-49_-32 | GGCGGGAGGGGCGGCACT | 507 |
| c.-32-48_-31 | AGGCGGGAGGGGCGGCAC | 508 |
| c.-32-47_-30 | GAGGCGGGAGGGGCGGCA | 509 |
| c.-32-46_-29 | GGAGGCGGGAGGGGCGGC | 510 |
| c.-32-45_-28 | GGGAGGCGGGAGGGGCGG | 511 |
| c.-32-75_-51 | GGCTCTCAAAGCAGCTCTGAGACAT | 512 |
| c.-32-77_-53 | GGGGCTCTCAAAGCAGCTCTGAGAC | 513 |
| c.-32-75_-51 | ACGGGGCTCTCAAAGCAGCTCTGAG | 514 |
| c.-32-73_-49 | TCACGGGGCTCTCAAAGCAGCTCTG | 515 |
| c.-32-71_-47 | ACTCACGGGGCTCTCAAAGCAGCTC | 516 |
| c.-32-69_-45 | GCACTCACGGGGCTCTCAAAGCAGC | 517 |
| c.-32-67_-43 | CGGCACTCACGGGGCTCTCAAAGCA | 518 |
| c.-32-65_-41 | GGCGGCACTCACGGGGCTCTCAAAG | 519 |
| c.-32-63_-39 | GGGGCGGCACTCACGGGGCTCTCAA | 520 |
| c.-32-61_-37 | GAGGGGCGGCACTCACGGGGCTCTC | 521 |
| c.-32-59_-35 | GGGAGGGGCGGCACTCACGGGGCTC | 522 |
| c.-32-57_-33 | GCGGGAGGGGCGGCACTCACGGGGC | 523 |
| c.-32-55_-31 | AGGCGGGAGGGGCGGCACTCACGGG | 524 |
| c.-32-53_-29 | GGAGGCGGGAGGGGCGGCACTCACG | 525 |
| c.-32-51_-27 | AGGGAGGCGGGAGGGGCGGCACTCA | 526 |
| c.-32-49_-25 | GCAGGGAGGCGGGAGGGGCGGCACT | 527 |
| c.-32-47_-23 | CAGCAGGGAGGCGGGAGGGGCGGCA | 528 |
| c.-32-45_-21 | CTCAGCAGGGAGGCGGGAGGGGCGG | 529 |
| c.-32-43_-19 | GGCTCAGCAGGGAGGCGGGAGGGGC | 530 |
| c.-32-41_-17 | CGGGCTCAGCAGGGAGGCGGGAGGG | 531 |
| c.-32-39_-15 | AGCGGGCTCAGCAGGGAGGCGGGAG | 532 |
| c.-32-37_-13 | AAAGCGGGCTCAGCAGGGAGGCGGG | 533 |
| c.-32-35_-11 | AGAAAGCGGGCTCAGCAGGGAGGCG | 534 |
| c.-32-33_-09 | GAAGAAAGCGGGCTCAGCAGGGAGG | 535 |

TABLE 12-continued

AONs targeting the cryptic donor splice site, e.g. targeting SEQ ID NO: 171.

| Sequence in GAA to which AON anneals | AON sequence 5' → 3' | SEQ ID NO |
|---|---|---|
| c.-32-31_-07 | GAGAAGAAAGCGGGCTCAGCAGGGA | 536 |
| c.-32-29_-05 | GGGAGAAGAAAGCGGGCTCAGCAGG | 537 |
| c.-32-27_-03 | GCGGGAGAAGAAAGCGGGCTCAGCA | 538 |
| c.-32-25_-01 | CTGCGGGAGAAGAAAGCGGGCTCAG | 539 |
| c.-32-23_+01 | GCCTGCGGGAGAAGAAAGCGGGCTC | 540 |
| c.-32-21_+03 | AGGCCTGCGGGAGAAGAAAGCGGGC | 541 |
| c.-32-40_+16 | ACTCCCATGGTTGGAGATGGCCTGG | 542 |
| c.-32-42_+18 | TCACTCCCATGGTTGGAGATGGCCT | 543 |
| c.-32-44_+20 | CCTCACTCCCATGGTTGGAGATGGC | 544 |
| c.-32+46_+22 | TGCCTCACTCCCATGGTTGGAGATG | 545 |
| c.-32+48_+24 | GGTGCCTCACTCCCATGGTTGGAGA | 546 |
| c.-32+50_+26 | CGGGTGCCTCACTCCCATGGTTGGA | 547 |
| c.-32+52_+28 | GGCGGGTGCCTCACTCCCATGGTTG | 548 |
| c.-32+54_+30 | AGGGCGGGTGCCTCACTCCCATGGT | 549 |
| c.-32+56_+32 | GCAGGGCGGGTGCCTCACTCCCATG | 550 |
| c.-32+58_+34 | GAGCAGGGCGGGTGCCTCACTCCCA | 551 |
| c.-32+60_+36 | GGGAGCAGGGCGGGTGCCTCACTCC | 552 |
| c.-32+62_+38 | GTGGGAGCAGGGCGGGTGCCTCACT | 553 |
| c.-32+64_+40 | CGGTGGGAGCAGGGCGGGTGCCTCA | 554 |
| c.-32+66_+42 | GCCGGTGGGAGCAGGGCGGGTGCCT | 555 |
| c.-32+68_+44 | GAGCCGGTGGGAGCAGGGCGGGTGC | 556 |
| c.-32+70_+46 | AGGAGCCGGTGGGAGCAGGGCGGGT | 557 |
| c.-32+72_+48 | CCAGGAGCCGGTGGGAGCAGGGCGG | 558 |
| c.-32+74_+50 | GGCCAGGAGCCGGTGGGAGCAGGGC | 559 |
| c.-32+76_+52 | ACGGCCAGGAGCCGGTGGGAGCAGG | 560 |
| c.-32+78_+54 | AGACGGCCAGGAGCCGGTGGGAGCA | 561 |
| c.-32+80_+56 | GCAGACGGCCAGGAGCCGGTGGGAG | 562 |
| c.-32+82_+58 | GCGCAGACGGCCAGGAGCCGGTGGG | 563 |
| c.-32+84_+60 | GGGCGCAGACGGCCAGGAGCCGGTG | 564 |
| c.-32+86_+62 | GAGGGCGCAGACGGCCAGGAGCCGG | 565 |
| c.-32+88_+64 | ACGAGGGCGCAGACGGCCAGGAGCC | 566 |
| c.-32+90_+66 | ACACGAGGGCGCAGACGGCCAGGAG | 567 |
| c.-32+92_+68 | GGACACGAGGGCGCAGACGGCCAGG | 568 |
| c.-32+94_+70 | AAGGACACGAGGGCGCAGACGGCCA | 569 |
| c.-32+96_+72 | CCAAGGACACGAGGGCGCAGACGGC | 570 |
| c.-32+98_+74 | TGCCAAGGACACGAGGGCGCAGACG | 571 |
| c.-32-80_-56 | GCTCTCAAAGCAGCTCTGAGACATC | 572 |

TABLE 12-continued

AONs targeting the cryptic donor splice site, e.g. targeting SEQ ID NO: 171.

| Sequence in GAA to which AON anneals | AON sequence 5' → 3' | SEQ ID NO |
|---|---|---|
| c.-32-78_-54 | GGGCTCTCAAAGCAGCTCTGAGACA | 573 |
| c.-32-72_-48 | CTCACGGGGCTCTCAAAGCAGCTCT | 574 |
| c.-32-70_-46 | CACTCACGGGGCTCTCAAAGCAGCT | 575 |
| c.-32-68_-44 | GGCACTCACGGGGCTCTCAAAGCAG | 576 |
| c.-32-66_-42 | GCGGCACTCACGGGGCTCTCAAAGC | 577 |
| c.-32-64_-40 | GGGCGGCACTCACGGGGCTCTCAAA | 578 |
| c.-32-62_-38 | AGGGGCGGCACTCACGGGGCTCTCA | 579 |
| c.-32-60_-36 | GGAGGGGCGGCACTCACGGGGCTCT | 580 |
| c.-32-58_-34 | CGGGAGGGGCGGCACTCACGGGGCT | 581 |
| c.-32-56_-32 | GGCGGGAGGGGCGGCACTCACGGGG | 582 |
| c.-32-54_-30 | GAGGCGGGAGGGGCGGCACTCACGG | 583 |
| c.-32-52_-28 | GGGAGGCGGGAGGGGCGGCACTCAC | 584 |
| c.-32-50_-26 | CAGGGAGGCGGGAGGGGCGGCACTC | 585 |
| c.-32-48_-24 | AGCAGGGAGGCGGGAGGGGCGGCAC | 586 |
| c.-32-46_-22 | TCAGCAGGGAGGCGGGAGGGGCGGC | 587 |
| c.-32-44_-20 | GCTCAGCAGGGAGGCGGGAGGGGCG | 588 |
| c.-32-42_-18 | GGGCTCAGCAGGGAGGCGGGAGGGG | 589 |
| c.-32-40_-16 | GCGGGCTCAGCAGGGAGGCGGGAGG | 590 |
| c.-32-38_-14 | AAGCGGGCTCAGCAGGGAGGCGGGA | 591 |
| c.-32-36_-12 | GAAAGCGGGCTCAGCAGGGAGGCGG | 592 |
| c.-32-34_-10 | AAGAAAGCGGGCTCAGCAGGGAGGC | 593 |
| c.-32-32_-8 | AGAAGAAAGCGGGCTCAGCAGGGAG | 594 |
| c.-32-30_-6 | GGAGAAGAAAGCGGGCTCAGCAGGG | 595 |
| c.-32-28_-4 | CGGGAGAAGAAAGCGGGCTCAGCAG | 596 |
| c.-32-26_-2 | TGCGGGAGAAGAAAGCGGGCTCAGC | 597 |
| c.-32-24_+1 | CCTGCGGGAGAAGAAAGCGGGCTCA | 598 |
| c.-32-22_+3 | GGCCTGCGGGAGAAGAAAGCGGGCT | 599 |
| c.-32-20_+5 | CAGGCCTGCGGGAGAAGAAAGCGGG | 600 |
| c.-32-76_-52 | CGGGGCTCTCAAAGCAGCTCTGAGA | 601 |
| c.-32-74_-50 | CACGGGGCTCTCAAAGCAGCTCTGA | 602 |

Further preferred but exemplary AONs for use in aspects of the present invention comprise the AONs as displayed in Table 13, targeting alternative aberrant splicing sites in the GAA gene.

TABLE 13

Further exemplary AONs useful in aspects of the present invention.

| Sequence in GAA to which AON anneals | AON sequence 5' → 3' | SEQ ID NO |
|---|---|---|
| c.-32-319_-300 | CCAAACAGCTGTCGCCTGGG | 603 |
| c.-32-299_-280 | AGGTAGACACTTGAAACAGG | 604 |
| c.-32-279_-260 | CCCAGGAAGACCAGCAAGGC | 605 |
| c.-32-259_-240 | TCAAACACGCTTAGAATGTC | 606 |
| c.-32-239_-220 | GTCTGCTAAAATGTTACAAA | 607 |
| c.-32-139_-120 | AGGTGGCCAGGGTGGGTGTT | 608 |
| c.-32-119_-100 | GCACCCAGGCAGGTGGGGTA | 609 |
| c.-32-99_-80 | CAACCGCGGCTGGCACTGCA | 610 |
| c.-32-19_-0 | CCTGCGGGAGAAGAAAGCGG | 611 |
| c.-30_-12 | GCCTGGACAGCTCCTACAGG | 612 |
| c.-10_+9 | CACTCCCATGGTTGGAGATG | 613 |
| c.10_+29 | TGGGAGCAGGGCGGGTGCCT | 614 |
| c.30_+49 | CGCAGACGGCCAGGAGCCGG | 615 |
| c.50_+69 | GGTTGCCAAGGACACGAGGG | 616 |
| c.70_+89 | ATGTGCCCCAGGAGTGCAGC | 617 |
| c.90_+109 | GCAGGAAATCATGGAGTAG | 618 |
| c.110_+129 | ACTCAGCTCTCGGGGAACCA | 619 |
| c.130_+149 | TCCAGGACTGGGGAGGAGCC | 620 |
| c.150_+169 | GGTGAGCTGGGTGAGTCTCC | 621 |
| c.170_+189 | TGGTCTGCTGGCTCCCTGCT | 622 |
| c.190_+209 | GCCTGGGCATCCCGGGGCCC | 623 |
| c.210_+229 | CTCTGGGACGGCCGGGGTGT | 624 |
| c.230_+249 | GTCGCACTGTGTGGGCACTG | 625 |
| c.250_+269 | AAGCGGCTGTTGGGGGGGAC | 626 |
| c.270_+289 | CCTTGTCAGGGGCGCAATCG | 627 |
| c.290_+309 | GCACTGTTCCTGGGTGATGG | 628 |
| c.310_+329 | TAGCAACAGCCGCGGGCCTC | 629 |
| c.330_+349 | GCCCCTGCTTTGCAGGGATG | 630 |
| c.350_+369 | CCCCATCTGGGCTCCCTGCA | 631 |
| c.370_+389 | GGGAAGAAGCACCAGGGCTG | 632 |
| c.390_+409 | TGTAGCTGGGGTAGCTGGGT | 633 |
| c.410_+429 | GGAGCTCAGGTTCTCCAGCT | 634 |
| c.430_+449 | GCCGTGTAGCCCATTTCAGA | 635 |
| c.450_+469 | GGGTGGTACGGGTCAGGGTG | 636 |
| c.470_+489 | GTCCTTGGGGAAGAAGGTGG | 637 |

TABLE 13-continued

Further exemplary AONs useful in aspects of the present invention.

| Sequence in GAA to which AON anneals | AON sequence 5' → 3' | SEQ ID NO |
|---|---|---|
| c.490_+509 | TCCAGCCGCAGGGTCAGGAT | 638 |
| c.510_+529 | TCTCAGTCTCCATCATCACG | 639 |
| c.530_+546 | GTGAAGTGGAGGCGGT | 640 |

In embodiments of aspects of this invention, AONs may be used that target specific mutations in the GAA gene or gene product that affect the splicing of the gene product, in particular, that result in aberrant splicing of exon 2. Exemplary AONs useful in embodiments of that aspect of the invention are displayed in Table 14. These include AON sequences designed to block the region surrounding the identified splice element.

TABLE 14

Further exemplary AONs useful in aspects of the present invention.

| variants that affect aberrant splicing of exon 2 caused by IVS1 in GAA exon 1-3 minigene system | Aon sequence designed to block the region surrounding the identified splice element (5' → 3') | SEQ ID NO |
|---|---|---|
| c.-32-102 C > T | CACCCAGGCAGGTGGGGTAAGGTGG | 641 |
| | AGCACCCAGGCAGGTGGGGTAAGGT | 642 |
| | GCAGCACCCAGGCAGGTGGGGTAAG | 643 |
| | CTGCAGCACCCAGGCAGGTGGGGTA | 644 |
| | CACTGCAGCACCCAGGCAGGTGGGG | 645 |
| | GGCACTGCAGCACCCAGGCAGGTGG | 646 |
| | CTGGCACTGCAGCACCCAGGCAGGT | 647 |
| | GGCTGGCACTGCAGCACCCAGGCAG | 648 |
| | GCGGCTGGCACTGCAGCACCCAGGC | 649 |
| | CCGCGGCTGGCACTGCAGCACCCAG | 650 |
| | TCAACCGCGGCTGGCACTGCAGCAC | 651 |
| | ACCCAGGCAGGTGGGGTAAGGTGGC | 652 |
| | GCACCCAGGCAGGTGGGGTAAGGTG | 653 |
| | CAGCACCCAGGCAGGTGGGGTAAGG | 654 |
| | TGCAGCACCCAGGCAGGTGGGGTAA | 655 |
| | ACTGCAGCACCCAGGCAGGTGGGGT | 656 |
| | GCACTGCAGCACCCAGGCAGGTGGG | 657 |
| | TGGCACTGCAGCACCCAGGCAGGTG | 658 |
| | GCTGGCACTGCAGCACCCAGGCAGG | 659 |
| | CGGCTGGCACTGCAGCACCCAGGCA | 660 |
| | CGCGGCTGGCACTGCAGCACCCAGG | 661 |
| | ACCGCGGCTGGCACTGCAGCACCCA | 662 |
| | CAACCGCGGCTGGCACTGCAGCACC | 663 |
| | ATCAACCGCGGCTGGCACTGCAGCA | 664 |
| c.7G > A, c.11G > A, c.15_17AAA, C.17C > T, c.19_21AAA, c.26_28AAA, c.33_35AAA, c.39 G > A, c.42C > T | CTCCCATGGTTGGAGATGGCCTGGA | 665 |
| | CACTCCCATGGTTGGAGATGGCCTG | 666 |
| | CTCACTCCCATGGTTGGAGATGGCC | 667 |
| | GCCTCACTCCCATGGTTGGAGATGG | 668 |
| | GTGCCTCACTCCCATGGTTGGAGAT | 669 |
| | GGGTGCCTCACTCCCATGGTTGGAG | 670 |
| | GCGGGTGCCTCACTCCCATGGTTGG | 671 |
| | GGGCGGGTGCCTCACTCCCATGGTT | 672 |
| | CAGGGCGGGTGCCTCACTCCCATGG | 673 |
| | AGCAGGGCGGGTGCCTCACTCCCAT | 674 |
| | GGAGCAGGGCGGGTGCCTCACTCCC | 675 |
| | TGGGAGCAGGGCGGGTGCCTCACTC | 676 |
| | GGTGGGAGCAGGGCGGGTGCCTCAC | 677 |
| | CCGGTGGGAGCAGGGCGGGTGCCTC | 678 |
| | AGCCGGTGGGAGCAGGGCGGGTGCC | 679 |
| | GGAGCCGGTGGGAGCAGGGCGGGTG | 680 |
| | CAGGAGCCGGTGGGAGCAGGGCGGG | 681 |
| | GCCAGGAGCCGGTGGGAGCAGGGCG | 682 |

TABLE 14-continued

Further exemplary AONs useful in aspects of the present invention.

| variants that affect aberrant splicing of exon 2 caused by IVS1 in GAA exon 1-3 minigene system | Aon sequence designed to block the region surrounding the identified splice element (5' → 3') | SEQ ID NO |
|---|---|---|
| | CGGCCAGGAGCCGGTGGGAGCAGGG | 683 |
| | GACGGCCAGGAGCCGGTGGGAGCAG | 684 |
| | CAGACGGCCAGGAGCCGGTGGGAGC | 685 |
| | CGCAGACGGCCAGGAGCCGGTGGGA | 686 |
| | GGCGCAGACGGCCAGGAGCCGGTGG | 687 |
| | AGGGCGCAGACGGCCAGGAGCCGGT | 688 |
| | CGAGGGCGCAGACGGCCAGGAGCCG | 689 |
| | CACGAGGGCGCAGACGGCCAGGAGC | 690 |
| | GACACGAGGGCGCAGACGGCCAGGA | 691 |
| | AGGACACGAGGGCGCAGACGGCCAG | 692 |
| | CAAGGACACGAGGGCGCAGACGGCC | 693 |
| | GCCAAGGACACGAGGGCGCAGACGG | 694 |
| | TTGCCAAGGACACGAGGGCGCAGAC | 695 |
| c.90C > T, c.112G > A, c.137C > T, c.164C > T | GGATGTGCCCCAGGAGTGCAGCGGT | 696 |
| | TAGGATGTGCCCCAGGAGTGCAGCG | 697 |
| | AGTAGGATGTGCCCCAGGAGTGCAG | 698 |
| | GGAGTAGGATGTGCCCCAGGAGTGC | 699 |
| | ATGGAGTAGGATGTGCCCCAGGAGT | 700 |
| | TCATGGAGTAGGATGTGCCCCAGGA | 701 |
| | AATCATGGAGTAGGATGTGCCCCAG | 702 |
| | GAAATCATGGAGTAGGATGTGCCCC | 703 |
| | AGGAAATCATGGAGTAGGATGTGCC | 704 |
| | GCAGGAAATCATGGAGTAGGATGTG | 705 |
| | CAGCAGGAAATCATGGAGTAGGATG | 706 |
| | ACCAGCAGGAAATCATGGAGTAGGA | 707 |
| | GAACCAGCAGGAAATCATGGAGTAG | 708 |
| | GGGAACCAGCAGGAAATCATGGAGT | 709 |
| | CGGGGAACCAGCAGGAAATCATGGA | 710 |
| | CTCGGGGAACCAGCAGGAAATCATG | 711 |
| | CTCTCGGGGAACCAGCAGGAAATCA | 712 |
| | AGCTCTCGGGGAACCAGCAGGAAAT | 713 |
| | TCAGCTCTCGGGGAACCAGCAGGAA | 714 |
| | ACTCAGCTCTCGGGGAACCAGCAGG | 715 |
| | CCACTCAGCTCTCGGGGAACCAGCA | 716 |
| | AGCCACTCAGCTCTCGGGGAACCAG | 717 |
| | GGAGCCACTCAGCTCTCGGGGAACC | 718 |
| | GAGGAGCCACTCAGCTCTCGGGGAA | 719 |
| | GGGAGGAGCCACTCAGCTCTCGGGG | 720 |
| | TGGGGAGGAGCCACTCAGCTCTCGG | 721 |
| | ACTGGGGAGGAGCCACTCAGCTCTC | 722 |
| | GGACTGGGGAGGAGCCACTCAGCTC | 723 |
| | CAGGACTGGGGAGGAGCCACTCAGC | 724 |
| | TCCAGGACTGGGGAGGAGCCACTCA | 725 |
| | CCTCCAGGACTGGGGAGGAGCCACT | 726 |
| | CTCCTCCAGGACTGGGGAGGAGCCA | 727 |
| | GTCTCCTCCAGGACTGGGGAGGAGC | 728 |
| | GAGTCTCCTCCAGGACTGGGGAGGA | 729 |
| | GTGAGTCTCCTCCAGGACTGGGGAG | 730 |
| | GGGTGAGTCTCCTCCAGGACTGGGG | 731 |
| | CTGGGTGAGTCTCCTCCAGGACTGG | 732 |
| | AGCTGGGTGAGTCTCCTCCAGGACT | 733 |
| | TGAGCTGGGTGAGTCTCCTCCAGGA | 734 |
| | GGTGAGCTGGGTGAGTCTCCTCCAG | 735 |
| | CTGGTGAGCTGGGTGAGTCTCCTCC | 736 |
| | TGCTGGTGAGCTGGGTGAGTCTCCT | 737 |
| | CCTGCTGGTGAGCTGGGTGAGTCTC | 738 |
| | TCCCTGCTGGTGAGCTGGGTGAGTC | 739 |
| | GCTCCCTGCTGGTGAGCTGGGTGAG | 740 |
| | TGGCTCCCTGCTGGTGAGCTGGGTG | 741 |
| | GCTGGCTCCCTGCTGGTGAGCTGGG | 742 |
| | CTGCTGGCTCCCTGCTGGTGAGCTG | 743 |
| | GTCTGCTGGCTCCCTGCTGGTGAGC | 744 |
| | GATGTGCCCCAGGAGTGCAGCGGTT | 745 |
| | AGGATGTGCCCCAGGAGTGCAGCGG | 746 |
| | GTAGGATGTGCCCCAGGAGTGCAGC | 747 |
| | GAGTAGGATGTGCCCCAGGAGTGCA | 748 |
| | TGGAGTAGGATGTGCCCCAGGAGTG | 749 |
| | CATGGAGTAGGATGTGCCCCAGGAG | 750 |
| | ATCATGGAGTAGGATGTGCCCCAGG | 751 |
| | AAATCATGGAGTAGGATGTGCCCCA | 752 |
| | GGAAATCATGGAGTAGGATGTGCCC | 753 |
| | CAGGAAATCATGGAGTAGGATGTGC | 754 |
| | AGCAGGAAATCATGGAGTAGGATGT | 755 |
| | CCAGCAGGAAATCATGGAGTAGGAT | 756 |
| | AACCAGCAGGAAATCATGGAGTAGG | 757 |
| | GGAACCAGCAGGAAATCATGGAGTA | 758 |
| | GGGGAACCAGCAGGAAATCATGGAG | 759 |
| | TCGGGGAACCAGCAGGAAATCATGG | 760 |
| | TCTCGGGGAACCAGCAGGAAATCAT | 761 |
| | GCTCTCGGGGAACCAGCAGGAAATC | 762 |
| | CAGCTCTCGGGGAACCAGCAGGAAA | 763 |
| | CTCAGCTCTCGGGGAACCAGCAGGA | 764 |
| | CACTCAGCTCTCGGGGAACCAGCAG | 765 |
| | GCCACTCAGCTCTCGGGGAACCAGC | 766 |
| | GAGCCACTCAGCTCTCGGGGAACCA | 767 |
| | AGGAGCCACTCAGCTCTCGGGGAAC | 768 |
| | GGAGGAGCCACTCAGCTCTCGGGGA | 769 |
| | GGGGAGGAGCCACTCAGCTCTCGGG | 770 |
| | CTGGGGAGGAGCCACTCAGCTCTCG | 771 |
| | GACTGGGGAGGAGCCACTCAGCTCT | 772 |
| | AGGACTGGGGAGGAGCCACTCAGCT | 773 |
| | CCAGGACTGGGGAGGAGCCACTCAG | 774 |
| | CTCCAGGACTGGGGAGGAGCCACTC | 775 |
| | TCCTCCAGGACTGGGGAGGAGCCAC | 776 |
| | TCTCCTCCAGGACTGGGGAGGAGCC | 777 |
| | AGTCTCCTCCAGGACTGGGGAGGAG | 778 |
| | TGAGTCTCCTCCAGGACTGGGGAGG | 779 |
| | GGTGAGTCTCCTCCAGGACTGGGGA | 780 |
| | TGGGTGAGTCTCCTCCAGGACTGGG | 781 |
| | GCTGGGTGAGTCTCCTCCAGGACTG | 782 |
| | GAGCTGGGTGAGTCTCCTCCAGGAC | 783 |
| | GTGAGCTGGGTGAGTCTCCTCCAGG | 784 |
| | TGGTGAGCTGGGTGAGTCTCCTCCA | 785 |
| | GCTGGTGAGCTGGGTGAGTCTCCTC | 786 |
| | CTGCTGGTGAGCTGGGTGAGTCTCC | 787 |
| | CCCTGCTGGTGAGCTGGGTGAGTCT | 788 |
| | CTCCCTGCTGGTGAGCTGGGTGAGT | 789 |
| | GGCTCCCTGCTGGTGAGCTGGGTGA | 790 |
| | CTGGCTCCCTGCTGGTGAGCTGGGT | 791 |
| | TGCTGGCTCCCTGCTGGTGAGCTGG | 792 |
| | TCTGCTGGCTCCCTGCTGGTGAGCT | 793 |
| | GGTCTGCTGGCTCCCTGCTGGTGAG | 794 |
| c.348G > A, c.373C > T | AGCCCCTGCTTTGCAGGGATGTAGC | 795 |
| | GCAGCCCCTGCTTTGCAGGGATGTA | 796 |
| | CTGCAGCCCCTGCTTTGCAGGGATG | 797 |
| | CCCTGCAGCCCCTGCTTTGCAGGGA | 798 |
| | CTCCCTGCAGCCCCTGCTTTGCAGG | 799 |
| | GGCTCCCTGCAGCCCCTGCTTTGCA | 800 |
| | TGGGCTCCCTGCAGCCCCTGCTTTG | 801 |
| | TCTGGGCTCCCTGCAGCCCCTGCTT | 802 |
| | CATCTGGGCTCCCTGCAGCCCCTGC | 803 |
| | CCCATCTGGGCTCCCTGCAGCCCCT | 804 |
| | GCCCCATCTGGGCTCCCTGCAGCCC | 805 |
| | CTGCCCCATCTGGGCTCCCTGCAGC | 806 |
| | GGCTGCCCCATCTGGGCTCCCTGCA | 807 |
| | AGGGCTGCCCCATCTGGGCTCCCTG | 808 |
| | CCAGGGCTGCCCCATCTGGGCTCCC | 809 |
| | CACCAGGGCTGCCCCATCTGGGCTC | 810 |
| | AGCACCAGGGCTGCCCCATCTGGGC | 811 |
| | GAAGCACCAGGGCTGCCCCATCTGG | 812 |
| | AAGAAGCACCAGGGCTGCCCCATCT | 813 |
| | GGAAGAAGCACCAGGGCTGCCCCAT | 814 |
| | TGGGAAGAAGCACCAGGGCTGCCCC | 815 |
| | GGTGGGAAGAAGCACCAGGGCTGCC | 816 |
| | TGGGTGGGAAGAAGCACCAGGGCTG | 817 |
| | GCTGGGTGGGAAGAAGCACCAGGGC | 818 |
| | GCCCCTGCTTTGCAGGATGTAGCA | 819 |
| | CAGCCCCTGCTTTGCAGGGATGTAG | 820 |

TABLE 14-continued

Further exemplary AONs useful in aspects of the present invention.

| variants that affect aberrant splicing of exon 2 caused by IVS1 in GAA exon 1-3 minigene system | Aon sequence designed to block the region surrounding the identified splice element (5' → 3') | SEQ ID NO |
|---|---|---|
| | TGCAGCCCCTGCTTTGCAGGGATGT | 821 |
| | CCTGCAGCCCCTGCTTTGCAGGGAT | 822 |
| | TCCCTGCAGCCCCTGCTTTGCAGGG | 823 |
| | GCTCCCTGCAGCCCCTGCTTTGCAG | 824 |
| | GGGCTCCCTGCAGCCCCTGCTTTGC | 825 |
| | CTGGGCTCCCTGCAGCCCCTGCTTT | 826 |
| | ATCTGGGCTCCCTGCAGCCCCTGCT | 827 |
| | CCATCTGGGCTCCCTGCAGCCCCTG | 828 |
| | CCCCATCTGGGCTCCCTGCAGCCCC | 829 |
| | TGCCCCATCTGGGCTCCCTGCAGCC | 830 |
| | GCTGCCCCATCTGGGCTCCCTGCAG | 831 |
| | GGGCTGCCCCATCTGGGCTCCCTGC | 832 |
| | CAGGGCTGCCCCATCTGGGCTCCCT | 833 |
| | ACCAGGGCTGCCCCATCTGGGCTCC | 834 |
| | GCACCAGGGCTGCCCCATCTGGGCT | 835 |
| | AAGCACCAGGGCTGCCCCATCTGGG | 836 |
| | AGAAGCACCAGGGCTGCCCCATCTG | 837 |
| | GAAGAAGCACCAGGGCTGCCCCATC | 838 |
| | GGGAAGAAGCACCAGGGCTGCCCCA | 839 |
| | GTGGGAAGAAGCACCAGGGCTGCCC | 840 |
| | GGGTGGGAAGAAGCACCAGGGCTGC | 841 |
| | CTGGGTGGGAAGAAGCACCAGGGCT | 842 |
| | AGCTGGGTGGGAAGAAGCACCAGGG | 843 |
| c.413T > A | CAGCTTGTAGCTGGGGTAGCTGGGT | 844 |
| | TCCAGCTTGTAGCTGGGGTAGCTGG | 845 |
| | TCTCCAGCTTGTAGCTGGGGTAGCT | 846 |
| | GTTCTCCAGCTTGTAGCTGGGGTAG | 847 |
| | AGGTTCTCCAGCTTGTAGCTGGGGT | 848 |
| | TCAGGTTCTCCAGCTTGTAGCTGGG | 849 |
| | GCTCAGGTTCTCCAGCTTGTAGCTG | 850 |
| | GAGCTCAGGTTCTCCAGCTTGTAGC | 851 |
| | AGGAGCTCAGGTTCTCCAGCTTGTA | 852 |
| | AGAGGAGCTCAGGTTCTCCAGCTTG | 853 |
| | TCAGAGGAGCTCAGGTTCTCCAGCT | 854 |
| | TTTCAGAGGAGCTCAGGTTCTCCAG | 855 |
| | AGCTTGTAGCTGGGGTAGCTGGGTG | 856 |
| | CCAGCTTGTAGCTGGGGTAGCTGGG | 857 |
| | CTCCAGCTTGTAGCTGGGGTAGCTG | 858 |
| | TTCTCCAGCTTGTAGCTGGGGTAGC | 859 |
| | GGTTCTCCAGCTTGTAGCTGGGGTA | 860 |
| | CAGGTTCTCCAGCTTGTAGCTGGGG | 861 |
| | CTCAGGTTCTCCAGCTTGTAGCTGG | 862 |
| | AGCTCAGGTTCTCCAGCTTGTAGCT | 863 |
| | GGAGCTCAGGTTCTCCAGCTTGTAG | 864 |
| | GAGGAGCTCAGGTTCTCCAGCTTGT | 865 |
| | CAGAGGAGCTCAGGTTCTCCAGCTT | 866 |
| | TTCAGAGGAGCTCAGGTTCTCCAGC | 867 |
| | ATTTCAGAGGAGCTCAGGTTCTCCA | 868 |
| c.469C > T, c.476T > C, c.476T > G, c.478T > G, c.482C > T | GGGGTGGTACGGGTCAGGGTGGCCG | 869 |
| | TGGGGGTGGTACGGGTCAGGGTGGC | 870 |
| | GGTGGGGGTGGTACGGGTCAGGGTG | 871 |
| | AAGGTGGGGGTGGTACGGGTCAGGG | 872 |
| | AGAAGGTGGGGGTGGTACGGGTCAG | 873 |
| | GAAGAAGGTGGGGGTGGTACGGGTC | 874 |
| | GGGAAGAAGGTGGGGGTGGTACGGG | 875 |
| | TGGGGAAGAAGGTGGGGGTGGTACG | 876 |
| | CTTGGGGAAGAAGGTGGGGGTGGTA | 878 |
| | TGTCCTTGGGGAAGAAGGTGGGGGT | 879 |
| | GATGTCCTTGGGGAAGAAGGTGGGG | 880 |
| | AGGATGTCCTTGGGGAAGAAGGTGG | 881 |
| | TCAGGATGTCCTTGGGGAAGAAGGT | 882 |
| | GGTCAGGATGTCCTTGGGGAAGAAG | 883 |
| | AGGGTCAGGATGTCCTTGGGGAAGA | 884 |
| | GCAGGGTCAGGATGTCCTTGGGGAA | 885 |
| | CCGCAGGGTCAGGATGTCCTTGGGG | 886 |
| | AGCCGCAGGGTCAGGATGTCCTTGG | 887 |
| | GGGTGGTACGGGTCAGGGTGGCCGT | 888 |
| | GGGGGTGGTACGGGTCAGGGTGGCC | 889 |
| | GTGGGGGTGGTACGGGTCAGGGTGG | 890 |
| | AGGTGGGGGTGGTACGGGTCAGGGT | 891 |
| | GAAGGTGGGGGTGGTACGGGTCAGG | 892 |
| | AAGAAGGTGGGGGTGGTACGGGTCA | 893 |
| | GGAAGAAGGTGGGGGTGGTACGGGT | 894 |
| | GGGGAAGAAGGTGGGGGTGGTACGG | 895 |
| | TTGGGGAAGAAGGTGGGGGTGGTAC | 896 |
| | CCTTGGGGAAGAAGGTGGGGGTGGT | 897 |
| | GTCCTTGGGGAAGAAGGTGGGGGTG | 898 |
| | ATGTCCTTGGGGAAGAAGGTGGGGG | 899 |
| | GGATGTCCTTGGGGAAGAAGGTGGG | 900 |
| | CAGGATGTCCTTGGGGAAGAAGGTG | 901 |
| | GTCAGGATGTCCTTGGGGAAGAAGG | 902 |
| | GGGTCAGGATGTCCTTGGGGAAGAA | 903 |
| | CAGGGTCAGGATGTCCTTGGGGAAG | 904 |
| | CGCAGGGTCAGGATGTCCTTGGGGA | 905 |
| | GCCGCAGGGTCAGGATGTCCTTGGG | 906 |
| | CAGCCGCAGGGTCAGGATGTCCTTG | 907 |
| c.510C > T, c.515T > A, c.520G > A | CGTCCAGCCGCAGGGTCAGGATGTC | 908 |
| | CACGTCCAGCCGCAGGGTCAGGATG | 909 |
| | ATCACGTCCAGCCGCAGGGTCAGGA | 910 |
| | TCATCACGTCCAGCCGCAGGGTCAG | 911 |
| | CATCATCACGTCCAGCCGCAGGGTC | 912 |
| | TCCATCATCACGTCCAGCCGCAGGG | 913 |
| | TCTCCATCATCACGTCCAGCCGCAG | 914 |
| | AGTCTCCATCATCACGTCCAGCCGC | 915 |
| | TCAGTCTCCATCATCACGTCCAGCC | 916 |
| | TCTCAGTCTCCATCATCACGTCCAG | 917 |
| | GTTCTCAGTCTCCATCATCACGTCC | 918 |
| | CGGTTCTCAGTCTCCATCATCACGT | 919 |
| | GGCGGTTCTCAGTCTCCATCATCAC | 920 |
| | GAGGCGGTTCTCAGTCTCCATCATC | 921 |
| | TGGAGGCGGTTCTCAGTCTCCATCA | 922 |
| | AGTGGAGGCGGTTCTCAGTCTCCAT | 923 |
| | GAAGTGGAGGCGGTTCTCAGTCTCC | 924 |
| | GTCCAGCCGCAGGGTCAGGATGTCC | 925 |
| | ACGTCCAGCCGCAGGGTCAGGATGT | 926 |
| | TCACGTCCAGCCGCAGGGTCAGGAT | 927 |
| | CATCACGTCCAGCCGCAGGGTCAGG | 928 |
| | ATCATCACGTCCAGCCGCAGGGTCA | 929 |
| | CCATCATCACGTCCAGCCGCAGGGT | 930 |
| | CTCCATCATCACGTCCAGCCGCAGG | 931 |
| | GTCTCCATCATCACGTCCAGCCGCA | 932 |
| | CAGTCTCCATCATCACGTCCAGCCG | 933 |
| | CTCAGTCTCCATCATCACGTCCAGC | 934 |
| | TTCTCAGTCTCCATCATCACGTCCA | 935 |
| | GGTTCTCAGTCTCCATCATCACGTC | 936 |
| | GCGGTTCTCAGTCTCCATCATCACG | 937 |
| | AGGCGGTTCTCAGTCTCCATCATCA | 938 |
| | GGAGGCGGTTCTCAGTCTCCATCAT | 939 |
| | GTGGAGGCGGTTCTCAGTCTCCATC | 940 |
| | AAGTGGAGGCGGTTCTCAGTCTCCA | 941 |
| | TGAAGTGGAGGCGGTTCTCAGTCTC | 942 |
| c.546 + 11C > T, c.546 + 14G > A, c.546 + 19G > A, c.546 + 23C > A | TGCCCTGCCCACCGTGAAGTGGAGG | 943 |
| | CCTGCCCTGCCCACCGTGAAGTGGA | 944 |
| | CCCCTGCCCTGCCCACCGTGAAGTG | 945 |
| | CGCCCCTGCCCTGCCCACCGTGAAG | 946 |
| | CCCGCCCCTGCCCTGCCCACCGTGA | 947 |
| | GCCCTGCCCACCGTGAAGTGGAGGC | 948 |
| | CTGCCCTGCCCACCGTGAAGTGGAG | 949 |
| | CCCTGCCCTGCCCACCGTGAAGTGG | 950 |
| | GCCCCTGCCCTGCCCACCGTGAAGT | 951 |
| | CCGCCCCTGCCCTGCCCACCGTGAA | 952 |
| | CCCCGCCCCTGCCCTGCCCACCGTG | 953 |
| | GCCCCCGCCCCTGCCCTGCCCACCG | 954 |
| | CCGCCCCCGCCCCTGCCCTGCCCAC | 955 |
| | CGCCGCCCCCGCCCCTGCCCTGCCC | 956 |
| | GCCGCCGCCCCCGCCCCTGCCCTGC | 957 |

TABLE 14-continued

Further exemplary AONs useful in aspects of the present invention.

| variants that affect aberrant splicing of exon 2 caused by IVS1 in GAA exon 1-3 minigene system | Aon sequence designed to block the region surrounding the identified splice element (5' → 3') | SEQ ID NO |
|---|---|---|
| | TGGCCGCCGCCCCCGCCCCTGCCCT | 958 |
| | CCTGGCCGCCGCCCCCGCCCCTGCC | 959 |
| | GCCCTGGCCGCCGCCCCCGCCCCTG | 960 |
| | CTGCCCTGGCCGCCGCCCCCGCCCC | 961 |
| | CTCTGCCCTGGCCGCCGCCCCCGCC | 962 |
| | CCCTCTGCCCTGGCCGCCGCCCCCG | 963 |
| | CACCCTCTGCCCTGGCCGCCGCCCC | 964 |
| | CGCACCCTCTGCCCTGGCCGCCGCC | 965 |
| | CGCGCACCCTCTGCCCTGGCCGCCG | 966 |
| | CCCCCGCCCCTGCCCTGCCCACCGT | 967 |
| | CGCCCCCGCCCCTGCCCTGCCCACC | 968 |
| | GCCGCCCCCGCCCCTGCCCTGCCCA | 969 |
| | CCGCCGCCCCCGCCCCTGCCCTGCC | 970 |
| | GGCCGCCGCCCCCGCCCCTGCCCTG | 971 |
| | CTGGCCGCCGCCCCCGCCCCTGCCC | 972 |
| | CCCTGGCCGCCGCCCCCGCCCCTGC | 973 |
| | TGCCCTGGCCGCCGCCCCCGCCCCT | 974 |
| | TCTGCCCTGGCCGCCGCCCCCGCCC | 975 |
| | CCTCTGCCCTGGCCGCCGCCCCCGC | 976 |
| | ACCCTCTGCCCTGGCCGCCGCCCCC | 977 |
| | GCACCCTCTGCCCTGGCCGCCGCCC | 978 |
| | GCGCACCCTCTGCCCTGGCCGCCGGC | 979 |
| c.547 - 6 | AGAGATGGGGGTTTATTGATGTTCC | 980 |
| | GAAGAGATGGGGGTTTATTGATGTT | 981 |
| | TAGAAGAGATGGGGGTTTATTGATG | 982 |
| | TCTAGAAGAGATGGGGGTTTATTGA | 983 |
| | GATCTAGAAGAGATGGGGGTTTATT | 984 |
| | TTGATCTAGAAGAGATGGGGGTTTA | 985 |
| | CTTTGATCTAGAAGAGATGGGGGTT | 986 |
| | ATCTTTGATCTAGAAGAGATGGGGG | 987 |
| | GGATCTTTGATCTAGAAGAGATGGG | 988 |
| | CTGGATCTTTGATCTAGAAGAGATG | 989 |
| | AGCTGGATCTTTGATCTAGAAGAGA | 990 |
| | TTAGCTGGATCTTTGATCTAGAAGA | 991 |
| | TGTTAGCTGGATCTTTGATCTAGAA | 992 |

In the above Table, the sequences are 25 nucleotides long however longer variants or shorter fragment are also envisioned. Optionally, in embodiments of aspects of the present invention, the antisense oligomeric compounds are selected from the group of AONs of SEQ ID NO: 603-992 and fragments and variants thereof having at least 80% sequence identity. Optionally, in embodiments of aspects of the present invention, the antisense oligomeric compounds are selected from the group of SEQ ID NO: 603-992 and fragments and variants thereof having at least 80%.83%, 85%, 87%, 90%, 92%, 93%, 94%, 95%, 96%, 97%, 98%, 99%, 99.2%, 99.3%, 99.4%, 99.5%, 99.6%, 99.7% sequence identity to SEQ ID NO: 603-992.

The present invention is also directed to sequences that are at least 80% identical to SEQ ID NO: 603-992, preferably at least 85% identical to SEQ ID NO: 603-992, more preferably at least 88% identical to SEQ ID NO: 603-992, still more preferably at least 90% identical to SEQ ID NO: 603-992, even, more preferably at least 91% identical to SEQ ID NO: 603-992, and even more preferably at least 92% identical to SEQ ID NO: 603-992, at least 93%, at least 94%, at least 95%, at least 96%, at, least 97%, at least, 98% or even more preferably at least 99% identical to SEQ ID NO: 603-992.

Optionally, in embodiments of aspects of the present invention, the antisense oligomeric compounds are selected from the group of fragments SEQ ID NO: 603-640 or 641-992, wherein the fragment is 16, 17, 18, 19, 20, 21, 22, 23, or 24 nucleotides long. Optionally, in embodiments of aspects of the present invention the antisense oligomeric compounds are selected from the group of fragments SEQ ID NO: 603-640 or 641-992, wherein the fragment is 17, 18, 19, 20, 21, or 22 nucleotides long. Optionally, in embodiments of aspects of the present invention, the antisense oligomeric compounds are selected from the group of fragments SEQ ID NO: 603-640 or 641-992, wherein the fragment is 19, 20, or 21 nucleotides long.

In a further alternative, or additional embodiment of aspects of the invention, the antisense oligomeric compounds of the invention target GAA gene sequences or sequences of gene products thereof, capable of modulating the splicing by promotion of exon 6 inclusion or intron 6 exclusion, including SEQ ID NOs: 993-2040, Again, these AONs may be 16, 17, 18, 19, 20, 21, 22, 23, 24 or more, such as 25 or 30 nucleotides in length.

TABLE 15

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.956-25_-1 | CTGGAAGGGAAGCAGCTCTGGGGTT | 993 |
| c.956-24_956 | TCTGGAAGGGAAGCAGCTCTGGGGT | 994 |
| c.956-23_957 | ATCTGGAAGGGAAGCAGCTCTGGGG | 995 |
| c.956-22_958 | CATCTGGAAGGGAAGCAGCTCTGGG | 996 |
| c.956-21_959 | ACATCTGGAAGGGAAGCAGCTCTGG | 997 |
| c.956-20_960 | CACATCTGGAAGGGAAGCAGCTCTG | 998 |
| c.956-19_961 | CCACATCTGGAAGGGAAGCAGCTCT | 999 |
| c.956-18_962 | ACCACATCTGGAAGGGAAGCAGCTC | 1000 |
| c.956-17_963 | GACCACATCTGGAAGGGAAGCAGCT | 1001 |
| c.956-16_964 | GGACCACATCTGGAAGGGAAGCAGC | 1002 |
| c.956-15_965 | AGGACCACATCTGGAAGGGAAGCAG | 1003 |
| c.956-14_966 | CAGGACCACATCTGGAAGGGAAGCA | 1004 |
| c.956-13_967 | GCAGGACCACATCTGGAAGGGAAGC | 1005 |
| c.956-12_968 | TGCAGGACCACATCTGGAAGGGAAG | 1006 |
| c.956-11_969 | CTGCAGGACCACATCTGGAAGGGAA | 1007 |
| c.956-10_970 | GCTGCAGGACCACATCTGGAAGGGA | 1008 |
| c.956-9_971 | GGCTGCAGGACCACATCTGGAAGGG | 1009 |
| c.956-8_972 | CGGCTGCAGGACCACATCTGGAAGG | 1010 |
| c.956-7_973 | TCGGCTGCAGGACCACATCTGGAAG | 1011 |
| c.956-6_974 | CTCGGCTGCAGGACCACATCTGGAA | 1012 |
| c.956-5_975 | GCTCGGCTGCAGGACCACATCTGGA | 1013 |
| c.956-4_976 | GGCTCGGCTGCAGGACCACATCTGG | 1014 |
| c.956-3_977 | GGGCTCGGCTGCAGGACCACATCTG | 1015 |
| c.956-2_978 | AGGGCTCGGCTGCAGGACCACATCT | 1016 |
| c.956-1_979 | CAGGGCTCGGCTGCAGGACCACATC | 1017 |
| c.956_980 | GCAGGGCTCGGCTGCAGGACCACAT | 1018 |
| c.957_981 | GGCAGGGCTCGGCTGCAGGACCACA | 1019 |
| c.958_982 | GGGCAGGGCTCGGCTGCAGGACCAC | 1020 |
| c.959_983 | AGGGCAGGGCTCGGCTGCAGGACCA | 1021 |
| c.960_984 | AAGGGCAGGGCTCGGCTGCAGGACC | 1022 |
| c.961_985 | TAAGGGCAGGGCTCGGCTGCAGGAC | 1023 |
| c.962_986 | CTAAGGGCAGGGCTCGGCTGCAGGA | 1024 |
| c.963_987 | GCTAAGGGCAGGGCTCGGCTGCAGG | 1025 |
| c.964_988 | AGCTAAGGGCAGGGCTCGGCTGCAG | 1026 |
| c.965_989 | CAGCTAAGGGCAGGGCTCGGCTGCA | 1027 |
| c.966_990 | CCAGCTAAGGGCAGGGCTCGGCTGC | 1028 |
| c.967_991 | TCCAGCTAAGGGCAGGGCTCGGCTG | 1029 |
| c.968_992 | CTCCAGCTAAGGGCAGGGCTCGGCT | 1030 |
| c.969_993 | CCTCCAGCTAAGGGCAGGGCTCGGC | 1031 |
| c.970_994 | ACCTCCAGCTAAGGGCAGGGCTCGG | 1032 |
| c.971_995 | GACCTCCAGCTAAGGGCAGGGCTCG | 1033 |
| c.972_996 | CGACCTCCAGCTAAGGGCAGGGCTC | 1034 |
| c.973_997 | TCGACCTCCAGCTAAGGGCAGGGCT | 1035 |
| c.974_998 | GTCGACCTCCAGCTAAGGGCAGGGC | 1036 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.975_999 | TGTCGACCTCCAGCTAAGGGCAGGG | 1037 |
| c.976_1000 | CTGTCGACCTCCAGCTAAGGGCAGG | 1038 |
| c.977_1001 | CCTGTCGACCTCCAGCTAAGGGCAG | 1039 |
| c.978_1002 | ACCTGTCGACCTCCAGCTAAGGGCA | 1040 |
| c.979_1003 | CACCTGTCGACCTCCAGCTAAGGGC | 1041 |
| c.980_1004 | CCACCTGTCGACCTCCAGCTAAGGG | 1042 |
| c.981_1005 | CCCACCTGTCGACCTCCAGCTAAGG | 1043 |
| c.982_1006 | TCCCACCTGTCGACCTCCAGCTAAG | 1044 |
| c.983_1007 | ATCCCACCTGTCGACCTCCAGCTAA | 1045 |
| c.984_1008 | GATCCCACCTGTCGACCTCCAGCTA | 1046 |
| c.985_1009 | GGATCCCACCTGTCGACCTCCAGCT | 1047 |
| c.986_1010 | AGGATCCCACCTGTCGACCTCCAGC | 1048 |
| c.987_1011 | CAGGATCCCACCTGTCGACCTCCAG | 1049 |
| c.988_1012 | CCAGGATCCCACCTGTCGACCTCCA | 1050 |
| c.989_1013 | TCCAGGATCCCACCTGTCGACCTCC | 1051 |
| c.990_1014 | ATCCAGGATCCCACCTGTCGACCTC | 1052 |
| c.991_1015 | CATCCAGGATCCCACCTGTCGACCT | 1053 |
| c.992_1016 | ACATCCAGGATCCCACCTGTCGACC | 1054 |
| c.993_1017 | GACATCCAGGATCCCACCTGTCGAC | 1055 |
| c.994_1018 | AGACATCCAGGATCCCACCTGTCGA | 1056 |
| c.995_1019 | TAGACATCCAGGATCCCACCTGTCG | 1057 |
| c.996_1020 | GTAGACATCCAGGATCCCACCTGTC | 1058 |
| c.997_1021 | TGTAGACATCCAGGATCCCACCTGT | 1059 |
| c.998_1022 | ATGTAGACATCCAGGATCCCACCTG | 1060 |
| c.999_1023 | GATGTAGACATCCAGGATCCCACCT | 1061 |
| c.1000_1024 | AGATGTAGACATCCAGGATCCCACC | 1062 |
| c.1001_1025 | AAGATGTAGACATCCAGGATCCCAC | 1063 |
| c.1002_1026 | GAAGATGTAGACATCCAGGATCCCA | 1064 |
| c.1003_1027 | GGAAGATGTAGACATCCAGGATCCC | 1065 |
| c.1004_1028 | AGGAAGATGTAGACATCCAGGATCC | 1066 |
| c.1005_1029 | CAGGAAGATGTAGACATCCAGGATC | 1067 |
| c.1006_1030 | CCAGGAAGATGTAGACATCCAGGAT | 1068 |
| c.1007_1031 | CCCAGGAAGATGTAGACATCCAGGA | 1069 |
| c.1008_1032 | GCCCAGGAAGATGTAGACATCCAGG | 1070 |
| c.1009_1033 | GGCCCAGGAAGATGTAGACATCCAG | 1071 |
| c.1010_1034 | GGGCCCAGGAAGATGTAGACATCCA | 1072 |
| c.1011_1035 | TGGGCCCAGGAAGATGTAGACATCC | 1073 |
| c.1012_1036 | CTGGGCCCAGGAAGATGTAGACATC | 1074 |
| c.1013_1037 | TCTGGGCCCAGGAAGATGTAGACAT | 1075 |
| c.1014_1038 | CTCTGGGCCCAGGAAGATGTAGACA | 1076 |
| c.1015_1039 | GCTCTGGGCCCAGGAAGATGTAGAC | 1077 |
| c.1016_1040 | GGCTCTGGGCCCAGGAAGATGTAGA | 1078 |
| c.1017_1041 | GGGCTCTGGGCCCAGGAAGATGTAG | 1079 |
| c.1018_1042 | TGGGCTCTGGGCCCAGGAAGATGTA | 1080 |
| c.1019_1043 | TTGGGCTCTGGGCCCAGGAAGATGT | 1081 |
| c.1020_1044 | CTTGGGCTCTGGGCCCAGGAAGATG | 1082 |
| c.1021_1045 | TCTTGGGCTCTGGGCCCAGGAAGAT | 1083 |
| c.1022_1046 | CTCTTGGGCTCTGGGCCCAGGAAGA | 1084 |
| c.1023_1047 | GCTCTTGGGCTCTGGGCCCAGGAAG | 1085 |
| c.1024_1048 | CGCTCTTGGGCTCTGGGCCCAGGAA | 1086 |
| c.1025_1049 | ACGCTCTTGGGCTCTGGGCCCAGGA | 1087 |
| c.1026_1050 | CACGCTCTTGGGCTCTGGGCCCAGG | 1088 |
| c.1027_1051 | CCACGCTCTTGGGCTCTGGGCCCAG | 1089 |
| c.1028_1052 | ACCACGCTCTTGGGCTCTGGGCCCA | 1090 |
| c.1029_1053 | CACCACGCTCTTGGGCTCTGGGCCC | 1091 |
| c.1030_1054 | GCACCACGCTCTTGGGCTCTGGGCC | 1092 |
| c.1031_1055 | TGCACCACGCTCTTGGGCTCTGGGC | 1093 |
| c.1032_1056 | CTGCACCACGCTCTTGGGCTCTGGG | 1094 |
| c.1033_1057 | GCTGCACCACGCTCTTGGGCTCTGG | 1095 |
| c.1034_1058 | TGCTGCACCACGCTCTTGGGCTCTG | 1096 |
| c.1035_1059 | CTGCTGCACCACGCTCTTGGGCTCT | 1097 |
| c.1036_1060 | ACTGCTGCACCACGCTCTTGGGCTC | 1098 |
| c.1037_1061 | TACTGCTGCACCACGCTCTTGGGCT | 1099 |
| c.1038_1062 | GTACTGCTGCACCACGCTCTTGGGC | 1100 |
| c.1039_1063 | GGTACTGCTGCACCACGCTCTTGGG | 1101 |
| c.1040_1064 | AGGTACTGCTGCACCACGCTCTTGG | 1102 |
| c.1041_1065 | CAGGTACTGCTGCACCACGCTCTTG | 1103 |
| c.1042_1066 | CCAGGTACTGCTGCACCACGCTCTT | 1104 |
| c.1043_1067 | TCCAGGTACTGCTGCACCACGCTCT | 1105 |
| c.1044_1068 | GTCCAGGTACTGCTGCACCACGCTC | 1106 |
| c.1045_1069 | CGTCCAGGTACTGCTGCACCACGCT | 1107 |
| c.1046_1070 | ACGTCCAGGTACTGCTGCACCAGGC | 1108 |
| c.1047_1071 | AACGTCCAGGTACTGCTGCACCACG | 1109 |
| c.1048_1072 | CAACGTCCAGGTACTGCTGCACCAC | 1110 |
| c.1049_1073 | ACAACGTCCAGGTACTGCTGCACCA | 1111 |
| c.1050_1074 | CACAACGTCCAGGTACTGCTGCACC | 1112 |
| c.1051_1075 | CCACAACGTCCAGGTACTGCTGCAC | 1113 |
| c.1052_1075+1 | CCCACAACGTCCAGGTACTGCTGCA | 1114 |
| c.1053_1075+2 | ACCCACAACGTCCAGGTACTGCTGC | 1115 |
| c.1054_1075+3 | TACCCACAACGTCCAGGTACTGCTG | 1116 |
| c.1055_1075+4 | CTACCCACAACGTCCAGGTACTGCT | 1117 |
| c.1056_1075+5 | CCTACCCACAACGTCCAGGTACTGC | 1118 |
| c.1057_1075+6 | CCCTACCCACAACGTCCAGGTACTG | 1119 |
| c.1058_1075+7 | GCCCTACCCACAACGTCCAGGTACT | 1120 |
| c.1059_1075+8 | GGCCCTACCCACAACGTCCAGGTAC | 1121 |
| c.1060_1075+9 | AGGCCCTACCCACAACGTCCAGGTA | 1122 |
| c.1061_1075+10 | CAGGCCCTACCCACAACGTCCAGGT | 1123 |
| c.1062_1075+11 | GCAGGCCCTACCCACAACGTCCAGG | 1124 |
| c.1063_1075+12 | AGCAGGCCCTACCCACAACGTCCAG | 1125 |
| c.1064_1075+13 | GAGCAGGCCCTACCCACAACGTCCA | 1126 |
| c.1065_1075+14 | GGAGCAGGCCCTACCCACAACGTCC | 1127 |
| c.1066_1075+15 | GGGAGCAGGCCCTACCCACAACGTC | 1128 |
| c.1067_1075+16 | AGGGAGCAGGCCCTACCCACAACGT | 1129 |
| c.1068_1075+17 | CAGGGAGCAGGCCCTACCCACAACG | 1130 |
| c.1069_1075+18 | CCAGGGAGCAGGCCCTACCCACAAC | 1131 |
| c.1070_1075+19 | GCCAGGGAGCAGGCCCTACCCACAA | 1132 |
| c.1071_1075+20 | GGCCAGGGAGCAGGCCCTACCCACA | 1133 |
| c.1072_1075+21 | CGGCCAGGGAGCAGGCCCTACCCAC | 1134 |
| c.1073_1075+22 | GCGGCCAGGGAGCAGGCCCTACCCA | 1135 |
| c.1074_1075+23 | CGCGGCCAGGGAGCAGGCCCTACCC | 1136 |
| c.1075_1075+24 | CCGCGGCCAGGGAGCAGGCCCTACC | 1137 |
| C.1075+1_+25 | GCCGCGGCCAGGGAGCAGGCCCTAC | 1138 |
| C.1075+2_+26 | GGCCGCGGCCAGGGAGCAGGCCCTA | 1139 |
| C.1075+3_+27 | GGGCCGCGGCCAGGGAGCAGGCCCT | 1140 |
| C.1075+4_+28 | GGGGCCGCGGCCAGGGAGCAGGCCC | 1141 |
| C.1075+5_+29 | GGGGGCCGCGGCCAGGGAGCAGGCC | 1142 |
| C.1075+6_+30 | CGGGGGCCGCGGCCAGGGAGCAGGC | 1143 |
| C.1075+7_+31 | GCGGGGGCCGCGGCCAGGGAGCAGG | 1144 |
| C.1075+8_+32 | GGCGGGGGCCGCGGCCAGGGAGCAG | 1145 |
| C.1075+9_+33 | GGGCGGGGGCCGCGGCCAGGGAGCA | 1146 |
| C.1075+10_+34 | GGGGCGGGGGCCGCGGCCAGGGAGC | 1147 |
| C.1075+11_+35 | TGGGGCGGGGGCCGCGGCCAGGGAG | 1148 |
| C.1075+12_+36 | TTGGGGCGGGGGCCGCGGCCAGGGA | 1149 |
| C.1075+13_+37 | CTTGGGGCGGGGGCCGCGGCCAGGG | 1150 |
| C.1075+14_+38 | CCTTGGGGCGGGGGCCGCGGCCAGG | 1151 |
| C.1075+15_+39 | GCCTTGGGGCGGGGGCCGCGGCCAG | 1152 |
| C.1075+16_+40 | AGCCTTGGGGCGGGGGCCGCGGCCA | 1153 |
| C.1075+17_1076-39 | GAGCCTTGGGGCGGGGGCCGCGGCC | 1154 |
| C.1075+18_1076-38 | GGAGCCTTGGGGCGGGGGCCGCGGC | 1155 |
| C.1075+19_1076-37 | GGGAGCCTTGGGGCGGGGGCCGCGG | 1156 |
| C.1075+20_1076-36 | AGGGAGCCTTGGGGCGGGGGCCGCG | 1157 |
| C.1075+21_1076-35 | GAGGGAGCCTTGGGGCGGGGGCCGC | 1158 |
| C.1075+22_1076-34 | GGAGGGAGCCTTGGGGCGGGGGCCG | 1159 |
| C.1075+23_1076-33 | AGGAGGGAGCCTTGGGGCGGGGGCC | 1160 |
| C.1075+24_1076-32 | GAGGAGGGAGCCTTGGGGCGGGGGC | 1161 |
| C.1075+25_1076-31 | GGAGGAGGGAGCCTTGGGGCGGGGG | 1162 |
| C.1075+26_1076-30 | GGGAGGAGGGAGCCTTGGGGCGGGG | 1163 |
| C.1075+27_1076-29 | AGGGAGGAGGGAGCCTTGGGGCGGG | 1164 |
| C.1075+28_1076-28 | GAGGGAGGAGGGAGCCTTGGGGCGG | 1165 |
| C.1075+29_1076-27 | GGAGGGAGGAGGGAGCCTTGGGGCG | 1166 |
| C.1075+30_1076-26 | GGGAGGGAGGAGGGAGCCTTGGGGC | 1167 |
| C.1075+31_1076-25 | AGGGAGGGAGGAGGGAGCCTTGGGG | 1168 |
| C.1075+32_1076-24 | GAGGGAGGGAGGAGGGAGCCTTGGG | 1169 |
| C.1075+33_1076-23 | TGAGGGAGGGAGGAGGGAGCCTTGG | 1170 |
| C.1075+34_1076-22 | ATGAGGGAGGGAGGAGGGAGCCTTG | 1171 |
| C.1075+35_1076-21 | CATGAGGGAGGGAGGAGGGAGCCTT | 1172 |
| C.1075+36_1076-20 | TCATGAGGGAGGGAGGAGGGAGCCT | 1173 |
| C.1075+37_1076-19 | TTCATGAGGGAGGGAGGAGGGAGCC | 1174 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| C.1075+38_1076-18 | CTTCATGAGGGAGGGAGGAGGGAGC | 1175 |
| C.1075+39_1076-17 | ACTTCATGAGGGAGGGAGGAGGGAG | 1176 |
| C.1075+40_1076-16 | GACTTCATGAGGGAGGGAGGAGGGA | 1177 |
| c.1076-39_-15 | CGACTTCATGAGGGAGGGAGGAGGG | 1178 |
| c.1076-38_-14 | CCGACTTCATGAGGGAGGGAGGAGG | 1179 |
| c.1076-37_-13 | GCCGACTTCATGAGGGAGGGAGGAG | 1180 |
| c.1076-36_-12 | CGCCGACTTCATGAGGGAGGGAGGA | 1181 |
| c.1076-35_-11 | ACGCCGACTTCATGAGGGAGGGAGG | 1182 |
| c.1076-34_-10 | AACGCCGACTTCATGAGGGAGGGAG | 1183 |
| c.1076-33_-9 | CAACGCCGACTTCATGAGGGAGGGA | 1184 |
| c.1076-32_-8 | CCAACGCCGACTTCATGAGGGAGGG | 1185 |
| c.1076-31_-7 | GCCAACGCCGACTTCATGAGGGAGG | 1186 |
| c.1076-30_-6 | GGCCAACGCCGACTTCATGAGGGAG | 1187 |
| c.1076-29_-5 | AGGCCAACGCCGACTTCATGAGGGA | 1188 |
| c.1076-28_-4 | CAGGCCAACGCCGACTTCATGAGGG | 1189 |
| c.1076-27_-3 | GCAGGCCAACGCCGACTTCATGAGG | 1190 |
| c.1076-26_-2 | TGCAGGCCAACGCCGACTTCATGAG | 1191 |
| c.1076-25_-1 | CTGCAGGCCAACGCCGACTTCATGA | 1192 |
| c.1076-24_1076 | CCTGCAGGCCAACGCCGACTTCATG | 1193 |
| c.1076-23_1077 | TCCTGCAGGCCAACGCCGACTTCAT | 1194 |
| c.1076-22_1078 | ATCCTGCAGGCCAACGCCGACTTCA | 1195 |
| c.1076-21_1079 | TATCCTGCAGGCCAACGCCGACTTC | 1196 |
| c.1076-20_1080 | GTATCCTGCAGGCCAACGCCGACTT | 1197 |
| c.1076-19_1081 | GGTATCCTGCAGGCCAACGCCGACT | 1198 |
| c.1076-18_1082 | GGGTATCCTGCAGGCCAACGCCGAC | 1199 |
| c.1076-17_1083 | CGGGTATCCTGCAGGCCAACGCCGA | 1200 |
| c.1076-16_1084 | ACGGGTATCCTGCAGGCCAACGCCG | 1201 |
| c.1076-15_1085 | AACGGGTATCCTGCAGGCCAACGCC | 1202 |
| c.1076-14_1086 | GAACGGGTATCCTGCAGGCCAACGC | 1203 |
| c.1076-13_1087 | TGAACGGGTATCCTGCAGGCCAACG | 1204 |
| c.1076-12_1088 | ATGAACGGGTATCCTGCAGGCCAAC | 1205 |
| c.1076-11_1089 | CATGAACGGGTATCCTGCAGGCCAA | 1206 |
| c.1076-10_1090 | GCATGAACGGGTATCCTGCAGGCCA | 1207 |
| c.1076-9_1091 | GGCATGAACGGGTATCCTGCAGGCC | 1208 |
| c.1076-8_1092 | CGGCATGAACGGGTATCCTGCAGGC | 1209 |
| c.1076-7_1093 | GCGGCATGAACGGGTATCCTGCAGG | 1210 |
| c.1076-6_1094 | GGCGGCATGAACGGGTATCCTGCAG | 1211 |
| c.1076-5_1095 | TGGCGGCATGAACGGGTATCCTGCA | 1212 |
| c.1076-4_1096 | ATGGCGGCATGAACGGGTATCCTGC | 1213 |
| c.1076-3_1097 | TATGGCGGCATGAACGGGTATCCTG | 1214 |
| c.1076-2_1098 | GTATGGCGGCATGAACGGGTATCCT | 1215 |
| c.1076-1_1099 | AGTATGGCGGCATGAACGGGTATCC | 1216 |
| c.1076_1100 | CAGTATGGCGGCATGAACGGGTATC | 1217 |
| c.1077_1101 | CCAGTATGGCGGCATGAACGGGTAT | 1218 |
| c.1078_1102 | CCCAGTATGGCGGCATGAACGGGTA | 1219 |
| c.1079_1103 | CCCCAGTATGGCGGCATGAACGGGT | 1220 |
| c.1080_1104 | GCCCCAGTATGGCGGCATGAACGGG | 1221 |
| c.1081_1105 | GGCCCCAGTATGGCGGCATGAACGG | 1222 |
| c.1082_1106 | AGGCCCCAGTATGGCGGCATGAACG | 1223 |
| c.1083_1107 | CAGGCCCCAGTATGGCGGCATGAAC | 1224 |
| c.1084_1108 | CCAGGCCCCAGTATGGCGGCATGAA | 1225 |
| c.1085_1109 | CCCAGGCCCCAGTATGGCGGCATGA | 1226 |
| c.1086_1110 | GCCCAGGCCCCAGTATGGCGGCATG | 1227 |
| c.1087_1111 | AGCCCAGGCCCCAGTATGGCGGCAT | 1228 |
| c.1088_1112 | AAGCCCAGGCCCCAGTATGGCGGCA | 1229 |
| c.1089_1113 | GAAGCCCAGGCCCCAGTATGGCGGC | 1230 |
| c.1090_1114 | GGAAGCCCAGGCCCCAGTATGGCGG | 1231 |
| c.1091_1115 | TGGAAGCCCAGGCCCCAGTATGGCG | 1232 |
| c.1092_1116 | GTGGAAGCCCAGGCCCCAGTATGGC | 1233 |
| c.1093_1117 | GGTGGAAGCCCAGGCCCCAGTATGG | 1234 |
| c.1094_1118 | AGGTGGAAGCCCAGGCCCCAGTATG | 1235 |
| c.1095_1119 | CAGGTGGAAGCCCAGGCCCCAGTAT | 1236 |
| c.1096_1120 | ACAGGTGGAAGCCCAGGCCCCAGTA | 1237 |
| c.1097_1121 | CACAGGTGGAAGCCCAGGCCCCAGT | 1238 |
| c.1098_1122 | GCACAGGTGGAAGCCCAGGCCCCAG | 1239 |
| c.1099_1123 | GGCACAGGTGGAAGCCCAGGCCCCA | 1240 |
| c.1100_1124 | CGGCACAGGTGGAAGCCCAGGCCCC | 1241 |
| c.1101_1125 | GCGGCACAGGTGGAAGCCCAGGCCC | 1242 |
| c.1102_1126 | AGCGGCACAGGTGGAAGCCCAGGCC | 1243 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.1103_1127 | CAGCGGCACAGGTGGAAGCCCAGGC | 1244 |
| c.1104_1128 | CCAGCGGCACAGGTGGAAGCCCAGG | 1245 |
| c.1105_1129 | CCCAGCGGCACAGGTGGAAGCCCAG | 1246 |
| c.1106_1130 | CCCCAGCGGCACAGGTGGAAGCCCA | 1247 |
| c.1107_1131 | GCCCCAGCGGCACAGGTGGAAGCCC | 1248 |
| c.1108_1132 | AGCCCCAGCGGCACAGGTGGAAGCC | 1249 |
| c.1109_1133 | TAGCCCCAGCGGCACAGGTGGAAGC | 1250 |
| c.1110_1134 | GTAGCCCCAGCGGCACAGGTGGAAG | 1251 |
| c.1111_1135 | AGTAGCCCCAGCGGCACAGGTGGAA | 1252 |
| c.1112_1136 | GAGTAGCCCCAGCGGCACAGGTGGA | 1253 |
| c.1113_1137 | GGAGTAGCCCCAGCGGCACAGGTGG | 1254 |
| c.1114_1138 | AGGAGTAGCCCCAGCGGCACAGGTG | 1255 |
| c.1115_1139 | GAGGAGTAGCCCCAGCGGCACAGGT | 1256 |
| c.1116_1140 | GGAGGAGTAGCCCCAGCGGCACAGG | 1257 |
| c.1117_1141 | TGGAGGAGTAGCCCCAGCGGCACAG | 1258 |
| c.1118_1142 | GTGGAGGAGTAGCCCCAGCGGCACA | 1259 |
| c.1119_1143 | GGTGGAGGAGTAGCCCCAGCGGCAC | 1260 |
| c.1120_1144 | CGGTGGAGGAGTAGCCCCAGCGGCA | 1261 |
| c.1121_1145 | GCGGTGGAGGAGTAGCCCCAGCGGC | 1262 |
| c.1122_1146 | AGCGGTGGAGGAGTAGCCCCAGCGG | 1263 |
| c.1123_1147 | TAGCGGTGGAGGAGTAGCCCCAGCG | 1264 |
| c.1124_1148 | ATAGCGGTGGAGGAGTAGCCCCAGC | 1265 |
| c.1125_1149 | GATAGCGGTGGAGGAGTAGCCCCAG | 1266 |
| c.1126_1150 | TGATAGCGGTGGAGGAGTAGCCCCA | 1267 |
| c.1127_1151 | GTGATAGCGGTGGAGGAGTAGCCCC | 1268 |
| c.1128_1152 | GGTGATAGCGGTGGAGGAGTAGCCC | 1269 |
| c.1129_1153 | GGGTGATAGCGGTGGAGGAGTAGCC | 1270 |
| c.1130_1154 | CGGGTGATAGCGGTGGAGGAGTAGC | 1271 |
| c.1131_1155 | GCGGGTGATAGCGGTGGAGGAGTAG | 1272 |
| c.1132_1156 | GGCGGGTGATAGCGGTGGAGGAGTA | 1273 |
| c.1133_1157 | TGGCGGGTGATAGCGGTGGAGGAGT | 1274 |
| c.1134_1158 | CTGGCGGGTGATAGCGGTGGAGGAG | 1275 |
| c.1135_1159 | CCTGGCGGGTGATAGCGGTGGAGGA | 1276 |
| c.1136_1160 | ACCTGGCGGGTGATAGCGGTGGAGG | 1277 |
| c.1137_1161 | CACCTGGCGGGTGATAGCGGTGGAG | 1278 |
| c.1138_1162 | CCACCTGGCGGGTGATAGCGGTGGA | 1279 |
| c.1139_1163 | ACCACCTGGCGGGTGATAGCGGTGG | 1280 |
| c.1140_1164 | CACCACCTGGCGGGTGATAGCGGTG | 1281 |
| c.1141_1165 | CCACCACCTGGCGGGTGATAGCGCT | 1282 |
| c.1142_1166 | TCCACCACCTGGCGGGTGATAGCGG | 1283 |
| c.1143_1167 | CTCCACCACCTGGCGGGTGATAGCG | 1284 |
| c.1144_1168 | TCTCCACCACCTGGCGGGTGATAGC | 1285 |
| c.1145_1169 | TTCTCCACCACCTGGCGGGTGATAG | 1286 |
| c.1146_1170 | GTTCTCCACCACCTGGCGGGTGATA | 1287 |
| c.1147_1171 | TGTTCTCCACCACCTGGCGGGTGAT | 1288 |
| c.1148_1172 | ATGTTCTCCACCACCTGGCGGGTGA | 1289 |
| c.1149_1173 | CATGTTCTCCACCACCTGGCGGGTG | 1290 |
| c.1150_1174 | TCATGTTCTCCACCACCTGGCGGGT | 1291 |
| c.1151_1175 | GTCATGTTCTCCACCACCTGGCGGG | 1292 |
| c.1152_1176 | GGTCATGTTCTCCACCACCTGGCGG | 1293 |
| c.1153_1177 | TGGTCATGTTCTCCACCACCTGGCG | 1294 |
| c.1154_1178 | CTGGTCATGTTCTCCACCACCTGGC | 1295 |
| c.1155_1179 | CCTGGTCATGTTCTCCACCACCTGG | 1296 |
| c.1156_1180 | CCCTGGTCATGTTCTCCACCACCTG | 1297 |
| c.1157_1181 | GCCCTGGTCATGTTCTCCACCACCT | 1298 |
| c.1158_1182 | GGCCCTGGTCATGTTCTCCACCACC | 1299 |
| c.1159_1183 | GGGCCCTGGTCATGTTCTCCACCAC | 1300 |
| c.1160_1184 | TGGGCCCTGGTCATGTTCTCCACCA | 1301 |
| c.1161_1185 | GTGGGCCCTGGTCATGTTCTCCACC | 1302 |
| c.1162_1186 | AGTGGGCCCTGGTCATGTTCTCCAC | 1303 |
| c.1163_1187 | AAGTGGGCCCTGGTCATGTTCTCCA | 1304 |
| c.1164_1188 | GAAGTGGGCCCTGGTCATGTTCTCC | 1305 |
| c.1165_1189 | GGAAGTGGGCCCTGGTCATGTTCTC | 1306 |
| c.1166_1190 | GGGAAGTGGGCCCTGGTCATGTTCT | 1307 |
| c.1167_1191 | GGGGAAGTGGGCCCTGGTCATGTTC | 1308 |
| c.1168_1192 | GGGGGAAGTGGGCCCTGGTCATGTT | 1309 |
| c.1169_1193 | AGGGGGAAGTGGGCCCTGGTCATGT | 1310 |
| c.1170_1194 | CAGGGGGAAGTGGGCCCTGGTCATG | 1311 |
| c.1171_1194+1 | CCAGGGGGAAGTGGGCCCTGGTCAT | 1312 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.1172_1194+2 | ACCAGGGGGAAGTGGGCCCTGGTCA | 1313 |
| c.1173_1194+3 | CACCAGGGGGAAGTGGGCCCTGGTC | 1314 |
| c.1174_1194+4 | TCACCAGGGGGAAGTGGGCCCTGGT | 1315 |
| c.1175_1194+5 | CTCACCAGGGGGAAGTGGGCCCTGG | 1316 |
| c.1176_1194+6 | ACTCACCAGGGGGAAGTGGGCCCTG | 1317 |
| c.1177_1194+7 | AACTCACCAGGGGGAAGTGGGCCCT | 1318 |
| c.1178_1194+8 | CAACTCACCAGGGGGAAGTGGGCCC | 1319 |
| c.1179_1194+9 | CCAACTCACCAGGGGGAAGTGGGCC | 1320 |
| c.1180_1194+10 | CCCAACTCACCAGGGGGAAGTGGGC | 1321 |
| c.1181_1194+11 | CCCCAACTCACCAGGGGGAAGTGGG | 1322 |
| c.1182_1194+12 | ACCCCAACTCACCAGGGGGAAGTGG | 1323 |
| c.1183_1194+13 | CACCCCAACTCACCAGGGGGAAGTG | 1324 |
| c.1184_1194+14 | CCACCCCAACTCACCAGGGGGAAGT | 1325 |
| c.1185_1194+15 | ACCACCCCAACTCACCAGGGGGAAG | 1326 |
| c.1186_1194+16 | CACCACCCCAACTCACCAGGGGGAA | 1327 |
| c.1187_1194+17 | CCACCACCCCAACTCACCAGGGGGA | 1328 |
| c.1188_1194+18 | GCCACCACCCCAACTCACCAGGGGG | 1329 |
| c.1189_1194+19 | TGCCACCACCCCAACTCACCAGGGG | 1330 |
| c.1190_1194+20 | CTGCCACCACCCCAACTCACCAGGG | 1331 |
| c.1191_1194+21 | CCTGCCACCACCCCAACTCACCAGG | 1332 |
| c.1192_1194+22 | CCCTGCCACCACCCCAACTCACCAG | 1333 |
| c.1193_1194+23 | CCCCTGCCACCACCCCAACTCACCA | 1334 |
| c.1194_1194+24 | TCCCCTGCCACCACCCCAACTCACC | 1335 |
| c.1194+1_+25 | CTCCCCTGCCACCACCCCAACTCAC | 1336 |
| c.956-25_-5 | AAGGGAAGCAGCTCTGGGGTT | 1337 |
| c.956-24_-4 | GAAGGGAAGCAGCTCTGGGGT | 1338 |
| c.956-23_-3 | GGAAGGGAAGCAGCTCTGGGG | 1339 |
| c.956-22_-2 | TGGAAGGGAAGCAGCTCTGGG | 1340 |
| c.956-21_-1 | CTGGAAGGGAAGCAGCTCTGG | 1341 |
| c.956-20_956 | TCTGGAAGGGAAGCAGCTCTG | 1342 |
| c.956-19_957 | ATCTGGAAGGGAAGCAGCTCT | 1343 |
| c.956-18_958 | CATCTGGAAGGGAAGCAGCTC | 1344 |
| c.956-17_959 | ACATCTGGAAGGGAAGCAGCT | 1345 |
| c.956-16_960 | CACATCTGGAAGGGAAGCAGC | 1346 |
| c.956-15_961 | CCACATCTGGAAGGGAAGCAG | 1347 |
| c.956-14_962 | ACCACATCTGGAAGGGAAGCA | 1348 |
| c.956-13_963 | GACCACATCTGGAAGGGAAGC | 1349 |
| c.956-12_964 | GGACCACATCTGGAAGGGAAG | 1350 |
| c.956-11_965 | AGGACCACATCTGGAAGGGAA | 1351 |
| c.956-10_966 | CAGGACCACATCTGGAAGGGA | 1352 |
| c.956-9_967 | GCAGGACCACATCTGGAAGGG | 1353 |
| c.956-8_968 | TGCAGGACCACATCTGGAAGG | 1354 |
| c.956-7_969 | CTGCAGGACCACATCTGGAAG | 1355 |
| c.956-6_970 | GCTGCAGGACCACATCTGGAA | 1356 |
| c.956-5_971 | GGCTGCAGGACCACATCTGGA | 1357 |
| c.956-4_972 | CGGCTGCAGGACCACATCTGG | 1358 |
| c.956-3_973 | TCGGCTGCAGGACCACATCTG | 1359 |
| c.956-2_974 | CTCGGCTGCAGGACCACATCT | 1360 |
| c.956-1_975 | GCTCGGCTGCAGGACCACATC | 1361 |
| c.956_976 | GGCTCGGCTGCAGGACCACAT | 1362 |
| c.957_977 | GGGCTCGGCTGCAGGACCACA | 1363 |
| c.958_978 | AGGGCTCGGCTGCAGGACCAC | 1364 |
| c.959_979 | CAGGGCTCGGCTGCAGGACCA | 1365 |
| c.960_980 | GCAGGGCTCGGCTGCAGGACC | 1366 |
| c.961_981 | GGCAGGGCTCGGCTGCAGGAC | 1367 |
| c.962_982 | GGGCAGGGCTCGGCTGCAGGA | 1368 |
| c.963_983 | AGGGCAGGGCTCGGCTGCAGG | 1369 |
| c.964_984 | AAGGGCAGGGCTCGGCTGCAG | 1370 |
| c.965_985 | TAAGGGCAGGGCTCGGCTGCA | 1371 |
| c.966_986 | CTAAGGGCAGGGCTCGGCTGC | 1372 |
| c.967_987 | GCTAAGGGCAGGGCTCGGCTG | 1373 |
| c.968_988 | AGCTAAGGGCAGGGCTCGGCT | 1374 |
| c.969_989 | CAGCTAAGGGCAGGGCTCGGC | 1375 |
| c.970_990 | CCAGCTAAGGGCAGGGCTCGG | 1376 |
| c.971_991 | TCCAGCTAAGGGCAGGGCTCG | 1377 |
| c.972_992 | CTCCAGCTAAGGGCAGGGCTC | 1378 |
| c.973_993 | CCTCCAGCTAAGGGCAGGGCT | 1379 |
| c.974_994 | ACCTCCAGCTAAGGGCAGGGC | 1380 |
| c.975_995 | GACCTCCAGCTAAGGGCAGGG | 1381 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.976_996 | CGACCTCCAGCTAAGGGCAGG | 1382 |
| c.977_997 | TCGACCTCCAGCTAAGGGCAG | 1383 |
| c.978_998 | GTCGACCTCCAGCTAAGGGCA | 1384 |
| c.979_999 | TGTCGACCTCCAGCTAAGGGC | 1385 |
| c.980_1000 | CTGTCGACCTCCAGCTAAGGG | 1386 |
| c.981_1001 | CCTGTCGACCTCCAGCTAACG | 1387 |
| c.982_1002 | ACCTGTCGACCTCCAGCTAAG | 1388 |
| c.983_1003 | CACCTGTCGACCTCCAGCTAA | 1389 |
| c.984_1004 | CCACCTGTCGACCTCCAGCTA | 1390 |
| c.985_1005 | CCCACCTGTCGACCTCCAGCT | 1391 |
| c.986_1006 | TCCCACCTGTCGACCTCCAGC | 1392 |
| c.987_1007 | ATCCCACCTGTCGACCTCCAG | 1393 |
| c.988_1008 | GATCCCACCTGTCGACCTCCA | 1394 |
| c.989_1009 | GGATCCCACCTGTCGACCTCC | 1395 |
| c.990_1010 | AGGATCCCACCTGTCGACCTC | 1396 |
| c.991_1011 | CAGGATCCCACCTGTCGACCT | 1397 |
| c.992_1012 | CCAGGATCCCACCTGTCGACC | 1398 |
| c.993_1013 | TCCAGGATCCCACCTGTCGAC | 1399 |
| c.994_1014 | ATCCAGGATCCCACCTGTCGA | 1400 |
| c.995_1015 | CATCCAGGATCCCACCTGTCG | 1401 |
| c.996_1016 | ACATCCAGGATCCCACCTGTC | 1402 |
| c.997_1017 | GACATCCAGGATCCCACCTGT | 1403 |
| c.998_1018 | AGACATCCAGGATCCCACCTG | 1404 |
| c.999_1019 | TAGACATCCAGGATCCCACCT | 1405 |
| c.1000_1020 | GTAGACATCCAGGATCCCACC | 1406 |
| c.1001_1021 | TGTAGACATCCAGGATCCCAC | 1407 |
| c.1002_1022 | ATGTAGACATCCAGGATCCCA | 1408 |
| c.1003_1023 | GATGTAGACATCCAGGATCCC | 1409 |
| c.1004_1024 | AGATGTAGACATCCAGGATCC | 1410 |
| c.1005_1025 | AAGATGTAGACATCCAGGATC | 1411 |
| c.1006_1026 | GAAGATGTAGACATCCAGGAT | 1412 |
| c.1007_1027 | GGAAGATGTAGACATCCAGGA | 1413 |
| c.1008_1028 | AGGAAGATGTAGACATCCAGG | 1414 |
| c.1009_1029 | CAGGAAGATGTAGACATCCAG | 1415 |
| c.1010_1030 | CCAGGAAGATGTAGACATCCA | 1416 |
| c.1011_1031 | CCCAGGAAGATGTAGACATCC | 1417 |
| c.1012_1032 | GCCCAGGAAGATGTAGACATC | 1418 |
| c.1013_1033 | GGCCCAGGAAGATGTAGACAT | 1419 |
| c.1014_1034 | GGGCCCAGGAAGATGTAGACA | 1420 |
| c.1015_1035 | TGGGCCCAGGAAGATGTAGAC | 1421 |
| c.1016_1036 | CTGGGCCCAGGAAGATGTAGA | 1422 |
| c.1017_1037 | TCTGGGCCCAGGAAGATGTAG | 1423 |
| c.1018_1038 | CTCTGGGCCCAGGAAGATGTA | 1424 |
| c.1019_1039 | GCTCTGGGCCCAGGAAGATGT | 1425 |
| c.1020_1040 | GGCTCTGGGCCCAGGAAGATG | 1426 |
| c.1021_1041 | GGGCTCTGGGCCCAGGAAGAT | 1427 |
| c.1022_1042 | TGGGCTCTGGGCCCAGGAAGA | 1428 |
| c.1023_1043 | TTGGGCTCTGGGCCCAGGAAG | 1429 |
| c.1024_1044 | CTTGGGCTCTGGGCCCAGGAA | 1430 |
| c.1025_1045 | TCTTGGGCTCTGGGCCCAGGA | 1431 |
| c.1026_1046 | CTCTTGGGCTCTGGGCCCAGG | 1432 |
| c.1027_1047 | GCTCTTGGGCTCTGGGCCCAG | 1433 |
| c.1028_1048 | CGCTCTTGGGCTCTGGGCCCA | 1434 |
| c.1029_1049 | ACGCTCTTGGGCTCTGGGCCC | 1435 |
| c.1030_1050 | CACGCTCTTGGGCTCTGGGCC | 1436 |
| c.1031_1051 | CCACGCTCTTGGGCTCTGGGC | 1437 |
| c.1032_1052 | ACCACGCTCTTGGGCTCTGGG | 1438 |
| c.1033_1053 | CACCACGCTCTTGGGCTCTGG | 1439 |
| c.1034_1054 | GCACCACGCTCTTGGGCTCTG | 1440 |
| c.1035_1055 | TGCACCACGCTCTTGGGCTCT | 1441 |
| c.1036_1056 | CTGCACCACGCTCTTGGGCTC | 1442 |
| c.1037_1057 | GCTGCACCACGCTCTTGGGCT | 1443 |
| c.1038_1058 | TGCTGCACCACGCTCTTGGGC | 1444 |
| c.1039_1059 | CTGCTGCACCACGCTCTTGGG | 1445 |
| c.1040_1060 | ACTGCTGCACCACGCTCTTGG | 1446 |
| c.1041_1061 | TACTGCTGCACCACGCTCTTG | 1447 |
| c.1042_1062 | GTACTGCTGCACCACGCTCTT | 1448 |
| c.1043_1063 | GGTACTGCTGCACCACGCTCT | 1449 |
| c.1044_1064 | AGGTACTGCTGCACCACGCTC | 1450 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.1045_1065 | CAGGTACTGCTGCACCACGCT | 1451 |
| c.1046_1066 | CCAGGTACTGCTGCACCACGC | 1452 |
| c.1047_1067 | TCCAGGTACTGCTGCACCACG | 1453 |
| c.1048_1068 | GTCCAGGTACTGCTGCACCAC | 1454 |
| c.1049_1069 | CGTCCAGGTACTGCTGCACCA | 1455 |
| c.1050_1070 | ACGTCCAGCTACTGCTGCACC | 1456 |
| c.1051_1071 | AACGTCCAGGTACTGCTGCAC | 1457 |
| c.1052_1072 | CAACGTCCAGGTACTGCTGCA | 1458 |
| c.1053_1073 | ACAACGTCCAGGTACTGCTGC | 1459 |
| c.1054_1074 | CACAACGTCCAGGTACTGCTG | 1460 |
| c.1055_1075 | CCACAACGTCCAGGTACTGCT | 1461 |
| c.1056_1075+1 | CCCACAACGTCCAGGTACTGC | 1462 |
| c.1057_1075+2 | ACCCACAACGTCCAGGTACTG | 1463 |
| c.1058_1075+3 | TACCCACAACGTCCAGGTACT | 1464 |
| c.1059_1075+4 | CTACCCACAACGTCCAGGTAC | 1465 |
| c.1060_1075+5 | CCTACCCACAACGTCCAGGTA | 1466 |
| c.1061_1075+6 | CCCTACCCACAACGTCCAGGT | 1467 |
| c.1062_1075+7 | GCCCTACCCACAACGTCCAGG | 1468 |
| c.1063_1075+8 | GGCCCTACCCACAACGTCCAG | 1469 |
| c.1064_1075+9 | AGGCCCTACCCACAACGTCCA | 1470 |
| c.1065_1075+10 | CAGGCCCTACCCACAACGTCC | 1471 |
| c.1066_1075+11 | GCAGGCCCTACCCACAACGTC | 1472 |
| c.1067_1075+12 | AGCAGGCCCTACCCACAACGT | 1473 |
| c.1068_1075+13 | GAGCAGGCCCTACCCACAACG | 1474 |
| c.1069_1075+14 | GGAGCAGGCCCTACCCACAAC | 1475 |
| c.1070_1075+15 | GGGAGCAGGCCCTACCCACAA | 1476 |
| c.1071_1075+16 | AGGGAGCAGGCCCTACCCACA | 1477 |
| c.1072_1075+17 | CAGGGAGCAGGCCCTACCCAC | 1478 |
| c.1073_1075+18 | CCAGGGAGCAGGCCCTACCCA | 1479 |
| c.1074_1075+19 | GCCAGGGAGCAGGCCCTACCC | 1480 |
| c.1075_1075+20 | GGCCAGGGAGCAGGCCCTACC | 1481 |
| c.1075+1_+21 | CGGCCAGGGAGCAGGCCCTAC | 1482 |
| c.1075+2_+22 | GCGGCCAGGGAGCAGGCCCTA | 1483 |
| c.1075+3_+23 | CGCGGCCAGGGAGCAGGCCCT | 1484 |
| c.1075+4_+24 | CCGCGGCCAGGGAGCAGGCCC | 1485 |
| c.1075+5_+25 | GCCGCGGCCAGGGAGCAGGCC | 1486 |
| c.1075+6_+26 | GGCCGCGGCCAGGGAGCAGGC | 1487 |
| c.1075+7_+27 | GGGCCGCGGCCAGGGAGCAGG | 1488 |
| c.1075+8_+28 | GGGGCCGCGGCCAGGGAGCAG | 1489 |
| c.1075+9_+29 | GGGGGCCGCGGCCAGGGAGCA | 1490 |
| c.1075+10_+30 | CGGGGGCCGCGGCCAGGGAGC | 1491 |
| c.1075+11_+31 | GCGGGGGCCGCGGCCAGGGAG | 1492 |
| c.1075+12_+32 | GGCGGGGGCCGCGGCCAGGGA | 1493 |
| c.1075+13_+33 | GGGCGGGGGCCGCGGCCAGGG | 1494 |
| c.1075+14_+34 | GGGGCGGGGGCCGCGGCCAGG | 1495 |
| c.1075+15_+35 | TGGGGCGGGGGCCGCGGCCAG | 1496 |
| c.1075+16_+36 | TTGGGGCGGGGGCCGCGGCCA | 1497 |
| c.1075+17_+37 | CTTGGGGCGGGGGCCGCGGCC | 1498 |
| c.1075+18_+38 | CCTTGGGGCGGGGGCCGCGGC | 1499 |
| c.1075+19_+39 | GCCTTGGGGCGGGGGCCGCGG | 1500 |
| c.1075+20_+40 | AGCCTTGGGGCGGGGGCCGCG | 1501 |
| c.1075+21_1076-39 | GAGCCTTGGGGCGGGGGCCGC | 1502 |
| c.1075+22_1076-38 | GGAGCCTTGGGGCGGGGGCCG | 1503 |
| c.1075+23_1076-37 | GGGAGCCTTGGGGCGGGGGCC | 1504 |
| c.1075+24_1076-36 | AGGGAGCCTTGGGGCGGGGGC | 1505 |
| c.1075+25_1076-35 | GAGGGAGCCTTGGGGCGGGGG | 1506 |
| c.1075+26_1076-34 | GGAGGGAGCCTTGGGGCGGGG | 1507 |
| c.1075+27_1076-33 | AGGAGGGAGCCTTGGGGCGGG | 1508 |
| c.1075+28_1076-32 | GAGGAGGGAGCCTTGGGGCGG | 1509 |
| c.1075+29_1076-31 | GGAGGAGGGAGCCTTGGGGCG | 1510 |
| c.1075+30_1076-30 | GGGAGGAGGGAGCCTTGGGGC | 1511 |
| c.1075+31_1076-29 | AGGGAGGAGGGAGCCTTGGGG | 1512 |
| c.1075+32_1076-28 | GAGGGAGGAGGGAGCCTTGGG | 1513 |
| c.1075+33_1076-27 | GGAGGGAGGAGGGAGCCTTGG | 1514 |
| c.1075+34_1076-26 | GGGAGGGAGGAGGGAGCCTTG | 1515 |
| c.1075+35_1076-25 | AGGGAGGGAGGAGGGAGCCTT | 1516 |
| c.1075+36_1076-24 | GAGGGAGGGAGGAGGGAGCCT | 1517 |
| c.1075+37_1076-23 | TGAGGGAGGGAGGAGGGAGCC | 1518 |
| c.1075+38_1076-22 | ATGAGGGAGGGAGGAGGGAGC | 1519 |
| c.1075+39_1076-21 | CATGAGGGAGGGAGGAGGGAG | 1520 |
| c.1075+40_1076-20 | TCATGAGGGAGGGAGGAGGGA | 1521 |
| c.1076-39_-19 | TTCATGAGGGAGGGAGGAGGG | 1522 |
| c.1076-38_-18 | CTTCATGAGGGAGGGAGGAGG | 1523 |
| c.1076-37_-17 | ACTTCATGAGGGAGGGAGGAG | 1524 |
| c.1076-36_-16 | GACTTCATGAGGGAGGGAGGA | 1525 |
| c.1076-35_-15 | CGACTTCATGAGGGAGGGAGG | 1526 |
| c.1076-34_-14 | CCGACTTCATGAGGGAGGGAG | 1527 |
| c.1076-33_-13 | GCCGACTTCATGAGCCAGGGA | 1528 |
| c.1076-32_-12 | CGCCGACTTCATGAGGGAGGG | 1529 |
| c.1076-31_-11 | ACGCCGACTTCATGAGGGAGG | 1530 |
| c.1076-30_-10 | AACGCCGACTTCATGAGGGAG | 1531 |
| c.1076-29_-9 | CAACGCCGACTTCATGAGGGA | 1532 |
| c.1076-28_-8 | CCAACGCCGACTTCATGAGGG | 1533 |
| c.1076-27_-7 | GCCAACGCCGACTTCATGAGG | 1534 |
| c.1076-26_-6 | GGCCAACGCCGACTTCATGAG | 1535 |
| c.1076-25_-5 | AGGCCAACGCCGACTTCATGA | 1536 |
| c.1076-24_-4 | CAGGCCAACGCCGACTTCATG | 1537 |
| c.1076-23_-3 | GCAGGCCAACGCCGACTTCAT | 1538 |
| c.1076-22_-2 | TGCAGGCCAACGCCGACTTCA | 1539 |
| c.1076-21_-1 | CTGCAGGCCAACGCCGACTTC | 1540 |
| c.1076-20_1076 | CCTGCAGGCCAACGCCGACTT | 1541 |
| c.1076-19_1077 | TCCTGCAGGCCAACGCCGACT | 1542 |
| c.1076-18_1078 | ATCCTGCAGGCCAACGCCGAC | 1543 |
| c.1076-17_1079 | TATCCTGCAGGCCAACGCCGA | 1544 |
| c.1076-16_1080 | GTATCCTGCAGGCCAACGCCG | 1545 |
| c.1076-15_1081 | GGTATCCTGCAGGCCAACGCC | 1546 |
| c.1076-14_1082 | GGGTATCCTGCAGGCCAACGC | 1547 |
| c.1076-13_1083 | CGGGTATCCTGCAGGCCAACG | 1548 |
| c.1076-12_1084 | ACGGGTATCCTGCAGGCCAAC | 1549 |
| c.1076-11_1085 | AACGGGTATCCTGCAGGCCAA | 1550 |
| c.1076-10_1086 | GAACGGGTATCCTGCAGGCCA | 1551 |
| c.1076-9_1087 | TGAACGGGTATCCTGCAGGCC | 1552 |
| c.1076-8_1088 | ATGAACGGGTATCCTGCAGGC | 1553 |
| c.1076-7_1089 | CATGAACGGGTATCCTGCAGG | 1554 |
| c.1076-6_1090 | GCATGAACGGGTATCCTGCAG | 1555 |
| c.1076-5_1091 | GGCATGAACGGGTATCCTGCA | 1556 |
| c.1076-4_1092 | CGGCATGAACGGGTATCCTGC | 1557 |
| c.1076-3_1093 | GCGGCATGAACGGGTATCCTG | 1558 |
| c.1076-2_1094 | GGCGGCATGAACGGGTATCCT | 1559 |
| c.1076-1_1095 | TGGCGGCATGAACGGGTATCC | 1560 |
| c.1076_1096 | ATGGCGGCATGAACGGGTATC | 1561 |
| c.1077_1097 | TATGGCGGCATGAACGGGTAT | 1562 |
| c.1078_1098 | GTATGGCGGCATGAACGGGTA | 1563 |
| c.1079_1099 | AGTATGGCGGCATGAACGGGT | 1564 |
| c.1080_1100 | CAGTATGGCGGCATGAACGGG | 1565 |
| c.1081_1101 | CCAGTATGGCGGCATGAACGG | 1566 |
| c.1082_1102 | CCCAGTATGGCGGCATGAACG | 1567 |
| c.1083_1103 | CCCCAGTATGGCGGCATGAAC | 1568 |
| c.1084_1104 | GCCCCAGTATGGCGGCATGAA | 1569 |
| c.1085_1105 | GGCCCCAGTATGGCGGCATGA | 1570 |
| c.1086_1106 | AGGCCCCAGTATGGCGGCATG | 1571 |
| c.1087_1107 | CAGGCCCCAGTATGGCGGCAT | 1572 |
| c.1088_1108 | CCAGGCCCCAGTATGGCGGCA | 1573 |
| c.1089_1109 | cccaggccccagtatggcggc | 1574 |
| c.1090_1110 | GCCCAGGCCCCAGTATGGCGG | 1575 |
| c.1091_1111 | AGCCCAGGCCCCAGTATGGCG | 1576 |
| c.1092_1112 | AAGCCCAGGCCCCAGTATGGC | 1577 |
| c.1093_1113 | GAAGCCCAGGCCCCAGTATGG | 1578 |
| c.1094_1114 | GGAAGCCCAGGCCCCAGTATG | 1579 |
| c.1095_1115 | TGGAAGCCCAGGCCCCAGTAT | 1580 |
| c.1096_1116 | GTGGAAGCCCAGGCCCCAGTA | 1581 |
| c.1097_1117 | GGTGGAAGCCCAGGCCCCAGT | 1582 |
| c.1098_1118 | AGGTGGAAGCCCAGGCCCCAG | 1583 |
| c.1099_1119 | CAGGTGGAAGCCCAGGCCCCA | 1584 |
| c.1100_1120 | ACAGGTGGAAGCCCAGGCCCC | 1585 |
| c.1101_1121 | CACAGGTGGAAGCCCAGGCCC | 1586 |
| c.1102_1122 | GCACAGGTGGAAGCCCAGGCC | 1587 |
| c.1103_1123 | GGCACAGGTGGAAGCCCAGGC | 1588 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.1104_1124 | CGGCACAGGTGGAAGCCCAGG | 1589 |
| c.1105_1125 | GCGGCACAGGTGGAAGCCCAG | 1590 |
| c.1106_1126 | AGCGGCACAGGTGGAAGCCCA | 1591 |
| c.1107_1127 | CAGCGGCACAGGTGGAAGCCC | 1592 |
| c.1108_1128 | CCAGCGGCACAGGTGGAAGCC | 1593 |
| c.1109_1129 | CCCAGCGGCACAGGTGGAAGC | 1594 |
| c.1110_1130 | CCCCAGCGGCACAGGTGGAAG | 1595 |
| c.1101_1131 | GCCCCAGCGGCACAGGTGGAA | 1596 |
| c.1112_1132 | AGCCCCAGCGGCACAGGTGGA | 1597 |
| c.1113_1133 | TAGCCCCAGCGGCACAGGTGG | 1598 |
| c.1114_1134 | GTAGCCCCAGCGGCACAGGTG | 1599 |
| c.1115_1135 | AGTAGCCCCAGCGGCACAGGT | 1600 |
| c.1116_1136 | GAGTAGCCCCAGCGGCACAGG | 1601 |
| c.1117_1137 | GGAGTAGCCCCAGCGGCACAG | 1602 |
| c.1118_1138 | AGGAGTAGCCCCAGCCGCACA | 1603 |
| c.1119_1139 | GAGGAGTAGCCCCAGCGGCAC | 1604 |
| c.1120_1140 | GGAGGAGTAGCCCCAGCGGCA | 1605 |
| c.1121_1141 | TGGAGGAGTAGCCCCAGCGGC | 1606 |
| c.1122_1142 | GTGGAGGAGTAGCCCCAGCGG | 1607 |
| c.1123_1143 | GGTGGAGGAGTAGCCCCAGCG | 1608 |
| c.1124_1144 | CGGTGGAGGAGTAGCCCCAGC | 1609 |
| c.1125_1145 | GCCGTGGAGGAGTAGCCCCAG | 1610 |
| c.1126_1146 | AGCGGTGGAGGAGTAGCCCCA | 1611 |
| c.1127_1147 | TAGCGGTGGAGGAGTAGCCCC | 1612 |
| c.1128_1148 | ATAGCGGTGGAGGAGTAGCCC | 1613 |
| c.1129_1149 | GATAGCGGTGGAGGAGTAGCC | 1614 |
| c.1130_1150 | TGATAGCGGTGGAGGAGTAGC | 1615 |
| c.1131_1151 | GTGATAGCGGTGGAGGAGTAG | 1616 |
| c.1132_1152 | GGTGATAGCCGTGGAGGAGTA | 1617 |
| c.1133_1153 | GGGTGATAGCGGTGGAGGAGT | 1618 |
| c.1134_1154 | CGGGTGATAGCCGTGGAGGAG | 1619 |
| c.1135_1155 | GCGGGTGATAGCGGTGGAGGA | 1620 |
| c.1136_1156 | GGCGGGTGATAGCGGTGGAGG | 1621 |
| c.1137_1157 | TGGCGGGTGATAGCGGTGGAG | 1622 |
| c.1138_1158 | CTGGCGGGTGATAGCGGTGGA | 1623 |
| c.1139_1159 | CCTGGCGGGTGATAGCGGTGG | 1624 |
| c.1140_1160 | ACCTGGCGGGTGATAGCGGTG | 1625 |
| c.1141_1161 | CACCTGGCGGGTGATAGCGGT | 1626 |
| c.1142_1162 | CCACCTGGCGGGTGATAGCGG | 1627 |
| c.1143_1163 | ACCACCTGGCGGGTGATAGCG | 1628 |
| c.1144_1164 | CACCACCTGGCGGGTGATAGC | 1629 |
| c.1145_1165 | CCACCACCTGGCGGGTGATAG | 1630 |
| c.1146_1166 | TCCACCACCTGGCGGGTGATA | 1631 |
| c.1147_1167 | CTCCACCACCTGGCGGGTGAT | 1632 |
| c.1148_1168 | TCTCCACCACCTGGCGGGTGA | 1633 |
| c.1149_1169 | TTCTCCACCACCTGGCGGGTG | 1634 |
| c.1150_1170 | GTTCTCCACCACCTGGCGGGT | 1635 |
| c.1151_1171 | TGTTCTCCACCACCTGGCGGG | 1636 |
| c.1152_1172 | ATGTTCTCCACCACCTGGCGG | 1637 |
| c.1153_1173 | CATGTTCTCCACCACCTGGCG | 1638 |
| c.1154_1174 | TCATGTTCTCCACCACCTGGC | 1639 |
| c.1155_1175 | GTCATGTTCTCCACCACCTGG | 1640 |
| c.1156_1176 | GGTCATGTTCTCCACCACCTG | 1641 |
| c.1157_1177 | TGGTCATGTTCTCCACCACCT | 1642 |
| c.1158_1178 | CTGGTCATGTTCTCCACCACC | 1643 |
| c.1159_1179 | CCTGGTCATGTTCTCCACCAC | 1644 |
| c.1160_1180 | CCCTGGTCATGTTCTCCACCA | 1645 |
| c.1161_1181 | GCCCTGGTCATGTTCTCCACC | 1646 |
| c.1162_1182 | GGCCCTGGTCATGTTCTCCAC | 1647 |
| c.1163_1183 | GGGCCCTGGTCATGTTCTCCA | 1648 |
| c.1164_1184 | TGGGCCCTGGTCATGTTCTCC | 1649 |
| c.1165_1185 | GTGGGCCCTGGTCATGTTCTC | 1650 |
| c.1166_1186 | AGTGGGCCCTGGTCATGTTCT | 1651 |
| c.1167_1187 | AAGTGGGCCCTGGTCATGTTC | 1652 |
| c.1168_1188 | GAAGTGGGCCCTGGTCATGTT | 1653 |
| c.1169_1189 | GGAAGTGGGCCCTGGTCATGT | 1654 |
| c.1170_1190 | GGGAAGTGGGCCCTGGTCATG | 1655 |
| c.1171_1191 | GGGGAAGTGGGCCCTGGTCAT | 1656 |
| c.1172_1192 | GGGGGAAGTGGGCCCTGGTCA | 1657 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.1173_1193 | AGGGGGAAGTGGGCCCTGGTC | 1658 |
| c.1174_1194 | CAGGGGGAAGTGGGCCCTGGT | 1659 |
| c.1175_1194+1 | CCAGGGGGAAGTGGGCCCTGG | 1660 |
| c.1176_1194+2 | ACCAGGGGGAAGTGGGCCCTG | 1661 |
| c.1177_1194+3 | CACCAGGGGGAAGTGGGCCCT | 1662 |
| c.1178_1194+4 | TCACCAGGGGGAAGTGGGCCC | 1663 |
| c.1179_1194+5 | CTCACCAGGGGGAAGTGGGCC | 1664 |
| c.1180_1194+6 | ACTCACCAGGGGGAAGTGGGC | 1665 |
| c.1181_1194+7 | AACTCACCAGGGGGAAGTGGG | 1666 |
| c.1182_1194+8 | CAACTCACCAGGGGGAAGTGG | 1667 |
| c.1183_1194+9 | CCAACTCACCAGGGGGAAGTG | 1668 |
| c.1184_1194+10 | CCCAACTCACCAGGGGGAAGT | 1669 |
| c.1185_1194+11 | CCCCAACTCACCAGGGGGAAG | 1670 |
| c.1186_1194+12 | ACCCCAACTCACCAGGGGGAA | 1671 |
| c.1187_1194+13 | CACCCCAACTCACCAGGGGGA | 1672 |
| c.1188_1194+14 | CCACCCCAACTCACCAGGGGG | 1673 |
| c.1189_1194+15 | ACCACCCCAACTCACCAGGGG | 1674 |
| c.1190_1194+16 | CACCACCCCAACTCACCAGGG | 1675 |
| c.1191_1194+17 | CCACCACCCCAACTCACCAGG | 1676 |
| c.1192_1194+18 | GCCACCACCCCAACTCACCAG | 1677 |
| c.1193_1194+19 | TGCCACCACCCCAACTCACCA | 1678 |
| c.1194_1194+20 | CTGCCACCACCCCAACTCACC | 1679 |
| c.1194+1_+21 | CCTGCCACCACCCCAACTCAC | 1680 |
| c.1194+2_+22 | CCCTGCCACCACCCCAACTCA | 1681 |
| c.1194+3_+23 | CCCCTGCCACCACCCCAACTC | 1682 |
| c.1194+4_+24 | TCCCCTGCCACCACCCCAACT | 1683 |
| c.1194+5_+25 | CTCCCCTGCCACCACCCCAAC | 1684 |
| c.956-25_-8 | GGAAGCAGCTCTGGGGTT | 1685 |
| c.956-24_-7 | GGGAAGCAGCTCTGGGGT | 1686 |
| c.956-23_-6 | AGGGAAGCAGCTCTGGGG | 1687 |
| c.956-22_-5 | AAGGGAAGCAGCTCTGGG | 1688 |
| c.956-21_-4 | GAAGGGAAGCAGCTCTGG | 1689 |
| c.956-20_-3 | GGAAGGGAAGCAGCTCTG | 1690 |
| c.956-19_-2 | TGGAAGGGAAGCAGCTCT | 1691 |
| c.956-18_-1 | CTGGAAGGGAAGCAGCTC | 1692 |
| c.956-17_956 | TCTGGAAGGGAAGCAGCT | 1693 |
| c.956-16_957 | ATCTGGAAGGGAAGCAGC | 1694 |
| c.956-15_958 | CATCTGGAAGGGAAGCAG | 1695 |
| c.956-14_959 | ACATCTGGAAGGGAAGCA | 1696 |
| c.956-13_960 | CACATCTGGAAGGGAAGC | 1697 |
| c.956-12_961 | CCACATCTGGAAGGGAAG | 1698 |
| c.956-11_962 | ACCACATCTGGAAGGGAA | 1699 |
| c.956-10_963 | GACCACATCTGGAAGGGA | 1700 |
| c.956-9_964 | GGACCACATCTGGAAGGG | 1701 |
| c.956-8_965 | AGGACCACATCTGGAAGG | 1702 |
| c.956-7_966 | CAGGACCACATCTGGAAG | 1703 |
| c.956-6_967 | GCAGGACCACATCTGGAA | 1704 |
| c.956-5_968 | TGCAGGACCACATCTGGA | 1705 |
| c.956-4_969 | CTGCAGGACCACATCTGG | 1706 |
| c.956-3_970 | GCTGCAGGACCACATCTG | 1707 |
| c.956-2_971 | GGCTGCAGGACCACATCT | 1708 |
| c.956-1_972 | CGGCTGCAGGACCACATC | 1709 |
| c.956_973 | TCGGCTGCAGGACCACAT | 1710 |
| c.957_974 | CTCGGCTGCAGGACCACA | 1711 |
| c.958_975 | GCTCGGCTGCAGGACCAC | 1712 |
| c.959_976 | GGCTCGGCTGCAGGACCA | 1713 |
| c.960_977 | GGGCTCGGCTGCAGGACC | 1714 |
| c.961_978 | AGGGCTCGGCTGCAGGAC | 1715 |
| c.962_979 | CAGGGCTCGGCTGCAGGA | 1716 |
| c.963_980 | GCAGGGCTCGGCTGCAGG | 1717 |
| c.964_981 | GGCAGGGCTCGGCTGCAG | 1718 |
| c.965_982 | GGGCAGGGCTCGGCTGCA | 1719 |
| c.966_983 | AGGGCAGGGCTCGGCTGC | 1720 |
| c.967_984 | AAGGGCAGGGCTCGGCTG | 1721 |
| c.968_985 | TAAGGGCAGGGCTCGGCT | 1722 |
| c.969_986 | CTAAGGGCAGGGCTCGGC | 1723 |
| c.970_987 | GCTAAGGGCAGGGCTCGG | 1724 |
| c.971_988 | AGCTAAGGGCAGGGCTCG | 1725 |
| c.972_989 | CAGCTAAGGGCAGGGCTC | 1726 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.973_990 | CCAGCTAAGGGCAGGGCT | 1727 |
| c.974_991 | TCCAGCTAAGGGCAGGGC | 1728 |
| c.975_992 | CTCCAGCTAAGGGCAGGG | 1729 |
| c.976_993 | CCTCCAGCTAAGGGCAGG | 1730 |
| c.977_994 | ACCTCCAGCTAAGGGCAG | 1731 |
| c.978_995 | GACCTCCAGCTAAGGGCA | 1732 |
| c.979_996 | CGACCTCCAGCTAAGGGC | 1733 |
| c.980_997 | TCGACCTCCAGCTAAGGG | 1734 |
| c.981_998 | GTCGACCTCCAGCTAAGG | 1735 |
| c.982_999 | TGTCGACCTCCAGCTAAG | 1736 |
| c.983_1000 | CTGTCGACCTCCAGCTAA | 1737 |
| c.984_1001 | CCTGTCGACCTCCAGCTA | 1738 |
| c.985_1002 | ACCTGTCGACCTCCAGCT | 1739 |
| c.986_1003 | CACCTGTCGACCTCCAGC | 1740 |
| c.987_1004 | CCACCTGTCGACCTCCAG | 1741 |
| c.988_1005 | CCCACCTGTCGACCTCCA | 1742 |
| c.989_1006 | TCCCACCTGTCGACCTCC | 1743 |
| c.990_1007 | ATCCCACCTGTCGACCTC | 1744 |
| c.991_1008 | GATCCCACCTGTCGACCT | 1745 |
| c.992_1009 | GGATCCCACCTGTCGACC | 1746 |
| c.993_1010 | AGGATCCCACCTGTCGAC | 1747 |
| c.994_1011 | CAGGATCCCACCTGTCGA | 1748 |
| c.995_1012 | CCAGGATCCCACCTGTCG | 1749 |
| c.996_1013 | TCCAGGATCCCACCTGTC | 1750 |
| c.997_1014 | ATCCAGGATCCCACCTGT | 1751 |
| c.998_1015 | CATCCAGGATCCCACCTG | 1752 |
| c.999_1016 | ACATCCAGGATCCCACCT | 1753 |
| c.1000_1017 | GACATCCAGGATCCCACC | 1754 |
| c.1001_1018 | AGACATCCAGGATCCCAC | 1755 |
| c.1002_1019 | TAGACATCCAGGATCCCA | 1756 |
| c.1003_1020 | GTAGACATCCAGGATCCC | 1757 |
| c.1004_1021 | TGTAGACATCCAGGATCC | 1758 |
| c.1005_1022 | ATGTAGACATCCAGGATC | 1759 |
| c.1006_1023 | GATGTAGACATCCAGGAT | 1760 |
| c.1007_1024 | AGATGTAGACATCCAGGA | 1761 |
| c.1008_1025 | AAGATGTAGACATCCAGG | 1762 |
| c.1009_1026 | GAAGATGTAGACATCCAG | 1763 |
| c.1010_1027 | GGAAGATGTAGACATCCA | 1764 |
| c.1011_1028 | AGGAAGATGTAGACATCC | 1765 |
| c.1012_1029 | CAGGAAGATGTAGACATC | 1766 |
| c.1013_1030 | CCAGGAAGATGTAGACAT | 1767 |
| c.1014_1031 | CCCAGGAAGATGTAGACA | 1768 |
| c.1015_1032 | GCCCAGGAAGATGTAGAC | 1769 |
| c.1016_1033 | GGCCCAGGAAGATGTAGA | 1770 |
| c.1017_1034 | GGGCCCAGGAAGATGTAG | 1771 |
| c.1018_1035 | TGGGCCCAGGAAGATGTA | 1772 |
| c.1019_1036 | CTGGGCCCAGGAAGATGT | 1773 |
| c.1020_1037 | TCTGGGCCCAGGAAGATG | 1774 |
| c.1021_1038 | CTCTGGGCCCAGGAAGAT | 1775 |
| c.1022_1039 | GCTCTGGGCCCAGGAAGA | 1776 |
| c.1023_1040 | GGCTCTGGGCCCAGGAAG | 1777 |
| c.1024_1041 | GGGCTCTGGGCCCAGGAA | 1778 |
| c.1025_1042 | TGGGCTCTGGGCCCAGGA | 1779 |
| c.1026_1043 | TTGGGCTCTGGGCCCAGG | 1780 |
| c.1027_1044 | CTTGGGCTCTGGGCCCAG | 1781 |
| c.1028_1045 | TCTTGGGCTCTGGGCCCA | 1782 |
| c.1029_1046 | CTCTTGGGCTCTGGGCCC | 1783 |
| c.1030_1047 | GCTCTTGGGCTCTGGGCC | 1784 |
| c.1031_1048 | CGCTCTTGGGCTCTGGGC | 1785 |
| c.1032_1049 | ACGCTCTTGGGCTCTGGG | 1786 |
| c.1033_1050 | CACGCTCTTGGGCTCTGG | 1787 |
| c.1034_1051 | CCACGCTCTTGGGCTCTG | 1788 |
| c.1035_1052 | ACCACGCTCTTGGGCTCT | 1789 |
| c.1036_1053 | CACCACGCTCTTGGGCTC | 1790 |
| c.1037_1054 | GCACCACGCTCTTGGGCT | 1791 |
| c.1038_1055 | TGCACCACGCTCTTGGGC | 1792 |
| c.1039_1056 | CTGCACCACGCTCTTGGG | 1793 |
| c.1040_1057 | GCTGCACCACGCTCTTGG | 1794 |
| c.1041_1058 | TGCTGCACCACGCTCTTG | 1795 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.1042_1059 | CTGCTGCACCACGCTCTT | 1796 |
| c.1043_1060 | ACTGCTGCACCACGCTCT | 1797 |
| c.1044_1061 | TACTGCTGCACCACGCTC | 1798 |
| c.1045_1062 | GTACTGCTGCACCACGCT | 1799 |
| c.1046_1063 | GGTACTGCTGCACCACGC | 1800 |
| c.1047_1064 | AGGTACTGCTGCACCACG | 1801 |
| c.1048_1065 | CAGGTACTGCTGCACCAC | 1802 |
| c.1049_1066 | CCAGGTACTGCTGCACCA | 1803 |
| c.1050_1067 | TCCAGGTACTGCTGCACC | 1804 |
| c.1051_1068 | GTCCAGGTACTGCTGCAC | 1805 |
| c.1052_1069 | CGTCCAGGTACTGCTGCA | 1806 |
| c.1053_1070 | ACGTCCAGGTACTGCTGC | 1807 |
| c.1054_1071 | AACGTCCAGGTACTGCTG | 1808 |
| c.1055_1072 | CAACGTCCAGGTACTGCT | 1809 |
| c.1056_1073 | ACAACGTCCAGGTACTGC | 1810 |
| c.1057_1074 | CACAACGTCCAGGTACTG | 1811 |
| c.1058_1075 | CCACAACGTCCAGGTACT | 1812 |
| c.1059_1075+1 | CCCACAACGTCCAGGTAC | 1813 |
| c.1060_1075+2 | ACCCACAACGTCCAGGTA | 1814 |
| c.1061_1075+3 | TACCCACAACGTCCAGGT | 1815 |
| c.1062_1075+4 | CTACCCACAACGTCCAGG | 1816 |
| c.1063_1075+5 | CCTACCCACAACGTCCAG | 1817 |
| c.1064_1075+6 | CCCTACCCACAACGTCCA | 1818 |
| c.1065_1075+7 | GCCCTACCCACAACGTCC | 1819 |
| c.1066_1075+8 | GGCCCTACCCACAACGTC | 1820 |
| c.1067_1075+9 | AGGCCCTACCCACAACGT | 1821 |
| c.1068_1075+10 | CAGGCCCTACCCACAACG | 1822 |
| c.1069_1075+11 | GCAGGCCCTACCCACAAC | 1823 |
| c.1070_1075+12 | AGCAGGCCCTACCCACAA | 1824 |
| c.1071_1075+13 | GAGCAGGCCCTACCCACA | 1825 |
| c.1072_1075+14 | GGAGCAGGCCCTACCCAC | 1826 |
| c.1073_1075+15 | GGGAGCAGGCCCTACCCA | 1827 |
| c.1074_1075+16 | AGGGAGCAGGCCCTACCC | 1828 |
| c.1075_1075+17 | CAGGGAGCAGGCCCTACC | 1829 |
| c.1075+1_+18 | CCAGGGAGCAGGCCCTAC | 1830 |
| c.1075+2_+19 | GCCAGGGAGCAGGCCCTA | 1831 |
| c.1075+3_+20 | GGCCAGGGAGCAGGCCCT | 1832 |
| c.1075+4_+21 | GGGCCAGGGAGCACGCCC | 1833 |
| c.1075+5_+22 | GCGGCCAGGGAGCAGGCC | 1834 |
| c.1075+6_+23 | CGCGGCCAGGGAGCAGGC | 1835 |
| c.1075+7_+24 | CCGCGGCCAGGGAGCAGG | 1836 |
| c.1075+8_+25 | GCCGCGGCCAGGGAGCAG | 1837 |
| c.1075+9_+26 | GGCCGCGGCCAGGGAGCA | 1838 |
| c.1075+10_+27 | GGGCCGCGGCCAGGGAGC | 1839 |
| c.1075+11_+28 | GGGGCCGCGGCCAGGGAG | 1840 |
| c.1075+12_+29 | GGGGGCCGCGGCCAGGGA | 1841 |
| c.1075+13_+30 | CGGGGGCCGCGGCCAGGG | 1842 |
| c.1075+14_+31 | GCGGGGGCCGCGGCCAGG | 1843 |
| c.1075+15_+32 | GGCGGGGGCCGCGGCCAG | 1844 |
| c.1075+16_+33 | GGGCGGGGGCCGCGGCCA | 1845 |
| c.1075+17_+34 | GGGGCGGGGGCCGCGGCC | 1846 |
| c.1075+18_+35 | TGGGGCGGGGGCCGCGGC | 1847 |
| c.1075+19_+36 | TTGGGGCGGGGGCCGCGG | 1848 |
| c.1075+20_+37 | CTTGGGGCGGGGGCCGCG | 1849 |
| c.1075+21_+38 | CCTTGGGGCGGGGGCCGC | 1850 |
| c.1075+22_+39 | GCCTTGGGGCGGGGGCCG | 1851 |
| c.1075+23_+40 | AGCCTTGGGGCGGGGGCC | 1852 |
| c.1075+24_1076-39 | GAGCCTTGGGGCGGGGGC | 1853 |
| c.1075+25_1076-38 | GGAGCCTTGGGGCGGGGG | 1854 |
| c.1075+26_1076-37 | GGGAGCCTTGGGGCGGGG | 1855 |
| c.1075+27_1076-36 | AGGGAGCCTTGGGGCGGG | 1856 |
| c.1075+28_1076-35 | GAGGGAGCCTTGGGGCGG | 1857 |
| c.1075+29_1076-34 | GGAGGGAGCCTTGGGGCG | 1858 |
| c.1075+30_1076-33 | AGGAGGGAGCCTTGGGGC | 1859 |
| c.1075+31_1076-32 | GAGGAGGGAGCCTTGGGG | 1860 |
| c.1075+32_1076-31 | GGAGGAGGGAGCCTTGGG | 1861 |
| c.1075+33_1076-30 | GGGAGGAGGGAGCCTTGG | 1862 |
| c.1075+34_1076-29 | AGGGAGGAGGGAGCCTTG | 1863 |
| c.1075+35_1076-28 | GAGGGAGGAGGGAGCCTT | 1864 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.1075+36_1076-27 | GGAGGGAGGAGGGAGCCT | 1865 |
| c.1075+37_1076-26 | GGGAGGGAGGAGGGAGCC | 1866 |
| c.1075+38_1076-25 | AGGGAGGGAGGAGGGAGC | 1867 |
| c.1075+39_1076-24 | GAGGGAGGGAGGAGGGAG | 1868 |
| c.1075+40_1076-23 | TGAGGGAGGGAGGAGGGA | 1869 |
| c.1076-39_-22 | ATGAGGGAGGGAGGAGGG | 1870 |
| c.1076-38_-21 | CATGAGGGAGGGAGGAGG | 1871 |
| c.1076-37_-20 | TCATGAGGGAGGGAGGAG | 1872 |
| c.1076-36_-19 | TTCATGAGGGAGGGAGGA | 1873 |
| c.1076-35_-18 | CTTCATGAGGGAGCGAGG | 1874 |
| c.1076-34_-17 | ACTTCATGAGGGAGGGAG | 1875 |
| c.1076-33_-16 | GACTTCATGAGGGAGGGA | 1876 |
| c.1076-32_-15 | CGACTTCATGAGGGAGGG | 1877 |
| c.1076-31_-14 | CCGACTTCATGAGGGAGG | 1878 |
| c.1076-30_-13 | GCCGACTTCATGAGGGAG | 1879 |
| c.1076-29_-12 | CGCCGACTTCATGAGGGA | 1880 |
| c.1076-28_-11 | ACGCCGACTTCATGAGGG | 1881 |
| c.1076-27_-10 | AACGCCGACTTCATGAGG | 1882 |
| c.1076-26_-9 | CAACGCCGACTTCATGAG | 1883 |
| c.1076-25_-8 | CCAACGCCGACTTCATGA | 1884 |
| c.1076-24_-7 | GCCAACGCCGACTTCATG | 1885 |
| c.1076-23_-6 | GGCCAACGCCGACTTCAT | 1886 |
| c.1076-22_-5 | AGGCCAACGCCGACTTCA | 1887 |
| c.1076-21_-4 | CAGGCCAACGCCGACTTC | 1888 |
| c.1076-20_-3 | GCAGGCCAACGCCGACTT | 1889 |
| c.1076-19_-2 | TGCAGGCCAACGCCGACT | 1890 |
| c.1076-18_-1 | CTGCAGGCCAACGCCGAC | 1891 |
| c.1076-17_1076 | CCTGCAGGCCAACGCCGA | 1892 |
| c.1076-16_1077 | TCCTGCAGGCCAACGCCG | 1893 |
| c.1076-15_1078 | ATCCTGCAGGCCAACGCC | 1894 |
| c.1076-14_1079 | TATCCTGCAGGCCAACGC | 1895 |
| c.1076-13_1080 | GTATCCTGCAGGCCAACG | 1896 |
| c.1076-12_1081 | GGTATCCTGCAGGCCAAC | 1897 |
| c.1076-11_1082 | GGGTATCCTGCAGGCCAA | 1898 |
| c.1076-10_1083 | CGGGTATCCTGCAGGCCA | 1899 |
| c.1076-9_1084 | ACGGGTATCCTGCAGCCC | 1900 |
| c.1076-8_1085 | AACGGGTATCCTGCAGGC | 1901 |
| c.1076-7_1086 | GAACGGGTATCCTGCAGG | 1902 |
| c.1076-6_1087 | TGAACGGGTATCCTGCAG | 1903 |
| c.1076-5_1088 | ATGAACGGGTATCCTGCA | 1904 |
| c.1076-4_1089 | CATGAACGGGTATCCTGC | 1905 |
| c.1076-3_1090 | GCATGAACGGGTATCCTG | 1906 |
| c.1076-2_1091 | GGCATGAACGGGTATCCT | 1907 |
| c.1076-1_1092 | CGGCATGAACGGGTATCC | 1908 |
| c.1076_1093 | GCGGCATGAACGGGTATC | 1909 |
| c.1077_1094 | GGCGGCATGAACGGGTAT | 1910 |
| c.1078_1095 | TGGCGGCATGAACGGGTA | 1911 |
| c.1079_1096 | ATGGCGGCATGAACGGGT | 1912 |
| c.1080_1097 | TATGGCGGCATGAACGGG | 1913 |
| c.1081_1098 | GTATGGCGGCATGAACGG | 1914 |
| c.1082_1099 | AGTATGGCGGCATGAACG | 1915 |
| c.1083_1100 | CAGTATGGCGGCATGAAC | 1916 |
| c.1084_1101 | CCAGTATGGCGGCATGAA | 1917 |
| c.1085_1102 | CCCAGTATGGCGGCATGA | 1918 |
| c.1086_1103 | CCCCAGTATGGCGGCATG | 1919 |
| c.1087_1104 | GCCCCAGTATGGCGGCAT | 1920 |
| c.1088_1105 | GGCCCCAGTATGGCGGCA | 1921 |
| c.1089_1106 | AGGCCCCAGTATGGCGGC | 1922 |
| c.1090_1107 | CAGGCCCCAGTATGGCGG | 1923 |
| c.1091_1108 | CCAGGCCCCAGTATGGCG | 1924 |
| c.1092_1109 | CCCAGGCCCCAGTATGGC | 1925 |
| c.1093_1110 | GCCCAGGCCCCAGTATGG | 1926 |
| c.1094_1111 | AGCCCAGGCCCCAGTATG | 1927 |
| c.1095_1112 | AAGCCCAGGCCCCAGTAT | 1928 |
| c.1096_1113 | GAAGCCCAGGCCCCAGTA | 1929 |
| c.1097_1114 | GGAAGCCCAGGCCCCAGT | 1930 |
| c.1098_1115 | TGGAAGCCCAGGCCCCAG | 1931 |
| c.1099_1116 | GTGGAAGCCCAGGCCCCA | 1932 |
| c.1100_1117 | GGTGGAAGCCCAGGCCCC | 1933 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.1101_1118 | AGGTGGAAGCCCAGGCCC | 1934 |
| c.1102_1119 | CAGGTGGAAGCCCAGGCC | 1935 |
| c.1103_1120 | ACAGGTGGAAGCCCAGGC | 1936 |
| c.1104_1121 | CACAGGTGGAAGCCCAGG | 1937 |
| c.1105_1122 | GCACAGGTGGAAGCCCAG | 1938 |
| c.1106_1123 | GGCACAGGTGGAAGCCCA | 1939 |
| c.1107_1124 | CGGCACAGGTGGAAGCCC | 1940 |
| c.1108_1125 | GCGGCACAGGTGGAAGCC | 1941 |
| c.1109_1126 | AGCGGCACAGGTGGAAGC | 1942 |
| c.1110_1127 | CAGCGGCACAGGTGGAAG | 1943 |
| c.1111_1128 | CCAGCGGCACAGGTGGAA | 1944 |
| c.1112_1129 | CCCAGCGGCACAGGTGGA | 1945 |
| c.1113_1130 | CCCCAGCGGCACAGGTGG | 1946 |
| c.1114_1131 | GCCCCAGCGGCACAGGTG | 1947 |
| c.1115_1132 | AGCCCCAGCGGCACAGGT | 1948 |
| c.1116_1133 | TAGCCCCAGCGGCACAGG | 1949 |
| c.1117_1134 | GTAGCCCCAGCGGCACAG | 1950 |
| c.1118_1135 | AGTAGCCCCAGCGGCACA | 1951 |
| c.1119_1136 | GAGTAGCCCCAGCGGCAC | 1952 |
| c.1120_1137 | GGAGTAGCCCCAGCGGCA | 1953 |
| c.1121_1138 | AGGAGTAGCCCCAGCGGC | 1954 |
| c.1122_1139 | GAGGAGTAGCCCCAGCGG | 1955 |
| c.1123_1140 | GGAGGAGTAGCCCCAGCG | 1956 |
| c.1124_1141 | TGGAGGAGTAGCCCCAGC | 1957 |
| c.1125_1142 | GTGGAGGAGTAGCCCCAG | 1958 |
| c.1126_1143 | GGTGGAGGAGTAGCCCCA | 1959 |
| c.1127_1144 | CGGTGGAGGAGTAGCCCC | 1960 |
| c.1128_1145 | GCGGTGGAGGAGTAGCCC | 1961 |
| c.1129_1146 | AGCGGTGGAGGAGTAGCC | 1962 |
| c.1130_1147 | TAGCGCTGGAGGAGTAGC | 1963 |
| c.1131_1148 | ATAGCGGTGGAGGAGTAG | 1964 |
| c.1132_1149 | GATAGCGGTGGAGGAGTA | 1965 |
| c.1133_1150 | TGATAGCGGTGGAGGAGT | 1966 |
| c.1134_1151 | GTGATAGCGGTGGAGGAG | 1967 |
| c.1135_1152 | GGTGATAGCGGTGGAGGA | 1968 |
| c.1136_1153 | GGGTGATAGCGGTGGAGG | 1969 |
| c.1137_1154 | CGGGTGATAGCGGTGGAG | 1970 |
| c.1138_1155 | GCGGGTGATAGCGGTGGA | 1971 |
| c.1139_1156 | GGCGGGTGATAGCGGTGG | 1972 |
| c.1140_1157 | TGGCGGGTGATAGCGGTG | 1973 |
| c.1141_1158 | CTGGCGGGTGATAGCGGT | 1974 |
| c.1142_1159 | CCTGGCGGGTGATAGCGG | 1975 |
| c.1143_1160 | ACCTGGCGGGTGATAGCG | 1976 |
| c.1144_1161 | CACCTGGCGGGTGATAGC | 1977 |
| c.1145_1162 | CCACCTGGCGGGTGATAG | 1978 |
| c.1146_1163 | ACCACCTGGCGGGTGATA | 1979 |
| c.1147_1164 | CACCACCTGGCGGGTGAT | 1980 |
| c.1148_1165 | CCACCACCTGGCGGGTGA | 1981 |
| c.1149_1166 | TCCACCACCTGGCGGGTG | 1982 |
| c.1150_1167 | CTCCACCACCTGGCGGGT | 1983 |
| c.1151_1168 | TCTCCACCACCTGGCGGG | 1984 |
| c.1152_1169 | TTCTCCACCACCTGGCGG | 1985 |
| c.1153_1170 | GTTCTCCACCACCTGGCG | 1986 |
| c.1154_1171 | TGTTCTCCACCACCTGGC | 1987 |
| c.1155_1172 | ATGTTCTCCACCACCTGG | 1988 |
| c.1156_1173 | CATGTTCTCCACCACCTG | 1989 |
| c.1157_1174 | TCATGTTCTCCACCACCT | 1990 |
| c.1158_1175 | GTCATGTTCTCCACCACC | 1991 |
| c.1159_1176 | GGTCATGTTCTCCACCAC | 1992 |
| c.1160_1170 | TGGTCATGTTCTCCACCA | 1993 |
| c.1161_1178 | CTGGTCATGTTCTCCACC | 1994 |
| c.1162_1179 | CCTGGTCATGTTCTCCAC | 1995 |
| c.1163_1180 | CCCTGGTCATGTTCTCCA | 1996 |
| c.1164_1181 | GCCCTGGTCATGTTCTCC | 1997 |
| c.1165_1182 | GGCCCTGGTCATGTTCTC | 1998 |
| c.1166_1183 | GGGCCCTGGTCATGTTCT | 1999 |
| c.1167_1184 | TGGGCCCTGGTCATGTTC | 2000 |
| c.1168_1185 | GTGGGCCCTGGTCATGTT | 2001 |
| c.1169_1186 | AGTGGGCCCTGGTCATGT | 2002 |

TABLE 15-continued

Exemplary antisense oligomeric compounds of the invention targeting GAA gene sequences or sequences of gene products thereof, and capable of modulating the splicing by promotion of exon 6 inclusion or intron 6 exclusion.

| Sequence in cDNA to which AON anneals for intron 6 exclusion | AON sequence 5' → 3' | Seq ID |
|---|---|---|
| c.1170_1187 | AAGTGGGCCCTGGTCATG | 2003 |
| c.1171_1188 | GAAGTGGGCCCTGGTCAT | 2004 |
| c.1172_1189 | GGAAGTGGGCCCTGGTCA | 2005 |
| c.1173_1190 | GGGAAGTGGGCCCTGGTC | 2006 |
| c.1174_1191 | GGGGAAGTGGGCCCTGGT | 2007 |
| c.1175_1192 | GGGGGAAGTGGGCCCTGG | 2008 |
| c.1176_1193 | AGGGGGAAGTGGGCCCTG | 2009 |
| c.1177_1194 | CAGGGGGAAGTGGGCCCT | 2010 |
| c.1178_1194+1 | CCAGGGGGAAGTGGGCCC | 2011 |
| c.1179_1194+2 | ACCAGGGGGAAGTGGGCC | 2012 |
| c.1180_1194+3 | CACCAGGGGGAAGTGGGC | 2013 |
| c.1181_1194+4 | TCACCAGGGGGAAGTGGG | 2014 |
| c.1182_1194+5 | CTCACCAGGGGGAAGTGG | 2015 |
| c.1183_1194+6 | ACTCACCAGGGGGAAGTG | 2016 |
| c.1184_1194+7 | AACTCACCAGGGGGAAGT | 2017 |
| c.1185_1194+8 | CAACTCACCAGGGGGAAG | 2018 |
| c.1186_1194+9 | CCAACTCACCAGGGGGAA | 2019 |
| c.1187_1194+10 | CCCAACTCACCAGGGGGA | 2020 |
| c.1188_1194+11 | CCCCAACTCACCAGGGGG | 2021 |
| c.1189_1194+12 | ACCCCAACTCACCAGGGG | 2022 |
| c.1190_1194+13 | CACCCCAACTCACCAGGG | 2023 |
| c.1191_1194+14 | CCACCCCAACTCACCAGG | 2024 |
| c.1192_1194+15 | ACCACCCCAACTCACCAG | 2025 |
| c.1193_1194+16 | CACCACCCCAACTCACCA | 2026 |
| c.1194_1194+17 | CCACCACCCCAACTCACC | 2027 |
| c.1194+1_+18 | GCCACCACCCCAACTCAC | 2028 |
| c.1194+2_+19 | TGCCACCACCCCAACTCA | 2029 |
| c.1194+3_+20 | CTGCCACCACCCCAACTC | 2030 |
| c.1194+4_+21 | CCTGCCACCACCCCAACT | 2031 |
| c.1194+5_+22 | CCCTGCCACCACCCCAAC | 2032 |
| c.1194+6_+23 | CCCCTGCCACCACCCCAA | 2033 |
| c.1194+7_+24 | TCCCCTGCCACCACCCCA | 2034 |
| c.1194+8_+25 | CTCCCCTGCCACCACCCC | 2035 |
| GAA_c.2190-357_-333 | TCAGTCAAGTATCTGGAAAGTACGA | 2036 |
| GAA_c.2190-355_-335 | AGTCAAGTATCTGGAAAGTAC | 2037 |
| GAA_c.2149_1273 | GGAAGTCCCGGAAGCCAACCTTGTT | 2038 |
| GAA_c.1552-46_-26 | TGACTCTGCCCAGAGTGAGGA | 2039 |
| GAA_c.1755-112_-88 | AGCTTTCTGGGATGAGGCAGAGGCT | 2040 |

In a preferred embodiment of aspects of the invention, the antisense oligomeric compound are 8 to 80 nucleotides in length, 9 to 0.50 nucleotides in length, 10 to 30 nucleotides in length, 12 to 30 nucleotides in length, 15 to 25 nucleotides in length or about 20 nucleotides in length. One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment of the invention and/or embodiments thereof, the antisense compounds comprise 13 to 80 nucleotides. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

In one embodiment of the invention and/or embodiments thereof, the antisense compounds comprise 13 to 50 nucleotides. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleotides.

In one embodiment of the invention and/or embodiments thereof, the antisense compounds comprise 13 to 30 nucleotides. One having ordinary skill in the art will appreciate that this embodies antisense compounds of 13, 14, 15, 16, 17, 18, 19, 20, 21, 22, 23, 24, 25, 26, 27, 28, 29 or 30 nucleotides.

In one embodiment of the invention and/or embodiments thereof, the antisense compounds comprise 20 to 30 nucleotides. One having ordinary skill in the art will appreciate that this embodies antisense compounds of 20, 21, 22, 23, 24, 25, 26, 27, 28, 29, or 30 nucleotides.

In one embodiment of the invention and/or embodiments thereof, the antisense compounds comprise 15 to 25 nucleotides. One having ordinary skill in the art will appreciate that this embodies antisense compounds of 15, 16, 17, 18, 19, 20, 21, 22, 23, 24 or 25.

In one embodiment of the invention and/or embodiments thereof, the antisense compounds comprise 20 nucleotides.

In one embodiment of the invention and/or embodiments thereof, the antisense compounds comprise 19 nucleotides.

In one embodiment of the invention and/or embodiments thereof, the antisense compounds comprise 18 nucleotides.

In one embodiment of the invention and/or embodiments thereof, the antisense compounds comprise 17 nucleotides.

In one embodiment of the invention and/or embodiments thereof, the antisense compounds comprise 16 nucleotides.

In one embodiment of the invention and/or embodiments thereof, the antisense compounds comprise 15 nucleotides.

In one embodiment of the invention and/or embodiments thereof, the antisense compounds comprise 14 nucleotides.

In one embodiment of the invention and/or embodiments thereof, the antisense compounds comprise 13 nucleotides.

In one embodiment of the invention and/or embodiments thereof, compounds include oligonucleotide sequences that comprise at least 8 consecutive nucleotides from one of the antisense compounds as claimed, preferably at least 9 consecutive nucleotides from one of the antisense compounds as claimed, more preferably at least 10 consecutive nucleotides from one of the antisense compounds as claimed, more preferably at least 11 consecutive nucleotides from one of the antisense compounds as claimed, more preferably at least 12 consecutive nucleotides from one of the antisense compounds as claimed, more preferably at least 13 consecutive nucleotides from one of the antisense compounds as claimed, more preferably at least 14 consecutive nucleotides from one of the antisense compounds as claimed, more preferably at least 15 consecutive nucleotides from one of the antisense compounds as claimed, more preferably at least 16 consecutive nucleotides from one of the antisense compounds as claimed, more preferably at least 17 consecutive nucleotides from one of the antisense compounds as claimed, more preferably at least 18 consecutive nucleotides from one of the antisense compounds as claimed, more preferably at least 19 consecutive nucleotides from one of the antisense compounds as claimed, more preferably at least 20 consecutive nucleotides from one of the antisense compounds as claimed.

Any remaining nucleotides from the oligonucleotides may be oligonucleotides that improve resistance to Rnase H, cell-targeting sequences, cell penetrating sequences, marker sequences or any other sequences.

One having skill in the art armed with the antisense compounds disclosed herein will be able, without undue experimentation, to identify further antisense compounds.

In order for an antisense oligonucleotide to achieve therapeutic success, oligonucleotide chemistry must allow for adequate cellular uptake (Kurreck, J. (2003) Eur. J. Biochem. 270:1628-1644). Splicing oligonucleotides have traditionally been comprised of uniform modifications that render the oligonucleotide RNA-like, and thus resistant to cleavage by RNase H, which is critical to achieve modulation of splicing. Provided herein are (pairs of) antisense compounds for modulation of splicing.

In a preferred embodiment of the invention and/or embodiments thereof, the antisense compounds are chimeric, with regions of RNA-like and DNA-like chemistry. Despite regions of DNA-like chemistry, the chimeric compounds are preferably RNase H-resistant and effectively modulate splicing of target mRNA in vitro and in vivo. In another preferred embodiment the disclosed antisense oligomeric compounds show enhanced cellular uptake and greater pharmacologic activity compared with uniformly modified oligonucleotides.

Contemplated herein are antisense oligomeric compound which are targeted to a splice site of a target mRNA or to splicing repressor sequences, or to splicing enhancer sequences. Optionally to splicing repressor sequences. Splice sites include aberrant and cryptic splice sites.

One skilled in the art recognizes that the inclusion of mismatches is possible without eliminating the activity of the antisense compound. Compounds provided herein are therefore directed to those antisense compounds that may contain up to about 20% nucleotides that disrupt base pairing of the antisense compound to the target. Preferably the compounds contain no more than about 15%, more preferably not more than about 10%, most preferably not more than 5% or no mismatches. The remaining nucleotides do not disrupt hybridization (e.g., universal bases).

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of the skill in the art is capable of determining an appropriate number of mismatches between oligonucleotides, or between an oligonucleotide and a target nucleic acid, such as by determining melting temperature.

It is known by a skilled person that hybridization to a target mRNA depends on the conditions. "Stringent hybridization conditions" or "stringent conditions" refer to conditions under which an oligomeric compound will hybridize to its target, sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

Antisense compounds, or a portion thereof, may have a defined percent identity to a SEQ ID NO as used herein, a sequence is identical to the sequence disclosed herein if it has the same nucleobase pairing ability. For example, an RNA which contains uracil in place of thymidine in the disclosed sequences would be considered identical as they both pair with adenine. This identity may be over the entire length of the oligomeric compound, or in a portion of the antisense compound (e.g. nucleotides 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein are also contemplated. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed throughout the oligonucleotide, or both.

For example, a 16-mer having the same sequence as nucleotides 2-17 of a 20-mer is 80% identical to the 20-mer. Alternatively, a 20-mer containing four nucleotides not identical to the 20-mer is also 80% identical to the 20-mer. A 14-mer having the same sequence as nucleotides 1-14 of an 18-mer is 78% identical to the 18-mer. Such calculations are well within the ability of those skilled in the art.

The percent identity is based on the percent of nucleotides in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. The complement of an active target segment may constitute a single portion. In a preferred embodiment of the invention and/or embodiments thereof, the oligonucleotides are at least about 80%, more preferably at least about 85%, even more preferably at least about 90%, most, preferably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7310, 1992, incorporated herein by reference), a series of antisense oligomeric compounds of 13-25 nucleotides in length were tested for their ability to induce cleavage of a target RNA. Antisense oligomeric compounds of 25 nucleotides in length with 8 or 11 mismatch bases near the ends of the antisense oligomeric compounds were able to direct specific cleavage of the target mRNA, albeit to a lesser extent than the antisense oligomeric compounds that contained no mismatches. Similarly, target specific cleavage was achieved using a 13 nucleobase antisense oligomeric compounds, including those with 1 or 3 mismatches. Maher and Dolnick (Nuc. Acid. Res. 16:3341-3358, 1988, incorporated herein by reference) tested a series of tandem 14 nucleobase antisense oligomeric compounds, and a 28 and 42 nucleobase antisense oligomeric compounds comprised of the sequence of two or three of the tandem antisense oligomeric compounds, respectively, for their ability to arrest translation of human DHFR in a rabbit reticulocyte assay. Each of the three 14 nucleobase antisense oligomeric compounds alone were able to inhibit translation, albeit at a more modest level than the 28 or 42 nucleobase antisense oligomeric compounds. It is understood that antisense compounds can vary in length and percent complementarity to the target provided that they maintain the desired activity. Methods to determine desired activity are disclosed herein and well known to those skilled in the art. In a preferred embodiment, of the invention and/or embodiments thereof, the antisense oligomeric compounds have at least 80% complementarity to the target mRNA, more preferably at least 85% complementarity to the target mRNA, more preferably at least 90% complementarity to the target mRNA, more preferably at least 95% complementarity to the target mRNA, more preferably at least 96% complementarity to the target mRNA, more preferably at least 97% complementarity to the target mRNA, more preferably at least 98% complementarity to the target mRNA, more preferably at least 99% complementarity to the target mRNA, more preferably at least 100% complementarity to the target mRNA.

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

Antisense compounds provided herein may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C(R1)(R2) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-$(CH_2)_2$—O-2' bridge); and substituted sugars, especially 2'-substituted sugars having a 2'-F, 2'-$OCH_2$ or a 2'-$O(CH_2)_2$—OCH3 substituent group. Sugars can also be replaced with sugar mimetic groups among others. Methods for the preparations of modified sugars are well known to those skilled in the art. Suitable compounds can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are $O((CH_2)_nO)_mCH_3$, $O(CH_2)_nOCH_3$, $O(CH_2)_nNH_2$, $O(CH_2)_nCH_3$, $O(CH_2)_nON_2$, and $O(CH_2)_nON((CH2)nCH3)2$, where n and m are from 1 to about 10. Other oligonucleotides comprise one of the following at the 2' position: C1 to C10 lower alkyl, substituted lower alkyl, alkenyl, alkynyl, alkaryl, aralkyl. O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., Helv. Chim. Acta. 1995, 78, 486-504), i.e., an alkoxyalkoxy group. A further modification includes 2'-dimethylaminooxyethoxy, i.e., a $O(CH_2)ON(CH_3)_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—$((CH_2)_2$—O—$(CH_2)_2$—$N((CH_3)_2$. Other modifications include 2'-methoxy (2'-O—$CH_3$), 2'-aminopropoxy (2'-$OCH_2CH_2CH_2NH_2$), 2'-allyl (2'-$CH_2$—CH—$CH_2$), 2'-O-allyl (2'-O—$CH_2$—CH—$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,780; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

In one aspect of the present invention oligomeric compounds include nucleosides modified to induce a 3'-endo sugar conformation. A nucleoside can incorporate modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry.

In the present invention there is a preference for an RNA type duplex (A form helix, predominantly 3'-endo) as they are RNase H resistant. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984. Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2' deoxy-2'F-nucleosides (Kawasaki et al., J. Med. Chem. (1993), 36, 831-841), which adopts the 3'-endo conformation positioning the electronegative fluorine atom in the axial position. Representative 2'-substituent groups amenable to the present invention that give A-form conformational properties (3'-endo) to the resultant duplexes include 2'-O-alkyl, 2'-O-substituted alkyl and 2'-fluoro substituent groups. Other suitable substituent groups are various alkyl and aryl ethers and thioethers, amines and monoalkyl and dialkyl substituted amines.

Other modifications of the ribose ring, for example substitution at the 4'-position to give 4'-F modified nucleosides (Guillerm et al., Bioorganic and Medicinal Chemistry Letters (1995), 5, 1455-1460 and Owen et al. J. Org. Chem. (1976), 41, 3010-3017), or for example modification to yield methanocarba nucleoside analogs (Jacobson et al., J. Med. Chem. Lett. (2000), 43, 2196-2203 and Lee et al. Bioorganic and Medicinal Chemistry Letters (2001), 11, 1333-1337) also induce preference for the 3'-endo conformation. Along similar lines, one or more nucleosides may be modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA™. Morita et al, Bioorganic & Medicinal Chemistry Letters (2002), 12, 73-76.)

Preferred modification of the sugar are selected from the group consisting of 2'-O-methyl 2'-O-methoxyethyl, 2'-fluoro, 2'-dimethylaminooxyethoxy, 2'-dimethylaminoethoxyethoxy, 2'-guanidinium, 2'-O-guanidinium ethyl, 2'-carbamate, 2'-aminooxy, 2'-acetamido and locked nucleic acid. In one preferred embodiment, the sugar modification is 2'-O-methyl or 2'-O-methoxyethyl.

Oligomeric compounds can also include nucleobase (often referred to in the art as heterocylic base or simply as "base") modifications or substitutions. As used herein, "unmodified" or "natural" nucleotides include the purine bases adenine (A) and guanine (G), and the pyrimidine bases thymine (T), cytosine (C) and uracil (U). A "substitution" is the replacement of an unmodified or natural base with another unmodified or natural base. "Modified" nucleotides mean other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C[identical to]C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleotides include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one). Modified nucleotides may also include those in which the purine or pyrimidine base is replaced with other heterocycles, for example 7-deaza-adenine, 7-deazaguanosine, 2-aminopyridine and 2-pyridone. Further nucleotides include those disclosed in U.S. Pat. No. 3,687,808, those disclosed in The Concise Encyclopedia Of Polymer Science And Engineering, pages 858-859. Kroschwitz, J. I, ed. John Wiley & Sons, 1990, those disclosed by Englisch et al., Angewandte Chemie. International Edition, 1991, 30, 613, and those disclosed by Sanghvi. Y. S., Chapter 15, Antisense Research and Applications, pages 289-302, Crooke, S. T, and Lebleu, B, ed. CRC Press, 1993. Certain of these nucleotides are known to those skilled in the art as suitable for increasing the binding affinity of the compounds of the invention. These include 5-substituted pyrimidines, 6-azapyrimidines and N-2. N-6 and O-6 substituted purines, including 2-aminopropyladenine, 5-propynyluracil and 5-propynylcytosine, 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence.

Representative United States patents that teach the preparation of certain of the above noted modified nucleotides as well as other modified nucleotides include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941; and 5,750,692.

Oligomeric compounds of the present invention may also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al. Nucleosides and Nucleotides, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin. K-Y. Matteucci, M. Tetrahedron Lett. 1998, 39, 8385-838). Incorporated into oligonucleotides these base modifications were shown to hybridize with complementary guanine and the latter was also shown to hybridize with adenine and to enhance helical thermal stability by extended stacking interactions (also see U.S. Pre-Grant Publications 2003/0207804 and 2003/0175906).

Further helix-stabilizing properties have been observed when a cytosine analog/substitute has an aminoethoxy moiety attached to the rigid 1,3-diazaphenoxazine-2-one scaffold (Lin, K-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a ΔTm of up to 18° C., relative to 5-methyl cytosine, which is a high affinity enhancement for a single modification. On the other hand, the gain in helical stability does not compromise the specificity of the oligonucleotides.

Further tricyclic heterocyclic compounds and methods of using them that are amenable to use in the present invention are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf. J. J.; Olson, P.; Grant, D.; Lin. K.-Y.; Wagner, R. W.; Matteucci, M. Proc. Natl. Acad. Sci. USA. 1999, 96, 3513-3518).

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,00; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. Pre-Grant Publication 20030158403.

The compounds described herein may include internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH—N($CH_3$)—O—$CH_2$—), thiodiester (—O—C(O)—S—), thionocarbamate (—O—C(O)(NH)—S—); siloxane (—O—Si$(H)_2$—O—); and N,N'-dimethylhydrazine (—$CH_2$—N($CH_3$)—N($CH_3$)—). Modified internucleoside linkages, compared to natural phosphodiester linkages, can be used to alter, typically increase, nuclease resistance of the antisense compound. Internucleoside linkages having a chiral atom may be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

Suitable modified internucleoside linking groups are for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, phosphonoacetate and thiophosphonoacetate (see Sheehan et al. Nucleic Acids Research, 2003, 31(14), 4109-4118 and Dellinger et al., J. Am. Chem. Soc., 2003, 125, 940-950), selenctphosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., J. Am. Chem. Soc., 1994, 116, 3143-3144). N3'-P5'-phosphoramidates have been studied with some success in vivo to specifically down regulate the expression of the c-myc gene (Skorski et al., Proc. Natl. Acad. Sci. 1997, 94, 3966-3971; and Faira et al., Nat. Biotechnol., 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,28,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments of the invention, oligomeric compounds may have one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone). —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(—O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones: formacetyl and thioformacetyl backbones; methylene formacetyl and thioformacetyl backbones; riboacetyl backbones: alkene containing backbones: sulfamate backbones: methyleneimino and methylenehydrazino backbones; sulfonate and sulfonamide backbones: amide backbones; and others having mixed N, O, S and $CH_2$ component, parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,77; 5,470,967; 5,489,677; 5,541,307; 5,561,225; 5,596,086; 5,002,240; 5,610,289; 5,602,240; 5,608,046; 5,610,289; 5,618,704; 5,623,070; 5,663,312; 5,633,360; 5,677,437; 5,792,608; 5,646,269 and 5,677,439.

In a preferred embodiment of the invention and/or embodiments thereof the internucleoside linkage is phosphorothioate, or phosphorodiamidate It is further intended that multiple modifications can be made to one or more of the oligomeric compounds of the invention at multiple sites of one or more monomeric subunits (nucleosides are suitable) and/or internucleoside linkages to enhance properties such as but not limited to activity in a selected application.

The synthesis of numerous of the modified nucleosides amenable to the present invention are known in the art (see for example. Chemistry of Nucleosides and Nucleotides Vol 1-3, ed. Leroy B. Townsend, 1988. Plenum press). The conformation of modified nucleosides and their oligomers can be estimated by various methods routine to those skilled in the art such as molecular dynamics calculations, nuclear magnetic resonance spectroscopy and CD measurements.

In a preferred embodiment of the invention and/or embodiments thereof, the oligomeric compounds of the present invention are morpholino phosphorothioates, or phosphorodiamidate morpholino.

Another group of oligomeric compounds includes oligonucleotide mimetics. As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al. Nuc Acid Res. 2000, 28:2911-14, incorporated herein by reference). Methods of synthesis of sugar, nucleoside and nucleobase mimetics are well known to those skilled in the art. The heterocyclic base moiety or a modified heterocyclic base moiety is preferably maintained for hybridization with an appropriate target nucleic acid.

The compounds described herein may contain one or more asymmetric centers and thus give rise to enantiomers, diastereomers, and other stereoisomeric configurations that may be defined, in terms of absolute stereochemistry, as (R) or (S). [alpha] or [beta], or as (D) or (L) such as for amino acids et al. The present disclosure is meant to include all such possible isomers, as well as their racemic and optically pure forms.

One such oligomeric compound, an oligonucleotide mimetic that has been shown to have excellent hybridization properties, is referred to as a peptide nucleic acid (PNA) (Nielsen et al., Science, 1991, 254, 1497-1500). PNAs have favorable hybridization properties, high biological stability and are electrostatically neutral molecules. PNA compounds have been used to correct aberrant splicing in a transgenic mouse model (Sazani et al. Nat. Biotechnol., 2002, 20, 1228-1233). In PNA oligomeric compounds, the sugar-backbone of an oligonucleotide is replaced with an amide containing backbone, in particular an aminoethylglycine backbone. The nucleotides are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262. PNA compounds can be obtained commercially from Applied Biosystems (Foster City, Calif. USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule. A polyarginine tail may be a suitable for enhancing cell penetration.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. Morpholino-based oligomeric compounds are non-ionic mimetics of oligo-nucleotides which are less likely to form undesired interactions with cellular proteins (Dwaine A. Braasch and David R. Corey, Biochemistry, 2002, 41(14), 4503-4510). Morpholino-based oligomeric compounds have been studied in zebrafish embryos (see: Genesis, volume 30, issue 3, 2001 and Heasman, J., Dev. Biol. 2002, 243, 209-214). Further studies of morpholino-based oligomeric compounds have also been reported (Nasevicius et al. Nat. Genet., 2000, 26, 216-220; and Lacerra et al., Proc. Natl. Acad. Sci. 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(—O)(N$(CH_3)_2$)—O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids (CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al. J. Am. Chem. Soc. 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. coli* RNase H resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby firming a 2'-C,4'-C-oxymethylene linkage to form the bicyclic sugar moiety (reviewed in Elayadi et al., Curr. Opinion Invens. Drugs, 2001, 2, 558-561; Braasch et al. Chem. Biol. 2001, 8 1-7; and Orum et al., Curr. Opinion Mol. Ther., 2001, 3, 239243; see also U.S. Pat. Nos. 6,268,490 and 6,670,461). The linkage can be a methylene (—CH—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm=+3 to +10[deg.] C.), stability towards 3'-exonucleolytic degradation and good solubility properties. LNAs are commercially available from ProLigo (Paris. France and Boulder, Colo. USA).

An isomer of LNA that has also been studied is α-L-LNA which has been shown to have superior stability against a 3'-exonuclease. The α-L-LNAs were incorporated into antisense gapmers and chimeras that showed potent antisense activity (Frieden et al., Nucleic Acids Research, 2003, 21, 6365-6372).

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11° C.) toward DNA complements. The universality of LNA-mediated hybridization has been stressed by the formation of exceedingly stable LNA:LNA duplexes. The RNA-mimicking of LNA was reflected with regard to the N-type conformational restrict ion of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp.LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA-LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Potent and nontoxic antisense oligonucleotides containing LNAs have been described (Wahlestedt et al. Proc. Natl. Acad. Sc U.S.A. 2000, 97, 5033-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished. Further successful in vive studies involving LNA's have shown knock-down of the rat delta opioid receptor without toxicity (Wahlestedt et al. Proc. Natl. Acad. Sci., 2000, 97, 5633-5638) and in another study showed a blockage of the translation of the large subunit of RNA polymerase II (Fluiter et al., Nucleic Acids Res. 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al. Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al. WO 99/14226). Furthermore, synthesis of 2'-amino-LNA, a novel conformationally restricted high-affinity oligonucleotide analog has been described in the art (Singh et al. J. Org. Chem., 1998, 63, 10035-10039). In addition, 2'-amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-α-L-threose nucleic acid (TNA) was directed to the question of whether a DNA polymerase existed that would copy the TNA. It was found that certain DNA polymerases are able to copy limited stretches of a TNA template (reported in Chemical and Engineering News, 2003, 81, 9). In another study it was determined that. TNA is capable of antiparallel Watson-Crick base pairing with complementary DNA, RNA and TNA oligonucleotides (Chaput et al., J. Am. Chem. Soc., 2003, 125, 856-857).

In one study (3',2')-α-L-threose nucleic acid was prepared and compared to the 2' and 3' amidate analogs (Wu et al., Organic Letters, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al. Helv. Chim. Acta, 1997, 80, 2426-2439; Steffens et al., J. Am. Chem. Soc. 1999, 121, 3249-3255; Renneberg et al., J. Am. Chem. Soc. 2002, 124, 5993-6002; and Renneberg et al. Nucleic acids res., 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Another modification of the oligomeric compounds of the invention involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligomeric compounds of the invention may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al. WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5' cap" present at, the 5' end of native mRNA molecules. In non-limiting examples, the 5'-cap includes inverted abasic residue (moiety), 4',5'-methylene nucleotide: 1-(beta-D-erythrofuranosyl) nucleotide, 4'-thio nucleotide, carbocyclic nucleotide; 1,5-anhydrohexitol nucleotide: L-nucleotides; α-nucleotides: modified base nucleotide; phosphorodithioate linkage; threo-pentofuranosyl nucleotide; acyclic 3',4'-seco nucleotide: acyclic 3,4-dihydroxybutyl nucleotide: acyclic 3,5-dihydroxypentyl riucleotide, 3'-3'-inverted nucleotide moiety: 3'-3'-inverted abasic moiety; 3'-2'-inverted nucleotide moiety: 3'-2'-inverted abasic moiety: 1,4-butanediol phosphate; 3'-phosphoramidate: hexylphosphate; aminohexyl phosphate: 3'-phosphate: 3'-phosphorothioate; phosphorodithioate: or bridging or non-bridging methylphosphonate moiety (for more details see Wincott et al. International PCT publication No. WO 97/26270).

Particularly suitable 3'-cap structures include, for example 4',5'-methylene nucleotide; 1-(beta-D-erythrofuranosyl) nucleotide: 4'-thio nucleotide, carbocyclic nucleotide: 5'-amino-alkyl phosphate: 1,3-diamino-2-propyl phosphate, 3-aminopropyl phosphate; 6-aminohexyl phosphate: 1,2-aminododecyl phosphate; hydroxypropyl phosphate; 1,5-anhydrohexitol nucleotide; L-nucleotide; α-nucleotide: modified base nucleotide: phosphorodithioate; threo-pentofuranosyl nucleotide; acyclic 3',4'-seco nucleotide; 3,4-dihydroxybutyl nucleotide: 3,5-dihydroxypentyl nucleotide, 5'-5'-inverted nucleotide moiety: 5'-5'-inverted abasic moiety: 5'-phosphoramidate; 5'-phosphorothioate; 1,4-butanediol phosphate: 5'-amino: bridging and/or non-bridging 5'-phosphoramidate, phosphorothioate and/or phosphorodithioate, bridging or non-bridging methylphosphonate and 5'-mercapto moieties (for more details see Beaucage and Tyer, 1993. Tetrahedron 49, 1925).

Further 3' and 5'-stabilizing groups that can be used to cap one or both ends of an oligomeric compound to impart nuclease si ability include those disclosed in WO 03/004602 published on Jan. 16, 2003.

In certain embodiments, oligomeric compounds, may be conjugated with a wide variety of different positively charged polymers. Examples of positively charged polymers include peptides, such as argine rich peptides (Examples of positively charged peptides that may be used in the practice of the invention include $R_9F_2C$; $(RXR)_4XB$ (where X can be any amino acid); $R_5F_2R_4C$; $(RFF)_3$; Tat proteins, such as TAT sequence CYGRKKRRQRRR; and $(RFF)_3R$, cationic polymers, such as dendrimeric octaguanindine polymer, and other positively charged molecules as known in the art for conjugation to antisense oligonucleotide compounds. In one embodiment of the invention and/or embodiments thereof, the antisense oligonucleotides are conjugated with positively charged polymer comprising a polymer having a molecular weight that is from about 1,000 to 20,000 Daltons, and preferably from about 5,000 to 10,000 Daltons. Another example of positively charged polymers is polyethylenimine (PEI) with multiple positively charged amine groups in its branched or unbranched chains. PEI has else been widely used as gene and oligomer delivery vesicle.

In a preferred embodiment of the invention and/or embodiments thereof the oligomeric compounds are modified with cell penetrating sequences. Suitable cell penetrating sequences include cell penetrating peptides, such as TAT peptide, MPG, Pep-1, MAP, fusogenic, antimicrobial peptides (AMPs), bacteriocidal peptides, fungicidal peptides, virucidal peptides.

Cell-penetrating peptides (CPPs) are short peptides that, facilitate cellular uptake of the particles of the invention. The particle of the invention is associated with the CPP peptides either through chemical linkage via covalent bonds or through non-covalent interactions. The function of the CPPs are to deliver the particles into cells, a process that commonly occurs through endocytosis with the cargo delivered to the endosomes of living mammalian cells. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake.

An exemplary cell penetrating peptide is the trans-activating transcriptional activator (Tat) from Human Immunodeficiency Virus 1 (IV-1) that can be efficiently taken up from the surrounding media by numerous cell types in culture. Other cell penetrating peptides are MPG. Pep-1, transportan, peneiratin, CADY, TP, TP10, arginine octamer, polyarginine sequences. Arg8, VP22 HSV-1 structural protein, SAP Proline-rich motifs, Vectocell® peptides, hCT (9-32). SynB, Pvec, and PPTG1. Cell penetrating peptides may be cationic, essentially containing clusters of polyarginine in their primary sequence or amphipathic. CPPs are generally peptides of less than 30 amino acids, derived from natural or unnatural protein or chimeric sequences.

In suitable embodiments, the oligomeric compounds are incorporated or otherwise associated with nanoparticles. Nanoparticles may suitably modified for targeting specific cells and optimised for penetrating cells. A skilled person is aware of methods to employ nanoparticles for oligomeric compounds delivery to cells.

Suitable particle are gold particles or silver particles.

Optionally the nanoparticles are made from material selected from the group consisting of gelatine, hydrophilic gelatine, Arg-Gly-Asp-Polyethylenglycol-stearic acid-chitosan, mesoporous silica.

Optionally the nanoparticles are made from protein selected from the group consisting of Hematoporphyrin-Bovine serum albumin, Heat-liable enterotoxin subunit B-Bovine serum albumin, Apotransferin-Bovine serum albumin, Apotransferrin-Lactoferrin, Chitosan-retinoic acid-Albumin, 30Kc19-human-serum-albumin.

Optionally the nanoparticles are made from a polymer selected from the group consisting of Poly(lactic-co-glyoclic acid). Poly(lactic-co-glyoclic acid)-Chitosan, Poly(lactic-co-glyoclic acid)-eudragit, Poly (lactic acid)-F127-Poly (lactic acid), Polycaprolactone-eudragit RS, Polyacrylic acid, Thiolated Polyacrylic acid, Chitosan, Chitosan-Hydroxy propyl Methyl cellulose Phthalate, Chitosan-PGA-DTPA. Trimethyl chitosan-cysteine conjugate, Lauryl-succinyl-Chitosan, Dextran-poloxamer-Chitosan-albumin. Dextran sulfate-Chitosan, Cholic acid modified dextran sulfate, Alginate-dextran sulfate-Chitosan-albumin, Alginate, Thiolated-Eudragit, Poly-N-isopropylacrylamide. Poly(lactic-co-glyoclic acid), Polyethylenglycol-dithiodipropionate-hyaluronic acid, polycaprolactone. Galactose-Chitosan, O-carboxymethyl-chitosan-Galactose, hyaluronic acid-Galactose, Galactosylated-chitosan-polycaprolactone. Galactosylated-chitosan, poly(alkylene oxide)-poly(propylacrylic acid), Poly (lactic acid), (poly(ethylene imine)), Poly(lactic-co-glyoclic acid).

Optionally the oligomeric compounds, enzyme, and/or nucleic acid encoding for the enzyme are incorporated or otherwise associated with extracellular vesicles (EV). Extracellular vesicles (EVs) are small vesicles, which are secreted by prokaryotic and eukaryotic cells One may distinguish between three classes of EVs, namely apoptotic bodies (ABs), microvesicles (MVs) and exosomes. Exosomes or extracellular vesicles are derived from cells. The cells may any kind of cell that is capable of producing exosomes. The cells may be patient derived or from donors, cells in culture or heterologous systems from animals or plants. Preferably the exosomes or extracellular vesicles are derived from the human cells. Several approaches may be used for the loading of exosomal or extracellular vesical carriers with therapeutic cargo.

(A) loading naïve exosomes or extracellular vesicles isolated from parental cells ex vitro:

(B) loading parental cells with enzyme, nucleic acid encoding the enzyme and/or antisense oligomeric compound, which is then released in exosomes or extracellular vesicles; and finally, (C) transfecting/infecting parental cells with DNA encoding enzyme, and/or antisense oligomeric compound, which are then released in exosomes or extracellular vesicles. Exosomes possess an intrinsic ability to cross biological barriers, including the most difficult to penetrate: the blood brain barrier (BBB).

Optionally the exosomes or extracellular vesicles comprise the enzyme or GAA. Optionally the exosomes or extracellular vesicles comprise the mRNA for the enzyme or GAA. Optionally the exosomes or extracellular vesicles comprise the antisense oligomeric compound. Optionally the exosomes or extracellular vesicles comprise a DNA construct encoding for the antisense oligomeric compound.

Optionally the oligomeric compounds, enzyme, and/or nucleic acid encoding for the enzyme are incorporated or otherwise associated with micelles.

Optionally the oligomeric compounds, enzyme, and/or nucleic acid encoding for the enzyme are incorporated or otherwise associated with liposomes.

Optionally the oligomeric compounds, enzyme, and/or nucleic acid encoding for the enzyme are incorporated or otherwise associated with microparticles.

In suitable embodiments of the present invention, the oligomeric compounds are modified with an endosomal escape agent moiety. The endocytic pathway is a major uptake mechanism of cells. Compounds taken up by the endocytic pathway become entrapped in endosomes and may be degraded by specific enzymes in the lysosome. This may be desired or not desired depending on the purpose. If uptake by the endosomes is not desired, an endosomal escape agent may be used. Suitable endosomal escape agents may be chloroquine. TAT peptide.

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid.

Chimeric oligomeric compounds of the invention can be formed as composite structures of two or more oligonucleotides, modified oligonucleotide, oligonucleosides, oligonucleotide mimetics, or regions or portions thereof. Such compounds have also been referred to in the art as hybrids or gapmers. Representative United States patents that, teach the preparation of such hybrid structures include, but are not limited to, U.S. Pat. Nos. 5,013,830; 5,149,797; 5,220,007;

5,256,775; 5,366,878; 5,403,711; 5,491,133; 5,565,350; 5,623,065; 5,652,355; 5,652,356; and 5,700,922.

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytityl-2'-deoxy-N4-benzoyl-5-methylcytidine penultimate intermediate for 5-methyl dC amidite, (5'-O-(4,4'-Dimethoxytriphenylmethyl)-2'-deoxy-N4-benzoyl-5-methylcytidin-3'-O-yl)-2-cyanoethyl-N,N-diisopropylphosphoramidite (5-methyl dC amidite), 2'-Fluonxleoxyadenosine, 2'-Fluorodeoxyguanosine, 2'-Fluorouridine, 2'-Fluorodeoxycyidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N<4>-benzoyl-5-methyl-cytidine penultimate intermediate. (5'-O-(4,4'-Dimethoxytriphenylmethyl)-2'-O-(2-methoxyethyl)-N<4>-benzoyl-5-methylcytidin-3'-O-yl)-2-cyanoethyl-N,N-diisopropylphospophoramidite (MOE 5-Me-C amidite), (5'-O-(4,4'-Dimethoxytriphenylmethyl)-2'-O-(2-methoxyethyl)-N<6>-benzoyladenosin-3'-O-yl)-2-cyanoethyl-N,N-diisopropylphosphoramidite (MOE A amdite). (5'-O-(4,4'-Dimethoxytriphenylmethyl)-2'-O-(2-methoxyethyl)-N<4>-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O<2>-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O-(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et, al. Nucleic Acids Research, 1993, 21, 3197-3203) using commercially available phosphoramidites (Glen Research, Sterling Va. or ChemGenes, Needham, Mass.).

2-fluoro oligonucleotides can be synthesized routinely as described (Kawasaki, et, al., J. Med. Chem., 1993, 36, 831-841) and U.S. Pat. No. 5,670,033.

2'-O-Methoxyethyl-substituted nucleoside amidites can be prepared routinely as per the methods of Martin, P., Helvetica Chimica Acta, 1995, 78, 486-504.

Aminooxyethyl and dimethylaminooxyethyl amidites can be prepared routinely as per the methods of U.S. Pat. No. 6,127,533.

Phosphorothioate-containing oligonucleotides (P-S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or 5,366,878.

Alkylphosphonothioate oligonucleotides can be prepared as described in published PCT applications WO 94/17093 and WO 94/02499.

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-Thio-containing oligonucleotides can be synthesized as described in U.S. Pat. No. 5,639,873.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P—O or P—S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Peptide nucleic acids (PNAs) can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. Nos. 5,539,082, 5,700,922, 5,719,262, 6,559,279 and 6,762,281.

Oligomeric compounds can incorporate at least one 2'-O-protected nucleoside prepared according to methods routine in the art. After incorporation and appropriate deprotection the 2'-O-protected nucleoside will be converted to a ribonucleoside at the position of incorporation. The number and position of the 2-ribonucleoside units in the final oligomeric compound may vary from one at any site or the strategy can be used to prepare up to a full 2'-OH modified oligomeric compound.

The main RNA synthesis strategies that are presently being used commercially include 5'-[beta]-DMT-2'-O-t-butyldimethylsilyl (TBDMS), 5'-O-DMT-2'-[1(2-fluorophenyl)-4-methoxypiperidin-4-yl](FPMP), 2'-O-[(triisopropylsilyl)oxy]methyl (2'-O—$CH_2$—O—Si(iPr)3 (TOM), and the 5'-O-silyl ether-2'-ACE (5'-O-bis(trimethylsiloxy)cyclododecyloxysilyl ether (DOD)-2'-O-bis(2-acetoxyethoxy) methyl (ACE). Some companies currently offering RNA products include Pierce Nucleic Acid Technologies (Milwaukee, Wis.). Dharmacon Research Inc. (a subsidiary of Fisher Scientific. Lafayette. Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the oligomeric compounds of the present invention.

All of the aforementioned RNA synthesis strategies are amenable to the oligomeric compounds of the present invention. Strategies that would be a hybrid of the above e.g. using a 5'-protecting group from one strategy with a 2'-O-protecting from another strategy is also contemplated herein.

Chimeric oligonucleotides, chimeric oligonucleosides and mixed chimeric oligonucleotides/oligonucleosides can be synthesized according to U.S. Pat. No. 5,623,065.

Chimeric oligomeric compounds exhibiting enhanced cellular uptake and greater pharmacologic activity may be made in accordance to U.S. Pat. No. 8,501,703.

Another form of oligomeric compounds comprise tricyclo-DNA (tc-DNA) antisense oligonucleotides. Tricyclo-DNA nucleotides are nucleotides modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Antisense oligomeric compound that contains between 6-22 tricyclo nucleotides in length, in particular between 8-20 tricyclo nucleotides, more particularly between 10 and 18 or between 11 and 18 tricyclo nucleotides are suitable. See e.g. WO2010115993 for examples of tricyclo-DNA (tc-DNA) antisense oligonucleotides. For the present invention this means that any sequence of 8-20, preferably 10-18, more preferably 11-18, more preferably 12, 13, 14, 15, 16 or 17 nucleotides as depicted in any of the above Tables may be useful when such a sequence is in tc-DNA form.

Oligomerization of modified and unmodified nucleosides can be routinely performed according to literature procedures for DNA (Protocols for Oligonucleotides and Analogs, Ed. Agrawal (1993). Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al. Tetrahedron (2001), 57, 5707-5713).

Antisense compounds can be conveniently and routinely made through the well-known technique of solid phase synthesis. Equipment, for such synthesis is sold by several vendors including, for example, Applied Biosystems (Foster City. Calif.). Any other means for such synthesis known in the art may additionally or alternatively be employed. It is well known to use similar techniques to prepare oligonucleotides such as the phosphorothioates and alkylated derivatives. The disclosure is not limited by the method of antisense compound synthesis.

Methods of oligonucleotide purification and analysis are known to those skilled in the art. Analysis methods include capillary electrophoresis (CE) and electrospray-mass spectroscopy. Such synthesis and analysis methods can be performed in multi-well plates. The methods described herein are not limited by the method of oligomer purification.

In a preferred embodiment of the invention and/or embodiments thereof, the antisense compounds provided herein are resistant to RNase H degradation.

In one embodiment of the invention and/or embodiments thereof, the antisense compounds comprise at least one modified nucleotide. In another embodiment, the antisense compounds comprise a modified nucleotide at each position. In yet another embodiment, the antisense compounds are uniformly modified at each position.

Modulation of splicing can be assayed in a variety of ways known in the art. Target mRNA levels can be quantitated by, e.g., Northern blot analysis, competitive polymerase chain reaction (PCR), or real-time PCR. RNA analysis can be performed on total cellular RNA or poly(A)+mRNA by methods known in the art. Methods of RNA isolation are taught in, for example, Ausubel. F. M, et al. Current Protocols in Molecular Biology. Volume 1, pp. 4.1.1-4.2.9 and 4.5.1-4.5.3. John Wiley & Sons, Inc., 1993.

Northern blot analysis is routine in the art and is taught in, for example, Ausubel, F. M. et al. Current Protocols in Molecular Biology, Volume 1, pp. 4.2.1-4.2.9, John Wiley & Sons. Inc., 1990. Real-time quantitative (PCR) can be conveniently accomplished using the commercially available ABI PRISM™ 7700 Sequence Detect ion System, available from PE-Applied Biosystems, Foster City, Calif. and used according to manufacturer's instructions.

Levels of a protein encoded by a target mRNA can be quantitated in a variety of ways well known in the art, such as immunoprecipitation, Western blot analysis (immunoblotting), ELISA or fluorescence-activated cell sorting (FACS). Antibodies directed to a protein encoded by a target mRNA can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M, et al. Current Protocols in Molecular Biology. Volume 2, pp. 11.12.1-11.12.9, John Wiley & Sons, Inc., 1997. Preparation of monoclonal antibodies is taught in, for example. Ausubel, F. M, et al. Current Protocols in Molecular Biology. Volume 2, pp. 11.4.1-11.11.5. John Wiley & Sons, Inc., 1997.

Immunoprecipitation methods are standard in the art and can be found at, for example, Ausubel, F. M, et al., Current Protocols in Molecular Biology, Volume 2, pp. 10.16.1-10.16.11, John Wiley & Sons. Inc., 1998. Western blot (immunoblot) analysis is standard in the art and can be found at, for example, Ausubel. F. M, et al. Current Protocols in Molecular Biology, Volume 2, pp. 10.8.1-10.8.21, John Wiley & Sons. Inc., 1997. Enzyme-linked immunosorbent assays (ELISA) are standard in the art and can be found at, for example, Ausubel. F. M, et al., Current Protocols in Molecular Biology, Volume 2, pp. 11.2.1-11.2.22, John Wiley & Sons, Inc., 1991.

The effect of the oligomeric compounds of the present invention may be analysed by RT PCT, qPCR, flanking exon PCR and/or a method comprising flanking exon PCR on each internal exon corresponding to the mRNA to obtain one or more flanking exon amplification products, and detecting the presence and length of the said flanking exon amplification products, and further quantifying of each protein encoding exon of said mRNA.

The oligomeric compounds provided herein may be utilized for therapeutics or research. Furthermore, antisense compounds, which are able to inhibit gene expression or modulate splicing with specificity, may be used to elucidate the function of particular genes or gene products or to distinguish between functions of various members of a biological pathway. In a preferred embodiment of the invention and/or embodiments thereof the oligomeric compounds are used for the treatment of Pompe disease. In a preferred embodiment of the invention and/or embodiments thereof the oligomeric compounds are used in research of the function of the GAA gene.

Compounds described herein can be used to modulate splicing of a target mRNA in metazoans, preferably mammals, more preferably human. In one non-limiting embodiment of the invention and/or embodiments thereof, the methods comprise the step of administering to said animal an effective amount of an antisense compound that modulates splicing of a target mRNA.

For example, modulation of splicing of a target mRNA can be measured by determining levels of mRNA splicing products in a bodily fluid, tissue, organ of cells of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues, organs or cells include, but are not limited to, blood (e.g., hematopoietic cells, such as human hematopoietic progenitor cells, human hematopoietic stem cells. CD34+ cells CD4+ cells), lymphocytes and other blood lineage cells, skin, hone marrow, spleen, thymus, lymph node, brain, spinal cord, heart, skeletal muscle, liver, connective tissue, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues, organs and cells can be routinely obtained by biopsy. In some alternative situations, samples of tissues or organs can be recovered from an animal after death. In a preferred embodiment of the invention and/or embodiments thereof modulation of splicing is measured in fibroblast, preferably primary fibroblasts, preferably primary fibroblasts from patients suffering from Pompe disease.

Next to use of a single oligomeric compound as herein described, or a pair of AONs targeted to the (cryptic) splice sites of one and the same pseudo-exon, it is also possible to use combinations of one AON or a pair of AONs as described above with any other AON targeted to a different area of the gene or even another gene for therapy against a different aberrant splicing variant. Accordingly, the AONs of the present invention may be readily combined with one or more AONs that are directed against another splice mutation of Pompe disease, such as AONs directed against one or more of the following mutations c.-32-13T>G, c.-32-3C>G c.-32-102T>C, c.-32-56C>T, c.-32-46G>A, c.-32-28C>A, c.-32-28C>T, c.-32-21G>A, c.7G>A, c.11G>A, c.15-17AAA, c.17C>T, c.19-21AAA, c.26-28AAA, c.33-35AAA, c.39G>A, c.42C>T, c.90C>T, c.112G>A, c.137C>T, c.164C>T, c.348G>A, c.373C>T, c.413T>A, c.469C>T, c.476T>C, c.476T>G, c.478T>G, c.482C>T, c.510C>T, c.515T>A, c.520G>A, c.546+11C>T, c.546+14G>A, c.546+19G>A, c.546+23C>A, c.547-6, c.1071, c.1254, c.1552-30, c.1256A>T, c.1551+1G>T, c.546G>T, 0.17C>T, c.469C>T, c.546+23C>A, c.-32-102T>C, c.-32-56C>T, c.11G>A, c.112G>A, c.137C>T. AONs against these mutations have been disclosed in co-pending application WO 2015/190922, more specifically SEQ ID NOs 2-33, 37-40 and 41-540 as disclosed therein.

It is further envisaged that the mutations listed in Table 16 and mutations in the neighborhood of these mutations also are accompanied by the introduction of a natural pseudo-exon. These then can be dealt with in the same manner as discussed above.

TABLE 16

| mutations that lead to the inclusion of a pseudo-exon. |
|---|
| c.546G > A |
| c.546G > T |
| c.546G > C |
| c.546 + 1G > T |
| c.546 + 2T > C |
| c.546 + 2_5deltggg |
| c.546 + 5G > T |
| c.546 + 24G > A |
| c.546 + 45G > C |
| c.547 − 67C > G |
| c.547 − 39T > G |

Advantageously AONs that prevent pseudo-exon expression for the mutations listed in Table 16 may be combined with the AONs or pairs of AONs of the invention.

It is further preferred to combine the AONs or pairs of AONs according to the present invention with the compounds mentioned in e.g. WO 2015/035231 (especially the tricycle-phosphorothiate compounds described therein) or described in WO 2015/036451.

Next to AONs directed to the therapy of Pompe disease, the AONs or pairs of AONs described above may be readily combined with AONs that are meant as a therapy for aberrant splicing in other diseases, such as selected from the group consisting of mucopolysaccharidoses (MPS I, MPS II, MPS IV), familial dysautonomia, congenital disorder of glycosylation (CDGIA), ataxia telangiectasia, spinal muscular atrophy, medium-chain acyl-CoA dehydrogenase (MCAD) deficiency, cystic fibrosis. Factor VII deficiency. Fanconi anemia, Hutchinson-Gilford progeria syndrome, growth hormone insensitivity, hyperphenylalaninemia (HPABH4A). Menkes disease, hypobetalipoproteinemia (FHBL), megalencephalic leukoencephalopathy with subcortical cysts (MLC1), methylmalonic aciduria, frontotemporal dementia, Parkinsonism related to chromosome 17 (FTDP-17), Alzheimer's disease, tauopathies, myotonic dystrophy, afibrinogenemia. Bardet-Biedl syndrome, β-thalassemia, muscular dystrophies, such as Duchenne muscular dystrophy, myopathy with lactic acidosis, neurofibromatosis, Fukuyama congenital muscular dystrophy, muscle wasting diseases, dystrophic epidermolysis bullosa, Myoshi myopathy, retinitis pigmentosa, ocular albinism type 1, hypercholesterolemia, Hemaophilis A, propionic academia. Prader-Willi syndrome, Niemann-Pick type C, Usher syndrome, autosomal dominant polycystic kidney disease (ADPKD), cancer such as solid tumours, retinitis pigmentosa, viral infections such as HIV, Zika, hepatitis, encephalitis, yellow fever, infectious diseases like malaria or Lyme disease.

It can also be imagined that different genes are targeted with AONs for the same disease. For example, Genzyme has published AONs to reduce levels of glycogen synthase (Clayton. N. P. et al., 2014. Mol. Ther. Nucleic Acids. October 28; 3:e206, doi: 10.1038/mtna.2014.57). They hope to reduce synthesis of cytoplasmic glycogen in this way, and this should be a so-called substrate reduction therapy The AONs of the present, invention may be suitably combined with these.

Further therapy based on the AONs of the present invention may be readily combined with enzymatic replacement therapy (ERT) to improve the treatment of Pompe Disease. Compounds for ERT are generally known and used an may be the compounds mentioned in co-pending application PCT/NL2015/050849 such as GAA, Myozyme®, Lumizyme®, neoGAA, Gilt GAA (BMN-701), or oxyrane optionally in combination with genistein, deoxynojirimycin-HCl, N-butyl-deoxynojirimycin. $C_{10}H_{19}NO_4$, $C_{12}H_{23}NO_4$ (as disclosed in this co-pending application), a combination of rituximab and methotrexate. All ERT schedules mentioned in PCT/NL2015/050849 in combination with the AONs of the present invention may be used in the dosage schemes and amounts as have been mentioned therein.

The effects of treatment with the oligomeric compounds can be assessed by measuring biomarkers associated with modulation of splicing of a target mRNA in the aforementioned fluids, tissues or organs, collected from an animal contacted with one or more compounds, by routine clinical methods known in the art. These biomarkers include but are not limited to: glucose, cholesterol, lipoproteins, triglycerides, free fatty acids and other markers of glucose and lipid metabolism: liver transaminases, bilirubin, albumin, blood urea nitrogen, creatine, creatinine and other markers of kidney and liver function; interleukins, tumor necrosis factors, intracellular adhesion molecules, C-reactive protein and other markers of inflammation: testosterone, estrogen and other hormones; tumor markers; vitamins, minerals and electrolytes. In a preferred embodiment of the invention and/or embodiments thereof the biomarker is glycogen.

The compounds disclosed herein can be utilized in pharmaceutical compositions by adding an effective amount of a compound to a suitable pharmaceutically acceptable diluent or carrier. The compounds can also be used in the manufacture of a medicament for the treatment of diseases and disorders related to alterations in splicing. In a preferred embodiment of the invention and/or embodiments thereof, the disease is Pompe disease.

Methods whereby bodily fluids, organs or tissues are contacted with an effective amount of one or more of the antisense compounds or compositions of the disclosure are also contemplated. Bodily fluids, organs or tissues can be contacted with one or more of the compounds of the disclosure resulting in modulation of splicing of target mRNA in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

A sufficient amount of an antisense oligomeric compound to be administered will be an amount that is sufficient to induce amelioration of unwanted disease symptoms. Such an amount may vary inter alia depending on such factors as the gender, age, weight, overall physical condition, of the patient, etc, and may be determined on a case by case basis. The amount may also vary according to the type of condition being treated, and the other components of a treatment protocol (e.g. administration of other medicaments such as steroids, etc.). The amount may also vary according to the method of administration such as systemically or locally.

Typical dosage amounts of the antisense oligonucleotide molecules in pharmaceutical formulations may range from about 0.05 to 1000 mg/kg body weight, and in particular from about 5 to 500 mg/kg body weight. In one embodiment of the invention and/or embodiments thereof, the dosage amount is from about 50 to 300) mg/kg body weight once in 2 weeks, or once or twice a week, or any frequency required to achieve therapeutic effect. Suitably amounts are from 3-50 mg/kg, more suitably 10-40 mg/kg, more suitably 15-25 mg/kg.

Optionally the enzyme or said nucleic acid encoding for said enzyme as used in ERT is administered in a dose of about 1-100 mg/kg/week, optionally 2-90 mg/kg/week, 3-80 mg/kg/week, 5-75 mg/kg/week, 7-70 mg/kg/week, 10-60 mg/kg/week, 12-55 mg/kg/week, 15-50 mg/kg/week, 17-45 mg/kg/week, 20-40 mg/kg/week, 22-35 mg/kg/week, 25-30 mg/kg/week, wherein kg refers to the body weight. Alternative preferred dosage regimens for ERT are 5-80 mg/kg body weight per week, preferably per 2 weeks, more preferably per 3, 4, or 5 weeks or more. Thus, the dosage may be spread out over a longer period, thereby reducing the costs of ERT. For example the enzyme and antisense oligomeric compound are administered once every two weeks, once every 3 weeks, once every 4 weeks, or even over longer intervals, such as 5, 6, 7 or 8 weeks or more. This has now become possible by the combination of AON therapy as disclosed herein.

Alternative preferred dosage regimens for AONs are Optionally said antisense oligomeric compound is administered in a dose of about 0.05 to 1000 mg/kg, optionally about 0.1 to 900 mg/kg, 1-800 mg/kg, 2-750 mg/kg, 3-700 mg/kg, 4-600 mg/kg, 5-500 mg/kg, 7 to 450 mg/kg, 10 to 400 mg/kg, 12 to 350 mg/kg, 15 to 300 mg/kg, 17 to 250 mg/kg, 20 to 220 mg/kg, 22 to 200 mg/kg, 25 to 180 mg/kg, 30 to 150 mg/kg, 35 to 125 mg/kg, 40 to 100 mg/kg, 45 to 75 mg/kg, 50-70 mg/kg.

The combination of the 2 dosage regimes (of ERT and AON therapy) ensures that the intracellular enzyme concentration of GAA enzyme using a defined ERT dosage is significantly increased at that dosage. Hence, the amount of ERT can me reduced by combined administration of AONs as defined herein. There was hitherto no indication in the art that ERT dosages could be reduced in the presence of AON therapy. Also, significantly longer administration intervals may be used for ERT when using combined administration of AONs as defined herein, since the levels of intracellular enzymes are significantly increased, even to levels that may be considered normal (e.g. healthy patient) levels. The terms “significantly longer” and “significantly increased” refer to a duration that is prolonged, or a level that is increased at least 5%, preferably at least 10%, 20%, 30%, 40%, 50%, or more, such as 70% or 80% increased.

The dosage administered will, of course, vary depending on the use and known factors such as the pharmacodynamic characteristics of the active ingredient; age, health, and weight of the recipient; nature and extent of symptoms, kind of concurrent treatment, frequency of treatment, and the effect desired. The recipient may be any type of mammal, but is preferably a human. In one embodiment of the invention and/or embodiments thereof, dosage forms (compositions) of the inventive pharmaceutical composition may contain about 1 microgram to 50,000 micrograms of active ingredient per unit, and in particular, from about 10 to 10,000 micrograms of active ingredient per unit. (if here a unit means a vial or one package for one injection, then it will be much higher, up to 15 g if the weight of a patient is 50 kg) For intravenous delivery, a unit dose of the pharmaceutical formulation will generally contain from 0.5 to 500 micrograms per kg body weight and preferably will contain from 5 to 300 micrograms, in particular 10, 15, 20, 30, 40, 50, 100, 200, or 300 micrograms per kg body weight ([mu]g/kg body weight) of the antisense oligonucleotide molecule. Preferred intravenous dosage ranges from 10 ng to 2000 µg, preferably 3 to 300 µg, more preferably 10 to 100 µg of compound per kg of body weight. Alternatively the unit dose may contain from 2 to 20 milligrams of the antisense oligonucleotide molecule and be administered in multiples, if desired, to give the preceding daily dose. In these pharmaceutical compositions, the antisense oligonucleotide molecule will ordinarily be present in an amount of about 0.5.95% by weight based on the total weight of the composition.

In one particular embodiment, it should be recognized that the dosage can be raised or lowered based on individual patient response. It will be appreciated that the actual amounts of antisense oligonucleotide molecule used will vary according to the specific antisense oligonucleotide molecule being utilized, the particular compositions formulated, the mode of application, and the particular site of administration.

Preferably the compounds are administered daily, once every 2 days, once every 3 days, once a week, once every two weeks, or once every month.

In another preferred embodiment the administration is only one time, e.g. when using a viral vector.

If a viral-based delivery of antisense oligomeric compounds is chosen, suitable (loses will depend on different factors such as the viral strain that is employed, the route of delivery (intramuscular, intravenous, intra-arterial or other), Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the antisense oligomeric compounds of the invention will likely be administered on multiple occasions, that may be, depending on the results obtained, several days apart, several weeks apart, or several months apart, or even several years apart.

Those of skill in the art will recognize that there are many ways to determine or measure a level of functionality of a protein, and to determine a level of increase or decrease of functionality e.g. in response to a treatment protocol. Such methods include but are not limited to measuring or detecting an activity of the protein, etc. Such measurements are generally made in comparison to a standard or control or "normal" sample. In addition, when the protein's lack of functionality is involved in a disease process, disease symptoms may be monitored and/or measured in order to indirectly detect the presence or absence of a correctly functioning protein, or to gauge the success of a treatment protocol intended to remedy the lack of functioning of the protein. In preferred embodiment the functionality of the GAA protein is measured. This is suitably performed with an enzymatic activity assays as is well known to a skilled person.

In a particular embodiment of the invention and/or embodiments thereof, antisense oligonucleotides of the invention may be delivered in vivo alone or in association with a vector. In its broadest sense, a "vector" is any vehicle capable of facilitating the transfer of the antisense oligonucleotide of the invention to the cells. Preferably, the vector transports the nucleic acid to cells with reduced degradation relative to the extent of degradation that would result in the absence of the vector. In general, the vectors useful in the invention include, but are not limited to, naked plasmids, non viral delivery systems (electroporation, sonoporation, cationic transfection agents, liposomes, etc. . . . ), phagemids, viruses, other vehicles derived from viral or bacterial sources that have been manipulated by the insertion or incorporation of the antisense oligonucleotide nucleic acid sequences. Viral vectors are a preferred type of vector and include, but are not limited to nucleic acid sequences from the following viruses: RNA or DNA viruses such as a retrovirus (as for example moloney murine leukemia virus and lentiviral derived vectors), harvey murine sarcoma virus, murine mammary tumor virus, and rous sarcoma virus; adenovirus, adeno-associated virus: SV40-type viruses: polyoma viruses; Epstein-Barr viruses; papilloma viruses; herpes virus; vaccinia virus: polio virus. One can readily employ other vectors not named but known to the art.

Preferred viral vectors according to the invention include adenoviruses and adeno-associated (AAV) viruses, which are DNA viruses that have already been approved for human use in gene therapy. Actually 12 different AAV serotypes (AAV1 to 12) are known, each with different tissue tropisms (Wu, Z Mol Ther 2006: 14:316-27). Recombinant AAV are derived from the dependent parvovirus AAV (Choi, V W J Virol 2005; 79:6801-07). The adeno-associated virus type 1 to 12 can be engineered to be replication deficient and is capable of infecting a wide range of cell types and species (Wu, Z Mol Ther 2006: 14:316.27). It further has advantages such as, heat and lipid solvent stability; high transduction frequencies in cells of diverse lineages, including hemopoietic cells; and lack of superinfection inhibition thus allowing multiple series of transductions. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al. 1989. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by, intranasal sprays or drops, rectal suppository and orally. Preferably, said DNA plasmid is injected intramuscular, or intravenous. It may also be administered into the epidermis or a mucosal surface using a gene-gun. The plasmids may be given in an aqueous solution, dried onto gold particles or in association with another DNA delivery system including but not limited to liposomes, dendrimers, cochleates and microencapsulation.

In a preferred embodiment of the invention and/or embodiments thereof, the antisense oligonucleotide nucleic acid sequence is under the control of a heterologous regulatory region, e.g., a heterologous promoter. The promoter can also be, e.g., a viral promoter, such as CMV promoter or any synthetic promoters.

In a preferred embodiment of the invention and/or embodiments thereof, the vector may code for more than one antisense oligomeric compound. Each antisense oligomeric compound is directed to different targets.

Pharmaceutical compositions comprising the antisense compounds described herein may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleotides that are cleaved (e.g., by incorporating phosphodiester backbone linkages at the ends) to produce the active compound.

The term "pharmaceutically acceptable salts" refers to physiologically and pharmaceutically acceptable salts of the compounds: i.e., salts that retain the desired biological activity of the parent compound and do not impart undesired toxicological effects thereto. Sodium salts of antisense oligonucleotides are useful and are well accepted for therapeutic administration to humans. In another embodiment of the invention and/or embodiments thereof, sodium salts of dsRNA compounds are also provided.

The antisense compounds described herein may also be admixed, encapsulated, conjugated or otherwise associated with other molecules, molecule structures or mixtures of compounds.

The present disclosure also includes pharmaceutical compositions and formulations which include the antisense compounds described herein. The pharmaceutical compositions may be administered in a number of ways depending upon whether local or systemic treatment is desired and upon the area to be treated. In a preferred embodiment of the invention and/or embodiments thereof, administration is intramuscular or intravenous.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a preferred embodiment of the invention and/or embodiments thereof, the pharmaceutical formulations are prepared for intramuscular administration in an appropriate solvent, e.g., water or normal saline, possibly in a sterile formulation, with carriers or other agents.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc. when combined with a nucleic acid and the other components of a given pharmaceutical composition.

Compositions provided herein may contain two or more antisense compounds. In another related embodiment, compositions may contain one or more antisense compounds, particularly oligonucleotides, targeted to SEQ ID NO: 1 and/or targeted to SEQ ID NO: 180 and one or more additional antisense compounds targeted to a further nucleic acid target, which may relevant to the patient to be treated. Alternatively, compositions provided herein can contain two or more antisense compounds targeted to different regions of the same nucleic acid target. Two or more combined compounds may be used together or sequentially. Compositions can also be combined with other non-antisense compound therapeutic agents.

The antisense oligomeric compound described herein may be in admixture with excipients suitable for the manufacture of aqueous suspensions. Such excipients are suspending agents, for example polyvinylpyrrolidone, sodium carboxymethylcellulose, methylcellulose, hydropropylmethylcellulose, sodium alginate, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions may also contain one or more preservatives, for example ethyl, or n-propyl p-hydroxybenzoate. Dispersible powders and granules suitable for preparation of an aqueous suspension by the addition of water provide the active ingredient in admixture with a dispersing or wetting agent, suspending agent and one or more preservatives, antisense oligomeric compound compositions may be in the form of a sterile injectable aqueous or oleaginous suspension. Suspensions may be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono or diglycerides. In addition, fatty acids such as oleic acid find use in the preparation of injectables.

The present disclosure also includes antisense oligomeric compound compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences (Mack Publishing Co., A. R. Gennaro edit., 1985). For example, preservatives and stabilizers can be provided. These include sodium benzoate, sorbic acid and esters of p-hydroxybenzoic acid. In addition, antioxidants and suspending agents can be used.

Pharmaceutical compositions of this disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxy ethylene sorbitan monooleate.

The antisense oligomeric compound of this disclosure may be administered to a patient by any standard means, with or without stabilizers, buffers, or the like, to form a composition suitable for treatment. When it is desired to use a liposome delivery mechanism, standard protocols for formation of liposomes can be followed. Thus the antisense oligomeric compound of the present disclosure may be administered in any form, for example intramuscular or by local, systemic, or intrathecal injection.

This disclosure also features the use of antisense oligomeric compound compositions comprising surface-modified liposomes containing poly(ethylene glycol) lipids (PEG-modified, or long-circulating liposomes or stealth liposomes). These formulations offer a method for increasing the accumulation of antisense oligomeric compound in target tissues. This class of drug carriers resists opsonization and elimination by the mononuclear phagocytic system (MPS or RES), thereby enabling longer blood circulation times and enhanced tissue exposure for the encapsulated antisense oligomeric compound (Lasic et al. Chem. Rev. 95:2601-2627 (1995) and Ishiwata et al, Chem. Pharm. Bull. 43:1005-1011 (1995). Long-circulating liposomes enhance the pharmacokinetics and pharmacodynamics of antisense oligomeric compound, particularly compared to conventional cationic liposomes which are known to accumulate in tissues of the MPS (Liu et al, J. Biol. Chem. 42:24864-24870 (1995); Choi et al, PCT Publication No. WO 96/10391; Ansell et al, PCT Publication No. WO 96/10390; Holland et al, PCT Publication No. WO 96/10392). Long-circulating liposomes are also likely to protect antisense oligomeric compound from nuclease degradation to a greater extent compared to cationic liposomes, based on their ability to avoid accumulation in metabolically aggressive MPS tissues such as the liver and spleen.

Following administration of the antisense oligomeric compound compositions according to the formulations and methods of this disclosure, test subjects will exhibit, about a 10% up to about a 99% reduction in one or more symptoms associated with the disease or disorder being treated, as compared to placebo-treated or other suitable control subjects.

The invention is further described by the following numbered paragraphs:

1. Composition for use for the treatment of Pompe disease, said composition comprising an enzyme or nucleic acid encoding for said enzyme suitable for Enzyme Replacement Therapy for Pompe disease, wherein said treatment is a combination of the administration of said enzyme or said nucleic acid encoding for said enzyme and the administration of an antisense oligomeric compound that modulates the splicing of acid α-glucosidase (GAA) enzyme.

2. Treatment, of Pompe disease by administration of an enzyme or nucleic acid encoding for said enzyme suitable for Enzyme Replacement Therapy for Pompe disease in combination with the administration of an antisense oligomeric compound that modulates the splicing of acid α-glucosidase (GAA) enzyme gene.

3. Composition according to paragraph 1 or treatment according to paragraph 2 wherein the antisense oligomeric compound modulates aberrant splicing of acid α-glucosidase (GAA) enzyme gene, Optionally by an activity selected from the group consisting of promotion of exon inclusion, inhibition of a cryptic splicing site, inhibition of intron inclusion, recovering of reading frame, inhibition of splicing silencer sequence, activation of spicing enhancer sequence or any combination thereof.

4. Composition according to any of paragraphs 1, 3 or treatment according to any of paragraphs 2, 3 wherein the antisense oligomeric compound targets a nucleic acid sequence of the GAA gene selected from the group consisting of SEQ ID NO: 1-266 or targets a single nucleotide polymorphism of SEQ ID NO: 1-266.

5. Composition according to any of paragraphs 1, 3-4 or treatment according to any of paragraphs 2-4 wherein said enzyme or said nucleic acid encoding for said enzyme and the antisense oligomeric compound is administered simultaneously or separately.

6. Composition according to any of paragraphs 1, 3-5 or treatment according to any of paragraphs 2-5 wherein said enzyme or said nucleic acid encoding for said enzyme and said antisense oligomeric compound are present in one treatment composition or in separate treatment compositions.

7. Composition according to any of paragraphs 1 or 3-6 or treatment according to any of paragraph 2-6 wherein the administration route is selected from the group consisting of oral, parenteral, intravenous, intraarterial, subcutaneous, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation, or combinations thereof, optionally intravenous.

8. Composition according to any of paragraphs 1 or 3-7 or treatment according to any of paragraph 2-7 wherein the administration route of said enzyme or said nucleic acid encoding for said enzyme and the administration route of said antisense oligomeric compound are the same or different.

9. Composition according to any of paragraphs 1 or 3-8 or treatment according to any of paragraph 2-8 wherein said enzyme or said nucleic acid encoding for said enzyme is administered once every 1 week or once every 2 weeks, or once every 3 weeks.

10. Composition according to any of paragraphs 1 or 3-9 or treatment according to any of paragraph 2-9 wherein said antisense oligomeric compound is administered once every week, once every 2 week or once every 4 weeks, or once every 6 weeks.

11. Composition according to any of paragraphs 1 or 3-10 or treatment according to any of paragraph 2-10 wherein said enzyme or said nucleic acid encoding for said enzyme is administered in a dose of about 1-100 mg/kg, optionally 2-90 mg/kg, 3-80 mg/kg, 5-75 mg/kg, 7-70 mg/kg, 10-60 mg/kg, 12-55 mg/kg, 15-50 mg/kg, 17-45 mg/kg, 20-40 mg/kg, 22-35 mg/kg, 25-30 mg/kg.

12. Composition according to any of paragraphs 1 or 3-11 or treatment according to any of paragraph 2-11 wherein said antisense oligomeric compound is administered in dose of about 0.05 to 1000 mg/kg, optionally about 0.1 to 900 mg/kg, 1,800 mg/kg, 2-750 mg/kg, 3-700 mg/kg, 4-600 mg/kg, 5,500 mg/kg, 7 to 450 mg/kg, 10 to 400 mg/kg, 12 to 350 mg/kg, 15 to 300 mg/kg, 17 to 250 mg/kg, 20 to 220 mg/kg, 22 to 200 mg/kg, 25 to 180 mg/kg, 30 to 150 mg/kg, 35 to 125 mg/kg, 40 to 100 mg/kg, 45 to 75 mg/kg, 50-70 mg/kg, preferably 0.1 to 100 mg/kg, 1-100 mg/kg, 2-100 mg/kg, 3-100 mg/kg, 4-100 mg/kg, 5-100 mg/kg, 7 to 100 mg/kg, 10 to 100 mg/kg, 10-75 mg/kg, 12 to 75 mg/kg, 15 to 75 mg/kg, 15-40 mg/kg, 15-30 mg/kg, 17 to 30 mg/kg, 20 to 30 mg/kg, 22 to 25 mg/kg 13. Composition according to any of paragraphs 1 or 3-12 or treatment according to any of paragraph 2-12 wherein the said enzyme or said nucleic acid encoding for said enzyme or said antisense oligomeric compound is administered in combination with a chaperone such as a Active Site-Specific Chaperone (ASSC).

15. (Composition according to any of paragraphs 1 or 3-14 or treatment according to any of paragraph 2-14 wherein the administration is in combination with cell penetrating peptides.

16. Composition according to any of paragraphs 1 or 3-15 or treatment according to any of paragraph 2-15 wherein said enzyme is an acid α-glucosidase (GAA) enzyme, or any modification, variant, analogue, fragment, portion, or functional derivative, thereof.

17. Composition according to any of paragraphs 1 or 3-16 or treatment according to any of paragraph 2-16 wherein said enzyme is selected from the group consisting of a recombinant human GAA, Myozyme, Lumizyme, neoGAA, Gilt GAA (BMN-701), or oxyrane.

18 Composition according to any of paragraphs 1 or 3-17 or treatment according to any of paragraph 2-17 wherein the composition comprises more than one antisense oligomeric compound.

19. Composition according to any of paragraphs 1 or 3-18 or treatment according to any of paragraph 2-18 wherein the antisense oligomeric compound is selected from the group comprising SEQ ID NO: 267-2040, complements thereof, and sequences having at least 80% identity thereof.

20. Composition according to any of paragraphs 1 or 3-19 or treatment according to any of paragraph 2-19 wherein the antisense oligomeric compound is complementary to a sequence selected from the group comprising SEQ ID NO: 1-266, and sequences having at least 80% identity thereof.

21. Composition according to any of paragraphs 1 or 3-20 or treatment according to any of paragraph 2-20 wherein at least one of the nucleotides of the is antisense oligomeric compound is modified Optionally the oligomeric compound is uniformly modified.

22. Composition according to any of paragraphs 1 or 3-21 or treatment according to any of paragraph 2-21 wherein the sugar of one or more nucleotides of the is antisense oligomeric compound is modified. Optionally the sugar modification is 2'-O-methyl or 2'-O-methoxyethyl.

23 Composition according to any of paragraphs 1 or 3-22 or treatment according to any of paragraph 2-22 wherein the base of one or more nucleotides of the antisense oligomeric compound is modified.

24. Composition according to any of paragraphs 1 or 3.23 or treatment according to any of paragraph 2-23 wherein the backbone of the antisense oligomeric compound is modified, Optionally wherein the modified oligomeric compound is a morpholino phosphorothioate, or a morpholino phosphorodiamidate, or tricyclo-DNA.

25. Composition according to paragraph any of 1 or 3-24 or treatment according to any of paragraph 2-24 wherein the antisense oligomeric compound is SEQ ID NO: 277 or SEQ ID NO: 298.

26. Composition according to paragraph any of 1 or 3-25 or treatment according to any of paragraph 2-25 wherein the antisense oligomeric compound and/or the enzyme or nucleic acid coding for said enzyme is carried in a carrier selected from the group of exosomes, nanoparticles, micelles, liposomes, or microparticles.

27. A pharmaceutical composition comprising at least one antisense oligomeric compound as defined in any of paragraph 1-26 and an enzyme as defined in any of paragraphs 1-26, 28. A pharmaceutical composition according to paragraph 27 wherein said composition further comprises a pharmaceutical acceptable excipient and/or a cell delivery agent.

29. A pharmaceutical composition according to paragraph 27 or 28 wherein the composition further comprises a chaperone such as a Active Site-Specific Chaperone (ASSC).

31. A pharmaceutical composition according to any of paragraphs 27 to 30 wherein the composition further comprises at least one cell penetrating peptide.

32. A pharmaceutical composition according to any of paragraphs 27 to 31 wherein the wherein said enzyme is an acid α-glucosidase (GAA) enzyme, or any modification, variant, analogue, fragment, portion, or functional derivative, thereof.

33. A pharmaceutical composition according to any of paragraphs 27 to 32 wherein the composition comprises enzyme in an amount of about 5-25 mg/mL enzyme.

34. A pharmaceutical composition according to any of paragraphs 27 to 33 wherein the composition comprises antisense oligomeric compound in an amount of −25 mg/mL.

35. A pharmaceutical composition according to any of paragraphs 27 to 34 wherein the composition comprises a carrier selected from the group consisting of exosomes, nanoparticles, micelles, liposomes, microparticles.

36. Antisense oligomeric compound comprising sequences selected from the group comprising SEQ ID NO: 2036-2040 and sequences having at least 80% identity thereof.

37. Antisense oligomeric compound as described in paragraph 36 for use in the treatment Pompe disease.

38. Antisense oligomeric compound as described in any of the paragraphs 36-37 wherein at least one of the nucleotides is modified Optionally the oligomeric compound is uniformly modified.

39. Antisense oligomeric compound as described in any of the paragraphs 36-38 wherein the sugar of one or more nucleotides is modified, Optionally the sugar modification is 2'-O-methyl or 2'-O-methoxyethyl.

40. Antisense oligomeric compound as described in any of the paragraphs 36-.39 wherein the base of one or more nucleotides is modified.

41. Antisense oligomeric compound as described in any of the paragraphs 36-40 wherein the backbone of the oligomeric compound is modified, Optionally is morpholino phosphorothioates, or morpholino phosphorodiamidate, or tricyclo DNA.

42. A method of modulating splicing of GAA pre-mRNA in a cell comprising: contacting the cell with an antisense oligomeric compound as described in any paragraph 36-41.

43. Method for treating Pompe disease in a patient comprising administering said patient with an effective amount of an antisense oligomeric compound according to any of paragraph 36-41.
44. Method to restore the function of GAA in a cell wherein said method comprises the step of administration of an antisense oligomeric compound according to any of paragraph 36.41.
45. Method of correcting abnormal gene expression in a cell, preferably a muscular or muscle cell, of a subject, the method comprising administering to the subject an antisense oligomeric compound according to any of paragraph 36-41.
46. Method according to any of paragraph 42-45 wherein the cell or the patient comprises at least one mutation selected from the group c.-:2-13T>G, c.-32-3C>G, c.547-6, c.1071, c.1254, and c.1552-:30, Optionally the cell or patient comprises mutation c.-32-3C>G or c.-32-13T>G.
47. Method according to any of paragraph 42-46 wherein exon inclusion is accomplished, preferably inclusion of exon 2.
48. A pharmaceutical composition comprising at least one antisense oligomeric compound according to any of paragraph 36-41
49. A pharmaceutical composition according to paragraph 48 wherein said composition furl her comprises a pharmaceutical acceptable excipient and/or a cell delivery agent.
50. A method for repairing aberrant splicing, wherein such aberrant splicing is caused by the expression of a natural pseudo exon, comprising blocking of either the natural cryptic 3' splice site or the natural cryptic 5' splice site of said natural pseudo exon with an antisense oligomeric compound (AON).
51. A method for repairing aberrant splicing, wherein such aberrant splicing is caused by the expression of a natural pseudo exon, comprising providing a pair of AONs, in which the first AON is directed to the acceptor splice site of said natural pseudo exon (i.e. 3' splice site of the natural pseudo exon) and wherein the second AON is directed to the donor splice site of said natural pseudo exon (i.e. the 5 splice site of the natural pseudo exon), wherein the application of said pair of AONs provides for a silencing of the expression of the natural pseudo exon, and promotes canonical splicing.
52. A method according to paragraph 50 or 51, wherein said natural pseudo exon is comprised in an intron of a gene.
53. A method according to paragraph 50 or 51, wherein the aberrant splicing causes a disease selected from the group consisting of mucopolysaccharidoses (MIPS I, MPS II, MPS IV), familial dysautonomia, congenital disorder of glycosylation (CDG1A), ataxia telangiectasia, spinal muscular atrophy, medium-chain acyl-CoA dehydrogenase (MCAD) deficiency, cystic fibrosis, Factor VII deficiency, Fanconi anemia, Hutchinson-Gilford progeria syndrome, growth hormone insensitivity, hyperphenylalaninemia (HPABH4A). Menkes disease, hypobetalipoproteinemia (FHBL), megalencephalic leukoencephalopathy with subcortical cysts (MLC1), methylmalonic aciduria, frontotemporal dementia, Parkinsonism related to chromosome 17 (FTDP-17). Alzheimer's disease, tauopathies, myotonic dystrophy, afibrinogenemia, Bardet-Biedl syndrome, δ-thalassemia, muscular dystrophies, such as Duchenne muscular dystrophy, myopathy with lactic acidosis, neurofibromatosis. Fukuyama congenital muscular dystrophy, muscle wasting diseases, dystrophic epidermolysis bullosa, Myoshi myopathy, retinitis pigmentosa, ocular albinism type 1, hypercholesterolemia. Hemaophilis A, propionic academia, Prader-Willi syndrome, Niemann-Pick type C, Usher syndrome, autosomal dominant polycystic kidney disease (ADPKD), cancer such as solid tumours, retinitis pigmentosa, viral infections such as HIV, Zika, hepatitis, encephalitis, yellow fever, infectious diseases like malaria or Lyme disease.
54. A method according to paragraph 53, wherein the disease is Pompe disease.
55. A method according to paragraph 54, wherein the Pompe disease is characterized by the IVS1 mutation.
56. A method according to paragraph 55, wherein an AON is directed against the natural cryptic donor splice site chosen from the sequences SEQ ID NO: 171.-20.
57. A method according to paragraph 55, wherein an AON is directed against the natural cryptic acceptor site chosen from the sequences SEQ ID NO: 1-170.
58. A method according to paragraph 56 or 57 wherein the AON is chosen from the sequences SEQ ID NO: 267-445 or sequences that have an identity of 80% with said sequences.
59. A method according to paragraph 56 or 57,wherein the AON is chosen from the sequences SEQ ID NO: 446-602 or sequences that have an identity of 80% with said sequences.
60. A method according to any of paragraphs 5-59, wherein a pair of AONs is formed by selecting a first AON from the sequences of SEQ ID NO: 267-445 or sequences that have an identity of 80% with said sequences and a second AON from the sequences of SEQ ID NO: 446-602 or sequences that have an identity of 80% with said sequences.
61. A method according to paragraph 60, wherein the pair of AONs is SEQ ID NO: 578 and one of SEQ ID NO: 277 and 298.
62. Antisense oligomeric compound targeting SEQ ID NO:1 or SEQ ID NO: 171.
63. Antisense oligomeric compound targeting any of the sequences of SEQ ID NO: 2-170 or SEQ ID NO: 172-260.
64. A pair of antisense oligomeric compounds of which a first AON targets one of the sequences of SEQ ID NO: 1-170 and of which the second AON targets one of the sequences of SEQ ID NO: 171-260.
65. An AON according to paragraph 62 or 63 selected from the sequences of SEQ ID NO: 446-602, sequences that are complementary to said sequences or sequences that have an identity of 80% with said sequences or the complementary sequences and a second AON from the sequences of SEQ ID NO: 267-445, sequences that are complementary to said sequences or sequences that have an identity of 80% with said sequences or the complementary sequences.
66. A pair of AONs according to paragraph 64, of which a first, member is selected from the sequences of SEQ ID NO: 267-445, sequences that are complementary to said sequences or sequences that have an identity of 80% with said sequences or the complementary sequences and of which a second AON is selected from the sequences of SEQ ID NO: 446-602, sequences that are complementary to said sequences or sequences that have an identity of 80% with said sequences or the complementary sequences
67. An AON according to paragraph 62 or 63 selected from the sequences of SEQ ID NO: 267-445, sequences that are complementary to said sequences or sequences that have an identity of 80% with said sequences or the complementary sequences and a second AON from the sequences of SEQ ID NO: 446-602, sequences that are complementary to said sequences or sequences that have an identity of 80% with said sequences or the complementary sequences for use in the treatment of Pompe disease, more preferably an AON selected from the group consisting of SEQ ID NO: 578. SEQ ID NO: 277 and 298, or sequences complimentary thereto or sequences having an identity of 80% with said sequences or the complementary sequences.

68. A pair of AONs according to paragraph 64, of which a first member is selected from the sequences of SEQ ID NO: 267-445, sequences that are complementary to said sequences or sequences that have an identity of 80% with said sequences or the complementary sequences and of which a second AON is selected from the sequences of SEQ ID NO: 4-46-602, sequences that are complementary to said sequences or sequences that have an identity of 80% with said sequences or the complementary sequences for use in the treatment of Pompe disease, more preferably wherein said pair comprises SEQ ID NO: 578, and one of SEQ ID NO: 277 and 298, or sequences complimentary thereto or sequences having an identity of 80% with said sequences or the complementary sequences.

69. An AON or pair of AONs according to any of paragraphs 62-66, or an AON or pair of AONs for use according to paragraphs 67 or 68 wherein each of said AONs is uniformly modified, preferably wherein the sugar of one or more nucleotides is modified, more preferably wherein the sugar modification is 2'-O-methyl or 2'-O-methoxyethy, or alternatively or in combination wherein the base of one or more nucleotides is modified, or alternatively or in combination wherein the backbone of the oligomeric compound is modified, more preferably wherein the backbone is morpholino phosphorothioates, or morpholino phosphorodiamidate.

70. A pharmaceutical composition comprising an AON or pair of AONs according to any of paragraph 62-66, preferably wherein said pharmaceutical composition further provides a pharmaceutical acceptable excipient and/or a cell delivery agent.

EXAMPLES

Example 1

Generation of Induced Pluripotent Stem Cells

Dermal fibroblasts from control 1 and two patients (1 and 2) with Pompe disease were obtained via skin biopsy with informed consent. The Institutional Review Board approved the study protocol. All patient and control primary cell lines were negative for HIV, hepatitis B, hepatitis C as tested by quantitative PCR analysis at the diagnostic department of Virology of the Erasmus MC Rotterdam. The Netherlands. Both patient cell lines contain the IVS1 mutation on one allele. The second allele was c.525delT for patient 1, and c.923A>C (his>pro) for patient 2, which both are established pathogenic GAA variants (www.pompecenter.nl). Primary fibroblasts were reprogrammed into iPS cells using a polycistronic lentiviral vector of Oct4, Sox2, Klf4, and c-Myc as described 54, iPS control 2 cell line was a gift from Christian Freund and Christine Mummery and has been characterized previously (26), iPS cells were cultured on γ-irradiated mouse embryonic feeder (MEF) cells. The culture medium consisted of DMEM/F12 medium (Invitrogen), 20% knockout serum replacement (Invitrogen), 1% non-essential amino acids (Gibco), 1% penicillin/streptomycin/L-glutamine (100×, Gibco), 2 mM β-mercaptoethanol (Invitrogen) and 20 ng/ml basic fibroblast growth factor (Peprotech).

Immunofluorescence

Cells were fixed with 4% paraformaldehyde (Merck) in PBS for 10 minutes at room temperature, washed with PBS and permeabilized for 5 minutes with 0.1% Triton X-100 (AppliChem) in PBS. Blocking was performed for 45 minutes at room temperature with blocking solution containing PBS-T (0.1% Tween, Sigma) with 3% BSA (Sigma). Primary antibodies (Supplementary Table 1) were diluted into 0.2% BSA in PBS-T and incubated either 1 hour at room temperature or overnight at 4° C. After incubation wells were washed three times for 5 minutes with PBS-T and incubated with the secondary antibodies (1:500, Alexa-Fluor-594-α-goat, Alexa-Fluor-488-α-mouse. Invitrogen) in PBS-T for 30 minutes at room temperature. The wells were subsequently washed two times for 5 minutes with PBS and incubated for 15 minutes with Hoechst (Thermo Scientific). Afterwards cells were embedded in Vectashield Mounting Medium (Vector).

Microarray Analysis

RNA samples to be analyzed by microarrays were prepared using RNeasy columns with on-column DNA digestion (Qiagen). 300 ng of total RNA per sample was used as input into a linear amplification protocol (Ambion), which involved synthesis of T7-linked double-stranded cDNA and 12 hours of in vitro transcription incorporating biotin-labelled nucleotides. Purified and labeled cRNA was then hybridized for 18 h onto HumanHT-12 v4 expression BeadChips (Illumina) following the manufacturers instructions. After recommended washing, chips were stained with streptavidin-Cy3 (GE Healthcare) and scanned using the iScan reader (Illumina) and accompanying software. Samples were exclusively hybridized as biological replicates. The bead intensities were mapped to gene information using BeadStudio 3.2 (Illumina). Background correction was performed using the Affymetrix Robust Multi-array Analysis (RMA) background correct ion model 55. Variance stabilization was performed using the log 2 scaling and gene expression normalization was calculated with the method implemented in the lumi package of R-Bioconductor. Data post-processing and graphics was performed with in-house developed functions in Matlab. Hierarchical clustering of genes and samples was performed with one minus correlation metric and the unweighted average distance (UPGMA) (also known as group average) linkage method. The microarray data have been deposited with accession number (in progress).

In Vitro Differentiation iPS colonies were washed once with PBS and treated for 45 minutes with 1 mg/ml collagenases IV (Invitrogen) at 37° C., scraped and centrifuged for 15 seconds at 800 rpm. The pellet was slowly dissolved into EB medium (iPS medium without FGF2) with 10 μM Y-27632 dihydrochloride (Ascent Scientific) and plated on low binding plates (Cyto one). For the endoderm condition 10 μM SB 431542 (Ascent Scientific) was added to the EB medium. Six days later EBs were plated in 12 wells coated with 0.1% gelatin (Sigma) for endoderm and mesoderm differentiation or with matrigel-coated plates for ectoderm differentiation in endo/mesoectoderm medium. Cells were fixed after 14 days of differentiation with 4% paraformaldehyde (Merck) in PBS for 5 minutes at room temperature and processed for immunofluorescence.

Karyotype Analysis iPS or myogenic progenitors were detached with TrypLe (Gibco) for 5 minutes at 37° C. The pellet was incubated with 10 μg/ml colcemid (Gibco) for 30 minutes at room temperature. Cells were then centrifuged for 10 minutes at 1100 rpm and resuspended into prewarmed 0.075 M KCL and incubated for 10 minutes at 37° C. After incubation cells were five times washed with fixation solution (3:1 methanol: acetic acid) and spread onto glass slides. Hoechst staining was performed as described above.

Differentiation of iPS Cells to Myogenic Progenitor Cells

Differentiation of iPS cells to myogenic progenitors cells was modified from Borchin et al. 5. Briefly, 0.6 mm large iPS colonies cultured in 10 cm dishes on MEF feeders were treated for 5 days with 3.5 μM CHIR99021 (Axon Medchem) in myogenic differentiation medium (DMEM/F12, 1×ITS-X and Penicillin/Streptomycin-Glutamine, all Gibco). After 5 days, CHIR99021 was removed and cells were cultured in myogenic differentiation medium containing 20 ng/ml FGF2 (Prepotech) for 14 days and switched for an additional 14 days to myogenic differentiation medium only. Fusion index represent the % of nuclei inside myofibers relative to the total number of nuclei. Five random fields at 20× magnification were counted.

FACS Sorting

Cells were washed once with PBS, detached for 5 minutes with TrypLe (Gibco) at 37° C., and filtered through a 0.45 μM FACS strainer (Falcon). Cells were stained with HNK-1-FITC (1:100. Aviva Systems Biology) and C-MET-APC (1:50, R&D Systems) for 30 minutes on ice in myogenic differentiation medium and washed three times with ice-cold 0.1% BSA in PBS before FACS sorting. Hoechst (33258. Life Technology) was used as viability marker.

Expansion of Myogenic Progenitor Cells

Hoechst/C-MET-positive cells were plated at 40,000 cells/well on ECM (Sigma Aldrich)-coated 48 wells plates in iPS-myogenic progenitor proliferation medium containing DMEM high glucose (Gibco) supplemented with 100 U/ml Penicillin/Streptomycin/Glutamine (Life Technology), 10% Fetal bovine serum (Hyclone, Thermo Scientific), 100 ng/ml FGF2 (Prepotech), and 1× RevitaCell™ Supplement (Gibco). Cells were passaged using 2× diluted TrypLe. For differentiation to skeletal muscle cells, myogenic progenitors were grown to 90% confluence and the medium was then replaced with myogenic differentiation medium (see above).

Modification of the U7 snRNA Vector for Intermediate Throughput Cloning of AON Sequences The U7 snRNA gene and promoter were amplified by PCR from female mouse genomic DNA using Fw-ms-U7snRNA-PstI and Rv-ms-U7snRNA-SalI primers, which included PstI and SalI overhang restriction sites. The PCR fragment (425 bp) was cloned into a pCRII-TOPO vector according to the manufacture's manual (Invitrogen). SMopt and NsiI sites were generated by site-directed mutagenesis according to an inner and outer primer design with Fw- and Rv-U7snRNA-SMopt or Fw- and Rv-U7snRNA-NsiI as inner primers and with Fw-M13 and Rv-M13 as outer primers (Table 9), and subcloned using the PstI and SalI sites in front of the polypurine tract fragment of the lentiviral vector used for reprogramming from which OSKM and the SF promoter were removed.

Cloning of AONs into the U7 snRNA Vector

AONs were inserted via PCR amplification using an forward primer that contained the desired antisense sequence and the unique NsiI restriction site and the reverse primer Rv-ms-U7snRNA-SalI. The amplified PCR product was purified by agarose gel electrophorese, extracted (gel extraction kit. Qiagen), digested with NsiI and SalI, purified (PCR purification kit, Qiagen), and cloned into the NsiI and SalI sites of the U7 snRNA vector. Clones were verified by sequencing with the Fw-ms-U7snRNA-PstI (Supplementary Table 3) and restriction enzyme digestion.

Cell Culture

HEK293T cells or human primary fibroblasts were cultured in Dulbecco's Modified Eagle's Medium (DMEM) high glucose (Gibco) supplemented with 100 U/ml Penicillin/Strepiomycin/Glutamine (Gibco) and 10% Fetal bovine serum (Hyclone, Thermo Scientific). Cells were passaged after reaching 80/90% confluence with TrypLE (Gibco). Human ES lines H1 and H9 were obtained from Wicell Research Institute, Madison, Wis. USA The identity of cell lines used in this study was confirmed by DNA sequence and microarray analyses. All cell lines were routinely tested for *mycoplasma* infection using the Myco-Alert™ *Mycoplasma* Detection Kit (Lonza) and were found negative.

Virus Production

Lentiviruses were produced by co-transfecting HEK293T cells at 80% confluency in a 10 cm culture dish with the lentivirus transfer vector (3 μg SF-OSKM or SF-U7snRNA vectors) and packaging plasmids (2 μg psPAX2 and 1 μg pVSV vectors) using Fugene 6 transfection according to manufacturers protocol (Promega). Lentiviruses were harvested from the medium after 72 hours of transfection and filtered using a 0.45 μm PDFV filter (Milipore). After filtering lentiviruses were concentrated by high speed centrifugation for 2 hours at 20000 rpm in a Beckman Coulter Ultracentrifuge with SW32 Ti rotor at 4° C. The supernatant was removed and the pellet was dissolved in 25 μl Dulbecco's Modified Eagle's medium Low Glucose (Invitrogen) per plate and stored in aliquots at −80° C.

P24 ELISA

Viral liters were determined with the HIV-1 p24 antigen ELISA kit (Retrotek) according to manufacturer's manual. Each virus was diluted 1:40000 and 1:100000 and the OD450 nm was measured with a varioskan (Thermos Scientific) reader.

Transduction of U7 snRNA Vectors

One day before infection $6\times10^4$ cells per single well of a 12 wells plate of patient 1-derived primary fibroblasts were seeded. One day later the cells were infected with 200 ng virus containing the SF-U7snRNA constructs, and after 24 hours cells were washed three times with PBS before adding fresh medium. After 4 days cells were washed with PBS and harvested with RLT buffer of the RNAeasy kit for RNA isolation (Qiagen). For GAA enzyme activity assay cells were harvested after 12 days.

Morpholino Transfections

Human fibroblasts or myogenic progenitors (day −1 or 0 of differentiation) were transfected with morpholino AONs using Endoporter reagent (Gene-Tools, LLC). Cells were plated out and grown to 90% confluency before transfection. Endoporter was used at a concentration of 4.5 μl per ml of medium. Morpholino was dissolved in sterile water to a concentration of 1 mM and the appropriate volume was added to each culture well. Cells were harvested after 3 to 5 days in culture.

RNA Isolation and cDNA Synthesis

RNA was extracted with the RNeasy mini kit with Dnase treatment (Qiagen) and was stored at −80° C., in RNase-free water. cDNA was synthesized from 500 ng RNA using iScript cDNA synthesis kit (Bio-Rad).

qPCR cDNA was diluted five, ten or twenty times and used with 7.5 μl iTaq Universersal SYBR Green Supermix (Bio-Rad) and 10 pmol/μl forward and reverse primers (Table 17) in a CFX96 real-time system (Bio-Rad). Ct values were related to amounts using standard curves of 4-6 dilutions. Quantification of expression was calculated relative to β-Actin expression in experiments where primary fibroblasts used, to expression of four markers (Myog, MyoD. LAMP1 and LAMP2) in experiments where myotubes were used, and to RNA input in experiments were multiple tissues (fibroblasts, myogenic progenitors and myotubes) were compared.

Flanking Exon RT-PCR

Ten times diluted cDNA with GC GAA Exon1-3 fw and CC GAA Exon 1-3 rv primers were used for RT-PCR with the Advantage GC 2 PCR kit (Clontech) and a GC-melt concentration of 0.5 M according to manufacturer's protocol. The whole GC-PCR reaction was analyzed on a 1.5% agarose gel containing 0.5 μg/ml ethidium bromide (Sigma).

GAA Enzyme Activity Assay

Cells were harvested with ice cold lysis buffer (50 mM Tris (pH 7.5), 100 mM NaCl, 50 mM NaF, 1% Triton X-100 and one tablet Protease Inhibitor Cocktail (cOmplete, with EDTA, Roche) and incubated for 10 minutes on ice. Samples were centrifuged at 14000 rpm for 10 minutes at 4° C. GAA enzyme activity was measured using 4-methylumbelliferyl α-D-glucopyranoside (Sigma) as substrate as described (21). Total protein concentration was determined using a BCA protein assay kit (Pierce, Thermo Scientific).

Statistical Analysis

All data represent mean+/−SD, and p-values refer to two-sided t-tests. Bonferroni multiple testing correction was applied where necessary. A p-value <0.05 was considered to be significant. Data showed normal variance. There was no power calculation in any of the experiments. No randomization method was used. No samples were excluded from the analyses. Experiments on expansion of iPS-derived muscle progenitors, differentiation into myotubes, and AON treatment have been performed at least two times. Investigators were not blinded to the identity of the samples.

TABLE 17

Primers used for qRT-PCR, RT-PC, cloning and sequencing

| Primer target | Sequence (5'-3') | Used for |
|---|---|---|
| β-Actin fw | AACCGCGAGAAGATGACCC | qPCR/ RT-PCR |
| β-Actin rv | GCCAGAGGCGTACAGGGATAG | qPCR/ RT-PCR |
| GAA Exon 1-2 fw | AAACTGAGGCACGGAGCG | qPCR |
| GAA Exon 1-2 rv | GAGTGCAGCGGTTGCCAA | qPCR |
| GAA Cryptic Exon 2 fw | GGCACGGAGCGGGACA | qPCR |
| GAA Cryptic Exon 2 rv | CTGTTAGCTGGATCTTTGATC GTG | qPCR |
| GAA Full Skip Exon 2 fw | AGGCACGGAGCGGATCA | qPCR |
| GAA Full Skip Exon 2 rv | TCGGAGAACTCCACGCTGTA | qPCR |
| GAA Pseudo Exon fw | AAACTGAGGCACGGAGCG | qPCR |
| GAA Pseudo Exon rv | GCAGCTCTGAGACATCAACCG | qPCR |
| α-Actinin fw | GAGACAGCGGCTAACAGGAT | qPCR |
| α-Actinin fw | ATTCCAAAAGCTCACTCGCT | qPCR |
| Six1 fw | GTCCAGAACCTCCCCTACTCC | qPCR |
| Six1 rv | CGAAAACCGGAGTCGGAACTT | qPCR |
| Six4 fw | CCATGCTGCTGGCTGTGGGAT | qPCR |
| Six4 rv | AGCAGTACAACACAGGTGCTC TTGC | qPCR |

TABLE 17-continued

Primers used for qRT-PCR, RT-PC, cloning and sequencing

| Primer target | Sequence (5'-3') | Used for |
|---|---|---|
| FGF2 fw | CAAAAACGGGGGCTTCTTCC | qPCR |
| FGF2 rv | GCCAGGTAACGGTTAGCACA | qPCR |
| Sox1 fw | GAGCTGCAACTTGGCCACGAC | qPCR |
| Sox1 rv | GAGACGGAGAGGAATTCAGAC | qPCR |
| MyoD fw | CACTCCGGTCCCAAATGTAG | qPCR |
| MyoD rv | TTCCCTGTAGCACCACACAC | qPCR |
| Myog fw | CACTCCCTCACCTCCATCGT | qPCR |
| Myog rv | CATCTGGGAAGGCCACAGA | qPCR |
| LAMP1 fw | GTGTTAGTGGCACCCAGGTC | qPCR |
| LAMP1 rv | GGAAGGCCTGTCTTGTTCAC | qPCR |
| LAMP2 fw | CCTGGATTGCGAATTTTACC | qPCR |
| LAMP2 rv | ATGGAATTCTGATGGCCAAA | qPCR |
| Fw-U7snRNA-smOPT | GCTCTTTTAGAATTTTTGGAG CAGGTTTTCTGACTTCG | Cloning |
| Rv-U7snRNA-smOPT | CGAAGTCAGAAAACCTGCTCC AAAAATTCTAAAAGAGC | Cloning |
| Fw-U7snRNA-Nsil | CCTGGCTCGCTACAGATGCAT AGGAGGACGGAGGACG | Cloning |
| Rv-U7snRNA-Nsil | CGTCCTCCGTCCTCCTATGCA TCTGTAGCGAGCCAGG | Cloning |
| M13 fw | GTAAAACGACGGGCCAG | Sequencing |
| M13 rv | CAGGAAACAGCTATGAC | Sequencing |
| GAA Exon1-3 fw | AGGTTCTCCTCGTCCGCCCGT TGTTCA | RT-PCR |
| GAA Exon1-3 rv | TCCAAGGGCACCTCGTAGCGC CTGTTA | RT-PCR |
| Fw-ms-U7snRNA-Pstl | GCGCCTGCAGTAACAACATAG GAGCTGTG | Cloning |
| Rv-ms-U7snRNA-Sall | GCGCGTCGACCAGATACGCGT TTCCTAGGA | Cloning |

Results

Figure 6A:
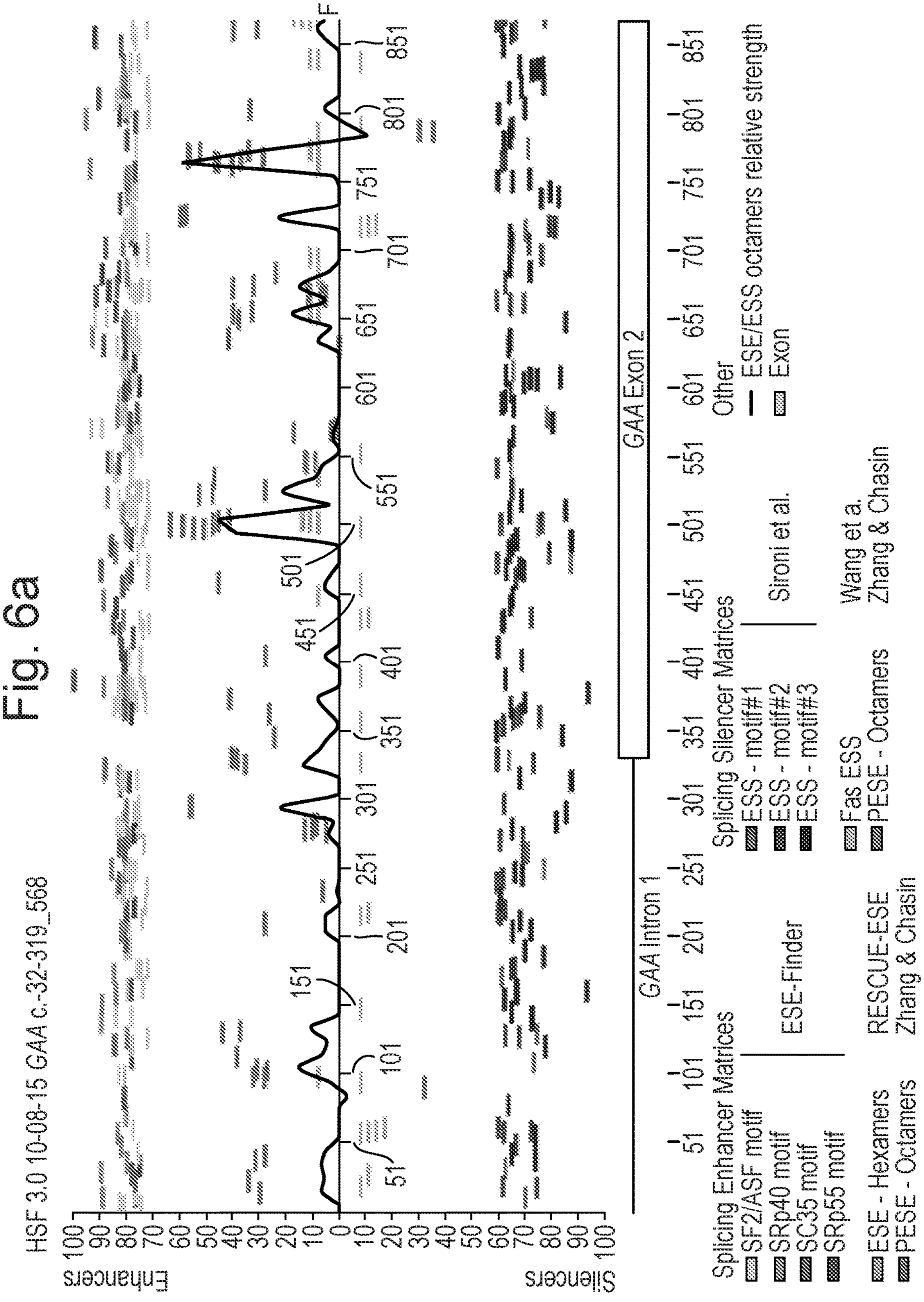

Our purpose was to promote exon 2 inclusion in cells from IVS1 patients to restore wild type GAA splicing. Primary fibroblasts from such patients show partial and complete skipping of exon 2 (FIG. 1*a*), as reported previously[23,24,25] We aimed to block a splicing repressor sequence using AONs. However, no splicing silencer sequences have been described so far for GAA. To identify silencers of exon 2 splicing, in silico prediction analysis was performed using Human Splicing Finder (http://www.umd.be/HSF/) (FIG. 6*a*). This yielded many possible hits that failed to overlap between different prediction algorithms, and it was unclear which hits should be used to design and synthesize rather expensive chemically stable AONs. This indicated the need to screen the GAA pre-mRNA for possible splicing regulatory motifs (FIG. 1*b*) in a functional and cost-effective assay.

Figure 6B:
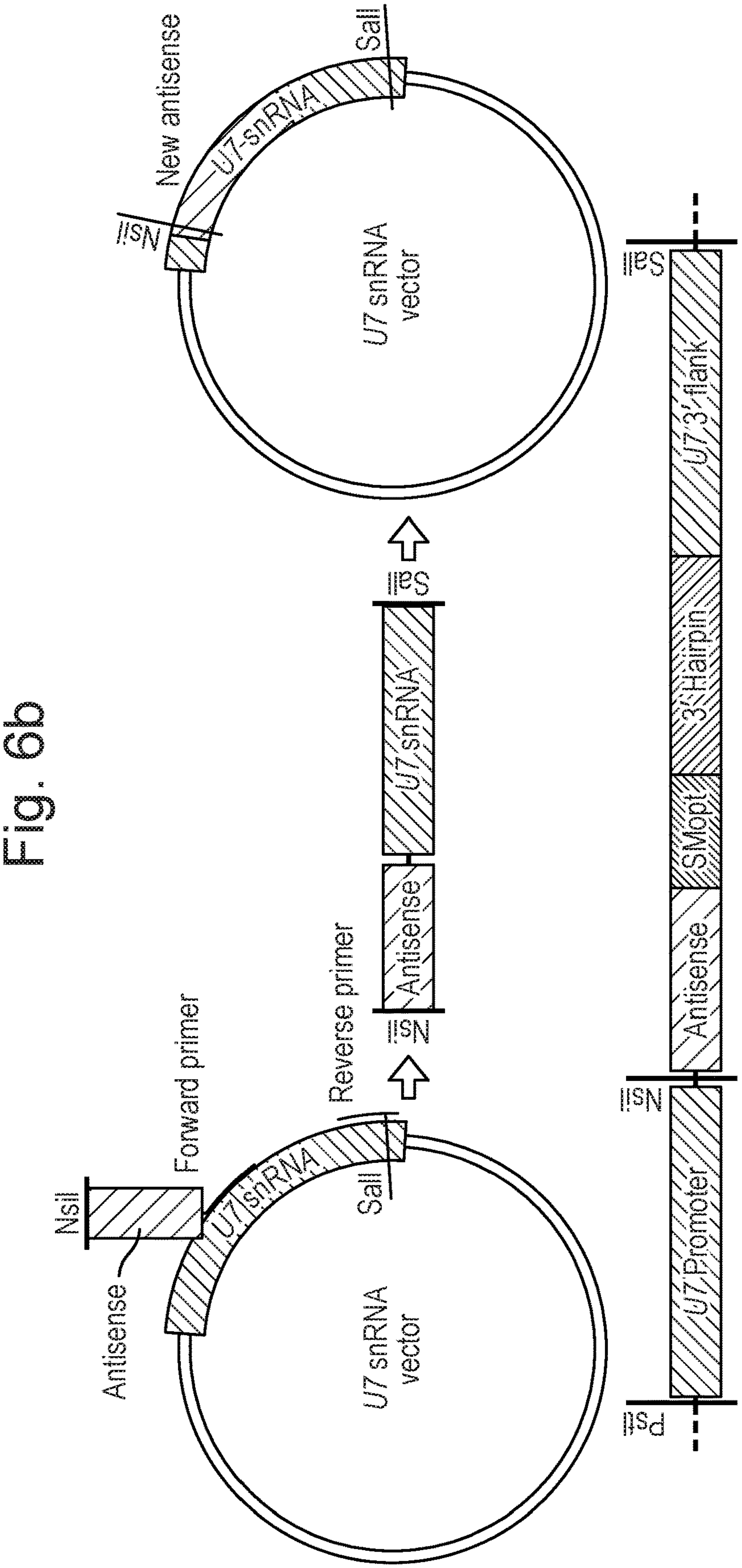
Figure 6C:
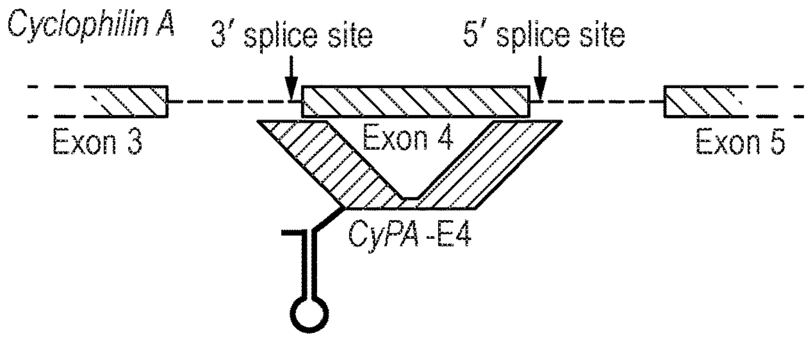
Figure 6D:
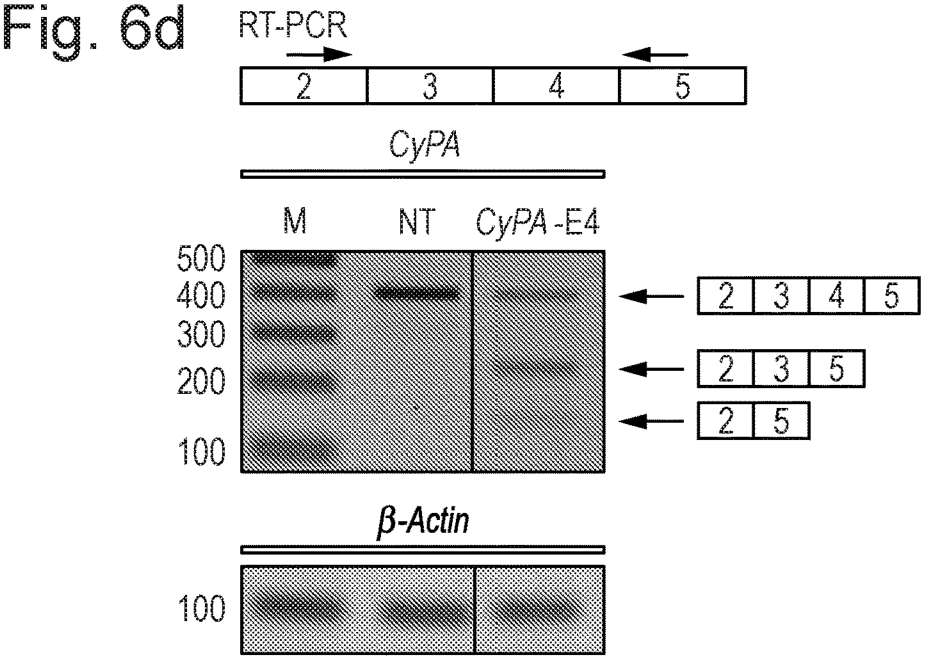
Figure 6E:
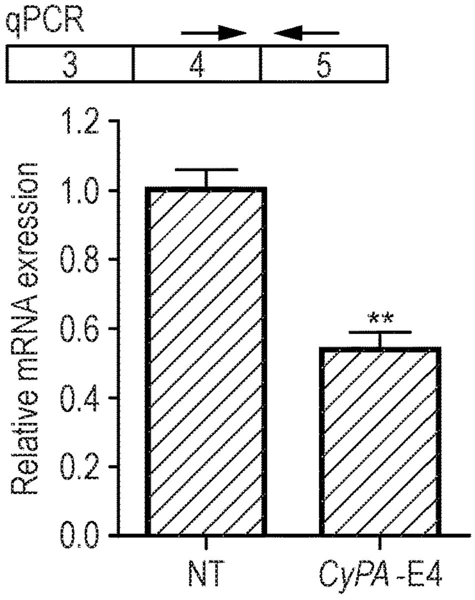
Figure 6F:
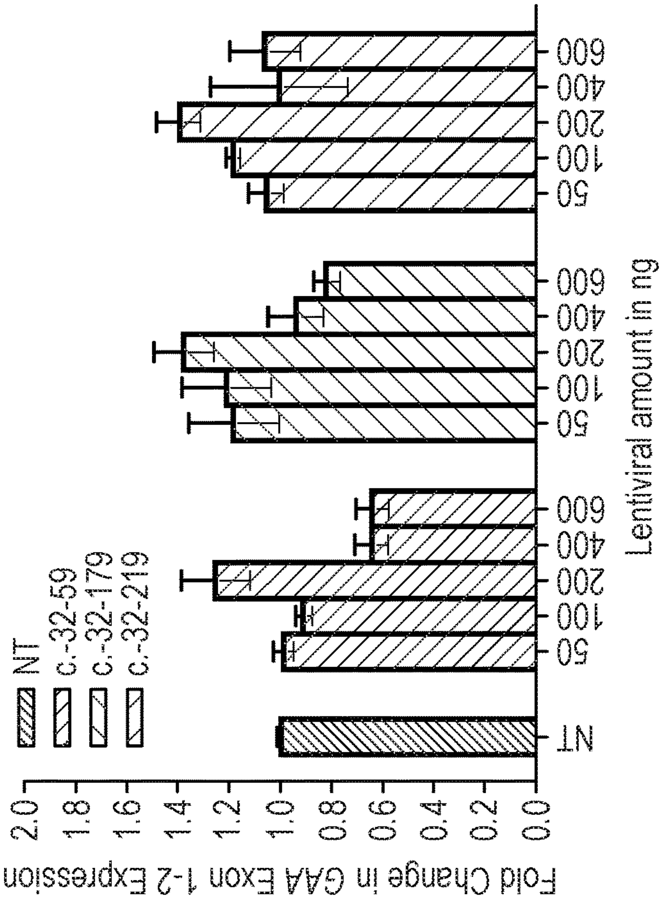

We used modified U7 snRNA to express AONs as shown previously[40,41]. This enables the expression of AONs in the nucleus that are stabilized by a stem loop that is provided by the snRNA (FIG. 1*b*, FIG. 6*c*). We aimed to test endogenous GAA splicing in primary cells, as these would be the closest to splicing regulation in vivo. Patient-derived primary fibroblasts, obtained via a skin biopsy, are routinely used for biochemical diagnosis of Pompe disease. GAA enzymatic activities of 1.20% of values indicate childhood/adult onset Pompe disease. Transfection of U7 snRNA expression constructs in primary cells was inefficient, preventing efficient modulation of endogenous splicing (data not shown). We therefore cloned the U7 snRNA cassette in a lentivirus and used lentiviral transduction, which resulted in ~100% transduction efficiency of primary fibroblasts. This vector was then modified by introduction of a NsiI site to allow 1-step cloning of AONs, introduced via a forward PCR primer, with a cloning success rate of >95% (FIG. 6*b*). We validated the lentiviral U7 snRNA system by promoting exon skipping of a control gene, cyclophilin A (CypA)42 in primary fibroblasts (FIG. 6*c*-*e*). We conclude that AONs expressed as U7 snRNAs using a lentivirus provides a fast and cheap method to screen putative target sites for splice-switching AONs in primary cells.

Figures 1D, 1E:
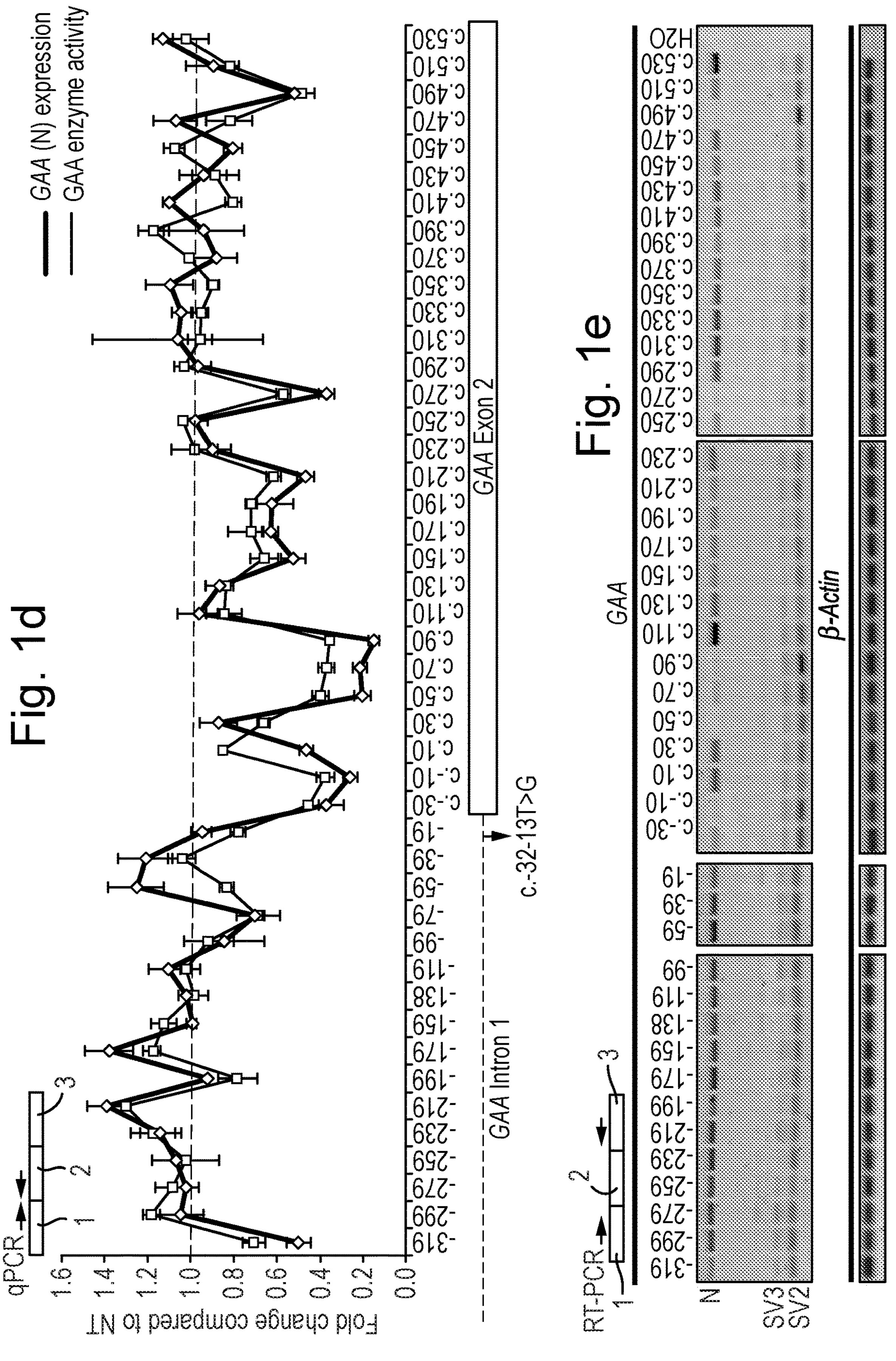
Figure 6G:
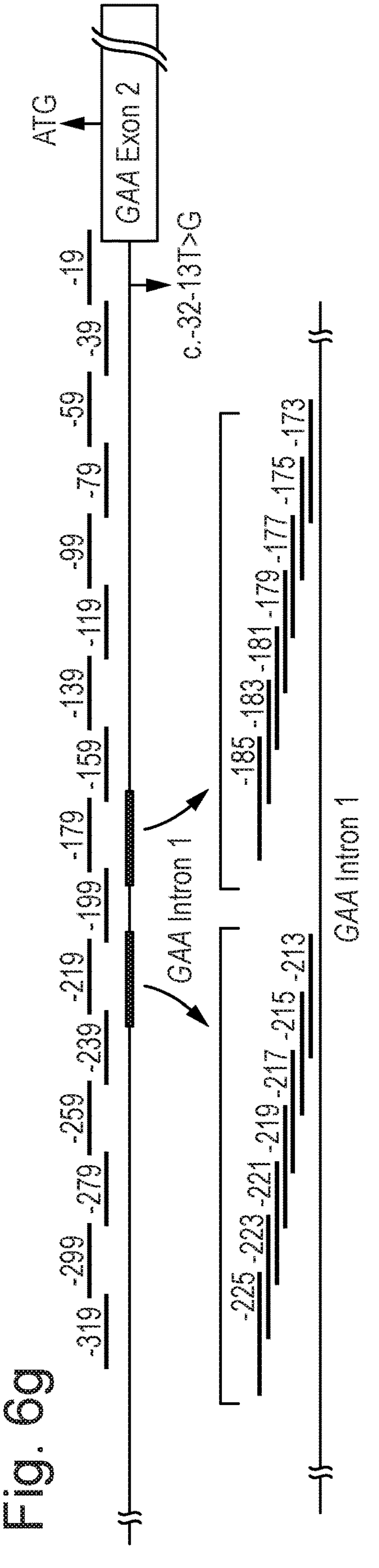
Figure 6H:
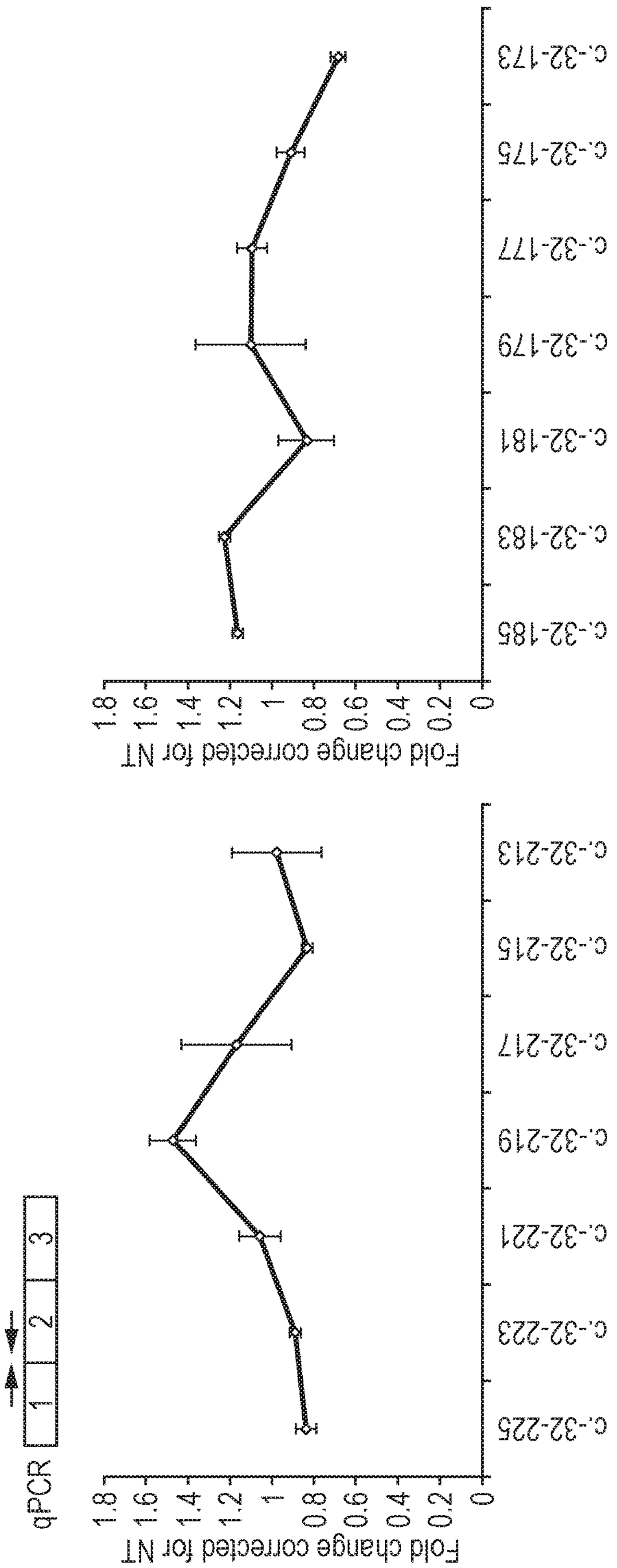
Figure 6I:
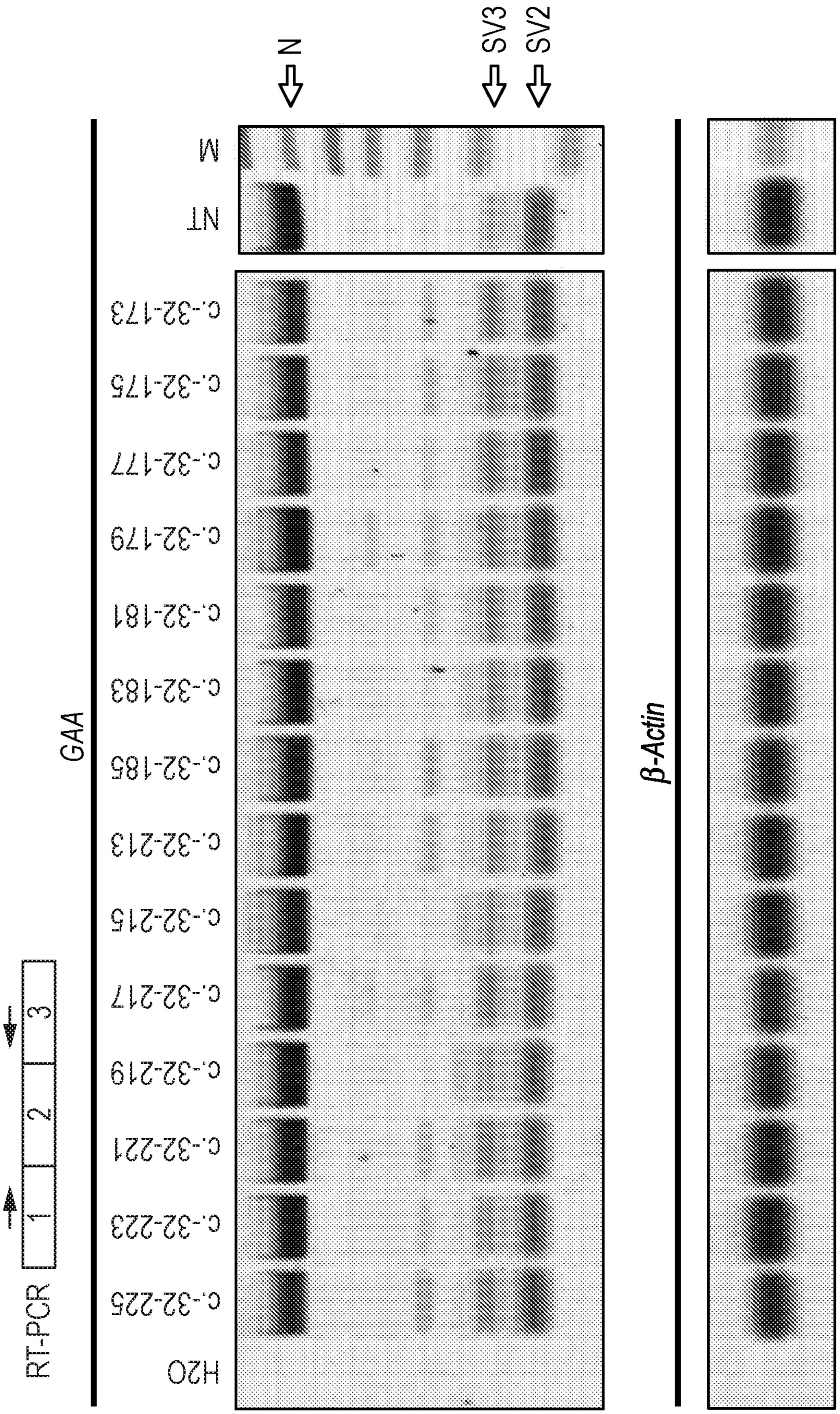

A screen was then performed in Pompe patient-derived fibroblasts in which AONs targeted the GAA pre-mRNA surrounding the IVS1 variant in a non-overlapping tiling arrangement, from c.-32-319 to c.530 (FIG. 1*c*). Three read outs were used: GAA mRNA expression by RT-qPCR and flanking exon PCR, and GAA enzyme activity (FIG. 1*d*,*e*). This resulted in the identification of two regions in intron 1 (c.-32-219 and c.-32-179) that acted as splicing silencer sequences and whose repression by AONs promoted exon 2 inclusion and GAA enzyme activity. Lentiviral-mediated U7 snRNA expression appeared to have a small window in which splicing modulation could be investigated, due to toxicity at high virus titers (FIG. 60*f*). We then performed a miniscreen around these targets using AONs that shifted 2 nt each, and this defined c.-32-179 and c.-32-179 as the peaks of the regions that acted as silencers of GAA exon 2 splicing (FIG. 6*g*-*i*).

To explore the possibility for the development of AONs that could be used in a clinical setting, we used phosphorodiamidate morpholino oligomer (PMO)-based AONs. In a validation experiment, exon 4 of CypA was efficiently skipped using AONs CypA 1 and CypA 2 that targeted the splice acceptor (FIG. 7*a*-*d*). No signs of toxicity were observed. This confirmed that PMO-based AONs are suitable for the modulation of splicing in primary fibroblasts, in agreement with previous reports[43,44].

Figures 7A, 7B:
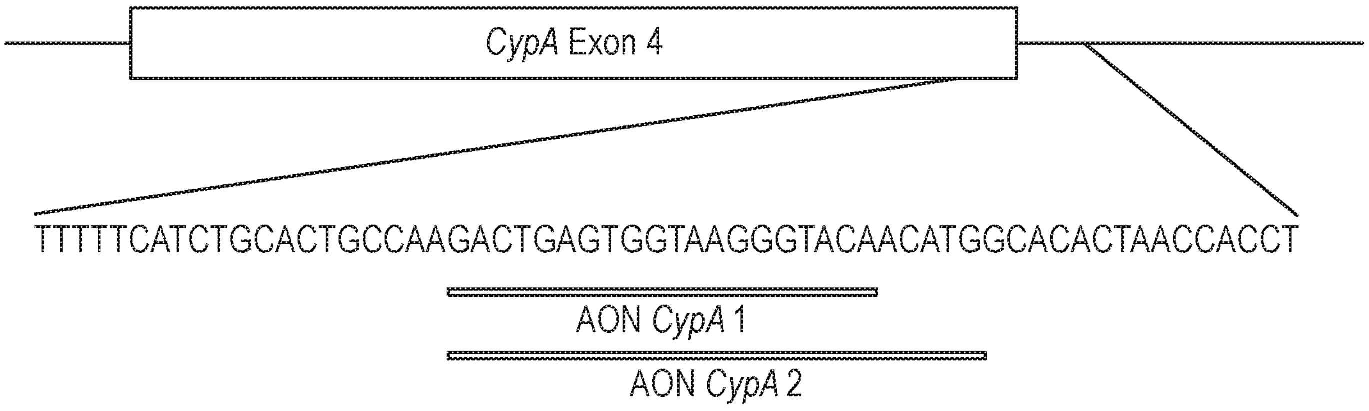
Figure 7C:
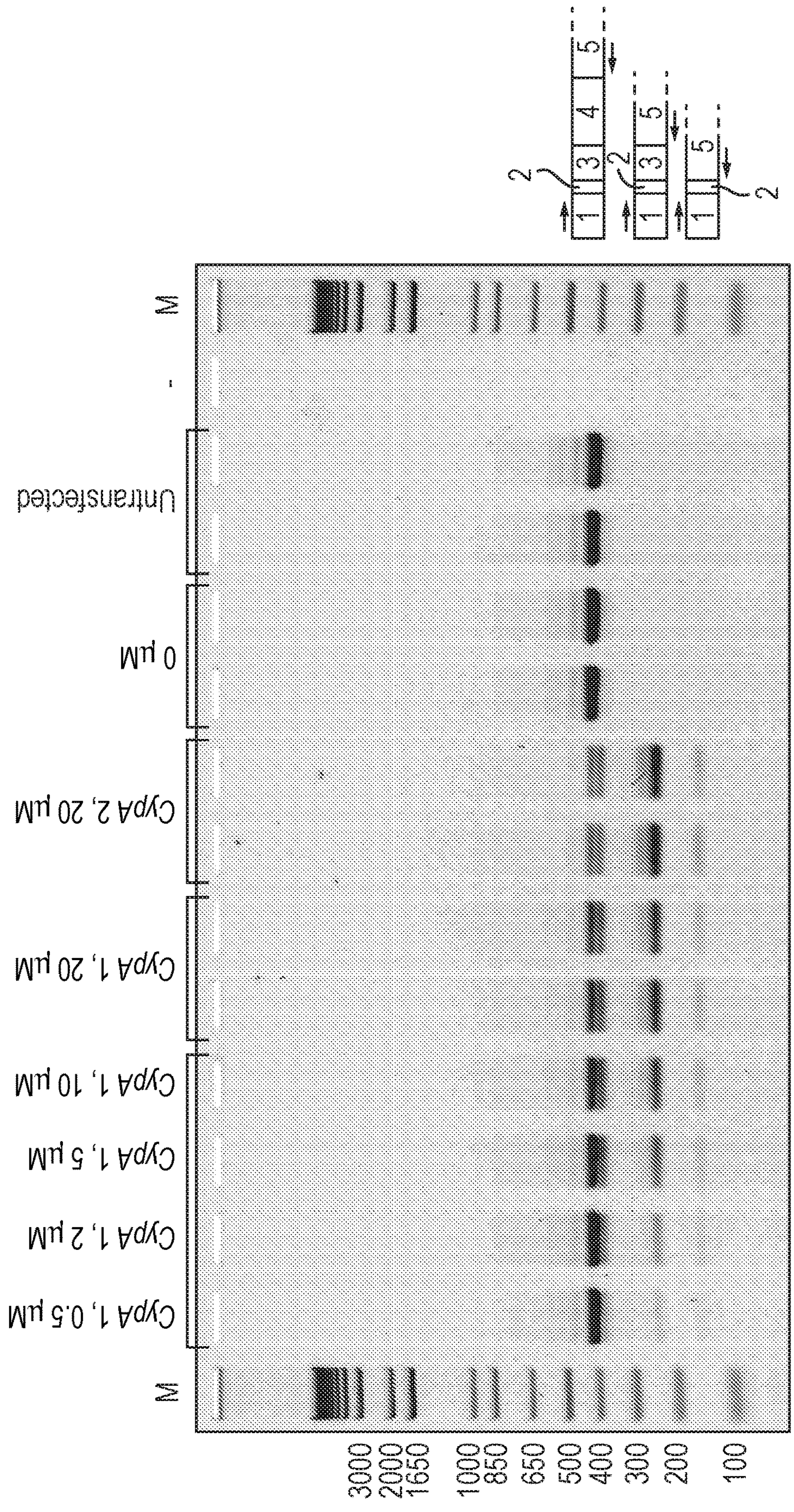
Figure 7D:
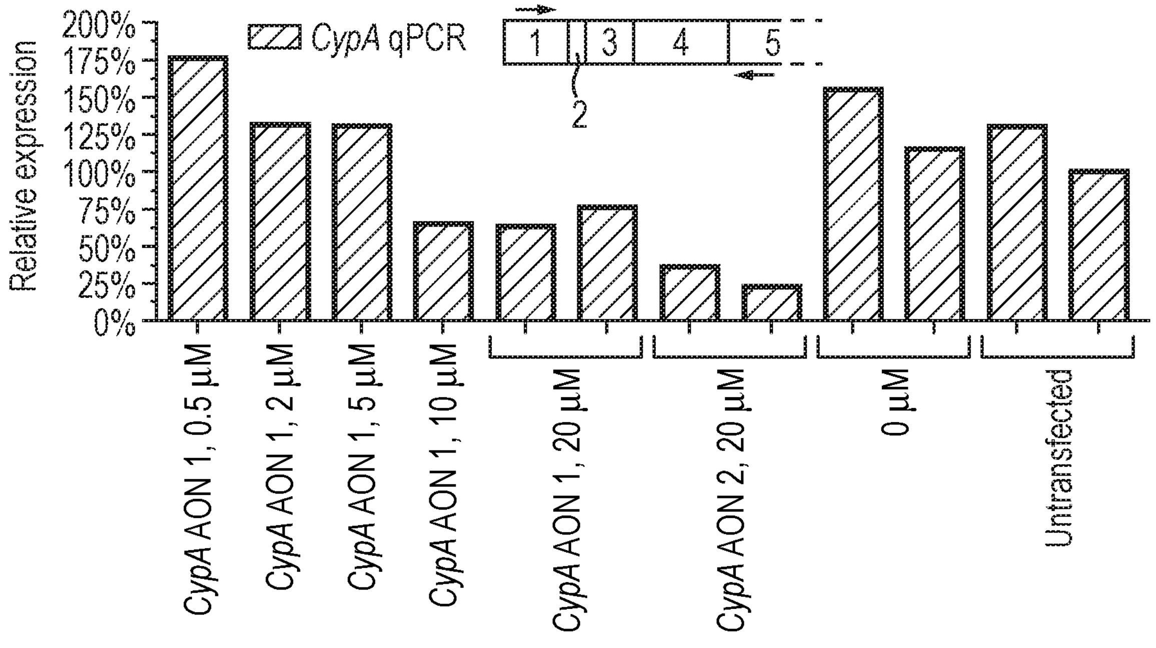
Figure 7E:
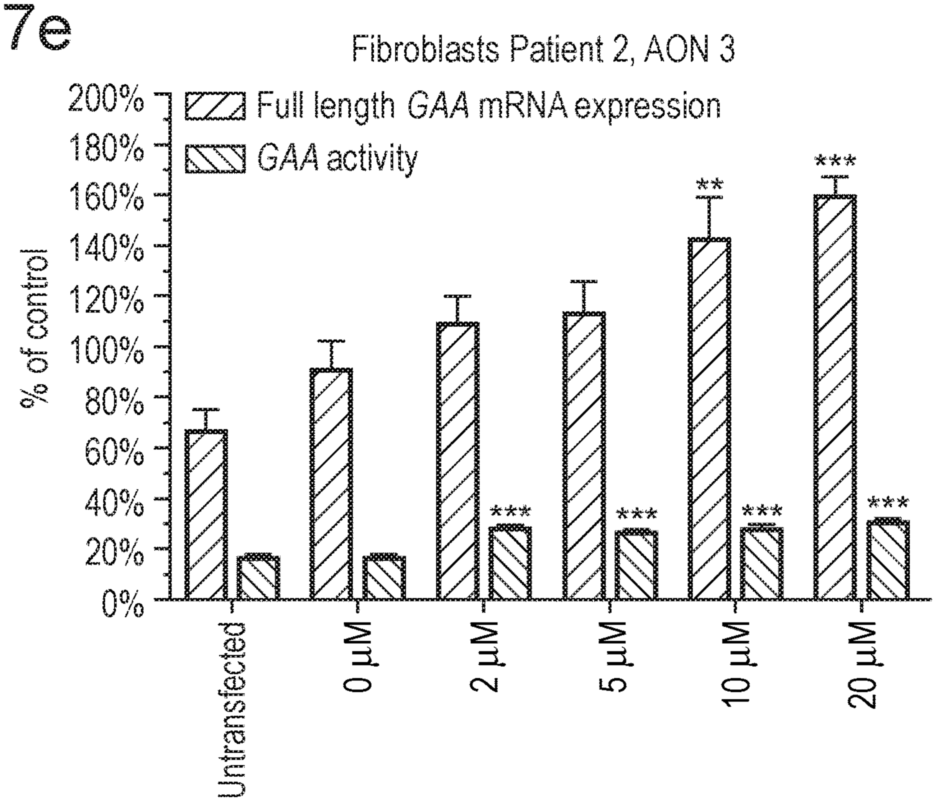
Figure 7F:
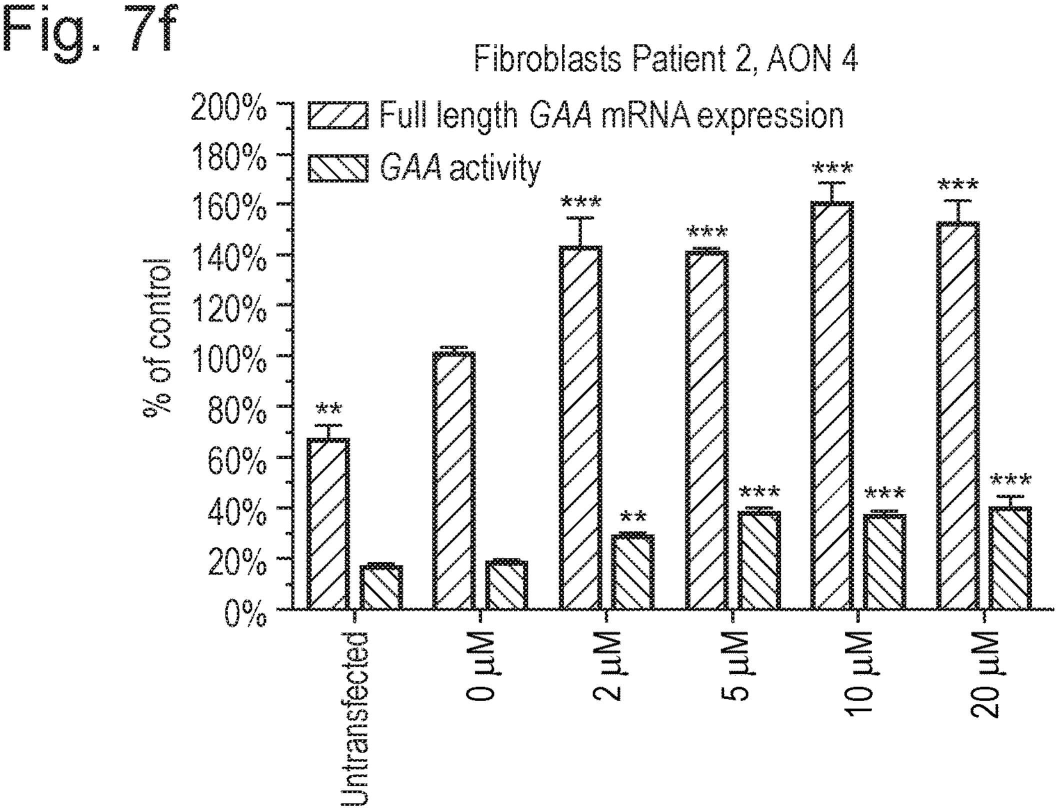

Next, we designed PMO AONs based on the results of the U7 snRNA screen, and tested these in fibroblasts derived from Pompe patient 1 (genotype IVS1, c.525delT; the second allele is not expressed) for promoting GAA exon 2 inclusion (FIG. 2*a*, FIG. 7*a*). The putative splicing silencer sequences at c.-32-219 and c.-32-179 were targeted using PMO-based AONs (FIG. 2*a*). Blocking of c.-32-179 using AON 3 (SEQ ID NO: 298) or AON 4 (SEQ ID NO: 277) resulted in promotion of exon 2 inclusion and enhancement of GAA enzymatic activity, while AON 1 (SEQ ID NO: 299) and AON 2 both of which targeted c.-32-219 were inactive (FIG. 2*b*-*e*). It is likely that blocking of c.-32-219 may require further optimization of PMO-AON sequences. AONs 3 and 4 also promoted exon inclusion and GAA enzymatic activity in fibroblasts from patient 2 (genotype IVS1, c.923A>C; the second allele is expressed)(FIG. 7*e*,*f*). The maximal possible enhancement of GAA enzyme activity using this approach is ~3.5-5 fold: patients with the IVS1 allele have ~10-15% leaky wild type splicing, and full restoration of this allele will amount to a maximum of 50% of healthy controls. AONs 3 and 4 promoted GAA exon 2 inclusion and GAA activity in fibroblasts with ~2.5 fold, indicating that these corrected 50-70% of exon 2 splicing.

Figure 2E:
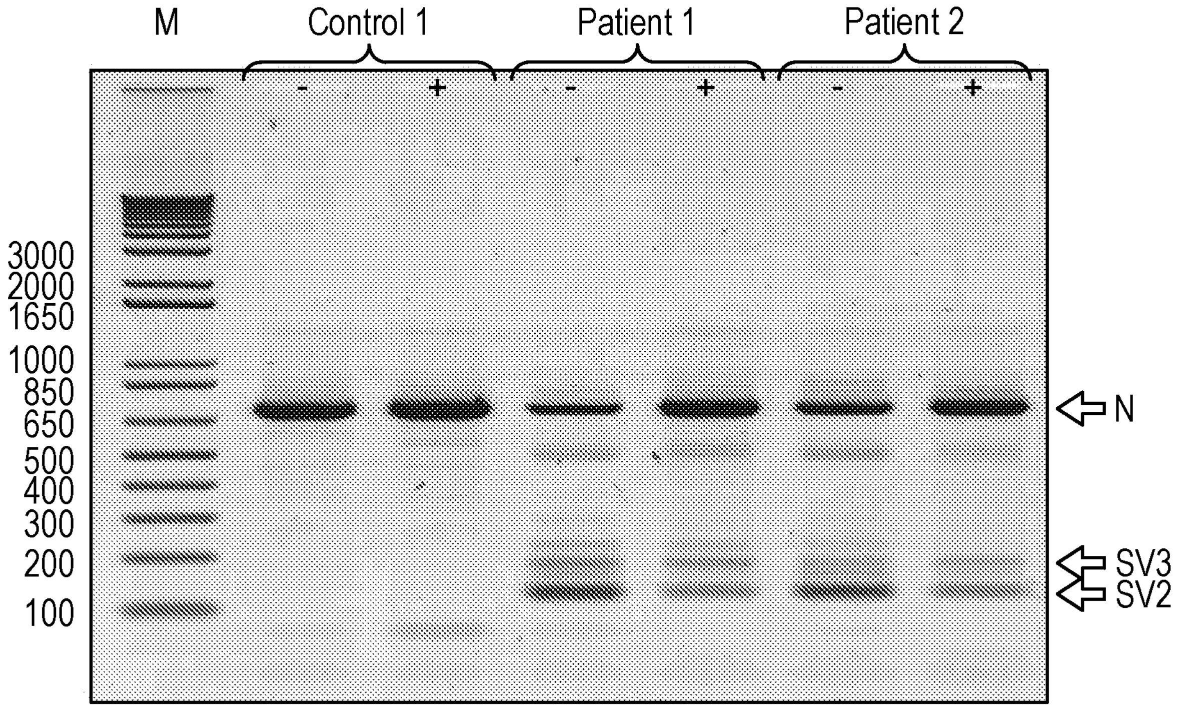
Figure 2F:
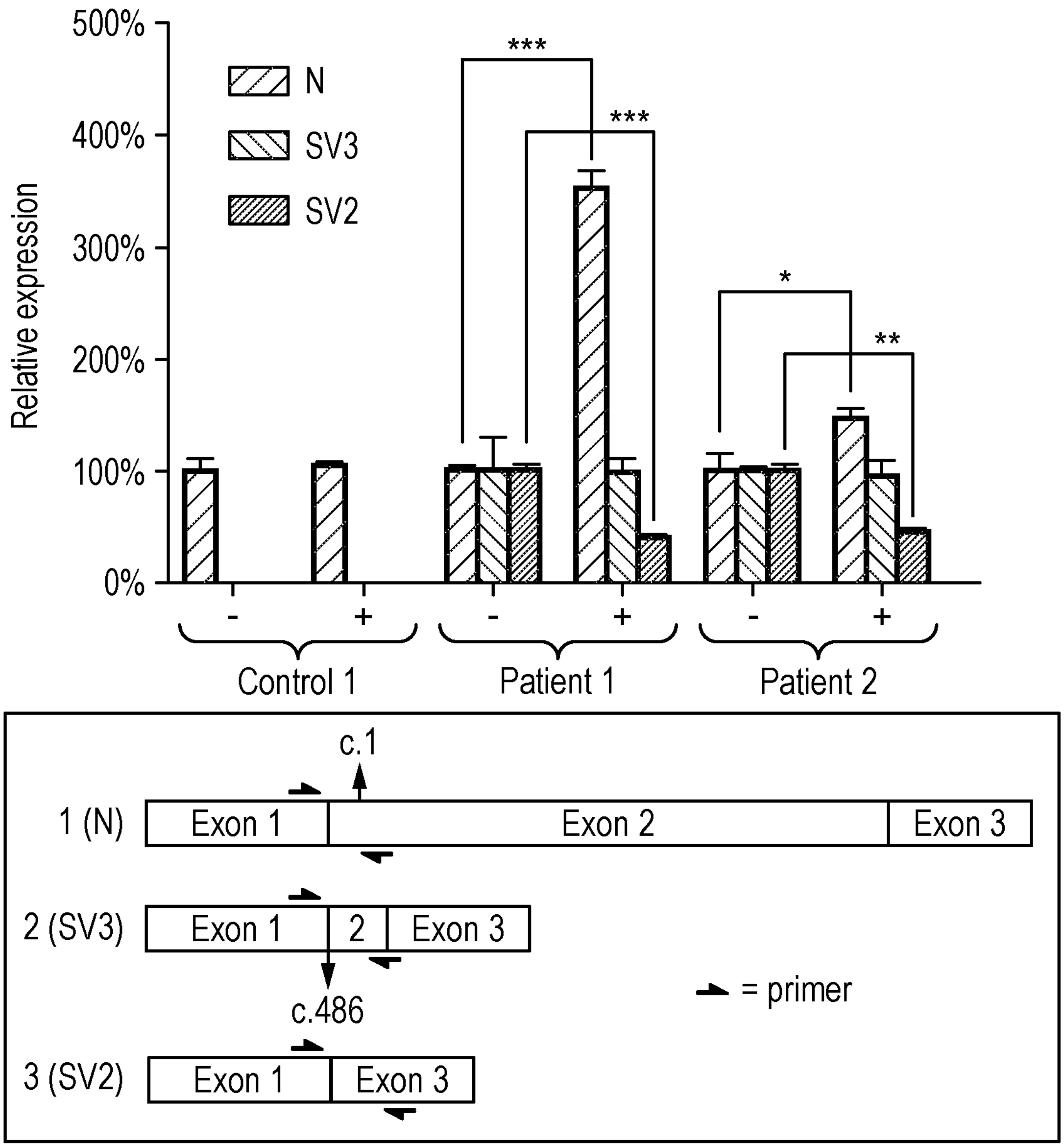

To confirm that AONs acted by modulating splicing rather than total GAA mRNA expression, splicing product-specific RT-qPCR analysis was performed. This showed that AONs 4 enhanced expression of wild type GAA mRNA while it repressed expression of aberrant splicing products SV2 and SV3 (FIG. 2*e*,*f*). In addition, AON 4 was ineffective in fibroblasts from a healthy control (FIG. 2*e*,*f*). Taken together, PMO AONs 3 and 4 were identified to promote exon 2 inclusion with 50-70% efficiency in fibroblasts from patients with the IVS1 GAA variant.

Splicing can occur in a tissue-specific manner, and it was unknown how the IVS1 variant and the putative splicing silencer would operate in differentiated skeletal muscle cells, which are affected in Pompe disease. To test this, we first used primary myoblasts derived from healthy controls and Pompe patients. However, these showed limited and heterogeneous capacity to proliferate and differentiate into multinucleated myotubes, which hindered the use of myoblasts for quantitative analysis of AONs (data not shown). A similar reduction of proliferation and differentiation capacity upon passaging of primary myoblasts has been reported previously[45].

Figure 8A:
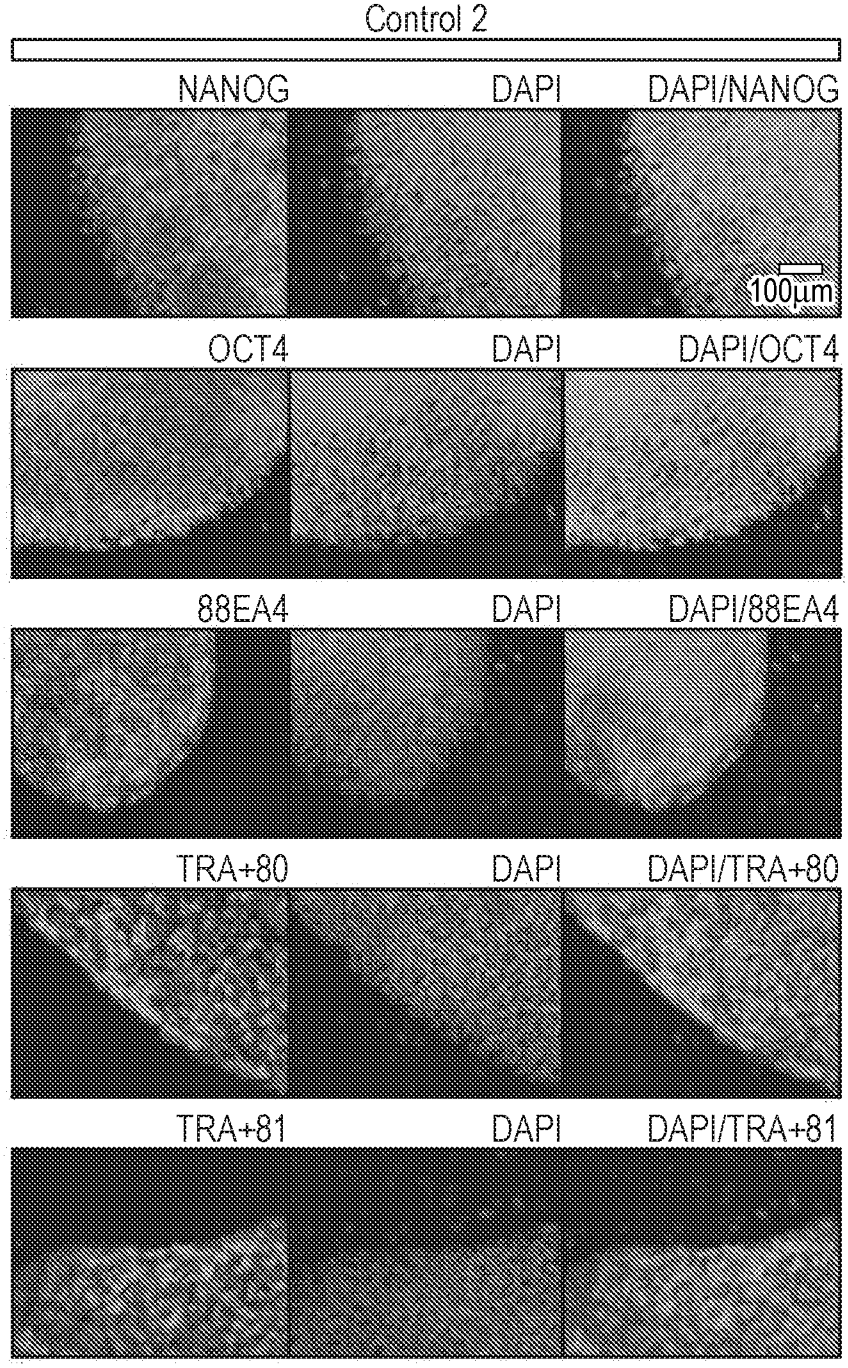
Figure 8B:
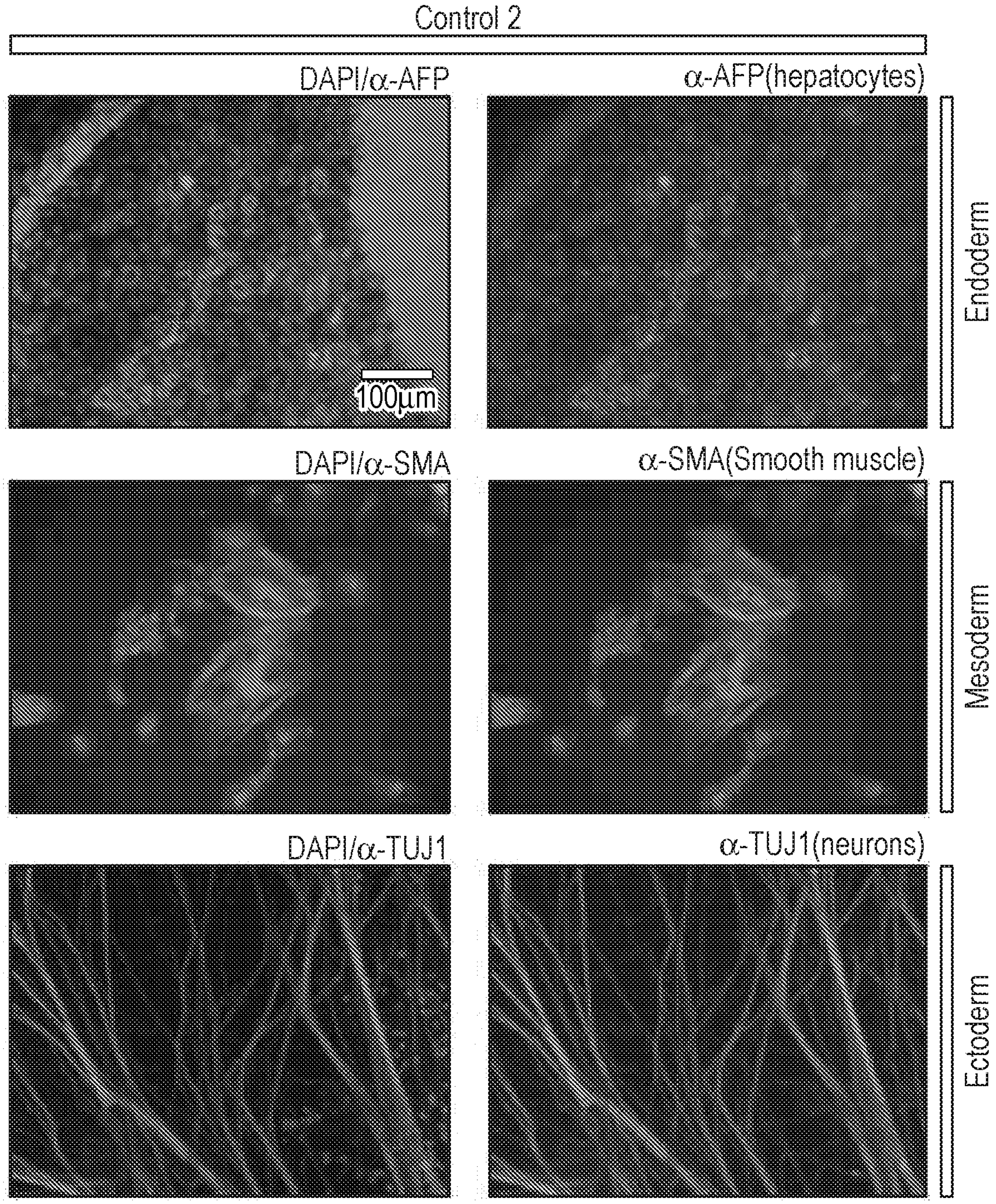
Figure 8C:
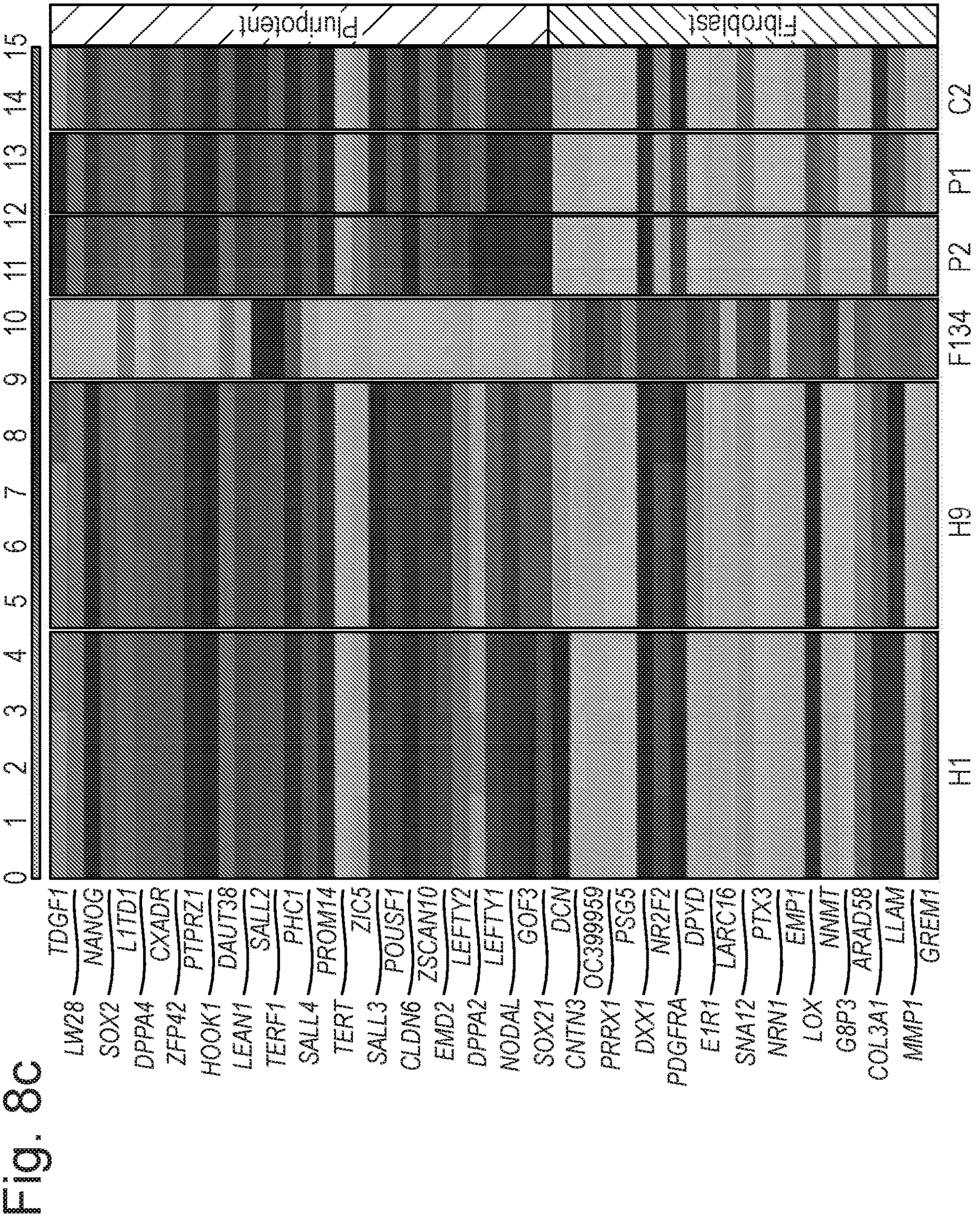
Figure 8D:
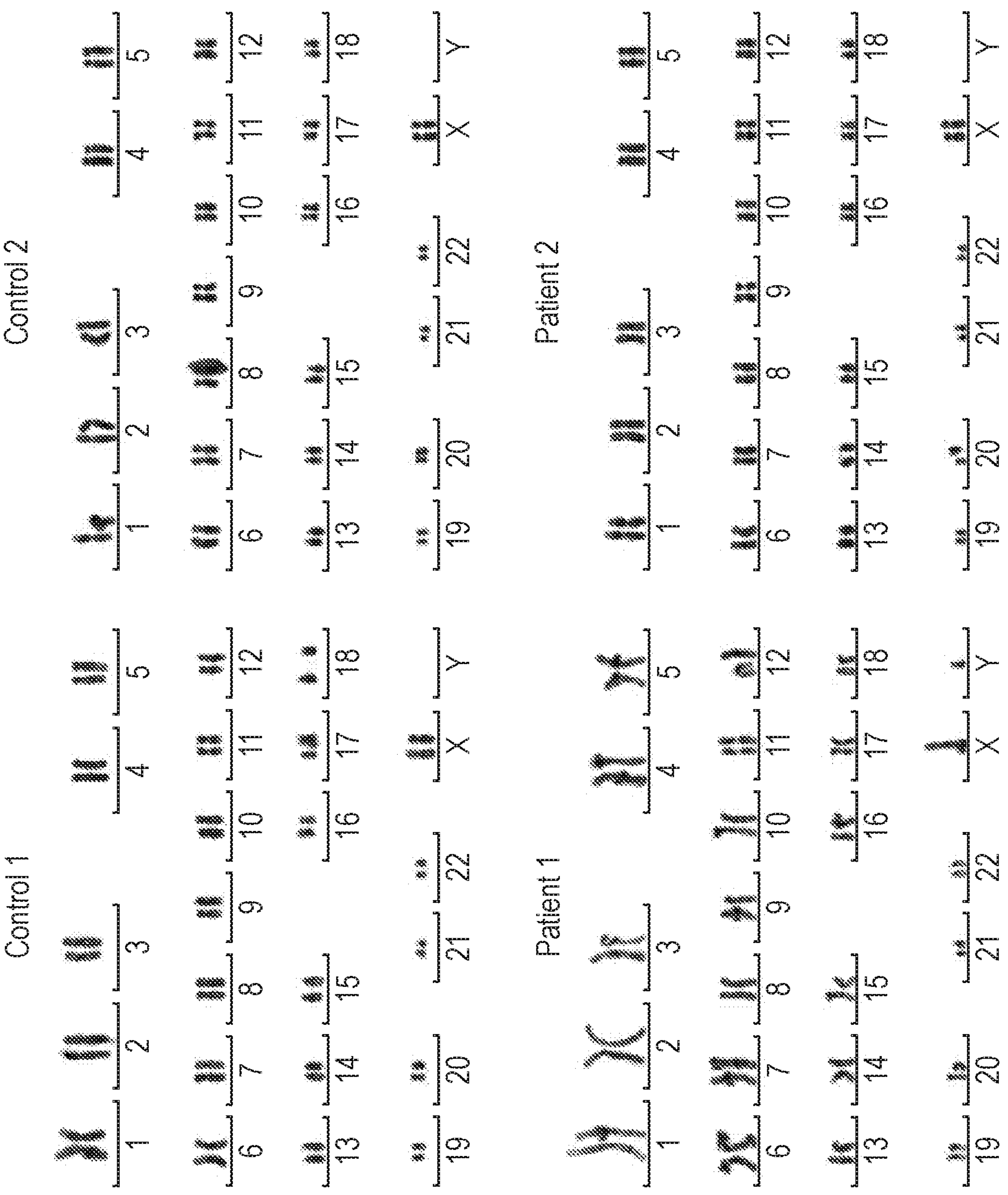
Figure 8E:
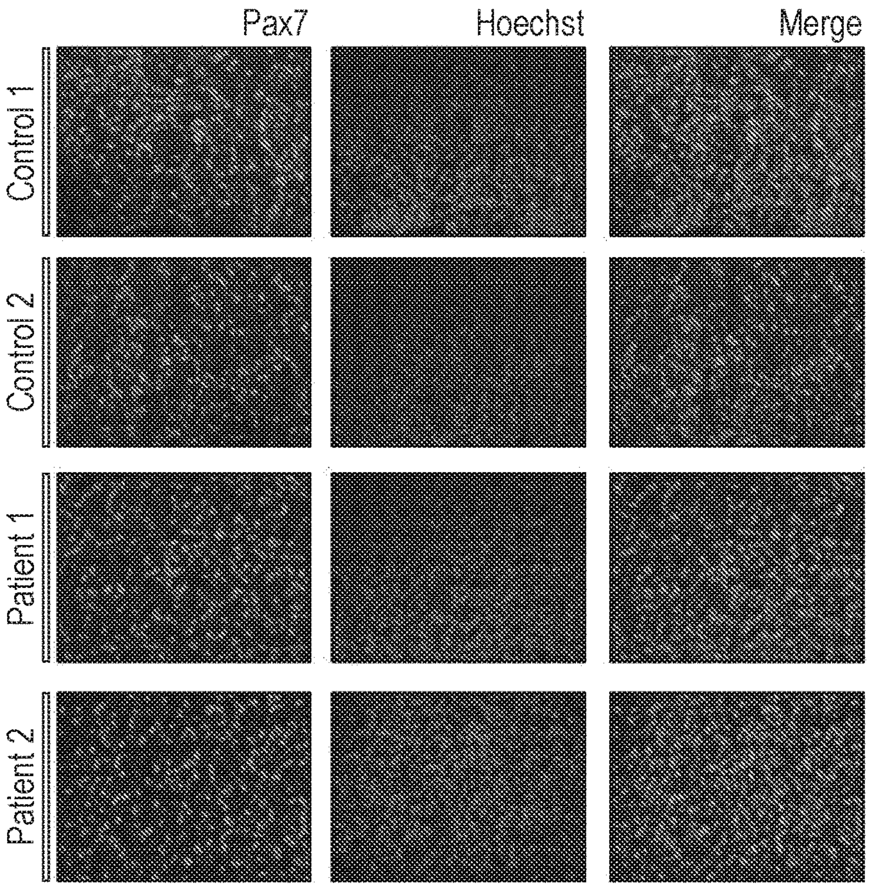
Figure 8F:
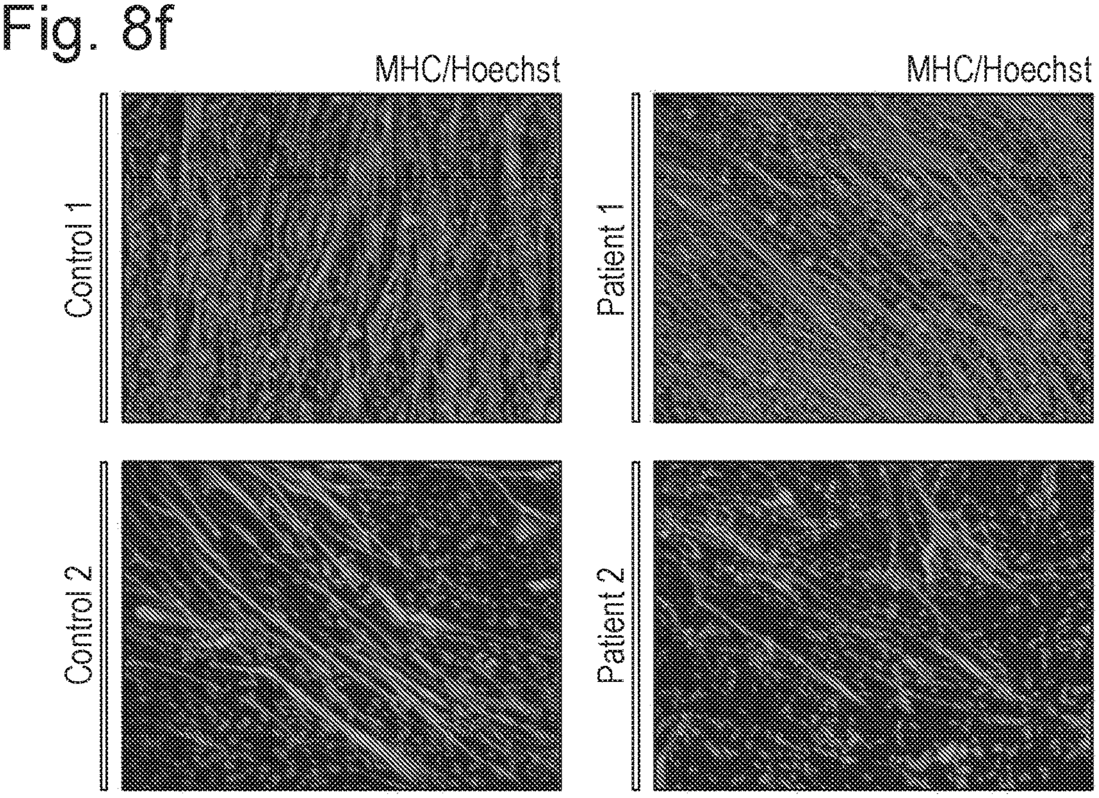

We therefore developed an in vitro model for childhood/adult Pompe disease using iPS cells (see also co-pending patent application NL 2017078). Reprogramming of fibroblasts and characterization of iPS cells are described in FIG. 8*a*-*d*, iPS cells from two patients and two healthy controls were differentiated into myogenic progenitors using a transgene-free protocol modified from Borchin et al.[37]. While this method yielded purified Pax7+ myogenic progenitors after a 35-day protocol (FIG. 8*e*), the recovery after FACS sorting was low. Between 50,000 and 500,000 cells could be purified starting from a full 10 cm dish of iPS cells, yielding only a few wells in a tissue culture dish that could be used for testing AONs. In addition, the capacity to differentiate into multinucleated myotubes varied largely between individual purifications (FIG. 8*f*). It was therefore not possible to reproducibly test the effect of AONs on splicing in freshly isolated iPS-derived myogenic progenitors.

Figure 3B:
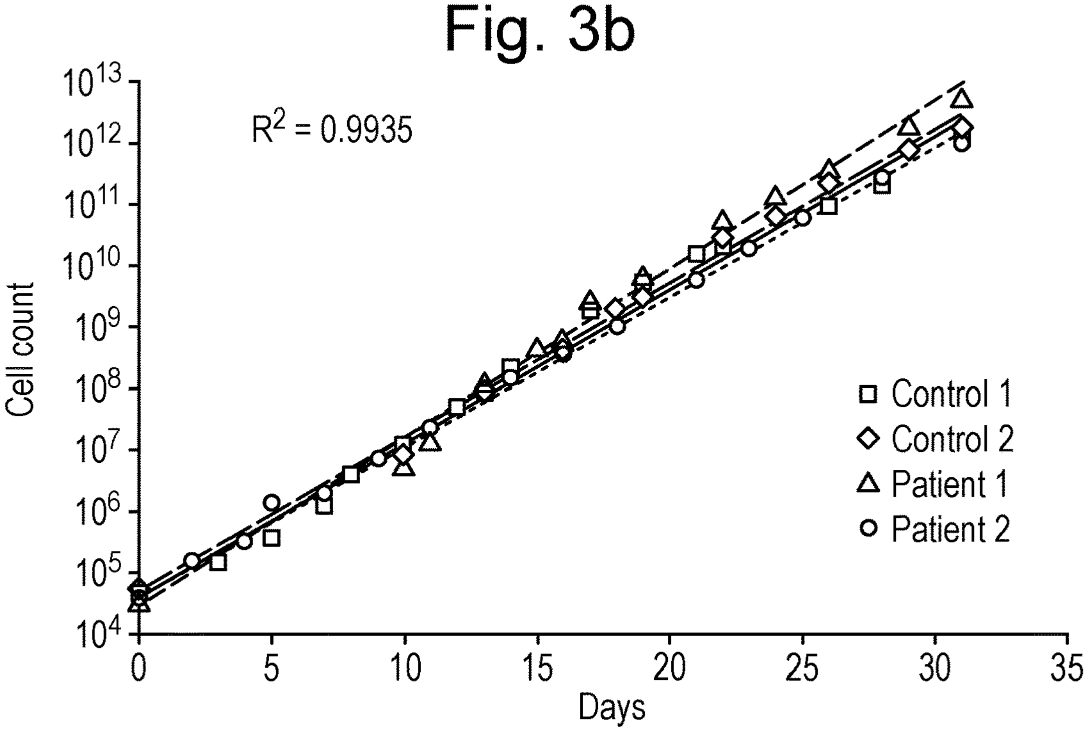
Figure 3C:
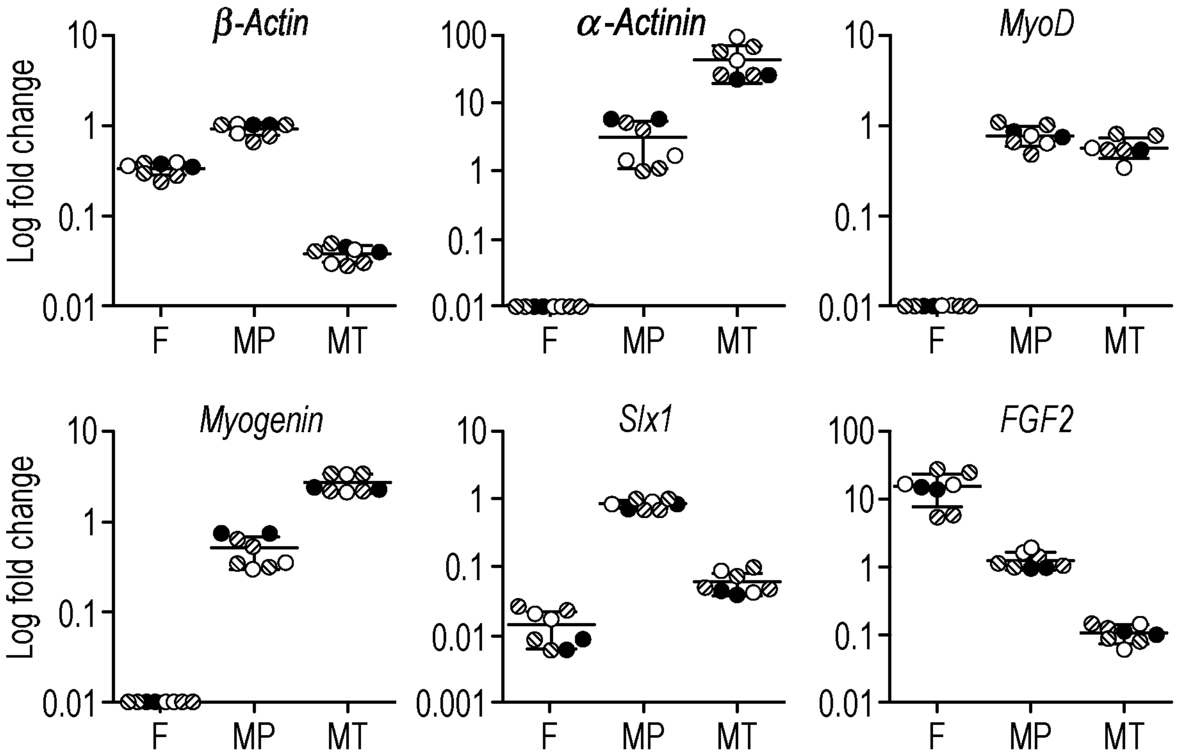
Figure 3D:
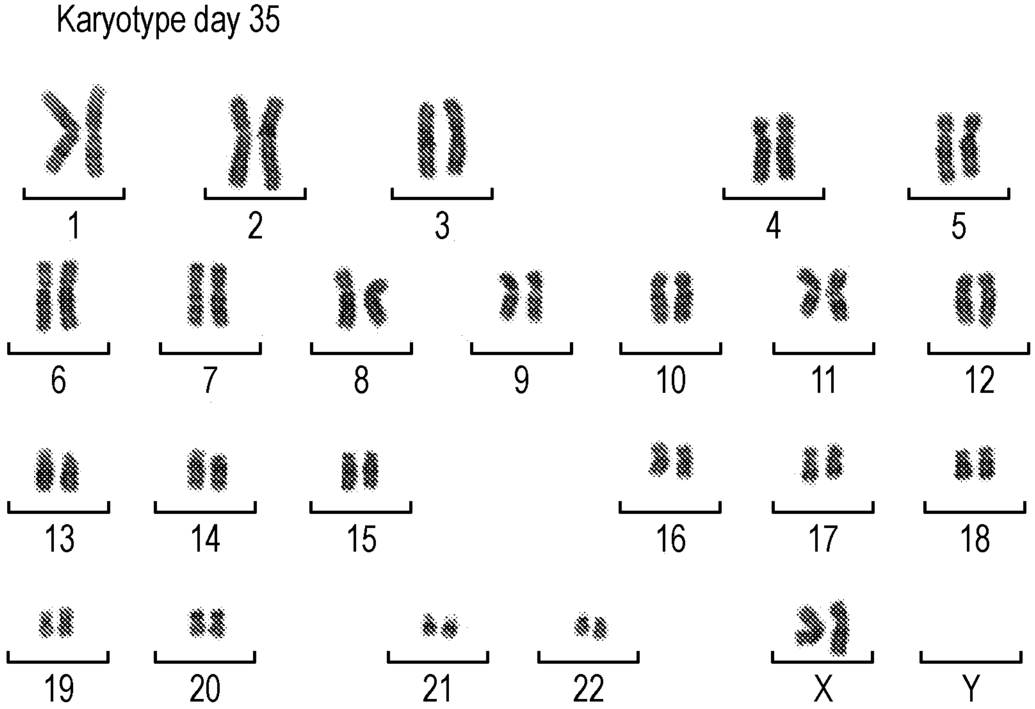
Figure 3E:
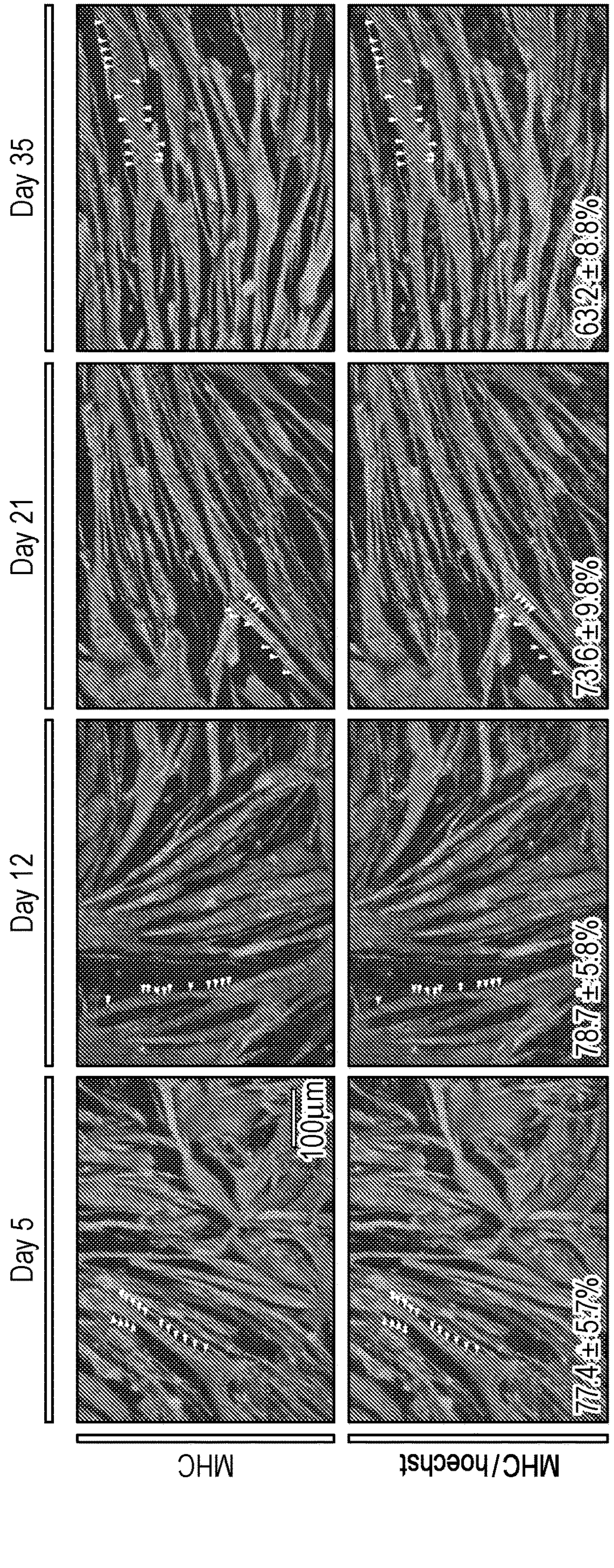
Figure 8G:
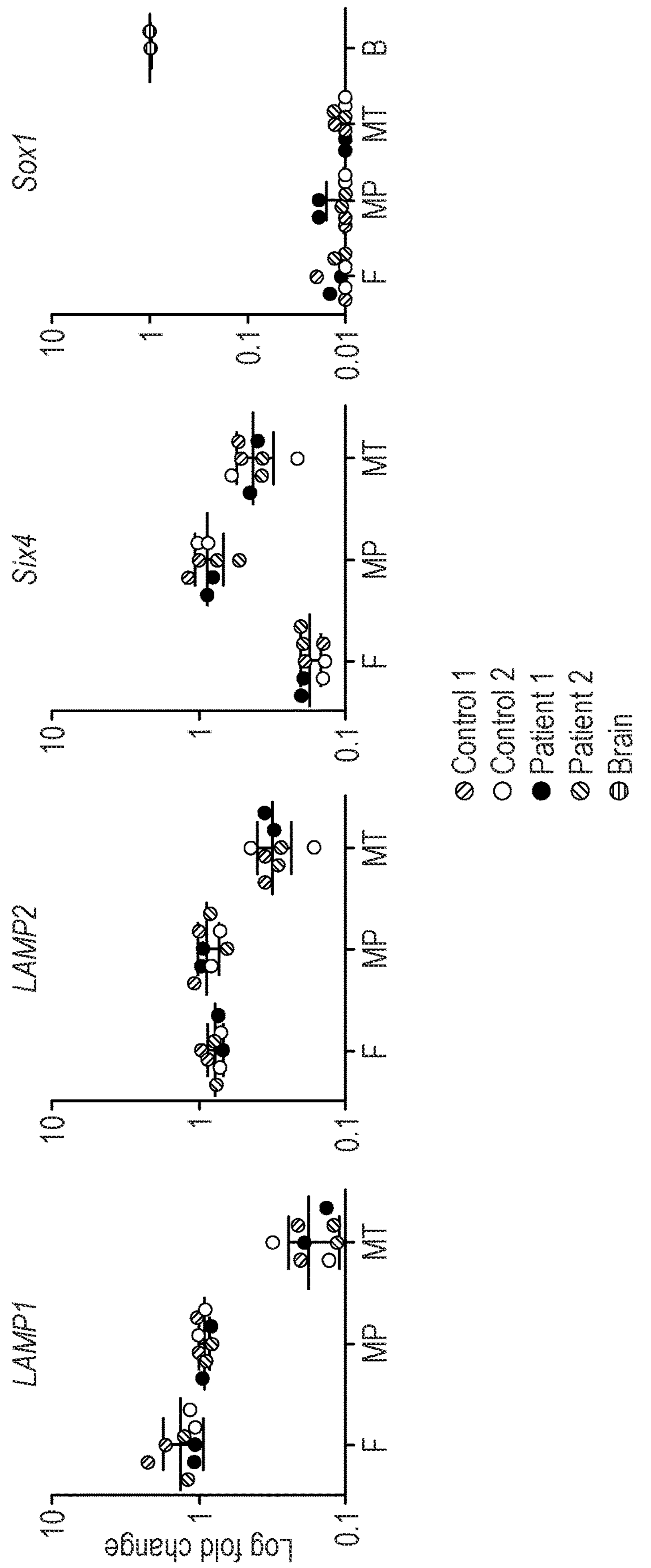
Figure 8H:
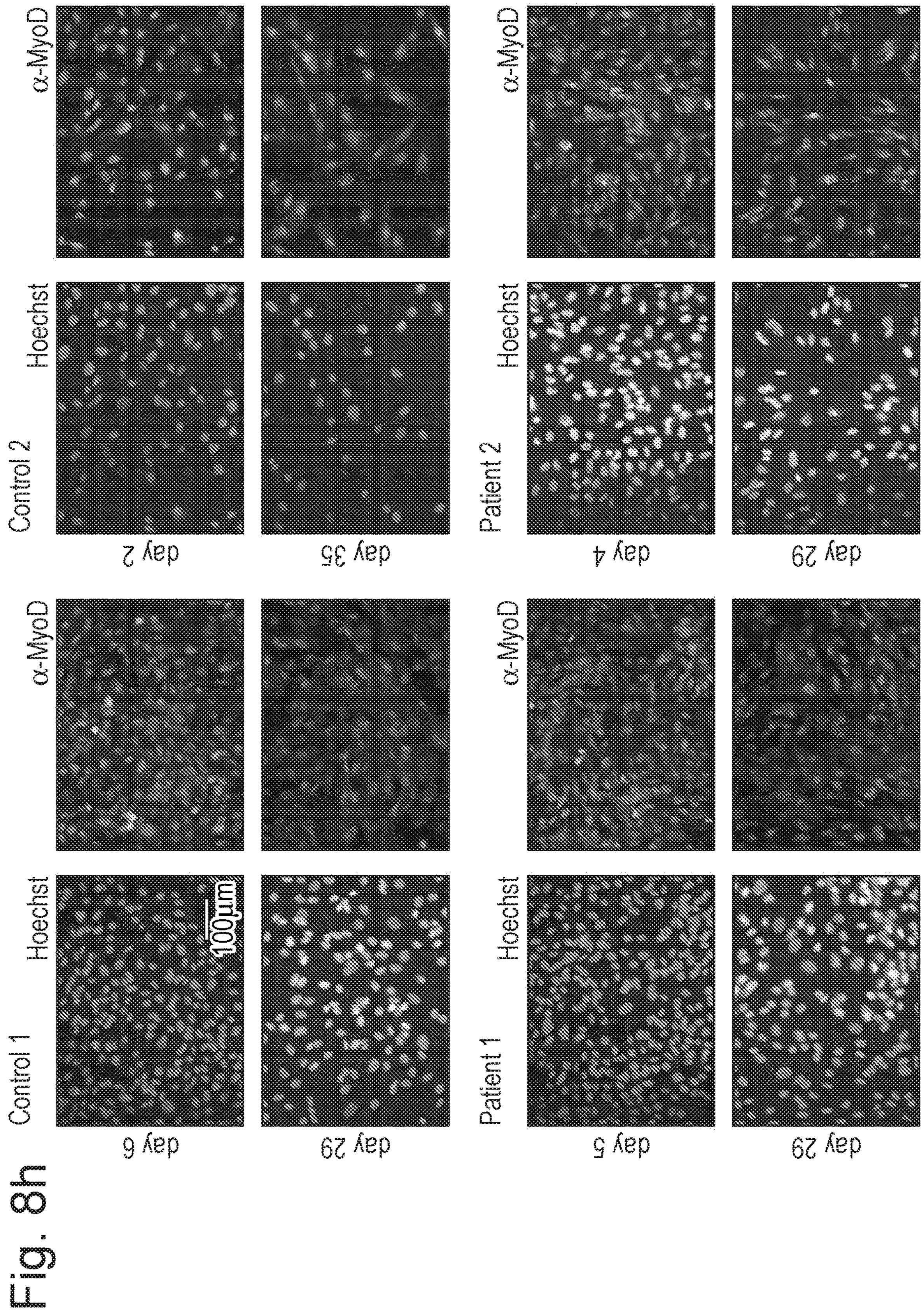
Figure 8I:
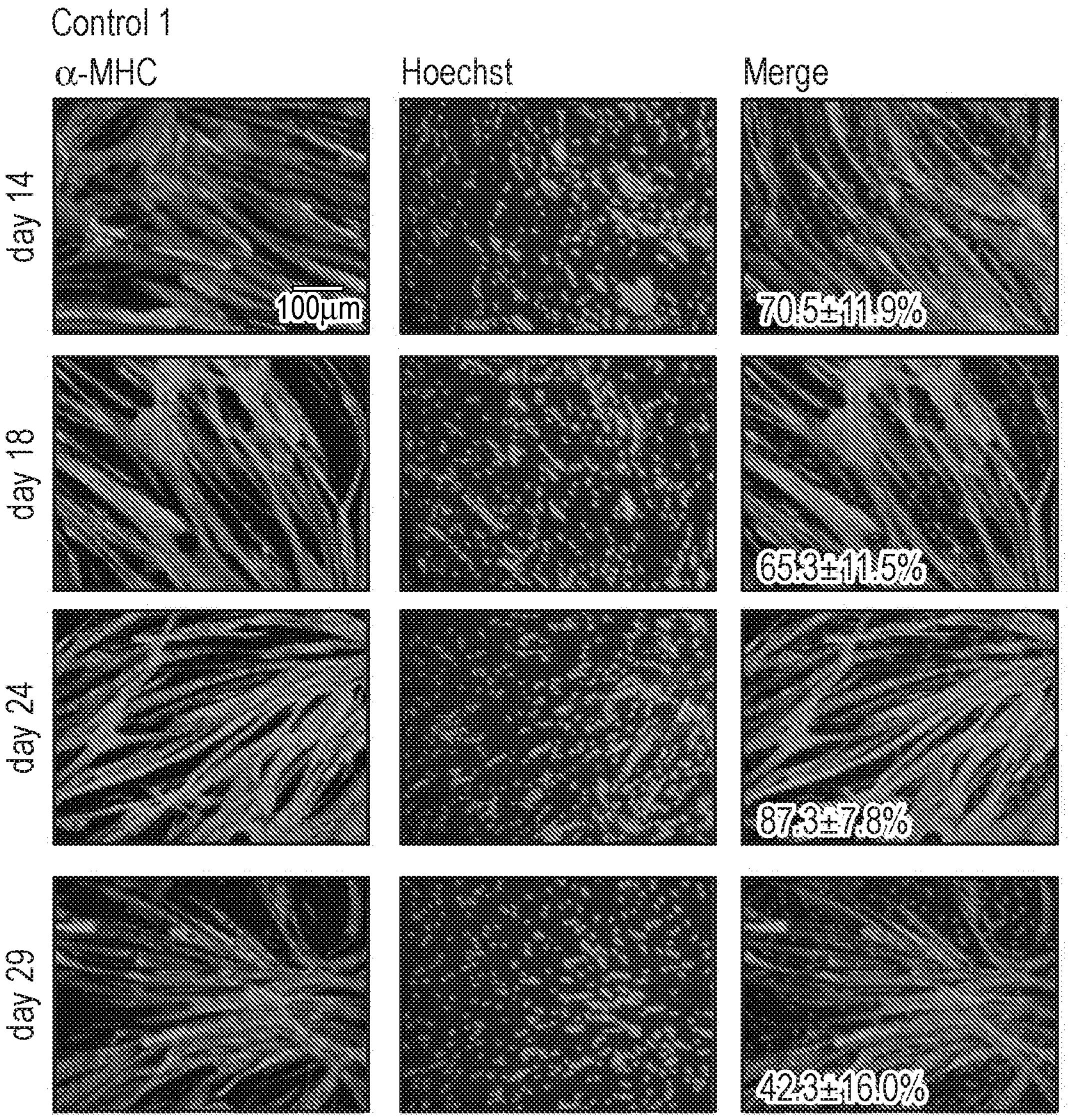
Figure 8J:
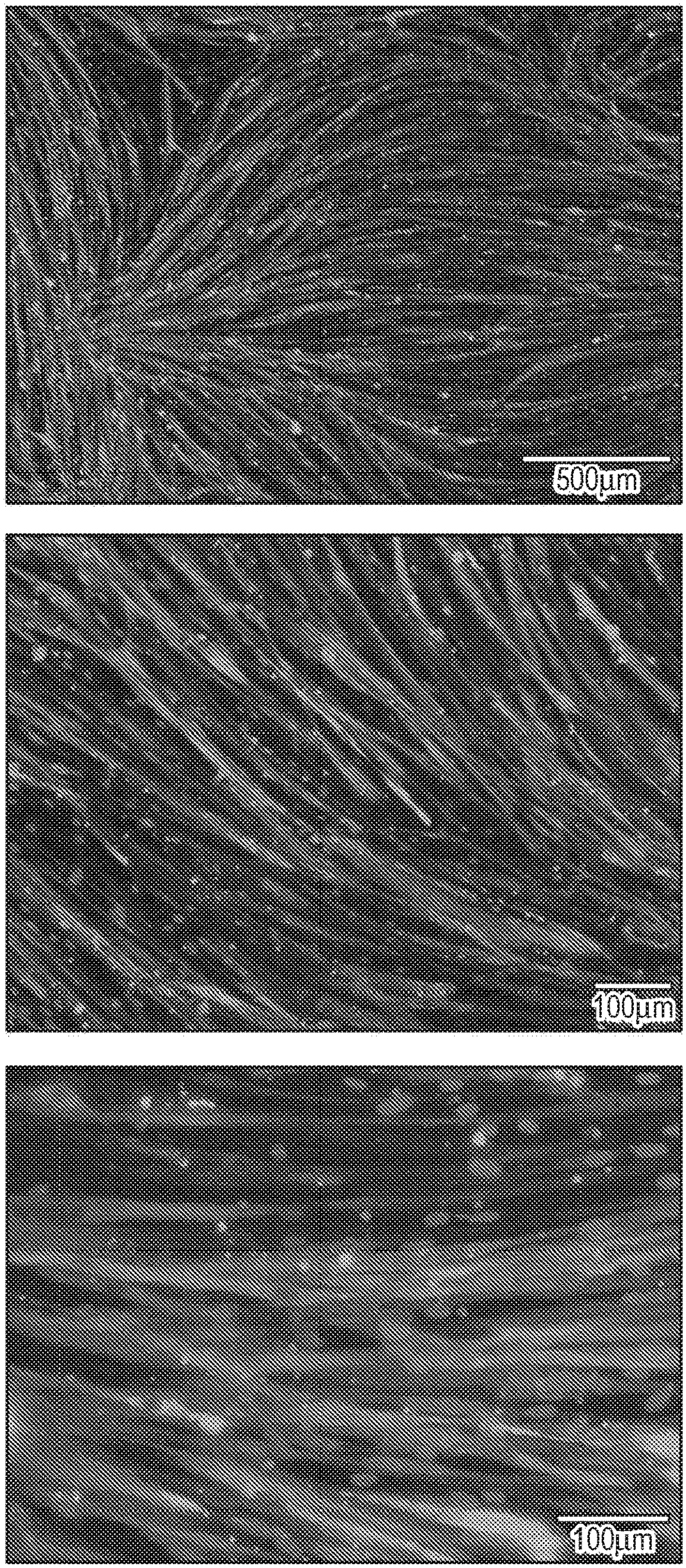

To address this, we tested cell culture conditions aiming to expand purified Pax7+ cells while maintaining proliferative and differentiation capacity. Out of 5 media tested medium 5 supported prolonged proliferation of myogenic cells (FIG. 3*a*). Critical components included DMEM as basal medium and FGF2, which supports proliferation. All 4 lines (2 Pompe patients, 2 healthy controls) could be expanded with nearly identical proliferation rates at an average of 29.4±1.3 hrs/cell cycle with at least $5\times10^7$ fold to yield at least $1\times10^{12}$ cells (FIG. 3*b*). At several time points during the expansion phase, cells could be frozen in viable state and used for subsequent expansion. Proliferating myogenic progenitors were characterized by high expression of the myogenic markers MyoD, Myogenin, Six1, and Six4, moderately high expression of the myogenic differentiation marker α-actinin and of FGF2, while the neural crest marker Sox1 was not expressed (FIG. 3*c*, FIG. 8*g*,*h*). Upon expansion, the karyotype remained normal (FIG. 3*d*). In addition, at any stage of expansion, cells could be differentiated into multinucleated myotubes in a highly reproducible manner (tested in >500 differentiations performed to date) (FIG. 3*e*, FIG. 8*i*). Multinucleated myotubes showed high expression of the myogenic differentiation markers Myosin Heavy Chain (MHC) (FIG. 3*e*) and α-actinin (FIG. 3*c*). The lysosomal markers LAMP1 and LAMP2 were expressed at similar levels in myogenic progenitors and myotubes from healthy controls and patients (FIG. 8*g*). This suggests that Pompe disease pathology, which includes enlarged lysosomes and elevated expression of LAMP1/2 in a subset of skeletal muscle fibers in patients[46], has not advanced to critical levels that affect lysosomal size and numbers in vitro, which is consistent with the late-onset phenotype of childhood/adult onset Pompe disease. We conclude that the expansion protocol reproducibly provided the amounts of purified iPS-derived myotubes that were required for the quantitative analysis of AONs on splicing.

Figure 4A:
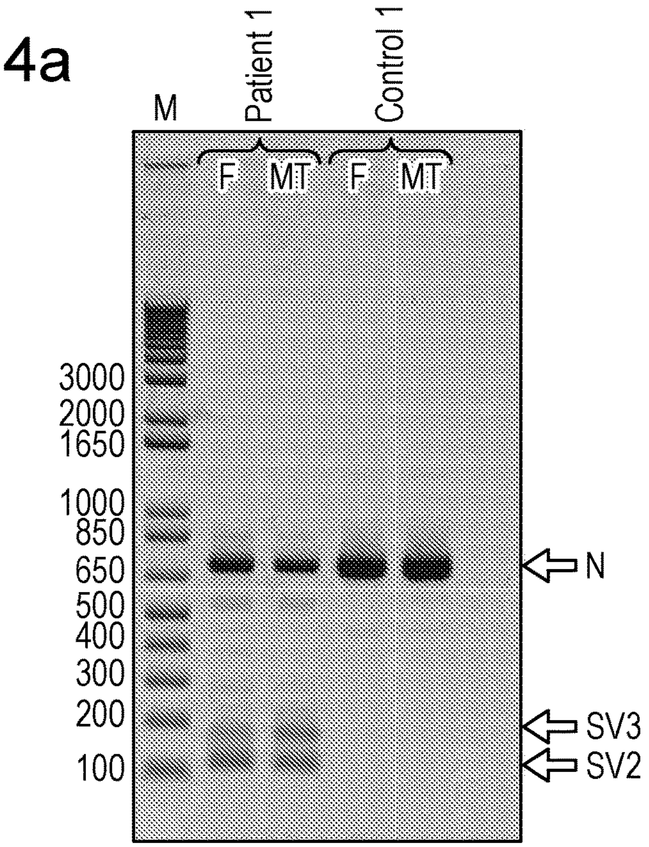
Figure 4B:
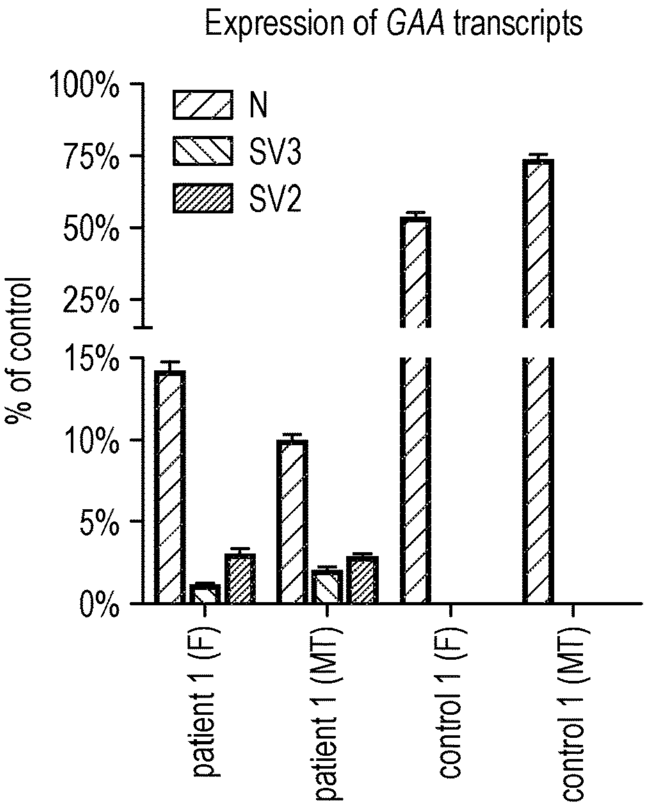

We expanded myogenic progenitors, differentiated them in a four-day protocol into multinucleated myotubes, and analyzed GAA splicing by flanking exon RT-PCR and quantitative RT-qPCR of splicing products. This showed leaky wild type splicing, and partial and complete skipping of exon 2 in patient-derived myotubes, but not in myotubes from healthy controls, similar to primary fibroblasts (FIG. 4*a,b*). This confirmed that the IVS1 variant caused aberrant splicing of exon 2 in skeletal muscle cells.

Figure 4C:
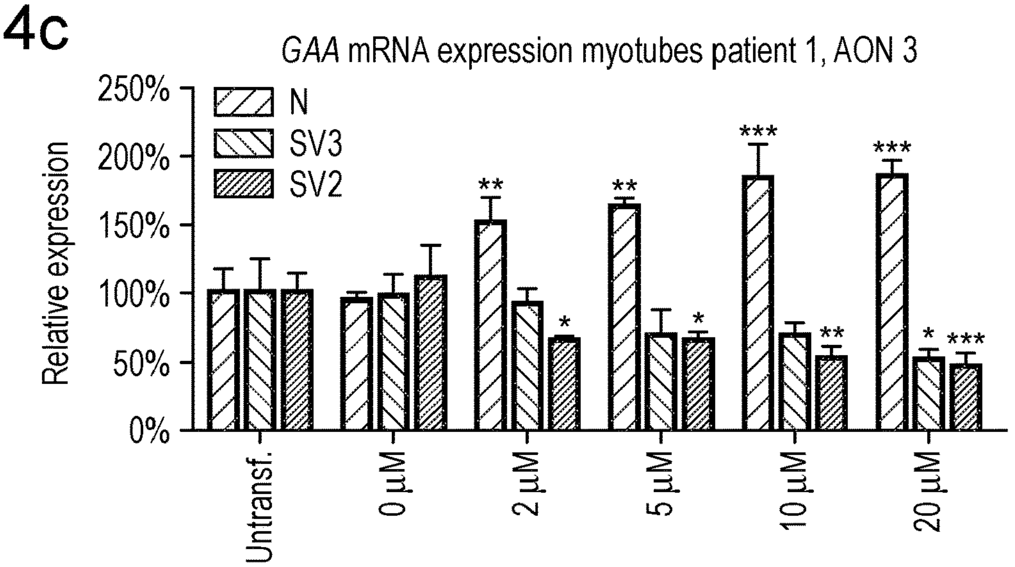
Figure 4D:
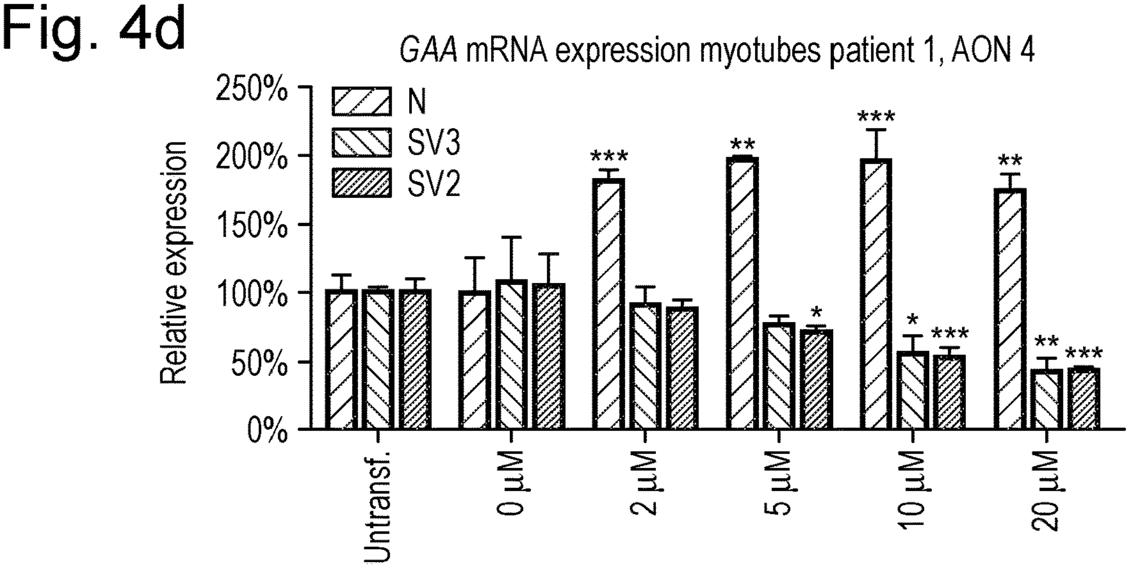
Figure 4E:
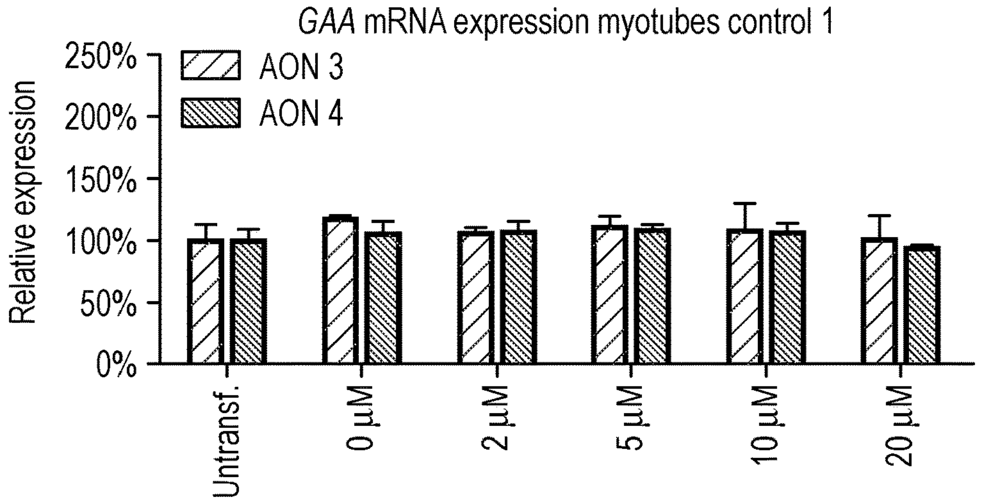
Figure 4F:
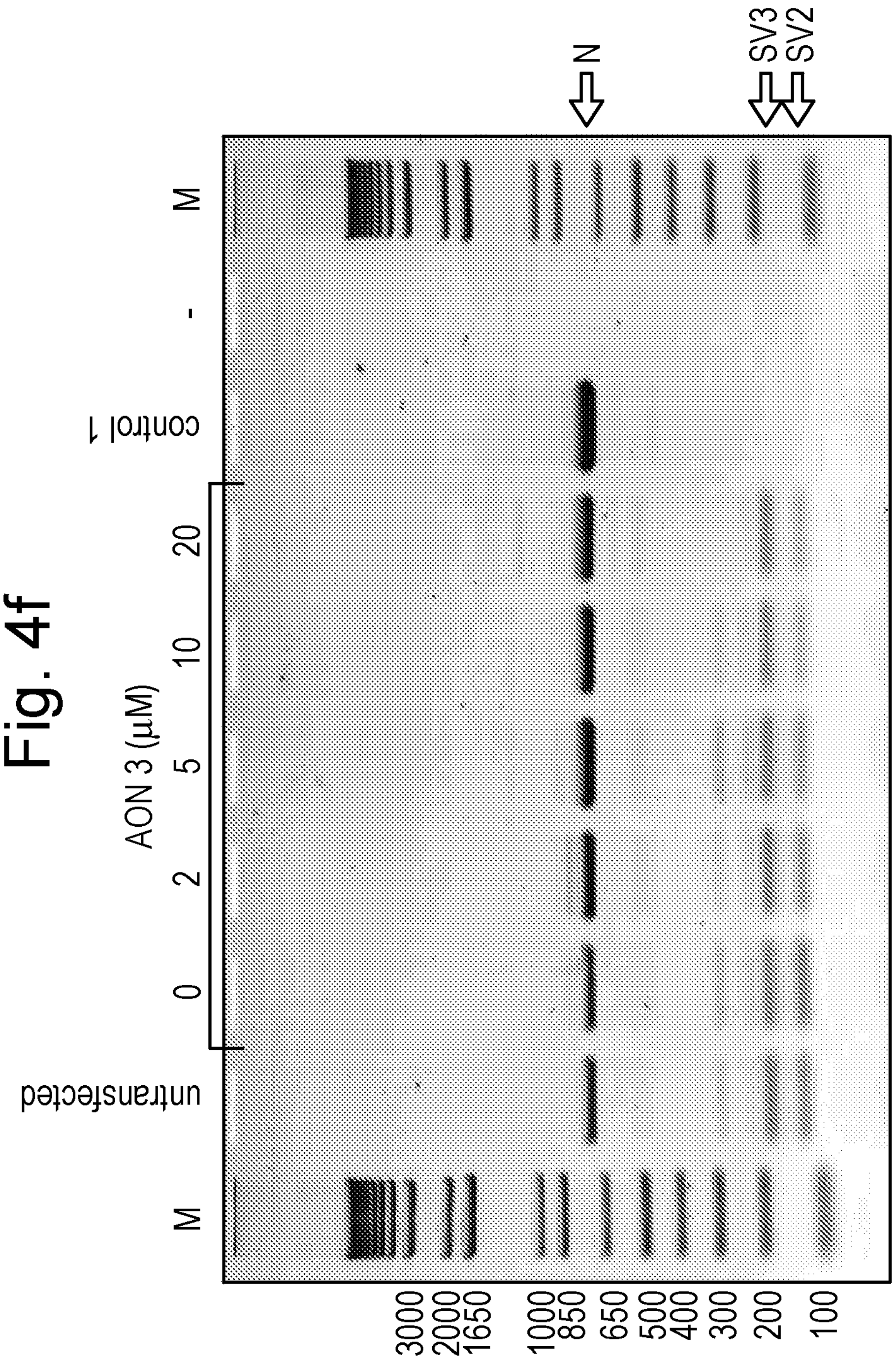
Figure 4G:
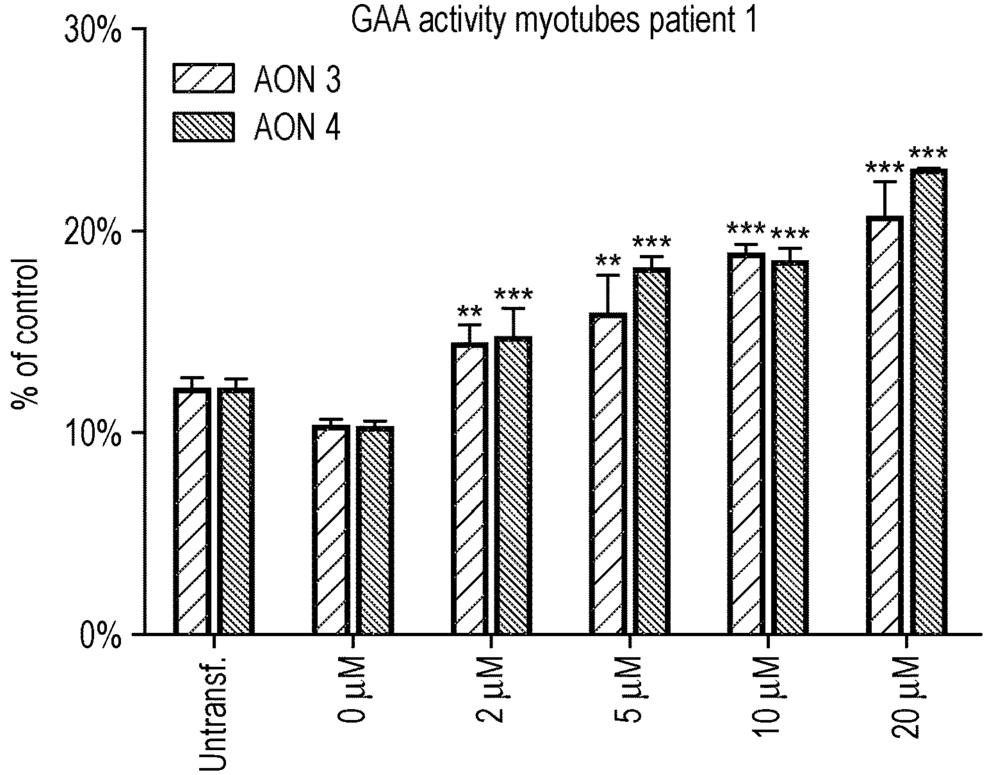
Figure 4H:
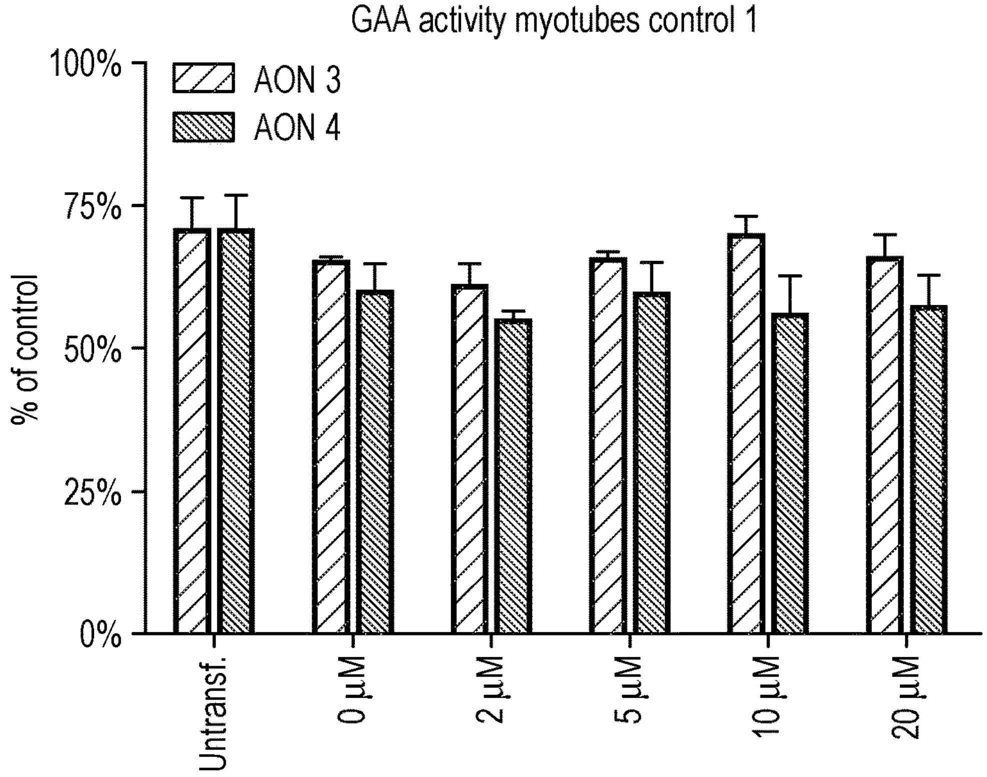
Figure 4I:
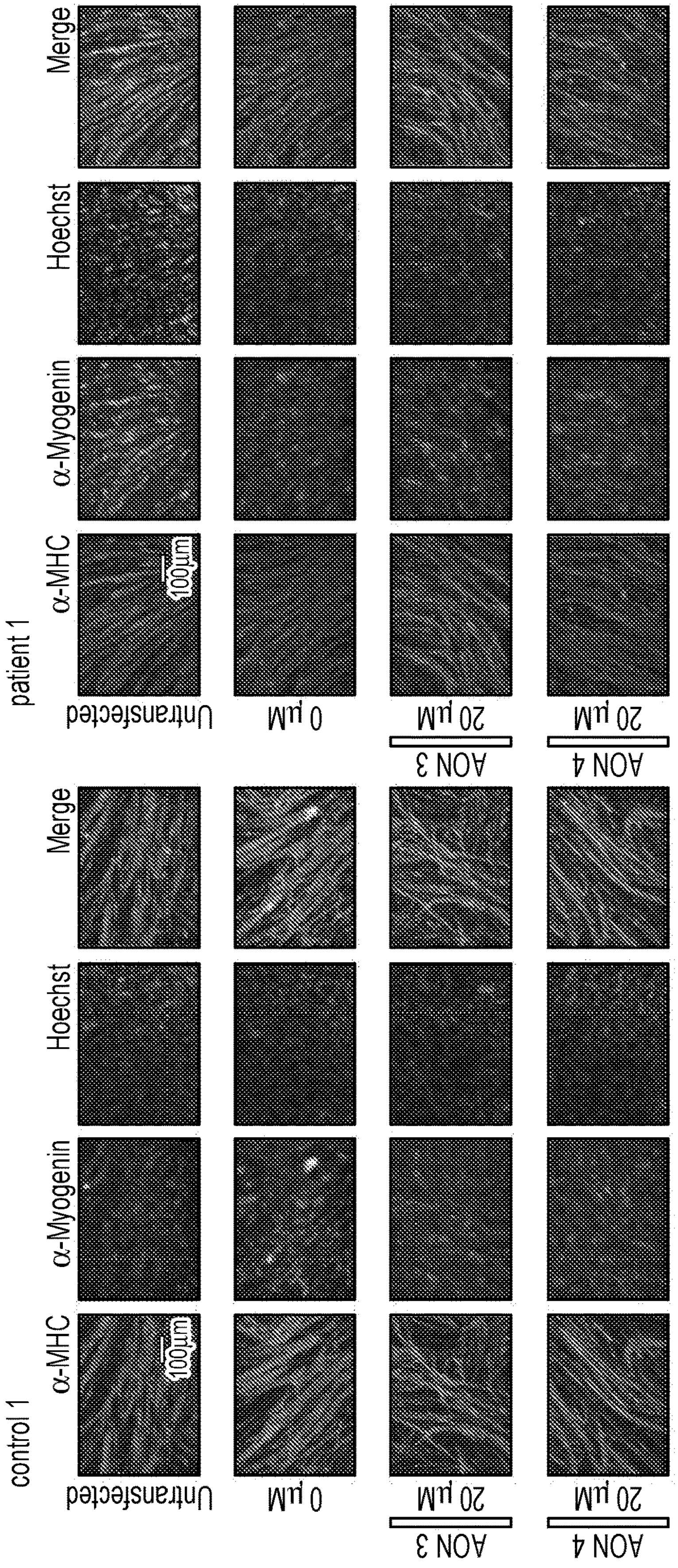
Figure 9A:
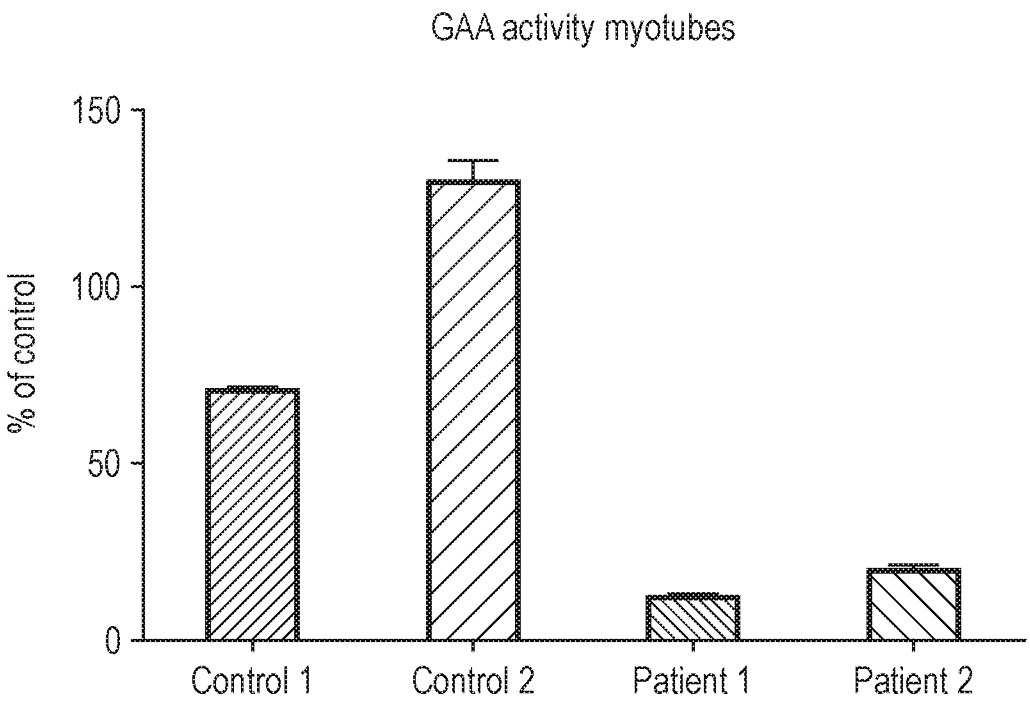
Figure 9B:
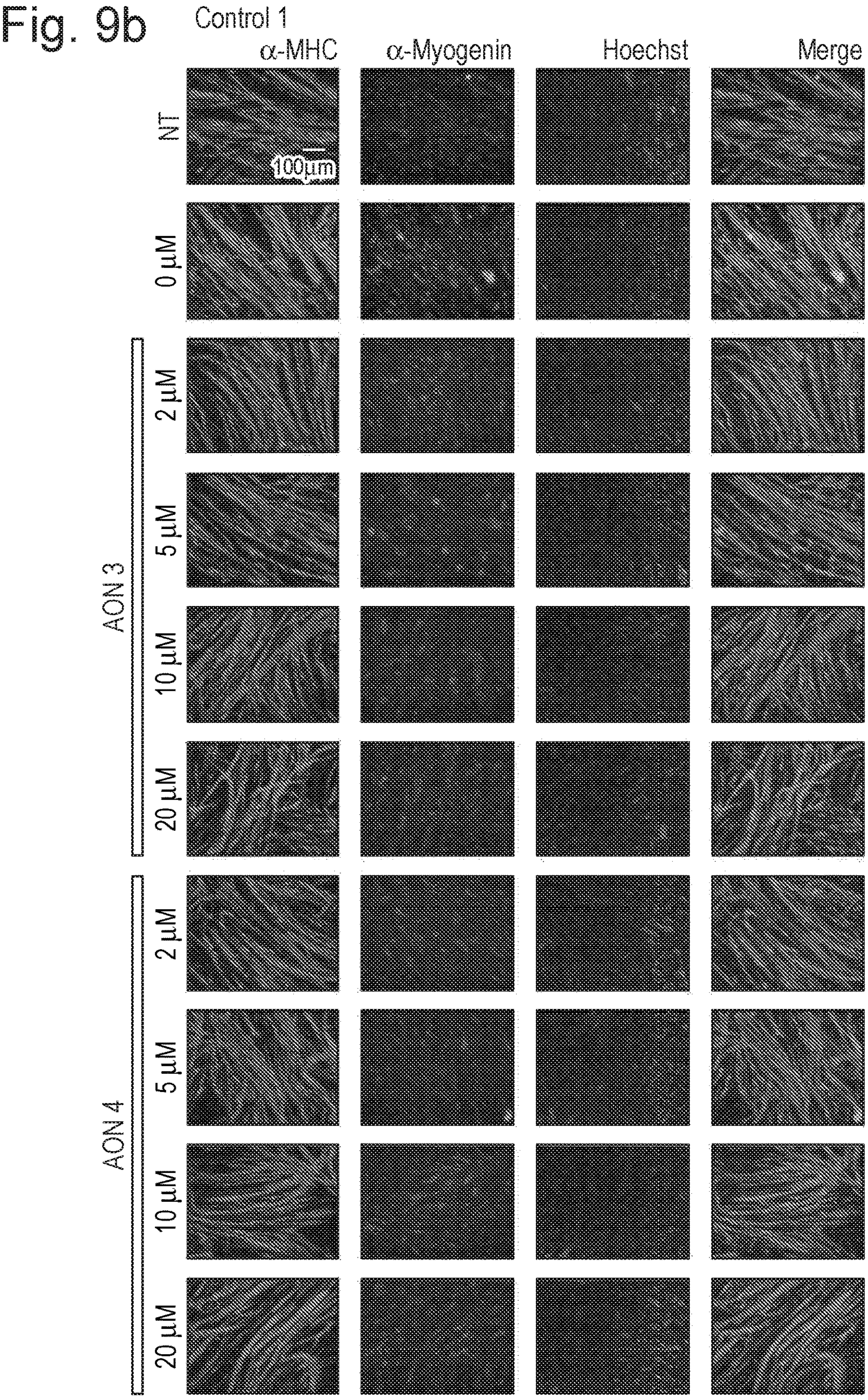
Figure 9B:
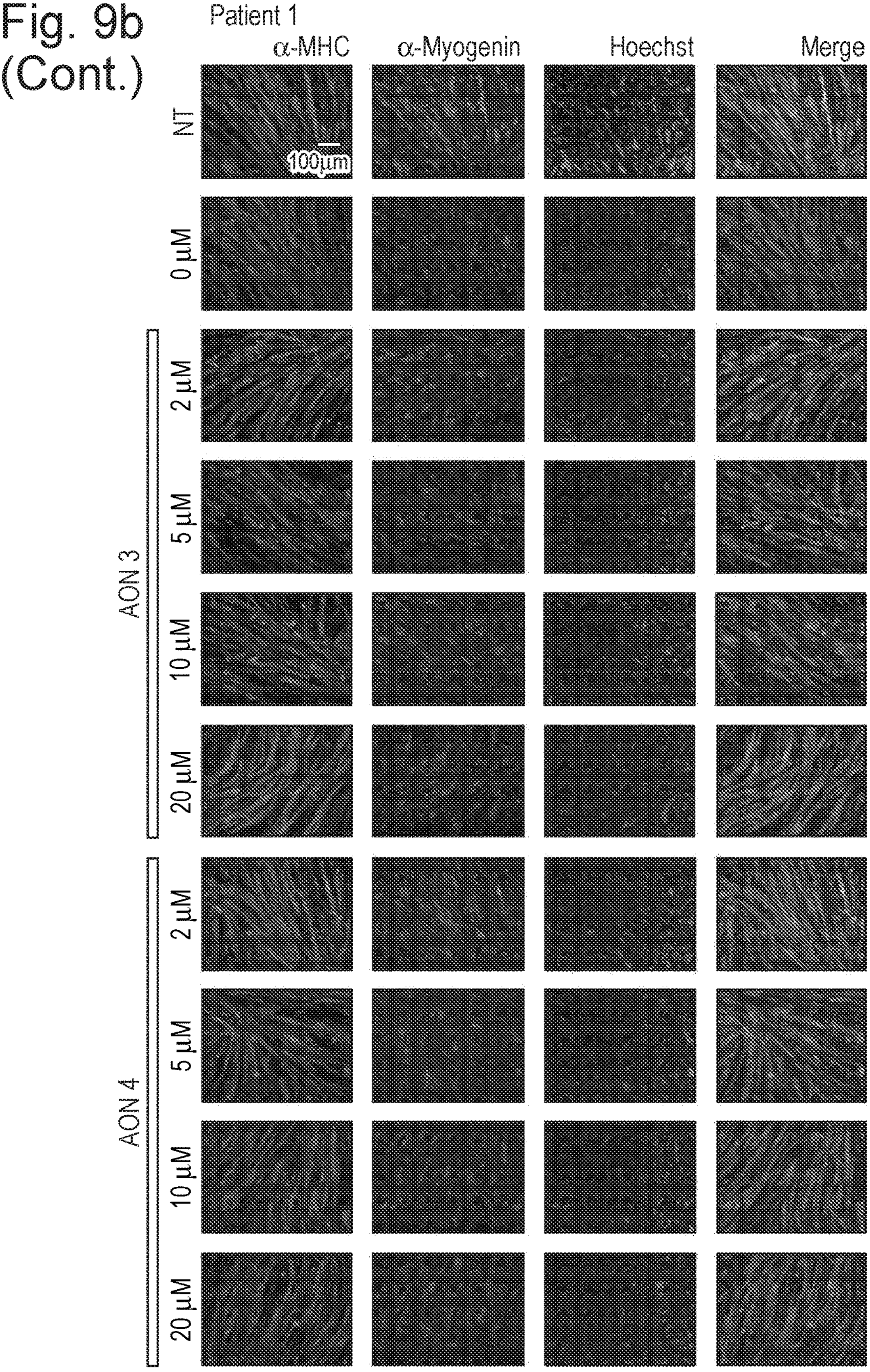
Figure 9C:
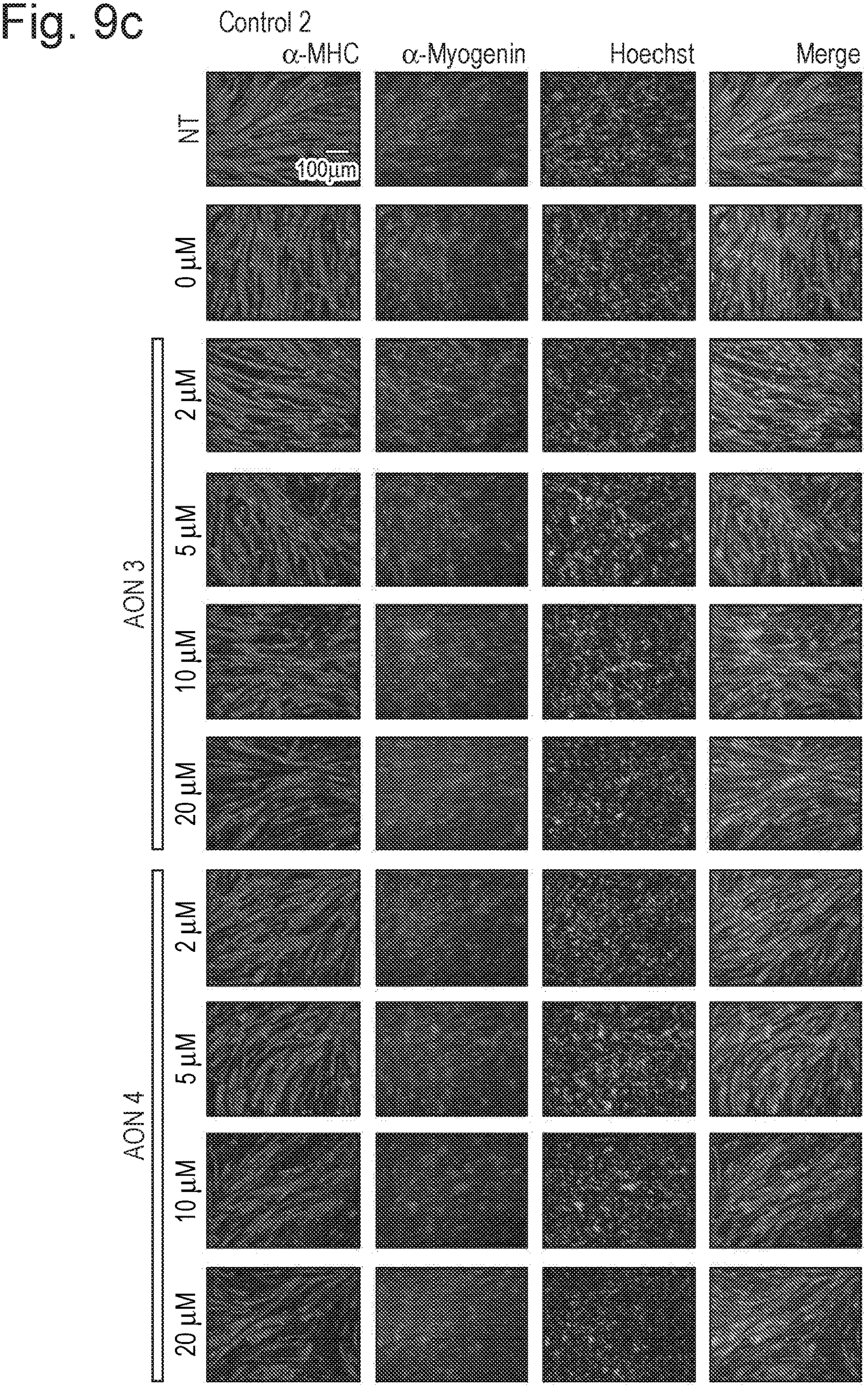
Figure 9C:
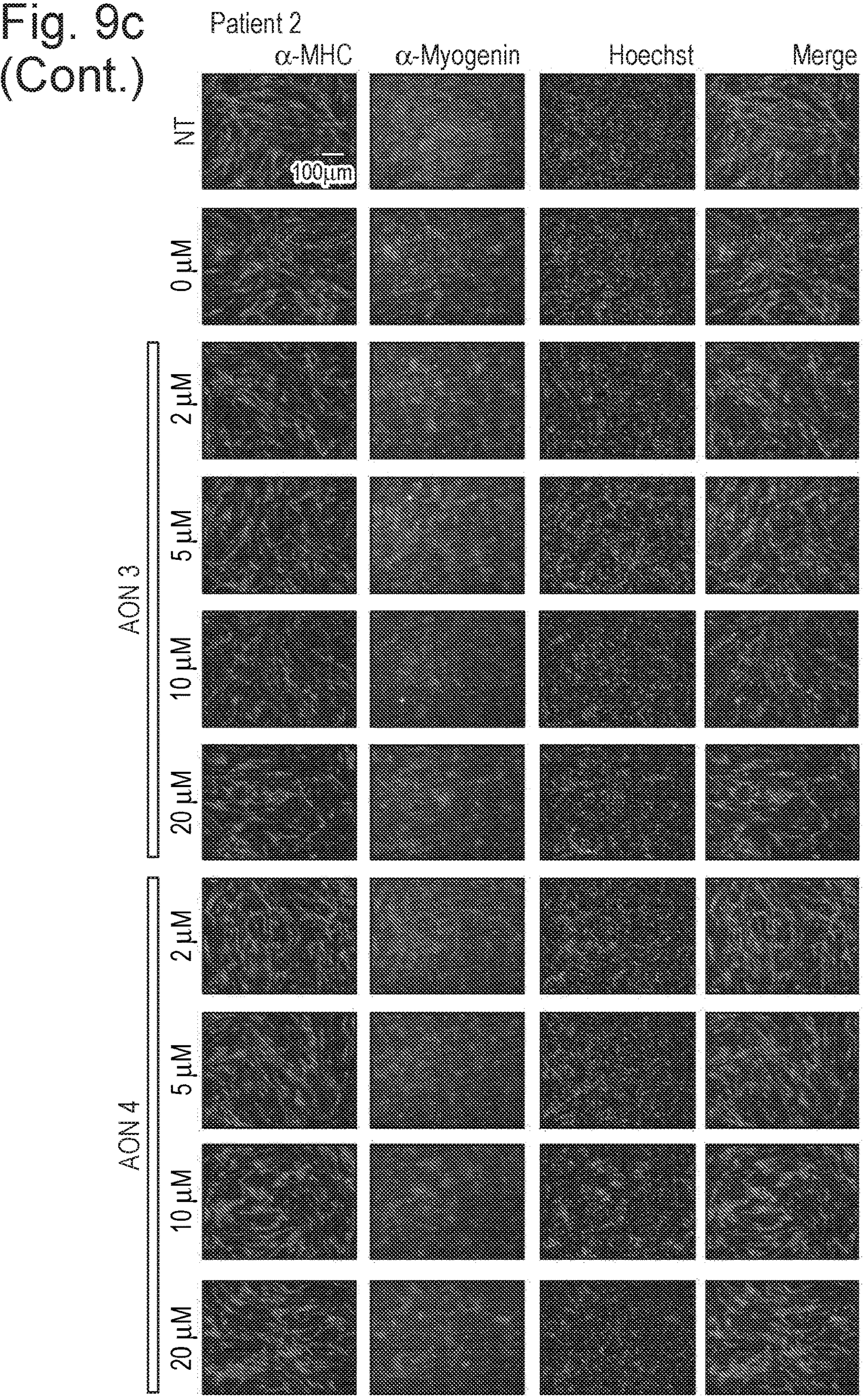
Figure 9D:
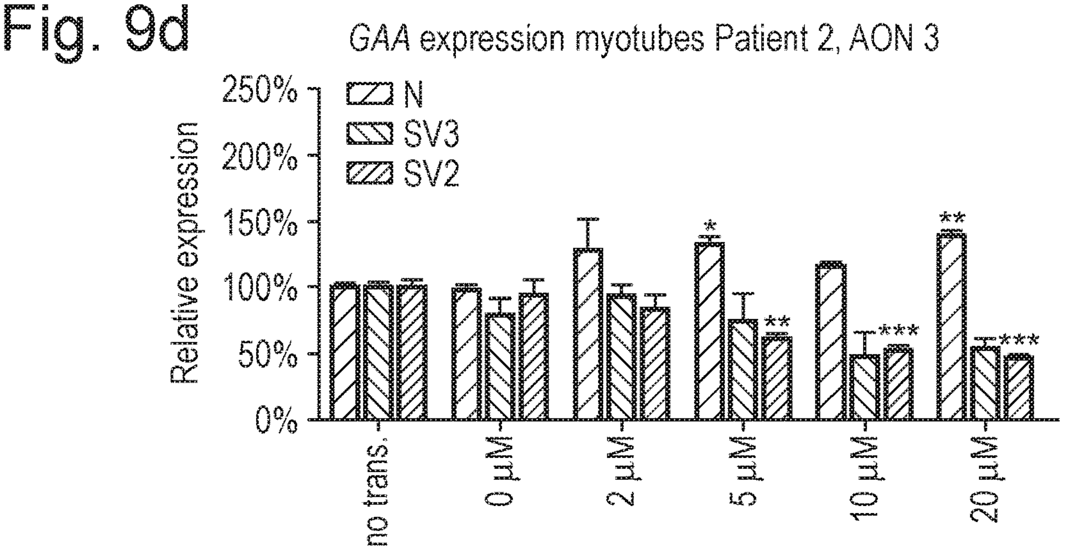
Figure 9E:
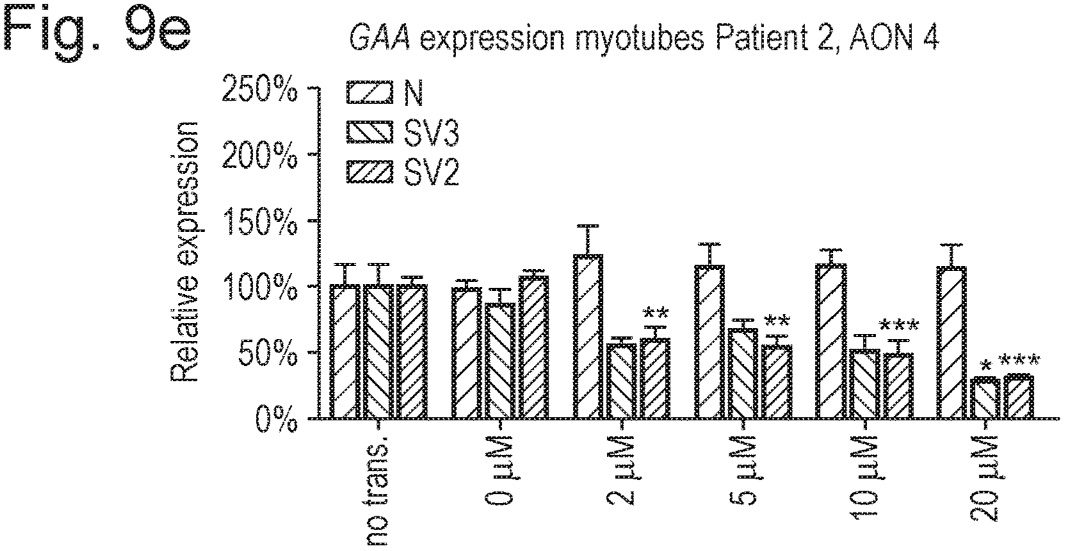
Figure 9F:
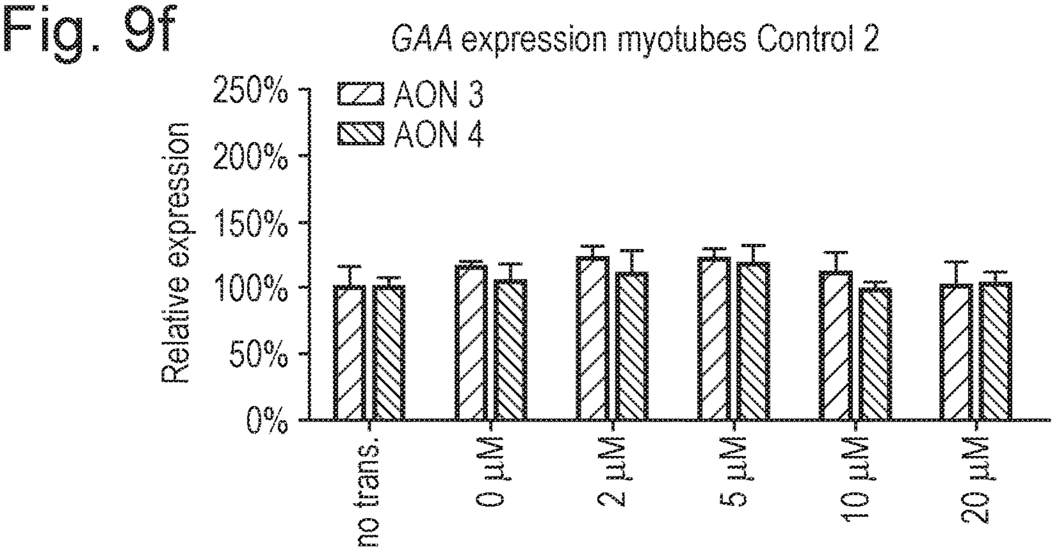
Figure 9G:
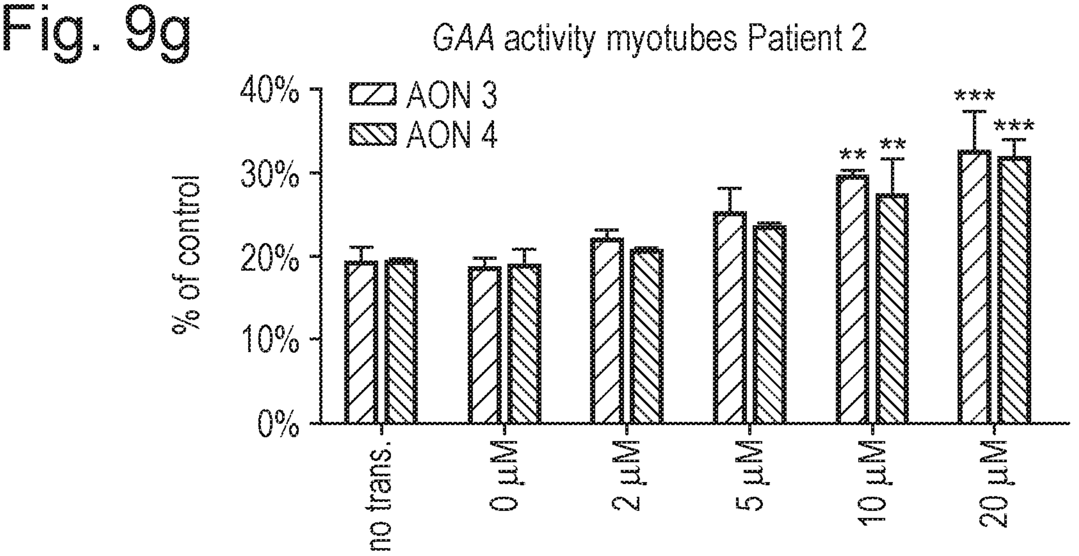
Figure 9H:
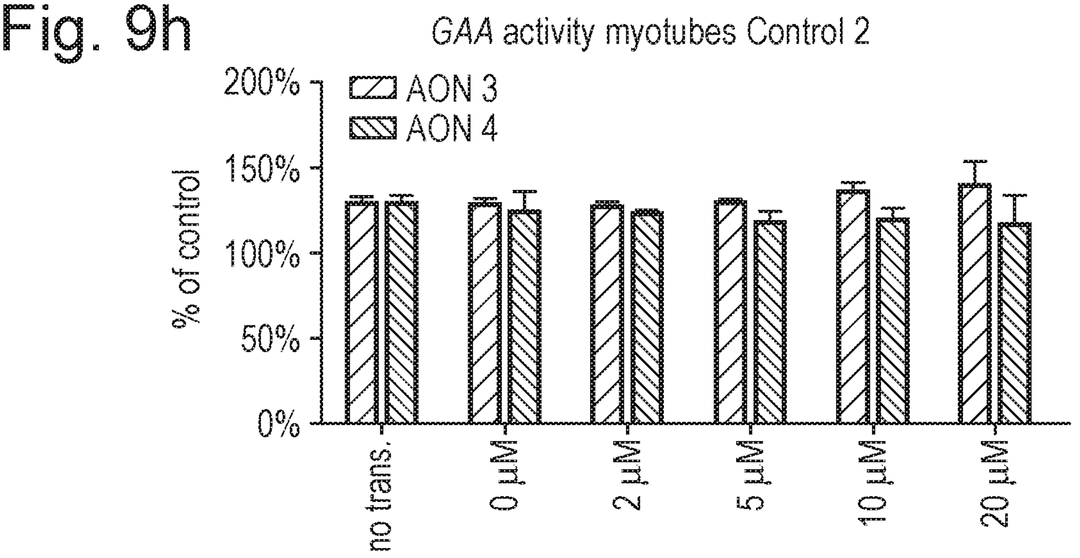
Figure 9I:
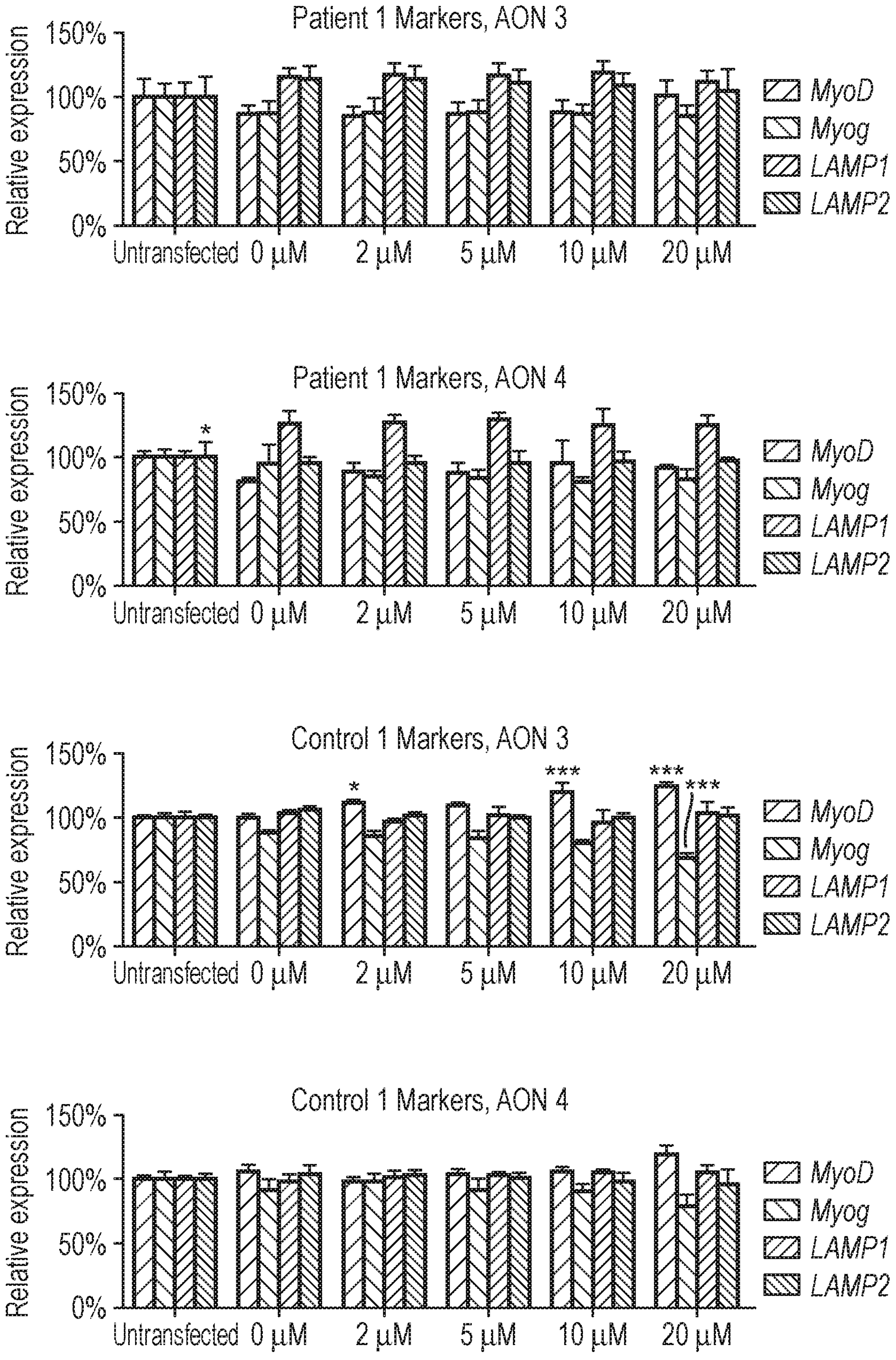
Figure 9I:
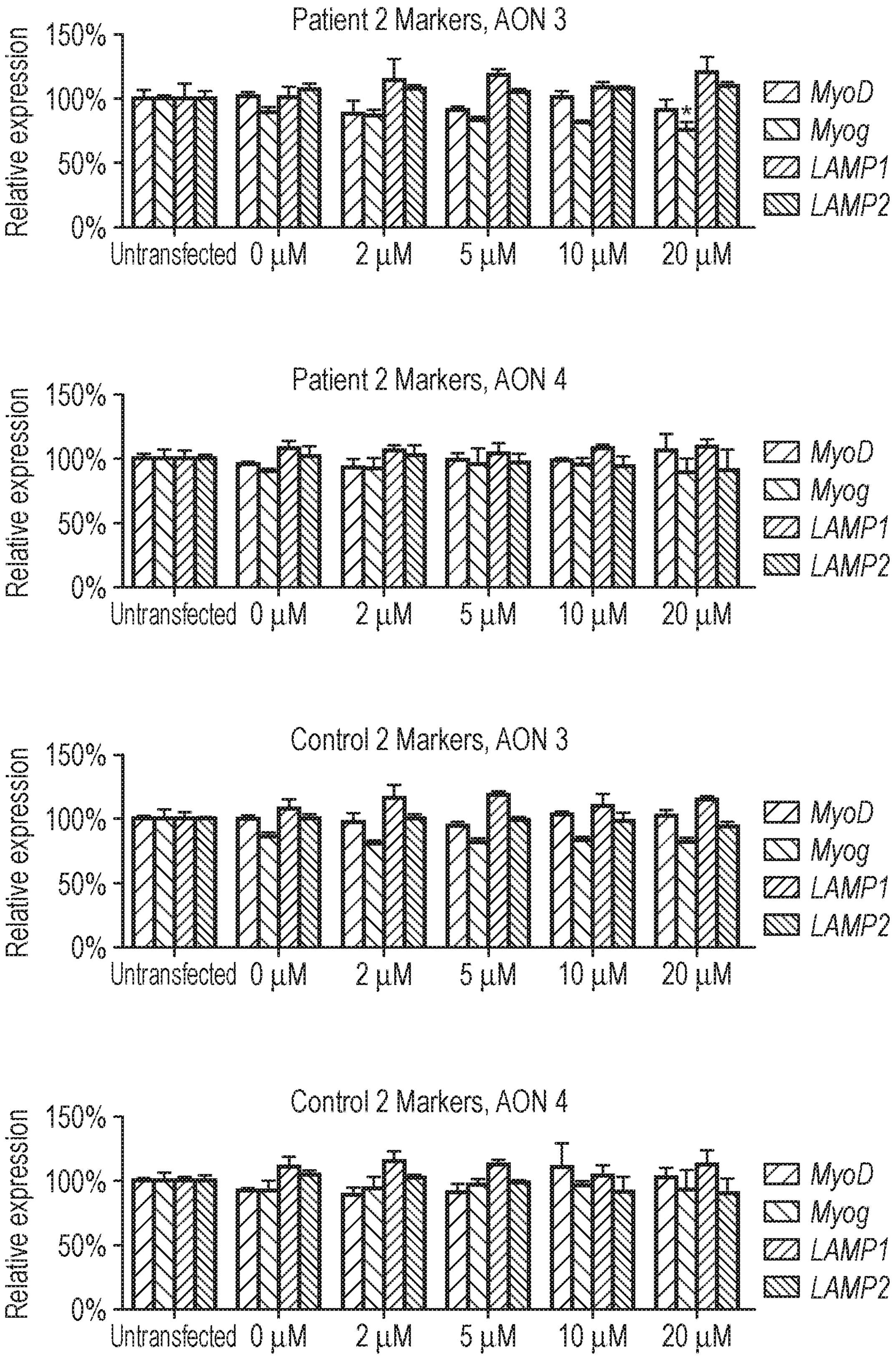

Next, we tested the effect of AONs 3 and 4 on exon 2 inclusion in myotubes (FIG. 4*c*, FIG. 9*a,b*). Treatment of patient-derived myotubes resulted in a concentration-dependent increase in wild type GAA splicing and a concomitant decrease in expression of aberrant splicing products SV2 and SV3, as shown by quantitative analysis of individual splicing products using RT-qPCR (FIG. 4*c,d, i*, FIG. 9*c,d*). In myotubes from healthy controls. AONs 3 and 4 did not affect GAA exon 2 splicing (FIG. 4*e*, FIG. 9*e*), indicating that these only restored normal splicing in the context of the IVS1 variant without promoting additional effects on GAA mRNA expression. This was confirmed by flanking exon RT-PCR analysis of exon 2 (FIG. 4*f*). Importantly, treatment of patient-derived myotubes with AONs 3 or 4 resulted in elevation of GAA enzyme activity above the disease threshold of 20% of healthy control levels (FIG. 4*g*, FIG. 9*f*), suggesting that these AONs are capable of restoring GAA enzyme levels to those present in healthy individuals. Treatment of myotubes from healthy controls did not affect GAA enzyme activity (FIG. 4*h*, FIG. 9*g*). We conclude that the splicing silencer sequence at c.-32-179 operates in skeletal muscle cells and that its inhibition by AONs can restore splicing in cells from Pompe patients carrying the IVS1 variant.

Figure 5A:
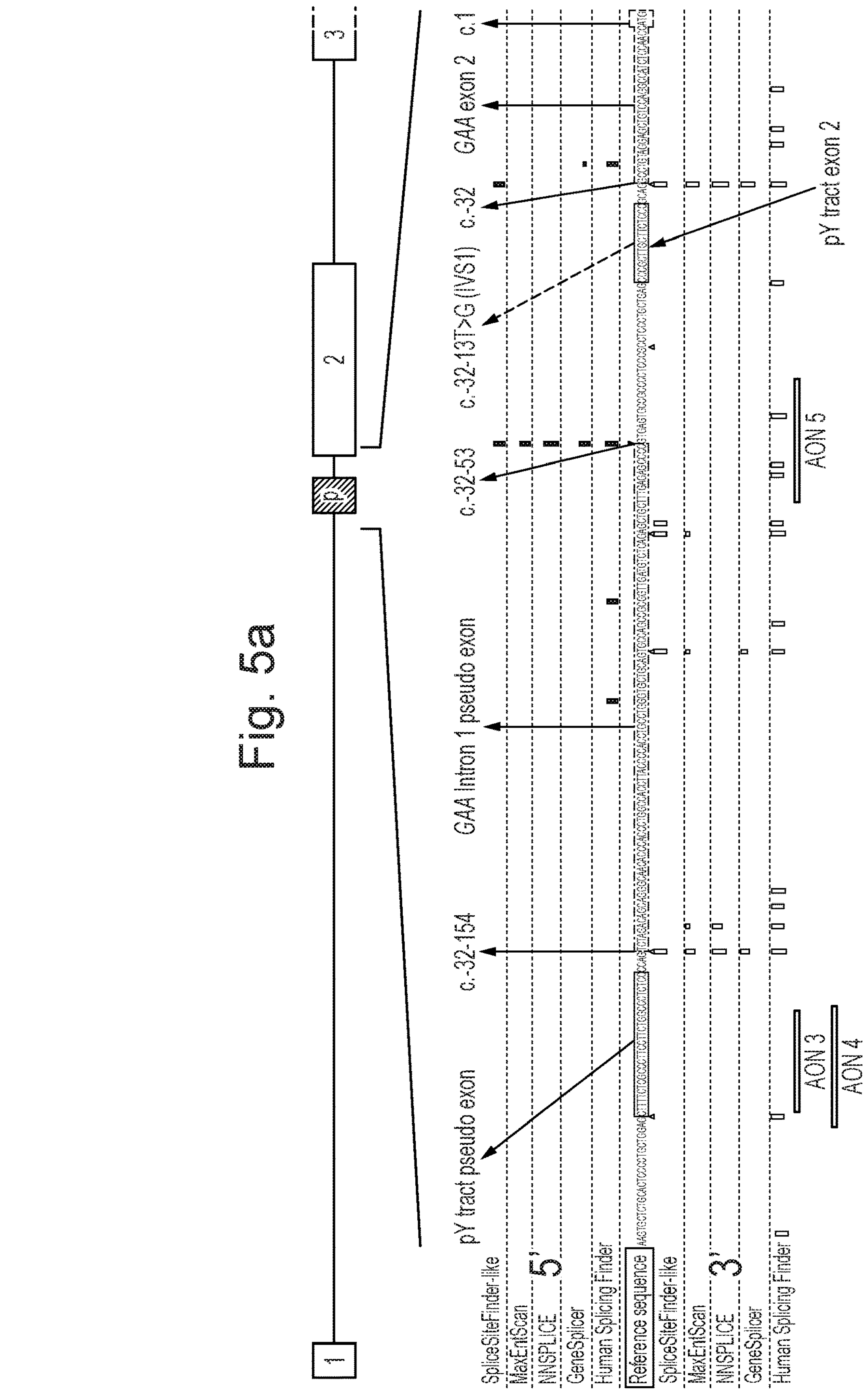
Figure 10A:
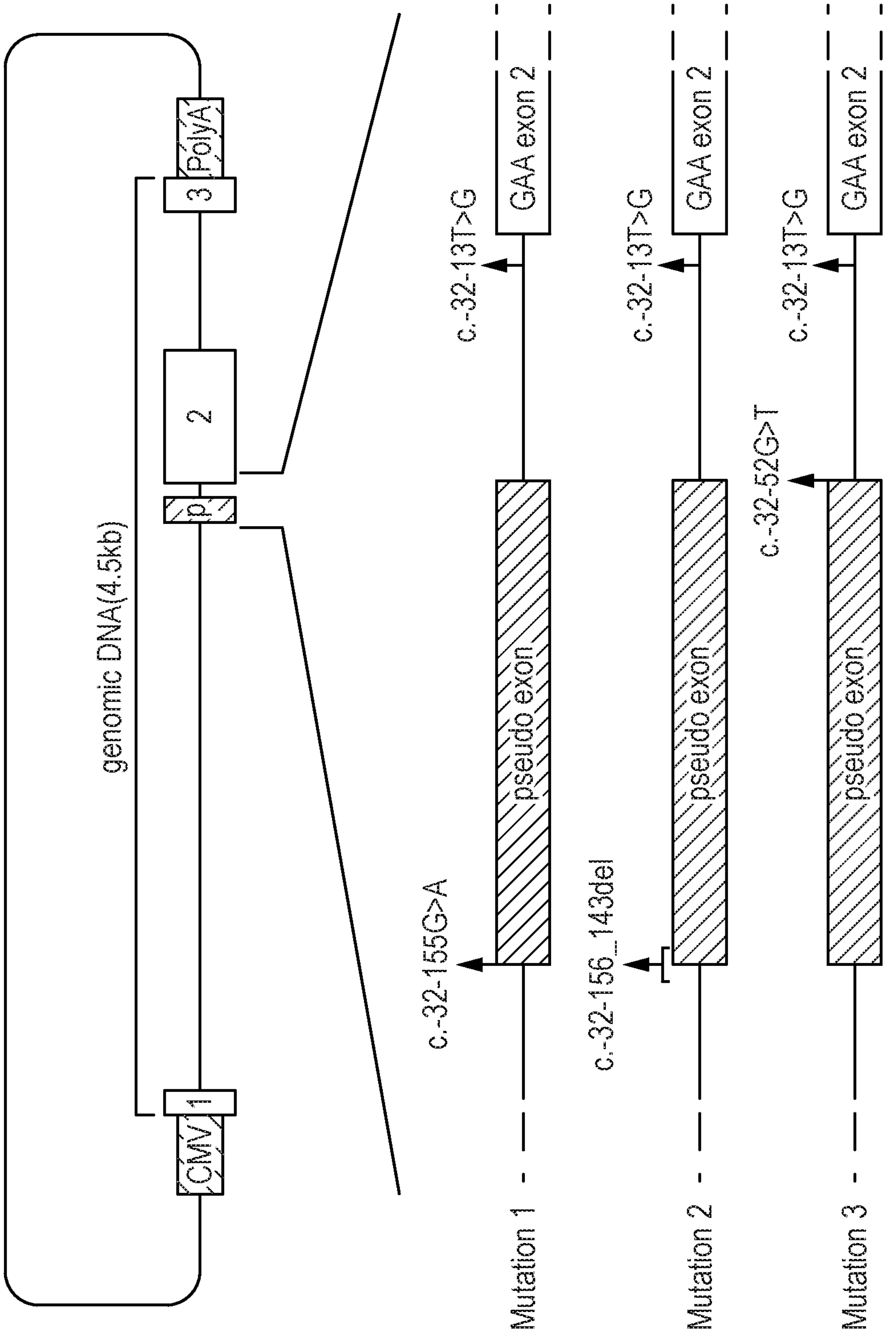
Figure 10B:
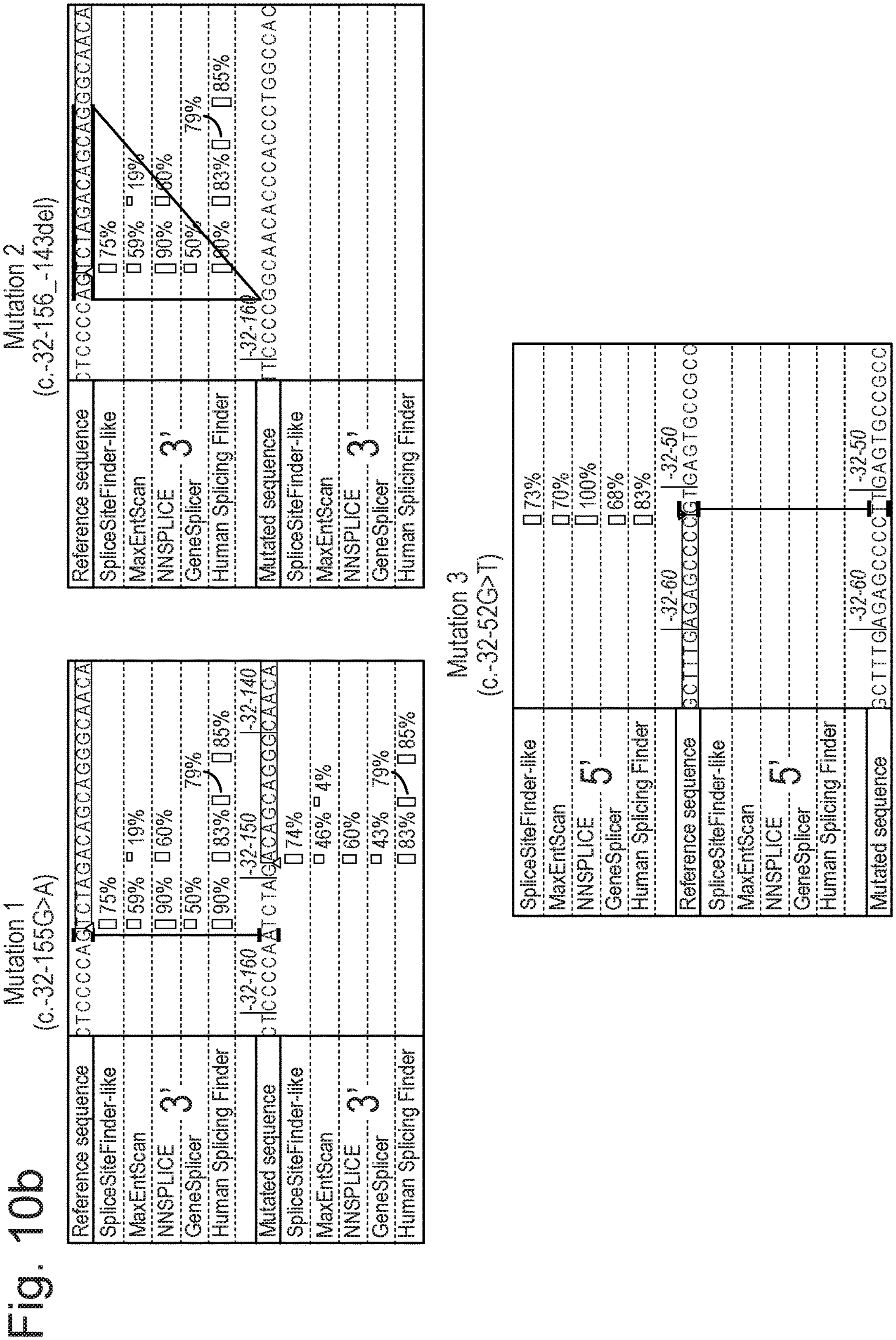
Figure 10C:
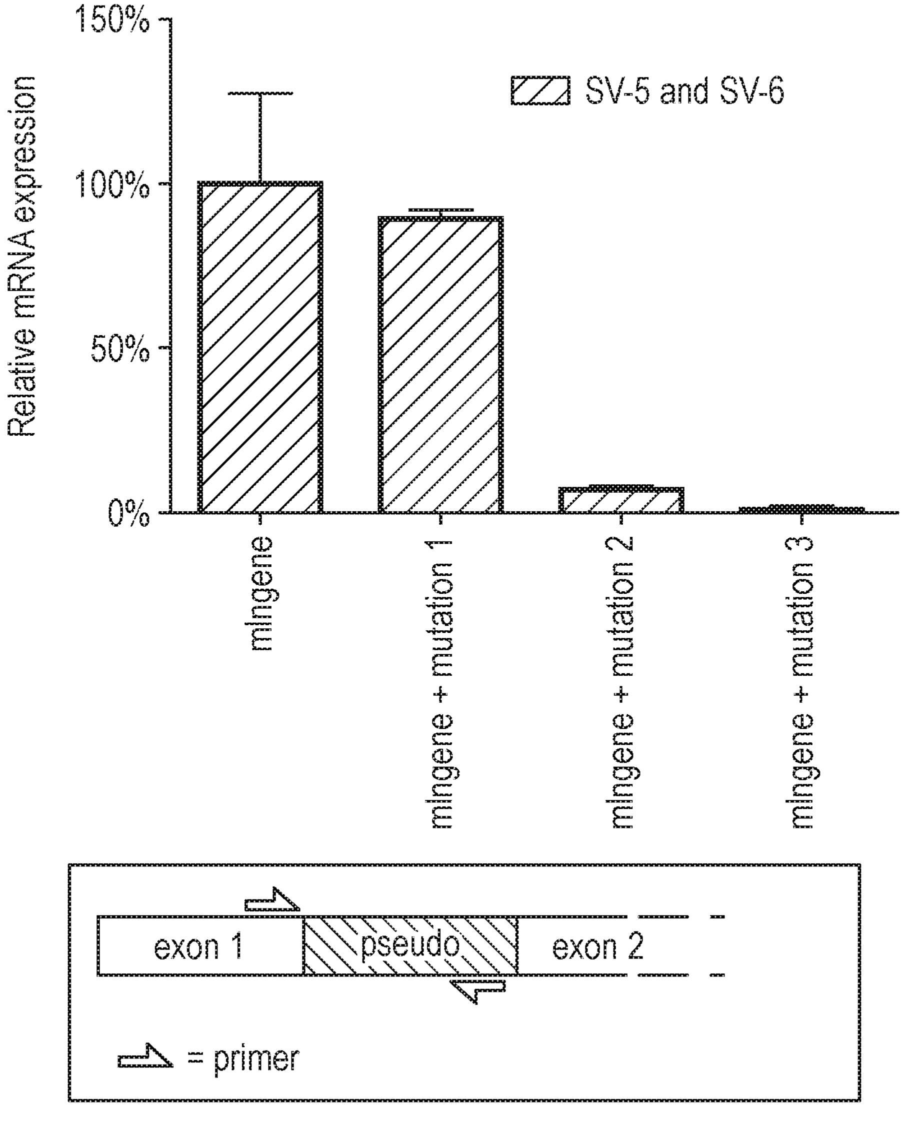
Figure 10D:
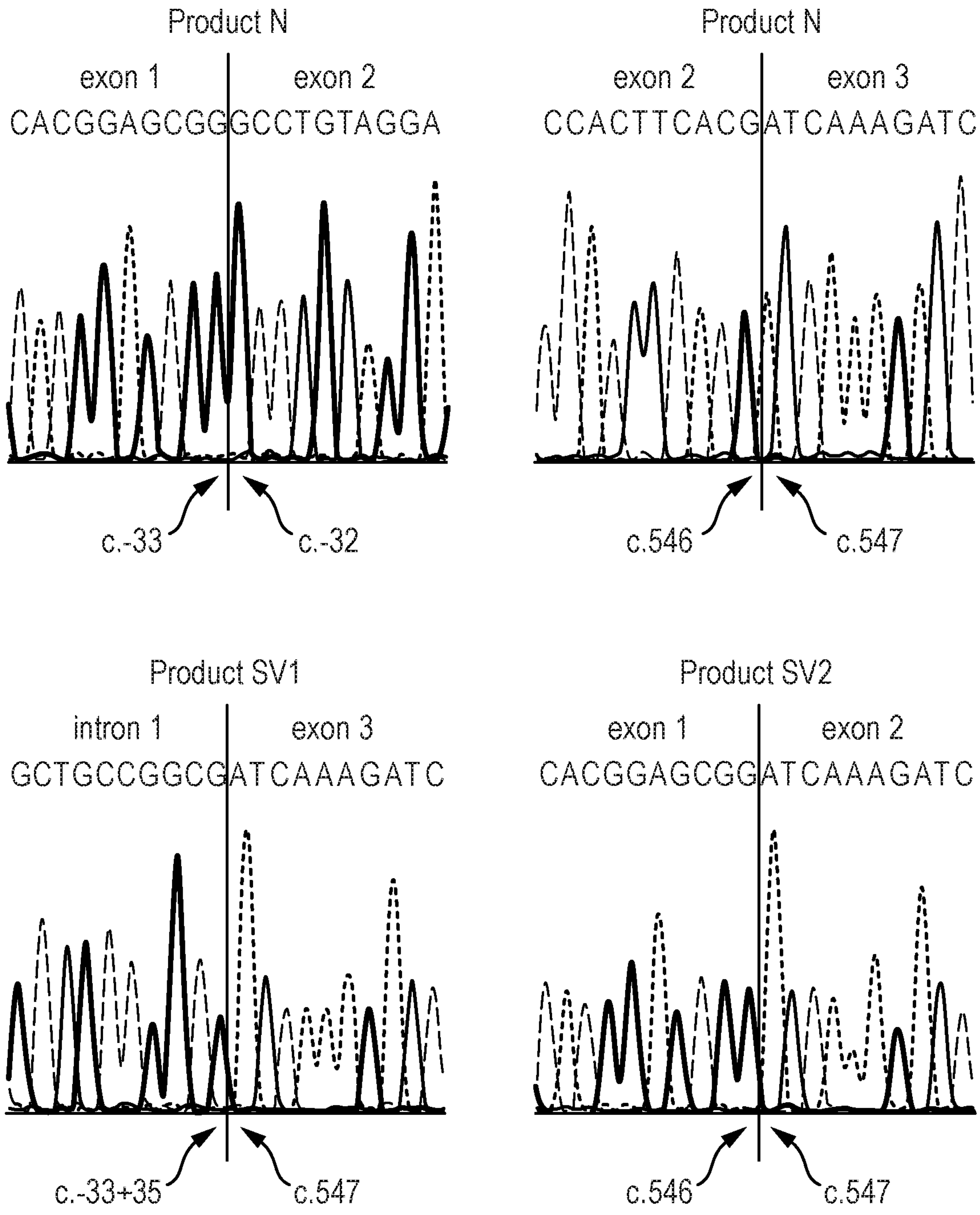

As it was unclear how AONs 3 and 4 restored exon 2 inclusion, we were interested to investigate their mechanism of action. We noted that the target sequence of these AONs showed similarity to a pY tract, which is usually present between 5-40 nucleotides upstream of a splice acceptor. We then performed in silico analysis of splice sites, and this predicted a strong natural cryptic splice acceptor site 12 nt downstream of the binding site for AONs 3 and 4 (FIG. 5*a*). One hundred and three nt further downstream, a strong natural cryptic splice donor was predicted. Together, these cryptic splice sites defined a hypothetical natural pseudo exon. Mutation of the predicted splice sites abolished inclusion of the pseudo exon in a minigene construct (FIG. 10*c-e*). This suggested the possibility that AONs 3 and 4 may act by inhibiting cryptic splicing rather than by repressing a putative ISS.

Figure 5B:
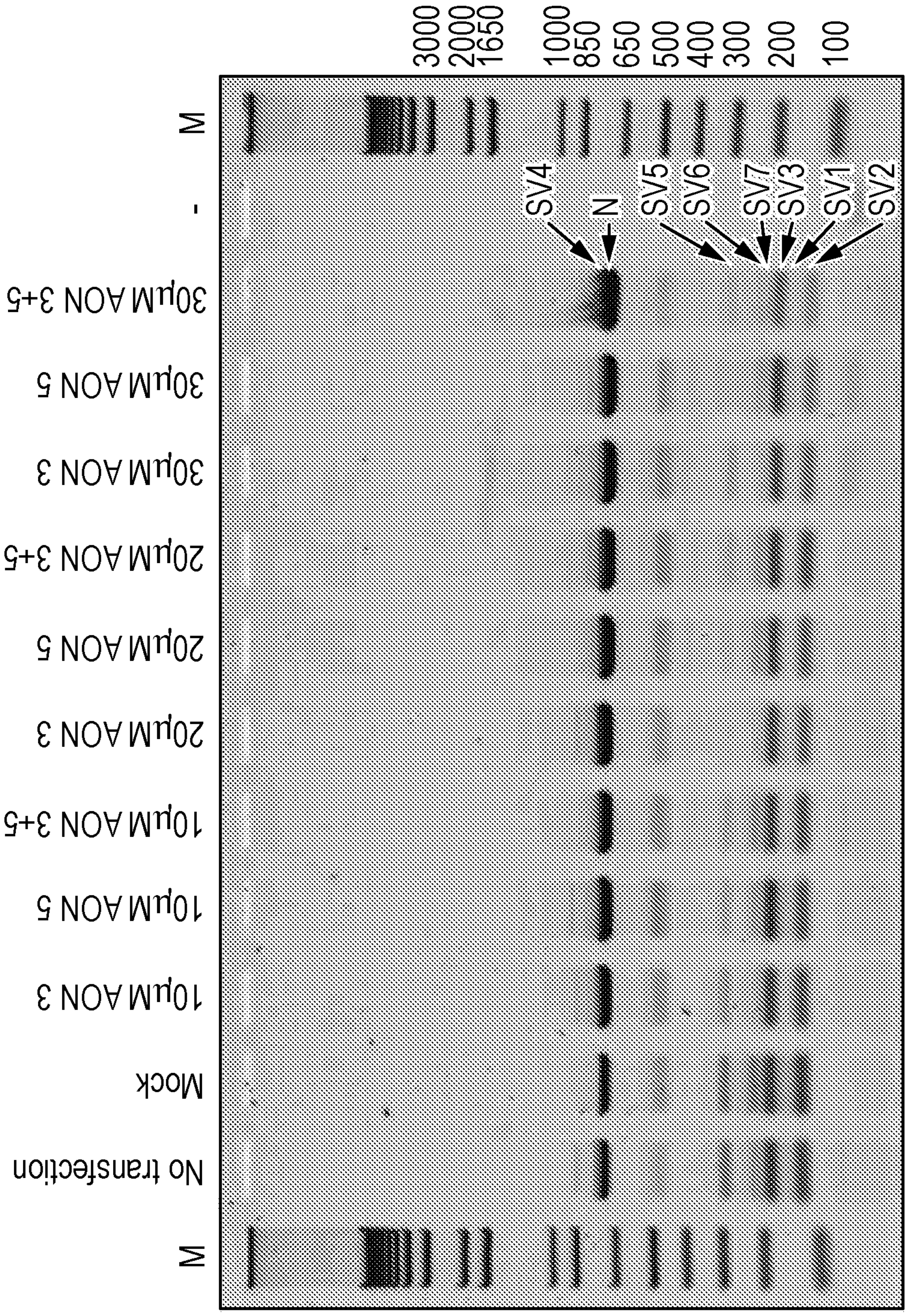

To test this, we first analyzed whether splice products comprising the pseudo exon exist in cells from Pompe patients. To this end, mRNA isolated from patient-derived myotubes was analyzed by flanking exon RT-PCR of exon 2, and PCR products were cloned in a TOPO vector. One hundred clones were analyzed by Sanger sequencing, and this resulted in the identification of 8 splice variants (FIG. 5*b,c*. Table 6, FIG. 10*a*). The predicted pseudo exon was indeed detected in two splice products, in which exon 2 was fully (SV6) or partially (SV5) skipped. Both products were likely subject to mRNA degradation due to the lack of the translation start codon, explaining their low abundance. Nevertheless, these could be identified on agarose gels following flanking exon PCR of exon 2 (FIG. 5*b*). Other low abundant splice products (SV1, SV4, and SV7) utilized a previously described cryptic splice donor nearby exon 123. However, these never contained the pseudo exon. We conclude that the predicted pseudo exon indeed exists in vive and that it is preferentially included in splice products in which exon 2 is partially or fully skipped due to the IVS1 variant.

Figure 5C:
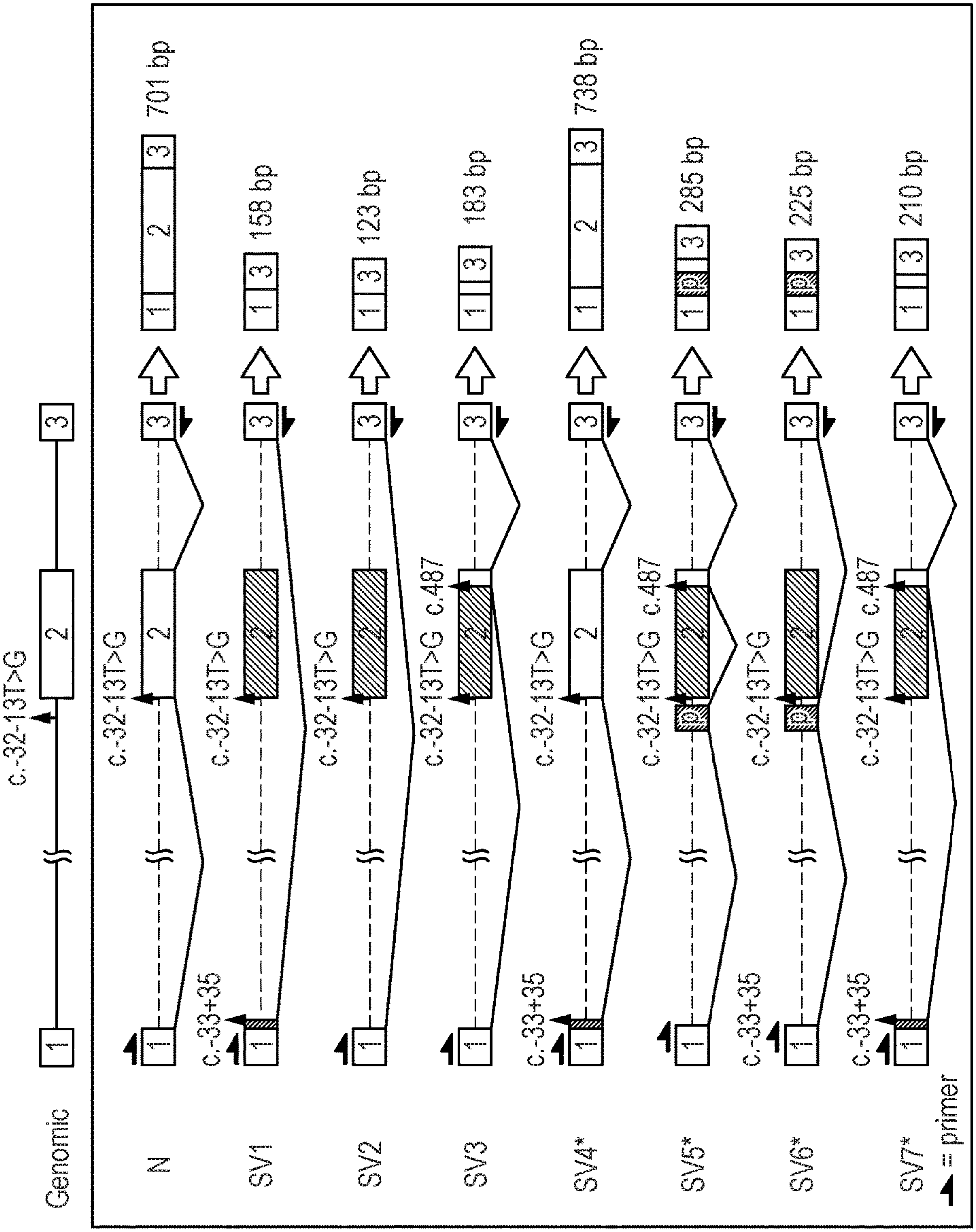
Figure 5D:
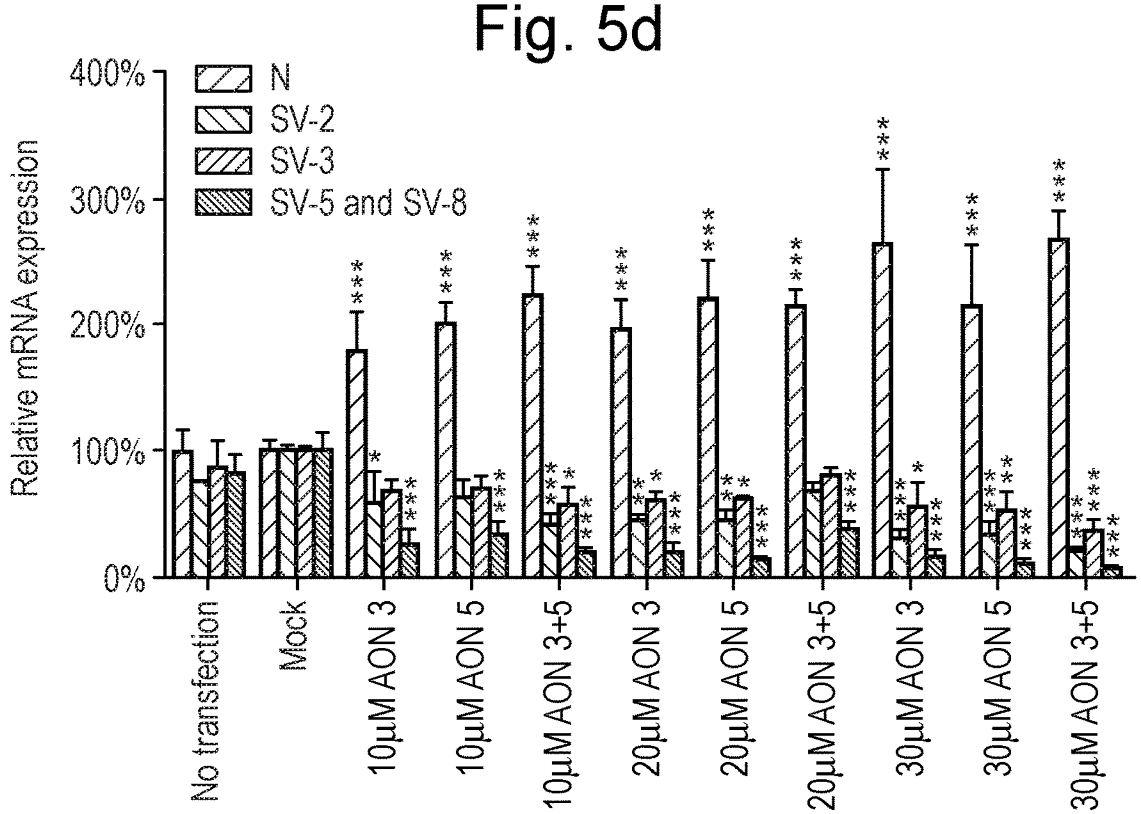
Figure 5E:
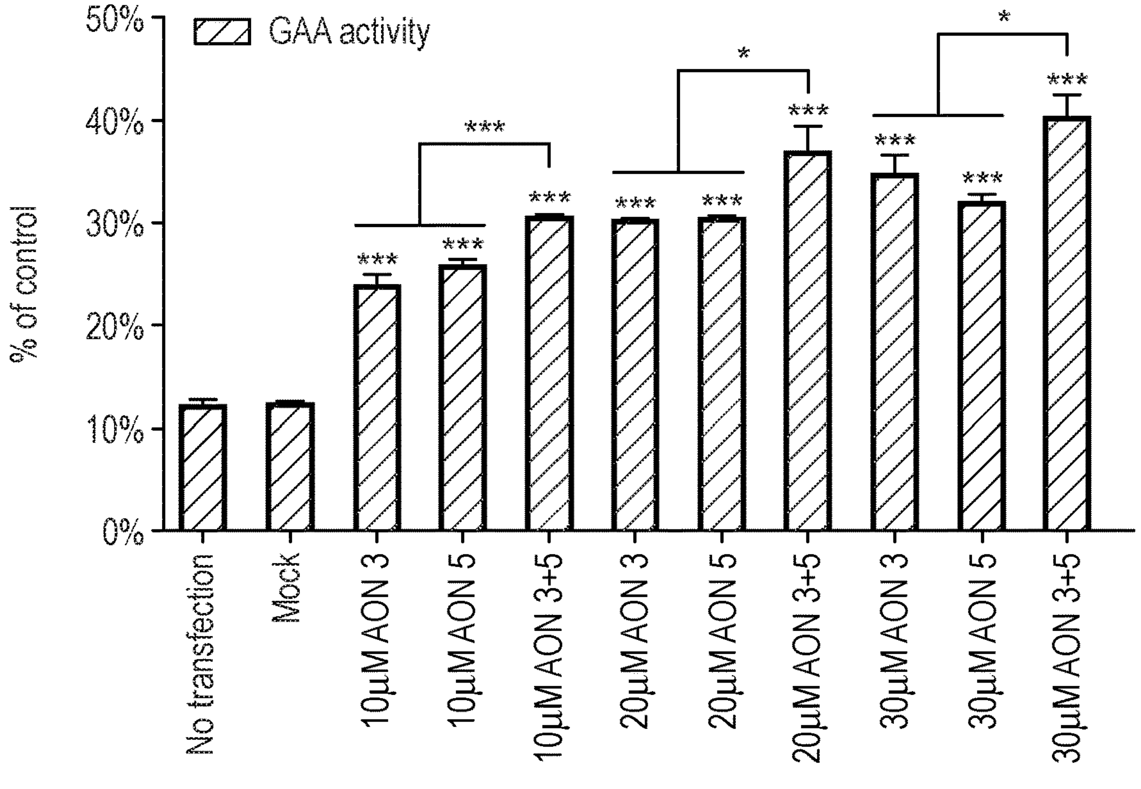
Figure 5F:
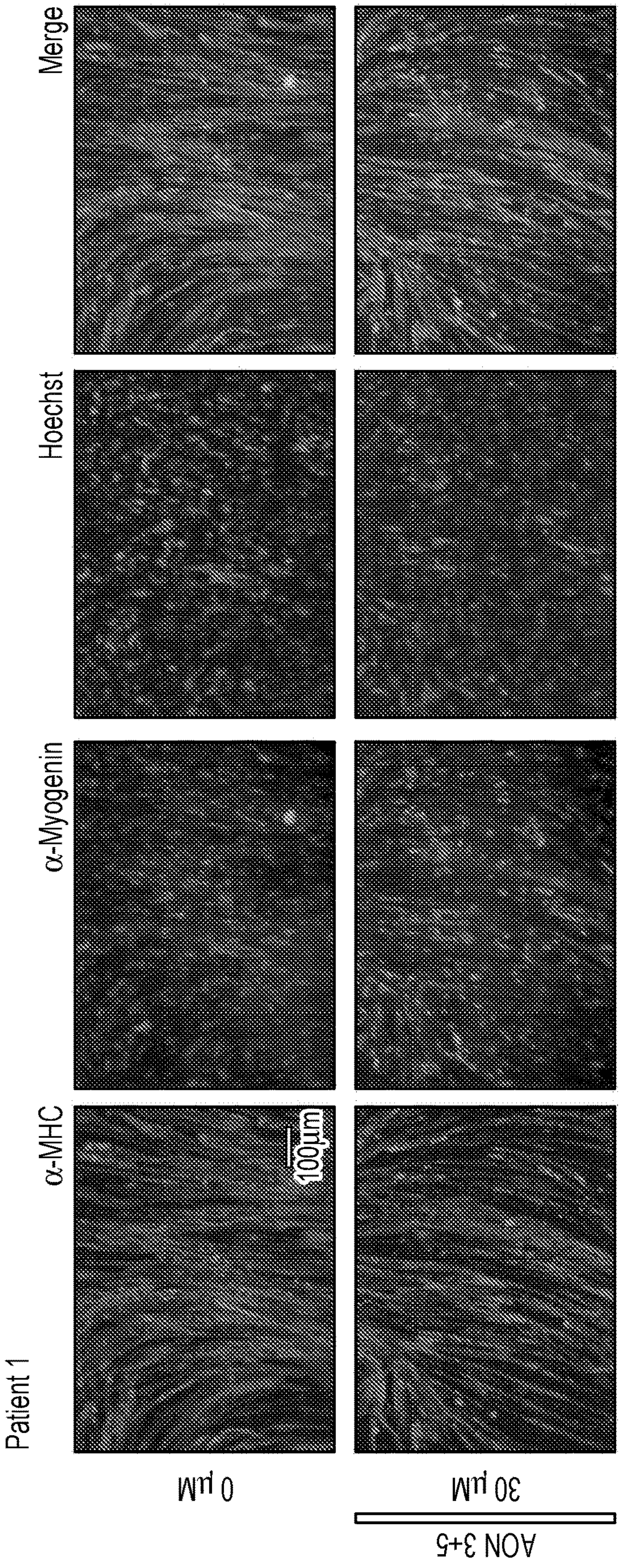

Short introns are unfavorable for successful splicing and have a typical minimum length of 70-80 nt. The length of the intron between the pseudo exon and exon 2 is 52 nt, which violates this rule. This suggested the possibility that inclusion of the pseudo exon competes with exon 2 inclusion, which is in agreement with the mutually exclusive inclusion of the pseudo exon or exon 2 in splice products. Such scenario explains why AONs 3 and 4 promote exon 2 inclusion, namely by repression of inclusion of the pseudo exon via interfering with the pY tract of the cryptic splice acceptor site. We hypothesized that repression of the cryptic splice donor would likewise promote exon 2 inclusion. To test this. AON 5 (SEQ ID NO: 578) was designed to target the cryptic splice donor site of the pseudo exon (FIG. 5*a*. FIG. 7*a*). In patient-derived myotubes. AON 5 promoted exon 2 inclusion (product N) and repressed inclusion of the pseudo exon (products SV5 and SV6), as shown by flanking exon RT-PCR and splicing product-specific RT-qPCR (FIG. 5*b,d*, and Supplementary FIG. 5*b*). AON 5 was equally effective in splicing correction compared to AON 3, in agreement with the idea that both AONs prevent utilization of the pseudo exon. GAA enzyme activity was enhanced by AON 5 to similar levels compared to AON 3 (FIG. 5*e*) and myotube differentiation was not altered by the AON treatment (FIG. 5*f*). These results suggest that the pseudo exon competes with exon 2 splicing and that pseudo exon skipping by AONs promotes exon 2 inclusion.

The identification of the pseudo exon offered an additional opt ion for splicing correction, namely by the simultaneous targeting of the cryptic splice acceptor and donor sites. To test this, a combination of AON3 plus AON 5 was tested in patient-derived myotubes. At the same total AON concentrations, the combination of AON 3 plus AON 5 showed higher efficacy than single AONs in promoting exon 2 inclusion and repressing aberrant exon 2 splicing (FIG. 5*c,d*).

We used TOPO cloning as above to analyze all products that arise from treatment with AON 3+AON 5 (Table 18). No additional products besides the 8 known splicing products were identified. Compared to mock treated cells, cells treated with AON 1+AON 5 showed an increase in the number of clones with a wild type exon 2 insert from 14 to 45 (3.2 fold), while the number of clones that contained the pseudo exon was reduced 6 fold from 6 to 1 (Table 18). GAA enzymatic activity was elevated by AON 3+AON 5 up to 3.3 fold (FIG. 5*e*). Following the calculation outlined above, this amounts to a highly efficient splicing correction of the IVS1 allele of 66-99%. We conclude that the simultaneous inhibition of the cryptic splice donor and acceptor sites of the pseudo exon is the most efficient way to promote exon 2 inclusion and is able to restore the majority of GAA enzymatic activity in patient-derived skeletal muscle cells towards healthy control levels.

TABLE 18 splice variants observed.

| Splice variant | colony count mock transfection | colony count transfection of 15 μM AON 3 and 5 |
|---|---|---|
| N | 14 | 45 |
| SV1 | 3 | 3 |
| SV2 | 44 | 16 |
| SV3 | 24 | 23 |
| SV4 | 0 | 2 |
| SV5 | 4 | 1 |
| SV6 | 2 | 0 |
| SV7 | 2 | 0 |
| total | 93 | 90 |

Example 2 In Vitro Experiments on ERT (Comparative)

In this experiment, patient-derived and healthy control subject-derived skeletal muscle cells were grown in a cell culture system as described in Example 1, after which these cells were treated with Myozyme® at several concentrations as ERT. The results are displayed in FIG. 11. This is a comparative experiment showing the effect of ERT alone.

Example 3. In Vitro Experiments on Combination of ERT and Antisense Therapy of ERT and Antisense Therapy: Effect of ERT Dosage Regimes In this experiment, IVS1 patient derived skeletal muscle cells from two Pompe patients (having a GAA IVS1 mutation on one allele and a fully deleterious GAA mutation on the other allele, as described in Example 1) were grown in a cell culture system as described above, after which the cells were treated with Myozyme® at several concentrations. Furthermore, the combination of Myozyme® at several concentrations with AON therapy at a fixed concentration was tested. The sequence of the AON 4 (5'-GCCAGAAGGAAGGGCGAGAAAAGCT-3'; SEQ ID NO: 277; target c.-32-190_-166) was used in this experiment. The concentration of AON used was 20 μM. The results are displayed in FIGS. 12 and 13.

The endogenous level of GAA is around 12 nmol 4-MU/hr/mg protein (y-axis intercept of ERT graph). It is clearly shown that without ERT, the AON therapy increases to a level of 40 nmol 4-MU/hr/mg protein. Treatment with ERT, using increasing amounts of exogenous enzyme, results in an activity ceiling of around 40 nmol 4-MU/hr/mg protein. It should be noted that an amount of around 200 nmol 4-MU/hr/mg protein mimics a treatment at a dose rate of 20 mg/kg body weight/2 weeks, which represents the clinically relevant ERT dosage. At this level. ERT reaches 20 nmol 4-MU/hr/mg protein at best. The combination with AON (constant administration of 20 microM of antisense oligonucleotide) at 200 nmol 4-MU/hr/mg protein of ERT results in a dramatic increase in the availability of intracellular protein to around (60 nmol 4-MU/hr/mg protein.

It is thus concluded that the increase in protein level using the combination of the invention is such that levels well in excess of 40 nmol 4-MU/hr/mg protein can be attained. The ERT therapeutic ceiling is thus increased by using ERT in combination with AON therapy. At the same time, this allows for the use of reduced concentrations of either AON, ERT, or both, which may add to a reduction of toxicity in the case of AON dosage, and a reduction in price in the case of ERT dosage, when using both in combination.

Example 4. In Vitro Experiments on Combination of ERT and Antisense Therapy: Effect of AON Dosage Regimes In this experiment, IVS1 patient derived skeletal muscle cells as described in Example 3 were grown in a cell culture system as described above, after which the cells were treated with Myozyme® at several concentrations and a fixed concentration of AON (20 μM). Furthermore, the combination of Myozyme® at fixed concentration (200 nmol 4-MU/hr/ml medium) was tested with several concentrations of AON. The sequence of the AON used in this experiment was AON 4 (5'-GCCAGAAGGAAGGQCGAGAAAAGCT-3; SeqID: 277, target c.-32-190_-166). The results are displayed in FIGS. 14-17.

Example 5. Definition of Splice Element Boundaries

In an attempt to define the downstream boundary of the target region of the splice acceptor site of the pseudo exon (SEQ ID NO: 1) and the upstream boundary of the target region of the splice donor site of the pseudo exon (SEQ ID NO 171), an experiment was conducted wherein the GAA enzyme activity was determined following administration of AONs covering the splice elements to in vitro cultured Pompe patient cells.

Nomenclature

Nomenclature according to HGVS guidelines was used to highlight specific locations within the GAA gene. NM00152.3 served as the reference sequence for GAA. Complementary DNA (cDNA) reference guidelines were used, in which c.1 represents the first nucleotide of the coding region within the GAA cDNA.

Primary Fibroblast and iPSC-Derived Myogenic Progenitor Cultures

Patient or healthy control cell lines have been cultured with informed consent. Fibroblast were cultured under standard conditions using medium containing DMEM High glucose (Gibco), 10% FBS, and 1% Penicillin/Streptomycin/Glutamate (Gibco), iPSC-derived myogenic progenitor cell lines were cultured as described previously (van der Wal et al, 2017). In short, cells were expanded in proliferation medium containing, DMEM High glucose (Gibco), 10% FBS, 1% Penicillin/Streptomycin/Glutamate (Gibco), and 100 ng/ml FGF2 (Peprotech). Myogenic progenitors were differentiated to myotubes using differentiation medium containing DMEM High glucose (Gibco), 1% ITS-x (Gibco), and 1% Penicillin/Streptomycin/Glutamate (Gibco). All cells were grown on plates coated with extracellular matrix (Sigma Aldrich). Cells were differentiated for four or five days before they were harvested for analysis.

Antisense Oligonucleotide Transfection

Phosphorodiamidate Morpholino oligomer (PMO) based antisense oligonucleotides (AONs) were ordered from Gene Tools. LLC and transfected in the myogenic progenitors using 4.5 μl Endoporter reagent (Gene Tools, LLC) per ml of proliferation medium according to the manusfactor's instructions. Transfection was carried out one day before start of differentiation. The concentration of the PMO-based AONs in the culture medium varied per experiment and is indicated in the figures and legends.

Treatment with rhGAA

Cultured iPS-derived skeletal muscle cells were grown in proliferation medium, and differentiated to myotubes as described above for 3-4 days. The medium was then replaced with medium containing DMEM High glucose (Gibco), 1% ITS-x (Invitrogen), 1% Penicillin/Streptomycin/Glutamate (Gibco), and 3 mM PIPES with the indicated concentrations of rhGAA (Myozyme®, Sanofi Genzyme). Cells were treated for one day, after which cells were rinsed three times with PBS and harvested for further analysis.

Measurement of GAA Enzymatic Activity

This was done as described in van der Wal et al., 2017. In short, cells were lysed using a lysis buffer containing 50 mM Tris (pH 7.5), 100 mM NaCl, 50 mM NaF, 1% Tx-100 and protease inhibitor cocktail (Roche). Total protein concentrations were measured using the BCA Protein Assay kit (Pierce). GAA enzymatic activity was tested using 4-Methylumbelliferyl α-D-glucoside (Sigma) as a substrate. After 1 hour, the reaction was stopped with a carbonate buffer (pH 10.4). Samples were measured on the Varioskan Flash Multimode Microplate Reader (Thermo). Results were normalized based on total protein.

The AONs used in this experiment are indicated in Table 19

TABLE 19 details of AONs highlighted in FIG. 5a.

| AON nr. | AON name and target location | AON sequence (5' to 3') | SEQ ID No. |
|---|---|---|---|
| 1 | c.-32-219_-200 | GAGTGCAGAGCACTTGCACA | 299 |
| 2 | c.-32-224_-200 | GAGTGCAGAGCACTTGCACAGTCTG | 2041 |
| 3 | c.-32-187_-167 | CCAGAAGGAAGGGCGAGAAAA | 298 |
| 4 | c.-32-190_-166 | GCCAGAAGGAAGGGCGAGAAAAGCT | 277 |
| 5 | c.-32-64_-40 | GGGCGGCACTCACGGGGCTCTCAAA | 578 |
| 6 | c.-32-170_-146 | CTGTCTAGACTGGGGAGAGGGCCAG | 326 |
| 7 | c.-32-113_-89 | CTGGCACTGCAGCACCCAGGCAGGT | 647 |
| 8 | c.-32-86_-62 | AAAGCAGCTCTGAGACATCAACCGC | 2042 |
| 9 | c.-32-75_-51 | ACGGGGCTCTCAAAGCAGCTCTGAG | 514 |
| 10 | c.-32-65_-41 | GGCGGCACTCACGGGGCTCTCAAAG | 519 |
| 11 | c.-32-27_-8 | AGAAGCAAGCGGGCTCAGCA | 2043 |
| 12 | c.5-25 | AGCAGGGCGGGTGCCTCACTC | 2044 |
| 13 | CypA c.165_173+11 | TGTACCCTTACCACTCAGTC | 2045 |

TABLE 20

AONs used in experiments.

| AON name and target location | AON sequence (5' to 3') | SeqID |
|---|---|---|
| c.-32-224_-200 | GAGTGCAGAGCACTTGCACAGTCTG | 2041 |
| c.-32-86_-62 | AAAGCAGCTCTGAGACATCAACCGC | 2042 |
| c.-32-27_-8 | AGAAGCAAGCGGGCTCAGCA | 2043 |
| c.5-25 | AGCAGGGCGGGTGCCTCACTC | 2044 |
| CypA c.165_173+11 | TGTACCCTTACCACTCAGTC | 2045 |

REFERENCES

1. Kaplan J C, Hamroun D. The 2015 version of the gene table of monogenic neuromuscular disorders (nuclear genome). Neuromuscul Disord 24, 1123-1153 (2014).
2. Van der Ploeg A T, Reuser A J. Pompe's disease. Lancet 372, 1342-1353 (2008).
3. Kishnani P S, Beckemeyer A A. New therapeutic approaches for Pompe disease: enzyme replacement therapy and beyond. Pediatr Endocrinol Rev 12 Suppl 1, 114-124 (2014).
4. Schoser B, et al. Survival and long-term outcomes in late-onset Pompe disease following alglucosidase alfa treatment: a systematic review and meta-analysis. J Neurol. (2016).
5. Van den flout H, Reuser A J, Vulto A G. Loonen M C, Cromme-Dijkhuis A, Van der Ploeg A T. Recombinant human alpha-glucosidase from rabbit milk in Pompe patients. Lancet 356, 397-398 (2000).
6. Van der Ploeg A T, et al. A randomized study of alglucosidase alfa in late-onset Pompe's disease. N Engl J Med 362, 1396-1406 (2010).
7. Gungor D, et al. Impact of enzyme replacement therapy on survival in adults with Pompe disease: results from a prospective international observational study. Orphanet J Rare Dis 8, 49 (2013).
8. Van der Ploeg A T, et al. Open-label extension study following the Late-Onset Treatment. Study (LOTS) of alglucosidase alfa. Mol (Genet Metab 107, 456-461 (2012).
9. Bembi B, et al. Long-term observational, non-randomized study of enzyme replacement therapy in late-onset glycogenosis type II. J Inherit Metab Dis 33, 727-735 (2010).
10. Orlikowski D, et al. Recombinant human acid alpha-glucosidase (rhGAA) in adult patients with severe respiratory failure due to Pompe disease. Neuromuscul Disord 21, 477-482 (2011).
11. Strothotte S, et al. Enzyme replacement therapy with alglucosidase alfa in 44 patients with late-onset glycogen storage disease type 2: 12-month results of an observational clinical trial. J Neurol 257, 91-97 (2010).
12. Angelini C, et. al. Observational clinical study in juvenile-adult glycogenosis type 2 patients undergoing enzyme replacement therapy for up to 4 years. J Neurol 259, 952-958 (2012).
13. Regnery C, et al. 36 months observational clinical study of 38 adult Pompe disease patients under alglucosidase alfa enzyme replacement therapy. J Inherit Metab Dis 35, 837-845 (2012).
14. Anderson L J, et al. Effectiveness of enzyme replacement therapy in adults with late-onset. Pompe disease: results from the NCS-LSD cohort study. J Inherit Metab Dis 37, 945-952 (2014).

15. De Vries J M, et al. Effect of enzyme therapy and prognostic factors in 69 adults with Pompe disease: an open-label single-center study. Orphanet J Rare Dis 7, 73 (2012).

16. De Vries J M, et al. High antibody liter in an adult with Pompe disease affects treatment with alglucosidase alfa. Mol Genet Metab 101, 338-345 (2010).

17. De Vries J M, et al. Pompe disease in adulthood: effects of antibody formation on enzyme replacement therapy. Genet Med, (2016).

18. Patel T T, Banugaria S G, Case L E, Wenninger S, Schoser B. Kishnani P S. The impact of antibodies in late-onset Pompe disease: a case series and literature review. Mol Genet Metab 106, 301-309 (2012).

19. Cardone M, et al. Abnormal mannose-6-phosphate receptor trafficking impairs recombinant alpha-glucosidase uptake in Pompe disease fibroblasts. Pathogenetics 1, 6 (2008).

20. Settembre C, Fraldi A, Rubinsztein D C, Ballabio A. Lysosomal storage diseases as disorders of autophagy. Autophagy 4, 113-114 (2008).

21. Fukuda T, et al. Autophagy and lysosomes in Pompe disease. Autophagy 2, 318-320 (2006).

22. Huie M L, et al. Aberrant splicing in adult onset glycogen storage disease type II (GSDII): molecular identification of an IVS1 (−13T->G) mutation in a majority of patients and a novel IVS10 (+1GT->CT) mutation. Hum Mol Genet 3, 2231-2236 (1994).

23. Boerkoel C F, et al. Leaky splicing mutation in the acid maltase gene is associated with delayed onset of glycogenosis type II. Am J Hum Genet 56, 887-897 (1995).

24. Dardis A, et al Functional characterization of the common c.-32-13T>G mutation of GAA gene: identification of potential therapeutic agents. Nucleic Acids Res 42, 1291-1302 (2014).

25. Bergsma A J. Kroos M. Hoogeveen-Westerveld M. Halley D, van der Ploeg A T, Pijnappel W W. Identification and characterization of aberrant GAA pre-mRNA splicing in pompe disease using a generic approach. Hum Mutat 36, 57-68 (2015).

26. McClorey G, Wood M J. An overview of the clinical application of antisense oligonucleotides for RNA-targeting therapies. Curr Opin Pharmacol 24, 52-58 (2015).

27. Jirka S. Aartsma-Rus A. An update on RNA-targeting therapies for neuromuscular disorders. Curr Opin Neurol 28, 515-521 (2015).

28. Rigo F, Seth P P. Bennett C F. Antisense oligonucleotide-based therapies for diseases caused by pre-mRNA processing defects. Adv Exp Med Biol 825, 303-352 (2014).

29. Havens M A, Hastings M L. Splice-switching antisense oligonucleotides as therapeutic drugs. Nucleic Acids Res, (2016).

30. Hua Y, Vickers T A, Okunola H L, Bennett C F, Krainer A R. Antisense masking of an hnRNP A1/A2 intronic splicing silencer corrects SMN2 splicing in transgenic mice. Am J Hum Genet 82, 834-848 (2008).

31. Lorson C L, Androphy E J. An exonic enhancer is required for inclusion of an essential exon in the SMA-determining gene SMN. Hum Mol Genet 9, 259-265 (2000).

32. Singh N K, Singh N N, Androphy E J, Singh R N. Splicing of a critical exon of human Survival Motor Neuron is regulated by a unique silencer element located in the last intron. Mol Cell Biol 26, 1333-1346 (2006).

33. Singh N N, Shishimorova M. Cao L C, Gangwani L. Singh R N. A short antisense oligonucleotide masking a unique intronic motif prevents skipping of a critical exon in spinal muscular atrophy. RNA Biol 6, 341-350 (2009).

34. Lee Y. Rio D C. Mechanisms and Regulation of Alternative Pre-mRNA Splicing. Annu Rev Biochem 84, 291-323 (2015).

35. Merkin J, Russell C, Chen P, Burge C B. Evolutionary dynamics of gene and isoform regulation in Mammalian tissues. Science 338, 1593-1599 (2012).

36. Nehlin J O, Just M, Rustan A C, Gaster M. Human myotubes from myoblast cultures undergoing senescence exhibit defects in glucose and lipid metabolism. Biogerontology 12, 349-365 (2011).

37. Borchin B, Chen J, Barberi T. Derivation and FACS-mediated purification of PAX3+/PAX7+ skeletal muscle precursors from human pluripotent stem cells. Stem Cell Reports 1, 620-631 (2013).

38. Shelton M. Kocharyan A. Liu J, Skerjanc I S, Stanford W L. Robust generation and expansion of skeletal muscle progenitors and myocytes from human pluripotent stem cells. Methods 101, 73-84 (2016).

39. Chal J., et al. Differentiation of pluripotent stem cells to muscle fiber to model Duchenne muscular dystrophy. Nat Biotechnol 33, 962-969 (2015).

40. Gorman L, Suter D, Emerick V, Schumperli D, Kole R. Stable alteration of pre-mRNA splicing patterns by modified U7 small nuclear RNAs. Proc Natl Acad Sci USA 95, 4929-4934 (1998).

41. Nlend R N, Schumperli D. Antisense genes to induce exon inclusion. Methods Mol Biol 867, 325-347 (2012).

42. Liu S, Asparuhova M, Brondani V, Ziekau I, Klimkait T, Schumperli D. Inhibition of HIV-1 multiplication by antisense U7 snRNAs and siRNAs targeting cyclophilin A. Nucleic Acids Res 32, 3752-3759 (2004).

43. Perez B, et al. Pseudoexon exclusion by antisense therapy in methylmalonic aciduria (MMAuria). Hum Mutat 30, 1676-1682 (2009).

44. Kollberg G, Holme E. Antisense oligonucleotide therapeutics for iron-sulphur cluster deficiency myopathy. Neuromuscul Disord 19, 833-836 (2009).

45. Bigot A, et al. Replicative aging down-regulates the myogenic regulatory factors in human myoblasts. Biol Cell 100, 189-199 (2008).

46. Drost M R, et al. Both type 1 and type 2a muscle fibers can respond to enzyme therapy in Pompe disease. Muscle Nerve 37, 251-255 (2008).

47. Droge C, Schaal H, Engelmann G, Wenning D, Haussinger D, Kubitz R. Exon-skipping and mRNA decay in human liver tissue: molecular consequences of pathogenic bile salt export pump mutations. Sci Rep 6, 24827 (2016).

48. Xue Y, et al. Exome Sequencing Identified a Splice Site Mutation in FHL1 that Causes Uruguay Syndrome, an X-Linked Disorder With Skeletal Muscle Hypertrophy and Premature Cardiac Death. Circ Cardiovasc Genet 9, 130-135 (2016).

49. Iida K, et al. A novel heterozygous splice site OPA1 mutation causes exon 10 skipping in Japanese patients with dominant optic atrophy. Ophthalmic Genet 37, 354-356 (2016).

50. Heilker R. Traub S. Reinhardt P, Scholer H R, Sterneckert J, iPS cell derived neuronal cells for drug discovery. Trends Pharmacol Sci 35, 510-519 (2014).

51. Takahashi K, et al. Induction of pluripotent stem cells from adult human fibroblasts by defined factors. Cell 131, 861-872 (2007).

52. Ebert A D, Liang P. Wu J C. Induced pluripotent stem cells as a disease modeling and drug screening platform. J Cardiovasc Pharmacol 60, 408-416 (2012).

53. Choi I Y, et al. Concordant but Varied Phenotypes among Duchenne Muscular Dystrophy Patient-Specific Myoblasts Derived using a Human iPSC-Based Model. Cell Rep 15, 2301-2312 (2016).

54. Warlich E, et al. Lentiviral vector design and imaging approaches to visualize the early stages of cellular reprogramming. Mol Ther 19, 782-789 (2011).

55. Irizarry R A, Bolstad B M, Collin F, Cope L M, Hobbs B, Speed T P. Summaries of Affymetrix GeneChip probe level data. Nucleic Acids Res 31, el5 (2003).

56. Gao K, Masuda A, Matsuura T, Ohno K. Human branch point consensus sequence is yUnAy. Nucleic Acids Res 36, 2257-2267 (2008).

The invention claimed is:

1. A method of treatment for Pompe disease comprising the administration to a subject in need thereof of a composition comprising a pharmaceutical combination of an enzyme or nucleic acid encoding said enzyme suitable for Enzyme Replacement Therapy for Pompe disease and an antisense oligomeric compound (AON) that repairs aberrant splicing of an acid a-glucosidase (GAA) gene product, wherein said treatment comprises the administration to a subject in need thereof of said enzyme or said nucleic acid encoding said enzyme in a dose of about 5-40 mg/kg body weight, in combination with said antisense oligomeric compound (AON) in a dose of about 10 ng-30 mg per kg of body weight.

2. The method according to claim 1, wherein said enzyme or said nucleic acid encoding said enzyme is administered every 2 weeks.

3. The method according to claim 1, wherein said antisense oligomeric compound (AON) is administered every 2 weeks.

4. The method according to claim 1, wherein said antisense oligomeric compound repairs said aberrant splicing by one of promotion of exon inclusion, inhibition of a cryptic splicing site, inhibition of intron inclusion, recovering of reading frame, inhibition of splicing silencer sequence, activation of spicing enhancer sequence and combinations thereof.

5. The method according to claim 1, wherein said Pompe disease is caused by the GAA IVS1 mutation c.-32-13T>G.

6. The method according to claim 5, wherein said AON is directed against the region surrounding and/or including the natural cryptic acceptor splice site indicated by SEQ ID NO:1, or a part thereof.

7. The method according to claim 6, wherein said AON is directed against the region surrounding and/or including the natural cryptic acceptor splice site indicated by SEQ ID NO:2046.

8. The method according to claim 5, wherein said AON is directed against the region surrounding and/or including the natural cryptic donor splice site indicated by SEQ ID NO:171, or a part thereof.

9. The method according to claim 6, wherein said AON directed against the natural cryptic acceptor splice site is selected from SEQ ID NOs: 267-298, SEQ ID NOs: 299-445 and sequences having a sequence identity of at least 80% therewith.

10. The method according to claim 8, wherein said AON directed against the natural cryptic donor splice site is selected from SEQ ID NOs: 446-602 and sequences having a sequence identity of at least 80% therewith.

11. The method according to claim 1, wherein said AON comprises a pair of two AONs formed by a first AON directed to the natural cryptic splice acceptor site, and by a second AON directed to the natural cryptic splice donor site.

12. The method according to claim 11, wherein the first AON is selected from the sequences of SEQ ID NOs: 267-298, SEQ ID NOs: 299-445, complementary sequences thereto and sequences having a sequence identity of at least 80% therewith.

13. The method according to claim 11, wherein the second AON is selected from the sequences of SEQ ID NOs: 446-602 complementary sequences thereto and sequences having a sequence identity of at least 80% therewith.

14. The method according to claim 11, wherein the pair of two AONs comprises:

- an AON selected from SEQ ID NOs: 514, 519, and 578 as the AON targeting the splice donor site or a sequence complimentary thereto or sequences having a sequence identity of at least 80% therewith or with the complementary sequence, and
- an AON selected from SEQ ID NOs: 277 and 298 as the AON targeting the splice acceptor site, or sequences complimentary thereto or sequences having a sequence identity of at least 80% therewith or with the complementary sequences.

15. The method according to claim 1, wherein said AON is selected from SEQ ID NOs: 641-992 and sequences having a sequence identity of at least 80% therewith.

16. The method according to claim 1, wherein said AON is selected from SEQ ID NOs: 603-640 and SEQ ID NOs: 993-2040 and sequences having a sequence identity of at least 80% therewith.

* * * * *